(12) United States Patent
Villarreal

(10) Patent No.: US 11,946,940 B2
(45) Date of Patent: Apr. 2, 2024

(54) SELECTION BIOMARKERS FOR PATIENT STRATIFICATION IN BODILY FLUIDS AND APPLYING PRECISION MEDICINE THROUGH NOVEL DIAGNOSTIC BIOMARKERS

(71) Applicant: LIFESTORY HEALTH, INC., Brookline, MA (US)

(72) Inventor: Anna Villarreal, Brookline, MA (US)

(73) Assignee: LIFESTORY HEALTH, INC., Brookline, MA (US)

( * ) Notice: Subject to any disclaimer, the term of this patent is extended or adjusted under 35 U.S.C. 154(b) by 634 days.

(21) Appl. No.: 16/753,418

(22) PCT Filed: Oct. 9, 2018

(86) PCT No.: PCT/US2018/055059
§ 371 (c)(1),
(2) Date: Apr. 3, 2020

(87) PCT Pub. No.: WO2019/074954
PCT Pub. Date: Apr. 18, 2019

(65) Prior Publication Data
US 2020/0309797 A1    Oct. 1, 2020

Related U.S. Application Data

(60) Provisional application No. 62/569,998, filed on Oct. 9, 2017.

(51) Int. Cl.
*G01N 33/72* (2006.01)
*G01N 33/68* (2006.01)

(52) U.S. Cl.
CPC ....... *G01N 33/723* (2013.01); *G01N 33/6848* (2013.01); *G01N 2333/805* (2013.01); *G01N 2560/00* (2013.01); *G01N 2800/042* (2013.01)

(58) Field of Classification Search
CPC ............ C12Q 2527/125; C12Q 1/6806; C12Q 1/686; C12Q 2521/107; C12Q 2531/113; C12Q 1/6851; C12N 15/1003; G01N 2333/805; G01N 2560/00; G01N 2800/042; G01N 33/6818; G01N 33/6848; G01N 33/723
See application file for complete search history.

(56) References Cited

U.S. PATENT DOCUMENTS

| 9,918,702 B2 * | 3/2018 | Tariyal | A61B 5/150755 |
| 10,973,496 B2 * | 4/2021 | Naseri | A61F 13/535 |
| 11,193,942 B2 * | 12/2021 | Villarreal | G01N 33/6893 |
| 2009/0093010 A1 * | 4/2009 | Nickerson | G01N 33/6893 435/23 |
| 2017/0363641 A1 * | 12/2017 | Villarreal | G01N 33/6893 |
| 2022/0299515 A1 * | 9/2022 | Villarreal | G01N 33/6848 |

FOREIGN PATENT DOCUMENTS

| WO | WO2016030687 | * | 3/2016 | G01N 33/68 |

OTHER PUBLICATIONS

Wang et al. "In-Depth Comparative Characterization of Hemoglobin Glycation in Normal and Diabetic Bloods by LC-MSMS", J Am Soc Mass Spectrom, vol. 25, pp. 758-766. (Year: 2014).*
Mak et al. Antibacterial hemoglobin peptides in human menstrual blood. Peptides, vol. 25, pp. 1839-1847 (Year: 2004).*

* cited by examiner

*Primary Examiner* — Marcela M Cordero Garcia
(74) *Attorney, Agent, or Firm* — E. Eric Mills; David S. Bradin; Maynard Nexsen PC

(57) ABSTRACT

The present invention relates to, in part, methods of improved healthcare in female subjects that, for example, rely on menstrual fluid sampling for applying selection biomarkers.

12 Claims, 109 Drawing Sheets
Specification includes a Sequence Listing.

Item name: Fingerprick 1 Channel name 1: Average Time 27.8397 min: TOF MS (400-4000) ESI+ : Max...
Item description:

Item name: Fingerprick 1 Channel name 1: Average Time 28.8288 min: TOF MS (400-4000) ESI+ : Max...
Item description:

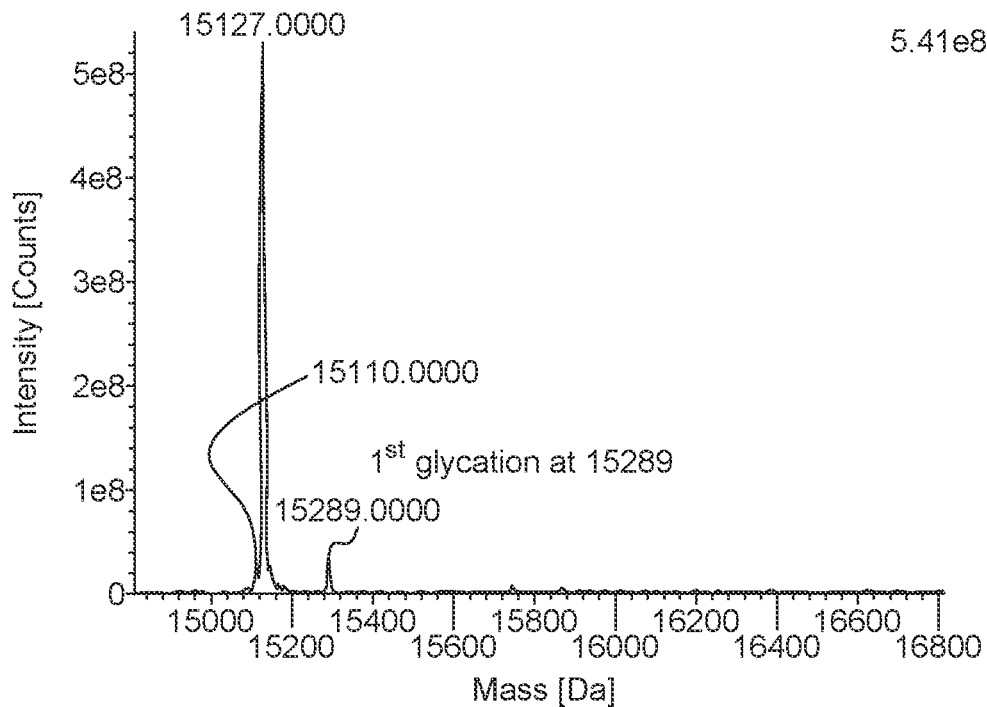
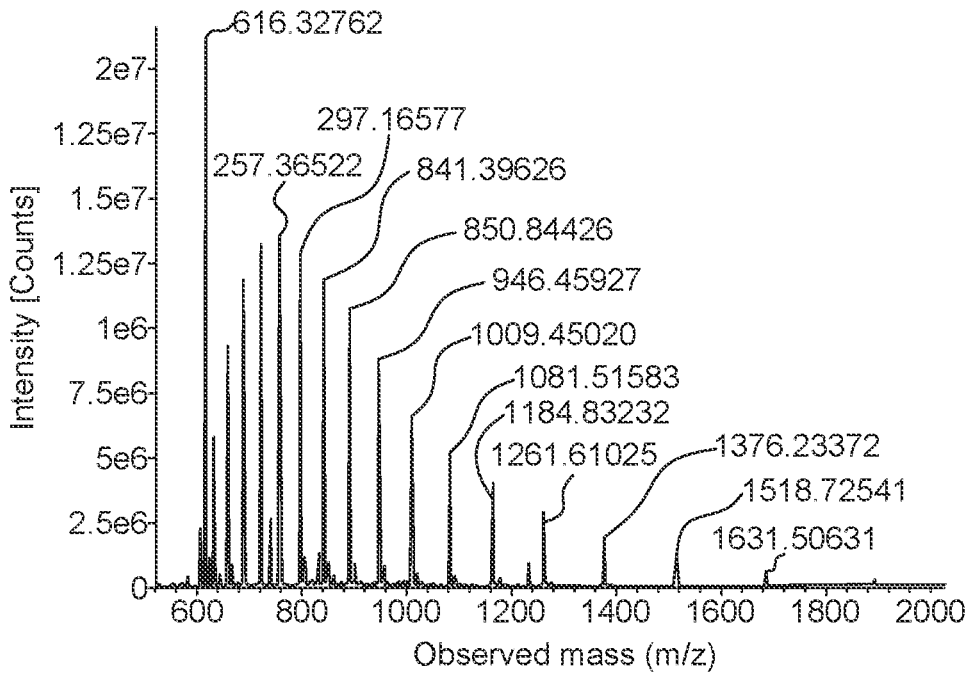
FIG. 11B

Modification Results

Components

| Identification | Peptide Sequence | Modification | Site | Delta (ppm) | Confidence Score | ID Type | RT(min) | M/Z | Charge State |
|---|---|---|---|---|---|---|---|---|---|
| Aa ▼ | Aa ▼ | Aa ▼ | Aa ▼ | ≡ ▼ | ≡ ▼ | Aa ▼ | ≡ ▼ | ≡ ▼ | ≡ ▼ |
| 1:V1-K8 = 951.50255m(K8+162.0480) | VHLTPEEK | 162.0480 | K8 | -15.91 | 98.8% | MS2 | 10.83 | 557.774 | 2 |
| 1:V1-K8 = 951.50255m(K8+162.0480) | VHLTPEEK | 162.0480 | K8 | -15.91 | 99.3% | MS2 | 10.83 | 1114.540 | 1 |
| 1:V1-K8 = 951.50255m(K8+162.0480) | VHLTPEEK | 162.0480 | K8 | -17.00 | 98.8% | MS2 | 10.83 | 372.184 | 3 |
| 1:V1-K8 = 951.50255m | VHLTPEEK | None | | -19.16 | 100.0% | MS2 | 10.57 | 467.749 | 2 |
| 1:V1-K8 = 951.50255m | VHLTPEEK | None | | -18.58 | 100.0% | Full | 10.57 | 952.492 | 1 |

| | Modification | Category | Comment | Normalized Time Shift | Predicted Time Shift | Peptides | Sequence | Confidence | Recovery | % Abundance HbA1c_standard_digest |
|---|---|---|---|---|---|---|---|---|---|---|
| ▼ | Aa ▼ | Aa ▼ | Aa ▼ | ≡ ▼ | ≡ ▼ | Aa ▼ | Aa ▼ | ≡ ▼ | ≡ ▼ | ≡ ▼ |
| 8 | K8+162.0480 | Unknown Modification | None | 1.2% | N/A | V1-K8 = 951.5025... | VHLTPEEK | 98.8% | 50.0% | 92.3510% |

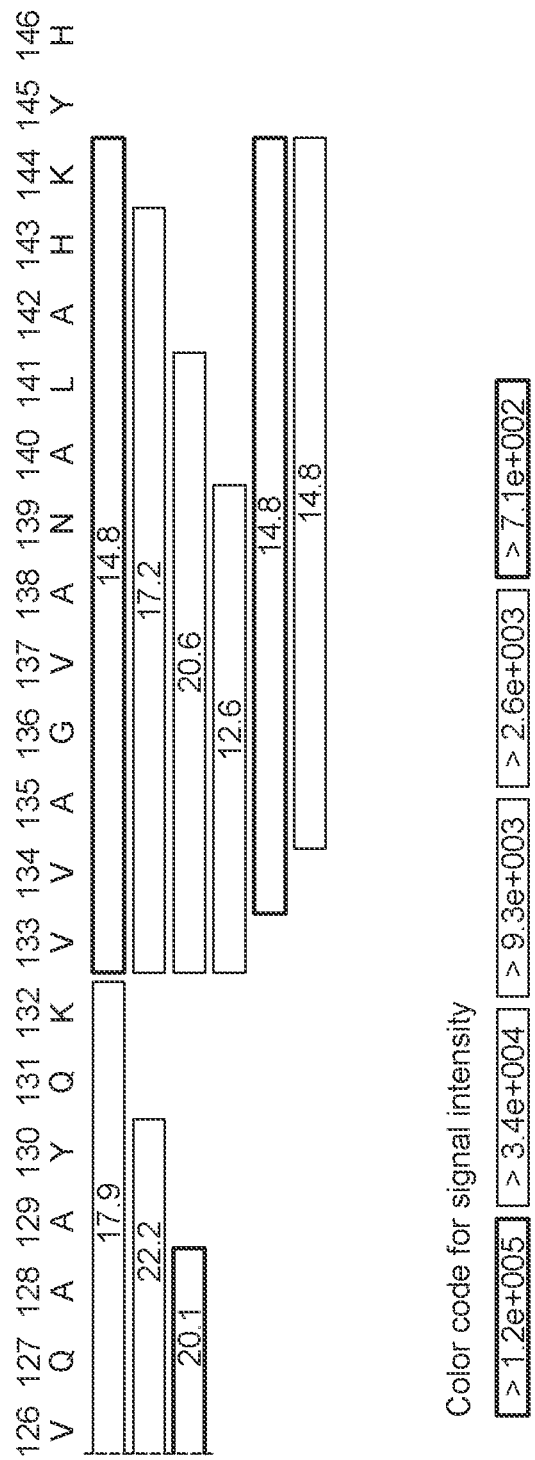
FIG. 13.BB

| Modification Results | | | | | | | |
|---|---|---|---|---|---|---|---|
| Components | | | | | | | Recalculate |
| | ▽ Level | No. | Identifaction | Peptide Sequence | Modifaction | Site | Delta (ppm) | Confidence Score |
| | Aa ▽ | ≡ ▼ | Aa ▼ | Aa ▼ | Aa ▽ | Aa ▽ | ≡ ▼ ▽ | ▼ ▽ |
| ⊞ 1 ☑ | Component | 96 | 1:V1-K8 = 951.50255m | VHLTPEEK | None | | -19.93 | 100% |
| ⊞ 2 ☑ | Component | 97 | 1:V1-K8 = 951.50255m | VHLTPEEK | None | | -19.35 | 100% |
| ⊞ 3 ☑ | Component | 114 | 1:V1-K8 = 951.50255m(K8+162.0497) | VHLTPEEK | 162.0497 | K8 | -16.99 | 100% |
| ▲ 4 ☑ | Component | 116 | 1:V1-K8 = 951.50255m(K8+162.0497) | VHLTPEEK | 162.0497 | K8 | -16.22 | 100% |

8  K8+162.0497  Unknown Modifica...  None  1.8%  N/A  V1-K8 = 951.5025...  VHLTPEEK  100%  19.3%  2.5170%

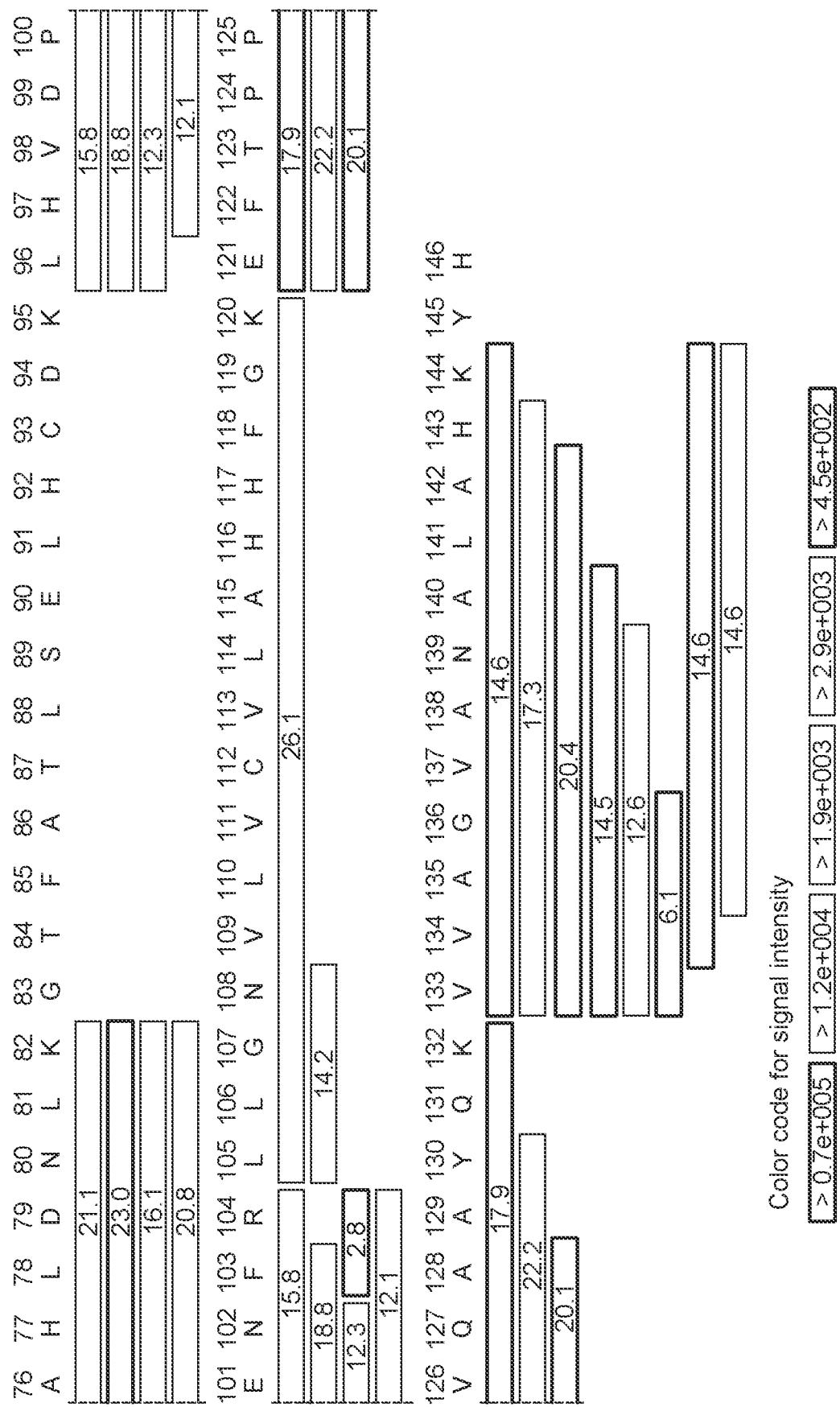
FIG. 14.BB

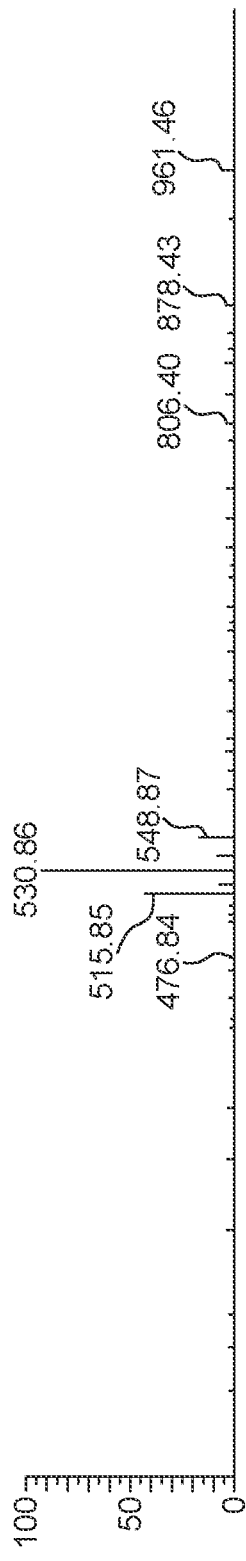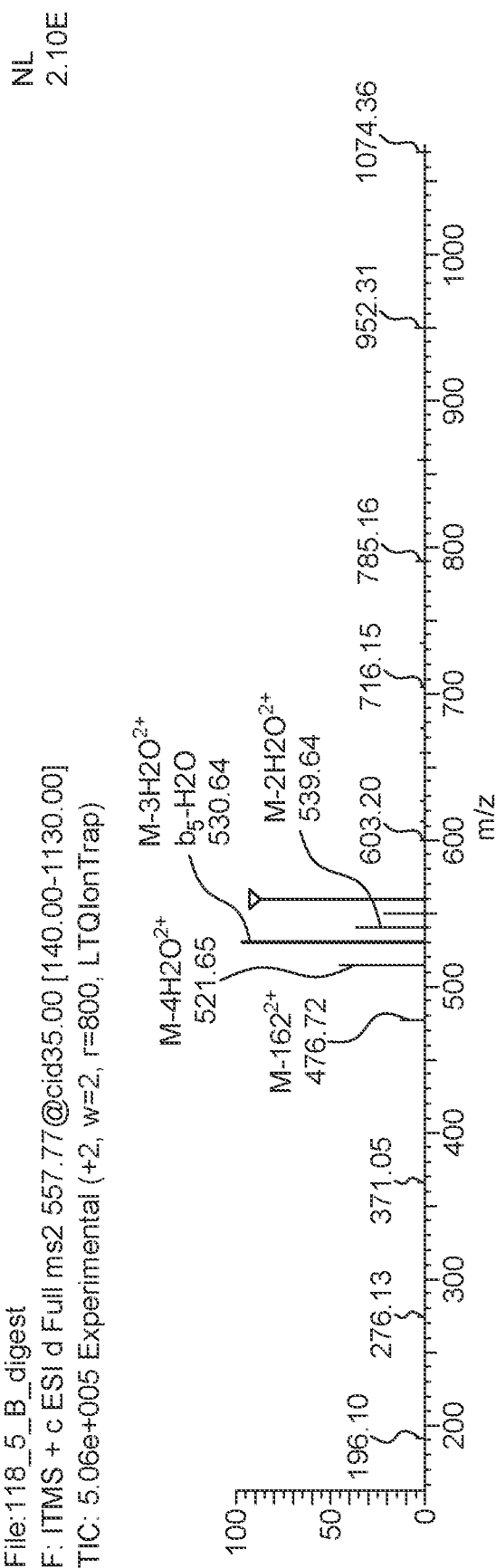
FIG. 14E

FIG. 15.AA

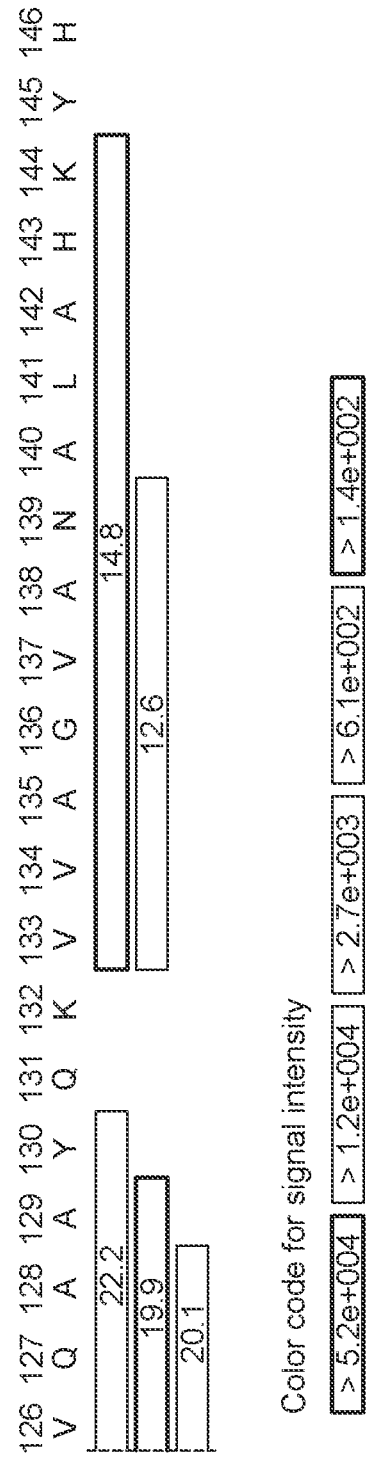
FIG. 15.AB

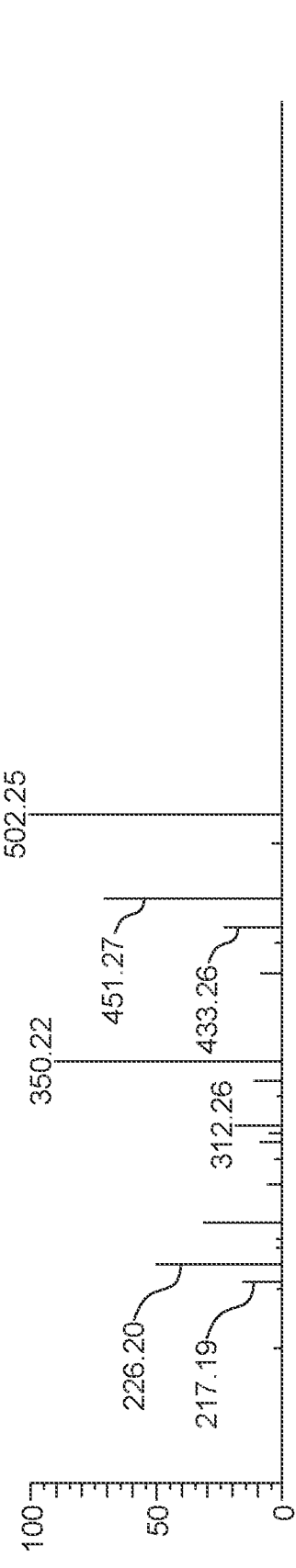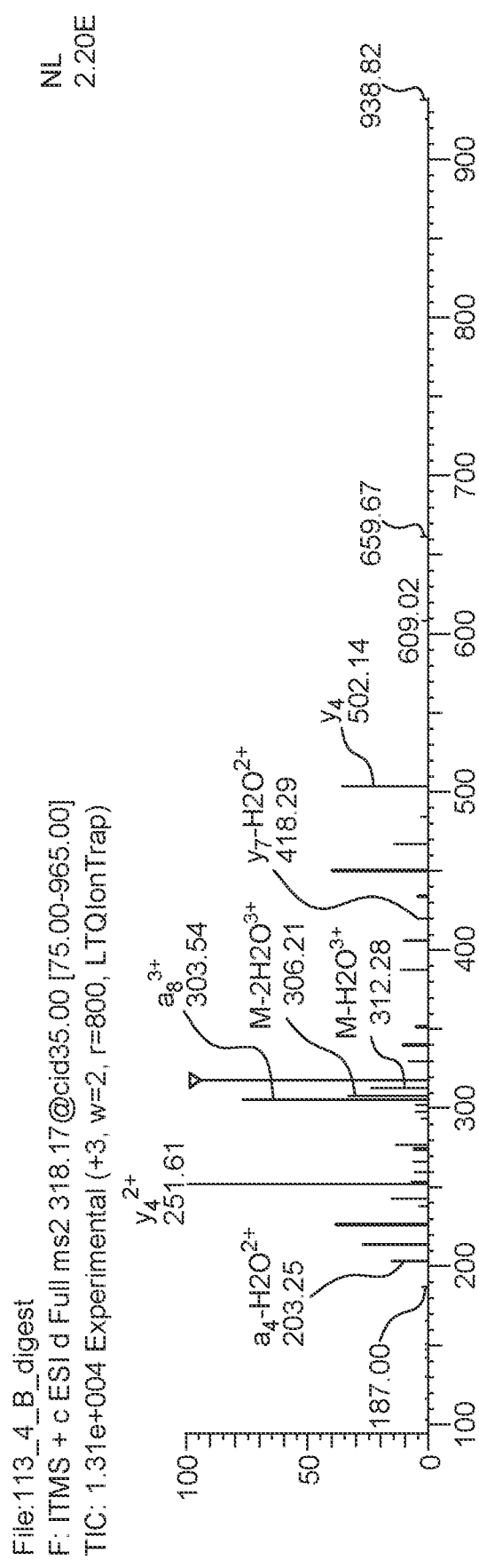
FIG. 15B

| PEPTIDE | MODIFIERS |
|---|---|
| GKVGAHAGEYGAE (SEQ ID No. 3) | Glycation [2] |
| SPADKTNVKAAWGKVGAHAGEYGAE (SEQ ID No. 4) | Glycation [?], Deamidation N [?]<br>Glycation (3) [5 9 14]<br>Deamidation N [?] |
| ADKTNVKAAWGKVGAHAGEYGAE (SEQ ID No. 5) | Glycation (2) [2?], Deamidation N [5] |
| SPADKTNVKAAWGKVGAHAGEYGAEALE (SEQ ID No. 6) | Glycation (3) [5 9 14] |
| PADKTNVKAAWGKVGAHAGEYGAEALE (SEQ ID No. 7) | Glycation (3) [4 8 13], Deamidation N [6] |
| TNVKAAWGKVGAHAGEYGAEALE (SEQ ID No. 8) | Glycation [?] |
| VLSPADKTNVKAAWGKVGAHAGEYGAEALERMFLS FPTTKTYFPHFDLSHGSAQVKGHGKKVADALTNAVA HVDDMPNALSALS (SEQ ID No. 9) | Glycation (5) [5?], Deamidation N (2) [2?] |
| VLSPADKTNVKAAWGKVGAHAGEYGAEALERMFLS FPTTKTYFPHFDLSHGSAQVKGHGKKVADALTNAVA HVDDMPNALSA (SEQ ID No. 10) | Glycation (5) [5?], Oxidation M [?] |
| VLSPADKTNVKAAWGKVGAHAGEYGAEALERMFLS FPTTKTYFPHFDLSHGSAQVKGHGKKVADALTNAVA HVDDMPNALS (SEQ ID No. 11) | Glycation (7) [7 11 16 40 56 60 61], Deamidation N [?] |
| VLSPADKTNVKAAWGKVGAHAGEYGAEALERMFLS FPTTKTYFPHFDLSHGSAQVKGHGKKVADALTNAV (SEQ ID No. 12) | Oxidation M [32] |

FIG. 16AA

| PEPTIDE | MODIFIERS |
|---|---|
| VLSPADKTNVKAAWGKVGAHAGEYGAEALERM (SEQ ID No. 13) | Glycation [?], Deamidation N [9], Oxidation M (32) Glycation (2) [2?], Deamidation N [9], Oxidation M (32) |
| GAHAGEYGAEALERMFLSFPTTKTYFPHFDLSHG SAQVKGHGKKVADALTNAVAHVDDMPNALSALSD LHAHKLRVDPVNFKLLLSHCLLVTLAAHLPAE (SEQ ID No. 14) | Carboxymethyl C [87], Glycation [?], Deamidation N (3) [51 61 80] |
| AHAGEYGAEALERMFLSFPTTKTYFPHFDLSHGSA QVKGHGKKVADALTNAVAHVDDMPNALSALSDLH AHKLRVDPVNFKLLLSHCLLVTLAAHLPAE (SEQ ID No. 15) | Carboxymethyl C [86], Glycation [?], Deamidation N (3) [50 60 79] |
| NVKAAWGKVGAHAGEYGAEALERMFLSFPTTKTY FPHFDLSHGSAQVKGHGKKVADALTNAVAHVDDM PNALSALSDLHAHKLRVDPVNFKLLLSHCLLVTLAAH LPAE (SEQ ID No. 16) | Carboxymethyl C [96], Deamidation N (3) [3?], Glycation (6) [6?], Oxidation M (2) [24 68] |
| VLSPADKTN (SEQ ID No. 17) | Glycation [7], Deamidation N [9] |
| VLSPADKT (SEQ ID No. 18) | Glycation [7] |
| KAAWGKVGAHAGE (SEQ ID No. 19) | Glycation [?] |
| WGKVGAHAGE (SEQ ID No. 20) | Glycation [3] |
| YGAEALERMFLSFPTTKTYFPHFDLSHGSAQVKG HGKKVADALTNAVAHVDDMPNALSALSDLHAHKL RVDPVNFKLLLSHCLLVTLAAHLPAE (SEQ ID No. 21) | Carboxymethyl C [81], Oxidation M (2) [9 53], Deamidation N [?] Carboxymethyl C [81], Oxidation M (2) [9 53], Glycation [?], Deamidation N [?] |

FIG. 16AB

| PEPTIDE | MODIFIERS |
|---|---|
| YGAEALERMFLSFPTTKTYFPHFDLSHGSAQV KGHGKKVADALTNAVAHVDDMPNALSALSDL HAHKLRVDPVN (SEQ ID No. 22) | Oxidation M (2) [9 53], Glycation (5) [17 33 37 38 67], Deamidation N [74] |
| YGAEALERMFLSFPTTKTYFPHFDLSHGSAQV KGHGKKVADALTNAVAHVDDMPNALSALSDL H (SEQ ID No. 23) | Oxidation M (2) [9 53], Glycation (3) [3?], Deamidation N [?] |
| YGAEALERMFLSFPTTKTYFPHFDLSHGSAQV KGHGKKVADALTNAVAHVDDMPNALSALSD (SEQ ID No. 24) | Deamidation N (2) [45 55] |
| YGAEALERMFLSFPTTKTYFPHFDLSHGSAQV KGHGKKVADALTNAVAHVDDMPNALS (SEQ ID No. 25) | Glycation (2) [2?], Deamidation N (2) [45 55] Oxidation M (2) [9 53], Glycation (2) [2?], Deamidation N [?] |
| YGAEALERMFLSFPTTKTYFPHFDLSHGSAQV KGHGKKVADALTNAVAHVDDMPN (SEQ ID No. 26) | Oxidation M [?], Glycation (4) [17 33 37 38], Deamidation N [?] |
| YGAEALERMFLSFPTTKTYFPHFDLSHGSAQV KGHGKKVADALTNAVAHV (SEQ ID No. 27) | Oxidation M [9], Glycation (4) [17 33 37 38] |
| YGAEALERMFLSFPTTKTYFPHFDLSHGSAQV KGHGKKVADALTN (SEQ ID No. 28) | Oxidation M [9], Glycation (4) [17 33 37 38], Deamidation N (45] Oxidation M [9], Glycation (4) [17 33 37 38] |
| YGAEALERMFLSFPTTKTYFPHFDLSHGSAQV KGHGKKVADALTNAVAHVDDMPNALSAISDLH AHKLRVDPVNFKLLSHCLLVTLAA (SEQ ID No. 29) | Carboxymethyl C [81], Oxidation M (2) [9 53], Glycation (4) [4?], Deamidation N (2) [2?] |
| YGAEALERMFLSFPTTKTY (SEQ ID No. 30) | Oxidation M [9], Glycation [17] |

FIG. 16AC

| PEPTIDE | MODIFIERS |
|---|---|
| YGAEALERMFLSFPTTKTYFPHFDLSHGSAQVKGHGKK VADALNAVAHVDDMPNALSAISDLHAHKLRVDPVNFKLL SHCLLV (SEQ ID No. 31) | Carboxymethyl C [81], Oxidation M [?], Glycation (6) [17 33 37 38 67 76], Deamidation N (3) [45 55 74] |
| AEALERMFLSFPTTKTYFPHFDLSHGSAQVKGHGKKVA DALTNAVAHVDDMPNALSALSDLHAHKLRVDPVNFKLL SHCLLVTLAAHLPAE (SEQ ID No. 32) | Carboxymethyl C [79], Glycation [?], Deamidation (2) [2?] |
| EALERMFLSFPTTKTYFPHFDLSHGSAQVKGHGKKVAD ALNAVAHVDDMPNALSALSDLHAHKLRVDPVNFKLLSH CLLVTLAAHLPAEFTPAVHASLDKFLASVSTVLTSKYR (SEQ ID No. 33) | Carboxymethyl C [78], Oxidation M (2) [6 50], Glycation (4) [4?] |
| ALERMFLSFPTTKTYFPHFDLSHGSAQVKGHGKKVADA LTNAVAHVDDMPNALSALSDLHAHKLRVDPVNFKLLSH CLLVTLAAHLPAE (SEQ ID No. 34) | Carboxymethyl C [77], Oxidation M [?], Deamidation N [?] |
| ALERMFLSFPTTKTYFPHFDLSHGSAQVKGHGKKVADA LTNAVAHVDDMPNALSALSDLHAHKLRVDPVNFKLLSH CLLVTLAAHLP (SEQ ID No. 35) | Carboxymethyl C [77], Oxidation M [?], Glycation (2) [2?], Deamidation N [?] |
| ALERMFLSFPTTKTYFPHFDLSHGSAQVKGHGKKVADA LTNAVAHVDDMPNALSALSDLHAHKLRVDPV (SEQ ID No. 36) | Oxidation M (2) [5 49], Glycation (4) [4?] |
| ALERMFLSFPTTKTYFPHFDLSHGSAQVKGHGKKVADA LTNAVAHVDDMPNALSALSDLHAHKLR (SEQ ID No. 37) | Oxidation M (2) [5 49], Glycation (4) [4?], Deamidation N [?] |
| ALERMFLSFPTTKTYFPHFDLSHGSAQVKGHGKKVADA LTNAVAHVDDMPNALSALSDLHAHKL (SEQ ID No. 38) | Glycation [?], Deamidation N [?] |
| ALERMFLSFPTTKTYFPHFDLSHGSAQVKGHGKKVADA LTNAVAHVDDMPNALSALSDLHAHK (SEQ ID No. 39) | Glycation (3) [3?], Deamidation N [?] |

FIG. 16AD

| PEPTIDE | MODIFIERS |
|---|---|
| ALERMFLSFPTTKTYFPHFDLSHGSAQVKGHGKKV ADALTNAVAHVDDMPNALSALSDLHAH (SEQ ID No. 40) | Oxidation M [?], Glycation (4) [13 29 33 34] |
| ALERMFLSFPTTKTYFPHFDLSHGSAQVKGHGKKV ADALTNAVAHVDDMPNALSALSDLH (SEQ ID No. 41) | Glycation (3) [3?] |
| ALERMFLSFPTTKTYFPHFDLSHGSAQVKGHGKKV ADALTNAVAHVDDMPNALSALS (SEQ ID No. 42) | Glycation (2) [2?], Deamidation N (2) [41 51] |
| ALERMFLSFPTTKTYFPHFDLSHGSAQVKGHGKKV ADALTNAVAHVDDMPNAL (SEQ ID No. 43) | Oxidation M [?], Glycation (4) [13 29 33 34], Deamidation N (2) [41 51] |
| ALERMFLSFPTTKTYFPHFDLSHGSAQVKGHGKKV ADALTNAVAHV (SEQ ID No. 44) | Oxidation M [5] |
| ALERMFLSFPTTKTYFPHFDLSHGSAQVKGHGKKV ADALTNAV (SEQ ID No. 45) | Deamidation N [41] Glycation [?] |
| ALERMFLSFPTTKTYFPHFDLSHGSAQVKGHGKKV ADALTNAVAHVDDMPNALSALSDLHAHKLRVDPVN FKLLSHCLLVTLA (SEQ ID No. 46) | Carboxymethyl C [77], Glycation (2) [2?], Deamidation N (3) [41 51 70] |
| ALERMFLSFPTTKTYFPHFDL (SEQ ID No. 47) | Glycation [13] |
| ALERMFLSFPT (SEQ ID No. 48) | Oxidation M [5] |
| ALERMFLSFPTTKTYFPHFDLSHGSAQVKGHGKKV ADALTNAVAHVDDMPNALSALSDLHAHKLRVDPVN FKLLSHCLLV (SEQ ID No. 49) | Carboxymethyl C [77], Oxidation M [?], Glycation (5) [5?], Deamidation N (2) [2?] |

FIG. 16AE

| PEPTIDE | MODIFIERS |
|---|---|
| ERMFLSFPTTKTYFPHFDLSHGSAQVKGHGKKVA DALTNAVAHVDDMPNALSALSDLHAHKLRVDPVN FKLLSHCLLVTLAAHLPAE (SEQ ID No. 50) | Carboxymethyl C [75], Glycation (4) [4?] |
| ALERMFLSFPTTKTYFPHFDLSHGSAQVKGHGKK VADALTNAVAHVDDMPNALSALSDLHAHKLRVDP VNFKLLSHCLLVTLAAHLPAEFTPAVHASLDKFLAS VSIVLTSKYR (SEQ ID No. 51) | Carboxymethyl C [77], Oxidation M [?], Glycation (5) [5?], Deamidation N (3) [41 51 70] |
| RMFLSFPTTKTYFPHFDLSHGSAQVKGHGKKVAD ALTNAVAHVDDMPNALSALSDLHAHKLRVDPVNF KLLSHCLLVTLAAHLPAE (SEQ ID No. 52) | Carboxymethyl C [74], Oxidation M (2) [2 46], Glycation [?], Deamidation N (2) [2?]<br>Carboxymethyl C [74], Oxidation M [?], Glycation (3) [3?] |
| YFPHFDLSHGSAQVKGHGKKVADALTNAVAHVDD MPNALSALSDLHAHKLRVDPVNFKLLSHCLLVTLA AHLPAEFTPAVHASLDKFLASVSTVLTSKYR (SEQ ID No. 53) | Carboxymethyl C [63], Glycation [?], Deamidation N [2?], Oxidation M [35] |
| HFDLSHGSAQVKGHGKKVADALTNAVAHVDDMP NALSALSDLHAHKLRVDPVNFKLLSHCLLVTLAAH LPAEFTPAVHASLDKFLASVSTVLTSKYR (SEQ ID No. 54) | Carboxymethyl C [60], Glycation (7) [12 16 17 46 55 83 95], Oxidation M [32], Carboxymethyl C [60], Glycation (3) [3?], Oxidation M [32], Carboxymethyl C [60], Glycation (3) [3?], Deamidation N (3) [24 34 53] |

FIG. 16AF

| PEPTIDE | MODIFIERS |
|---|---|
| LSHGSAQVKGHGKKVADALTNAVAHVDDMPNALSA LSDLHAHKLRVDPVNFKLLSHCLLVTLAAHLPAEFTP AVHASLDKFLASVSTVLTSKYR (SEQ ID No. 55) | Carboxymethyl C [57], Glycation (7) [9 13 14 43 52 80 92], Deamidation N [?], Oxidation M [29] |
| SHGSAQVKGHGKKVADALTNAVAHVDDMPNALSAL SDLHAHKLRVDPVNFKLLSHCLLVTLAAHLPAEFTPA VHASLDKFLASVSTVLTSKYR (SEQ ID No. 56) | Carboxymethyl C [56], Glycation (4) [4?], Oxidation M [28] |
| GSAQVKGHGKKVADALTNAVAHVDDMPNALSALSD LHAHKLRVDPVNFKLLSHCLLVTLAAHLPAEFTPAVH ASLDKFLASVSTVLTSKYR (SEQ ID No. 57) | Carboxymethyl C [54], Glycation (2) [2?], Deamidation [?] |
| SAQVKGHGKKVADALTNAVAHVDDMPNALSALSDL HAHKLRVDPVNFKLLSHCLLVTLAAHLPAEFTPAVHA SLDKFLASVSTVLTSKYR (SEQ ID No. 58) | Carboxymethyl C [53], Oxidation M [25] |
| AQVKGHGKKVADALTNAVAHVDDMPNALSALSDLH AHKLRVD'PVNFKLLSHCLLVTLAAHLPAEFTPAVHAS LDKFLASVSTVLTSKYR (SEQ ID No. 59) | Carboxymethyl C [52], Glycation (5) [5?], Oxidation M [24] Carboxymethyl C [52], Glycation (3) [3?], Deamidation N (3) [16 26 45], Oxidation M [24] |
| QVKGHGKKVADALTNAVAHVDDMPNALSALSDLHA HKLRVDPVNFKLLSHCLLVTLAAHLPAEFTPAVHASL DKFLASVSTVLTSKYR (SEQ ID No. 60) | Carboxymethyl C [51], Glycation (5) [5?], Deamidation (2) [2?] |
| GKKVADALTNAVAHVDDMPNALSALSDLHAHKLRVD PVNFKLLSHCLLVTLAAHLPAEFTPAVHASLDKFLAS VSTVLTSKYR (SEQ ID No. 61) | Carboxymethyl C [46], Glycation (4) [4?], Deamidation (2) [2?] Carboxymethyl C [46], Glycation (3) [3?], Deamidation (3) [10 20 39] |
| KVADALTNAVAHVDDMPNALSALSDLHAHKLRVDPV NFKLLSHCLLVTLAAHLPAEFTPAVHASLDKFLASVST VLTSKYR (SEQ ID No. 62) | Carboxymethyl C [44], Deamidation N (2) [2?], Oxidation M [16] |

FIG. 16BA

| PEPTIDE | MODIFIERS |
|---|---|
| ALTNAVAHVDDMPNALSALSDLHAHKLRVDPVNFKLL SHCLLVTLAAHLPAEFTPAVHASLDKFLASVSTVLTSKY R (SEQ ID No. 63) | Carboxymethyl C [40], Glycation (3) [3?] Carboxymethyl C [40], Deamidation N [?] Carboxymethyl C [40], Deamidation N (2) [2?], Glycation [?] |
| LTNAVAHVDDMPNALSALSDLHAHKLRVDPVNFKLLS HCLLVTLAAHLPAEFTPAVHASLDKFLASVSTVLTSKY R (SEQ ID No. 64) | Carboxymethyl C [39], Deamidation N (3) [31332], Glycation (2) [2?] |
| TNAVAHVDDMPNALSALSDLHAHKLRVDPVNFKLLSH CLLVTLAAHLPAEFTPAVHASLDKFLASVSTVLTSKYR (SEQ ID No. 65) | Carboxymethyl C [38], Oxidation M [10] |
| NAVAHVDDMPNALSALSDLHAHKLRVDPVNFKLLSHC LLVTLAAHLPAEFTPAVHASLDKFLASVSTVLTSKYR (SEQ ID No. 66) | Carboxymethyl C [37], Deamidation N (2) [2?], Oxidation M [9], Glycation (2) [2?] |
| SFPTTKTYFPHFDLSHGSAQVKGHGKKVADALTNAVA HVDDMPNALSALSDLHAHKLRVDPVNFKLLSHCLLVTL AAHLPAEFTPAVHASLDKFLASVSTVLTSKYR (SEQ ID No. 67) | Carboxymethyl C [70], Glycation (2) [2?] |
| MPNALSALSDLHAHKLRVDPVNFKLLSHCLLLVTLAAHL PAEFTPAVHASLDKFLASVSTVLTSKYR (SEQ ID No. 68) | Carboxymethyl C [29], Glycation (2) [2?] Carboxymethyl C [29], Deamidation N (2) [3 22], Glycation (2) [2?] |
| LSALSDLHAHKLRVDPVNFKLLSHCLLLVTLAAHLPAEFT PAVHASLDKFLASVSTVLTSKYR (SEQ ID No. 69) | Carboxymethyl C [25], Glycation (3) [3?] |
| SALSDLHAHKLRVDPVNFKLLSHCLLLVTLAAHLPAEFT PAVHASLDKFLASVSTVLTSKYR (SEQ ID No. 70) | Carboxymethyl C [24], Glycation [?], Deamidation N [17] Carboxymethyl C [24], Glycation (3) [3?] |

FIG. 16BB

| PEPTIDE | MODIFIERS |
|---|---|
| ALSDLHAHKLRVDPVNFKLLSHCLLVTLAAHLPAEFTPA VHASLDKFLASVSTVLTSKYR (SEQ ID No. 71) | Carboxymethyl C [23], Glycation (4) [9 18 46 58] Carboxymethyl C [23] |
| LSDLHAHKLRVDPVNFKLLSHCLLVTLAAHLPAEFTPAV HASLDKFLASVSTVLTSKYR (SEQ ID No. 72) | Carboxymethyl C [22], Glycation (4) [8 17 45 57] |
| AHKLRVDPVNFKLLSHCLLVTLAAHLPAEFTPAVHASLD KFLASVSTVLTSKYR (SEQ ID No. 73) | Carboxymethyl C [17], Glycation (4) [3 12 40 52] |
| KLRVDPVNFKLLSHCLLVTLAAHLPAEFTPAVHASLDKF LASVSTVLTSKYR (SEQ ID No. 74) | Carboxymethyl C [15], Glycation (3) [3?] |
| LRVDPVNFKLLSHCLLVTLAAHLPAEFTPAVHASLDKFL ASVSTVLTSKYR (SEQ ID No. 75) | Carboxymethyl C [14], Deamidation N [7], Glycation (3) [9 37 49] |
| DPVNFKLLSHCLLVTLAAHLPAEFTPAVHASLDKFLASV STVLTSKYR (SEQ ID No. 76) | Carboxymethyl C [11] |
| PVNFKLLSHCLLVTLAAHLPAEFTPAVHASLDKFLASVS TVLTSKYR (SEQ ID No. 77) | Carboxymethyl C [10] |
| NFKLLSHCLLVTLAAHLPAEFTPAVHASLDKFLASVSTV LTSKYR (SEQ ID No. 78) | Carboxymethyl C [8] |
| FKLLSHCLLVTLAAHLPAEFTPAVHASLDKFLASVSTVL TSKYR (SEQ ID No. 79) | Carboxymethyl C [7], Glycation (3) [2 30 42] |
| KLLSHCLLVTLAAHLPAEFTPAVHASLDKFLASVSTVLT SKYR (SEQ ID No. 80) | Carboxymethyl C [6], Glycation [?] |
| HCLLVTLAAHLPAEFTPAVHASLDKFLASVSTVLTSKYR (SEQ ID No. 81) | Carboxymethyl C [2], Glycation [?] |
| VTLAAHLPAEFTPAVHASLDKFLASVSTVLTSKYR (SEQ ID No. 82) | Glycation (2) [21 33] |

FIG. 16BC

| PEPTIDE | MODIFIERS |
|---|---|
| RMFLSFPTTKTYFPHFDLSHGSAQVKGHGKKVADAL TNAVAHVDDMPNALSALSDLHAHKLRVDPVNFK (SEQ ID No. 83) | Oxidation M (2) [2 46], Glycation (2) [2?], Deamidation N (2) [2?]<br>Oxidation M (2) [2 46], Glycation (3) [3?], Deamidation N (2) [2?] |
| RMFLSFPTTKTYFPHFDLSHGSAQVKGHGKKVADAL TNAVAHVDDMPNALSALSDLHAHKLRVDPVN (SEQ ID No. 84) | Oxidation M (2) [2 46], Glycation [?], Deamidation N [?] |
| RMFLSFPTTKTYFPHFDLSHGSAQVKGHGKKVADAL TNAVAHVDDMPNALSALSDLHAHKLRVDPV (SEQ ID No. 85) | Oxidation M (2) [2 46], Glycation (3) [3?], Deamidation N (2) [38 48] |
| RMFLSFPTTKTYFPHFDLSHGSAQVKGHGKKVADAL TNAVAHVDDMPNALSALSDLHAHKLRVD (SEQ ID No. 86) | Oxidation M [?], Glycation [?], Deamidation N [?]<br>Oxidation M [?], Glycation [?], Deamidation N (2) [38 48]<br>Oxidation M (2) [2 46], Glycation (3) [3?], Deamidation N [?] |
| RMFLSFPTTKTYFPHFDLSHGSAQVKGHGKKVADAL TNAVAHVDDMPNALSALSDLHAHKLR (SEQ ID No. 87) | Oxidation M [?], Glycation [?] |
| RMFLSFPTTKTYFPHFDLSHGSAQVKGHGKKVADAL TNAVAHVDDMPNALSALSD (SEQ ID No. 88) | Oxidation M (2) [2 46], Glycation (4) [10 26 30 31], Deamidation N (2) [38 48]<br>Oxidation M [?], Glycation (3) [3?], Deamidation N (2) [38 48] |
| RMFLSFPTTKTYFPHFDLSHGSAQVKGHGKKVADAL TNAVAHVDDMPNALSAL (SEQ ID No. 89) | Deamidation N [?]<br>Glycation [?], Deamidation N [?] |
| RMFLSFPTTKTYFPHFDLSHGSAQVKGHGKKVADAL TNAVAHVDDMPNALSA (SEQ ID No. 90) | Oxidation M [?], Glycation (3) [3?], Deamidation N [?] |
| RMFLSFPTTKTYFPHFDLSHGSAQVKGHGKKVADAL TNAVAHVDDMPNALS (SEQ ID No. 91) | Glycation (2) [21] |

FIG. 16BD

| PEPTIDE | MODIFIERS |
|---|---|
| RMFLSFPTTKTYFPHFDLSHGSAQVKGHGKKVADALT NAVAHVDDMPNA (SEQ ID No. 92) | Oxidation M [?], Deamidation N [?] |
| RMFLSFPTTKTYFPHFDLSHGSAQVKGHGKKVADALT NAVAHVDDM (SEQ ID No. 93) | Glycation [?], Deamidation N [38] |
| RMFLSFPTTKTYFPHFDLSHGSAQVKGHGKKVADALT NAVAHV (SEQ ID No. 94) | Glycation (2) [30 31] |
| RMFLSFPTTKTYFPHFDLSHGSAQVKGHGKKVADALT NAV (SEQ ID No. 95) | Oxidation M [2], Deamidation N [38] |
| RMFLSFPTTKTYFPHFDLSHGSAQVKGHGKKVADALT NA (SEQ ID No. 96) | Glycation (3) [31], Deamidation N [38] |
| RMFLSFPTTKTYFPHFDLSHGSAQVKGHGKKVADALT NAVAHVDDMPNALSALSDLHAHKLRVDPVNFKLLSHC LLVTLAA (SEQ ID No. 97) | Carboxymethyl C [74], Oxidation M (2) [2 46], Glycation (3) [37], Deamidation N (3) [38 48 67] |
| RMFLSFPTTKTYFPHFDLSHGSAQVKGHGKKVA (SEQ ID No. 98) | Oxidation M [2], Glycation (3) [3?] |
| RMFLSFPTTKTYFPHFDLSHGSAQVKGHGK (SEQ ID No. 99) | Oxidation M [2], Glycation [?] |
| RMFLSFPTTKTYFPHFDLSHGSAQVKGHGKKVADALT NAVAHVDDMPNALSALSDLHAHKLRVDPVNFKLLSHC LLVTLA (SEQ ID No. 100) | Carboxymethyl C [74], Oxidation M (2) [2 46], Glycation (5) [5?], Deamidation N (2) [2?] |
| RMFLSFP (SEQ ID No. 101) | Oxidation M [2] |
| RMFLS (SEQ ID No. 102) | Oxidation M [2] |
| MFLSFPTTKTYFPHFDLSHGSAQVKGHGKKVADALTN AVAHVDDMPNALSALSDLHAHKLRVDPVNFKLLSHCL LVTLAAHLPAE (SEQ ID No. 103) | Carboxymethyl C [73], Deamidation N (3) [37 47 66] Carboxymethyl C [73], Glycation [?], Deamidation N [?] Carboxymethyl C [73], Oxidation M [?], Glycation (6) [9 25 29 30 59 68], Deamidation N (3) [37 47 66] |

FIG. 16BE

| PEPTIDE | MODIFIERS |
|---|---|
| TYFPHFDLSHGSAQVKGHGKKVADALTNAVAHV DDMPNALSALSDLHAHKLRVDPVNFKLLSHCLL VTLAAHLPAE (SEQ ID No. 104) | Carboxymethyl C [64], Deamidation N (3) [28 38 57] Carboxymethyl C [64], Glycation (2) [2?], Deamidation N (3) [28 38 57], Oxidation M [36] Carboxymethyl C [64], Glycation (3) [3?], Oxidation M [36] |
| YFPHFDLSHGSAQVKGHGKKVADALTNAVAHV DDMPNALSALSDLHAHKLRVDPVNFKLLSHCLL VTLAAHLPAE (SEQ ID No. 105) | Carboxymethyl C [63], Glycation (2) [2?], Deamidation N (3) [27 37 56], Oxidation M [35] Carboxymethyl C [63], Glycation (2) [2?] |
| FPHFDLSHGSAQVKGHGKKVADALTNAVAHVD DMPNALSALSDLHAHKLRVDPVNFKLLSHCLLVT LAAHLPAE (SEQ ID No. 106) | Carboxymethyl C [62], Deamidation N (3) [26 36 55], Oxidation M [34] |
| HFDLSHGSAQVKGHGKKVADALTNAVAHVDDM PNALSALSDLHAHKLRVDPVNFKLLSHCLLVTLA AHLPAE (SEQ ID No. 107) | Carboxymethyl C [60], Oxidation M [32] |
| LSHGSAQVKGHGKKVADALTNAVAHVDDMPNA LSALSDLHAHKLRVDPVNFKLLSHCLLVTLAAHL PAE (SEQ ID No. 108) | Carboxymethyl C [57], Glycation [?] |
| HGSAQVKGHGKKVADALTNAVAHVDDMPNALS ALSDLHAHKLRVDPVNFKLLSHCLLVTLMHLPAE (SEQ ID No. 109) | Carboxymethyl C [55], Glycation (4) [4?], Deamidation N (2) [2?] Carboxymethyl C [55], Glycation (5) [7 11 12 41 50] |
| FLSFPTTKTYFPHFDLSHGSAQVKGHGKKVADA LTNAVAHVDDMPNALSALSDLHAHKLRVDPVNF KLLSHCLLVTLMHLPAE (SEQ ID No. 110) | Carboxymethyl C [72], Deamidation N (3) [36 46 65] |
| GSAQVKGHGKKVADALTNAVAHVDDMPNALSA LSDLHAHKLRVDPVNFKLLSHCLLVTLAAHLPAE (SEQ ID No. 111) | Carboxymethyl C [54], Glycation (5) [6 10 11 40 49], Deamidation N [?] |

FIG. 16BF

| PEPTIDE | MODIFIERS |
|---|---|
| QVKGHGKKVADALTNAVAHVDDMPNALSA LSDLHAHKLRVDPVNFKLLSHCLLVTLAAH LPAE (SEQ ID No. 112) | Carboxymethyl C [51], Deamidation N (3) [15 25 44] |
| VKGHGKKVADALTNAVAHVDDMPNALSAL SDLHAHKLRVDPVNFKLLSHCLLVTLAAHL PAE (SEQ ID No. 113) | Carboxymethyl C [50], Glycation (5) [2 6 7 36 45]<br>Carboxymethyl C [50], Glycation (3) [3?], Deamidation N (2) [2?],<br>Oxidation M [22]<br>Carboxymethyl C [50], Glycation (4) [4?], Deamidation N (2) [2?],<br>Oxidation M [22] Carboxymethyl C [50], Oxidation M [22]<br>Carboxymethyl C [50], Glycation (5) [2 6 7 36 45], Deamidation N (2) [2?] |
| KGHGKKVADALTNAVAHVDDMPNALSALS DLHAHKLRVDPVNFKLLSHCLLVTLAAHLP AE (SEQ ID No. 114) | Carboxymethyl C [49], Glycation (4) [4?]<br>Carboxymethyl C [49], Glycation (4) [4?], Deamidation N [?]<br>Carboxymethyl C [49], Glycation (5) [1 5 6 35 44], Deamidation N (2) [2?]<br>Carboxymethyl C [49], Glycation (5) [1 5 6 35 44], Deamidation N (3) [13 23 42]<br>Carboxymethyl C [49], Glycation (3) [3?], Deamidation N (3) [13 23 42], Oxidation M [21] |
| GHGKKVADALTNAVAHVDDMPNALSALSD LHAHKLRVDPVNFKLLSHCLLVTLAAHLPA E (SEQ ID No. 115) | Carboxymethyl C [48], Glycation (3) [3?], Deamidation N (2) [2?] |
| HGKKVADALTNAVAHVDDMPNALSALSDL HAHKLRVDPVNFKLLSHCLLVTLAAHLPAE (SEQ ID No. 116) | Carboxymethyl C [47], Glycation (4) [3 4 33 42], Deamidation N (3) [11 21 40]<br>Carboxymethyl C [47], Glycation (4) [3 4 33 42], Deamidation N (2) [2?]<br>Carboxymethyl C [47], Glycation (4) [3 4 33 42], Deamidation N [?] |

FIG. 16CA

| PEPTIDE | MODIFIERS |
|---|---|
| GKKVADALTNAVAHVDDMPNALSALSDLHAH KLRVDPVNFKLLSHCLLVTLAAHLPAE (SEQ ID No. 117) | Carboxymethyl C [46], Deamidation N (2) [2?] |
| KKVADALTNAVAHVDDMPNALSALSDLHAHK LRVDPVNFKLLSHCLLVTLAAHLPAE (SEQ ID No. 118) | Carboxymethyl C [45], Glycation (3) [3?] Carboxymethyl C [45], Oxidation M [17] Carboxymethyl C [45], Glycation (3) [3?], Deamidation N [?] Carboxymethyl C [45], Glycation (3) [3?], Deamidation N (2) [2?] |
| KVADALTNAVAHVDDMPNALSALSDLHAHKL RVDPVNFKLLSHCLLVTLAAHLPAE (SEQ ID No. 119) | Carboxymethyl C [44], Oxidation M [16] Carboxymethyl C [44], Glycation [?], Oxidation M [16] |
| VADALTNAVAHVDDMPNALSALSDLHAHKLR VDPVNFKLLSHCLLVTLAAHLPAE (SEQ ID No. 120) | Carboxymethyl C [43], Deamidation N [?], Glycation (2) [29 38] Carboxymethyl C [43], Glycation (2) [29 38] Carboxymethyl C [43], Oxidation M [15], Glycation (2) [29 38] Carboxymethyl C [43], Deamidation N (2) [2?], Glycation [?] Carboxymethyl C [43], Deamidation N [?], Oxidation M [15], Glycation [?] |
| ALTNAVAHVDDMPNALSALSDLHAHKLRVDP VNFKLLSHCLLVTLAAHLPAE (SEQ ID No. 121) | Carboxymethyl C [40], Deamidation N [?], Oxidation M [12], Glycation [?] |
| LTNAVAHVDDMPNALSALSDLHAHKLRVDPV NFKLLSHCLLVTLAAHLPAE (SEQ ID No. 122) | Carboxymethyl C [39], Oxidation M [11], Glycation [?] |
| TNAVAHVDDMPNALSALSDLHAHKLRVDPVN FKLLSHCLLVTLAAHLPAE (SEQ ID No. 123) | Carboxymethyl C [38], Deamidation N (2) [2?], Oxidation M [10] Carboxymethyl C [38], Deamidation N (3) [2 12 31] |
| AVAHVDDMPNALSALSDLHAHKLRVDPVNFK LLSHCLLVTLAAHLPAE (SEQ ID No. 124) | Carboxymethyl C [36], Oxidation M [8] |

FIG 16CB

| PEPTIDE | MODIFIERS |
|---|---|
| SFPTTKTYFPHFDLSHGSAQVKGHGKKVAD ALTNAVAHVDDMPNALSALSDLHAHKLRVD PVNFKLLSHCLLVTLAAHLPAE (SEQ ID No. 125) | Carboxymethyl C [70], Glycation (5) [5?], Oxidation M [42] |
| HVDDMPNALSALSDLHAHKLRVDPVNFKLL SHCLLVTLAAHLPAE (SEQ ID No. 126) | Carboxymethyl C [33], Oxidation M [5], Deamidation N [?], Glycation [?] |
| DMPNALSALSDLHAHKLRVDPVNFKLLSHC LLVTLAAHLPAE (SEQ ID No. 127) | Carboxymethyl C [30], Oxidation M [2] Carboxymethyl C [30], Deamidation N (2) [4 23], Glycation [?] |
| PNALSALSDLHAHKLRVDPVNFKLLSHCLLV TLAAHLPAE (SEQ ID No. 128) | Carboxymethyl C [28], Glycation (2) [14 23] |
| NALSALSDLHAHKLRVDPVNFKLLSHCLLVT LAAHLPAE (SEQ ID No. 129) | Carboxymethyl C [27], Glycation [?] |
| FPTTKTYFPHFDLSHGSAQVKGHGKKVADA LTNAVAHVDDMPNALSALSDLHAHKLRVDP VNFKLLSHCLLVTLAAHLPAE (SEQ ID No. 130) | Carboxymethyl C [69], Glycation (3) [3?], Deamidation N (2) [2?] Carboxymethyl C [69], Glycation (3) [3?], Deamidation N (3) [33 43 62] |
| SDLHAHKLRVDPVNFKLLSHCLLVTLAAHLP AE (SEQ ID No. 131) | Carboxymethyl C [21], Glycation [?] |
| HAHKLRVDPVNFKLLSHCLLVTLAAHLPAE (SEQ ID No. 132) | Carboxymethyl C [18], Glycation (2) [4 13] |
| FKLLSHCLLVTLAAHLPAE (SEQ ID No. 133) | Carboxymethyl C [7], Glycation [2] |
| TTKTYFPHFDLSHGSAQVKGHGKKVADALT NAVAHVDDMPNALSALSDLHAHKLRVDPVN FKLLSHCLLVTLAAHLPAE (SEQ ID No. 134) | Carboxymethyl C [67], Deamidation N (2) [2?] |

FIG. 16CC

| PEPTIDE | MODIFIERS |
|---|---|
| TKTYFPHFDLSHGSAQVKGHGKKVADAL TNAVAHVDDMPNALSALSDLHAHKLRVD PVNFKLLSHCLLVTLAAHLPAE (SEQ ID No. 135) | Carboxymethyl C [66], Glycation (5) [52], Carboxymethyl C [66], Glycation [?], Deamidation N [?], Oxidation M [38] |
| KTYFPHFDLSHGSAQVKGHGKKVADALT NAVAHVDDMPNALSALSDLHAHKLRVDP VNFKLLSHCLLVTLAAHLPAE (SEQ ID No. 136) | Carboxymethyl C [65], Glycation (3) [3?], Carboxymethyl C [65], Glycation (2) [2?], Deamidation N [2?], Oxidation M (37) |
| FLASVSTVLTSKYR (SEQ ID No. 137) | Glycation [12] |
| STVLTSKYR (SEQ ID No. 138) | Glycation [7] |
| TSKYR (SEQ ID No. 139) | Glycation [3] |
| AVHASLDKFLASVSTVLTSKYR (SEQ ID No. 140) | Glycation (2) [8 20] |

FIG. 16CD

| PEPTIDE | MODIFIERS |
|---|---|
| YPVEPFTESQSLTLTDVENLHLPLPLLQS (SEQ ID No. 141) | Deamidation N [19] |
| DMPIQAFLLYQEPVLGPV (SEQ ID No. 142) | Oxidation M [2] |
| DMPIQAFLLY (SEQ ID No. 143) | Oxidation M [2] |
| LEELNVPGEIVESLSSSEESITR (SEQ ID No. 144) | Deamidation N [5] |
| NVPGEIVESLSSSEESITR (SEQ ID No. 145) | Deamidation N [1] |
| GPIPNSLPQNIPPLTQTPVVVPPFLQPEVMGVSK (SEQ ID No. 146) | Deamidation N [?], Oxidation M [30] |
| PIPNSLPQNIPPLTQTPVVVPPFLQPEVMGVSK (SEQ ID No. 147) | oxidation M [29] |
| PFLQPEVMGVSK (SEQ ID No. 148) | Oxidation M [8] |
| PEVMGVSK (SEQ ID No. 149) | Oxidation M [4] |
| MGVSK (SEQ ID No. 150) | Oxidation M [1] |
| LVNELTEFA (SEQ ID No. 151) | Deamidation N [3] |
| LVNELTEF (SEQ ID No. 152) | Deamidation N [3] |
| LVNEL (SEQ ID No. 153) | Deamidation N [3] |
| VNELTEFAK (SEQ ID No. 154) | Deamidation N [2] |
| VADESHAGCEK (SEQ ID No. 155) | Carboxymethyl C [9] |
| FGDELCK (SEQ ID No. 156) | Carboxymethyl C [6] |
| LKPDPNTL (SEQ ID No. 157) | Deamidation N [6] |
| FYAPELLYYANK (SEQ ID No. 158) | Deamidation N [11] |
| PELLYYANK (SEQ ID No. 159) | Deamidation N [8] |
| YNGVFQECCQAEDK (SEQ ID No. 160) | Carboxymethyl C (2) [8 9] |
| YICDNQDTISSK (SEQ ID No. 161) | Carboxymethyl C [3] |
| ECCDKPLLE (SEQ ID No. 162) | Carboxymethyl C (2) [2 3] |
| CDKPLLEK (SEQ ID No. 163) | Carboxymethyl C (1) |
| DAIPEN (SEQ ID No. 164) | Deamidation N [6] |
| DAIPENLPPLTADFAE (SEQ ID No. 165) | Deamidation N [6] |
| DAIPENLPPLTADFA (SEQ ID No. 166) | Deamidation N [6] |
| DAIPENLPPLTADF (SEQ ID No. 167) | Deamidation N [6] |
| DAIPENLPPL (SEQ ID No. 168) | Deamidation N [6] |
| VDEPQNLIK (SEQ ID No. 169) | Deamidation N [6] |
| LGEYGFQNAL (SEQ ID No. 170) | Deamidation N [8] |

Fig. 17AA

| PEPTIDE | MODIFIERS |
|---|---|
| NALIVR (SEQ ID No. 171) | Deamidation N [1] |
| EDYLSLILNR (SEQ ID No. 172) | Deamidation N [9] |
| LFTFHADICTLP (SEQ ID No. 173) | Carboxymethyl C [9] |
| ADICTLPDTEK (SEQ ID No. 174) | Carboxymethyl C [4] |
| TVMENFVAFVDK (SEQ ID No. 175) | Oxidation M [3]<br>Deamidation N [5]<br>Oxidation M [3], Deamidation N [5] |
| TVMENF (SEQ ID No. 176) | Oxidation M [3] |
| VMENFVAFVDK (SEQ ID No. 177) | Oxidation M [2] |
| QCPFDEHVK (SEQ ID No. 178) | Carboxymethyl C [2] |
| FSQYLQQCPFDEHVK (SEQ ID No. 179) | Carboxymethyl C [8] |
| LCKVASLRETYGDMADCCE (SEQ ID No. 180) | Carboxymethyl C (3) [2 17 18], Glycation [3], Oxidation M [14] |
| LCKVASLRETYG (SEQ ID No. 181) | Carboxymethyl C [2] |
| LCKVASLRETY (SEQ ID No. 182) | Carboxymethyl C [2] |
| LCKVASLRET (SEQ ID No. 183) | Carboxymethyl C [2] |
| CKVASLRETYGDMADCCE (SEQ ID No. 184) | Carboxymethyl C (3) [1 16 17], Glycation [2] |
| KVASLRETYGDMADCCE (SEQ ID No. 185) | Carboxymethyl C (2) [15 16], Oxidation M [12] |
| ETYGDMADCCE (SEQ ID No. 186) | Carboxymethyl C (2) [9 10], Oxidation M [6] |
| VASLRETYGDMADCCEKQEPE (SEQ ID No. 187) | Carboxymethyl C (2) [14 15] |
| SLRETYGDMADCCEKQEPE (SEQ ID No. 188) | Carboxymethyl C (2) [12 13], Oxidation M [9], Glycation [15] |
| RETYGDMADCCEKQEPE (SEQ ID No. 189) | Carboxymethyl C (2) [10 11]<br>Carboxymethyl C (2) [10 11], Oxidation M [7], Glycation [13] |
| ETYGDMADCCEKQEPE (SEQ ID No. 190) | Carboxymethyl C (2) [9 10], Oxidation M [6], Glycation [12] |
| LCKVASLRETYGDMADCCEKQEPERN (SEQ ID No. 191) | Carboxymethyl C (3) [2 17 18], Glycation [?], Deamidation N [26] |
| LRETYGDMADCCEKQEPERNE (SEQ ID No. 192) | Carboxymethyl C (2) [11 12], Oxidation M [8] |
| RETYGDMADCCEKQEPERNE (SEQ ID No. 193) | Carboxymethyl C (2) [10 11], Oxidation M [7], Deamidation N [19]<br>Carboxymethyl C (2) [10 11], Glycation [13] |

FIG. 17AB

| PEPTIDE | MODIFIERS |
|---|---|
| ETYGDMADCCEKQEPERNE (SEQ ID No. 194) | Carboxymethyl C (2) [9 10], Oxidation M [6], Deamidation N [18]<br>Carboxymethyl C (2) [9 10], Deamidation N [18] |
| LCKVAS (SEQ ID No. 195) | Carboxymethyl C [2], Glycation [3]<br>Carboxymethyl C [2] |
| TYGDMADCCE (SEQ ID No. 196) | Carboxymethyl C (2) [8 9], Oxidation M [5] |
| TYGDMADCCEKQEP (SEQ ID No. 197) | Carboxymethyl C (2) [8 9], Glycation [11]<br>Carboxymethyl C (2) [8 9], Oxidation M [5] |
| TYGDMADCCEKQE (SEQ ID No. 198) | Carboxymethyl C (2) [8 9], Oxidation M [5], Glycation [11] |
| TYGDMADCCEKQ (SEQ ID No. 199) | Carboxymethyl C (2) [8 9], Oxidation M [5]<br>Carboxymethyl C (2) [8 9], Oxidation M [5], Glycation [11] |
| TYGDMADCCEK (SEQ ID No. 200) | Carboxymethyl C (2) [8 9], Oxidation M [5] |
| GDMADCCEKQEPE (SEQ ID No. 201) | Carboxymethyl C (2) [6 7]<br>Carboxymethyl C (2) [6 7], Oxidation M [3] |
| MADCCEKQEPE (SEQ ID No. 202) | Carboxymethyl C (2) [4 5] |
| ADCCEKQEPE (SEQ ID No. 203) | Carboxymethyl C (2) [3 4], Glycation [6]<br>Carboxymethyl C (2) [3 4] |
| CCEKQEPE (SEQ ID No. 204) | Carboxymethyl C (2) [1 2], Glycation [4]<br>Carboxymethyl C (2) [1 2] |
| TYGDMADCCEKQEPERNE (SEQ ID No. 205) | Carboxymethyl C (2) [8 9], Oxidation M [5], Deamidation N [17]<br>Carboxymethyl C (2) [8 9] |
| TYGDMADCCEKQEPERN (SEQ ID No. 206) | Carboxymethyl C (2) [8 9], Glycation [11], Deamidation N [17] |
| TYGDMADCCEKQEPER (SEQ ID No. 207) | Carboxymethyl C (2) [8 9], Oxidation M [5] |
| YGDMADCCEKQEPERNE (SEQ ID No. 208) | Carboxymethyl C (2) [7 8], Oxidation M [4], Deamidation N [16]<br>Carboxymethyl C (2) [7 8], Oxidation M [4], Glycation [10], Deamidation N [16]<br>Carboxymethyl C (2) [7 8] |
| GDMADCCEKQEPERNE (SEQ ID No. 209) | Carboxymethyl C (2) [6 7], Deamidation N [15]<br>Carboxymethyl C (2) [6 7], Glycation [9], Deamidation N [15] |

FIG. 17AC

| PEPTIDE | MODIFIERS |
|---|---|
| DMADCCEKQEPERNE (SEQ ID No. 210) | Carboxymethyl C (2) [5 6], Oxidation M [2], Glycation [8]<br>Carboxymethyl C (2) [5 6], Oxidation M [2], Glycation [8], Deamidation N [14] |
| MADCCEKQEPERNE (SEQ ID No. 211) | Carboxymethyl C (2) [4 5], Glycation [7], Deamidation N [13] |
| ADCCEKQEPERNE (SEQ ID No. 212) | Carboxymethyl C (2) [3 4]<br>Carboxymethyl C (2) [3 4], Glycation [6]<br>Carboxymethyl C (2) [3 4], Deamidation N [12] |
| CCEKQEPERNE (SEQ ID No. 213) | Carboxymethyl c (2) [1 2], Glycation [4], Deamidation N [10]<br>Carboxymethyl C (2) [1 2] |
| CEKQEPERNE (SEQ ID No. 214) | Carboxymethyl C [1], Deamidation N [9] |
| TYGDMADCCEKQEPERNECFLSHKDDSPDLPKLKPDPNTLCDE (SEQ ID No. 215) | Carboxymethyl C (4) [8 9 19 41], Oxidation M [5], Glycation (2) [2?]<br>Carboxymethyl C (4) [8 9 19 41], Oxidation M [5], Glycation (2) [2?], Deamidation N [?] |
| TYGDMADCCEKQEPERNECFLSHKDDSPDLPK (SEQ ID No. 216) | Carboxymethyl C (3) [8 9 19], Oxidation M [5], Glycation (3) [11 24 32] |
| TYGDMADCCEKQEPERNECFLSHKDDSPDLP (SEQ ID No. 217) | Carboxymethyl C (3) [8 9 19], Oxidation M [5], Deamidation N [17] |
| TYGDMADCCEKQEPERNECFLSHKDDSPDL (SEQ ID No. 218) | Carboxymethyl C (3) [8 9 19], Deamidation N [17] |
| TYGDMADCCEKQEPERNECFLSHKDDS (SEQ ID No. 219) | Carboxymethyl C (3) [8 9 19], Glycation (2) [11 24], Deamidation N [17]<br>Carboxymethyl C (3) [8 9 19], Glycation [?], Deamidation N [17] |
| TYGDMADCCEKQEPERNECFLSHKD (SEQ ID No. 220) | Carboxymethyl C (3) [8 9 19], Glycation [?] |
| TYGDMADCCEKQEPERNECFLSHKDDSPDLPKLKPDPNTLC (SEQ ID No. 221) | Carboxymethyl C (4) [8 9 19 41], Oxidation M [5], Glycation (4) [11 24 32 34], Deamidation N (2) [17 38]<br>Carboxymethyl C (4) {8 9 19 41], Glycation (4) [11 24 32 34], Deamidation N (2) [17 38] |
| TYGDMADCCEKQEPERNECFLSH (SEQ ID No. 222) | Carboxymethyl C (3) [8 9 19], Oxidation M [5], Glycation [11] |

FIG. 17 AD

| PEPTIDE | MODIFIERS |
|---|---|
| TYGDMADCCEKQEPERNECFLS (SEQ ID No. 223) | Carboxymethyl C (3) [8 9 19], Deamidation N [17]<br>Carboxymethyl C (3) [8 9 19] |
| TYGDMADCCEKQEPERNECFL (SEQ ID No. 224) | Carboxymethyl C (3) [8 9 19], Glycation [11]<br>Carboxymethyl C (3) [8 9 19], Oxidation M [5], Glycation [11]<br>Carboxymethyl C (3) [8 9 19] |
| TYGDMADCCEKQEPERNECF (SEQ ID No. 225) | Carboxymethyl C (3) [8 9 19], Deamidation N [17]<br>Carboxymethyl C (3) [8 9 19], Oxidation M [5]<br>Carboxymethyl C (3) [8 9 19], Glycation [11], Deamidation N [17] |
| TYGDMADCCEKQEPERNECFLSHKDDSPDLPKLKPDPNT (SEQ ID No. 226) | Carboxymethyl C (3) [8 9 19], Oxidation M [5], Glycation (4) [11 24 32 34], Deamidation N (2) [17 38]<br>Carboxymethyl C (3) [8 9 19], Glycation (4) [11 24 32 34], Deamidation N [?] |
| TYGDMADCCEKQEPERNECFLSHKDDSPDLPKLKPDPN (SEQ ID No. 227) | Carboxymethyl C (3) [8 9 19], Oxidation M [S], Glycation (3) [3?]<br>Carboxymethyl C (3) [8 9 19], Glycation (4) [11 24 32 34], Deamidation N [?] |
| YGDMADCCEKQEPERNECFLSHKDDSPDLPKLKPDPNTLCDE (SEQ ID No. 228) | Carboxymethyl C (4) [7 8 18 40], Oxidation M [4], Glycation (4) [10 23 31 33], Deamidation N (2) [16 37]<br>Carboxymethyl C (4) [7 8 18 40], Glycation (3) [3?], Deamidation N [?] |
| DMADCCEKQEPERNECFLSHKDDSPDLPKLKPDPNTLCDE (SEQ ID No. 229) | Carboxymethyl C (4) [5 6 16 38], Glycation (2) [2?], Deamidation N (2) [14 35] |
| DCCEKQEPERNECFLSHKDDSPDLPKLKPDPNTLCDE (SEQ ID No. 230) | Carboxymethyl C (4) [2 3 13 35], Glycation (3) [3?], Deamidation N (2) [11 32]<br>Carboxymethyl C (4) [2 3 13 35], Glycation (3) [3?], Deamidation N [?] |

FIG. 17 AE

| PEPTIDE | MODIFIERS |
|---|---|
| TYGDMADCC (SEQ ID No. 231) | Carboxymethyl C (2) [8 9], Oxidation M [5] Carboxymethyl C (2) [8 9] |
| TYGDMADC (SEQ ID No. 232) | Carboxymethyl C [8], Oxidation M [5] |
| TYGDMA (SEQ ID No. 233) | Oxidation M [5] |
| TYGDM (SEQ ID No. 234) | Oxidation M [5] |
| YGDMADCCE (SEQ ID No. 235) | Carboxymethyl C (2) [7 8], Oxidation M [4] |
| DMADCCE (SEQ ID No. 236) | Carboxymethyl C (2) [5 6] |
| MADCCE (SEQ ID No. 237) | Carboxymethyl C (2) [4 5], Oxidation M [1] |
| KQEPERNE (SEQ ID No. 238) | Glycation [1] |
| KQEPERN (SEQ ID No. 239) | Glycation [1], Deamidation N [7] Glycation [1] |
| EPERNE (SEQ ID No. 240) | Deamidation N [5] |
| ERNE (SEQ ID No. 241) | Deamidation N [3] |
| KQEPERNECFLSHKDDSPDLPKLKPDPNTLCDE (SEQ ID No. 242) | Carboxymethyl C (2) [9 31], Glycation (3) [3?], Deamidation N [?] |
| KQEPERNECFLSHKDDSPD (SEQ ID No. 243) | Carboxymethyl C [9], Glycation (2) [1 14], Deamidation N [7] |
| KQEPERNECFLSHKDDSP (SEQ ID No. 244) | Carboxymethyl C [9], Glycation (2) [1 14], Deamidation N [7] |
| KQEPERNEC (SEQ ID No. 245) | Carboxymethyl C [9], Deamidation N [7] Carboxymethyl C [9] Carboxymethyl C [9], Glycation [1], Deamidation N [7] |
| ERNECFLSHKDDSPDLPKLKPDPNTLCDEFKADE (SEQ ID No. 246) | Carboxymethyl C (2) [5 27], Deamidation N [?], Glycation (3) [3?] |
| KQEP (SEQ ID No. 247) | Glycation [1] |
| MKWVTFISLLLLFSSAYSRGVFRRDTHKSEIAHRFKDLG (SEQ ID No. 248) | Glycation [?] |
| MKWVTFISLLLLFSSAYSRGVFRRDTHKSEIAHRFKDL (SEQ ID No. 249) | Oxidation M [1], Glycation [?] |
| MKWVTFISLLLLFSSAYSRGVFRRDTHKSEIAHRFKD (SEQ ID No. 250) | Glycation (3) [2 28 36] |
| MKWVTFISLLLLFSSAYSRGVFRRDTHKSEIAHRFK (SEQ ID No. 251) | Oxidation M [1] |
| KWVTFISLLLLFSSAYSRGVFRRDTHKSEIAHRFKDLGE (SEQ ID No. 252) | Glycation (3) [1 27 35] |
| KSEIAHRFKDLGE (SEQ ID No. 253) | Glycation [?] |

FIG. 17BA

| PEPTIDE | MODIFIERS |
|---|---|
| MKWVTFISLLLLFSSAYSRGVFRRDTHKSEIAHRFKDLGEE (SEQ ID No. 254) | Oxidation M [1] |
| RNECFLSHKDDSPDLPKLKPDPNTLCDE (SEQ ID No. 255) | Carboxymethyl C (2) [4 26], Deamidation N [?] |
| RNECFLSHKDDSPD (SEQ ID No. 256) | Carboxymethyl C [4]<br>Carboxymethyl C [4], Glycation [9]<br>Carboxymethyl C [4], Deamidation N [2], Glycation [9] |
| RNECFLSHKDDSP (SEQ ID No. 257) | Carboxymethyl C [4] |
| RNECFLSHKD (SEQ ID No. 258) | Carboxymethyl C [4], Deamidation N [2], Glycation [9] |
| RNECFLSHK (SEQ ID No. 259) | Carboxymethyl C [4], Deamidation N [2], Glycation [9] |
| RNECF (SEQ ID No. 260) | Carboxymethyl C [4], Deamidation N [2] |
| RNEC (SEQ ID No. 261) | Carboxymethyl C [4] |
| RNECFLSHKDDSPDLPKLKPDPN (SEQ ID No. 262) | Carboxymethyl C [4], Deamidation N [?], Glycation (3) [9 17 19] |
| RNECFLSHKDDSPDLPKLKPDP (SEQ ID No. 263) | Carboxymethyl C [4], Deamidation N [2], Glycation (3) [9 17 19] |
| RNECFLSHKDDSPDLPKLKPD (SEQ ID No. 264) | Carboxymethyl C [4], Glycation (3) [9 17 19] |
| RNECFLSHKDDSPDLPKLK (SEQ ID No. 265) | Carboxymethyl C [4]<br>Carboxymethyl C [4], Deamidation N [2] |
| RNECFLSHKDDSPDLPKLKPDPNTLCDEFK (SEQ ID No. 266) | Carboxymethyl C (2) [4 26], Deamidation N [?], Glycation [?] |
| NECFLSHKDDSPDLPKLKPDPNTLCDEFKADE (SEQ ID No. 267) | Carboxymethyl C (2) [3 25], Deamidation N (2) [1 22], Glycation (4) [8 16 18 29]<br>Carboxymethyl C (2) [3 25], Deamidation N (2) [1 22], Glycation [?] |
| RNECFLSHKDDSPDLPKLKPDPNTLCDEFFKADEKKFWGKYLYE (SEQ ID No. 268) | Carboxymethyl C (2) [4 26], Deamidation N (2) [2 23] |
| NECFLSHKDDSPDLPKLKPDPNTLCDEFKADEKKFWGKYLYE (SEQ ID No. 269) | Carboxymethyl C (2) [3 25], Deamidation N (2) [1 22], Glycation (5) [5?] |
| THKSEIAHRFKDLGEE (SEQ ID No. 270) | Glycation (2) [3 11] |
| CFLSHKDDSPDLPKLKPDPNTLCDE (SEQ ID No. 271) | Carboxymethyl C (2) [1 23], Glycation (3) [6 14 16]<br>Carboxymethyl C (2) [1 23] |
| MKWVTFISLLLLFSSAYSRGVFRRDTHKSEIAHRFKDLGEEHFKGLVLIAFSQYLQQC (SEQ ID No. 272) | Carboxymethyl C [58], Oxidation M [1], Glycation (2) [2?] |
| CFLSHKDDSPDLPKLKPDPNTLCDEFKAD (SEQ ID No. 273) | Carboxymethyl C (2) [1 23], Deamidation N [20] |
| KLKPDPNTLCDEFKADE (SEQ ID No. 274) | Carboxymethyl C [10], Glycation (3) [1 3 14] |
| DPNTLCDEFKADE (SEQ ID No. 275) | Carboxymethyl C [6] |
| PNTLCDEFKADE (SEQ ID No. 276) | Carboxymethyl C [5], Glycation [9] |
| NTLCDEFKADE (SEQ ID No. 277) | Carboxymethyl C [4] |

FIG. 17BB

| PEPTIDE | MODIFIERS |
|---|---|
| CDEFKADE (SEQ ID No. 278) | Carboxymethyl C [1]<br>Carboxymethyl C [1], Glycation [5] |
| SPDLPKLKPDPNTLCDEFKADE (SEQ ID No. 279) | Carboxymethyl C [15], Glycation (3) [6 8 19] |
| PDLPKLKPDPNTLCDEFKADE (SEQ ID No. 280) | Carboxymethyl C [14] |
| CFLSHKDDSPDLPKLKPDPNTLCDEFKADEKKFWGKYLYE (SEQ ID No. 281) | Carboxymethyl C (2) [1 23], Glycation [?], Deamidation N [20]<br>Carboxymethyl C (2) [1 23], Glycation [?] |
| CFLSHKDDSPDLPKLKPDPNTLCDEFKADEKKFWG (SEQ ID No. 282) | Carboxymethyl C (2) [1 23] |
| CFLSHKDDSPDLPKLKPDPNTLCDEFKADEKK (SEQ ID No. 283) | Carboxymethyl C (2) [1 23], Glycation (4) [4?] |
| SHKDDSPDLPKLKPDPNTLCDEFKADEKKFWGKYLYE (SEQ ID No. 284) | Carboxymethyl C [20], Glycation [?] |
| CFLSHKDDSPDLPKLKPDPNTLCDEFKADEKKFWGKYLYEIARRHPYFYA (SEQ ID No. 285) | Carboxymethyl C (2) [1 23], Glycation (3) [3?], Deamidation N [20] |
| CFLSHKDDSPDLPKLKPDPNTLCDEFKADEKKFWGKYLYEIARRHPYF (SEQ ID No. 286) | Carboxymethyl C (2) [1 23], Glycation (7) [6 14 16 27 31 32 36] |
| LKPDPNTLCDEFKADEKKFWGKYLYEIARRHPYFYAPE (SEQ ID No. 287) | Carboxymethyl C [9] |
| PDPNTLCDEFKADEKKFWGKYLYEIARRHPYFYAPE (SEQ ID No. 288) | Carboxymethyl C [7], Deamidation N [4], Glycation (2) [2?] |
| HKDDSPDLPKLKPDPNTLCDEFKADEKKFWGKYLY EIARRH PYFYAPE (SEQ ID No. 289) | Carboxymethyl C [19], Glycation (6) [6?] |
| MKWVTFISLLLLFSSAYSRGVFRRDTHKSEIAHRFKDLGEEHFKGLVLIAF (SEQ ID No. 290) | Oxidation M [1], Glycation [?]<br>Glycation (4) [2 28 36 44] |
| CFLSHKDDSPDLP (SEQ ID No. 291) | Carboxymethyl C [1], Glycation [6] |
| CFLSHKDDSPDL (SEQ ID No. 292) | Carboxymethyl C [1], Glycation [6] |
| CFLSHKDDSPD (SEQ ID No. 293) | Carboxymethyl C [1], Glycation [6] |
| CFLSHKDDSP (SEQ ID No. 294) | Carboxymethyl C [1] |
| CFLSHKDDS (SEQ ID No. 295) | Carboxymethyl C [1], Glycation [6] |
| CFLSH (SEQ ID No. 296) | Carboxymethyl C [1] |
| CFLSHKDDSPDLPKLKPDPNT (SEQ ID No. 297) | Carboxymethyl C [1], Deamidation N [20] |
| DLPKLKPDPNTLCDE (SEQ ID No. 298) | Carboxymethyl C [13], Glycation [?] |
| KPDPNTLCDE (SEQ ID No. 299) | Carboxymethyl C [8], Glycation [1], Deamidation N [5] |
| PDPNTLCDE (SEQ ID No. 300) | Carboxymethyl C [7], Deamidation N [4] |
| DPNTLCDE (SEQ ID No. 301) | Carboxymethyl C [6]<br>Carboxymethyl C [6], Deamidation N [3] |
| PNTLCDE (SEQ ID No. 302) | Carboxymethyl C [5], Deamidation N [2]<br>Carboxymethyl C [5] |
| NTLCDE (SEQ ID No. 303) | Carboxymethyl C [4], Deamidation N [1] |

FIG. 17BC

| PEPTIDE | MODIFIERS |
|---|---|
| LCDE (SEQ ID No. 304) | Carboxymethyl C [2] |
| RDTHKSEIAHRFKDLGEEHFKGLVLIAFSQYLQQCPFDE (SEQ ID No. 305) | Carboxymethyl C [35], Glycation (3) [5 13 21] |
| HKDDSPDLPKLKPDPNTLCDE (SEQ ID No. 306) | Carboxymethyl C [19], Deamidation N [16]<br>Carboxymethyl C [19], Glycation [?], Deamidation N [16] |
| DDSPDLPKLKPDPNTLCDE (SEQ ID No. 307) | Carboxymethyl c [17], Glycation (2) [8 10] |
| FKADE (SEQ ID No. 308) | Glycation [2] |
| KADEKKFWGKYLYE (SEQ ID No. 309) | Glycation (3) [3?] |
| FKADEKKFWGKYLYEIARRHPYFYAP (SEQ ID No. 310) | Glycation [?] |
| FKADEKKFWGKYLYEIARRHPYFYA (SEQ ID No. 311) | Glycation (3) [3?]<br>Glycation (2) [2?] |
| EKKFWGKYLYEIARRHPYFYAPE (SEQ ID No. 312) | Glycation (3) [2 3 7] |
| FKADEKKFWGKYLYEIARRHPYFYAPELLYYANKYN (SEQ ID No. 313) | Glycation (5) [2 6 7 11 34], Deamidation N (2) [33 36] |
| KADEKKFWGKYLYEIARRHPYFYAPELLYYANKYNGVFQE (SEQ ID No. 314) | Glycation (5) [1 5 6 10 33], Deamidation N [?] |
| KADE (SEQ ID No. 315) | Glycation [1] |
| KKFWGKYLYEIARRHPYFYAPE (SEQ ID No. 316) | Glycation [?] |
| KKFWGKYLYEIARRHPYFYAPELLYYANKYNGVFQE (SEQ ID No. 317) | Glycation (3) [3?], Deamidation N (2) [28 31]<br>Deamidation N [?] |
| KFWGKYLYEIARRHPYFYAPELLYYANKYNGVFQE (SEQ ID No. 318) | Glycation (2) [2?], Deamidation N (2) [27 30] |
| GKYLYEIARRHPYFYAPELLYYANKYNGVFQE (SEQ ID No. 319) | Glycation (2) [2 25], Deamidation N (2) [24 27] |
| KYLYEIARRHPYFYAPELLYYANKYNGVFQECCQAE (SEQ ID No. 320) | Carboxymethyl C (2) [32 33], Glycation [?], Deamidation N (2) [23 26] |
| KKFWGKY (SEQ ID No. 321) | Glycation [?] |
| KYLYE (SEQ ID No. 322) | Glycation [1] |
| IARRHPYFYAPELLYYANKY (SEQ ID No. 323) | Glycation [19] |
| PELLYYANKYNGVFQE (SEQ ID No. 324) | Deamidation N [?], Glycation [9] |
| YAPELLYYANKYNGVFQE (SEQ ID No. 325) | Deamidation N [?], Glycation [11] |
| APELLYYANKYNGVFQE (SEQ ID No. 326) | Deamidation N [?] |
| IARRHPYFYAPELLYYANKYNGVFQECCQAE (SEQ ID No. 327) | Carboxymethyl C (2) [27 28], Glycation [19] |
| PELLYYANKYNGVFQECCQAE (SEQ ID No. 328) | Carboxymethyl C (2) [17 18], Deamidation N [?], Glycation [9] |

FIG. 17BD

| PEPTIDE | MODIFIERS |
|---|---|
| ELLYYANKYNGVFQECCQAE (SEQ ID No. 329) | Carboxymethyl c (2) [16 17], Deamidation N (2) [7 10]<br>Carboxymethyl C (2) [16 17], Deamidation N [?] |
| HPYFYAPELIYYANKYNGVFQECCQAE (SEQ ID No. 330) | Carboxymethyl C (2) [23 24], Deamidation N (2) [14 17], Glycation [15] |
| APELLYYANKYNGVFQECCQAE (SEQ ID No. 331) | Carboxymethyl C (2) [18 19], Deamidation N (2) [9 12] |
| IARRHPYFYAPELLYYANKYNGVFQECCQAEDKGACLLPKIE (SEQ ID No. 332) | Carboxymethyl C (3) [27 28 36], Deamidation N [?], Glycation (2) [2?] |
| IARRHPYFYAPELLYYANKYNGVFQECCQAEDKGACLLPK (SEQ ID No. 333) | Carboxymethyl C (3) [27 28 36], Deamidation N [?], Glycation [?] |
| LLYYANKYNGVFQECCQA (SEQ ID No. 334) | Carboxymethyl C (2) [15 16], Deamidation N [?], Glycation [7] |
| LLYYANKYNGVFQECC (SEQ ID No. 335) | Carboxymethyl C (2) [15 16], Deamidation N (2) [6 9], Glycation [7] |
| LYYANKYNGVFQECCQAE (SEQ ID No. 336) | Carboxymethyl C (2) [14 15], Deamidation N [?]<br>Carboxymethyl C (2) [14 15], Deamidation N [?], Glycation [6]<br>Carboxymethyl C (2) [14 15], Glycation [6] |
| VFQECCQAE (SEQ ID No. 337) | Carboxymethyl C (2) [5 6] |
| FQECCQAE (SEQ ID No. 338) | Carboxymethyl C (2) [4 5] |
| QECCQAE (SEQ ID No. 339) | Carboxymethyl C (2) [3 4] |
| ECCQAE (SEQ ID No. 340) | Carboxymethyl C (2) [2 3] |
| YANKYNGVFQECCQAE (SEQ ID No. 341) | Carboxymethyl C (2) [12 13], Deamidation N [?], Glycation [4]<br>Carboxymethyl C (2) [12 13], Deamidation N [?]<br>Carboxymethyl C (2) [12 13], Deamidation N (2) [3 6] |
| ANKYNGVFQECCQAE (SEQ ID No. 342) | Carboxymethyl C (2) [11 12] |
| NKYNGVFQECCQAE (SEQ ID No. 343) | Carboxymethyl C (2) [9 10], Glycation [1], Deamidation N [3] |
| KYNGVFQECQAE (SEQ ID No. 344) | Carboxymethyl C (2) [7 8], Deamidation N [1] |

FIG. 17BE

| PEPTIDE | MODIFIERS |
|---|---|
| NGVFQECCQAE (SEQ ID No. 345) | Carboxymethyl C (2) [7 8], Deamidation N [1] |
| GVFQECCQAE (SEQ ID No. 346) | Carboxymethyl C (2) [6 7] |
| LLYYANKYNGVFQECCQAEDKGACLLP (SEQ ID No. 347) | Carboxymethyl C (3) [15 16 24], Deamidation N (2) [6 9] |
| ECCQAEDKGACLLPKIE (SEQ ID No. 348) | Carboxymethyl C (3) [2 3 11]<br>Carboxymethyl C (3) [2 3 11], Glycation [?] |
| YNGVFQECCQAEDKGACLLPKIE (SEQ ID No. 349) | Carboxymethyl C (3) [8 9 17], Glycation [?] |
| FQECCQAEDKGACLLPKIETMRE (SEQ ID No. 350) | Carboxymethyl C (3) [4 5 13], Glycation (2) [10 17] |
| ECCQAEDKGACLLPKIETMRE (SEQ ID No. 351) | Carboxymethyl C (3) [2 3 11] |
| NKYNGVFQECCQAEDKGACLLPKIETMRE (SEQ ID No. 352) | Carboxymethyl C (3) [10 11 19], Deamidation N [?], Oxidation M |
| KYNGVFQECCQAEDKGACLLPKIETMRE (SEQ ID No. 353) | Carboxymethyl C (3) [9 10 18] |
| LLYYAN (SEQ ID No. 354) | Deamidation N [6] |
| YANKYNGVFQE (SEQ ID No. 355) | Deamidation N [?] |
| ANKYNGVFQE (SEQ ID No. 356) | Deamidation N (2) [2 5], Glycation [3]<br>Deamidation N [?], Glycation [3] |
| NKYNGVFQE (SEQ ID No. 357) | Glycation [2] |
| KYNGVFQE (SEQ ID No. 358) | Glycation [1], Deamidation N [3]<br>Deamidation N [3] |
| YNGVFQE (SEQ ID No. 359) | Deamidation N [2] |
| CCQAED (SEQ ID No. 360) | Carboxymethyl C (2) [1 2] |
| CCQAEDKGACL (SEQ ID No. 361) | Carboxymethyl C (3) [1 2 10], Glycation [7]<br>Carboxymethyl C (3) [1 2 10] |
| CCQAEDKGAC (SEQ ID No. 362) | Carboxymethyl C (3) [1 2 10] |
| CCQAEDKG (SEQ ID No. 363) | Carboxymethyl C (2) [12], Glycation [7]<br>Carboxymethyl C (2) [1 2] |
| CCQAEDK (SEQ ID No. 364) | Carboxymethyl C (2) [1 2], Glycation [7] |
| CCQAEDKGACLLPKIETM (SEQ ID No. 365) | Carboxymethyl C (3) [1 2 10], Glycation [?], Oxidation M [18] |
| AEDKGACLLPKIETMREKVLASSARQRLRCASIQKFGE (SEQ ID No. 366) | Carboxymethyl C (2) [7 30], Glycation (3) [3?] |
| CQAE (SEQ ID No. 367) | Carboxymethyl C [1] |
| MKWVTFISLL (SEQ ID No. 368) | Oxidation M [1] |
| MKWVTF (SEQ ID No. 369) | Glycation [2] |
| MKWVT (SEQ ID No. 370) | Oxidation M [1]<br>Oxidation M [1], Glycation [2] |
| MKWV (SEQ ID No. 371) | Oxidation M [1], Glycation [2] |
| MKWVTFISLLLLFSSAYSRGVF (SEQ ID No. 372) | Oxidation M [1] |
| FSSAYSRGVFRRDTHKSE (SEQ ID No. 373) | Glycation [16] |
| FRRDTHKSE (SEQ ID No. 374) | Glycation [7] |

FIG. 17CA

| PEPTIDE | MODIFIERS |
|---|---|
| HKSE (SEQ ID No. 375) | Glycation [2] |
| LLPKIETMRE (SEQ ID No. 376) | Glycation [4], Oxidation M [8] |
| IETMRE (SEQ ID No. 377) | Oxidation M [4] |
| DKGACLLPKIETMREKVLASSARQRLRCASIQKFGE (SEQ ID No. 378) | Carboxymethyl C (2) [5 28], Glycation (3) [3?], Oxidation M [13]<br>Carboxymethyl C (2) [5 28], Glycation (4) [2 9 16 33] |
| DKGACLLPKIETMREKVLASSARQRLR (SEQ ID No. 379) | Carboxymethyl C [5], Oxidation M [13] |
| KIETMREKVLASSARQRLRCASIQKFGERALKAWSVARLSQKFPKAE (SEQ ID No. 380) | Carboxymethyl C [20], Glycation (2) [2?] |
| IETMREKLASSARQRLRCASIQKFGERALKAWSVARLSQKFPKAE (SEQ ID No. 381) | Carboxymethyl C [19], Oxidation M [4], Glycation [?] |
| DKGACLLPKI (SEQ ID No. 382) | Carboxymethyl C [5] |
| DKGACLLP (SEQ ID No. 383) | Carboxymethyl C [5] |
| DKGACL (SEQ ID No. 384) | Carboxymethyl C [5]<br>Carboxymethyl C [5], Glycation [2] |
| DKGAC (SEQ ID No. 385) | Carboxymethyl C [5]<br>Carboxymethyl C [5], Glycation [2] |
| KGACLLPKIE (SEQ ID No. 386) | Carboxymethyl C [4], Glycation [?] |
| GACLLPKIE (SEQ ID No. 387) | Carboxymethyl C [3] |
| TMREKVLASSAR (SEQ ID No. 388) | Oxidation M [2] |
| TMREKVLASS (SEQ ID No. 389) | Oxidation M [2]<br>Oxidation M [2], Glycation [5] |
| TMREKVLAS (SEQ ID No. 390) | Oxidation M [2] |
| TMREKVLASSARQRLRCASIQKFGERALKAWSVARLSQKFPKAE (SEQ ID No. 391) | Carboxymethyl C [17], Oxidation M [2], Glycation [?] |
| MREKVLASSARQRLRCASIQKFGERALKAWSVARLSQKFPKAEFVE (SEQ ID No. 392) | Carboxymethyl C [16], Glycation (2) [2?] |
| KVLASSARQRLRCASIQKFGE (SEQ ID No. 393) | Carboxymethyl C [13], Glycation (2) [1 18] |
| KVLASSARQRLRCASIQKFGERALKAWSVA (SEQ ID No. 394) | Carboxymethyl C [13], Glycation (3) [1 18 25] |
| KVLASSARQRLRCASIQKFGERALKAWSVARLSQKF (SEQ ID No. 395) | Carboxymethyl C [13] |
| LRCASIQKFGERALKAWSVARLSQKFPKAE (SEQ ID No. 396) | Carboxymethyl C [3], Glycation (4) [8 15 25 28] |
| SARQRLRCASIQKFGERALKAWSVARLSQKFPKAE (SEQ ID No. 397) | Carboxymethyl C [8], Glycation (3) [3?] |
| VLASSARQRLRCASIQKFGERALKAWSVARLSQKFPKAEFVE (SEQ ID No. 398) | Carboxymethyl C [12] |
| KVLASSARQRLRCASIQKFGERALKAWSVARLSQKFPKAEFVEVTKLVTDLTKVHI (SEQ ID No. 399) | Carboxymethyl C [13], Glycation (6) [6?]<br>Carboxymethyl C [13] |

FIG. 17CB

| PEPTIDE | MODIFIERS |
|---|---|
| KVLASSARQRLRCASIQKFGERALKAWSVARLSQKFPKAEFVEVTKLVTDLTK (SEQ ID No. 400) | Carboxymethyl C [13], Glycation (2) [2?] |
| VLASSARQRLRCASIQKFGERALKAWSVARLSQKFPKAEFVEVTKLVTDLTKVHKI (SEQ ID No. 401) | Carboxymethyl C [12], Glycation (4) [4?] |
| LRCASIQKFGERALKAWSVARLSQKFPKAEFVEVTKLVTDLTKVHKE (SEQ ID No. 402) | Carboxymethyl C [3], Glycation (4) [4?] |
| SIQKFGERALKAWSVARLSQKFPKAEFVEVTKLVTDLTKVHKE (SEQ ID No. 403) | Glycation [?] |
| ERALKAWSVARLSQKFPKAEFVEVTKLVTDLTKVHKE (SEQ ID No. 404) | Glycation (2) [2?] |
| RQRLRCASIQKFGERALKAWSVARLSQKFPKAEFVEVTKLVTDLTKVHKE (SEQ ID No. 405) | Carboxymethyl C [6] |
| KVLASSARQRLRCASIQKFG (SEQ ID No. 406) | Carboxymethyl C [13], Glycation (2) [1 18] |
| VLASSARQRLRCASIQKFGE (SEQ ID No. 407) | Carboxymethyl C [12] |
| CASIQKFGE (SEQ ID No. 408) | Carboxymethyl C [1] |
| IQKFGE (SEQ ID No. 409) | Glycation [3] |
| KFPKAEFVE (SEQ ID No. 410) | Glycation [?] |
| KAEFVE (SEQ ID No. 411) | Glycation [1] |
| LSQKFPKAEFVEVTKLVTDLTKVHKE (SEQ ID No. 412) | Glycation (2) [2?] Glycation (4) [4?] |
| FPKAEFVEVTKLVTDLTKVHKECCHGDLLE (SEQ ID No. 413) | Carboxymethyl C (2) [23 24], Glycation (2) [2?] |
| ARLSQKFPKAEFVEVTKLVTDLTKVHKECCHGDLLE (SEQ ID No. 414) | Carboxymethyl C (2) [29 30] |
| RALKA (SEQ ID No. 415) | Glycation [4] |
| RALKAWSVARLS (SEQ ID No. 416) | Glycation [4] |
| AHRFKDLGEE (SEQ ID No. 417) | Glycation [5] |
| QKFPKAE (SEQ ID No. 418) | Glycation [?] |
| SVARLSQKFPKAE (SEQ ID No. 419) | Glycation [?] |
| RLSQKFPKAE (SEQ ID No. 420) | Glycation (2) [5 8] |
| FVEVTK (SEQ ID No. 421) | Glycation [6] |
| FVEVTKLVTDLTKVHKECCHGDLLECADDRADLAKYI (SEQ ID No. 422) | Carboxymethyl C (3) [18 19 26], Glycation (4) [6 13 16 35] |
| FVEVTKLVTDLTKVHKECCHGDLLECADDRADLAKYICDNQDTISSKL (SEQ ID No. 423) | Carboxymethyl C (4) [18 19 26 38], Glycation (4) [4?], Deamidation N [40] |
| FVEVTKLVTDLTKVHKECCHGDLLECADDRADLAKYICDNQDTISSK (SEQ ID No. 424) | Carboxymethyl C (4) [18 19 26 38], Glycation (4) [4?], Deamidation N [40] |
| FVEVTKLVTDLTKVHKECCHGDLLECADDRADLAKYICDNQDTI (SEQ ID No. 425) | Carboxymethyl C (4) [18 19 26 38], Glycation [?], Deamidation N [40] |

FIG. 17CC

| PEPTIDE | MODIFIERS |
|---|---|
| VTKLVTDLTKVHKECCHGDL (SEQ ID No. 426) | Carboxymethyl C (2) [15 16] |
| KECCHGDLLE (SEQ ID No. 427) | Carboxymethyl C (2) [3 4], Glycation [1] |
| VTKLVTDLTKVHKECCHGDLLECADDRADLAKYICDNQDTISS (SEQ ID No. 428) | Carboxymethyl C (4) [15 16 23 35], Glycation (2) [2?] |
| KECCHGDLLECADDRADLAKYICDNQDTISSKLKE (SEQ ID No. 429) | Carboxymethyl C (4) [3 4 11 23], Glycation [?] |
| KLVTDLTKVHKECCHGDLLECADDRADLAKYICDNQDTISSKLKE (SEQ ID No. 430) | Carboxymethyl C (4) [13 14 21 33], Glycation (6) [18 11 30 42 44] |
| DLTKVHKECCHGDLLECADDRADLAKYICDNQDTISSKLKE (SEQ ID No. 431) | Carboxymethyl C (4) [9 10 17 29], Glycation (4) [4?], Deamidation N [31] |
| KVHKECCHGDLLECADDRADLAKYICDNQDTISSKLKE (SEQ ID No. 432) | Carboxymethyl C (4) [6 7 14 26], Glycation [?], Deamidation N [28] |
| VTKLVTDLTKVHKECCHGDLLECADDRADLAKYICDNQDTISSKLKECCD (SEQ ID No. 433) | Carboxymethyl C (6) [15 16 23 35 48 49], Glycation (3) [3?] |
| KLVTDLTKVHKECCHGDLLECADDRADLAKYICDNQDTISSKLKECCDKPLLE (SEQ ID No. 434) | Carboxymethyl C (6) [13 14 21 33 46 47], Glycation (5) [5?] |
| LVTDLTKVHKECCHGDLLECADDRADLAKYICDNQDTISSKLKECCDKPLLE (SEQ ID No. 435) | Carboxymethyl C (6) [12 13 20 32 45 46], Glycation (2) [2?], Deamidation N [34] |
| DLTKVHKECCHGDLLECADDRADLAKYICDNQDTISSKLKECCDKPLLE (SEQ ID No. 436) | Carboxymethyl C (6) [9 10 17 29 42 43], Glycation [?], Deamidation N [31] |
| VTKLVTDL (SEQ ID No. 437) | Glycation [3] |
| VTKLVT (SEQ ID No. 438) | Glycation [3] |
| VTKLV (SEQ ID No. 439) | Glycation [3] |

FIG. 17CD

| PEPTIDE | MODIFIERS |
|---|---|
| KDLGEEHFKGLVLIAFSQYLQQCPFDEHVKLVNE (SEQ ID No. 440) | Carboxymethyl C [23], Deamidation N [33] |
| DLTKVHKE (SEQ ID No. 441) | Glycation (2) [4 7] |
| TKVHKE (SEQ ID No. 442) | Glycation (2) [2 5] |
| GEEHFKGLVLIAFSQYLQQCPFDEHVKLVNE (SEQ ID No. 443) | Carboxymethyl C [20], Glycation (2) [5 27], Deamidation N [30] |
| KVHKE (SEQ ID No. 444) | Glycation [?] Glycation (2) [1 4] |
| EEHFKGLVLIAFSQYLQQCPFDEHVKLVNE (SEQ ID No. 445) | Carboxymethyl C [19], Glycation [?] Carboxymethyl C [19], Glycation [?], Deamidation N [29] |
| CCHGDLLE (SEQ ID No. 446) | Carboxymethyl C (2) [1 2] |
| CCHGDLLECADDRADLAKYICDN (SEQ ID No. 447) | Carboxymethyl C (4) [1 2 9 21] |
| CCHGDLLECADDRAD (SEQ ID No. 448) | Carboxymethyl C (3) [1 2 9] |
| CCHGDLLECADD (SEQ ID No. 449) | Carboxymethyl C (3) [1 2 9] |
| CCHGDLLEC (SEQ ID No. 450) | Carboxymethyl C (3) [1 2 9] |
| CCHGDLLECADDRADLAKYICDNQDTISSK (SEQ ID No. 451) | Carboxymethyl C (4) [1 2 9 21], Glycation [?] Carboxymethyl C (4) [1 2 9 21] |
| GDLLECADDRADLAKYICDNQDTISSKLKE (SEQ ID No. 452) | Carboxymethyl C (2) [6 18], Glycation (3) [15 27 29] |
| CCHGDLLECADDRADLAKYICDNQDTISSKLKECCD (SEQ ID No. 453) | Carboxymethyl C (6) [1 2 9 21 34 35], Glycation (2) [2?], Deamidation N [23] |
| CCHGDLLECADDRADLAKYICDNQDTISSKLKECC (SEQ ID No. 454) | Carboxymethyl C (6) [1 2 9 21 34 35], Glycation (2) [2?], Deamidation N [23] |
| DLLECADDRADLAKYICDNQDTISSKLKECCDKPLLE (SEQ ID No. 455) | Carboxymethyl C (4) [5 17 30 31], Glycation (3) [3?], Deamidation N [19] |
| CCHGDLLECADDRADLAKYICDNQDTISSKLKECCDKPLLEKSHCI (SEQ ID No. 456) | Carboxymethyl C (7) [1 2 9 21 34 35 45], Glycation (3) [3?], Deamidation N [23] |
| CCHGDLL (SEQ ID No. 457) | Carboxymethyl C (2) [1 2] |
| CADDRADLAKYICDNQDTISSKLKECCDKPLL (SEQ ID No. 458) | Carboxymethyl C (4) [1 13 26 27], Glycation (3) [3?] |
| CADDRADLAKYICDNQDTISSKLKECCDK (SEQ ID No. 459) | Carboxymethyl C (4) [1 13 26 27], Glycation [?] |
| CADDRADLAKYICDNQDTISSKLKECCD (SEQ ID No. 460) | Carboxymethyl C (4) [1 13 26 27], Glycation (3) [10 22 24] |
| ECCDKPLLE (SEQ ID No. 461) | Carboxymethyl C (2) [2 3], Glycation [5] Carboxymethyl C (2) [2 3] |
| LAKYICDNQDTISSKLKECCDKPLLE (SEQ ID No. 462) | Carboxymethyl C (3) [6 19 20], Glycation (3) [3?] |
| AKYICDNQDTISSKLKECCDKPLLE (SEQ ID No. 463) | Carboxymethyl C (3) [5 18 19], Glycation (4) [2 14 16 21] |

FIG. 17DA

| PEPTIDE | MODIFIERS |
|---|---|
| CADDRADLAKYICDNQDTISSKLKECCDKPLLEKSHCIAE (SEQ ID No. 464) | Carboxymethyl C (5) [1 13 26 27 37], Deamidation N [15] |
| CADDRADLAKYICDNQDTISSKLKECCDKPLLEK (SEQ ID No. 465) | Carboxymethyl C (4) [1 13 26 27], Glycation (5) [10 22 24 29 34], Deamidation N [15] |
| NQDTISSKLKECCDKPLLEKSHCIAE (SEQ ID No. 466) | Carboxymethyl C (3) [12 13 23], Glycation (4) [8 10 15 20] |
| AKYICDNQDTISSKLKECCDKPLLEKSHCIAE (SEQ ID No. 467) | Carboxymethyl C (4) [5 18 19 29], Glycation (4) [4?], Deamidation N [7] |
| CADDRADLAKYICDNQDTISSKLKECCDKPLLEKSHCIAEVE (SEQ ID No. 468) | Carboxymethyl C (5) [1 13 26 27 37], Glycation [?] |
| ADLAKYICDNQDTISSKLKECCDKPLLEKSHCIAEVE (SEQ ID No. 469) | Carboxymethyl C (4) [8 21 22 32], Glycation (3) [3?] |
| CADDRADLAKY (SEQ ID No. 470) | Carboxymethyl C [1] |
| CADDRADLAK (SEQ ID No. 471) | Carboxymethyl C [1], Glycation [10] |
| CADDRAD (SEQ ID No. 472) | Carboxymethyl C [1] |
| CADDRA (SEQ ID No. 473) | Carboxymethyl C [1] |
| CADDRADLAKYICDNQDTISSKL (SEQ ID No. 474) | Carboxymethyl C (2) [1 13], Glycation (2) [10 22] |
| CADDR (SEQ ID No. 475) | Carboxymethyl C [1] |
| CADD (SEQ ID No. 476) | Carboxymethyl C [1] |
| CADDRADLAKYICDNQDTISSK (SEQ ID No. 477) | Carboxymethyl C (2) [1 13], Glycation (2) [10 22] |
| CADDRADLAKYICDNQD (SEQ ID No. 478) | Carboxymethyl C (2) [1 13], Deamidation N [15] |
| CADDRADLAKYICDNQ (SEQ ID No. 479) | Carboxymethyl C (2) [1 13], Deamidation N [15] |
| ISSKLKE (SEQ ID No. 480) | Glycation (2) [4 6] Glycation [?] |
| SKLKE (SEQ ID No. 481) | Glycation [?] |
| LLEKSHCIAE (SEQ ID No. 482) | Carboxymethyl C [7] Carboxymethyl C [6], Glycation [3] Carboxymethyl C [6] |
| CCDKPLLEKSHCIAEVE (SEQ ID No. 483) | Carboxymethyl C (3) [1 2 12] |
| CCDK (SEQ ID No. 484) | Carboxymethyl C (2) [1 2] |
| CDKPLLE (SEQ ID No. 485) | Carboxymethyl C [1], Glycation [3] |
| CIAEVE (SEQ ID No. 486) | Carboxymethyl C [1] |
| KSHCIAEVEK (SEQ ID No. 487) | Carboxymethyl C [4], Glycation (2) [1 10] |
| AEVEKDAIPE (SEQ ID No. 488) | Glycation [5] |
| KSHCIAEVEKDAIPENLPPLTADFAE (SEQ ID No. 489) | Carboxymethyl C [4], Glycation (2) [1 10], Deamidation N |
| KSHCIAEVEKDAIPENLPPL (SEQ ID No. 490) | Carboxymethyl C [4], Glycation [?], Deamidation N [16] |
| KSHCIA (SEQ ID No. 491) | Carboxymethyl C [4] |
| KSHC (SEQ ID No. 492) | Carboxymethyl C [4] Carboxymethyl C [4], Glycation [1] |
| HCIAE (SEQ ID No. 493) | Carboxymethyl C [2] |

FIG. 17DB

| PEPTIDE | MODIFIERS |
|---|---|
| CIAE (SEQ ID No. 494) | Carboxymethyl C [1] |
| HRFKDLGE (SEQ ID No. 495) | Glycation [4] |
| KDLGE (SEQ ID No. 496) | Glycation [1] |
| VEKDAIPE (SEQ ID No. 497) | Glycation [3] |
| VEKDAI (SEQ ID No. 498) | Glycation [3] |
| VEKDAIPEN (SEQ ID No. 499) | Glycation [3], Deamidation N [9] |
| VEKDAIPENLPPL (SEQ ID No. 500) | Deamidation N [9] |
| VEKDAIPENLPPLTADFAEDKDVCKNYQE (SEQ ID No. 501) | Carboxymethyl C [24], Glycation [?], Deamidation N [?] |
| KDAIPENLP (SEQ ID No. 502) | Glycation [1]<br>Glycation [1], Deamidation N [7] |
| NLPPLTADFAE (SEQ ID No. 503) | Deamidation N [1] |
| NLPPLTADFAEDKDVCKNYQ (SEQ ID No. 504) | Carboxymethyl C [16], Deamidation N [?], Glycation [?] |
| NLPPLTADFAEDKDVCKN (SEQ ID No. 505) | Carboxymethyl C [16], Deamidation N (2) [1 18], Glycation |
| EDKDVCKNYQE (SEQ ID No. 506) | Carboxymethyl C [6], Deamidation N [8] |
| PPLTADFAEDKDVCKNYQE (SEQ ID No. 507) | Carboxymethyl C [14], Glycation (2) [11 15], Deamidation |
| ADFAEDKDVCKNYQE (SEQ ID No. 508) | Carboxymethyl C [10], Glycation (2) [7 11] |
| FAEDKDVCKNYQE (SEQ ID No. 509) | Carboxymethyl C [8], Glycation [?] |
| AEDKDVCKNYQE (SEQ ID No. 510) | Carboxymethyl C [7], Deamidation N [9] |
| NLPPLTADFAEDKDVCKNYQEAKDAFL (SEQ ID No. 511) | Carboxymethyl C [16], Deamidation N (2) [1 18] |
| PLTADFAEDKDVCKNYQEAKDAFLGSFLYE (SEQ ID No. 512) | Carboxymethyl C [13] |
| AEDKDVCKNYQEAKDAFLGSFLYEYSRRHPE (SEQ ID No. 513) | Carboxymethyl C [7], Deamidation N [9]<br>Carboxymethyl C [7], Glycation (3) [4 8 14], Deamidation |
| NLPPLTA (SEQ ID No. 514) | Deamidation N [1] |
| NLPPL (SEQ ID No. 515) | Deamidation N [1] |
| NLPP (SEQ ID No. 516) | Deamidation N [1] |
| DKDVCKNYQEAKDAFLGSFLYE (SEQ ID No. 517) | Carboxymethyl C [5] |
| DKDVCKNYQEA (SEQ ID No. 518) | Carboxymethyl C [5] |
| DKDVCKNYQEAKD (SEQ ID No. 519) | Carboxymethyl C [5], Glycation (2) [2 ?] |
| DVCKNYQEAKDAFLGSFLYE (SEQ ID No. 520) | Carboxymethyl C [3]<br>Carboxymethyl C [3], Glycation (2) [4 10] |
| DVCKNYQEAKDAFLGSFLYEYSRRHPE (SEQ ID No. 521) | Carboxymethyl C [3], Deamidation N [5] |
| NYQEAKDAFLGSFLYEYSRRHPE (SEQ ID No. 522) | Deamidation N [1] |

FIG. 17DC

| PEPTIDE | MODIFIERS |
|---|---|
| DKDVCKNYQ (SEQ ID No. 523) | Carboxymethyl C [5], Deamidation N [7] |
| DKDVCKNY (SEQ ID No. 524) | Carboxymethyl C [5], Glycation [?], Deamidation N [7]<br>Carboxymethyl C [5], Deamidation N [7] |
| DKDVCKN (SEQ ID No. 525) | Carboxymethyl C [5], Glycation (2) [2 6], Deamidation N [7] |
| DKDVC (SEQ ID No. 526) | Carboxymethyl C [5] |
| DKDV (SEQ ID No. 527) | Glycation [2] |

FIG. 17DD

| PEPTIDE | MODIFIERS |
|---|---|
| DVCKNYQE (SEQ ID No. 528) | Carboxymethyl C [3], Glycation [4], Deamidation N [5]<br>Carboxymethyl C [3]<br>Carboxymethyl C [3], Deamidation N [5] |
| CKNYQE (SEQ ID No. 529) | Carboxymethyl C [1]<br>Carboxymethyl C [1], Deamidation N [3]<br>Carboxymethyl C [1], Glycation [2], Deamidation N [3]<br>Carboxymethyl C [1], Glycation [2] |
| KNYQE (SEQ ID No. 530) | Glycation [1], Deamidation N [2] |
| NYQE (SEQ ID No. 531) | Deamidation N [1] |
| KDAFLGSFLYEYSRRHPEYAVSVLLRLAKE (SEQ ID No. 532) | Glycation (2) [1 29] |
| AKDAFL (SEQ ID No. 533) | Glycation [2] |
| AKEYE (SEQ ID No. 534) | Glycation [2] |
| KEYEATLE (SEQ ID No. 535) | Glycation [1] |
| LLRLAKE (SEQ ID No. 536) | Glycation [6] |
| RLAKE (SEQ ID No. 537) | Glycation [4] |
| YEATLEECCAKDDPHACYSTVFDKLKHLVDEPQNLIKQNCDQFE (SEQ ID No. 538) | Carboxymethyl C (4) [8 9 17 40], Deamidation N [?]<br>Carboxymethyl C (4) [8 9 17 40], Glycation [?], Deamidation N [?] |
| YEATLEECCAKDDPHACYSTVFDKL (SEQ ID No. 539) | Carboxymethyl C (3) [8 9 17] |
| YEATLEECCAKDDPHACYST (SEQ ID No. 540) | Carboxymethyl C (3) [8 9 17], Glycation [11] |
| YEATLEECCAKDDPHACYS (SEQ ID No. 541) | Carboxymethyl C (3) [8 9 17] |
| YEATLEECCAKDDPH (SEQ ID No. 542) | Carboxymethyl C (2) [8 9] |
| YEATLEECCAKDDP (SEQ ID No. 543) | Carboxymethyl C (2) [8 9] |
| YEATLEECCAKDD (SEQ ID No. 544) | Carboxymethyl C (2) [8 9], Glycation [11] |
| YEATLEECCAKDDPHACYSTVFDKLKHLVDEPQNLIKQNC (SEQ ID No. 545) | Carboxymethyl C (4) [8 9 17 40], Deamidation N [?] |
| ATLEECCAKDDPHACYSTV (SEQ ID No. 546) | Carboxymethyl C (3) [6 7 15] |
| ATLEECCAKDDPHACYSTVFDKLKHLVDEPQNLIKQNCD (SEQ ID No. 547) | Carboxymethyl C (4) [6 7 15 38], Glycation (3) [3?], Deamidation N (2) [32 37] |
| ATLEECCAKDD (SEQ ID No. 548) | Carboxymethyl C (2) [6 7] |
| ATLEECCAKD (SEQ ID No. 549) | Carboxymethyl C (2) [6 7], Glycation [9] |
| ATLEECCA (SEQ ID No. 550) | Carboxymethyl C (2) [6 7] |
| ATLEEC (SEQ ID No. 551) | Carboxymethyl C [6] |
| ATLEECCAKDDPHACYSTVFDKLKHLVDEPQNLIKQN (SEQ ID No. 552) | Carboxymethyl C (3) [6 7 15], Glycation (4) [9 22 24 35], Deamidation N (2) [32 37] |

FIG. 17EA

| PEPTIDE | MODIFIERS |
|---|---|
| EECCAKDDPHACYSTVFDKLKHLVDEPQNLIKQNCDQFE (SEQ ID No. 553) | Carboxymethyl C (4) [3 4 12 35], Glycation (3) [3?] |
| ATLEECCAKDDPHACYSTVFDKLKHLVDEPQNLIKQNCDQFEKLGE (SEQ ID No. 554) | Carboxymethyl C (4) [6 7 15 38], Glycation (5) [9 22 24 35 43], Deamidation N [?] Carboxymethyl C (4) [6 7 15 38], Glycation (2) [2?], Deamidation N (2) [32 37] |
| LEECCAKDDPHACYSTVFDKLKHLVDEPQNLIKQNCDQFEKLGE (SEQ ID No. 555) | Carboxymethyl C (4) [4 5 13 36], Glycation (3) [3?] |
| ECCAKDDPHACYSTVFDKLKHLVDEPQNLIKQNCDQFE (SEQ ID No. 556) | Carboxymethyl C (4) [2 3 11 34], Glycation (2) [2?] |
| ECCAKDDPHACYSTVFDK (SEQ ID No. 557) | Carboxymethyl C (3) [2 3 11], Glycation [?] |
| ECCAKDDPHACYSTV (SEQ ID No. 558) | Carboxymethyl C (3) [2 3 11], Glycation [5] |
| ECCAKDDPHACYST (SEQ ID No. 559) | Carboxymethyl C (3) [2 3 11], Glycation [5] |
| ECCAKDDPHACY (SEQ ID No. 560) | Carboxymethyl C (3) [2 3 11] |
| ECCAKDDPHAC (SEQ ID No. 561) | Carboxymethyl C (3) [2 3 11] |
| ECCAKDDPHA (SEQ ID No. 562) | Carboxymethyl C (2) [2 3] Carboxymethyl C (2) [2 3], Glycation [5] |
| ECCAKDDPH (SEQ ID No. 563) | Carboxymethyl C (2) [2 3], Glycation [5] |
| ECCAKDDP (SEQ ID No. 564) | Carboxymethyl C (2) [2 3], Glycation [5] |
| ECCAKDD (SEQ ID No. 565) | Carboxymethyl C (2) [2 3], Glycation [5] |
| ECCAK (SEQ ID No. 566) | Carboxymethyl C (2) [2 3], Glycation [5] |
| ECCAKDDPHACYSTVFDKLKHLVDEPQNLI (SEQ ID No. 567) | Carboxymethyl C (3) [2 3 11], Glycation (3) [5 18 20], Deamidation N [28] |
| ECCAKDDPHACYSTVFDKLKHLVDEPQNLIKQNCDQFEKLGEYGFQNALIVRYTRKVPQVSTPTLVE (SEQ ID No. 568) | Carboxymethyl C (4) [2 3 11 34], Glycation (6) [5 18 20 31 39 56], Deamidation N[?] Carboxymethyl C (4) [2 3 11 34], Glycation (3) [3?], Deamidation N (2) [2?] Carboxymethyl C (4) [2 3 11 34], Glycation (6) [5 18 20 31 39 56] |
| ECCAKDDPHACYSTVFDKLKHLVDEPQNLIKQNCDQFEKLGEYGFQNALIVRYTR (SEQ ID No. 569) | Carboxymethyl C (4) [2 3 11 34], Deamidation N (3) [28 33 47] |
| ECCAKDDPHACYSTVFDKLKHLVDEPQNLIKQNCDQFEKLGEYGFQNALIVRY (SEQ ID No. 570) | Carboxymethyl C (4) [2 3 11 34], Glycation [?], Deamidation N [?] |
| ECCAKDDPHACYSTVFDKLKHLVDEPQNLIKQNCDQFEKLGEYGFQNALI (SEQ ID No. 571) | Carboxymethyl C (4) [2 3 11 34], Glycation (5) [5 18 20 31 39], Deamidation N [?] |

FIG. 17EB

| PEPTIDE | MODIFIERS |
|---|---|
| ECCAKDDPHACYSTVFDKLKHLVDEPQNLIKQNCDQFEKLGEYGFQNALIVRYTRKVPQVSTPTL (SEQ ID No. 572) | Carboxymethyl C (4) [2 3 11 34], Glycation (6) [5 18 20 31 39 56], Deamidation N (3) [28 33 47] Carboxymethyl C (4) [2 3 11 34], Glycation (5) [5?], Deamidation N [?] |
| ECCAKDDPHACYSTVFDKLKHLVDEPQNLIKQNCDQFEKLGEYGFQNALIVRYTRKVPQVSTPT (SEQ ID No. 573) | Carboxymethyl C (4) [2 3 11 34], Glycation (2) [2?], Deamidation N (2) [2?] Carboxymethyl C (4) [2 3 11 34], Glycation (6) [5 18 20 31 39 56], Deamidation N (3) [28 33 47] |
| ECCAKDDPHACYSTVFDKLKHLVDEPQNLIKQNCDQFEKLGEYGFQNALIVRYTRKVPQVSTP (SEQ ID No. 574) | Carboxymethyl C (4) [2 3 11 34], Glycation (6) [5 18 20 31 39 56], Deamidation N (3) [28 33 47] |
| ECCAKDDPHACYSTVFDKLKHLVDEPQNLIKQNCDQFEKLGEYGFQNALIVRYTRKVPQVST (SEQ ID No. 575) | Carboxymethyl C (4) [2 3 11 34], Glycation [?], Deamidation N [?] |
| ECCAKDDPHACYSTVFDKLKHLVDEPQNLIKQNCDQFEKLGEYGFQNALIVRYTRKVPQ (SEQ ID No. 576) | Carboxymethyl C (4) [2 3 11 34], Glycation (5) [5?], Deamidation N (3) [28 33 47] |
| CCAKDDPHACYSTVFDKLKHLVDEPQNLIKQNCDQFE (SEQ ID No. 577) | Carboxymethyl C (4) [1 2 10 33], Glycation (3) [3?], Deamidation N (2) [27 32] |
| CCAKDDPHACYSTVFDKLKHLVDEPQNLIKQNCDQFEKLG (SEQ ID No. 578) | Carboxymethyl C (4) [1 2 10 33], Glycation [?], Deamidation N [?] |
| CCAKDDPHACYSTVFDKLKHLVDEPQNLIKQNCDQFEKL (SEQ ID No. 579) | Carboxymethyl C (4) [1 2 10 33], Glycation [?], Deamidation N (2) [27 32] |
| CAKDDPHACYSTVFDKLKHLVDEPQNLIKQNCDQFEKLGE (SEQ ID No. 580) | Carboxymethyl C (3) [1 9 32], Deamidation N [?] Carboxymethyl C (3) [1 9 32], Deamidation N (2) [26 31] |
| VFDKLKHLVDEPQNLIKQNCDQFEKLGE (SEQ ID No. 581) | Carboxymethyl C [20], Glycation (2) [2?], Deamidation N [?] |
| LKHLVDEPQNLIKQNCDQFEKLGE (SEQ ID No. 582) | Carboxymethyl C [16], Deamidation N (2) [10 15] |
| KHLVDEPQNLIKQNCDQFEKLGE (SEQ ID No. 583) | Carboxymethyl C [15], Deamidation N (2) [9 14] |
| AKDDPHACYSTVFDKLKHLVDEPQNLIKQNCDQFEKLGE (SEQ ID No. 584) | Carboxymethyl C (2) [8 31], Deamidation N (2) [25 30] |
| PQNLIKQNCDQFEKLGE (SEQ ID No. 585) | Carboxymethyl C [9], Deamidation N (2) [3 8], Glycation (2) [6 14] |
| QNCDQFEKLGE (SEQ ID No. 586) | Carboxymethyl C [3] |
| NCDQFEKLGE (SEQ ID No. 587) | Carboxymethyl C [2], Deamidation N [1], Glycation [7] |
| CDQFEKLGE (SEQ ID No. 588) | Carboxymethyl C [1], Glycation [6] |
| DDPHACYSTVFDKLKHLVDEPQNLIKQNCDQFEKLGE (SEQ ID No. 589) | Carboxymethyl C (2) [6 29], Glycation (3) [3?], Deamidation N (2) [23 28] Carboxymethyl C (2) [6 29], Glycation (3) [3?] |

FIG. 17EC

| PEPTIDE | MODIFIERS |
|---|---|
| ACYSTVFDKLKHLVDEPQNLIKQNCDQFEK LGE (SEQ ID No. 590) | Carboxymethyl C (2) [2 25] |
| CCAKDDPHACYSTVFDKLKHLVDEPQNLIK QNCDQFEKLGEYGFQNAL (SEQ ID No. 591) | Carboxymethyl C (4) [1 2 10 33], Glycation (5) [5?] Carboxymethyl C (4) [1 2 10 33], Glycation (4) [4?], Deamidation N [?] Carboxymethyl C (4) [1 2 10 33], Glycation (5) [4 17 19 30 38], Deamidation N [?] |
| CCAKDDPHACYSTVFDKLKHLVDEPQNLIK QNCDQFEKLGEYGFQN (SEQ ID No. 592) | Carboxymethyl C (4) [1 2 10 33], Glycation (3) [3?] |
| CCAKDDPHACYSTVFDKLKHLVDEPQNLIK QNCDQFEKLGEYG (SEQ ID No. 593) | Carboxymethyl C (4) [1 2 10 33], Glycation [?], Deamidation N (2) [27 32] |
| TVFDKLKHLVDEPQNLIKQNCDQFEKLGEY GFQNALIVRYTRKVPQVSI (SEQ ID No. 594) | Carboxymethyl C [21], Glycation (5) [5 7 18 26 43], Deamidation N (3) [15 20 34] |
| DKLKHLVDEPQNLIKQNCDQFEKLGEYGFQ NALIVRYTRKVPQVSTPTL (SEQ ID No. 595) | Carboxymethyl C [18], Glycation (3) [3?], Deamidation N [?] Carboxymethyl C [18], Glycation (2) [2?], Deamidation N (3) [12 17 31] |
| LIKQNCDQFEKLGEYGFQNALIVRYTRKVP QVSTPTLVE (SEQ ID No. 596) | Carboxymethyl C [6], Glycation [?], Deamidation N [?] |
| QFEKLGEYGFQNALIVRYTRKVPQVSTPTL VE (SEQ ID No. 597) | Glycation (2) [4 21] |
| ACYSTVFDKLKHLVDEPQNLIKQNCDQFEK LGEYGFQNALIVRYTRKVP (SEQ ID No. 598) | Carboxymethyl C (2) [2 25], Deamidation N (2) [2?] Carboxymethyl C (2) [2 25], Glycation (4) [4?] |
| CYSTVFDKLKHLVDEPQNLIKQNCDQFEKL GEYGFQNALIVRYTRKVPC (SEQ ID No. 599) | Carboxymethyl C (2) [1 24], Glycation (3) [3?], Deamidation N [?] |
| CCAKDDPHACYSTVFDKLKHLVDEPQNLIK QNCDQFEKLGEYGFQNAL (SEQ ID No. 600) | Carboxymethyl C (6) [1 2 10 33 78 79], Glycation (6) [6?] Carboxymethyl C (4) [1 2 10 33], Glycation (7) [4 17 19 30 38 55 73], Deamidation Carboxymethyl C (6) [1 2 10 33 78 79], Glycation (3) [3?], Deamidation N (2) [2?] |
| VDEPQNLIKQNCDQFEKLGEYGFQNALIVR YTRKVPQVSTPTLVEVSRS (SEQ ID No. 601) | Carboxymethyl C (3) [12 57 58], Deamidation N [?], Glycation (5) [9 17 34 52 60] |
| EPQNLIKQNCDQFEKLGEYGFQNALIVRYT RKVPQVSTPTLVEVSRSLG (SEQ ID No. 602) | Carboxymethyl C (3) [10 55 56], Deamidation N [?] |
| NLIKQNCDQFEKLGEYGFQNALIVRYTRKVP QVSTPTLVEVSRSLGKVG (SEQ ID No. 603) | Carboxymethyl C (3) [7 52 53], Deamidation N (3) [1 6 20], Glycation (4) [4?] |

FIG. 17ED

| PEPTIDE | MODIFIERS |
|---|---|
| IKQNCDQFEKLGEYGFQNALIVRYTRKVPQVSTPTLVEVSRSLGKVGTR (SEQ ID No. 604) | Carboxymethyl C (3) [5 50 51], Glycation (3) [3?], Deamidation N (2) [4 18] |
| CCAKDDPHACYSTVFDK (SEQ ID No. 605) | Carboxymethyl C (3) [1 2 10], Glycation (2) [4 17] |
| CCAKDDPHACYSTVFD (SEQ ID No. 606) | Carboxymethyl C (3) [1 2 10], Glycation [4] |
| CCAKDDPHACYSTV (SEQ ID No. 607) | Carboxymethyl C (3) [1 2 10] |
| CCAKDDPHACYST (SEQ ID No. 608) | Carboxymethyl C (3) [1 2 10] |
| CCAKDDPHACYS (SEQ ID No. 609) | Carboxymethyl C (3) [1 2 10] |
| CCAKDDPH (SEQ ID No. 610) | Carboxymethyl C (2) [1 2], Glycation [4] |
| CCAKDDP (SEQ ID No. 611) | Carboxymethyl C (2) [1 2] |
| CCAKDD (SEQ ID No. 612) | Carboxymethyl C (2) [1 2], Glycation [4] Carboxymethyl C (2) [1 2] |
| CCAKD (SEQ ID No. 613) | Carboxymethyl C (2) [1 2] |
| CCAK (SEQ ID No. 614) | Carboxymethyl C (2) [1 2], Glycation [4] |
| CCAKDDPHACYSTVFDKLKHLVDEPQNLIKQNC (SEQ ID No. 615) | Carboxymethyl C (4) [1 2 10 33], Glycation (3) [3?], Deamidation N [?] |
| CCAKDDPHACYSTVFDKLKHLVDEPQNLI (SEQ ID No. 616) | Carboxymethyl C (3) [1 2 10], Glycation [?] |
| CAKDDPHACYSTVFDKLKHLVDEPQNLIKQNCDQFE (SEQ ID No. 617) | Carboxymethyl C (3) [19 32], Glycation [?], Deamidation N (2) [26 31] |
| KLKHLVDEPQNLIKQNCDQFE (SEQ ID No. 618) | Carboxymethyl C [17], Deamidation N (2) [11 16] |
| LKHLVDEPQNLIKQNCDQFE (SEQ ID No. 619) | Carboxymethyl C [16], Glycation (2) [2 13], Deamidation N (2) [10 15] |
| KHLVDEPQNLIKQNCDQFE (SEQ ID No. 620) | Carboxymethyl C [15], Glycation [?], Deamidation N (2) [9 14] Carboxymethyl C [15], Deamidation N (2) [9 14] |
| EPQNLIKQNCDQFE (SEQ ID No. 621) | Carboxymethyl C [10] Carboxymethyl C [10], Deamidation N [?], Glycation [7] |
| PQNLIKQNCDQFE (SEQ ID No. 622) | Carboxymethyl C [9] |
| QNLIKQNCDQFE (SEQ ID No. 623) | Carboxymethyl C [8], Glycation [5] |
| IKQNCDQFE (SEQ ID No. 624) | Carboxymethyl C [5] |
| KQNCDQFE (SEQ ID No. 625) | Carboxymethyl C [4], Deamidation N [3] Carboxymethyl C [4], Glycation [1] |
| HACYSTVFDKLKHLVDEPQNLIKQNCDQFE (SEQ ID No. 626) | Carboxymethyl C (2) [3 26], Glycation (2) [2?], Deamidation N (2) [20 25] |
| KLGEYGFQNA (SEQ ID No. 627) | Glycation [1], Deamidation N [9] |
| KLGEYG (SEQ ID No. 628) | Glycation [1] |

FIG. 17EE

| PEPTIDE | MODIFIERS |
|---|---|
| KLGEYGFQNALIVRYTRKVPQVS (SEQ ID No. 629) | Glycation [?] |
| KLGEYGFQNALIVRYTRKVPQVSTPTLVEVSRSLGKVGTRCCTKPE (SEQ ID No. 630) | Carboxymethyl C (2) [41 42], Glycation (3) [3?]<br>Carboxymethyl C (2) [41 42], Glycation [?], Deamidation N [9] |
| KLGEYGFQNALIVRYTRKVPQVSTPTLVEVSRSLGKVGTR (SEQ ID No. 631) | Glycation [?], Deamidation N [9] |
| GEYGFQNALIVRYTRKVPQVSTPTLVEVSRSLGKVGTRCCTKPE (SEQ ID No. 632) | Carboxymethyl C (2) [39 40], Deamidation N [7], Glycation (3) [16 34 42] |
| KLGEYGFQNALIVRYTRKVPQVSTPTLVEVSRSLGKVGTRCCTKPESE (SEQ ID No. 633) | Carboxymethyl C (2) [41 42], Deamidation N [9] |
| YGFQNALIVRYTRKVPQVSTPTLVEVSRSLGKVGT (SEQ ID No. 634) | Glycation [?] |
| FQNALIVRYTRKVPQVSTPTLVEVSRSLGKVGTRCCTKPE (SEQ ID No. 635) | Carboxymethyl C (2) [35 36], Glycation (3) [12 30 38] |
| QNALIVRYTRKVPQVSTPTLVEVSRSLGKVGTRCCTKPE (SEQ ID No. 636) | Carboxymethyl C (2) [34 35] |
| YGFQNALIVRYTRKVPQVSTPTLVEVSRSLGKVGTRCCTKPESE (SEQ ID No. 637) | Carboxymethyl C (2) [37 38], Deamidation N [5], Glycation [?] |
| TRKVPQVSTPTLVEVSRSLGKVGTRCCTKPESE (SEQ ID No. 638) | Carboxymethyl C (2) [26 27] |
| NALIVRYTRKVPQVSTPTLVEVSRSLGKVGTRCCTKPESE (SEQ ID No. 639) | Carboxymethyl C (2) [33 34], Glycation [?] |
| PQVSTPTLVEVSRSLGKVGTRCCTKPESERMPCTE (SEQ ID No. 640) | Carboxymethyl C (3) [22 23 33] |
| ALIVRYTRKVPQVSTPTLVEVSRSLGKVGTRCCTKPESERMPCTE (SEQ ID No. 641) | Carboxymethyl C (3) [32 33 43], Glycation [?] |
| YGFQN (SEQ ID No. 642) | Deamidation N [5] |
| RCCTKPESE (SEQ ID No. 643) | Carboxymethyl C (2) [2 3], Glycation [5] |
| CCTKPESE (SEQ ID No. 644) | Carboxymethyl C (2) [1 2]<br>Carboxymethyl C (2) [1 2], Glycation [4] |
| CTKPESE (SEQ ID No. 645) | Carboxymethyl C [1] |
| GKVGTRCCTKPESE (SEQ ID No. 646) | Carboxymethyl C (2) [7 8] |
| VGTRCCTKPESE (SEQ ID No. 647) | Carboxymethyl C (2) [5 6] |
| RCCTKPESERMPCTE (SEQ ID No. 648) | Carboxymethyl C (3) [23 13], Glycation [5], Oxidation M [11] |
| CCTKPESERMPCTE (SEQ ID No. 649) | Carboxymethyl C (3) [1 2 12] |
| TKPESERMPCTE (SEQ ID No. 650) | Carboxymethyl C [10], Glycation [2], Oxidation M [8] |
| PESERMPCTE (SEQ ID No. 651) | Carboxymethyl C [8], Oxidation M [6] |
| VGTRCCTKPESERMPCTE (SEQ ID No. 652) | Carboxymethyl C (3) [5 6 16]<br>Carboxymethyl C (3) [5 6 16], Oxidation M [14]<br>Carboxymethyl C (3) [5 6 16], Glycation [8] |

FIG. 17EF

| PEPTIDE | MODIFIERS |
|---|---|
| TRCCTKPESERMPCTE (SEQ ID No. 653) | Carboxymethyl C (3) [3 4 14] |
| SRSLGKVGTRCCTKPESERMPCTEDYLSLILNRLCVLHE (SEQ ID No. 654) | Carboxymethyl C (4) [11 12 22 35], Glycation (2) [6 14] |
| TKPESERMPCTEDYLSLILNRLCVLHE (SEQ ID No. 655) | Carboxymethyl C (2) [10 23], Oxidation M [8], Deamidation N [20] |
| LGKVGTRCCTKPESERMPCTEDYLSLILNRLCVLHE (SEQ ID No. 656) | Carboxymethyl C (4) [8 9 19 32] |
| GKVGTRCCTKPESERMPCTEDYLSLILNRLCVLHE (SEQ ID No. 657) | Carboxymethyl C (4) [7 8 18 31], Glycation (2) [2 10], Deamidation N [28] |
| VSRSLGKVGT (SEQ ID No. 658) | Glycation [7] |

FIG. 17EG

| PEPTIDE | MODIFIERS |
|---|---|
| RCCTKPE (SEQ ID No. 659) | Carboxymethyl C (2) [2 3]<br>Carboxymethyl C (2) [2 3], Glycation [5] |
| CCTKPE (SEQ ID No. 660) | Carboxymethyl C (2) [1 2] |
| VGTRCCTKPE (SEQ ID No. 661) | Carboxymethyl C (2) [5 6] |
| GTRCCTKPE (SEQ ID No. 662) | Carboxymethyl C (2) [4 5], Glycation [7]<br>Carboxymethyl C (2) [4 5] |
| SERMPCTE (SEQ ID No. 663) | Carboxymethyl C [6] |
| SERMPCT (SEQ ID No. 664) | Carboxymethyl C [6], Oxidation M [4] |
| ERMPCTE (SEQ ID No. 665) | Carboxymethyl C [5]<br>Carboxymethyl C [5], Oxidation M [3] |
| SERMPCTEDY (SEQ ID No. 666) | Carboxymethyl C [6], Oxidation M [4] |
| SERMPCTED (SEQ ID No. 667) | Carboxymethyl C [6] |
| RMPCTE (SEQ ID No. 668) | Carboxymethyl C [4], Oxidation M [2] |
| RMPCTEDYLS (SEQ ID No. 669) | Carboxymethyl C [4], Oxidation M [2] |
| RMPCTEDYL (SEQ ID No. 670) | Carboxymethyl C [4] |
| RMPCTEDY (SEQ ID No. 671) | Carboxymethyl C [4] |
| RMPCTED (SEQ ID No. 672) | Carboxymethyl C [4] |
| RMPCTEDYLSLILNRLCV (SEQ ID No. 673) | Carboxymethyl C (2) [4 17], Oxidation M [2], Deamidation N [14] |
| RMPCTEDYLSLILN (SEQ ID No. 674) | Carboxymethyl C [4], Oxidation M [2], Deamidation N [14] |
| MPCTEDYLSLILNRLCVLHEKTPVSEKVTKCCTE (SEQ ID No. 675) | Carboxymethyl C (4) [3 16 31 32], Oxidation M [1], Deamidation N [13], Glycation (2) [2?] |
| RMPCT (SEQ ID No. 676) | Carboxymethyl C [4] |
| RMPC (SEQ ID No. 677) | Carboxymethyl C [4], Oxidation M [2] |
| MPCTE (SEQ ID No. 678) | Carboxymethyl C [3]<br>Carboxymethyl C [3], Oxidation M [1] |
| QQCPFDEHVKLVNE (SEQ ID No. 679) | Carboxymethyl C [3] |
| PCTE (SEQ ID No. 680) | Carboxymethyl C [2] |
| FSQYLQQCPFDEHVKLVNE (SEQ ID No. 681) | Carboxymethyl C [8] |
| DYLSLILNRLCVLHEKTPVSE (SEQ ID No. 682) | Carboxymethyl C [11], Deamidation N [8], Glycation [16] |
| CVLHEKTPVSE (SEQ ID No. 683) | Carboxymethyl C [1] |
| DYLSLILNRLCVLHEKTPVSEKVTKCCTESLVNRRPCFSAL (SEQ ID No. 684) | Carboxymethyl C (4) [11 26 27 37], Deamidation N (2) [8 33], Glycation (2) [2?] |
| YLSLILNRLCVLHEKTPVSEKVTKCCTESLVNRRPCFSALTPDE (SEQ ID No. 685) | Carboxymethyl C (4) [10 25 26 36], Deamidation N (2) [7 32], Glycation (3) [15 21 24] |
| HEKTPVSEKVTKCCTESLVNRRPCFSALTPDE (SEQ ID No. 686) | Carboxymethyl C (3) [13 14 24], Glycation [?], Deamidation N [20] |
| LSLILNRLCVLHEKTPVSEKVTKCCTESLVNRRPCFSALTPDE (SEQ ID No. 687) | Carboxymethyl C (4) [9 24 25 35], Glycation [?] |
| SLILNRLCVLHEKTPVSEKVTKCCTESLVNRRPCFSALTPDE (SEQ ID No. 688) | Carboxymethyl C (4) [8 23 24 34], Deamidation N (2) [5 30] |
| DYLSLILNR (SEQ ID No. 689) | Deamidation N [8] |
| LNRLCVLHE (SEQ ID No. 690) | Carboxymethyl C [5] |

FIG. 17FA

| PEPTIDE | MODIFIERS |
|---|---|
| NRLCVLHE (SEQ ID No. 691) | Carboxymethyl C [4] |
| LCVLHE (SEQ ID No. 692) | Carboxymethyl C [2] |
| KTPVSE (SEQ ID No. 693) | Glycation [1] |
| KTPVSEKV (SEQ ID No. 694) | Glycation [?] |
| KTPVSEK (SEQ ID No. 695) | Glycation (2) [1 7] |
| VSEKVTKCCTE (SEQ ID No. 696) | Carboxymethyl C (2) [8 9], Glycation (2) [4 7] |
| SEKVTKCCTE (SEQ ID No. 697) | Carboxymethyl C (2) [7 8], Glycation (2) [3 6] |
| EKVTKCCTE (SEQ ID No. 698) | Carboxymethyl C (2) [6 7], Glycation (2) [2 5] |
| KTPVSEKVTKCCTESLVNRRPCFSALTPDE (SEQ ID No. 699) | Carboxymethyl C (3) [11 12 22], Glycation (3) [1 7 10], Deamidation N [18] |
| SEKVTKCCTESLVNRRPCFSALTPDE (SEQ ID No. 700) | Carboxymethyl C (3) [7 8 18], Glycation (2) [3 6] |
| SQYLQQCPFDEHVKLVNELTEFAKTCVADE (SEQ ID No. 701) | Carboxymethyl C (2) [7 26], Glycation [?] |
| EHVKLVNELTEFAKTCVADE (SEQ ID No. 702) | Carboxymethyl C [16], Glycation [?], Deamidation N [7] |
| KVTKCCTE (SEQ ID No. 703) | Carboxymethyl C (2) [5 6] |
| KVTKCCTESLV (SEQ ID No. 704) | Carboxymethyl C (2) [5 6] |
| KVTKCCTESL (SEQ ID No. 705) | Carboxymethyl C (2) [5 6] |
| KVTKCCTES (SEQ ID No. 706) | Carboxymethyl C (2) [5 6] |
| KVTKCCTESLVNRRPCFSALTPDETYVPKA (SEQ ID No. 707) | Carboxymethyl C (3) [5 6 16] |
| KVTKCCTESLVNRRPCFSALTPDETYVPK (SEQ ID No. 708) | Carboxymethyl C (3) [5 6 16], Deamidation N [12] |
| KVTKCCTESLVNRRPCFSALTPDETYVPKAFDEKLFTFHADICTLPDTE (SEQ ID No. 709) | Carboxymethyl C (4) [5 6 16 43], Glycation (4) [14 29 34], Deamidation N [12] |
| KVTKCCTESLVNRRPCFSALTPDETYVPKAFDEKLFTFHADICTLPD (SEQ ID No. 710) | Carboxymethyl C (4) [5 6 16 43], Glycation [?] Carboxymethyl C (4) [5 6 16 43], Glycation (2) [2?], Deamidation N [12] |
| CCTESLVNRRPCFSALTPDETYVPKAFDEKLFTFHADICTLPDTE (SEQ ID No. 711) | Carboxymethyl C (4) [1 2 12 39], Deamidation N [8], Glycation [?] |
| KVTKCCT (SEQ ID No. 712) | Carboxymethyl C (2) [5 6], Glycation (2) [14] |
| KVTKC (SEQ ID No. 713) | Carboxymethyl C [5], Glycation [?] |
| TKCCTE (SEQ ID No. 714) | Carboxymethyl C (2) [3 4], Glycation [2] Carboxymethyl C (2) [3 4] |
| KCCTE (SEQ ID No. 715) | Carboxymethyl C (2) [2 3], Glycation [1] |
| SLVNRRPCFSALTPDETYVPKAFDEKLFTFHADICTLPDT (SEQ ID No. 716) | Carboxymethyl C (2) [8 35], Glycation [?] |
| SLVNRRPCFSALTPDETYVPKAFDEKLFTFHA (SEQ ID No. 717) | Carboxymethyl C [8], Deamidation N [4] |
| LVNRRPCFSALTPDETYVPKAFDEKLFTFHADICTLPDTE (SEQ ID No. 718) | Carboxymethyl C (2) [7 34], Glycation (2) [20 25] Carboxymethyl C (2) [7 34], Deamidation N [3], Glycation [?] |

FIG. 17FB

| PEPTIDE | MODIFIERS |
|---|---|
| FSALTPDETYVPKAFDEKLFTFHADICTLPDTE (SEQ ID No. 719) | Carboxymethyl C [27] |
| LVNRRPCFSALTPDETYVPKAFDEKLFTFHADICTLPDTEKQIKKQ (SEQ ID No. 720) | Carboxymethyl C (2) [7 34], Deamidation N [3], Glycation (4) [41]<br>Carboxymethyl C (2) [7 34], Deamidation N [3], Glycation (5) [20 25 41 44 45] |
| VNRRPCFSALTPDETYVPKAFDEKLFTFHADICTLPDTEKQIKKQT (SEQ ID No. 721) | Carboxymethyl C (2) [6 33], Glycation (5) [19 24 40 43 44] |
| SLVNRRPC (SEQ ID No. 722) | Carboxymethyl C [8], Deamidation N [4] |
| HFKGLV (SEQ ID No. 723) | Glycation [3] |
| HFKG (SEQ ID No. 724) | Glycation [3] |
| QYLQQCPFDE (SEQ ID No. 725) | Carboxymethyl C [6] |
| LQQCPFDE (SEQ ID No. 726) | Carboxymethyl C [4] |
| QCPFDE (SEQ ID No. 727) | Carboxymethyl C [2] |
| TYVPKAFDEKLFTFHADICTL (SEQ ID No. 728) | Carboxymethyl C [19] |
| TYVPKAFDEKLFTFHADI (SEQ ID No. 729) | Glycation [?] |
| KAFDEKLFTFHADICTLPDTE (SEQ ID No. 730) | Carboxymethyl C [15], Glycation (2) [16] |
| AFDEKLFTFHADICTLPDTE (SEQ ID No. 731) | Carboxymethyl C [14] |
| TYVPKAFDEKLFTFHADICTLPDTEKQIKKQTALVELLKHKPK (SEQ ID No. 732) | Carboxymethyl C [19], Glycation (2) [2?] |
| TYVPKAFDEKLFTFHADICTLPDTEKQIKKQTALVELLK (SEQ ID No. 733) | Carboxymethyl C [19] |
| YVPKAFDEKLFTFHADICTLPDTEKQIKKQTALVELLKHKPKATE (SEQ ID No. 734) | Carboxymethyl C [18], Glycation [?] |
| TYVPKA (SEQ ID No. 735) | Glycation [5] |
| VPKAFDE (SEQ ID No. 736) | Glycation [3] |
| KLFTFHADICTLPDTEKQIKKQTALVE (SEQ ID No. 737) | Carboxymethyl C [10], Glycation (3) [3?] |
| TLPDTEKQIKKQTALVE (SEQ ID No. 738) | Glycation (2) [2?] |
| KLFTFHADICTLPDTEKQIKKQTALVELLKHKPKATE (SEQ ID No. 739) | Carboxymethyl C [10] |
| KLFTFHADICTLPDTEKQIKKQTALVELLKHKPKAT (SEQ ID No. 740) | Carboxymethyl C [10], Glycation (4) [4?]<br>Carboxymethyl C [10], Glycation (5) [5?] |
| KLFTFHADICTLPDTEKQIKKQTALVELLK (SEQ ID No. 741) | Carboxymethyl C [10] |
| TEKQIKKQTALVELLKHKPKATE (SEQ ID No. 742) | Glycation (5) [5?] |
| ADICTLPDTEKQIKKQTALVELLKHKPKATE (SEQ ID No. 743) | Carboxymethyl C [4], Glycation (3) [3?] |
| KLFTFHADICTLPDTEKQIKKQTALVELLKHKPKATEE (SEQ ID No. 744) | Carboxymethyl C [10], Glycation (7) [1 17 20 21 30 32 34]<br>Carboxymethyl C [10], Glycation (6) [6?] |
| TEKQIKKQTALVELLKHKPKATEE (SEQ ID No. 745) | Glycation (4) [4?] |

FIG. 17FC

| PEPTIDE | MODIFIERS |
|---|---|
| EKQIKKQTALVELLKHKPKATEE (SEQ ID No. 746) | Glycation (4) [4?] |
| TFHADICTLPDTEKQIKKQTALVELLKHK PKATEE (SEQ ID No. 747) | Carboxymethyl C [7], Glycation [?] |
| KLFT (SEQ ID No. 748) | Glycation [1] |
| FTFHADICTLPDTE (SEQ ID No. 749) | Carboxymethyl C [8] |
| HADICTLPDTE (SEQ ID No. 750) | Carboxymethyl C [5] |
| DICTLPDTE (SEQ ID No. 751) | Carboxymethyl C [3] |
| KQIKKQTALVE (SEQ ID No. 752) | Glycation (2) [2?] |
| KQIKKQTALVELLKHKPKAT (SEQ ID No. 753) | Glycation [?] |
| KQIKKQTALVELLKHKPKA (SEQ ID No. 754) | Glycation [?] |
| KQIKKQTALVELLKHKP (SEQ ID No. 755) | Glycation (4) [4?] |
| KQIKKQTALVELLKHK (SEQ ID No. 756) | Glycation (3) [3?] |
| KQIKKQTALVELLKH (SEQ ID No. 757) | Glycation (4) [1 4 5 14] |
| IKKQTALVELLKHKPKATE (SEQ ID No. 758) | Glycation (2) [2?] |
| KQTALVELLKHKPKATE (SEQ ID No. 759) | Glycation (3) [3?] |
| QTALVELLKHKPKATE (SEQ ID No. 760) | Glycation (3) [9 11 13] |
| KKQTALVELLKHKPKATEE (SEQ ID No. 761) | Glycation [?] |
| KQIKKQTALVELLKHKPKATEEQLKTVM (SEQ ID No. 762) | Glycation [?], Oxidation M [28] |
| KQIKKQTALVELLKHKPKATEEQLKT (SEQ ID No. 763) | Glycation (4) [4?] |
| KQIKKQTALVELLKHKPKATEEQLK (SEQ ID No. 764) | Glycation (5) [5?] |
| QIKKQTALVELLKHKPKATEEQLKTVME (SEQ ID No. 765) | Glycation [?], Oxidation M [27] |
| IKKQTALVELLKHKPKATEEQLKTVME (SEQ ID No. 766) | Glycation [?], Oxidation M [26] |
| QTALVELLKHKPKATEEQLKTVME (SEQ ID No. 767) | Glycation (4) [9 11 13 20], Oxidation M [23] |
| LVELLKHKPKATEEQLKTVME (SEQ ID No. 768) | Oxidation M [20] |
| VELLKHKPKATEEQLKTVME (SEQ ID No. 769) | Glycation (2) [2?], Oxidation M [20] Glycation [?] |
| KQIKK (SEQ ID No. 770) | Glycation (2) [2?] Glycation [?] |
| KQIK (SEQ ID No. 771) | Glycation [?] |
| KKQTALVE (SEQ ID No. 772) | Glycation [?] |
| LLHKPKATEE (SEQ ID No. 773) | Glycation [?] |
| LLKHKPKATEEQLKTVME (SEQ ID No. 774) | Oxidation M [17] Glycation (2) [2?] |

FIG. 17FD

| PEPTIDE | MODIFIERS |
|---|---|
| LKHKPKATEEQLKTVME (SEQ ID No. 775) | Glycation (3) [3?], Oxidation M [16] Glycation (4) [2 4 6 13] |
| EEQLKTVME (SEQ ID No. 776) | Glycation [5], Oxidation M [8] |
| LLKHKPKATEEQLKTVMENFV (SEQ ID No. 777) | Glycation [?], Deamidation N [19] Oxidation M [17], Deamidation N [19] |
| LLKHKPKATEEQLKTVMENFVAFVDKC C (SEQ ID No. 778) | Carboxymethyl C (2) [27 28], Glycation (4) [4?], Oxidation M [17] |
| LLKHKPKATEEQLKTVMENFVAFVDK (SEQ ID No. 779) | Glycation (3) [3?] |
| KATEEQLKTVMENFVAFVDKCCAADDK E (SEQ ID No. 780) | Carboxymethyl C (2) [21 22], Glycation (3) [3?], Oxidation M [11] |
| LLKHKPKAT (SEQ ID No. 781) | Glycation [?] |
| LLKH (SEQ ID No. 782) | Glycation [3] |
| LKHKPKATE (SEQ ID No. 783) | Glycation [?] |
| HKPKATE (SEQ ID No. 784) | Glycation [?] |
| KATE (SEQ ID No. 785) | Glycation [1] |
| EQLKT (SEQ ID No. 786) | Glycation [4] |
| EQLKTVMEN (SEQ ID No. 787) | Glycation [4] |
| EQLKTVMENFVAFVDKCCA (SEQ ID No. 788) | Carboxymethyl C (2) [17 18], Glycation [?], Deamidation N [9] |
| EQLKTVMENFVAFVDKCCAADDKEACF AVE (SEQ ID No. 789) | Carboxymethyl C (3) [17 18 26] |
| EQLKTVMENFVAFVDKCCAADDKEAC (SEQ ID No. 790) | Carboxymethyl C (3) [17 18 26], Glycation (3) [4 16 23], Deamidation N [9] |
| QLKTVME (SEQ ID No. 791) | Glycation [3], Oxidation M [6] |
| QLKTVMENFVAFVDKCCAADDKE (SEQ ID No. 792) | Carboxymethyl C (2) [16 17], Glycation (2) [2?], Oxidation M [6] |
| QLKTVMEN (SEQ ID No. 793) | Glycation [3], Oxidation M [6], Deamidation N [8] |
| QLKTVMENFVAFVDKCCA (SEQ ID No. 794) | Carboxymethyl C (2) [16 17], Glycation [?] |

FIG. 17FE

| PEPTIDE | MODIFIERS |
|---|---|
| QLKTVMENFVAFVDKCC (SEQ ID No. 795) | Carboxymethyl C (2) [16 17], Glycation [?], Oxidation M [6], Deamidation N [8] |
| LKTVMENFVAFVDKCCAADDKE (SEQ ID No. 796) | Carboxymethyl C (2) [15 16], Deamidation N [7] |
| KTVMENFVAFVDKCCAADDKE (SEQ ID No. 797) | Carboxymethyl C (2) [14 15], Glycation [?], Oxidation M [4] |
| VMENFVAFVDKCCAADDKE (SEQ ID No. 798) | Carboxymethyl C (2) [12 13], Deamidation N [4], Glycation [?]<br>Carboxymethyl C (2) [12 13], Deamidation N [4], Glycation (2) [11 18]<br>Carboxymethyl C (2) [12 13], Oxidation M [2], Glycation [?]<br>Carboxymethyl C (2) [12 13], Oxidation M [2], Deamidation N [4], Glycation (2) [11 18] |
| MENFVAFVDKCCAADDKE (SEQ ID No. 799) | Carboxymethyl C (2) [11 12], Deamidation N [3], Glycation (2) [10 17] |
| ENFVAFVDKCCAADDKE (SEQ ID No. 800) | Carboxymethyl C (2) [10 11], Deamidation N [2], Glycation (2) [9 16] |
| KTVMENFVAFVDKCCAADDKEACFAVE (SEQ ID No. 801) | Carboxymethyl C (3) [14 15 23], Glycation (3) [1 13 20], Deamidation N [6] |
| TVMENFVAFVDKCCAADDKEACFAVE (SEQ ID No. 802) | Carboxymethyl C (3) [13 14 22], Oxidation M [3], Glycation [?]<br>Carboxymethyl C (3) [13 14 22] |
| VMENFVAFVDKCCAADDKEACFAVE (SEQ ID No. 803) | Carboxymethyl C (3) [12 13 21], Oxidation M [2], Glycation (2) [11 18]<br>Carboxymethyl C (3) [12 13 21], Oxidation M [2], Glycation [?] |
| QLKTVMENFVAFVDKCCAADDKEACFAVEGPKLVV (SEQ ID No. 804) | Carboxymethyl C (3) [16 17 25], Deamidation N [8] |
| LKTVMENFVAFVDKCCAADDKEACFAVEGPKLVVSTQTALA (SEQ ID No. 805) | Carboxymethyl C (3) [15 16 24], Glycation (2) [2 ?], Deamidation N [7] |
| VMENFVAFVDKCCAADDKEACFAVEGPKLVVSTQTALA (SEQ ID No. 806) | Carboxymethyl C (3) [12 13 21], Deamidation N [4], Glycation (2) [2 ?]<br>Carboxymethyl C (3) [12 13 21], Oxidation M [2], Deamidation N [4], Glycation (2) [2 ?]<br>Carboxymethyl C (3) [12 13 21], Oxidation M [2], Glycation (3) [11 18 28] |
| QLKTVM (SEQ ID No. 807) | Oxidation M [6] |
| QLKTV (SEQ ID No. 808) | Glycation [3] |
| LKTVME (SEQ ID No. 809) | Glycation [2] |
| KTVME (SEQ ID No. 810) | Glycation [1]<br>Glycation [1], Oxidation M [4] |
| NFVAFVDKCCAADDKE (SEQ ID No. 811) | Carboxymethyl C (2) [9 10], Glycation [?] |
| HVKLVNELTE (SEQ ID No. 812) | Deamidation N [6] |
| NFVAFVDKCCAADDKEACFAVE (SEQ ID No. 813) | Carboxymethyl C (3) [9 10 18], Deamidation N [1], Glycation (2) [8 15]<br>Carboxymethyl C (3) [9 10 18], Deamidation N [1] |

FIG. 17GA

| PEPTIDE | MODIFIERS |
|---|---|
| NFVAFVDKCCAADDKEACF (SEQ ID No. 814) | Carboxymethyl C (3) [9 10 18], Glycation [?]<br>Carboxymethyl C (3) [9 10 18], Deamidation N [1], Glycation (2) [8 15] |
| NFVAFVDKCCAADDKEA (SEQ ID No. 815) | Carboxymethyl C (2) [9 10], Deamidation N [1], Glycation [?] |
| FVAFVDKCCAADDKEACFAVE (SEQ ID No. 816) | Carboxymethyl C (3) [8 9 17], Glycation [?] |
| ADDKEACFAVE (SEQ ID No. 817) | Carboxymethyl C [7] |
| DDKEACFAVE (SEQ ID No. 818) | Carboxymethyl C [6] |
| KEACFAVE (SEQ ID No. 819) | Carboxymethyl C [4], Glycation [1] |
| EACFAVE (SEQ ID No. 820) | Carboxymethyl C [3] |
| VDKCCAADDKEACFAVE (SEQ ID No. 821) | Carboxymethyl C (3) [4 5 13], Glycation (2) [3 10] |
| KCCAADDKEACFAVE (SEQ ID No. 822) | Carboxymethyl C (3) [2 3 11] |
| CCAADDKEACFAVE (SEQ ID No. 823) | Carboxymethyl C (3) [1 2 10], Glycation [7]<br>Carboxymethyl C (3) [1 2 10] |
| CAADDKEACFAVE (SEQ ID No. 824) | Carboxymethyl C (2) [1 9] |
| HVKLVNELT (SEQ ID No. 825) | Glycation [3] |
| NFVAFV (SEQ ID No. 826) | Deamidation N [1] |
| NFVAFVDKCCAADD (SEQ ID No. 827) | Carboxymethyl C (2) [9 10], Glycation [8] |
| HVKLVNEL (SEQ ID No. 828) | Deamidation N [6] |
| NFVAFVDKCCAAD (SEQ ID No. 829) | Carboxymethyl C (2) [9 10], Deamidation N [1], Glycation [8]<br>Carboxymethyl C (2) [9 10]<br>Carboxymethyl C (2) [9 10], Glycation [8] |
| FVAFVDKCCAADDKE (SEQ ID No. 830) | Carboxymethyl C (2) [8 9] |
| AADDKE (SEQ ID No. 831) | Glycation [5] |
| ADDKE (SEQ ID No. 832) | Glycation [4] |
| KLVNELTE (SEQ ID No. 833) | Glycation [1] |
| FVDKCCAADDKE (SEQ ID No. 834) | Carboxymethyl C (2) [5 6], Glycation [?]<br>Carboxymethyl C (2) [5 6], Glycation (2) [4 11] |
| DKCCAADDKE (SEQ ID No. 835) | Carboxymethyl C (2) [3 4]<br>Carboxymethyl C (2) [3 4], Glycation [?] |
| CAADDKE (SEQ ID No. 836) | Carboxymethyl C [1] |
| ACFAVE (SEQ ID No. 837) | Carboxymethyl C [2] |
| ACFAVEGPK (SEQ ID No. 838) | Carboxymethyl C [2], Glycation [9] |
| ACFAVEGP (SEQ ID No. 839) | Carboxymethyl C [2] |
| ACFAVEGPKLVV (SEQ ID No. 840) | Carboxymethyl C [2]<br>Carboxymethyl C [2], Glycation [9] |
| AVEGPKLVVSTQTALA (SEQ ID No. 841) | Glycation [6] |
| ACFA (SEQ ID No. 842) | Carboxymethyl C [2] |

FIG. 17GB

| PEPTIDE | MODIFIERS |
|---|---|
| CFAVE (SEQ ID No. 843) | Carboxymethyl C [1] |
| KLVNELTEFAKTCVADE (SEQ ID No. 844) | Carboxymethyl C [13], Glycation [?], Deamidation N [4] |
| GPKLVV (SEQ ID No. 845) | Glycation [3] |
| NELTEFAKTCVADESHAGCE (SEQ ID No. 846) | Carboxymethyl C (2) [10 19], Glycation [8] |
| HVKLVN (SEQ ID No. 847) | Glycation [3], Deamidation N [6] Deamidation N [6] |
| HVKLV (SEQ ID No. 848) | Glycation [3] |
| HVKL (SEQ ID No. 849) | Glycation [3] |
| VKLVNE (SEQ ID No. 850) | Deamidation N [5] |
| KLVNE (SEQ ID No. 851) | Glycation [1], Deamidation N [4] |
| LTEFAKTCVAD (SEQ ID No. 852) | Carboxymethyl C [8] |
| LTEFAKTC (SEQ ID No. 853) | Carboxymethyl C [8], Glycation [6] |
| LTEFAKT (SEQ ID No. 854) | Glycation [6] |
| LTEFAK (SEQ ID No. 855) | Glycation [6] |
| EFAKTCVADESHAGCE (SEQ ID No. 856) | Carboxymethyl C (2) [6 15] |
| FAKTCVADESH (SEQ ID No. 857) | Carboxymethyl C [5] |
| KTCVADESHAGCE (SEQ ID No. 858) | Carboxymethyl C (2) [3 12], Glycation [1] |
| TCVADESHAGCE (SEQ ID No. 859) | Carboxymethyl C (2) [2 11] |
| VADESHAGCE (SEQ ID No. 860) | Carboxymethyl C [9] |
| DESHAGCE (SEQ ID No. 861) | Carboxymethyl C [7] |
| ESHAGCE (SEQ ID No. 862) | Carboxymethyl C [6] |
| FAKTCVADESHAGCEKSLHTL (SEQ ID No. 863) | Carboxymethyl C (2) [5 14], Glycation [?] |
| FAKTCVADESHAGCEK (SEQ ID No. 864) | Carboxymethyl C (2) [5 14], Glycation (2) [3 16] |
| FAKTCVAD (SEQ ID No. 865) | Carboxymethyl C [5], Glycation [3] |
| FAKTCV (SEQ ID No. 866) | Carboxymethyl C [5], Glycation [3] |
| FAKTC (SEQ ID No. 867) | Carboxymethyl C [5], Glycation [3] |
| AKTCVADE (SEQ ID No. 868) | Carboxymethyl C [4], Glycation [2] |
| KTCVADE (SEQ ID No. 869) | Carboxymethyl C [3], Glycation [1] Carboxymethyl C [3] |
| TCVADE (SEQ ID No. 870) | Carboxymethyl C [2] |
| CVADE (SEQ ID No. 871) | Carboxymethyl C [1] |
| SHAGCE (SEQ ID No. 872) | Carboxymethyl C [5] |
| SHAGCEKSLHTLFGDELCKVASLRETYGDMADCC (SEQ ID No. 873) | Carboxymethyl C (4) [5 18 33 34], Glycation (?), Oxidation M |
| SHAGCEKSLHT (SEQ ID No. 874) | Carboxymethyl C [5] |
| SHAGCEKSLH (SEQ ID No. 875) | Carboxymethyl C [5], Glycation [7] |
| SHAGCEKS (SEQ ID No. 876) | Carboxymethyl C [5], Glycation [7] |

FIG. 17GC

| PEPTIDE | MODIFIERS |
|---|---|
| SHAGCEK (SEQ ID No. 877) | Carboxymethyl C [5]<br>Carboxymethyl C [5], Glycation [7] |
| SHAGC (SEQ ID No. 878) | Carboxymethyl C [5] |
| KSLHTLFGDELCKVASLRETYGDMADCCE (SEQ ID No. 879) | Carboxymethyl C (3) [12 27 28], Oxidation M [24] |
| GDELCKVASLRETYGDMADCCE (SEQ ID No. 880) | Carboxymethyl C (3) [5 20 21]<br>Carboxymethyl C (3) [5 20 21], Glycation (6), Oxidation M [1] |
| DELCKVASLRETYGDMADCCE (SEQ ID No. 881) | Carboxymethyl C (3) [4 19 20], Oxidation M [16] |
| ELCKVASLRETYGDMADCCE (SEQ ID No. 882) | Carboxymethyl C (3) [3 18 19], Glycation [4], Oxidation M [1]<br>Carboxymethyl C (3) [3 18 19], Glycation [4] |
| FGDELCKVASLRETYGDMADCCEKQEPE (SEQ ID No. 883) | Carboxymethyl C (3) [6 21 22], Glycation [?], Oxidation M [1] |
| KSLHTLFG (SEQ ID No. 884) | Glycation [1] |
| KSLHTLF (SEQ ID No. 885) | Glycation [1] |
| KSLHTL (SEQ ID No. 886) | Glycation [1] |

FIG. 17GD

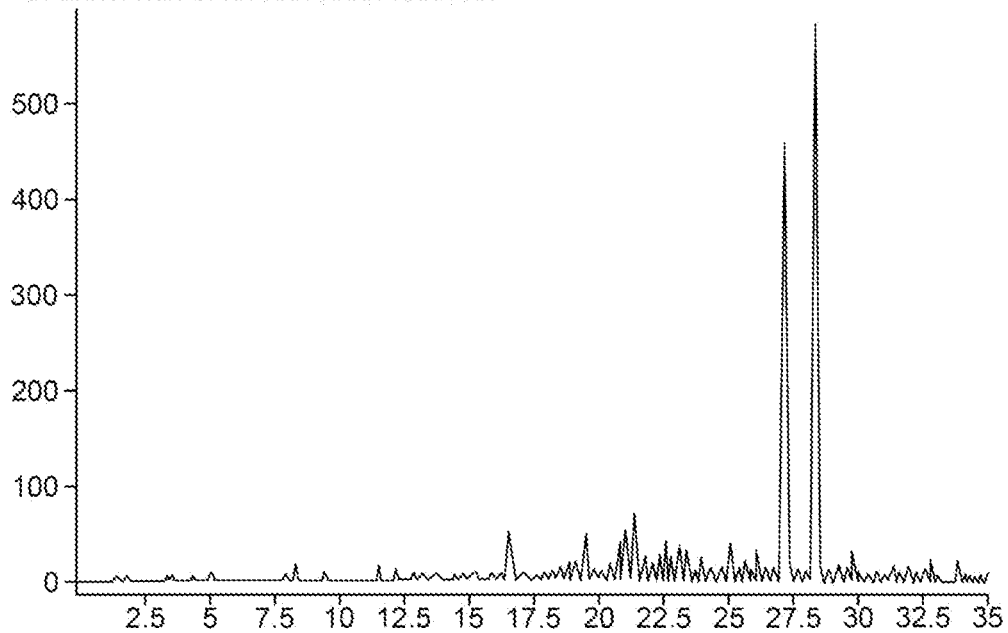
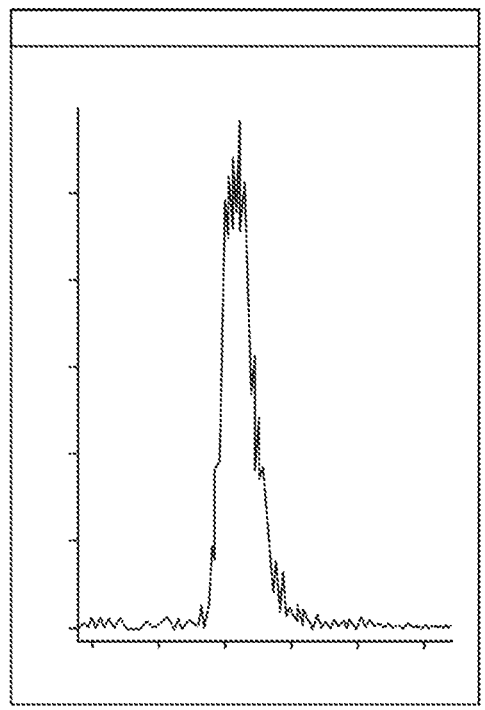
FIG. 18D

SELECTION BIOMARKERS FOR PATIENT STRATIFICATION IN BODILY FLUIDS AND APPLYING PRECISION MEDICINE THROUGH NOVEL DIAGNOSTIC BIOMARKERS

RELATED APPLICATIONS

This application claims priority to U.S. Provisional Application No. 62/569,998, titled "DIABETES AND PREDIABETES DETECTION IN MENSTRUAL FLUID" and filed Oct. 9, 2017, the entire contents of which are hereby incorporated by reference for all purposes.

REFERENCE TO AN ELECTRONIC SEQUENCE LISTING

The contents of the electronic sequence listing, Replacement_Sequence_Listing_ST25_9_1_23.txt, Size: 381 kilobytes, and Date of Creation: Sep. 1, 2023, is herein incorporated by reference in its entirety.

FIELD OF THE INVENTION

This invention relates to, in part, methods and devices that are useful for the treatment, prevention, and/or diagnosis, of various diseases in females, as well as female stratification through application of selection biomarkers and precision medicine using health-related biomarkers.

BACKGROUND

Healthcare is estimated to account for nearly twenty percent of the U.S. Gross Domestic Product (GDP)—an amount of almost three trillion US dollars. Considering the increased demand for healthcare the magnitude of this industry is expected to rise. With increased demand comes less access to health care practitioners either in the form of shorter visits or longer wait times to schedule an appointment. Further, the increased reliance on biomarkers for monitoring patient health and prescribing pharmaceuticals make accurate biomarker measurements a critical component for effective health care. New methods, devices, and systems capable of providing accurate biomarker measurements, without increasing demand on the current health care system, are needed. A three-fold higher likelihood of approval from Phase One was calculated for programs that utilized selection biomarkers (25.9%, n=512) versus programs that did not (8.4%, n=9,012). All four phase transition success rates were much higher for programs incorporating selection biomarkers versus those not incorporating selection biomarkers. Phase three transition success rates for selection biomarker programs were 76.5% (n=132) vs. only 55.0% (n=1,254) for nonselection biomarker programs—the largest percentage difference among the four phases of development. Patient enrollment at the molecular level is a more successful strategy than heterogeneous enrollment especially for female inclusion as the female biology is largely unknown and females remain excluded from many clinical studies.

Millions of women worldwide have a variety of healthcare needs largely unmet for many reasons. Some reasons are based on sociocultural, political and/or socioeconomical determinants, where women's health remains a minority focus for mainstream funding, discussion and solutions in nearly all global economic geographies.

Other reasons are as basic as the uniqueness of females and their biology. Unlike males, females will have different healthcare needs driven by various biological changes that occur throughout her life. It starts with pre-puberty, continues through puberty and adolescence, into early and mid-childbearing years and through menopause and beyond.

Many researchers have claimed that this amount of variability throughout a female's life makes it difficult to study, innovate and/or improve diagnostics and therapeutics specific to female health needs; and hence, we still have very little insight about the specifics of female biology to this day. In fact, it was only twenty-five years ago when the US Food & Drug Administration (US FDA) changed their policy from excluding women of child-bearing age from clinical studies to including them into clinical studies, and yet we still see instances where male biology (even in pre-clinical studies) remains the proxy for a drug's safety and efficacy.

To underscore the unknown and therefore the un-met needs for female patients, as well as costs incurred from current-day methods and approaches some of the most common diseases, we provide two examples:

More Women are Impacted by Cancer

The American Cancer Society estimates 1.7 MM new cases of cancer in 2018, of which 879K (52%) will be women—a majority because nearly 80K more women than men are impacted by female-prevalent breast and endocrine cancers. Further, there is a hypothesis that cancer develops at greater rates in women than in men possibly due to the cyclical nature of menstruation in combination with the effects of estrogen signaling which rapidly causes the biological development of a tumor-network.

Additionally, ~3.2 MM women between the ages of 18 and 45 were diagnosed or living with some of the most prevalent female-specific cancers (Breast, Endometrial, Lung, Ovarian, Cervical), representing a $15B annual cost in healthcare for this age group.

Early detection is the best detection, but not always easy, available or affordable. When we think about the nearly 900K women who will be diagnosed with cancer this year, and the million others who are living with cancer, we wonder: what if there were a regular, easy, affordable way for physicians to detect or even predict potential cancers, starting in our teenage years?

More Women are Impacted by Degenerative Diseases

Female-prevalent degenerative disease has twice the magnitude outlook as cancer, with ~6.5 MM women between the ages of 18 and 45 diagnosed or living with some of the most prevalent female-specific degenerative diseases (such as Type II Diabetes, Heart Disease, Early-Onset Alzheimer's), representing a $27B annual cost in healthcare for this age group. Diagnostic devices targeted for gynecological use are expected to display the highest future growth rate in North America. In 2015, the available market for diagnostics in women's health was ~$33B. By 2020 of the market growth is valued at $40.6B with a CAGR value of 4.2% over this time period. The American Cancer Society estimates that 51% of new cancer cases in 2018 will be women vs 49% men due to female-prevalent cancers such as endocrine, in which there is no screening test for women. Diagnostic solutions are not personalized enough for women; female biology is not widely understood yet.

SUMMARY OF THE INVENTION

This disclosure relates to methods and devices that enables physicians, healthcare providers, pharmaceutical companies and female patients to engage in patient stratification, apply precision medicine to therapeutic use, treatment, diagnosis and/or prognosis, and/or short and long-term health monitoring of important disease- or health-related biomarkers in a reliable, cost effective, and non-invasive manner.

In one aspect, the invention provides a method for evaluating one or more disease- or health-related biomarkers in a female subject, comprising: (a) obtaining a sample of the female subject's menstrual fluid; (b) measuring the presence, absence, or level of one or more disease- or health-related biomarkers in the sample; and (c) repeating with subsequent menstrual fluid. The trend and/or average levels of the biomarker(s) can be evaluated by the healthcare provider or patient to inform healthcare or lifestyle decisions, including in some embodiments the diagnosis of early stage disease, the state of chronic disease (e.g., controlled or uncontrolled), and/or patient stratification and precision medicine to the individual patient.

In some embodiments, the present methods inform a healthcare provider to make healthcare decisions and/or providing improved health care and/or informs a female subject to make improved health/lifestyle decisions.

In various embodiments, the method prevents unnecessary medical care visits, reduces or eliminates unnecessary diagnostic tests, reduces or eliminates unnecessary administration of therapeutic agents, improves the selection of diagnostic tests, and improves the selection of therapeutic agents.

Further, in various embodiments, the present methods provide baseline biomarker levels for the patient, as well as long term and short term trends in biomarker levels. Such baseline information or trends allow for more accurate and interpretable diagnostic and/or prognostic tests including, for example, when the baseline or trend health information is used to compare to a biomarker measurement at a single point of time (including, by way of non-limiting example, at a point of care, e.g., upon visit to a healthcare profession presenting symptoms of a disease or disorder). Additionally, baseline information may be used to apply precision medicine at a given point in time of the female patient's menstruating life, for example, between the onset of menses and menopause, a female's biology will significantly change and one can use such baseline information to properly dose medication, monitor the state of chronic disease, etc. In various embodiments, the methods provided herein comprise measurement of various disease- or health-related biomarkers that are used to direct healthcare decisions and/or personal health decisions. In particular, the present invention provides for biomarker measurements for which patient stratification through selection biomarkers and precision medicine is desired across a wide range of health states and various diseases.

Provided herein is a method of stratifying human female subject, comprising obtaining a sample of the female subject's menstrual fluid; separating proteins of the menstrual fluid; measuring the level of glycation of the hemoglobin subunit alpha in the sample; and assigning female subject to a category and using said category for clinical trial enrollment and medication dosing. A category is defined by the number of hemoglobin subunit alpha modifications present in the female subject's menstrual blood. Categories may also be confirmed by the number of modifications on other proteins present in the female subject's menstrual blood. Categories are numerically assigned and each subject within a category has specific and similar attributes related to the biological health of the female subjects in each category. For instance, a category of one, subjects will be dosed in similar quantities for medications as compared to other categories in which the dosing may be more or less. In some aspects, category assignments will rate the risk of future and current disease exacerbation within female subjects of that category. For instance, a category of four, subjects will be of higher risk for increased disease progression, as compared to a category one, in which female subjects will have a lower risk of disease progression.

Also provided herein is a method for evaluating hemoglobin subunit alpha in a female subject, comprising: obtaining a sample of the female subject's menstrual fluid; separating proteins of the menstrual fluid; measuring the presence, absence, or level of glycation of the hemoglobin subunit alpha in the sample; and repeating with subsequent menstrual fluid. A post-translation modification on any protein may be detected and correlated to various diseases. The hemoglobin subunit alpha may be positively identified from the sample through MS analysis. A post-translation modification on the hemoglobin subunit alpha may be detected. The post-translation modification on any protein may be detected and correlated to various diseases. The post-translation modification may be an advanced glycation event or glutathionylation. The menstrual fluid may be collected using a 903 dried blood spot collection card. The hemoglobin subunit alpha may be detected using LC-MS/MS peptide sequencing. The post-translational modification may be detected using LC-MS/MS peptide sequencing. The protein may be identified based on mass and site of modification may be identified based on residue. Multiple glycation events may be observed on the hemoglobin subunit alpha. The multiple glycation events may be indicative of the presence of diabetes or prediabetes. The female subject's menstrual fluid may be obtained using a device comprising a disposable cartridge, optionally inserted or insertable into a wireless enabled device. The device may be a home instrument. The menstrual blood may be collected and analyzed for about 3 months, or about 6 months, or about 9 months, or about 1 year, or about 2 years, or about 3 years, or about 4 years, or about 5 years, or about 6 years, or about 7 years, or about 8 years, or about 9 years, or about 10 years, or about 20 years, or about 30 years, or about 40 years, or about 50 years.

A method of detecting glycated hemoglobin on the alpha subunit in a female patient is provided, the method comprising: obtaining a menstrual fluid sample from a human female patient; and detecting whether glycation of hemoglobin alpha subunit is present in the menstrual fluid sample by using LC-MS/MS peptide sequencing.

A method of detecting modifications of any protein in a female patient is provided, the method comprising: obtaining a menstrual fluid sample from the female patient; and detecting whether modification on one or more proteins is present in the menstrual fluid sample by using LC-MS/MS peptide sequencing.

A method of diagnosing pre-diabetes or diabetes in a female patient is provided, the method comprising: obtaining a menstrual fluid sample from the female patient; detecting whether glycation of hemoglobin alpha subunit is present in the menstrual fluid sample by using LC-MS/MS peptide sequencing; and diagnosing the female patient with pre-diabetes or diabetes when the presence of one or more glycation events in the menstrual fluid sample is detected.

A method of diagnosing and treating pre-diabetes or diabetes in a female patient is provided, the method comprising: obtaining a menstrual fluid sample from the female patient; detecting whether glycation of hemoglobin alpha subunit is present in the menstrual fluid sample by using LC-MS/MS peptide sequencing; and diagnosing the female patient with pre-diabetes or diabetes when the presence of one or more glycation events in the menstrual fluid sample is detected; and administering an effective amount of insulin to the diagnosed female patient.

A method of medication dosing in a female patient is provided, the method comprising: obtaining a menstrual fluid sample from the female patient; measuring glycation of hemoglobin subunit alpha in the menstrual fluid sample; assigning the female patient to a category, as described in the claims; and administering an effective amount of medication to the patient.

BRIEF DESCRIPTION OF THE FIGURES

FIG. 5A shows total ion chromatogram, intact mass spectrum showing P1A, identified as hemoglobin subunit alpha and P2A, identified as hemoglobin subunit beta. FIG. 5B shows deconvoluted P1 A shows P1B as unmodified hemoglobin subunit beta and P2B as singly glycated hemoglobin (S.9%). FIG. 5C is deconvoluted P2A shows P1C as unmodified hemoglobin subunit beta and P2c as singly glycated hemoglobin (9S.4%).

FIG. 6A shows intact mass spectrum showing P1A, identified as hemoglobin subunit alpha and P2A, identified as hemoglobin subunit beta. FIG. 6B is a graph of deconvoluted P1A showing P1B as unmodified hemoglobin subunit beta, P2B as singly glycated hemoglobin (3.S %), P3B as doubly glycated (3.S %), P4B as triply glycated (3.8%), and PSB as quadruply glycated (1.3%). FIG. 6C is a graph of deconvoluted P2A showing P1C as unmodified hemoglobin subunit beta and P2C as singly glycated hemoglobin (3.2%), P3C as doubly glycated (3.7%), P4C as triply glycated (2.7%).

FIG. 7A shows intact mass spectrum showing P1 A, identified as hemoglobin subunit alpha and P2A, identified as hemoglobin subunit beta. FIG. 7B is a graph of deconvoluted P1A showing P1B as unmodified hemoglobin subunit beta, P2B as singly glycated hemoglobin (5.8). FIG. 7C is a graph of deconvoluted P2A showing P1C as unmodified hemoglobin subunit beta and P2C as singly glycated hemoglobin (4.7%).

FIGS. 11A-11D are graphs illustrating the analysis of a fingerprick blood sample compared to a menstrual blood sample and the contents of hemoglobin subunit alpha glycation. FIG. 11A shows intact mass spectrum from fingerpick blood of a single patient. FIG. 11B shows intact mass analysis from fingerpick blood of a singly glycated hemoglobin subunit alpha. FIG. 11C shows intact mass spectrum from menstrual blood taken from the same patient as represented in FIG. 11A and FIG. 11B. FIG. 11D shows intact mass spectrum showing an additional hemoglobin subunit alpha that is not found in the blood from the same patient's fingerprick sample.

FIG. 12A shows intact mass spectrum from fingerpick blood of a single patient. FIG. 12B shows intact mass analysis from fingerpick blood of a singly glycated hemoglobin subunit alpha. FIG. 12C shows intact mass spectrum from menstrual blood taken from the same patient as represented in FIG. 12A and FIG. 12B. FIG. 12D shows intact mass spectrum showing an additional hemoglobin subunit alpha that is not found in the blood from the same patient's fingerpick sample.

Figure 13:
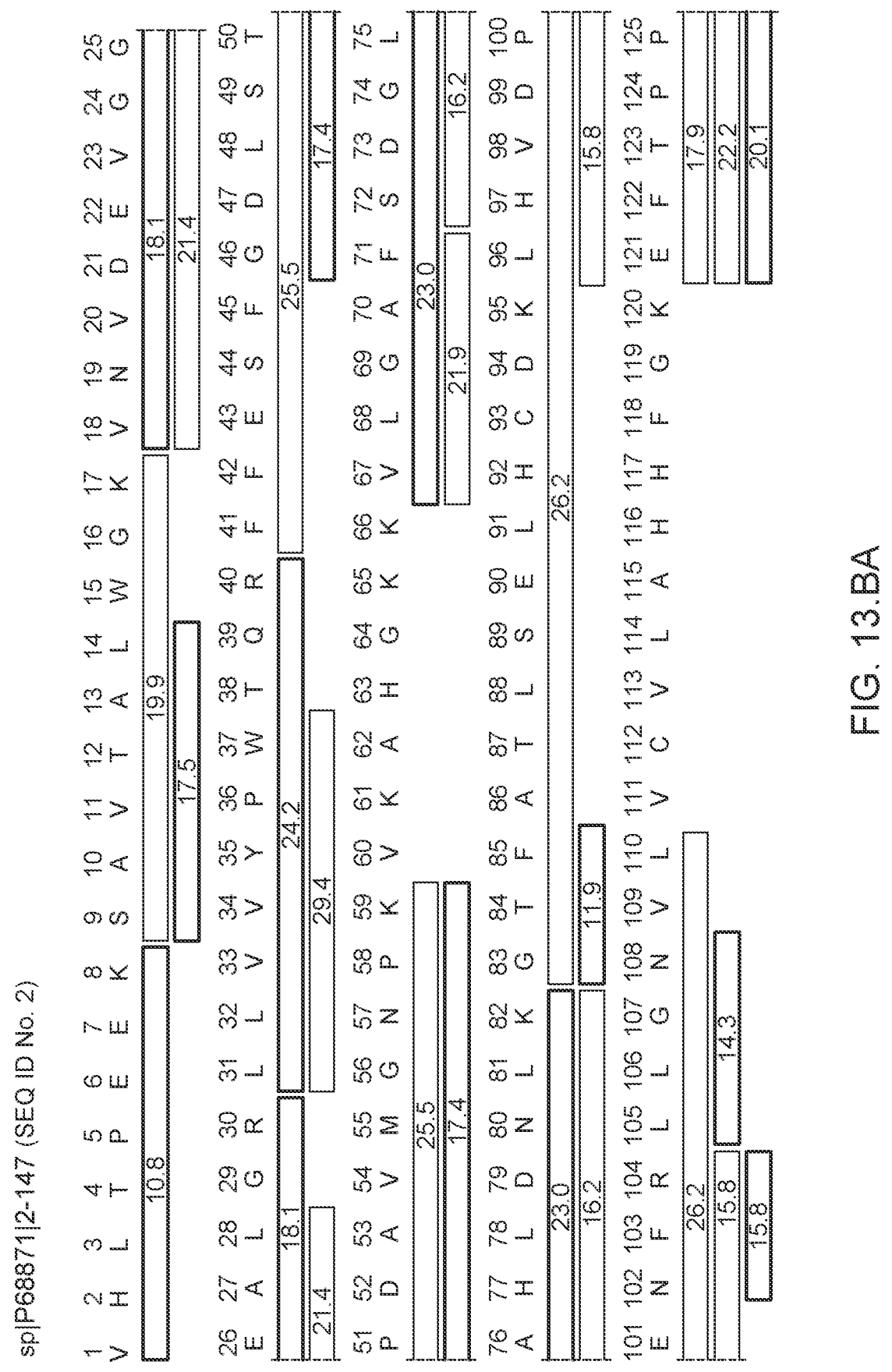

FIGS. 13A-13F are mass spectrometry reports from a single patient that illustrates hemoglobin subunit beta modified position as lysine eight (8), which is unreported in literature. FIG. 13A illustrates the authentic HbA1c standard hemoglobin subunit beta glycan modifications and the detection of a previously unreported glycation on Lysine-8. FIGS. 13BA and 13BB show the sequence coverage map in which 87% of the hemoglobin subunit beta is reported (Seq. Id. No. 2). FIG. 13C shows the fragment coverage map in which the average structural resolutions is equal to 1.6 residues. FIG. 13D shows both the deconvoluted scan spectra and the full scan spectra of the number of residues from FIG. 13C. FIG. 13E shows the fragment coverage map in which the average structural resolutions is equal to 8.0 residues and a sequence of VHLTPEEK. FIG. 13F shows both the deconvoluted scan spectra and the full scan spectra of the number of residues from FIG. 13E.

Figure 14:
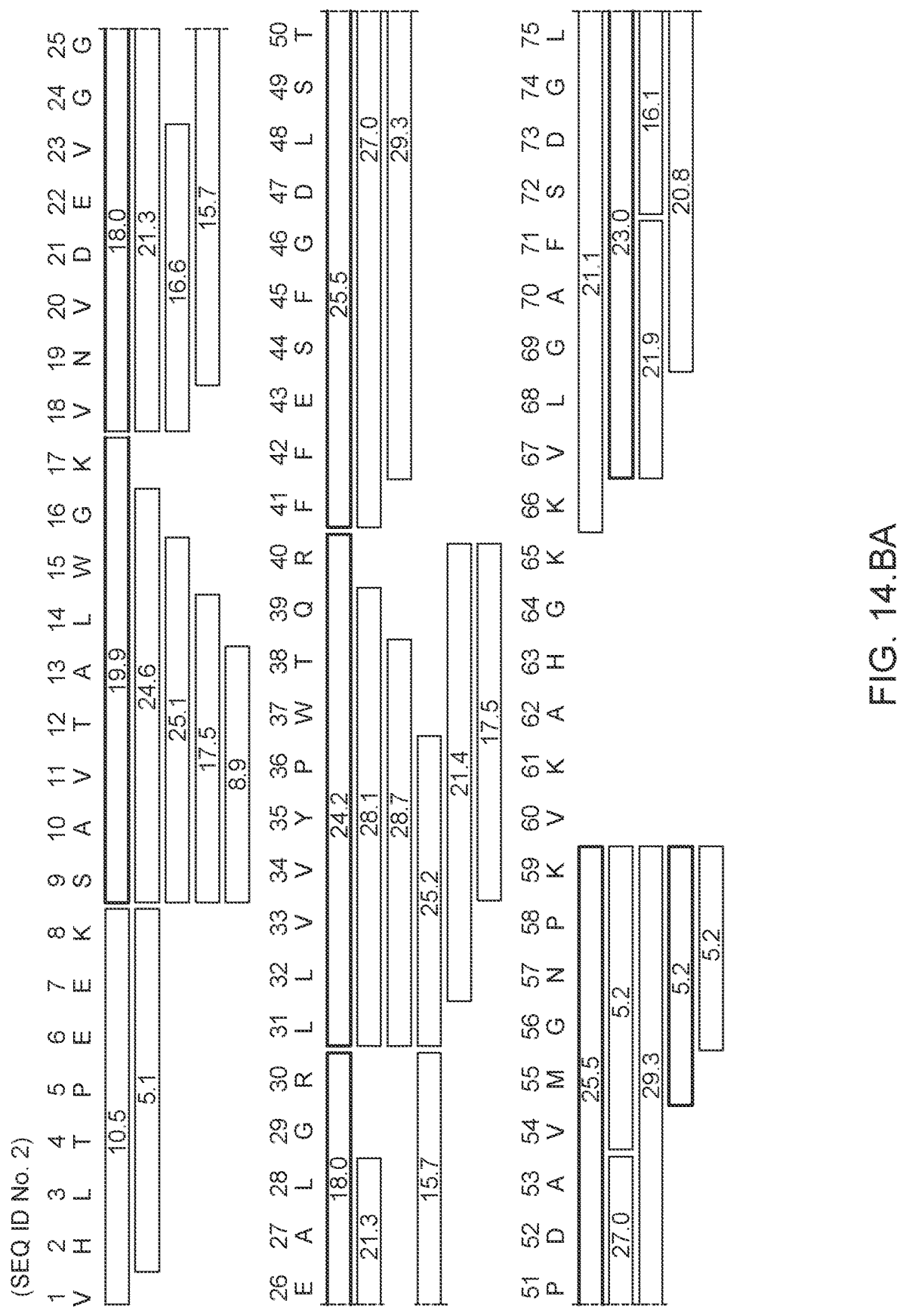

FIGS. 14A-14F are mass spectrometry reports from a second, and separate patient from FIG. 13A-F, that illustrates hemoglobin subunit beta modified position as lysine eight (8), which is unreported in literature. FIG. 14A illustrates the authentic HbA1c standard hemoglobin subunit beta glycan modifications and the detection of a previously unreported glycation on Lysine-8. FIGS. 14BA and 14BB show the sequence coverage map in which 86.5% of the hemoglobin subunit beta is reported (Seq. Id. No. 2). FIG. 14C shows the fragment coverage map in which the average structural resolutions is equal to 1.6 residues. FIG. 14D shows both the deconvoluted scan spectra and the full scan spectra of the number of residues from FIG. 14C. FIG. 14E shows the fragment coverage map in which the average structural resolutions is equal to 8.0 residues and a sequence of VHLTPEEK (SEQ ID No. 140). FIG. 14F shows both the deconvoluted scan spectra and the full scan spectra of the number of residues from FIG. 14E.

Figure 15:
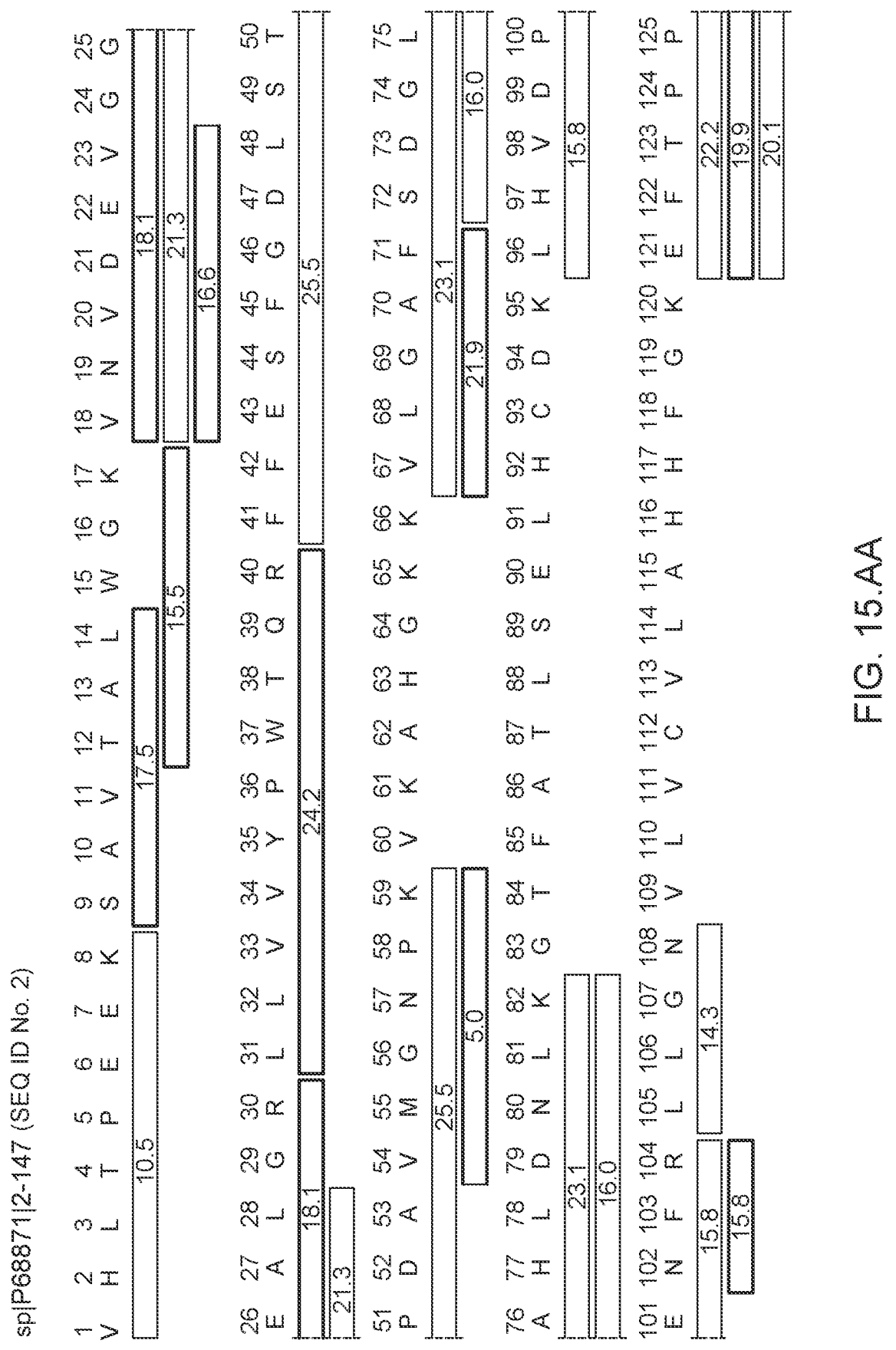
Figure 15C:
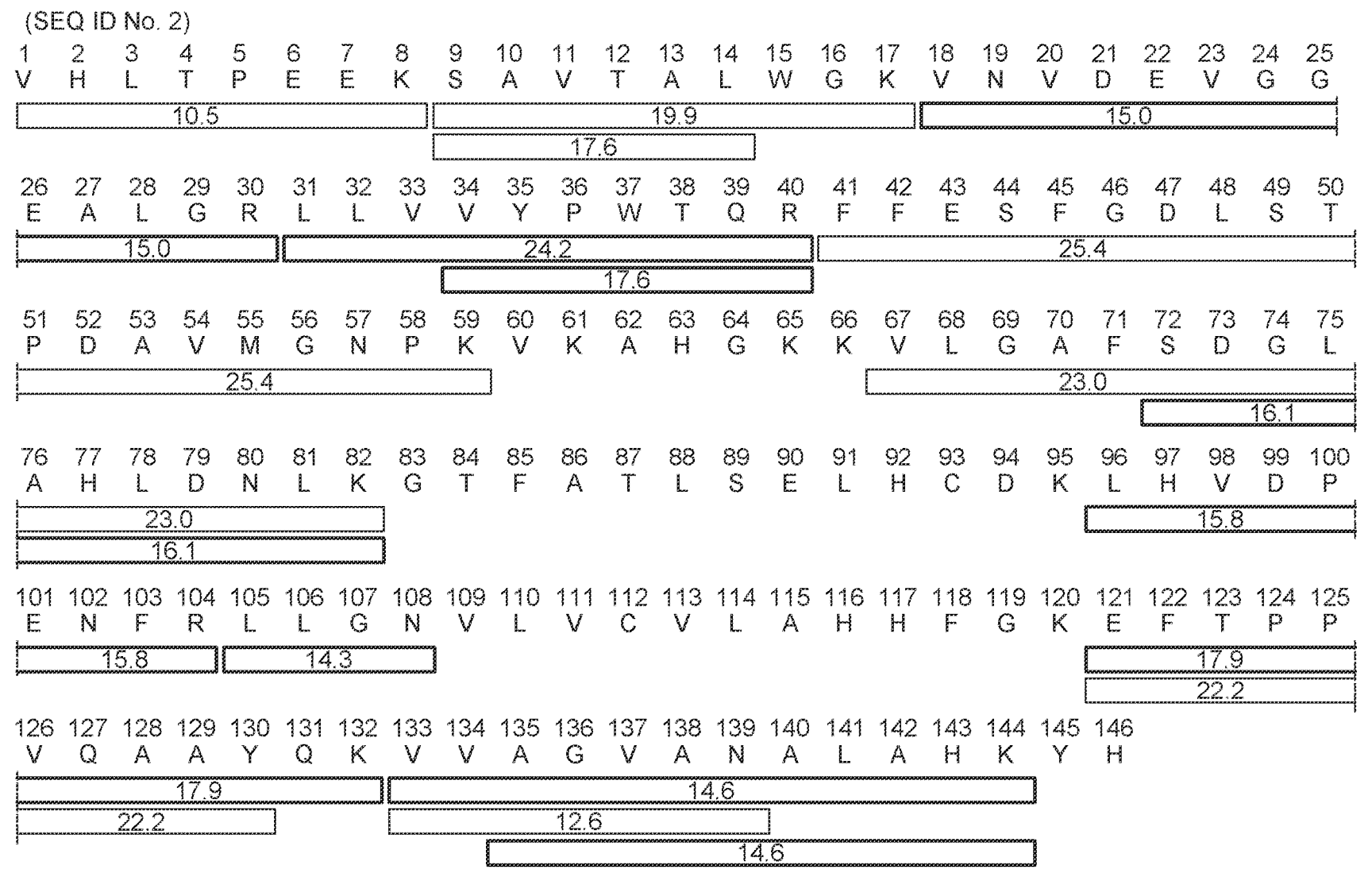

FIGS. 15AA-15F are mass spectrometry reports from three separate patients that illustrates that no glycations are found on hemoglobin subunit beta with between 75%-87% sequence coverage. FIGS. 15AA and 15AB show the sequence coverage map in which 75.3% of the hemoglobin subunit beta is reported (Seq. Id. No. 2). FIG. 15B shows the fragment coverage map in which the average structural resolutions is equal to 1.1 residues from the patient in FIG. 15AA. FIG. 15C shows the sequence coverage map from a separate female subject in which 76.7% of the hemoglobin subunit beta is reported (Seq. Id. No. 2).

FIGS. 16AA-16CD are a table representing the unique peptide sequences for the modified hemoglobin subunit alpha, including, the site of modification on the amino acid from the menstrual blood samples of multiple female subjects over a period. Seq. Id. Nos. 3-140 are shown in FIGS. 16AA-16CD.

FIGS. 17AA-17GD are a table representing the unique peptide sequences for five (5) additional modified biomarkers (Seq. Id. Nos. 141-886), including, the site of modification on the amino acid from the menstrual blood samples of multiple female subjects over a period. FIGS. 17AA-17GD serve as a proxy for the data for all other biomarkers.

FIG. 18A shows intact mass spectrum from the menstrual blood of a single female subject. FIG. 18B shows intact mass analysis from the female subjects menstrual represented in FIG. 18A as having an observed mass of −820 Da and an observed retention time of 36.21 minutes. FIG. 18C illustrates the unique peptide as ITPNLAEFAFSLYR (Seq. Id. No. 887). FIG. 18D shows intact mass spectrum from the menstrual blood of a single patient as different from the female subject in FIG. 18A.

FIG. 19A shows intact mass deconvoluted spectrum from the menstrual blood of a single female subject with 5.7% glutathionylation on hemoglobin subunit beta. FIG. 19B shows intact mass deconvoluted spectrum from the menstrual blood of a single female subject, separate from the female subject in FIG. 19A, with 12.1% glutathionylation on hemoglobin subunit beta. FIG. 19C shows intact mass deconvoluted spectrum from the menstrual blood of a single female subject, separate from the female subject in FIGS. 19A & 19B, with 6.3% glutathionylation on hemoglobin subunit beta. FIG. 19D shows intact mass deconvoluted spectrum from the menstrual blood of a single female subject, separate from the female subject in FIGS. 19A, 19B, 19C, with 8.2% glutathionylation on hemoglobin subunit beta.

FIG. 20A shows intact mass spectrum from the menstrual blood of a single female with 34 times glycated albumin. FIG. 20B shows intact mass spectrum from the menstrual blood of a single female subject, separate from the female subject in FIG. 20A, with 34 times glycated albumin.

DETAILED DESCRIPTION

Figure 1:
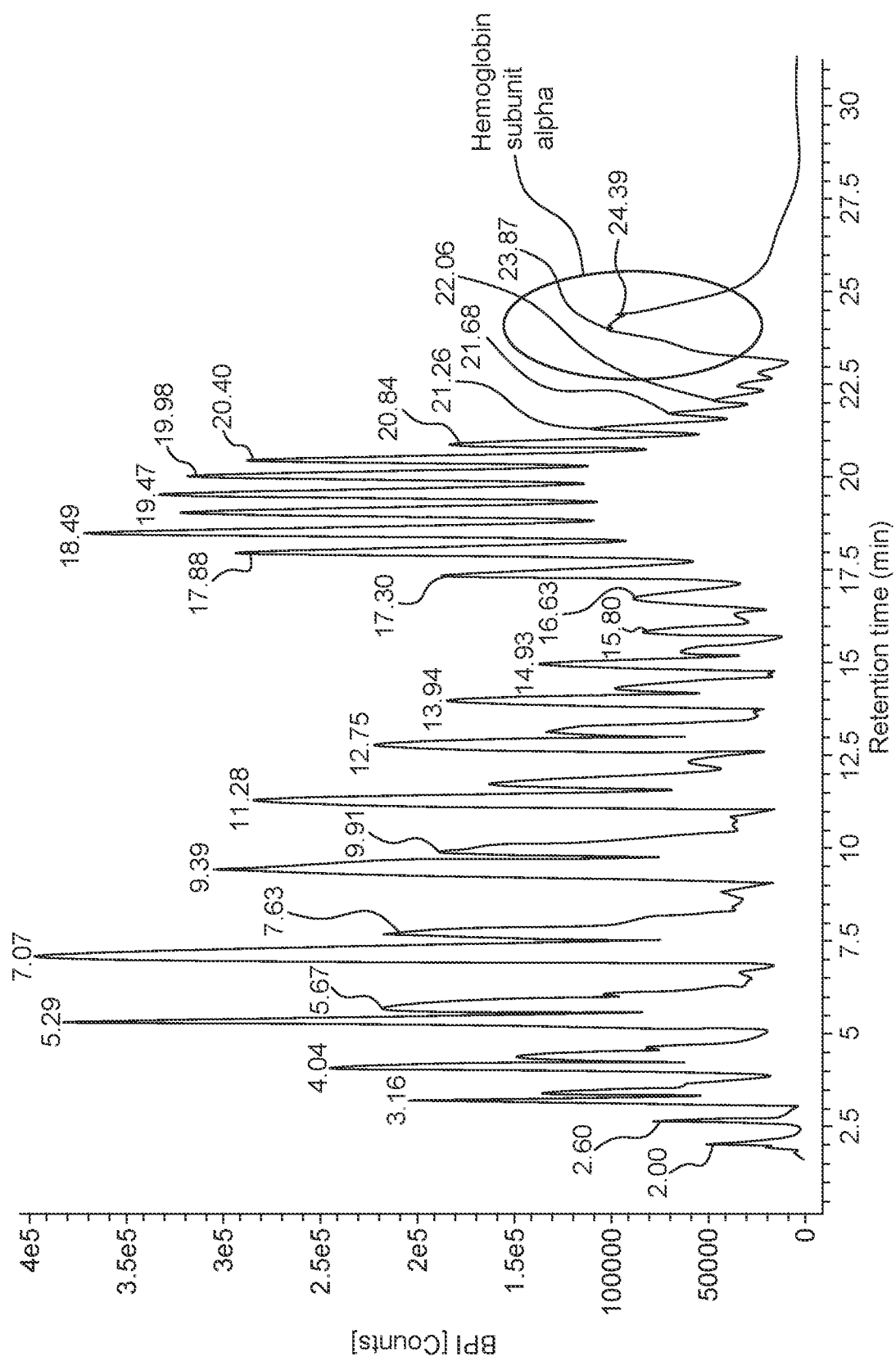
FIG. 1 is a graph showing intact mass spectrum of menstrual blood sample 1.
Figure 2:
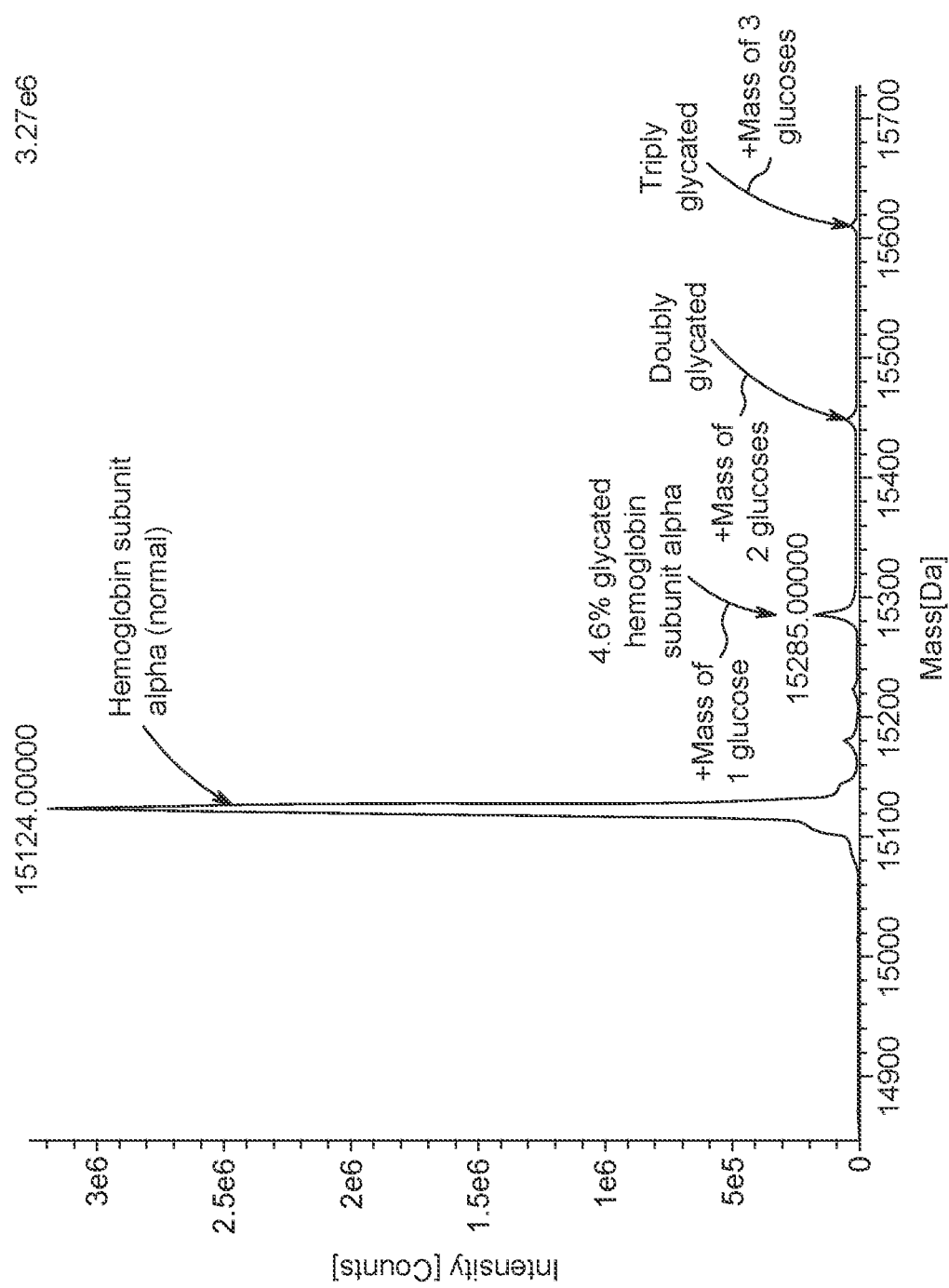
FIG. 2 is a graph showing deconvoluted hemoglobin subunit alpha with post translational glycation.
Figure 3:
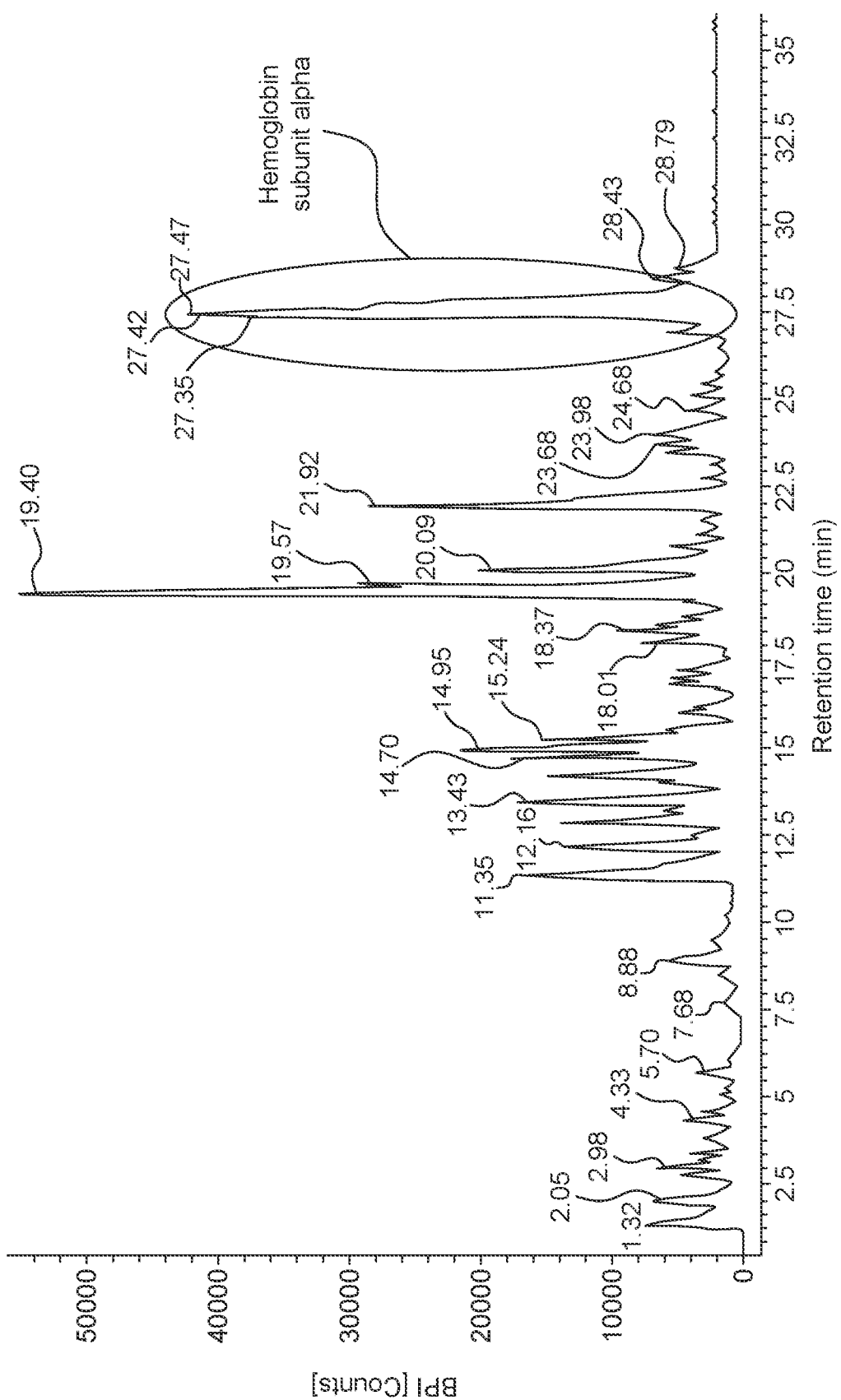
FIG. 3 is a graph showing intact mass spectrum of menstrual blood sample 2.
Figure 4:
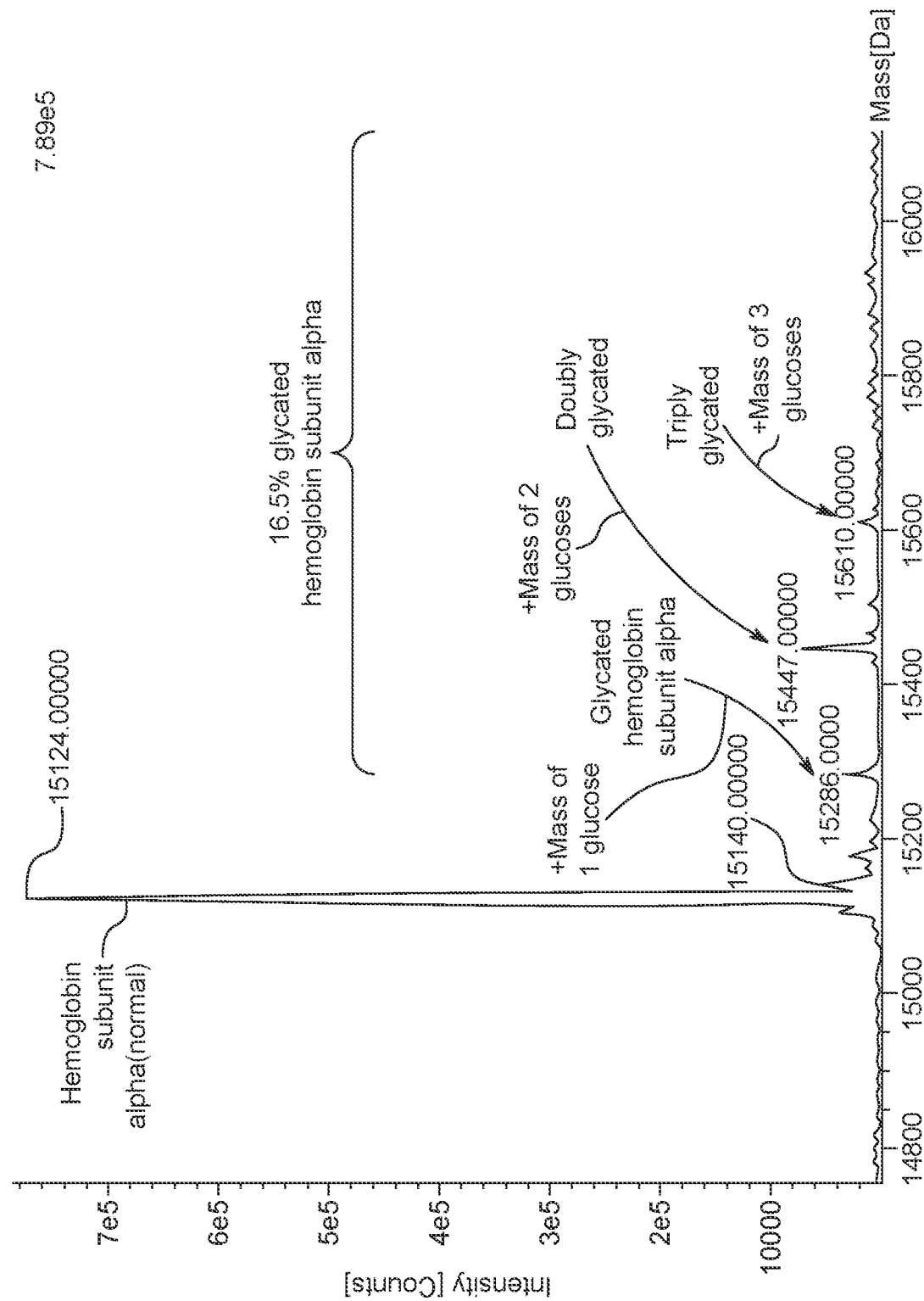
FIG. 4 is a graph showing deconvoluted hemoglobin subunit alpha with post translational glycation.

The genomic, proteomic and bio-informatic interplay has a central theme in disease progression and sex-bias that revolves around estrogen and cyclical spikes each month at menses.

The present invention is based, in part, on the discovery of novel detection systems and methods for detecting PTM's on proteins specifically, glycation, oxidation, carboxymethyl, deamidation and glutathionylation of the hemoglobin subunit a (alpha), alpha 1 antitrypsin, hemoglobin subunit beta, Lon protease homolog 2, peroxisomal, serotransferrin, peroxiredoxin-2, TANC1, Teashirt homolog 2, Glycodelin, FE65—Amyloid-beta A4 precursor protein-binding family B member 1, Albumin, and Bovine Casine. These unique methods described herein provide for a non-invasive and robust method of early and continuous detection of novel disease biomarkers for personalized medicine and patient stratification. The systems described herein solve the problem of early and easy detection, tracking, and treatment of women's diseases.

The presence of multiple PTM's on biomarkers in menstrual fluid are quite different from circulating blood. The menstrual cycle provides a unique and monthly trackable, yet non-invasive biopsy for menstruating women. Thus, monitoring menstrual fluid allows for the possibility of an easily assessed diagnosis of cancer, specifically, endometrial, breast and lung cancer, early detection of degenerative disease such as early on-set Alzheimer's and prediabetes, all with potentially global utility.

In addition to disease detection, the methods described herein allow for application of precision based on patient stratification techniques as well as selection biomarker usage. A new method of detecting biomarkers with multiple modification events, with positions on specific lysine residues is described herein. Novel modification patterns on proteins that appear to be unique to the blood found in menstrual fluid have been discovered.

The menstrual blood milieu presents an environment that can be analyzed quite differently than that from circulating blood. For example, the mean pH of the vagina is typically 4.0 to 4.5 during menstruation, rising slightly to blood's pH of 7.4 when menstrual blood is present. The exact effects of this unique environment on modified proteins in menstrual blood and the indications it may predict have previously gone uninvestigated without baseline studies such as those presented herein. Monitoring this information and correlating it to clinical information provides valuable data for diagnosis and/or treatment of patients in various states of disease progression, management and treatment.

In one aspect, the method comprises the steps of obtaining a sample of a human female's menstrual fluid, separating the proteins of the menstrual fluid, detecting protein profiles, identifying individual proteins, and elucidating biomarkers. Proteins can be positively identified from a complex menstrual fluid sample (e.g., dried menstrual fluid) through MS analysis. Unique post-translational modifications (e.g., advanced glycation events) can also be observed on the proteins that compare with standard tests for monitoring disease.

The proteins of the menstrual fluid can be collected using any commercially available blood sampling device that provides a consistent, uniform, and rapid collection of fluid. Health profiles are completed by all patients and where applicable and possible, patient medical records, health tracking device data, etc. will be included. Samples are collected in the patient's home according to LSH's Collection Protocol using EBF-Inc.'s 903 dried blood spot (DBS) collection device. Up to one-hundred and fifty microliters (150 uL) of menstrual blood is collected.

A multitude of proteins can be detected from the processed menstrual fluid including but not limited to, actin-binding, albumin, chaperone proteins, enzymes, antibodies, ribosomal proteins, structural proteins, transcription factors, and hemoglobin, using, for example, LC-MS/MS peptide sequencing.

The analyzation of unique modifications that have not been detected by current techniques are outlined herein.

First, the observed mass of the proteins is matched against its intensity output (e.g. mass-to-charge (mlz) ratio) versus intensity (e.g. current generated from multiplier) which generates the mass spectrum. The presence of ions are identified in a particular mass which enables the count of all amino acids in a protein element to be identified. The difference in peaks of these amino acids provide a residue in which we can compare masses with standard weights of amino acids to identify the presence of modification in different molecular samples. Through this process the ability to analyse biomarkers is achieved in order to gain overall health knowledge of the patient for example, presence of certain amino acids are related to human disease which ultimately points out the protein causing the disease.

Once analysed, precision medicine can be applied using a 1, 2, or 50 or more combined biomarkers per female subject to both early detect various diseases as well as apply treatment in a more precise manner to female patients. As described herein, each protein represents a single biomarker and a combination of biomarkers can be combined to provide more accurate measures including, diagnosis, prognosis, patient stratification and/or precision medicine.

In one aspect, hemoglobin and its subunits are detected. Post-translation modifications (e.g., glycation, glutathionylation) are detected during protein profiling experiments. For example, PTMs and hemoglobin identifications may be observed based on mass. Without wishing to be bound by theory, glutathionylation may be observed as a result of oxidative stress and/or glycation may be observed when high concentrations of sugars are present in the menstrual fluid sample. In some aspects, multiple glycation events (e.g., 1 to 4 or more events) are observed on the alpha subunits of hemoglobin.

In one aspect, PIP5K1a is detected, specifically observing the LEVAESEFTH peptide sequence (Seq. Id. No. 888) consistently. Increases in PIP5K1a in blood increase the risk of cancer due to cell proliferation, survival, invasion (Citation doi:10.1073/pnas.1107808109), and creation of invododia (Citation https://doi.org/10.1111/j.1349-7006.2010.01574.x). In addition to identification of PIP5K1a, post-translational modifications have been identified, including, but not limited to, glycyl lysine isopeptide at position 103 and phosphoserine at position 486. In one aspect, GRP-78 is detected and observed in (nine) 9 unique, reproducible, peptides.

Increases in this protein in blood are consistently linked to breast cancer, endometrial cancer, familial breast and ovarian cancer and pre-eclampsia. PTM's reported, including, but not limited to, Signal peptide—between positions 1 and 18; Polypeptide chain between positions 19 and 654; Modified residue at positions 86, 125, 160,213, 326, 353, 447, 518, 585, 591, 643 and 648; Cross-link at positions 352 and 353.

In one aspect, alpha 1 antitrypsin is detected. In two separate patients, alpha-1 antitrypsin, is detected by monitoring a characteristic peptide, observed in a range from 0.0166% to 0.047% of total peptide detected. In the first patient, 12 unique peptide sequences were matched in which one was confidently followed as ITPNLAEFAFSLYR (Seq. Id. No. 887) and exhibits 0.047% of entire peptide content analyzed in sample. In the second patient, 15 unique peptide sequences were matched in which one was confidently followed as ITPNLAEFAFSLYR (Seq. Id. No. 887) and exhibits 0.0166% of entire peptide content analyzed in sample. In one aspect, hemoglobin subunit beta is detected. Post-translation modifications (e.g. glutathionylation) are detected during protein profiling experiments. 28% of patient samples demonstrated modifications and 19 unique peptide sequences.

In one aspect, Ion protease homolog 2, peroxisomal is detected. In some aspects, upregulation is observed as a result of linkage to poor prognosis in cancer patients and tumor growth. Observed with one unique peptide sequence in seven samples.

In one aspect, serotransferrin is detected in 42% of patients with 14 unique peptide sequences and a signal peptide position of 1-19 and chain positions 20-698.

In one aspect, peroxiredoxin-2 is detected with four unique sequences and PTM's such as: Initiator methionine; Polypeptide chain—between positions 2 and 198; Modified residue at position 2, 112 and 182; Disulfide bond at position 51 and 172.

In one aspect, TANC-1 is detected in 57% of patients with three unique sequences and PTM's such as: Phosphorylated by MINK1 and TNIK upon stimulation by RAP2A.

In one aspect, teashirt homolog 2 is detected in 29% of patients with four unique sequences.

In one aspect, glycodelin is detected with four unique sequences and PTM's on signal peptide—position 1-18 and Glycosylations at positions 46 and 81; Disulfide bonds between positions 84 and 178 and between positions 124 and 137; Four distinct glycoforms A, C, F and S arise from different N-linked oligosaccharide chains at amino acid residues Asn-46 and Asn-81.

In one aspect, FE65-amyloid-beta A4 precursor protein-binding family B member 1 is detected with PTM's on polypeptide chain between positions 1 and 710; Modified residue at positions 517, 547 and 610.

In one aspect, albumin is detected with PTM's on Signal peptide positions 1-18; Propeptide 19-24; Glycosylations positions 36, 75, 161, 186, 223, 249, 257, 300, 305, 337, 341, 342, 347, 375, 402, 437, 463, 468, 518, 549, 558, 560, 569, 597 (plus additional reported). Disulfide bonds between positions: 77-86, 99-115, 114-125, 148-193, 192-201, 224-270, 269-277, 289-303, 302-313, 340-385, 384-393, 416-462, 461-472, 485-501, 500-511, 538-583, 582-591; Modified amino acid residues: Phosphoserine positions 29, 82, 89, 297, 443, 513; Phosphothreonine positions 107, 444, 446; N6-succinyllysine positions 229, 460, 543, 588; N6-methyllysine position 558.

In various embodiments, the present methods provide for protein combinations based on unique signatures based on PTM's found in menstrual blood that can be applied to improve personal healthcare and/or health decisions. Such protein profiling based on unique signatures found in each female patient is used to form a more complete subject's health history than standard point of care testing.

In one aspect, the method of detecting modified proteins and novel biomarkers in a female patient, comprises obtaining a menstrual fluid sample from a human female patient; and detecting whether modifications are present in the menstrual fluid sample by using LC-MS/MS peptide sequencing and analyzation techniques.

In various embodiments, the application of precision medicine is applied by using the female biology as the method of diagnosing various diseases and treating the female patient, which comprises obtaining a menstrual fluid sample from a human female patient; by first stratifying the patient based on the number of glycation of hemoglobin alpha subunit present in the menstrual fluid sample by using LC-MS/MS peptide sequencing; diagnosing the patient with disease when the presence of a set number of proteins and modification events in the menstrual fluid sample are detected; alerting patient to a lifestyle change and/or prompting the administering of an effective amount of medication to the diagnosed patient.

In one aspect, the method of diagnosing prediabetes and/or diabetes in its nascent stage in a female patient, comprises obtaining a menstrual fluid sample from a human female patient; detecting whether glycation of hemoglobin alpha subunit is present in the menstrual fluid sample by using LC-MS/MS peptide sequencing; and diagnosing the patient with prediabetes and/or diabetes when the presence of a set number of glycation events in the menstrual fluid sample is detected; alerting patient to a lifestyle change and/or prompting the administering of an effective amount of insulin to the diagnosed patient.

In one aspect, the method of diagnosing well characterized liver and/or lung disorders in its nascent stage in a female patient, comprises obtaining a menstrual fluid sample from a human female patient; detecting whether post translational modifications on Alpha 1-Antitrypsin are present in the menstrual fluid sample by using LC-MS/MS peptide sequencing; and diagnosing the patient with liver and/or lung disorders when the presence of a set number of modification events in the menstrual fluid sample are detected; alerting patient to a lifestyle change and/or prompting the administering of an effective amount of medication to the diagnosed patient.

In one aspect, the method of diagnosing any early stage disease and/or providing prognosis in a female patient, comprises obtaining menstrual fluid sample from a human female patient; detecting whether post-translational modifications are present in the menstrual fluid sample by using LC-MS/MS peptide sequencing;

In one aspect, the method of diagnosing overall health in a female patient, comprises obtaining a menstrual fluid sample from a human female patient; detecting whether glycation of hemoglobin alpha subunit is present in the menstrual fluid sample by using LC-MS/MS peptide sequencing; stratifying the patient based on the presence of a set number of glycation events in the menstrual fluid is detected; and assigning the patient into a category when the presence of a set number of glycation events in the menstrual fluid sample is detected; alerting patient to a lifestyle change and/or prompting the diagnosis of latent disease, potentially at risk of exacerbation, and/or prompting of an reevaluation of effective amount of medication to the diagnosed patient. As used herein, a category is defined by the number of hemoglobin subunit alpha modifications present in the female subject's menstrual blood. Categories may also be confirmed by the number of modifications on other proteins present in the female subject's menstrual blood. Categories are numerically assigned and each subject within a category has specific and similar attributes related to the biological health of the female subjects in each category. For instance, a category of one, subjects will be dosed in similar quantities for medications as compared to other categories in which the dosing may be more or less. In some aspects, category assignments will rate the risk of future and current disease exacerbation within female subjects of that category. For instance, a category of four, subjects will be of higher risk for increased disease progression, as compared to a category one, in which female subjects will have a lower risk of disease progression.

In one aspect, the application of precision medicine is applied by using the female biology as the method of diagnosing and treating pre-diabetes and/or diabetes in a patient, comprises obtaining a menstrual fluid sample from a human female patient; detecting whether glycation of hemoglobin alpha subunit is present in the menstrual fluid sample by using LC-MS/MS peptide sequencing; diagnosing the patient with diabetes when the presence of a set number of glycation events in the menstrual fluid sample is detected; alerting patient to a lifestyle change and/or prompting the administering of an effective amount of insulin to the diagnosed patient.

In various aspects, the application of precision medicine is applied by using the female biology as the method of diagnosing early stage disease in a patient, comprises obtaining a menstrual fluid sample from a human female patient; detecting whether protein modifications are present in the menstrual fluid sample by using LC-MS/MS peptide sequencing; diagnosing the patient with disease when the presence of a set number of modification events in the menstrual fluid sample are detected; alerting patient to a lifestyle change and/or prompting the administering of an effective amount of medication to the diagnosed patient.

In various embodiments, the present methods provide for repeated sampling of a female subject's menstrual fluid to allow for an accumulation of data over a period of weeks, months or years. Such data is used to form a more complete subject's health history than standard point of care testing. As described herein, such data allows for an improvement in personal healthcare and/or health decisions.

Also, in some embodiments, the present invention provides for a non-invasive method of monitoring one's health. For example, in various embodiments, the collection of menstrual fluid provides biomarker information (e.g., glycation and glutathionylation of hemoglobin subunit alpha) without the need for blood draws, etc. In some embodiments, the present methods allow for long term health monitoring without various deleterious side effects of standard monitoring including, by way of illustration, excessive bleeding, fainting, lightheadedness, hematoma, infection, pricking or stinging sensations, bruising, pain, throbbing, etc. In some embodiments, the non-invasive nature of the sample collection improves patient compliance and allows for a more complete set of data.

In various embodiments, the evaluation informs a healthcare provider to provide improved health care and/or informs the female subject to make improved health decisions. For example, subtle alterations (e.g., glycation and glutathionylation of hemoglobin subunit alpha) in one or more disease- or health-related biomarkers over time, away from a normal level, may provide an earlier indication of a disease or disorder than a test at a single point of time (including, by way of non-limiting example, at a point of care) test and before symptoms arise. Further, the repeated evaluations of the present methods allow for early detection of a disease or disorder as the evaluation is not driven by a symptom or sign on the subject part.

For instance, the repeated evaluation of menstrual fluid allows for increased healthcare vigilance and largely eliminates the need for reactive medical interventions. In some embodiments, the subject has a chronic disease such as diabetes and the state (e.g., controlled or uncontrolled) is monitored over time.

In some embodiments, the evaluation comprises any one of diagnosis, prognosis, and response to treatment. Diagnosis refers to the process of attempting to determine or identify a possible disease or disorder. Prognosis refers to the predicting of a likely outcome of a disease or disorder. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment (e.g. response to a therapeutic agent). Responses to treatment can be, by way of non-limiting example, pathological complete response, survival, and remission.

In various embodiments, the present invention pertains to the generation of a long term health history record that informs care. Accordingly, in various embodiments, the menstrual sample is obtained periodically. In some embodiments, the menstrual sample is obtained on a regular basis. For instance, sampling may occur about once every month, or about once every other month, or about once every 3 months, or about once every 6 months, or about once every 9 months, or about once every year. In some embodiments, about 1 to about 12, or about 2 to about 10, or about 3 to about 8 samples are evaluated per year.

Furthermore, in some embodiments the present methods are repeated long term to generate a large data set. For example, in some embodiments, the evaluation is repeated for about 3 months, or about 6 months, or about 9 months, or about 1 year, or about 2 years, or about 3 years, or about 4 years, or about 5 years, or about 6 years, or about 7 years, or about 8 years, or about 9 years, or about 10 years, or about 20 years, or about 30 years, or about 40 years, or about 50 years.

In various embodiments, the female subject's biomarker information (e.g., glycation and glutathionylation of hemoglobin subunit alpha) provides baseline health information, as well as long term and short term trends in biomarker levels. In various embodiments, the baseline or trend health information is used to compare to a biomarker measurement at a single point in time (e.g. at the point of care). Accordingly, in some embodiments, the present methods prevent or mitigate incorrect or missed diagnosis. In various embodiments, the present methods allow for one or more of reducing or eliminating unnecessary medical care visits, reducing or eliminating unnecessary diagnostic tests, reducing or eliminating unnecessary administration of therapeutic agents, improving the selection of appropriate diagnostic tests, and improving the selection of appropriate therapeutic agents.

In various embodiments, the present invention relates to various disease- or health-related biomarkers that are available in menstrual fluid. For example, the present invention provides for disease- or health-related biomarkers for which long term data is desirable. Further, in some embodiments, the disease- or health-related biomarkers of the present invention are those which are hindered by inconsistency when measured in a single point of time (including, by way of non-limiting example, at a point of care) scenario. Further still in some embodiments, the present disease- or health-related biomarkers include those which are surrogates for slowly developing and/or relatively symptom-free and/or chronic diseases.

In various embodiments, the evaluation is of glycation and glutathionylation of hemoglobin subunit alpha and is useful to screen for, diagnose, and monitor diabetes and pre-diabetes. For instance, a female subject at risk for type II diabetes may have repeated evaluation of these disease- or health-related biomarkers and such readings may direct lifestyle changes (e.g. increased exercise, improved diet) and/or treatments to avoid an onset or worsening of diabetes (e.g. administration of metformin to control blood glucose levels).

Further, the present methods, at least in situations of relatively controlled blood glucose, obviate a need for inconvenient blood glucose monitors that suffer from poor patient compliance due to, in part, their invasiveness (e.g. monitors requiring finger pricking for blood sampling). In some embodiments, the present methods show a gradual increase in glycation and glutathionylation of hemoglobin subunit alpha and allow for lifestyle changes or medical intervention to prevent, for example, the evaluation from normal to pre-diabetes or pre-diabetes to diabetes. Further, it is suggested that diabetic subjects maintain an HbA1c level of less than about 7% and the present methods allow for a non-invasive manner to monitor this. For example, if the periodic evaluations show HbA1c levels rising to 7% or above, medical intervention of lifestyle change may be ordered to mitigate detrimental effects (e.g. increased likelihood or onset of one or more of eye disease, heart disease, kidney disease, nerve damage, and stroke).

The methods described herein allow for the personalized and routine monitoring of menstrual fluid that could lead to the early detection and treatment of disease.

Assays

In one aspect, the invention relates to an assay (e.g., a diagnostic assay). The assay may utilize mass spectrometry to identify biomarkers and other major proteins (e.g., hemoglobin).

The assay described herein is capable of documenting multiple glycation events on the alpha subunits of hemoglobin. This stands in unique juxtaposition to the standard test for diabetes management, the HbA1c, which measures the concentration of singly glycated beta subunits of hemoglobin.

Intact mass analysis may be used to identify the alpha and beta subunits of a protein such as hemoglobin. Detailed analysis of the hemoglobin samples may show one or more glycations of alpha subunit, for example 1, 2, 3, 4, or more glycations, 1 to 4, 1 to 3, or 2 to 4 glycations may be observed. This assay may serve as a diagnostic assay for disease (e.g., diabetes) with routine testing of menstrual blood, or may serve as an assay for pre-diagnosis of diseases such as pre-diabetes and/or diabetes.

In some embodiments, the present invention relates to a device for collection of a female subject's menstrual fluid sample and uses thereof. In some embodiments, the device is a disposable cartridge which may be inserted into a wireless enabled device. In various embodiments, the device is a home instrument. In various embodiments, the device is operated by the patient, without the need for intervention by a medical professional.

Accordingly, in various embodiments, the patient is spared the inconvenience of scheduling an appointment in a medical clinical and may be able to institute sample collection at her convenience and without scheduling delays.

In various embodiments, the device is or comprises a sampling implement that provides a means to collect a sample from a subject. The sampling implement may be connected to a collection chamber via a sampling implement holder. In some embodiments, the sampling implement is disposed at the distal end of a shaft, which shaft can be solid, hollow or semi-permeable. In some embodiments, the sampling implement is a swab, a comb, a brush, a spatula, a rod, a foam, a flocculated substrate or a spun substrate.

In various embodiments, the device is associated with and/or integrated into one or more of a tampon, pad (menstrual napkin) or menstrual cup (see, e.g., International Patent Publication Nos. WO/2002/080827 and WO/2006/058409, the contents of which are hereby incorporated by reference).

In various embodiments, the collection of menstrual fluid may take place on one of the heaviest days of the donor's menstrual period which may be the first or second day. In various embodiments, the general area around the vagina may be cleansed with an aseptic cleaning pad prior to collection.

In various embodiments, a single sample or multiple samples may be collected. The sample or samples may be maintained at room temperature (about 15° C. to about 25° C.). In various embodiments, samples may be shipped to a laboratory so long as the sample or samples arrive at the laboratory within about 24 hours to about 72 hours of collection. Alternatively, samples may be refrigerated at about 1° C. to about 10° C.

In various embodiments, the sample may be subjected to centrifugation and either the supernatant or pellet may be analyzed.

In some embodiments, the present methods comprise contacting an agent that specifically binds a biomarker (e.g., glycated hemoglobin) with the menstrual sample. For example, such an agent may be an antibody. Illustrative, but non-limiting methods for evaluation include one or more of immunohistochemical staining, western blotting, in cell western, immunofluorescent staining, ELISA, and fluorescent activating cell sorting (FACS), or any other method described herein or known in the art.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, N Y, 1988), Harlow et al. (Using Antibodies, A Laboratory Manual, Cold Spring Harbor Laboratory, N Y, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the VL, VH, CL and CH domains; a F(ab)2 fragment, a bivalent fragment including two Fab fragments linked by a disulfide bridge at the hinge region; a Pd fragment consisting of the VH and CH domains; a Fv fragment consisting of the VL and VH domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

A person skilled in the art will appreciate that a number of methods can be used to detect or quantify the DNA/RNA levels of various disease- or health-related biomarkers (e.g., hemoglobin).

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP.

A person skilled in the art will appreciate that a number of methods can be used to detect or quantify the level of RNA products of the disease- or health-related biomarkers within a sample, including arrays, such as microarrays, RT-PCR (including quantitative PCR), nuclease protection assays and Northern blot analyses.

In various embodiments, the female subject is menstruating and thus generating sample for evaluation. In some embodiments, the female subject is non-menopausal or recently menopausal. In some embodiments, the female subject may be repeatedly evaluated until pregnancy and resume evaluation post-partum. In these embodiments, the female subject may be monitored for post-partum complications. For instance, the pre-pregnancy data may be used in comparison with post-partum data to monitor a restoration of pre-pregnancy health baselines.

In some embodiments, the female subject has an age in a range of from about 13 years to about 60 years. In some embodiments, the female subject is about 10 years old, or about 15 years old, or about 20 years old, or about 25 years old, or about 30 years old, or about 35 years old, or about 40 years old, or about 45 years old, or about 50 years old, or about 55 years old, or about 60 years old, or about 65 years old.

EXEMPLIFICATION

The following results are applicable to any of the other proteins and/or combination of proteins and modifications described herein.

Example 1-Mass Spectrometry Based Assay

Menstrual blood was analyzed for biomarkers using a shot gun proteomics approach. Eleven major proteins were identified and list above. By intact mass analysis, we were able to identify unique modifications to the 11 proteins. Upon detailed analysis of certain modifications such as the hemoglobin samples, we observed multiple glycations of the alpha subunit (1-4 glycans observed) in at least 389 patient samples. In comparison to a glycated hemoglobin control, we only observed glycation on the beta subunit and only a single glycation on the alpha subunit. Thus, the observation of the alpha-subunit of glycation was a unique finding in menstrual blood, in addition to the several other unique findings described herein. Glutathionylation on subunit beta of hemoglobin was also observed in at least 40 patient samples. Glutathionylation is sometimes seen in diabetic patients with microangiopathy.

Example 2-Immunological Assay for Biomarker Quantitation in MB

After identification of the modified proteins, we digested the protein using enzymes and subjected it to peptide mapping and post-translational analysis using mass spectrometry. The discovery of modified proteins are unique finds (described above), and further identification of the exact sites of modifications was used in a separate process described herein.

This procedure was employed to identity the location of particular modification events on 130 proteins, found in the menstrual fluid sample. Using this method, multiple specific locations of modification were identified.

Extraction of menstrual fluid from collection paper: Menstrual fluid-soaked filter paper portion (a spiral 6 cm in diameter) was extracted with 200 ul of 100 mM ammonium bicarbonate in a 1.5 ml Eppendorf tube. It was shaken at room temperature, 1000 RPM for 45 min.

Trypsin digest: 20 ng of lyophilized trypsin was prepared by adding 20 uL of buffer solution and mixing by pipetting. This solution was added to 20 uL of sample and incubated for 2 hours at 37 C. This samples was then subjected to MS/MS analysis.

Glu-C digest: 10 ng of lyophilized Glu-C was prepared by adding 10 uL of buffer solution and mixing by pipetting. This solution was added to 10 uL of sample and incubated for 2 hours at 37 C. This samples was then subjected to MS/MS analysis.

UPLC-MS method: Samples were separated on a C-18 reverse phase column over the course of 90 minutes. They were then injected into the ESI-Q-Tof Mass Spectrometer using standard parameters for MS analysis. The mass spec data collected in an entire sample run was analyzed via the UNIFI software package.

Data interpretation: All MS/MS peptide fragmentation data was interpreted using UNIFI software. Identification of peptide fragments containing K-linked modified events were identified and cross matched between the alternative digest methods.

Following the identification of proteoform(s) of interest using bottom-up and top-down MS proteomics workflows, we develop highly sensitive immunological assays for simple quantitation in MB.

To accomplish this, using the process described herein, a full protein purification regimen was used to isolate the proteoform(s) in sufficiently high concentrations for polyclonal antibody production. The exact steps of the regimen are informed by the results of each proteomics study but might include: size exclusion chromatography (SEC), ion exchange chromatography (IEC), preparative high-performance liquid chromatography (HPLC), isoelectric focusing (IEF), and/or affinity chromatography techniques (e.g. lectin affinity chromatography for glycosylated proteins).

After the proteoform(s) of interest are isolated in sufficient purity as determined by MS and quantities (~250-1000 µg), using standardized custom animal monospecific antibody production protocols offered by an assortment of companies such as Thermo Fisher Scientific (Waltham, MA), Abzena (Cambridge, UK), and GenScript (Piscataway, NJ), are used.

Monospecific antibody production is tailored to target proteoform-specific post-translational modifications to ensure singular binding of the developed antibody to the proteoform of interest in situ (aberrant post-translational modifications, such as glycosylation, have been well characterized in some cancer types). Finally, custom antibodies are chemically or enzymatically labelled as necessary for detection purposes (via colorimetry or fluorometry) in the immunological assay. The resulting assay is designed to be highly specific, easy-to-use, and produce rapid quantitative results.

Performance of developed assays through parallel ultra-high resolution mass spectrometry/ion mobility studies.

An antibody raised to the modified peptide on the protein will serve as a robust, inexpensive, diagnostic assay for reliable biomarkers for detection of disease, stratification, and assay kit(s).

Example 3-Glycated Hemoglobin Standard Analysis

This example shall be used as proxy for all proteins and modifications described herein as applying to all industry standard tests for various diseases and the usage of selection biomarkers.

The ability to observe multiple glycation events on menstrual fluid hemoglobin could be a promising diagnostic for prediabetes, as poor control of blood sugar would lead to such glycation events.

The goal of this experiment was to determine the position of the glycation events. For comparison, authenticated 96% natural HbA1c sample (abeam ab98306) was obtained and compared with a fingerpick sample from a patient. Under LC-MS conditions, separate alpha and beta subunits were observed. The hemoglobin A1e is a native protein and prepared from packed red blood cells, the protein arrives intact. The tetramer molecular weight was ~64 KDa, consisting of four subunits of approximately 16 KDa each. Analysis showed that this standard exhibited a level of 5.88% glycated hemoglobin subunit alpha. No signs of multiple glycation sites were observed. It also exhibited 95.4% glycated subunit beta, as authenticated.

Figure 5A:
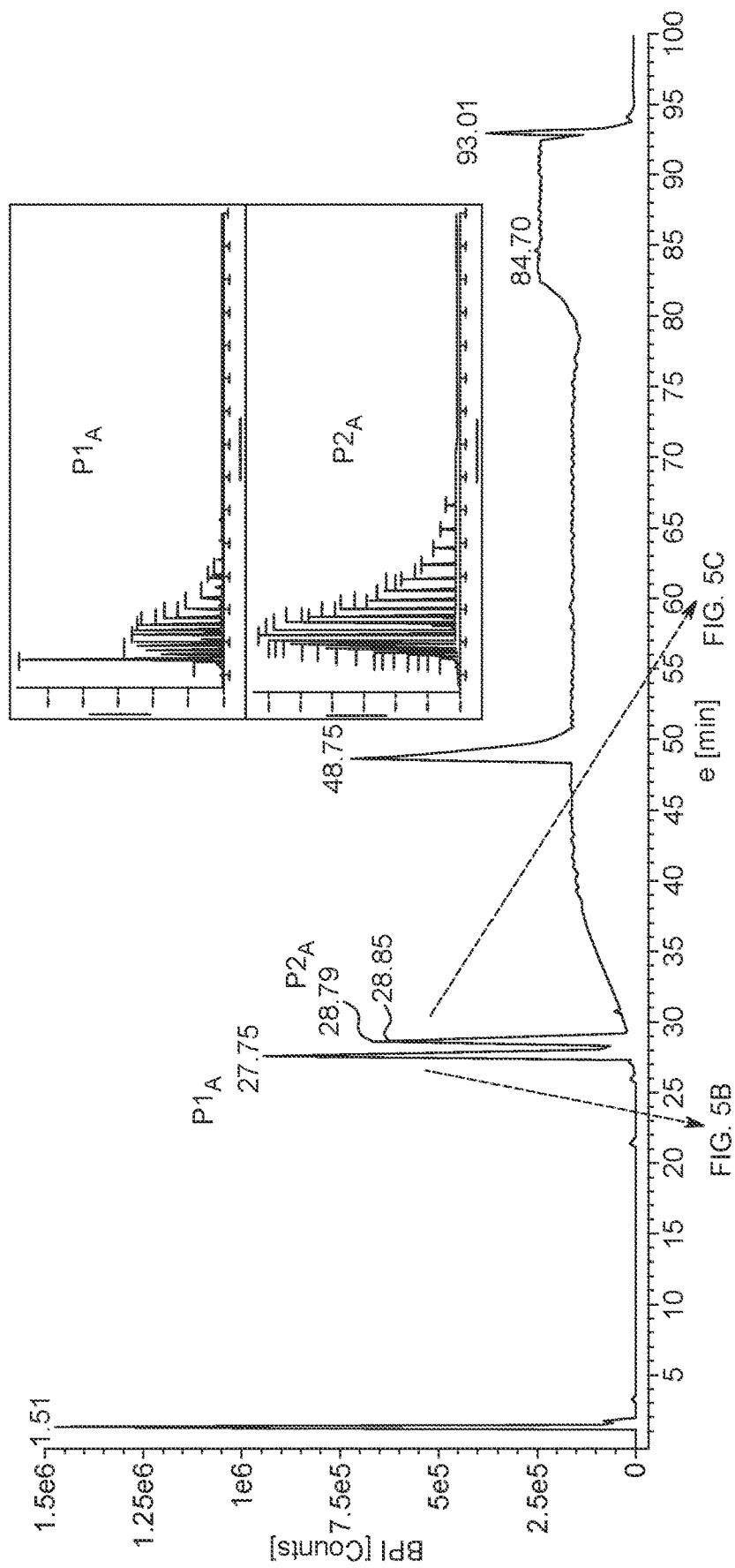
FIGS. 5A-5C are graphs illustrating the analysis of hemoglobin Ale standard (96%).
Figure 5B:
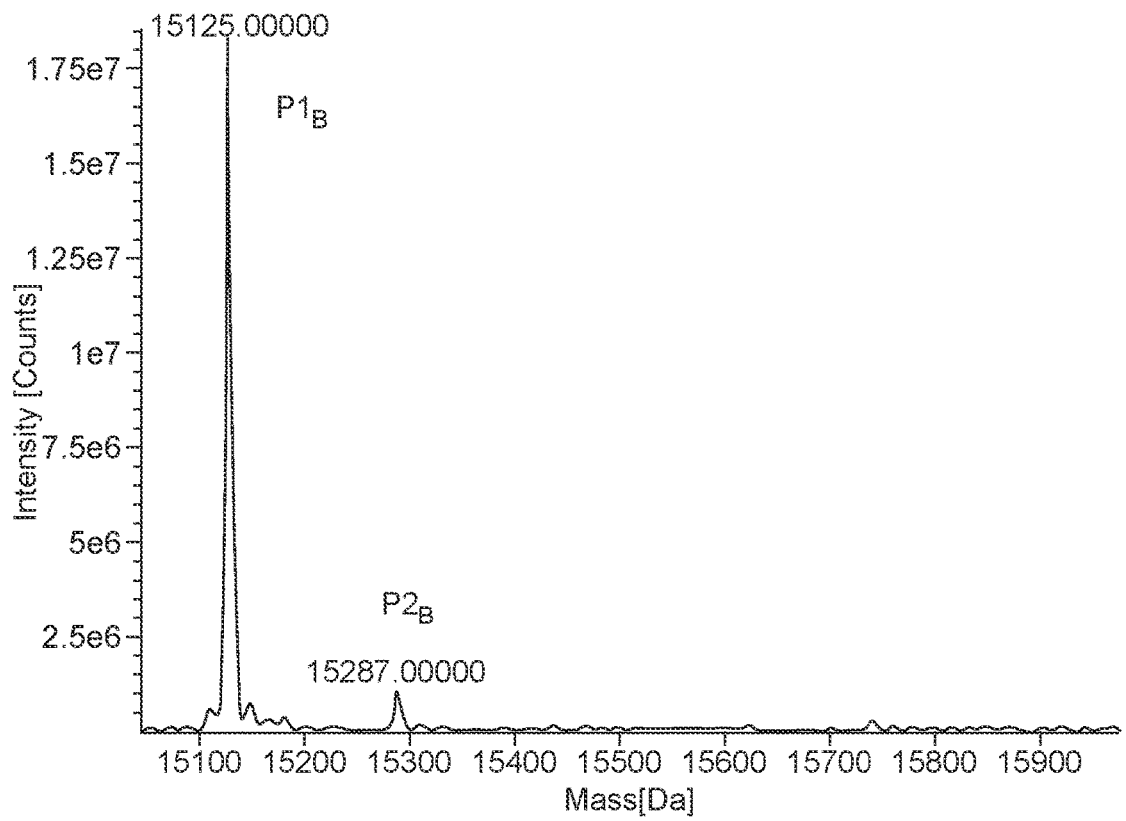
Figure 5C:
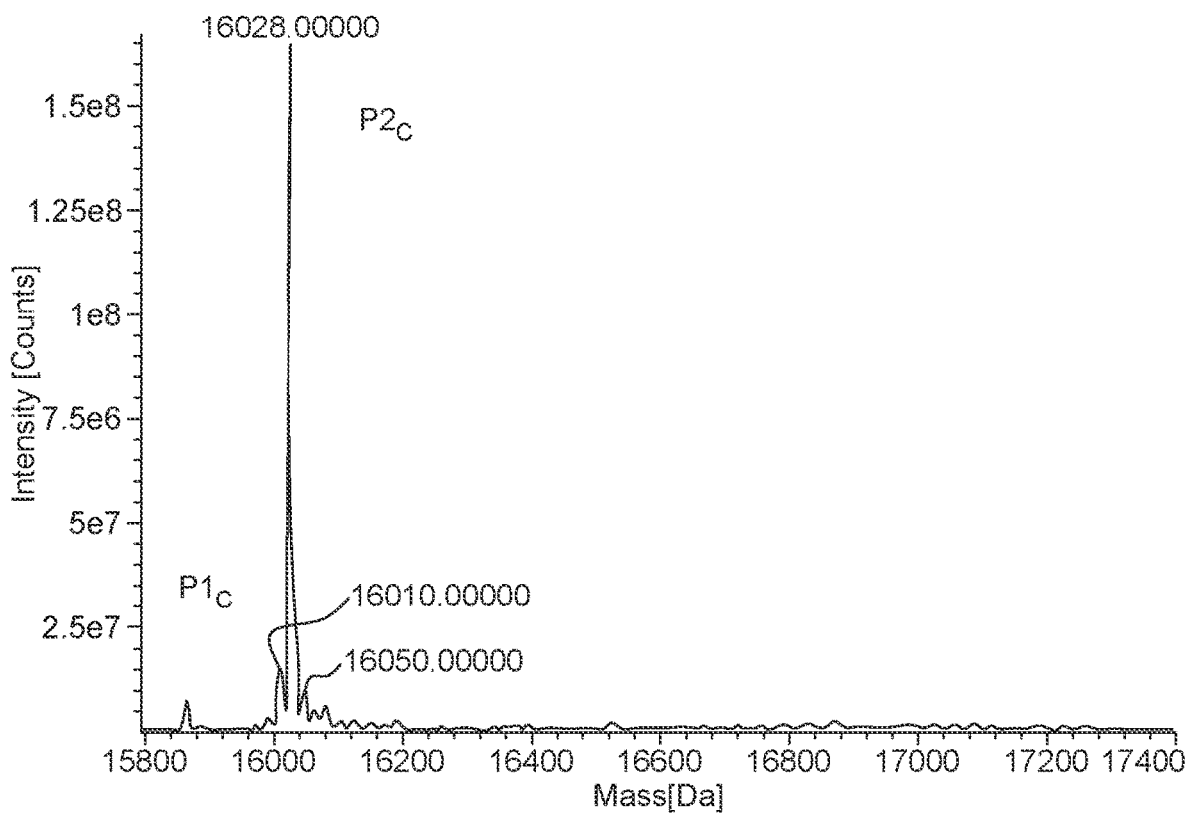
Figure 6A:
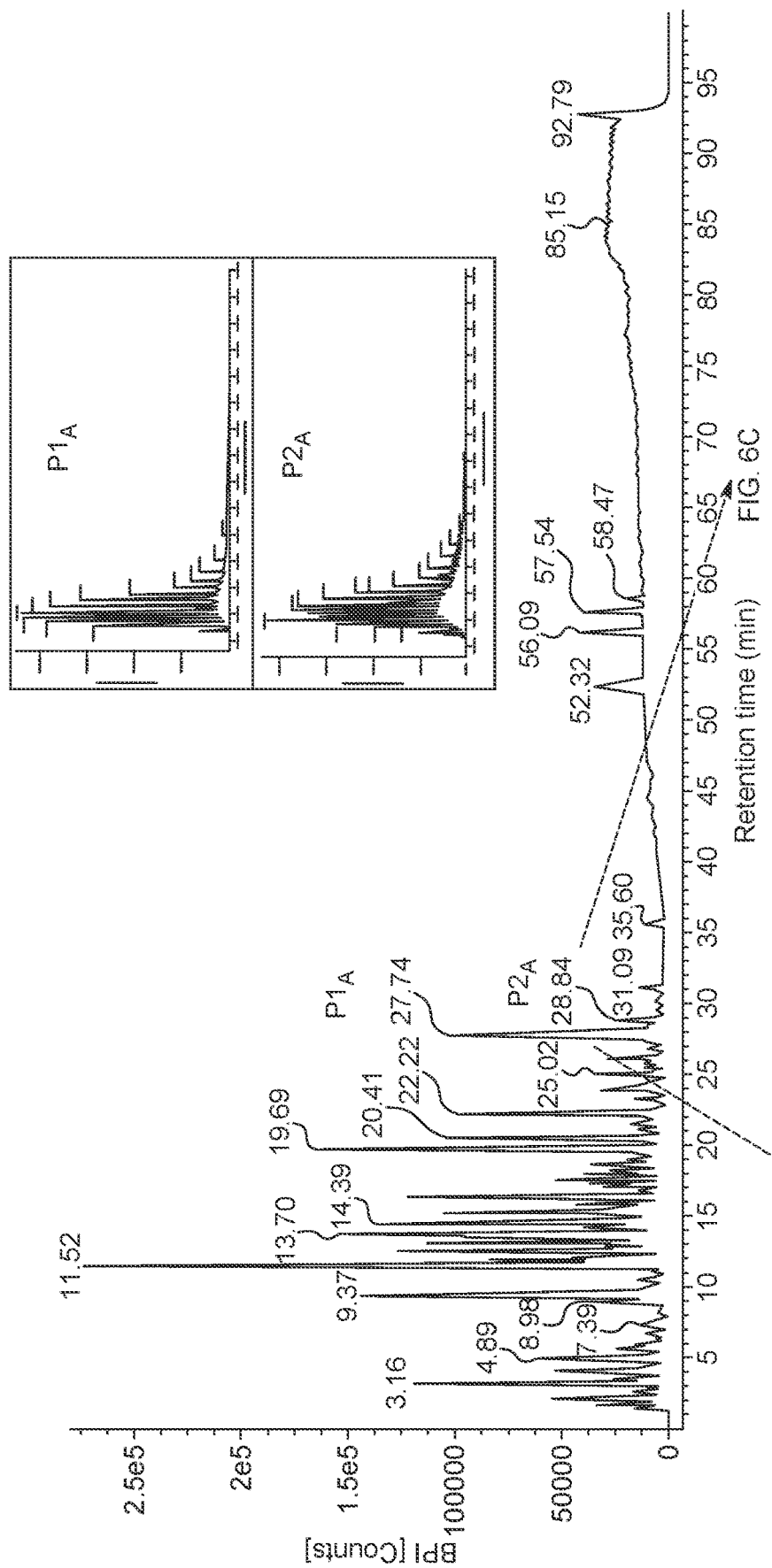
FIGS. 6A-6C are graphs illustrating the analysis of a menstrual blood sample.
Figure 6B:
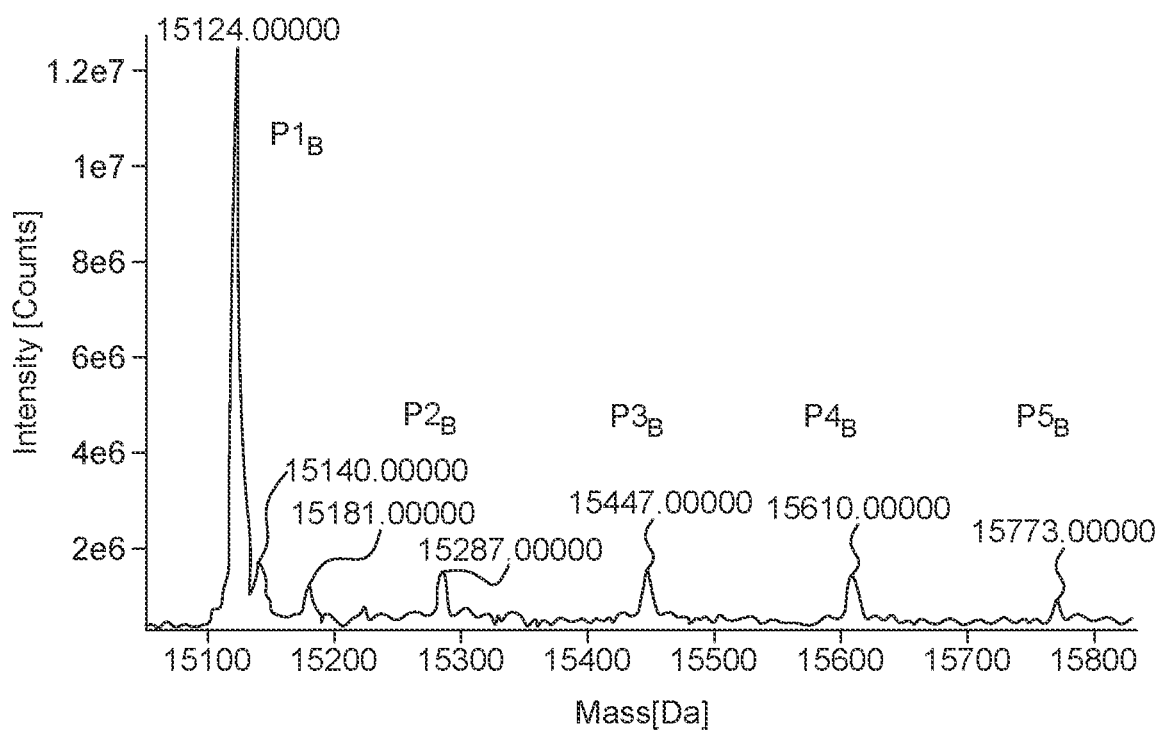
Figure 6C:
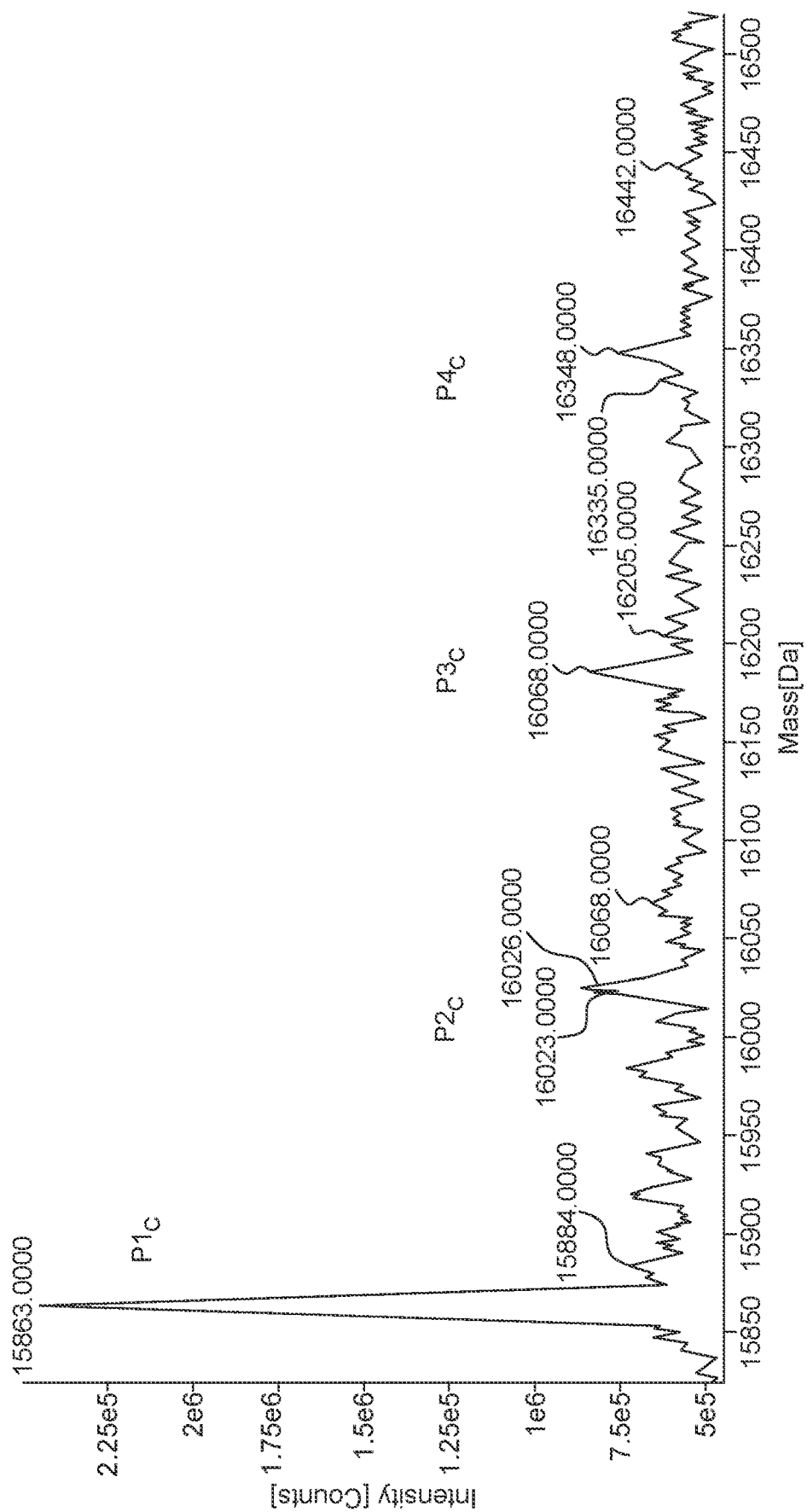
Figure 7A:
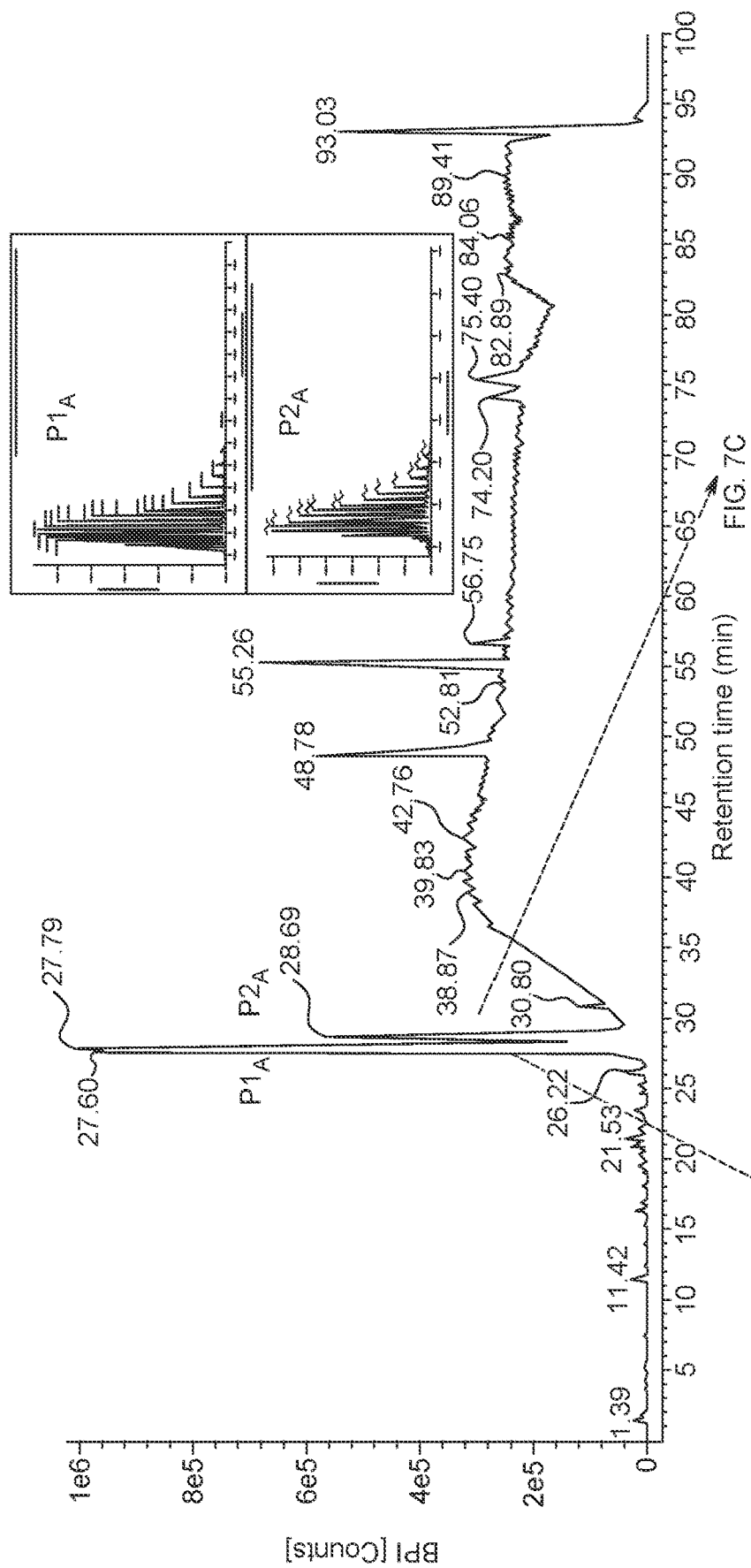
FIGS. 7A-7C are graphs illustrating the analysis of a fingerprick blood sample.
Figure 7B:
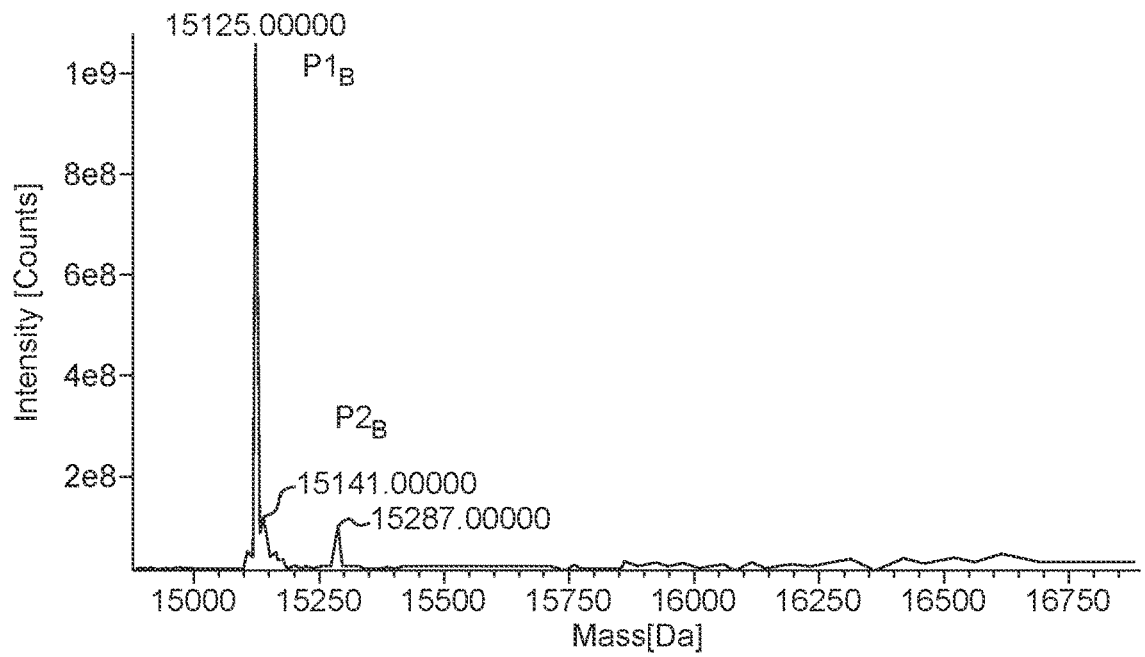
Figure 7C:
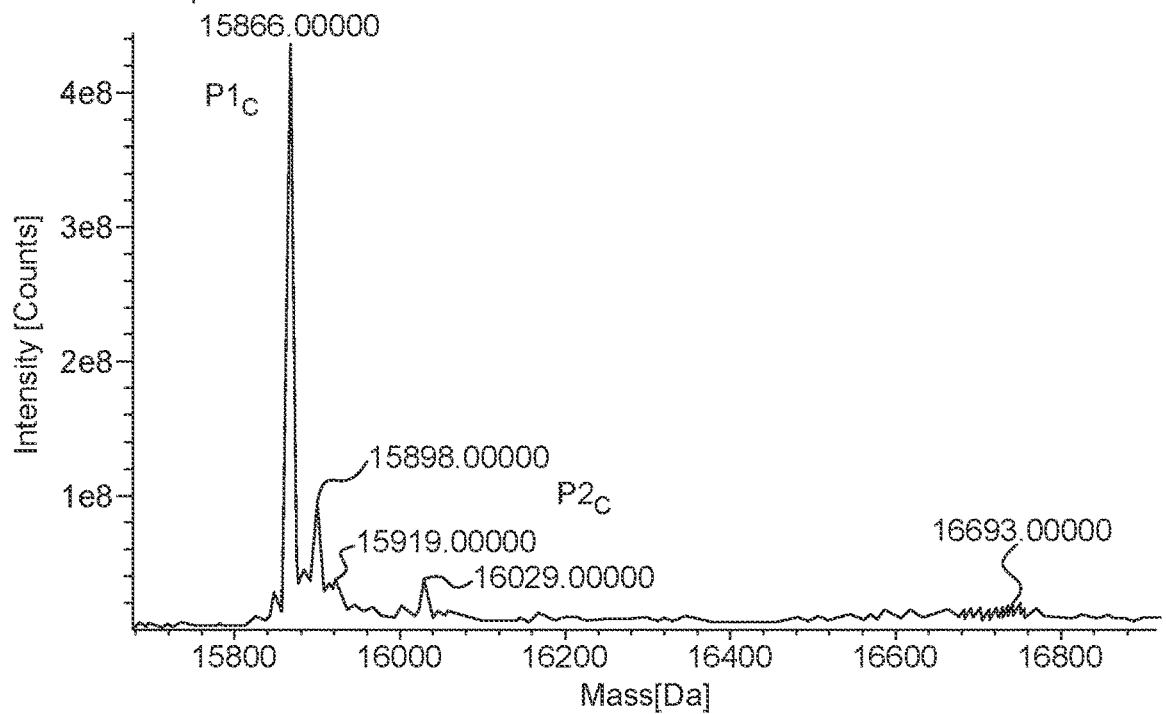
Figure 8:
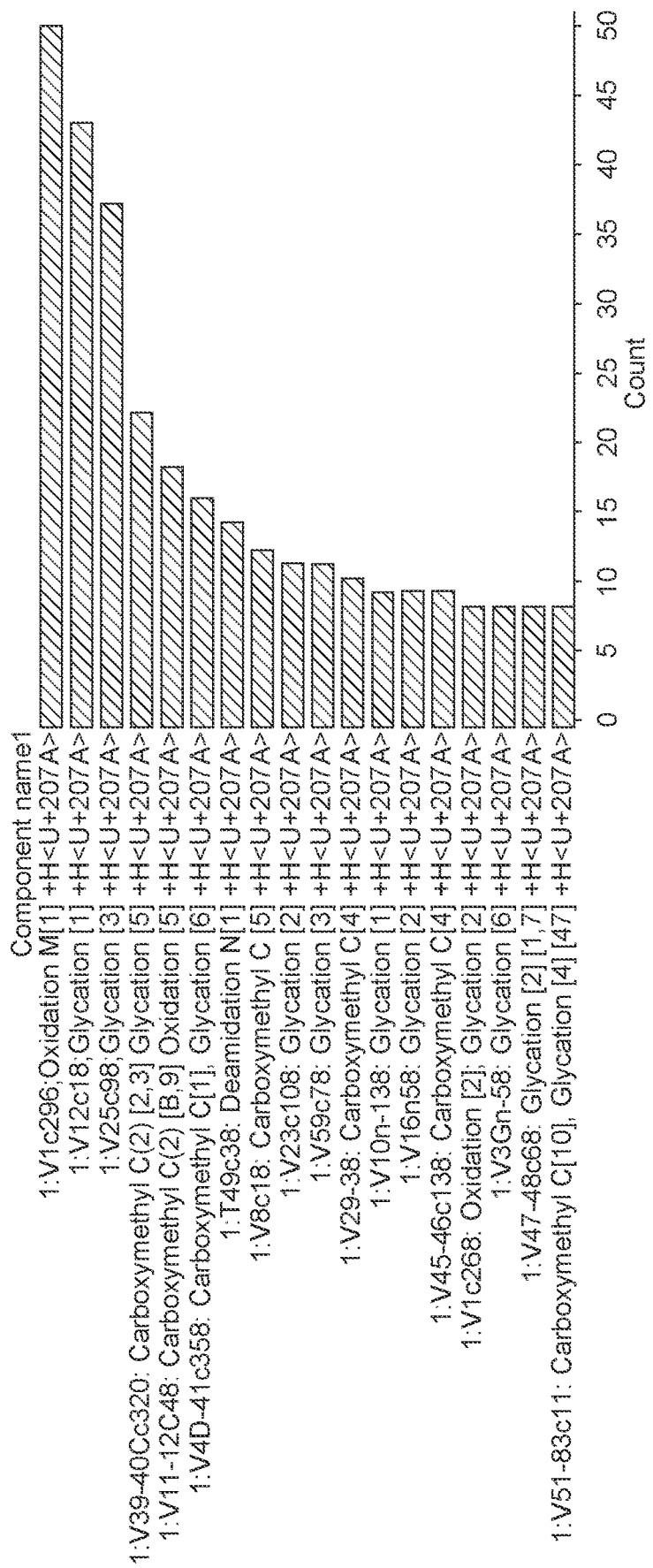
FIG. 8 illustrates a series of modifications found in menstrual blood and the location of the amino acid with the post-translational modifications (PTM's).
Figure 9:
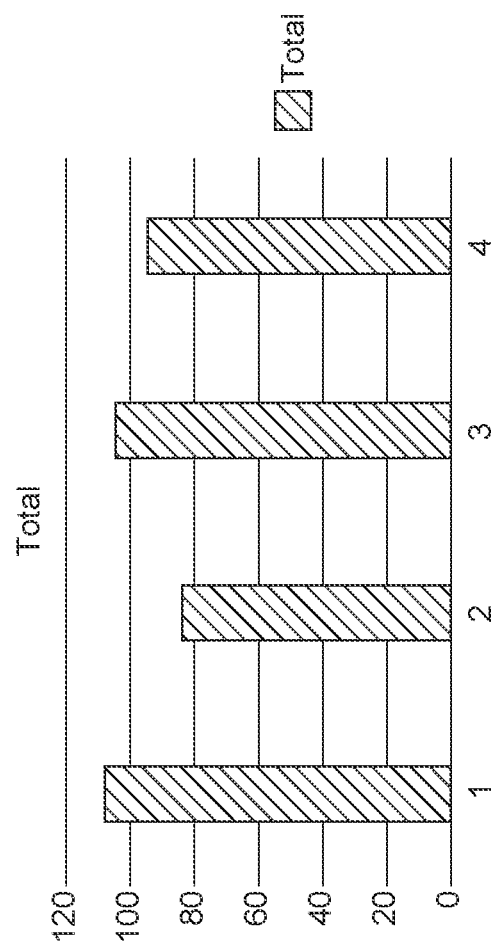
FIG. 9 represents data from 389 patients ascribing each patient to a category based on the level of glycations on the hemoglobin subunit alpha found in menstrual blood as set forth in the claims.
Figure 10:
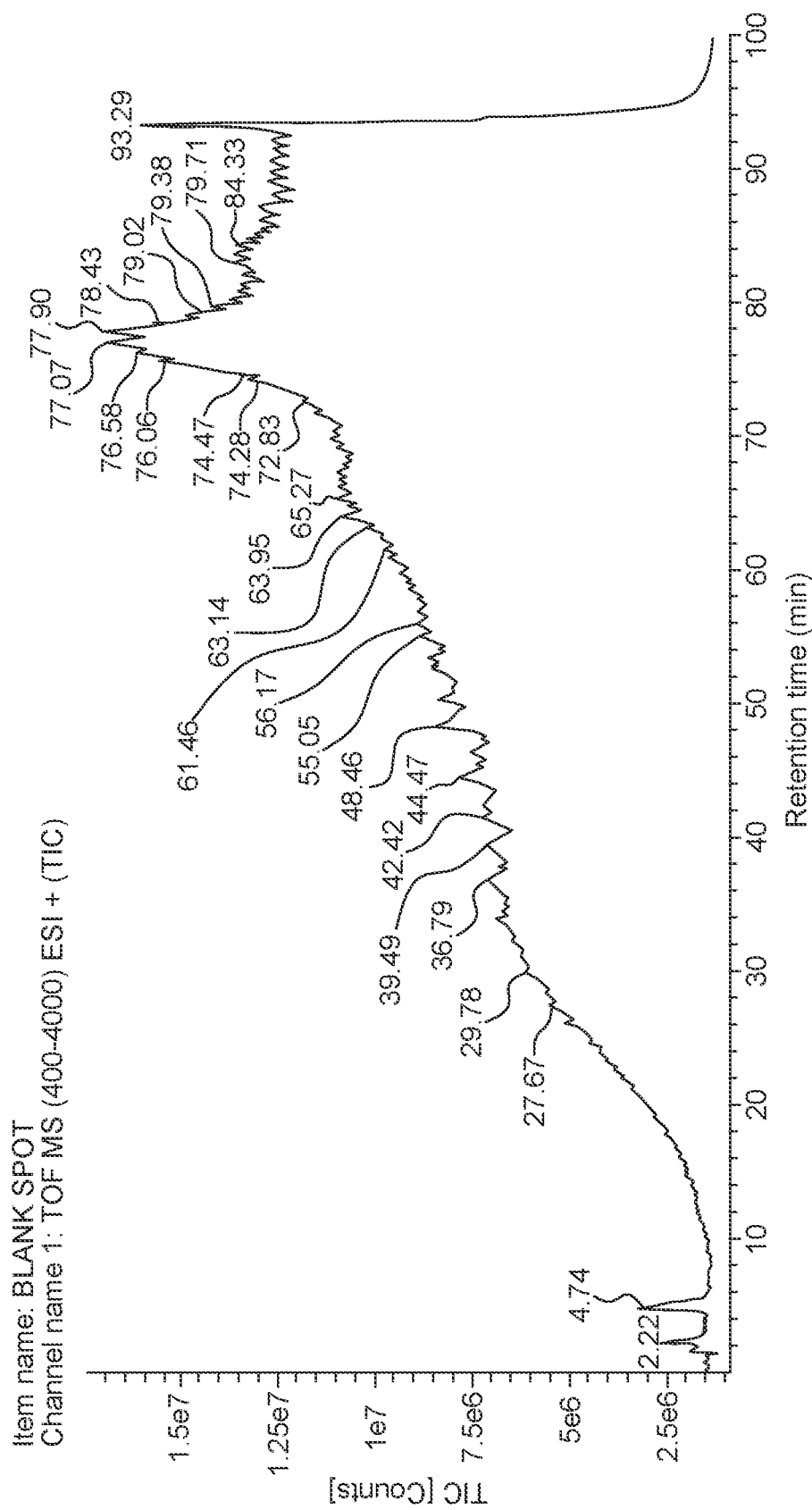
FIG. 10 is a graph of a blank dried blood spot collection card to illustrate the absence of any proteins without blood and/or menstrual fluid.
Figure 11A:
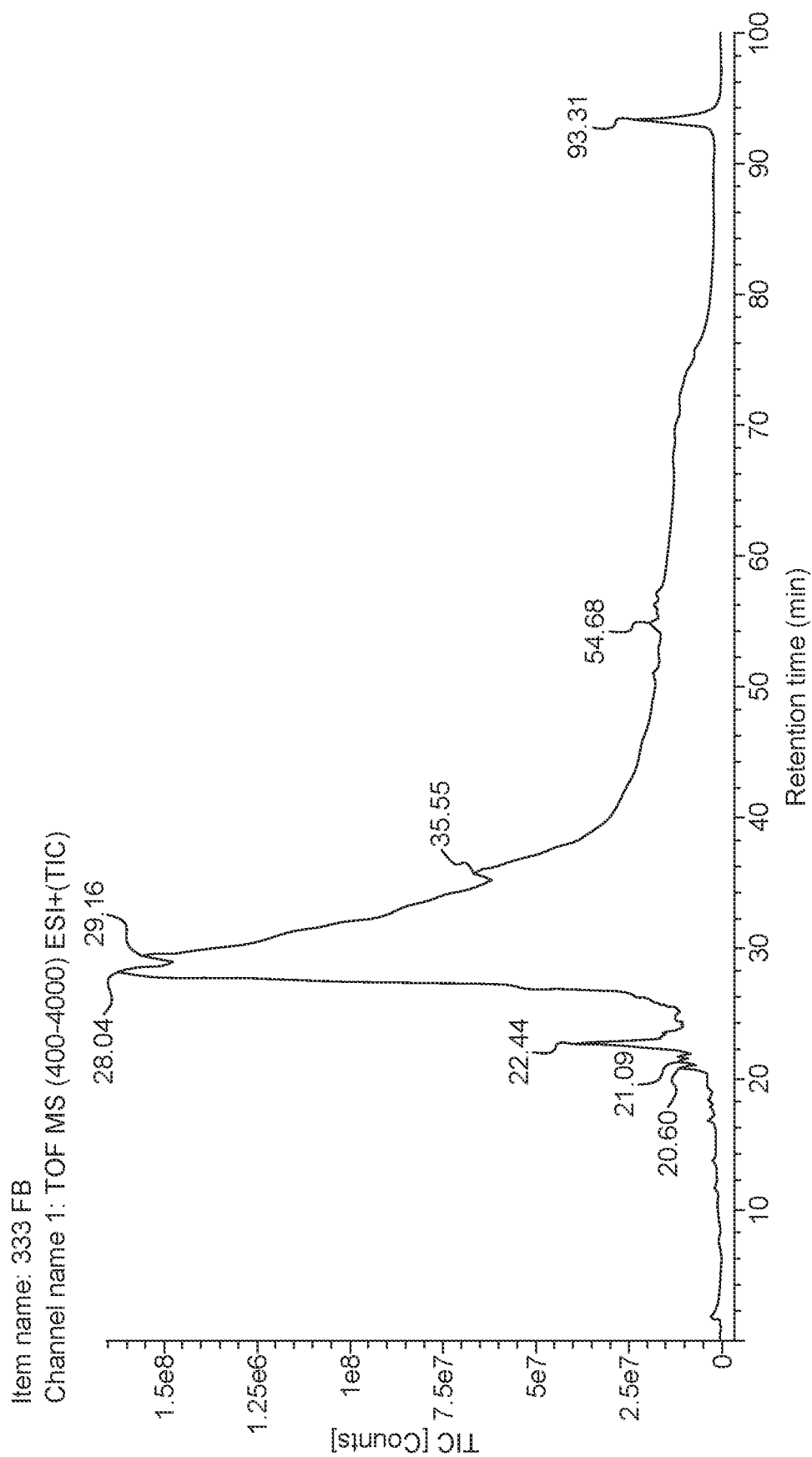
Figure 11C:
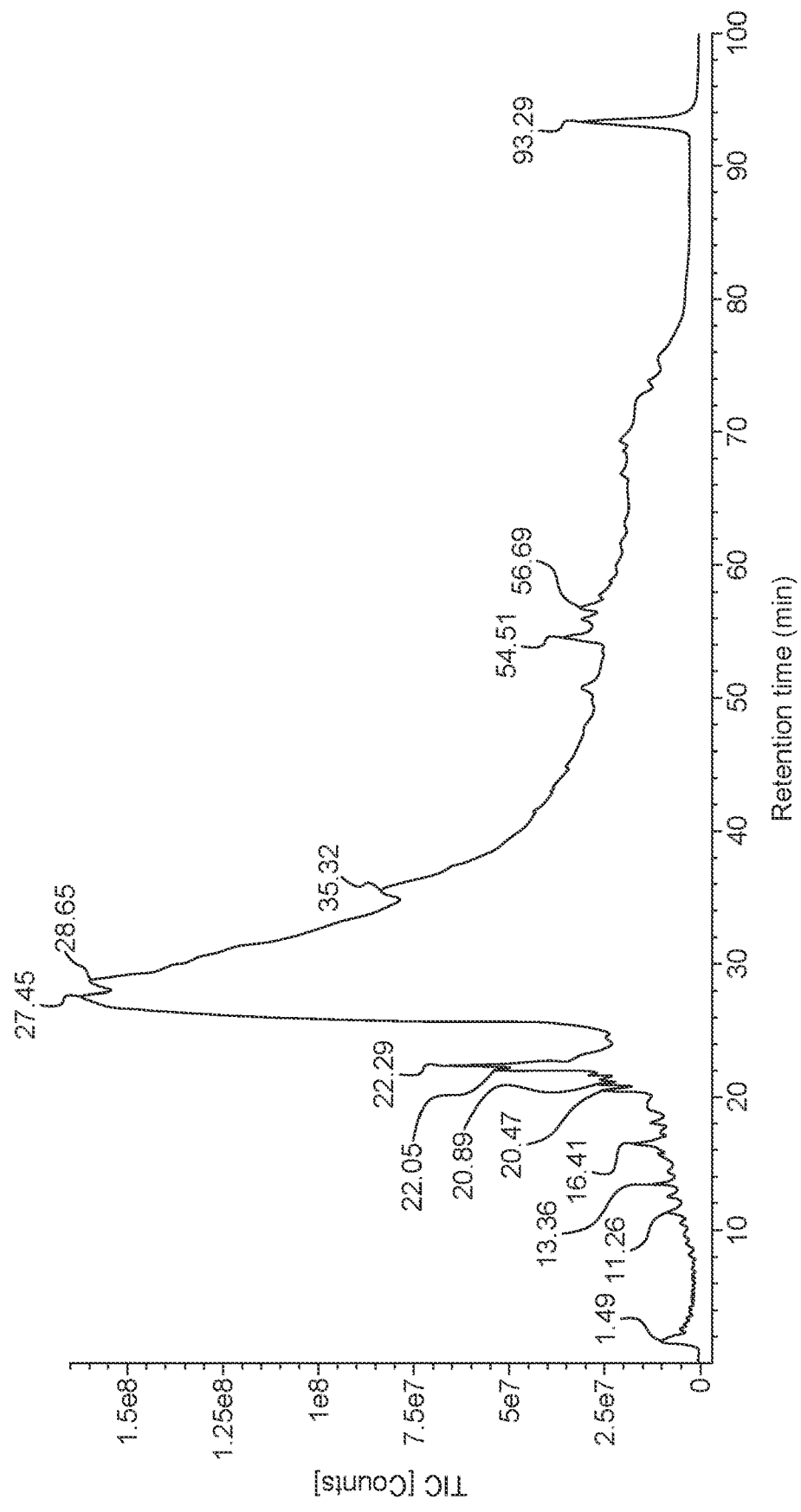
Figure 11D:
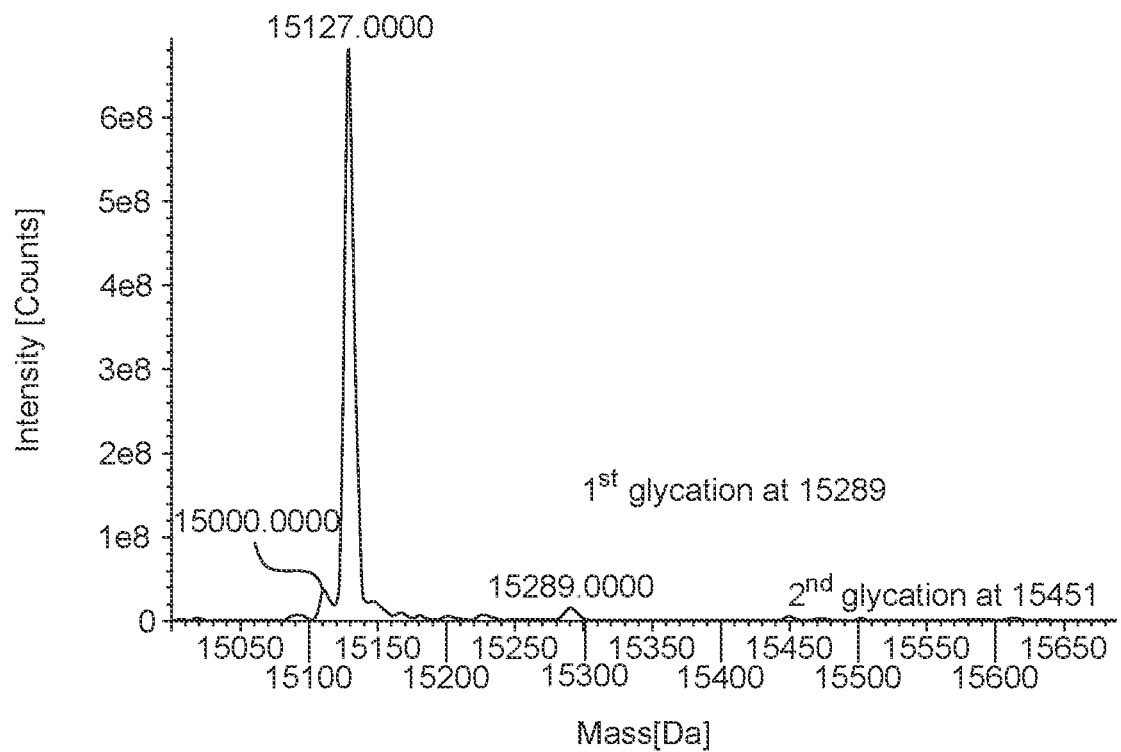
Figure 11D:
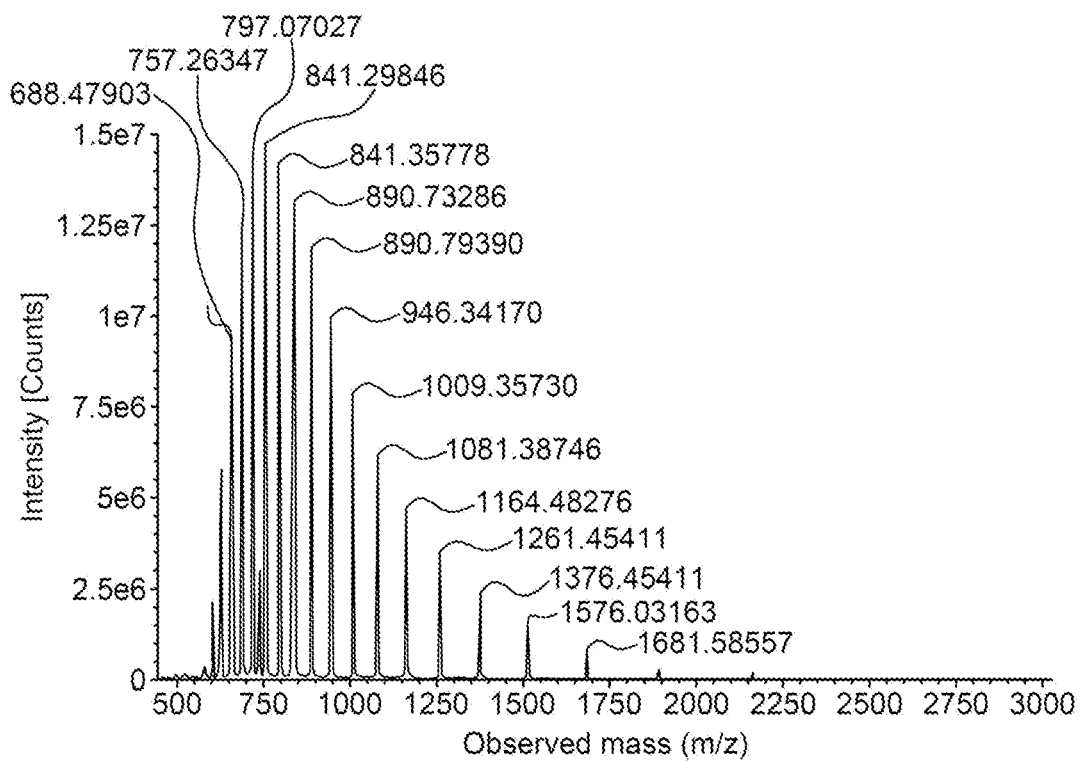
Figure 12A:
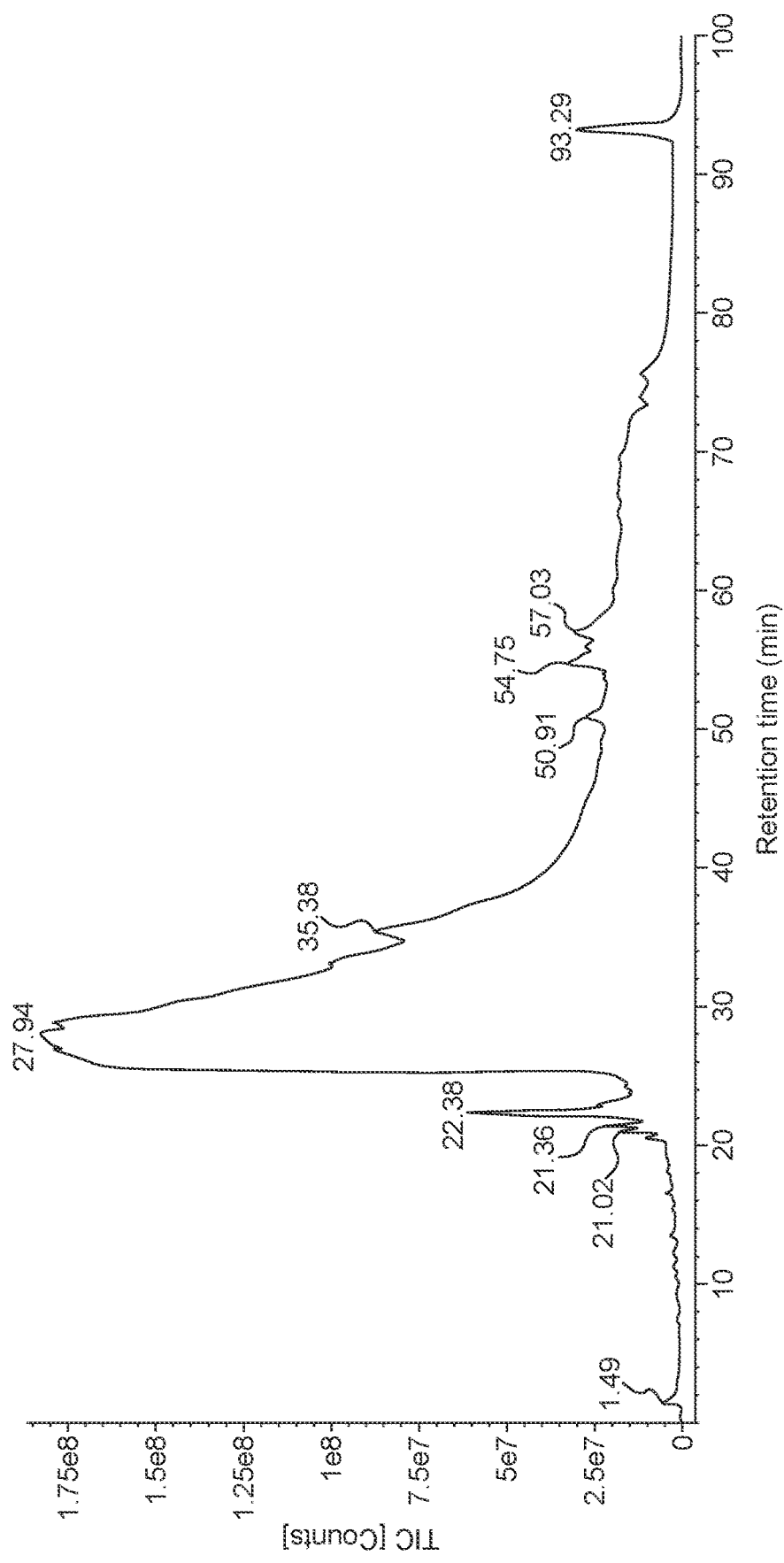
FIGS. 12A-12D are graphs illustrating the analysis of a fingerpick blood sample compared to a menstrual blood sample and the contents of alpha glycation, in a second female patient.
Figure 12B:
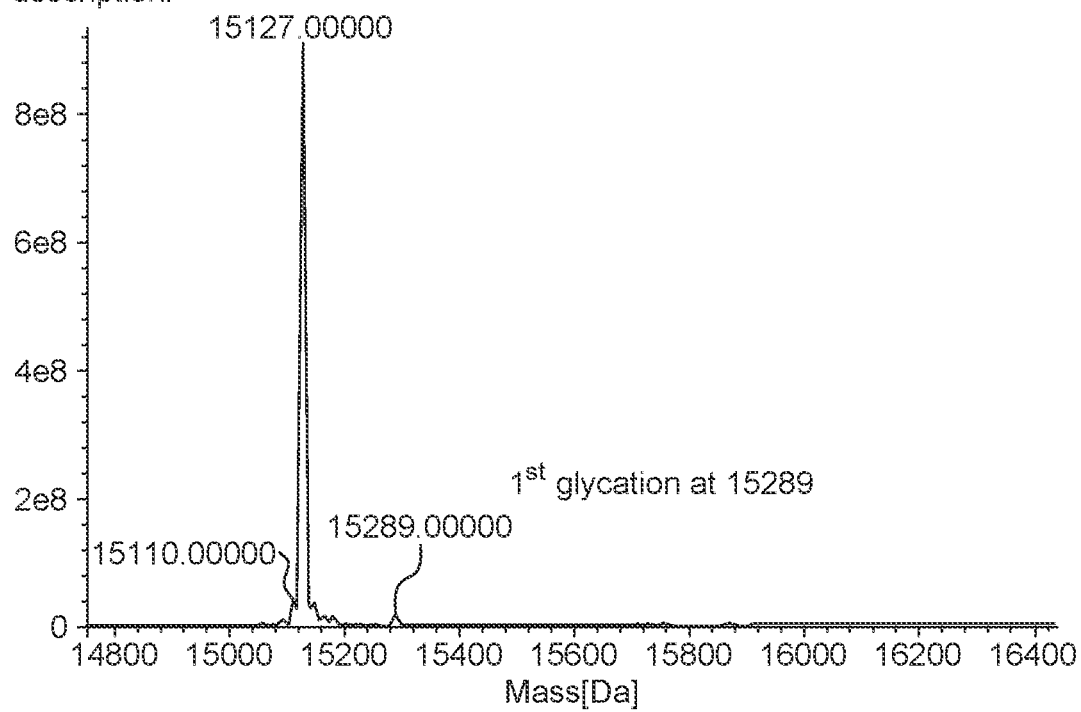
Figure 12B:
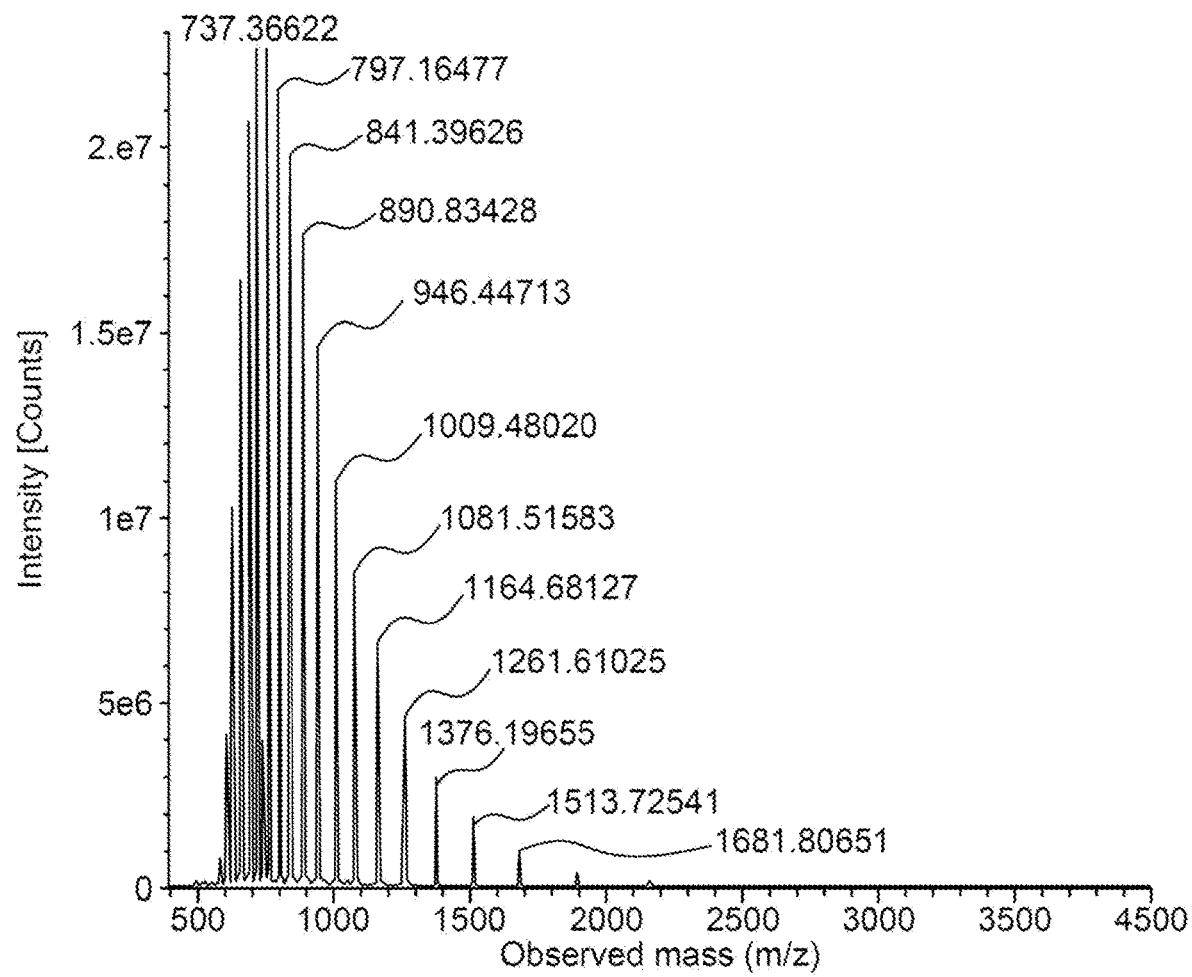
Figure 12C:
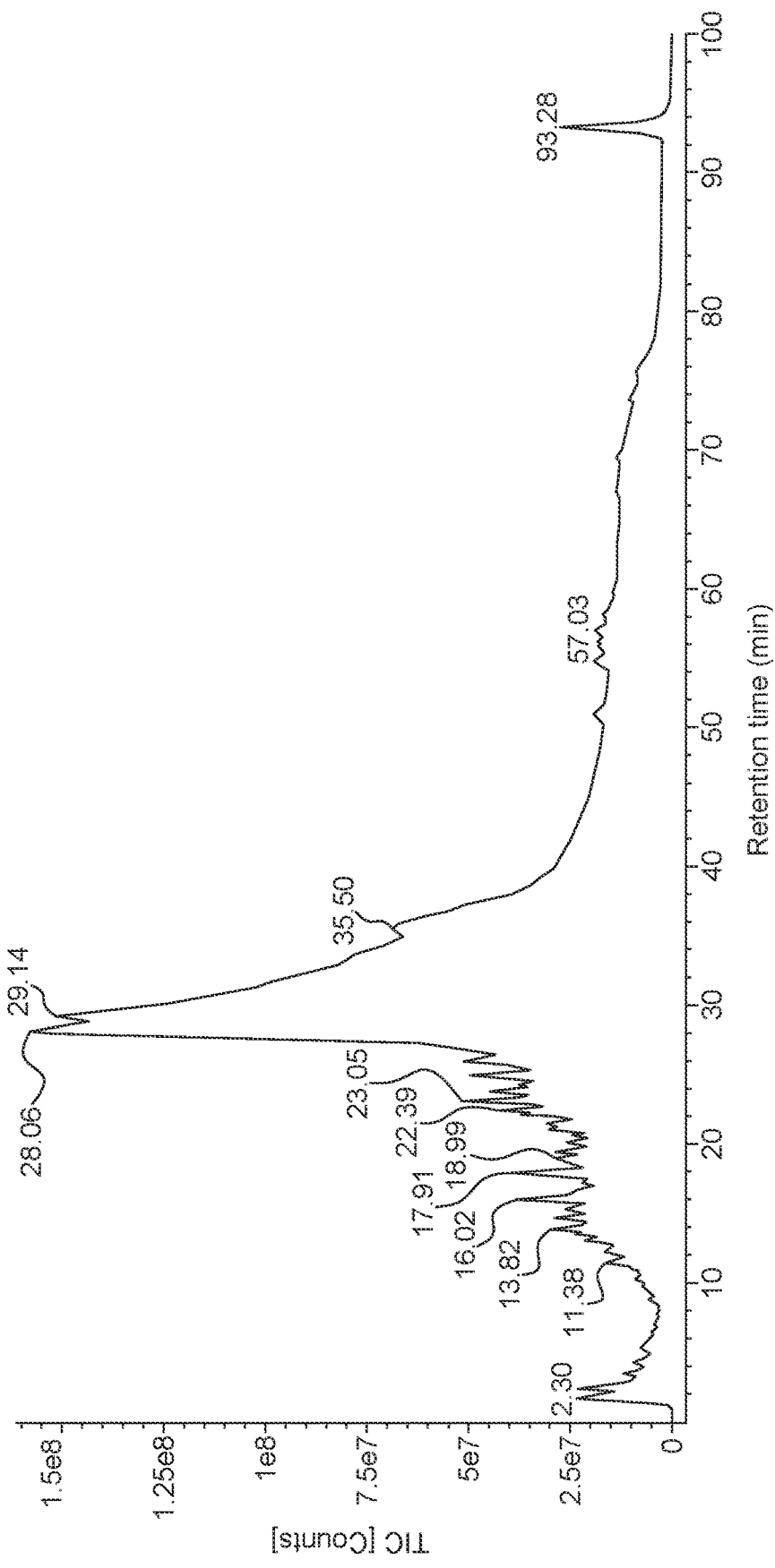
Figure 12D:
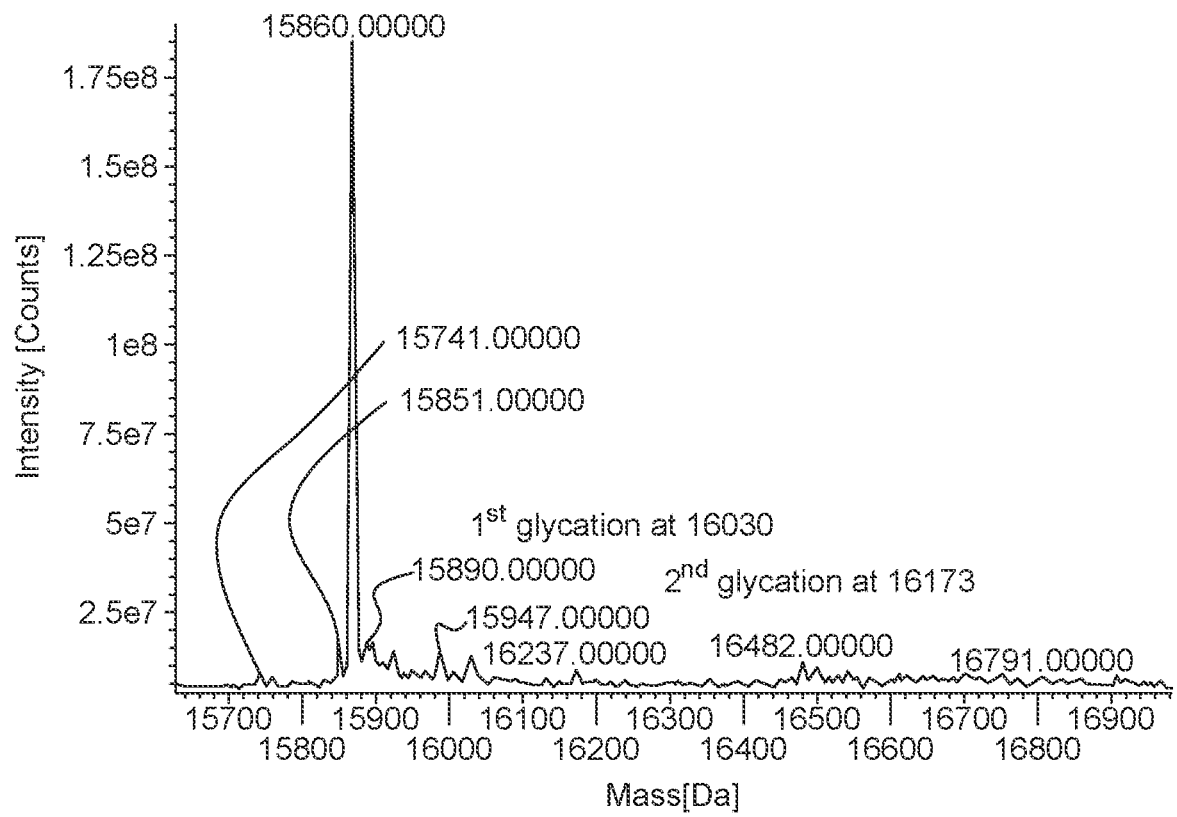
Figure 12D:
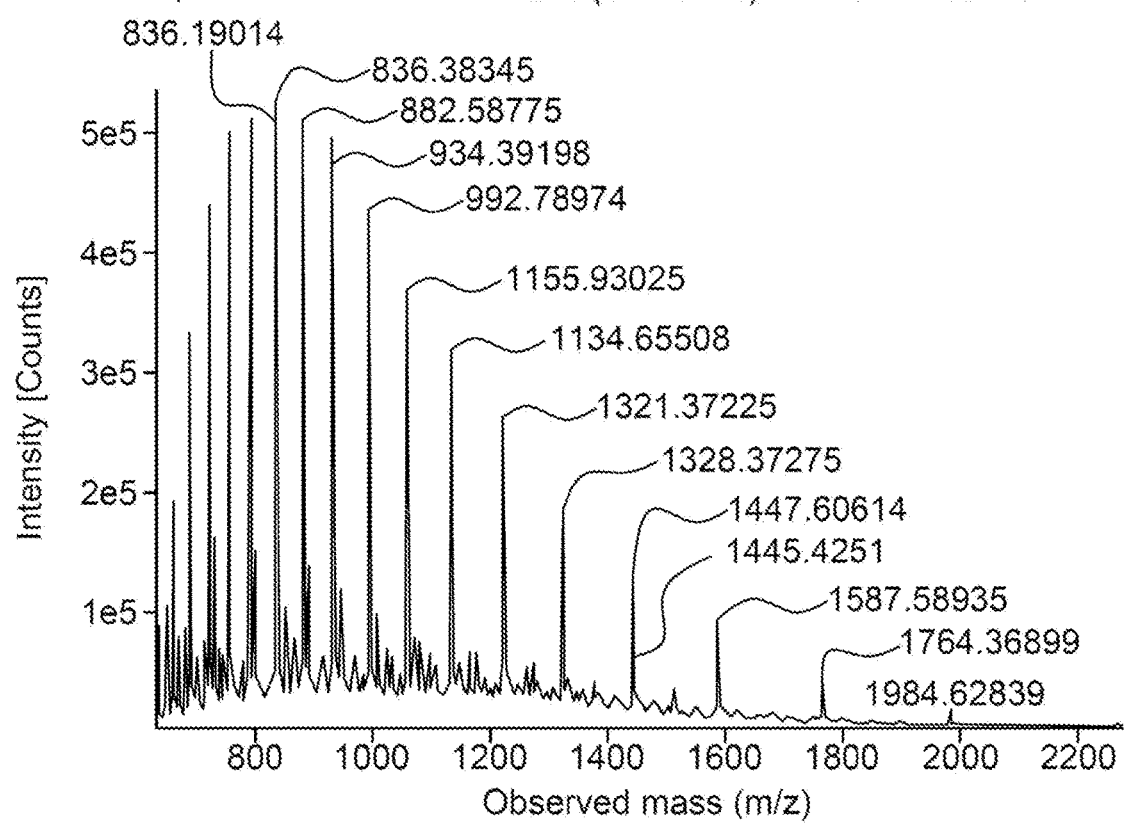
Figure 13C:
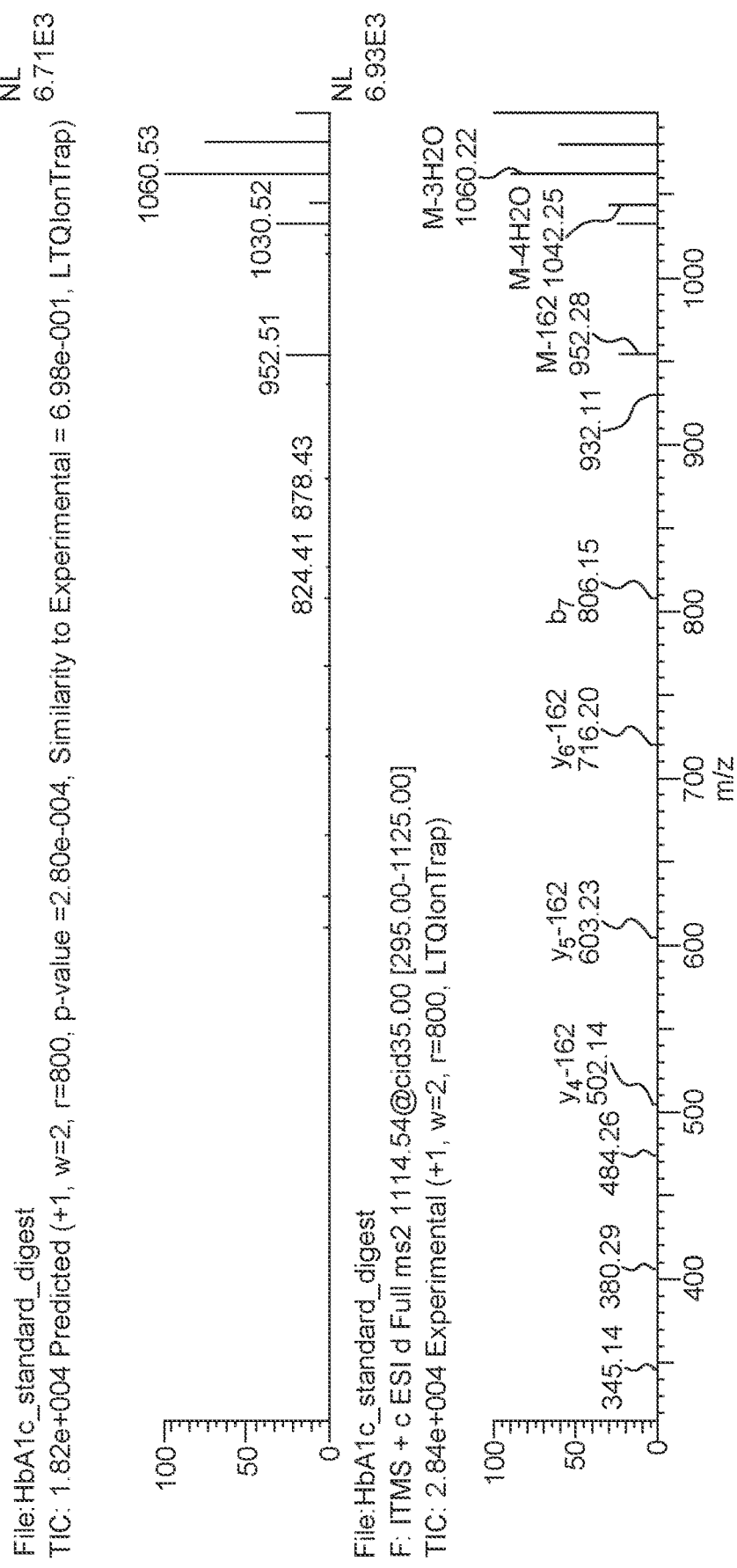
Figure 13D:
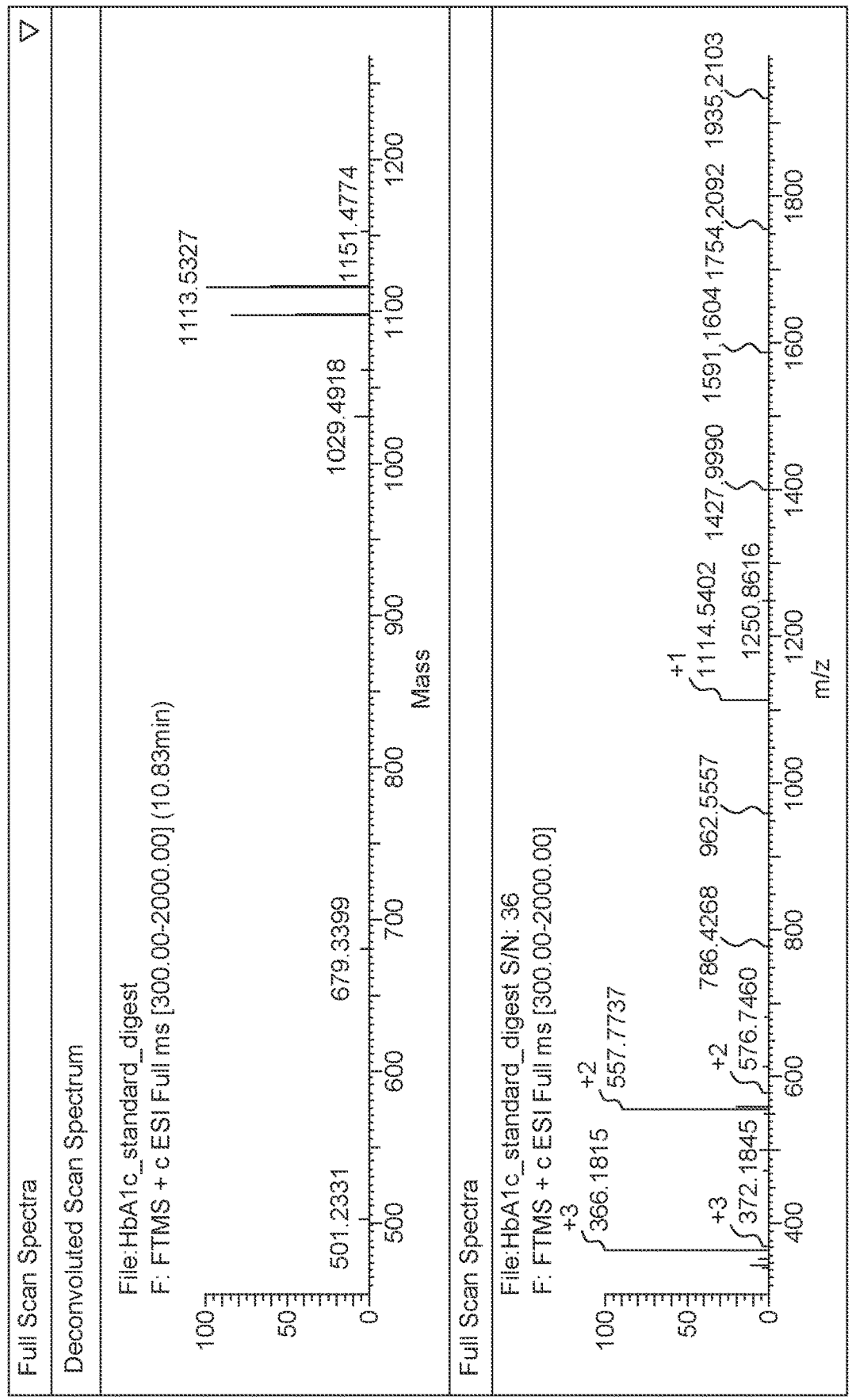
Figure 13E:
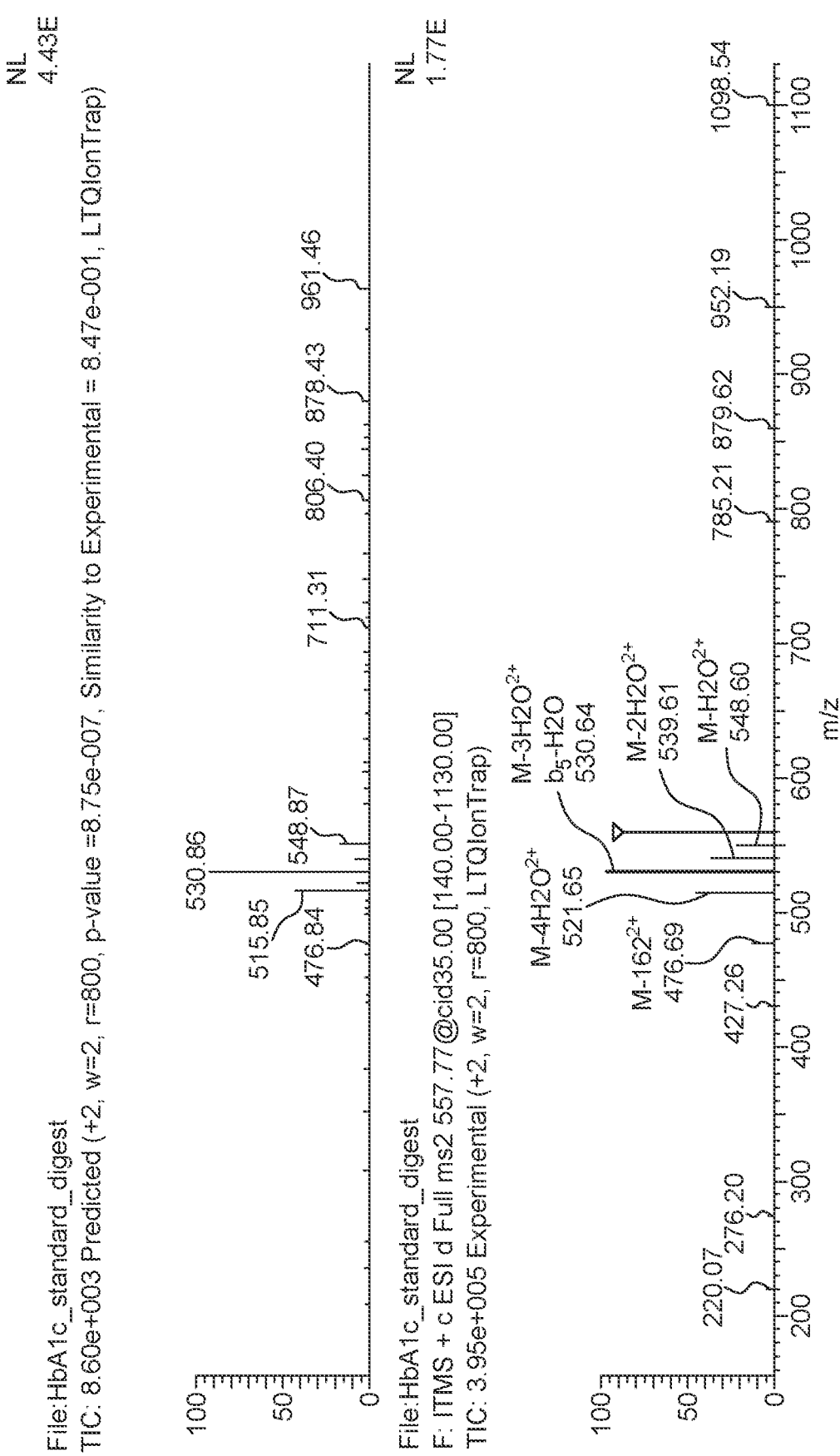
Figure 13F:
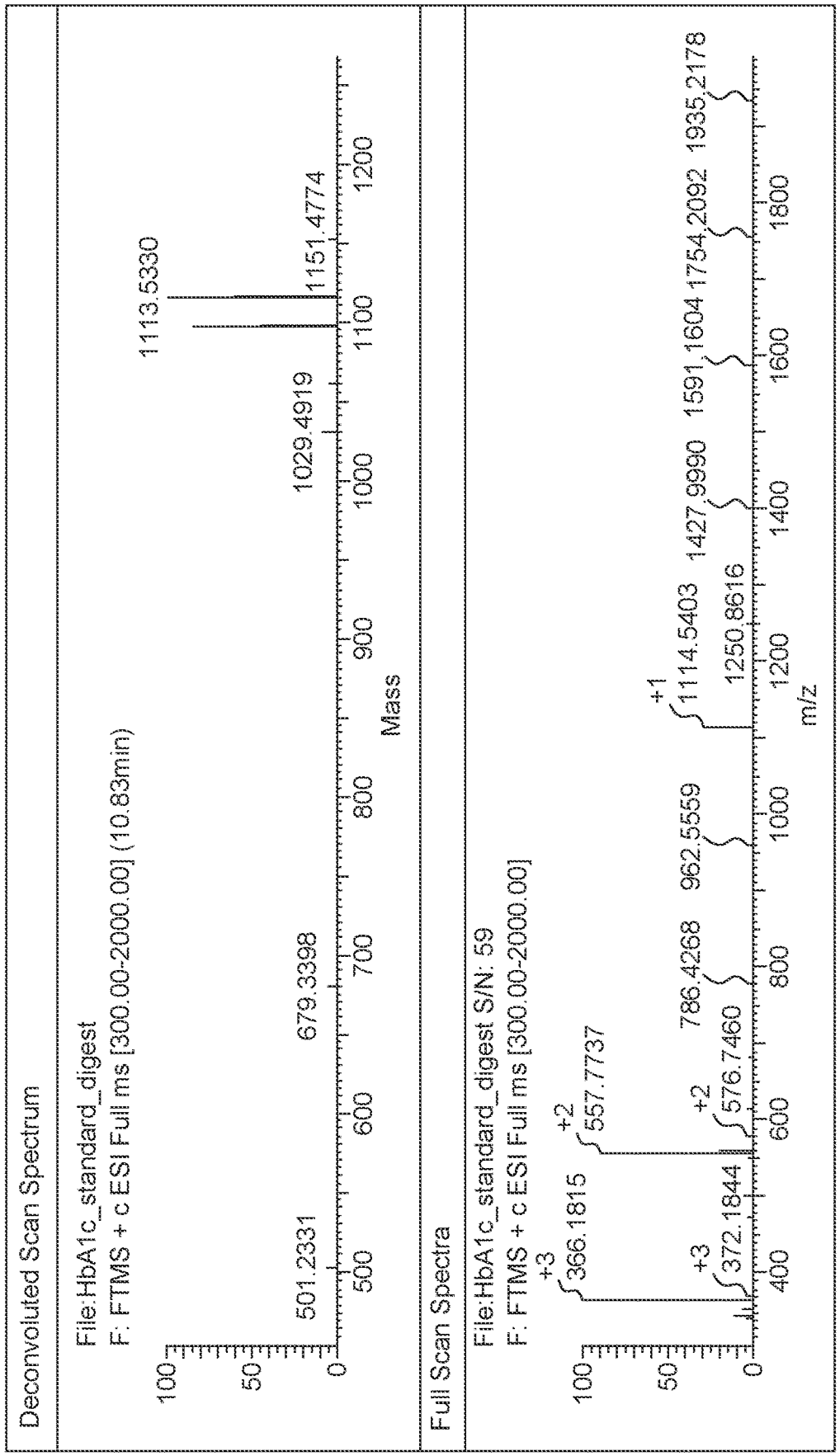
Figure 14C:
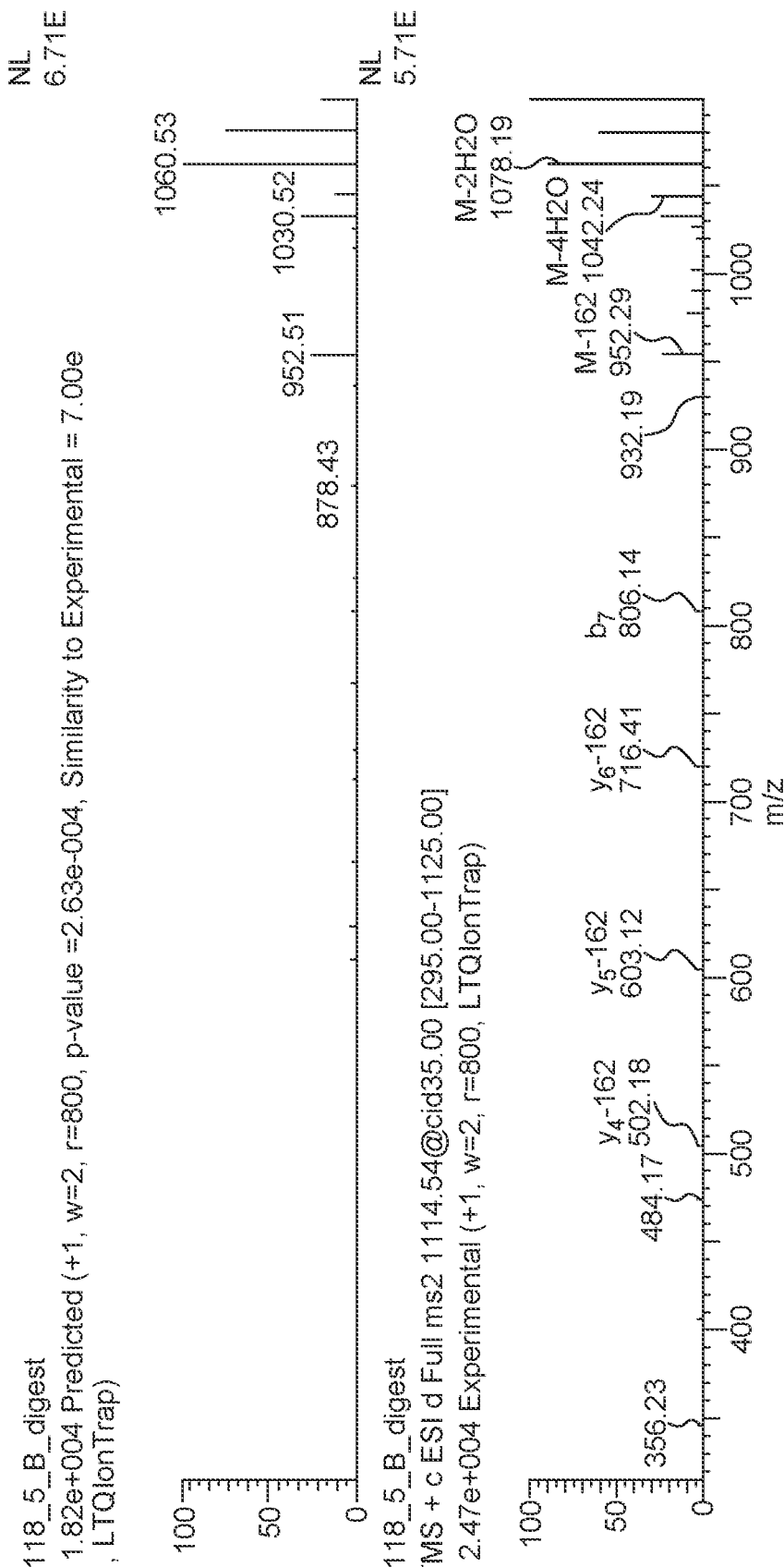
Figure 14D:
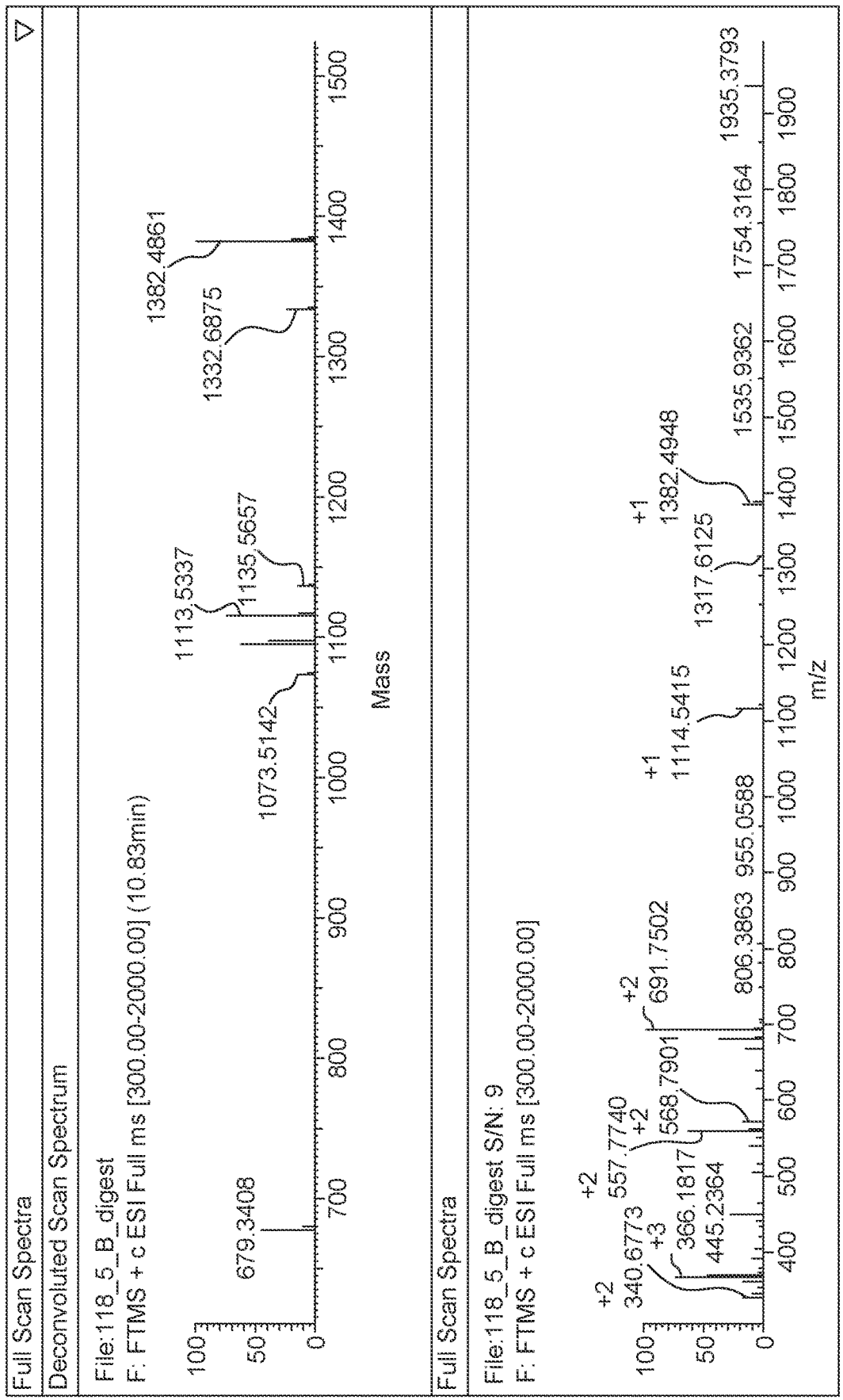
Figure 14F:
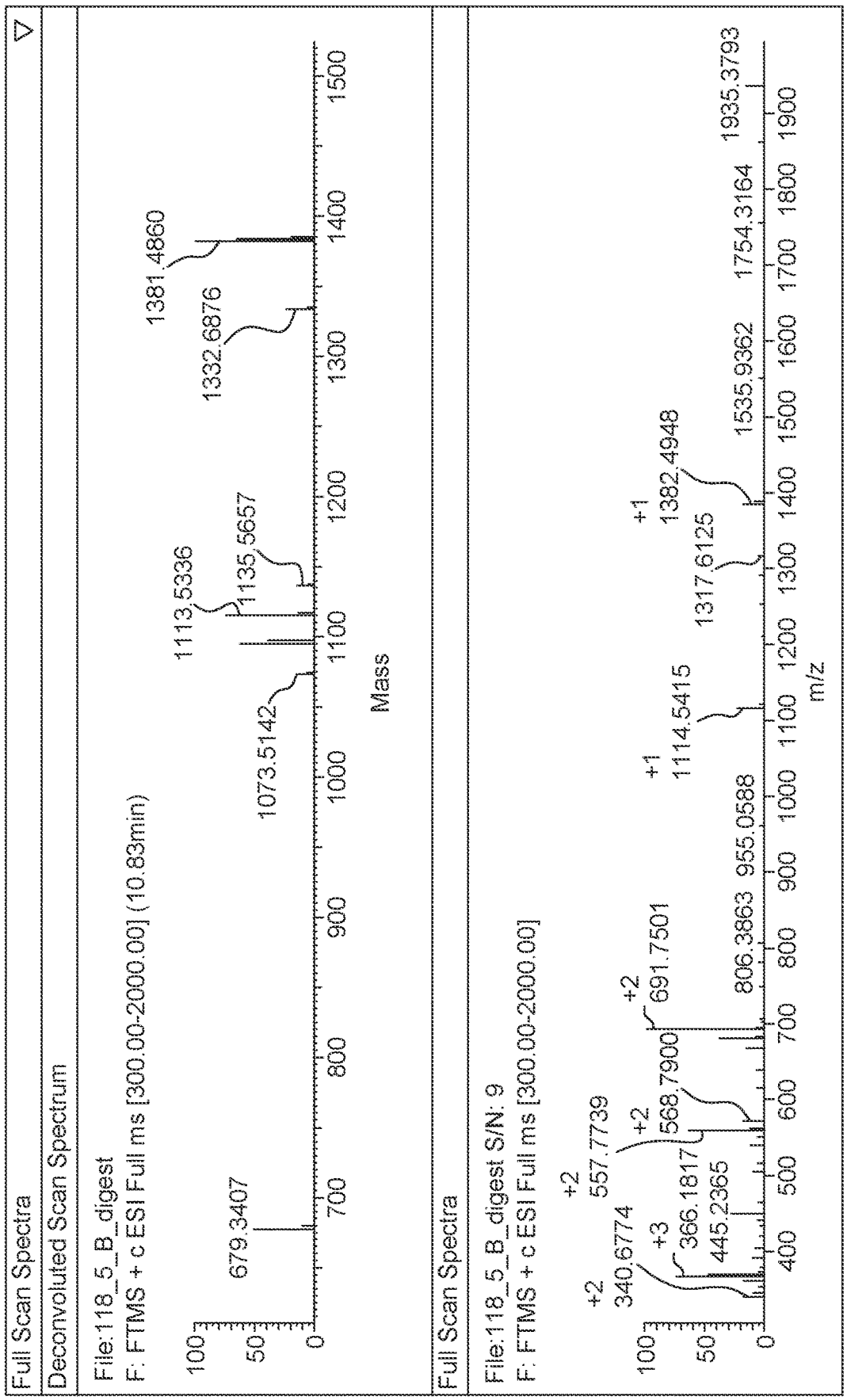
Figure 15D:
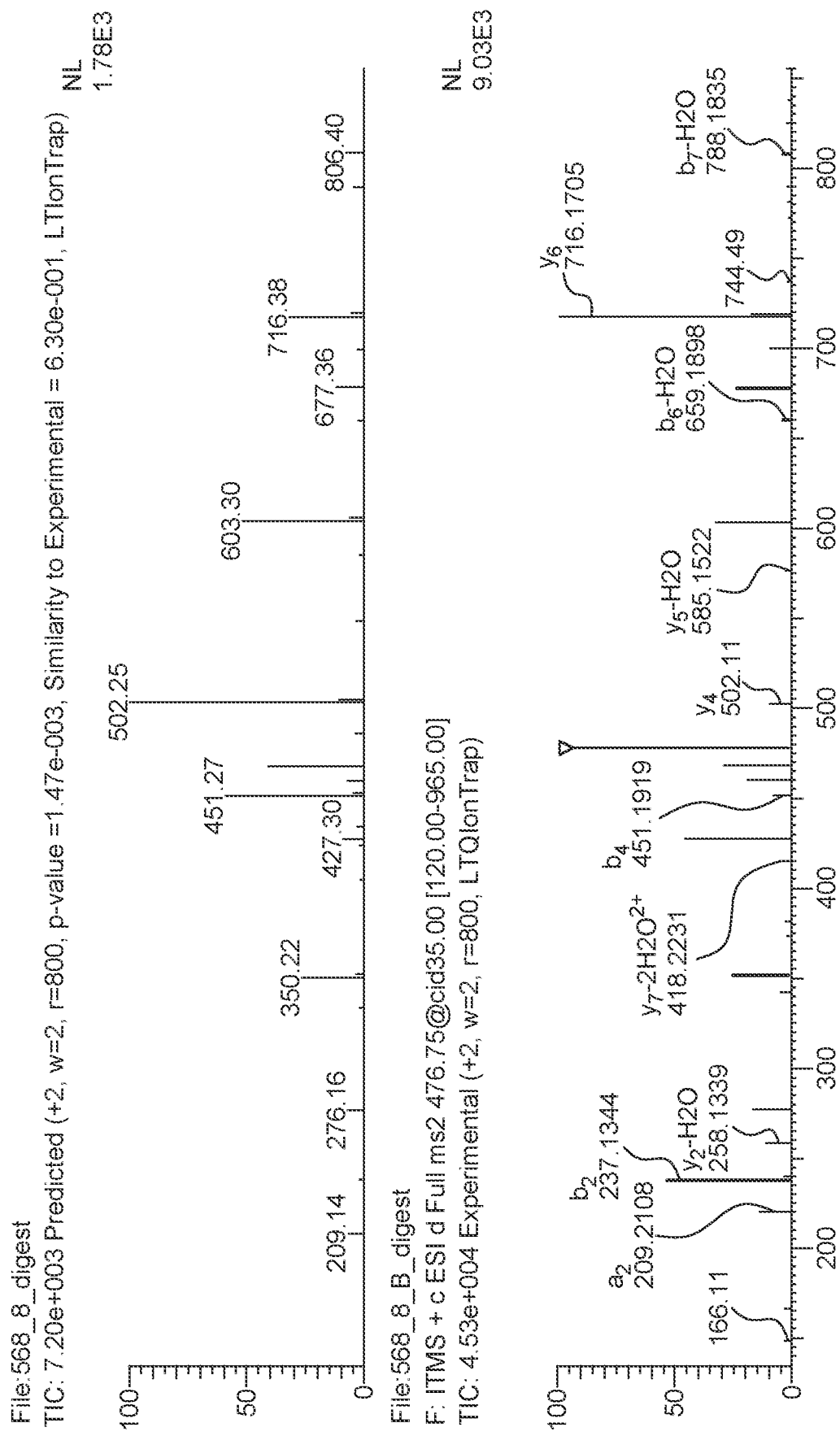
FIG. 15D shows the fragment coverage map in which the average structural resolutions is equal to 1.1 residues from the patient in FIG. 15C.
Figure 15E:
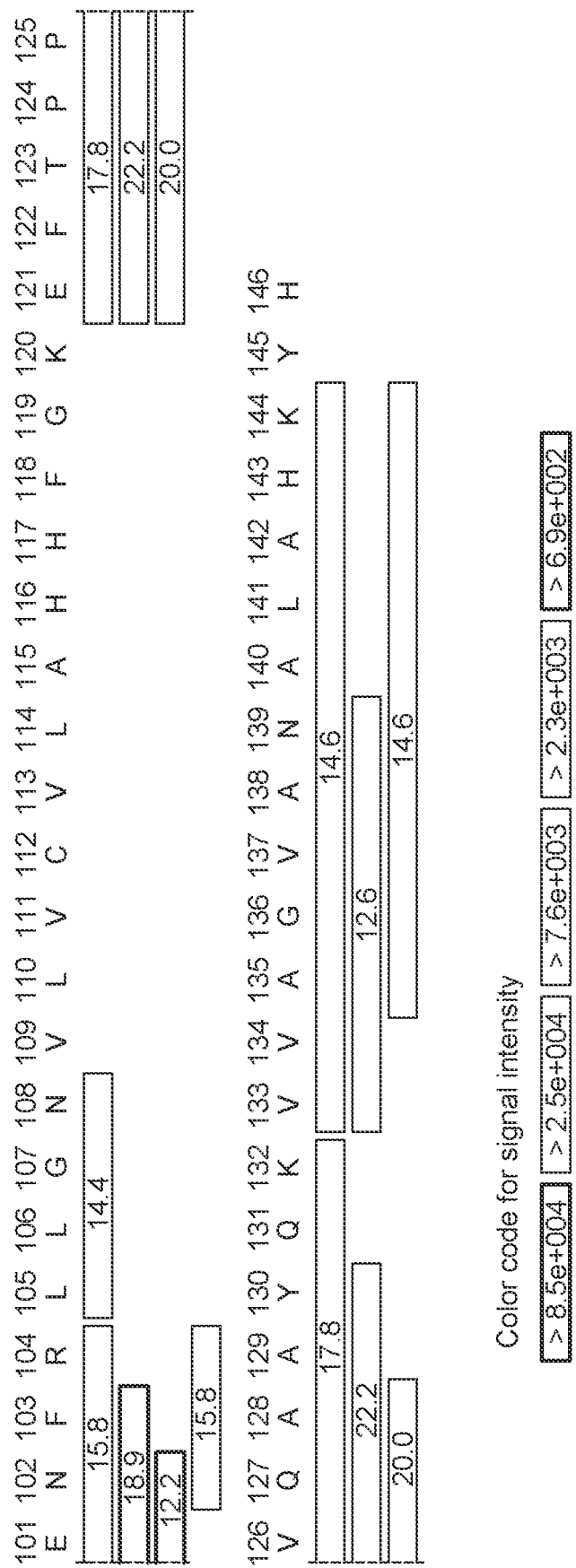
FIG. 15E shows the sequence coverage map from a separate female subject in which 76.7% of the hemoglobin subunit beta is reported (Seq. Id. No. 2).
Figure 15F:
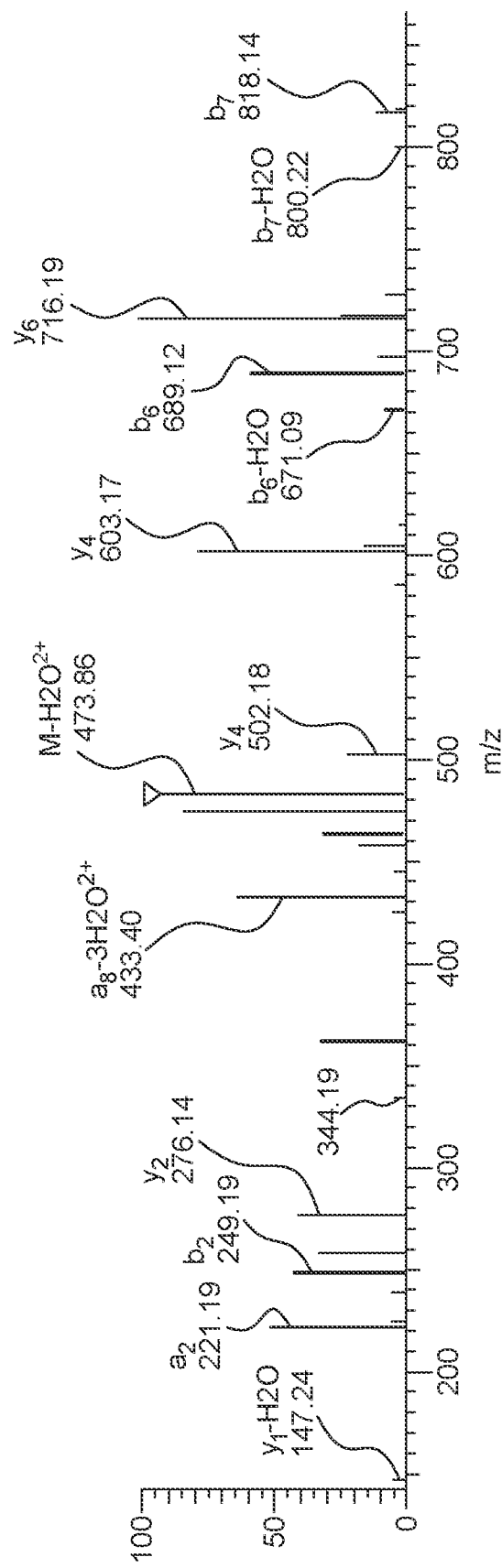
FIG. 15F shows the fragment coverage map in which the average structural resolutions is equal to 1.0 residues from the patient in FIG. 15E.
Figure 18A:
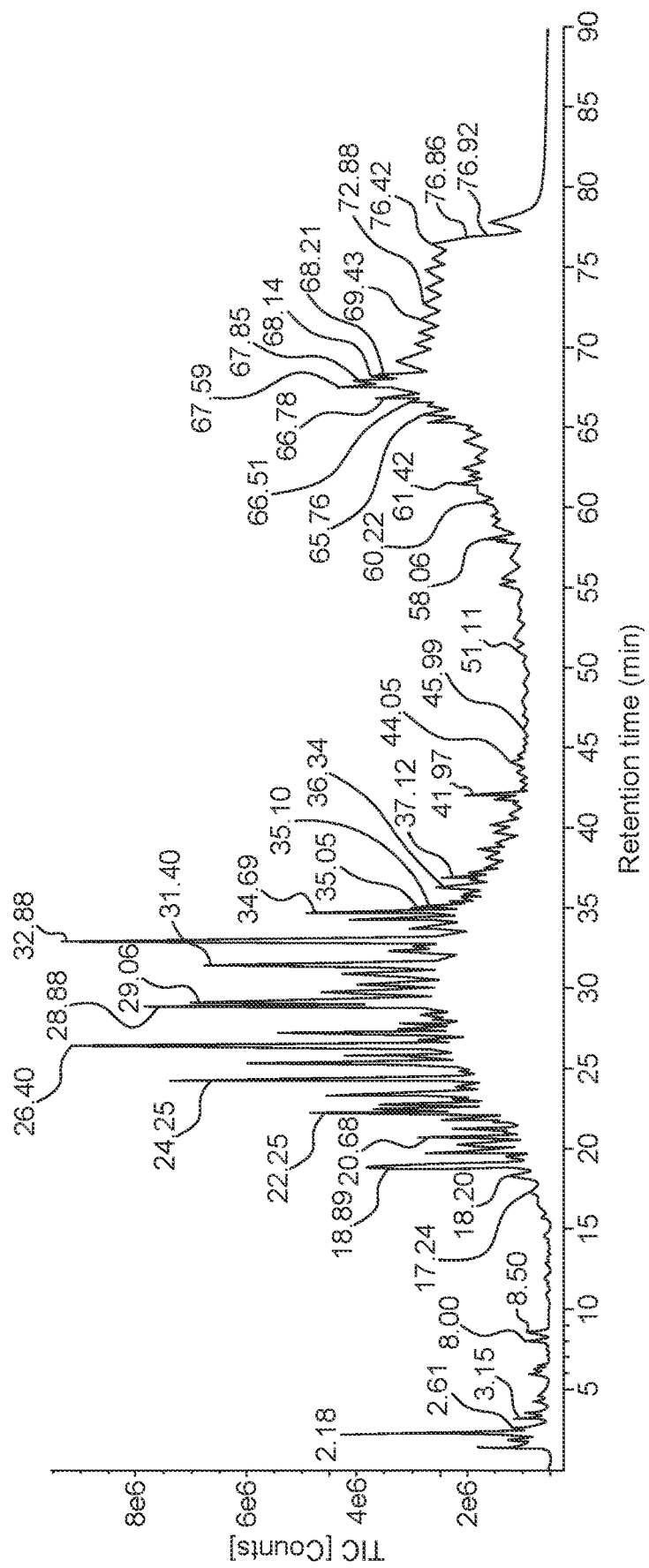
FIGS. 18A-18D illustrates mass spectrometry reports from two patients in which alpha-1 antitrypsin was detected by monitoring a characteristic peptide, observed with a range from 0.0166% to 0.047% of total peptide detected.
Figure 18B:
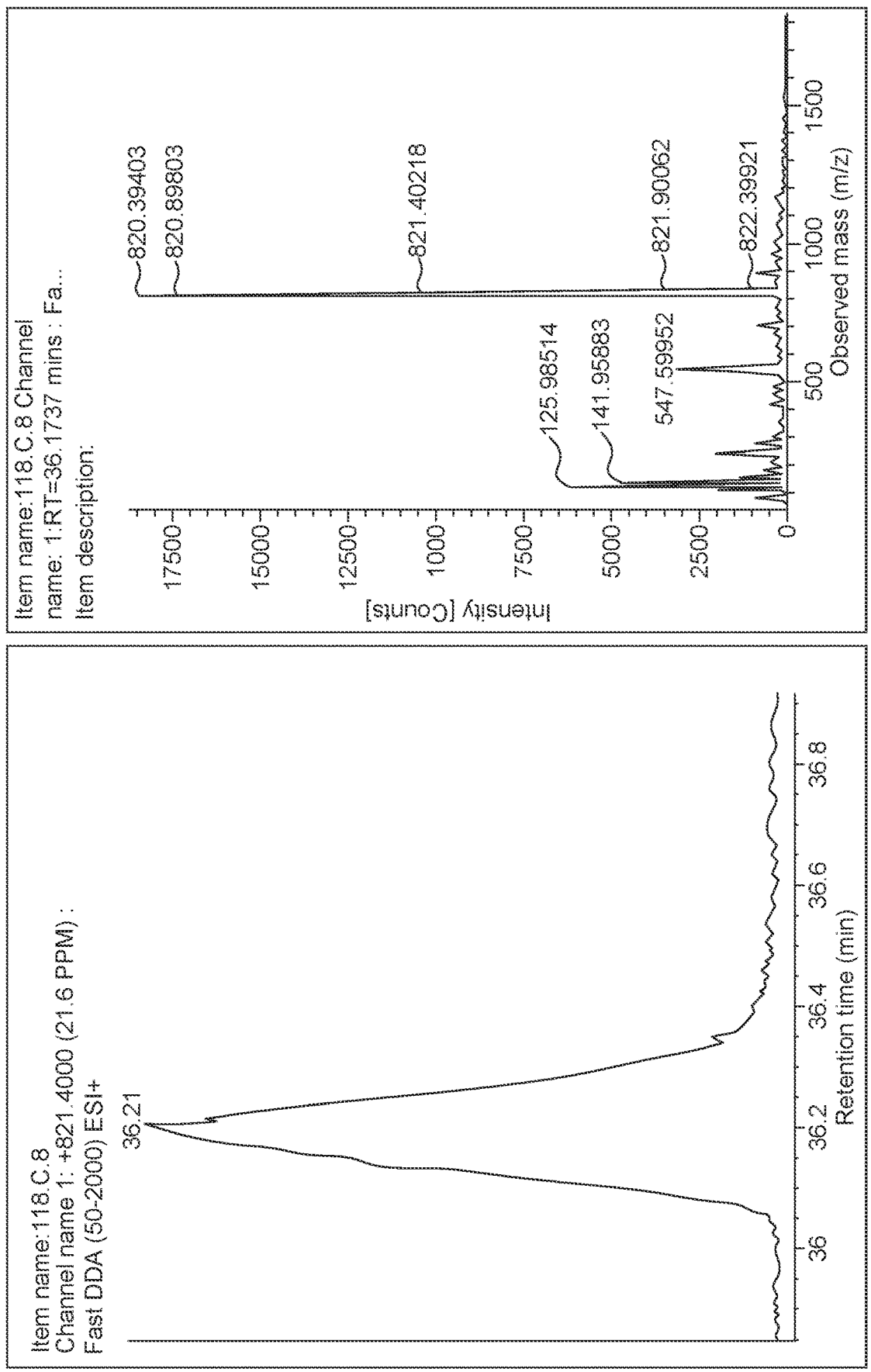
Figure 18C:
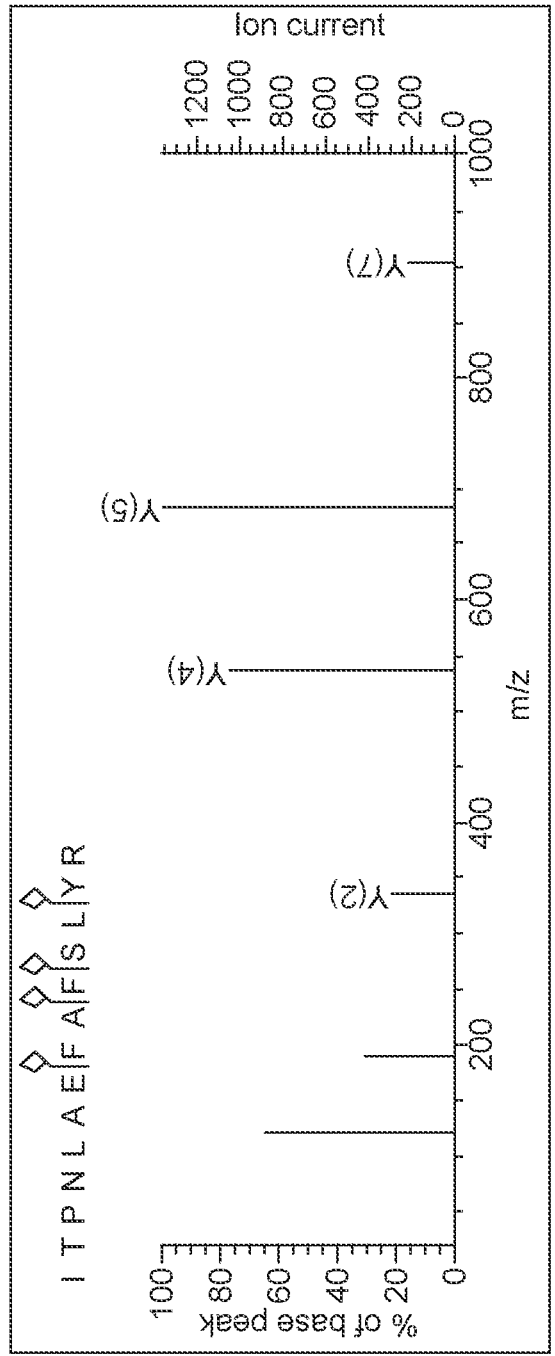
Figure 18D:
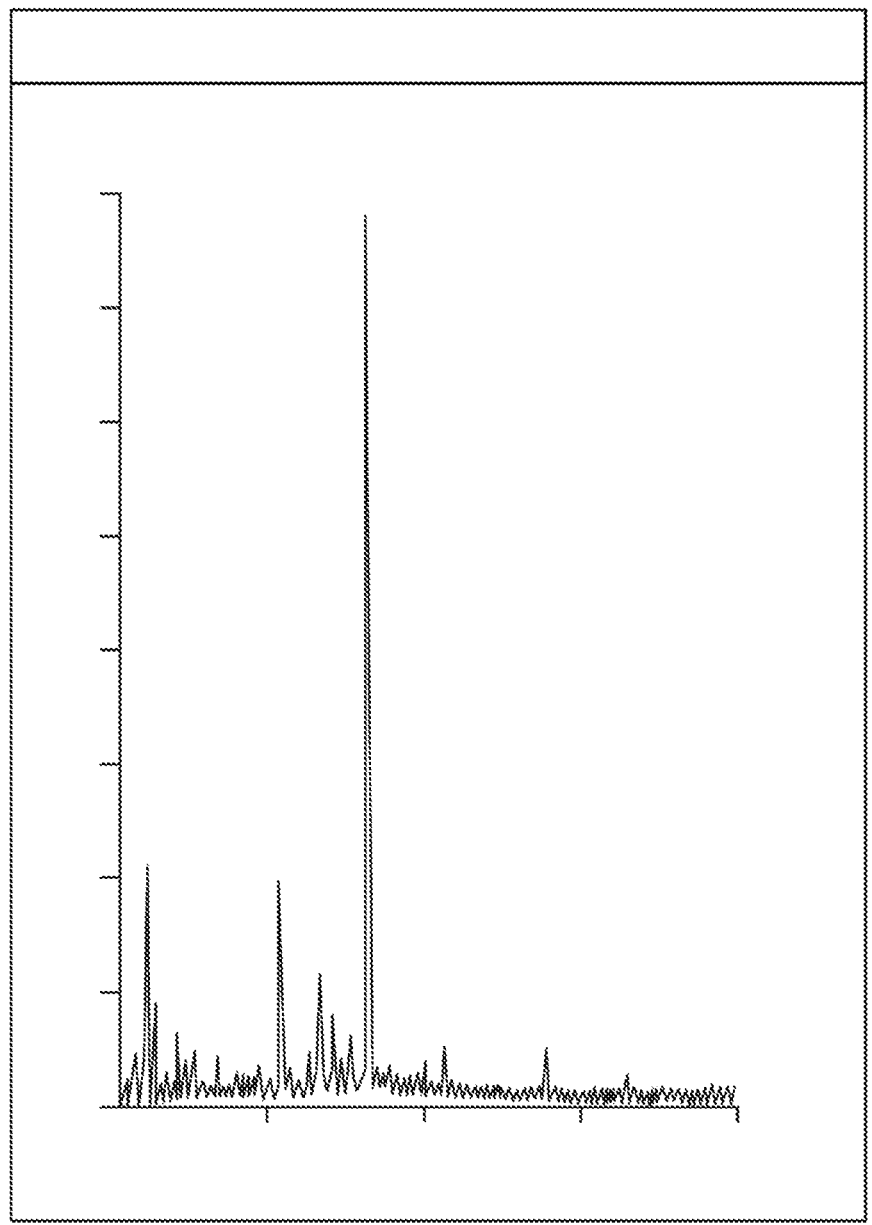
Figure 18D:
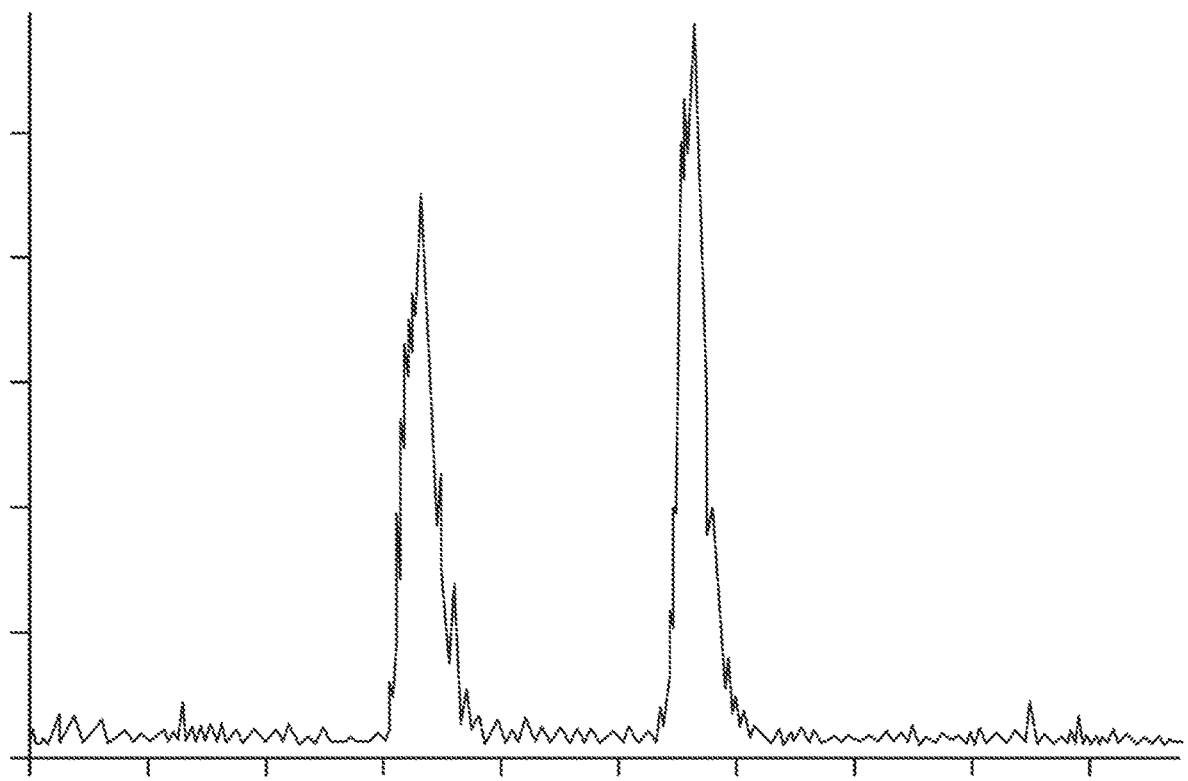
Figure 19A:
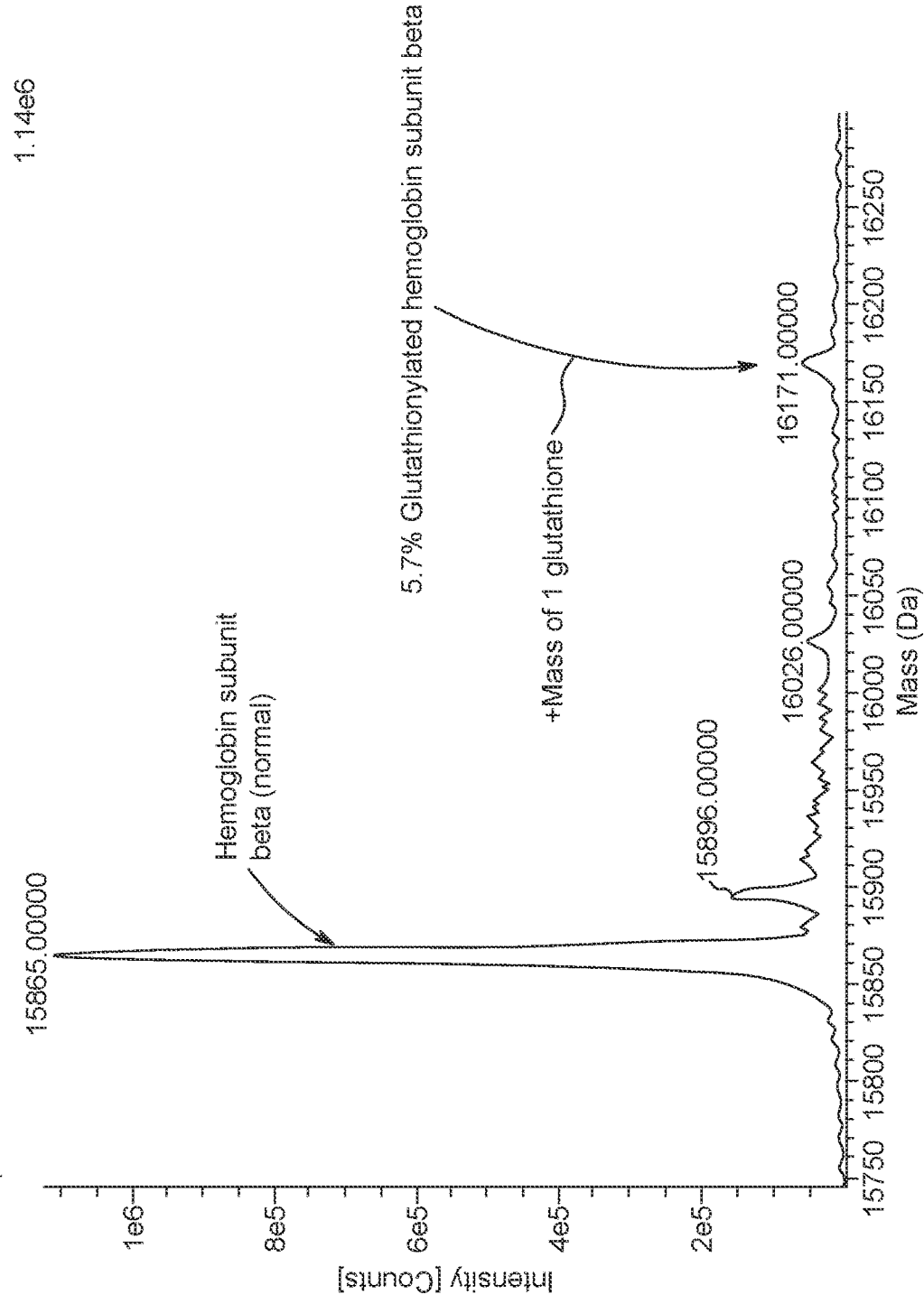
FIGS. 19A-19D are graphs representing the analysis of menstrual blood samples. The graphs are samples from four separate female subjects in which glutathionylation is detected and observed with a range from 5.7% to 12.1% glutathionylation of hemoglobin subunit beta.
Figure 19B:
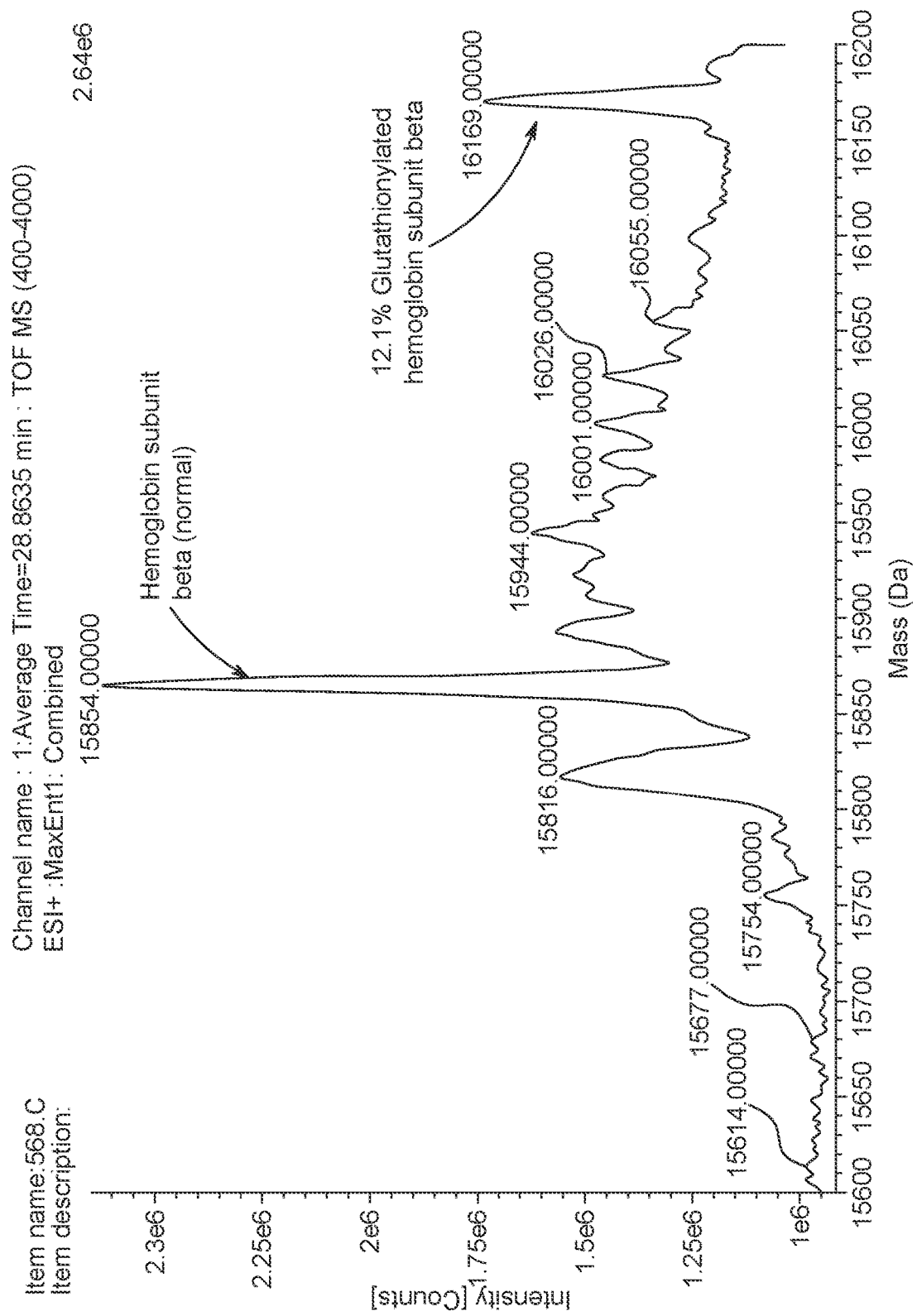
Figure 19C:
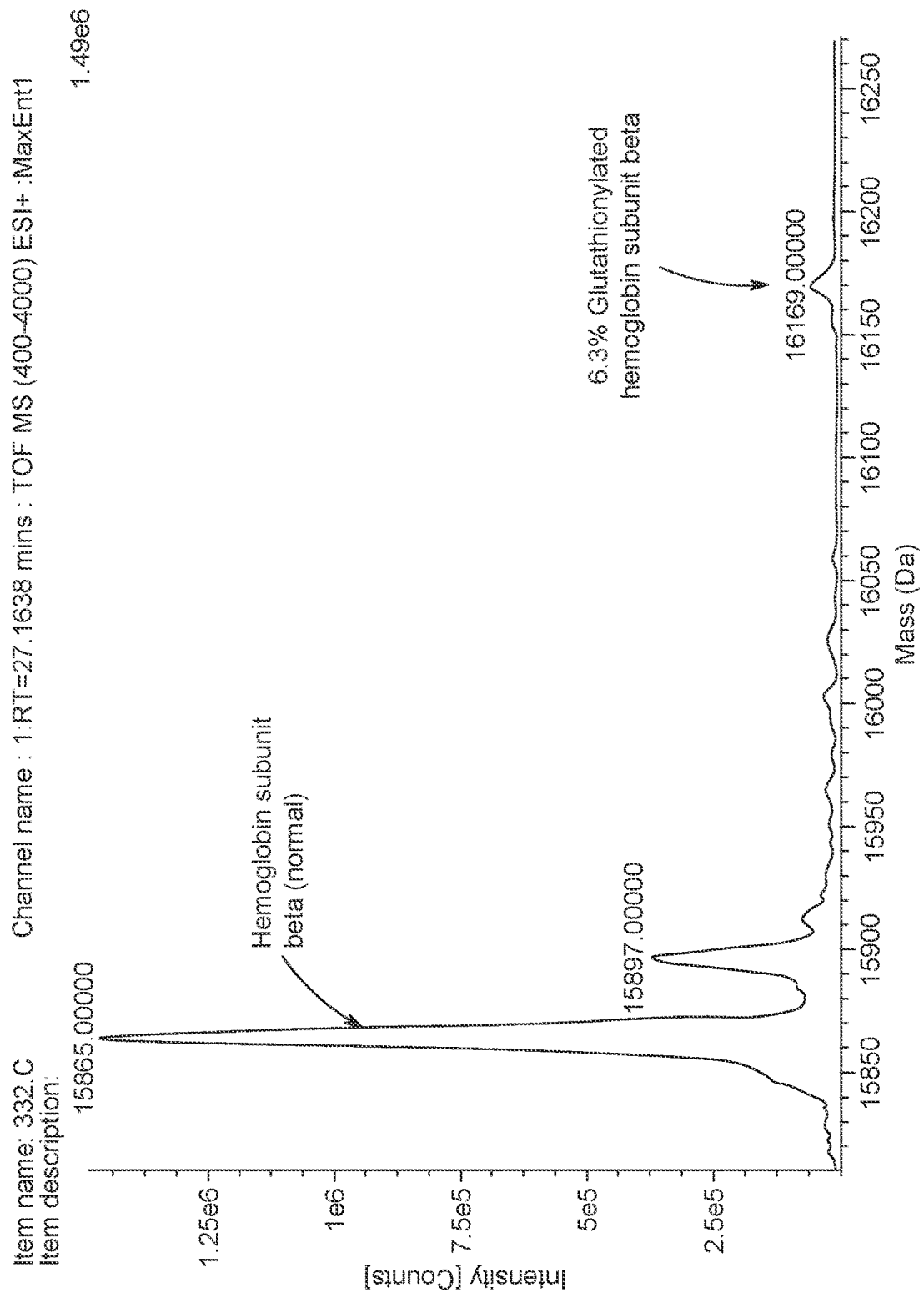
Figure 19D:
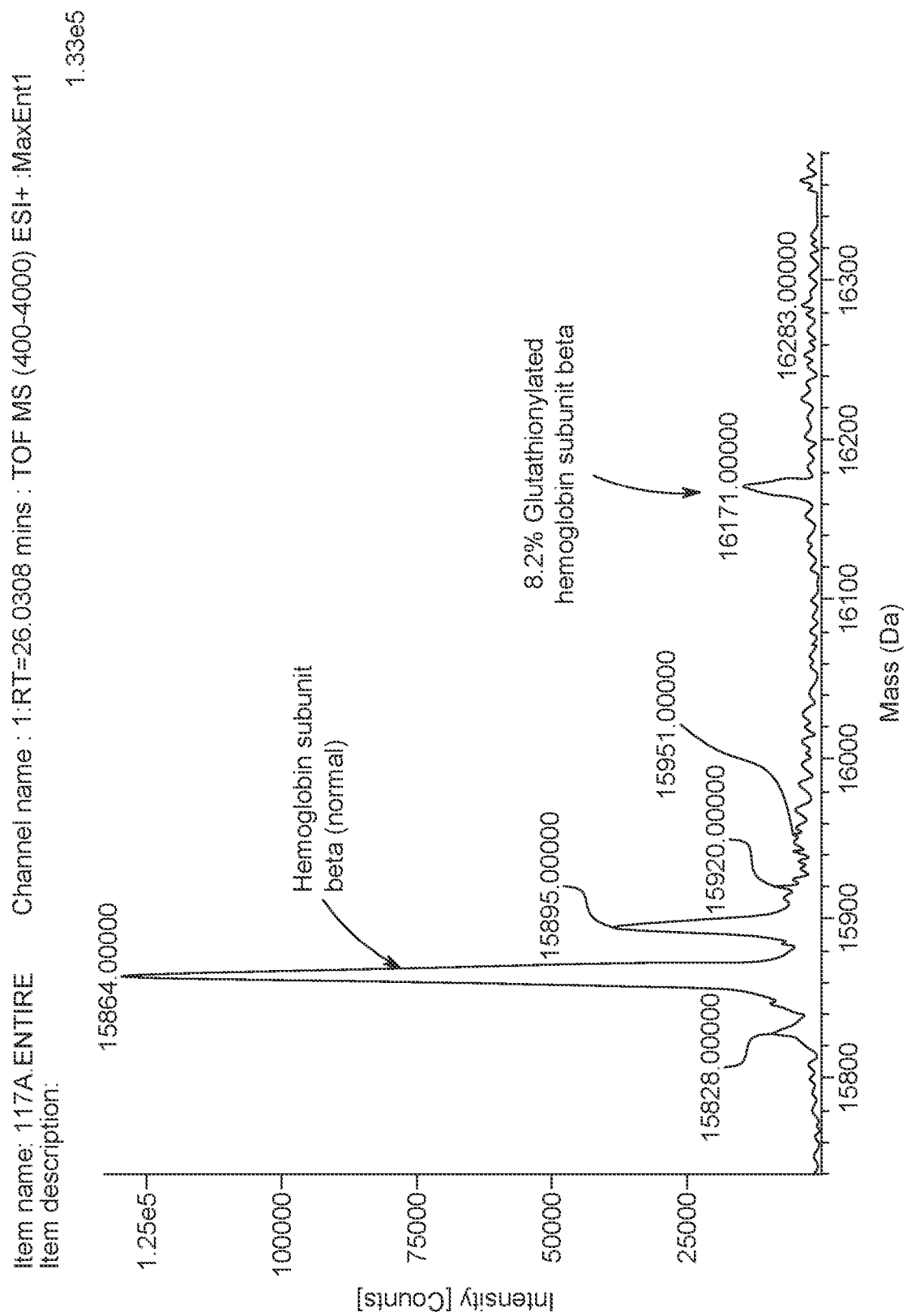
Figure 20A:
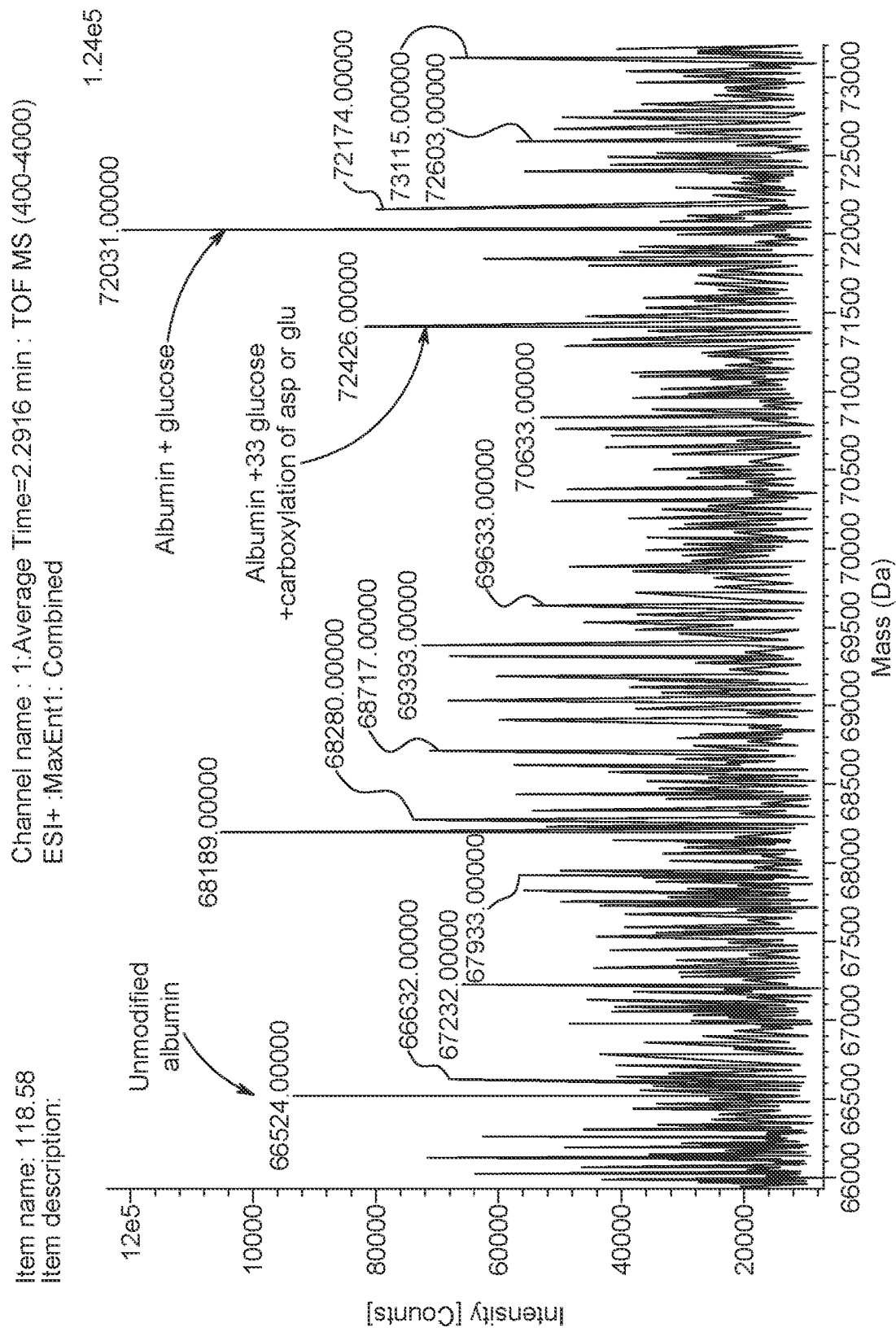
FIG. 20A-20B are graphs representing the analysis of menstrual blood samples. The graphs are samples from two separate patients in which glycated albumin is detected.
Figure 20B:
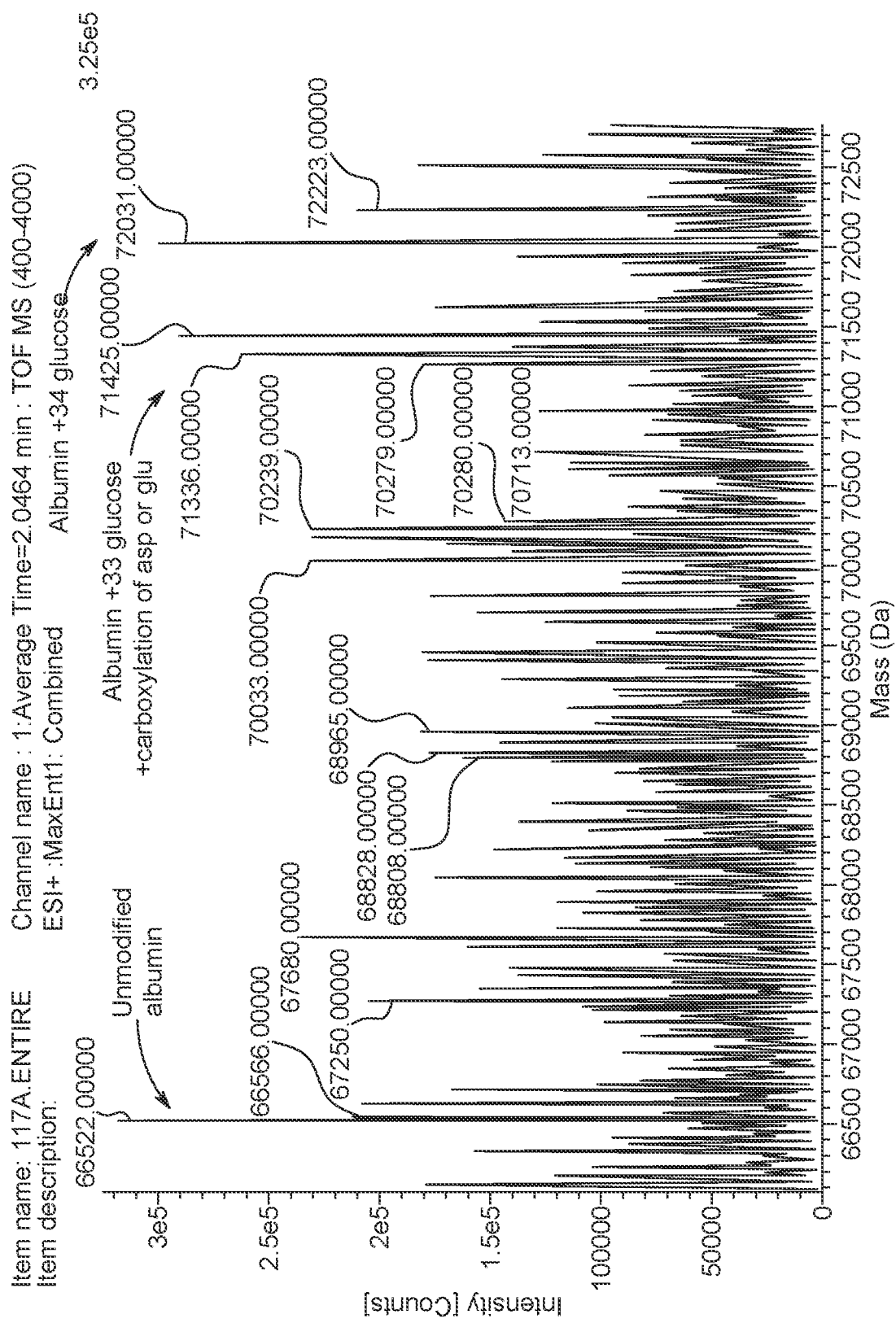

Intact protein analysis is shown in FIGS. 5A, 6A, and 7A.

While the hemoglobin subunits from fingerpick blood appeared to be glycated in a similar quantitative pattern as the HbA1c standard (1 glycation event per subunit), the menstrual fluid sample exhibited multiple glycation most clearly on the beta subunit. To investigate this phenomenon further, several menstrual fluid samples were subjected to alternative digestion (Glu-C and trypsin) and analyzed via QTOF MS/MS for the elucidation of the position of glycation. Fragment masses were detected that matched specific amino acid sequences in the hemoglobin subunit plus the mass of a glucose attached to a lysine.

Several of the sites of glycation on menstrual fluid hemoglobin subunit alpha I reported here were not detected as glycated in circulating blood. Thus, we can conclude that the additional sites are specific to menstrual blood hemoglobin subunit alpha, or at least they are the product of particularly high glucose gradients that might be present in the menstrual fluid milieu.

As suggested from the intact analysis, the predominate glycation on menstrual fluid hemoglobin was on the alpha subunit and thus the shear amount of glycated proteoforms allowed for positive identification of sites of glycation on that subunit.

What is claimed is:

1. A method of stratifying human female subject, comprising
    a. obtaining an initial sample of the female subject's menstrual fluid;
    b. separating proteins of the menstrual fluid;
    c. measuring the level of glycation, and, optionally, glutathionylation, of the hemoglobin subunit alpha in the sample and determining the number of glycation events, and, optionally, glutathionylation events on the hemoglobin alpha subunit;
    d. obtaining a subsequent sample of the female subject's menstrual fluid and performing the separating and measuring steps to determine the number of glycation events, and, optionally, glutathionylation events, on the hemoglobin alpha subunit in the subsequent sample; and
    e. assigning female subject to a category based on the number of glycation events, and, optionally glutathionylation events on the hemoglobin alpha subunit in the initial and subsequent sample of the female subject's menstrual fluid and using said category for clinical trial enrollment and/or medication dosing.

2. The method of claim 1, wherein the hemoglobin subunit alpha is positively identified from the sample through MS analysis.

3. The method of claim 1 wherein a post-translation modification of glycation and glutathionylation on the hemoglobin subunit alpha is detected.

4. The method of claim 1, wherein the initial and subsequent samples of menstrual fluid is collected using a 903 dried blood spot collection card.

5. The method of claim 1, wherein the hemoglobin subunit alpha is detected using LC-MS/MS peptide sequencing.

6. The method of claim 1, wherein multiple glycation and glutathionylation events are observed on the hemoglobin subunit alpha and assigning female subject to a category based on the number of glycation and glutathionylation events on the hemoglobin alpha subunit in the initial and subsequent sample of the female subject's menstrual fluid and using said category for clinical trial enrollment and medication dosing.

7. The method of claim 1, wherein the initial and subsequent samples of the female subject's menstrual fluid is obtained using a device comprising a disposable cartridge which is insertable into a wireless enabled device.

8. The method of claim 1, wherein the continued use of subsequent menstrual blood collection and analysis for about 3 months, or about 6 months, or about 9 months, or about 1 year, or about 2 years, or about 3 years, or about 4 years, or about 10 years, or about 20 years, or about 30 years, or about 40 years, or about 50 years is used to evaluate the increase, decrease or trend of the glycation, and, optionally, glutathionylation of the hemoglobin alpha subunit.

9. A method of detecting glycated, and, optionally, glutathionylated hemoglobin on the alpha subunit in a female patient, said method comprising:
    a. obtaining an initial menstrual fluid sample from a human female patient;
    b. detecting whether glycation, and, optionally, glutathionylation of hemoglobin alpha subunit is present in the initial menstrual fluid sample by using LC-MS/MS peptide sequencing;
    c. obtaining a subsequent menstrual fluid sample from a human female patient;
    d. detecting whether glycation, and, optionally, glutathionylation of hemoglobin alpha subunit is present in the subsequent menstrual fluid sample from a human female patient; and
    e. evaluating the increase, decrease or trend of the number of glycation events, and, optionally, glutathionylation events, on the hemoglobin alpha subunit in the initial and subsequent menstrual fluid samples to determine the diabetes and/or prediabetes status of the female patient.

10. The method of claim 9 for detecting modifications of any additional proteins on the hemoglobin alpha subunit in a female patient, said method further comprising:
    obtaining initial and subsequent menstrual fluid samples from the female patient; and
    detecting whether modification on one or more additional proteins is present in the initial and subsequent menstrual fluid sample samples by using LC-MS/MS peptide sequencing.

11. The method of claim 9 for diagnosing pre-diabetes or diabetes in a female patient, said method further comprising:
    a. obtaining initial and subsequent menstrual fluid samples from the female patient;
    b. detecting whether glycation, and, optionally, glutathionylation, of hemoglobin alpha subunit is present in the initial and subsequent menstrual fluid samples by using LC-MS/MS peptide sequencing; and
    c. diagnosing the female patient with pre-diabetes or diabetes when the presence of one or more glycation events, and, optionally, glutathionylation events, in the initial and subsequent menstrual fluid samples is detected.

12. A method of medication dosing for diabetes or pre-diabetes in a female patient, said method comprising:
    a. obtaining an initial and subsequent menstrual fluid sample from the female patient;
    b. measuring the amount of glycation, and, optionally, glutathionylation of hemoglobin subunit alpha in the initial and subsequent menstrual fluid samples;
    c. assigning the female patient to a category based on the amount of glycation, and, optionally, glutathionylation of hemoglobin subunit alpha in the initial and subsequent menstrual fluid samples and based on the increase or decrease in the amount of glycation, and, optionally, glutathionylation of hemoglobin subunit alpha in the initial and subsequent menstrual fluid samples; and
    d. administering an effective amount of medication for treating diabetes or prediabetes to the patient based on the category assigned to the patient.

* * * * *

SEQUENCE LISTING

<160> NUMBER OF SEQ ID NOS: 888

<210> SEQ ID NO 1
<211> LENGTH: 8
<212> TYPE: PRT
<213> ORGANISM: Homo sapiens

<400> SEQUENCE: 1

Val His Leu Thr Pro Glu Glu Lys
1               5

<210> SEQ ID NO 2
<211> LENGTH: 146
<212> TYPE: PRT
<213> ORGANISM: Homo sapiens

<400> SEQUENCE: 2

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 3

Gly Lys Val Gly Ala His Ala Gly Glu Tyr Gly Ala Glu
1               5                   10

<210> SEQ ID NO 4
<211> LENGTH: 25
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation [?]
<220> FEATURE:
<221> NAME/KEY: MOD_RES
<222> LOCATION: (5)..(14)
<223> OTHER INFORMATION: Glycation (3) [5 9 14]

```
<220> FEATURE:
<221> NAME/KEY: MOD_RES
<222> LOCATION: (7)..(7)
<223> OTHER INFORMATION: Deamidation N [5]

<400> SEQUENCE: 4

Ser Pro Ala Asp Lys Thr Asn Val Lys Ala Ala Trp Gly Lys Val Gly
1               5                   10                  15

Ala His Ala Gly Glu Tyr Gly Ala Glu
            20                  25

<210> SEQ ID NO 5
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation [2 ?]
<220> FEATURE:
<221> NAME/KEY: MOD_RES
<222> LOCATION: (5)..(5)
<223> OTHER INFORMATION: Deamidation N [5]

<400> SEQUENCE: 5

Ala Asp Lys Thr Asn Val Lys Ala Ala Trp Gly Lys Val Gly Ala His
1               5                   10                  15

Ala Gly Glu Tyr Gly Ala Glu
            20

<210> SEQ ID NO 6
<211> LENGTH: 28
<212> TYPE: PRT
<213> ORGANISM: Homo sapiens
<220> FEATURE:
<221> NAME/KEY: MOD_RES
<222> LOCATION: (5)..(14)
<223> OTHER INFORMATION: Glycation (3) [5 9 14]

<400> SEQUENCE: 6

Ser Pro Ala Asp Lys Thr Asn Val Lys Ala Ala Trp Gly Lys Val Gly
1               5                   10                  15

Ala His Ala Gly Glu Tyr Gly Ala Glu Ala Leu Glu
            20                  25

<210> SEQ ID NO 7
<211> LENGTH: 27
<212> TYPE: PRT
<213> ORGANISM: Homo sapiens
<220> FEATURE:
<221> NAME/KEY: MOD_RES
<222> LOCATION: (4)..(13)
<223> OTHER INFORMATION: Glycation (3) [4 8 13]
<220> FEATURE:
<221> NAME/KEY: MOD_RES
<222> LOCATION: (6)..(6)
<223> OTHER INFORMATION: Deamidation N [6]

<400> SEQUENCE: 7

Pro Ala Asp Lys Thr Asn Val Lys Ala Ala Trp Gly Lys Val Gly Ala
1               5                   10                  15

His Ala Gly Glu Tyr Gly Ala Glu Ala Leu Glu
            20                  25

<210> SEQ ID NO 8
<211> LENGTH: 23
<212> TYPE: PRT
```

```
<213> ORGANISM: Homo sapiens
<220> FEATURE:
<221> NAME/KEY: MOD_RES
<222> LOCATION: (1)..(23)
<223> OTHER INFORMATION: Glycation [?]

<400> SEQUENCE: 8

Thr Asn Val Lys Ala Ala Trp Gly Lys Val Gly Ala His Ala Gly Glu
1               5                   10                  15

Tyr Gly Ala Glu Ala Leu Glu
            20

<210> SEQ ID NO 9
<211> LENGTH: 84
<212> TYPE: PRT
<213> ORGANISM: Homo sapiens
<220> FEATURE:
<221> NAME/KEY: MOD_RES
<222> LOCATION: (1)..(84)
<223> OTHER INFORMATION: Glycation (5) [5?]
<220> FEATURE:
<221> NAME/KEY: MOD_RES
<222> LOCATION: (1)..(84)
<223> OTHER INFORMATION: Deamidation N (2) [2?]

<400> SEQUENCE: 9

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser

<210> SEQ ID NO 10
<211> LENGTH: 82
<212> TYPE: PRT
<213> ORGANISM: Homo sapiens
<220> FEATURE:
<221> NAME/KEY: MOD_RES
<222> LOCATION: (1)..(82)
<223> OTHER INFORMATION: Glycation (5) [5?]
<220> FEATURE:
<221> NAME/KEY: MOD_RES
<222> LOCATION: (1)..(82)
<223> OTHER INFORMATION: Oxidation M [?]

<400> SEQUENCE: 10

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala
```

```
<210> SEQ ID NO 11
<211> LENGTH: 81
<212> TYPE: PRT
<213> ORGANISM: Homo sapiens
<220> FEATURE:
<221> NAME/KEY: MOD_RES
<222> LOCATION: (1)..(81)
<223> OTHER INFORMATION: Deamidation N [?]
<220> FEATURE:
<221> NAME/KEY: MOD_RES
<222> LOCATION: (7)..(61)
<223> OTHER INFORMATION: Glycation (7) [7 11 16 40 56 60 61]

<400> SEQUENCE: 11

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser

<210> SEQ ID NO 12
<211> LENGTH: 70
<212> TYPE: PRT
<213> ORGANISM: Homo sapiens
<220> FEATURE:
<221> NAME/KEY: MOD_RES
<222> LOCATION: (32)..(32)
<223> OTHER INFORMATION: Oxidation M [32]

<400> SEQUENCE: 12

Val Leu Ser Pro Ala Asp Lys Thr Asn Val Lys Ala Ala Trp Gly Lys Val
1               5                   10                  15

Gly Ala His Ala Gly Glu Tyr Gly Ala Glu Ala Leu Glu Arg Met Phe
            20                  25                  30

Leu Ser Phe Pro Thr Thr Lys Thr Tyr Phe Pro His Phe Asp Leu Ser
        35                  40                  45

His Gly Ser Ala Gln Val Lys Gly His Gly Lys Lys Val Ala Asp Ala
    50                  55                  60                  65

Leu Thr Asn Ala Val
70

<210> SEQ ID NO 13
<211> LENGTH: 32
<212> TYPE: PRT
<213> ORGANISM: Homo sapiens
<220> FEATURE:
<221> NAME/KEY: MOD_RES
<222> LOCATION: (1)..(32)
<223> OTHER INFORMATION: Glycation [?]
<220> FEATURE:
<221> NAME/KEY: MOD_RES
<222> LOCATION: (1)..(32)
<223> OTHER INFORMATION: Glycation (2) [2?]
<220> FEATURE:
<221> NAME/KEY: MOD_RES
<222> LOCATION: (9)..(9)
<223> OTHER INFORMATION: Deamidation N [9]
<220> FEATURE:
```

```
<221> NAME/KEY: MOD_RES
<222> LOCATION: (32)..(32)
<223> OTHER INFORMATION: Oxidation M [32]

<400> SEQUENCE: 13

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

<210> SEQ ID NO 14
<211> LENGTH: 99
<212> TYPE: PRT
<213> ORGANISM: Homo sapiens
<220> FEATURE:
<221> NAME/KEY: MOD_RES
<222> LOCATION: (1)..(99)
<223> OTHER INFORMATION: Glycation [?]
<220> FEATURE:
<221> NAME/KEY: MOD_RES
<222> LOCATION: (51)..(80)
<223> OTHER INFORMATION: Deamidation N (3) [51 61 80]
<220> FEATURE:
<221> NAME/KEY: MOD_RES
<222> LOCATION: (87)..(87)
<223> OTHER INFORMATION: Carboxymethyl C [87]

<400> SEQUENCE: 14

Gly Ala His Ala Gly Glu Tyr Gly Ala Glu Ala Leu Glu Arg Met Phe
1               5                   10                  15

Leu Ser Phe Pro Thr Thr Lys Thr Tyr Phe Pro His Phe Asp Leu Ser
                20                  25                  30

His Gly Ser Ala Gln Val Lys Gly His Gly Lys Lys Val Ala Asp Ala
            35                  40                  45

Leu Thr Asn Ala Val Ala His Val Asp Asp Met Pro Asn Ala Leu Ser
        50                  55                  60

Ala Leu Ser Asp Leu His Ala His Lys Leu Arg Val Asp Pro Val Asn
65                  70                  75                  80

Phe Lys Leu Leu Ser His Cys Leu Leu Val Thr Leu Ala Ala His Leu
                85                  90                  95

Pro Ala Glu

<210> SEQ ID NO 15
<211> LENGTH: 98
<212> TYPE: PRT
<213> ORGANISM: Homo sapiens
<220> FEATURE:
<221> NAME/KEY: MOD_RES
<222> LOCATION: (1)..(98)
<223> OTHER INFORMATION: Glycation [?]
<220> FEATURE:
<221> NAME/KEY: MOD_RES
<222> LOCATION: (50)..(79)
<223> OTHER INFORMATION: Deamidation N (3) [50 60 79]
<220> FEATURE:
<221> NAME/KEY: MOD_RES
<222> LOCATION: (86)..(86)
<223> OTHER INFORMATION: Carboxymethyl C [86]

<400> SEQUENCE: 15

Ala His Ala Gly Glu Tyr Gly Ala Glu Ala Leu Glu Arg Met Phe Leu
1               5                   10                  15

Ser Phe Pro Thr Thr Lys Thr Tyr Phe Pro His Phe Asp Leu Ser His
                20                  25                  30

Gly Ser Ala Gln Val Lys Gly His Gly Lys Lys Val Ala Asp Ala Leu
```

```
                    35                  40                  45
Thr Asn Ala Val Ala His Val Asp Asp Met Pro Asn Ala Leu Ser Ala
             50                  55                  60

Leu Ser Asp Leu His Ala His Lys Leu Arg Val Asp Pro Val Asn Phe
65                  70                  75                  80

Lys Leu Leu Ser His Cys Leu Leu Val Thr Leu Ala Ala His Leu Pro
                85                  90                  95

Ala Glu

<210> SEQ ID NO 16
<211> LENGTH: 108
<212> TYPE: PRT
<213> ORGANISM: Homo sapiens
<220> FEATURE:
<221> NAME/KEY: MOD_RES
<222> LOCATION: (1)..(108)
<223> OTHER INFORMATION: Glycation (6) [6?]
<220> FEATURE:
<221> NAME/KEY: MOD_RES
<222> LOCATION: (1)..(108)
<223> OTHER INFORMATION: Deamidation N (3) [3?]
<220> FEATURE:
<221> NAME/KEY: MOD_RES
<222> LOCATION: (24)..(68)
<223> OTHER INFORMATION: Oxidation M (2) [24 68]
<220> FEATURE:
<221> NAME/KEY: MOD_RES
<222> LOCATION: (96)..(96)
<223> OTHER INFORMATION: Carboxymethyl C [96]

<400> SEQUENCE: 16

Asn Val Lys Ala Ala Trp Gly Lys Val Gly Ala His Ala Gly Glu Tyr
1               5                   10                  15

Gly Ala Glu Ala Leu Glu Arg Met Phe Leu Ser Phe Pro Thr Thr Lys
                20                  25                  30

Thr Tyr Phe Pro His Phe Asp Leu Ser His Gly Ser Ala Gln Val Lys
            35                  40                  45

Gly His Gly Lys Lys Val Ala Asp Ala Leu Thr Asn Ala Val Ala His
        50                  55                  60

Val Asp Asp Met Pro Asn Ala Leu Ser Ala Leu Ser Asp Leu His Ala
65                  70                  75                  80

His Lys Leu Arg Val Asp Pro Val Asn Phe Lys Leu Leu Ser His Cys
                85                  90                  95

Leu Leu Val Thr Leu Ala Ala His Leu Pro Ala Glu
            100                 105

<210> SEQ ID NO 17
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (9)..(9)
<223> OTHER INFORMATION: Deamidation N [9]

<400> SEQUENCE: 17

Val Leu Ser Pro Ala Asp Lys Thr Asn
1               5

<210> SEQ ID NO 18
```

```
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]

<400> SEQUENCE: 18

Val Leu Ser Pro Ala Asp Lys Thr
1               5

<210> SEQ ID NO 19
<211> LENGTH: 13
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Glycation [?]

<400> SEQUENCE: 19

Lys Ala Ala Trp Gly Lys Val Gly Ala His Ala Gly Glu
1               5                   10

<210> SEQ ID NO 20
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 20

Trp Gly Lys Val Gly Ala His Ala Gly Glu
1               5                   10

<210> SEQ ID NO 21
<211> LENGTH: 93
<212> TYPE: PRT
<213> ORGANISM: Homo sapiens
<220> FEATURE:
<221> NAME/KEY: MOD_RES
<222> LOCATION: (1)..(93)
<223> OTHER INFORMATION: Glycation [?]
<220> FEATURE:
<221> NAME/KEY: MOD_RES
<222> LOCATION: (1)..(93)
<223> OTHER INFORMATION: Deamidation N [?]
<220> FEATURE:
<221> NAME/KEY: MOD_RES
<222> LOCATION: (9)..(53)
<223> OTHER INFORMATION: Oxidation M (2) [9 53]
<220> FEATURE:
<221> NAME/KEY: MOD_RES
<222> LOCATION: (81)..(81)
<223> OTHER INFORMATION: Carboxymethyl C [81]

<400> SEQUENCE: 21

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn Ala Val Ala
        35                  40                  45

His Val Asp Asp Met Pro Asn Ala Leu Ser Ala Leu Ser Asp Leu His
    50                  55                  60
```

```
Ala His Lys Leu Arg Val Asp Pro Val Asn Phe Lys Leu Leu Ser His
 65                  70                  75                  80

Cys Leu Leu Val Thr Leu Ala Ala His Leu Pro Ala Glu
                 85                  90
```

<210> SEQ ID NO 22
<211> LENGTH: 74
<212> TYPE: PRT
<213> ORGANISM: Homo sapiens
<220> FEATURE:
<221> NAME/KEY: MOD_RES
<222> LOCATION: (9)..(53)
<223> OTHER INFORMATION: Oxidation M (2) [9 53]
<220> FEATURE:
<221> NAME/KEY: MOD_RES
<222> LOCATION: (17)..(67)
<223> OTHER INFORMATION: Glycation (5) [17 33 37 38 67]
<220> FEATURE:
<221> NAME/KEY: MOD_RES
<222> LOCATION: (74)..(74)
<223> OTHER INFORMATION: Deamidation N [74]

<400> SEQUENCE: 22

```
Tyr Gly Ala Glu Ala Leu Glu Arg Met Phe Leu Ser Phe Pro Thr Thr
 1               5                  10                  15

Lys Thr Tyr Phe Pro His Phe Asp Leu Ser His Gly Ser Ala Gln Val
                 20                  25                  30

Lys Gly His Gly Lys Lys Val Ala Asp Ala Leu Thr Asn Ala Val Ala
             35                  40                  45

His Val Asp Asp Met Pro Asn Ala Leu Ser Ala Leu Ser Asp Leu His
 50                  55                  60

Ala His Lys Leu Arg Val Asp Pro Val Asn
 65                  70
```

<210> SEQ ID NO 23
<211> LENGTH: 64
<212> TYPE: PRT
<213> ORGANISM: Homo sapiens
<220> FEATURE:
<221> NAME/KEY: MOD_RES
<222> LOCATION: (1)..(64)
<223> OTHER INFORMATION: Deamidation N [?]
<220> FEATURE:
<221> NAME/KEY: MOD_RES
<222> LOCATION: (1)..(64)
<223> OTHER INFORMATION: Glycation (3) [3?]
<220> FEATURE:
<221> NAME/KEY: MOD_RES
<222> LOCATION: (9)..(53)
<223> OTHER INFORMATION: Oxidation M (2) [9 53]

<400> SEQUENCE: 23

```
Tyr Gly Ala Glu Ala Leu Glu Arg Met Phe Leu Ser Phe Pro Thr Thr
 1               5                  10                  15

Lys Thr Tyr Phe Pro His Phe Asp Leu Ser His Gly Ser Ala Gln Val
                 20                  25                  30

Lys Gly His Gly Lys Lys Val Ala Asp Ala Leu Thr Asn Ala Val Ala
             35                  40                  45

His Val Asp Asp Met Pro Asn Ala Leu Ser Ala Leu Ser Asp Leu His
 50                  55                  60
```

<210> SEQ ID NO 24
<211> LENGTH: 62
<212> TYPE: PRT
<213> ORGANISM: Homo sapiens
<220> FEATURE:

-continued

```
<221> NAME/KEY: MOD_RES
<222> LOCATION: (45)..(55)
<223> OTHER INFORMATION: Deamidation N (2) [45 55]

<400> SEQUENCE: 24

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn Ala Val Ala
        35                  40                  45

His Val Asp Asp Met Pro Asn Ala Leu Ser Ala Leu Ser Asp
    50                  55                  60

<210> SEQ ID NO 25
<211> LENGTH: 58
<212> TYPE: PRT
<213> ORGANISM: Homo sapiens
<220> FEATURE:
<221> NAME/KEY: MOD_RES
<222> LOCATION: (1)..(58)
<223> OTHER INFORMATION: Glycation (2) [2?]
<220> FEATURE:
<221> NAME/KEY: MOD_RES
<222> LOCATION: (1)..(58)
<223> OTHER INFORMATION: Deamidation N [?]
<220> FEATURE:
<221> NAME/KEY: MOD_RES
<222> LOCATION: (9)..(53)
<223> OTHER INFORMATION: Oxidation M (2) [9 53]
<220> FEATURE:
<221> NAME/KEY: MOD_RES
<222> LOCATION: (45)..(55)
<223> OTHER INFORMATION: Deamidation N (2) [45 55]

<400> SEQUENCE: 25

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn Ala Val Ala
        35                  40                  45

His Val Asp Asp Met Pro Asn Ala Leu Ser
    50                  55

<210> SEQ ID NO 26
<211> LENGTH: 55
<212> TYPE: PRT
<213> ORGANISM: Homo sapiens
<220> FEATURE:
<221> NAME/KEY: MOD_RES
<222> LOCATION: (1)..(55)
<223> OTHER INFORMATION: Oxidation M [?]
<220> FEATURE:
<221> NAME/KEY: MOD_RES
<222> LOCATION: (1)..(55)
<223> OTHER INFORMATION: Deamidation N [?]
<220> FEATURE:
<221> NAME/KEY: MOD_RES
<222> LOCATION: (17)..(38)
<223> OTHER INFORMATION: Glycation (4) [17 33 37 38]

<400> SEQUENCE: 26

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30
```

```
Lys Gly His Gly Lys Lys Val Ala Asp Ala Leu Thr Asn Ala Val Ala
        35                  40                  45

His Val Asp Asp Met Pro Asn
    50                  55

<210> SEQ ID NO 27
<211> LENGTH: 50
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Oxidation M [9]
<220> FEATURE:
<221> NAME/KEY: MOD_RES
<222> LOCATION: (17)..(38)
<223> OTHER INFORMATION: Glycation (4) [17 33 37 38]

<400> SEQUENCE: 27

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn Ala Val Ala
        35                  40                  45

His Val
    50

<210> SEQ ID NO 28
<211> LENGTH: 45
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Oxidation M [9]
<220> FEATURE:
<221> NAME/KEY: MOD_RES
<222> LOCATION: (17)..(38)
<223> OTHER INFORMATION: Glycation (4) [17 33 37 38]
<220> FEATURE:
<221> NAME/KEY: MOD_RES
<222> LOCATION: (45)..(45)
<223> OTHER INFORMATION: Deamidation N [45]

<400> SEQUENCE: 28

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn
        35                  40                  45

<210> SEQ ID NO 29
<211> LENGTH: 88
<212> TYPE: PRT
<213> ORGANISM: Homo sapiens
<220> FEATURE:
<221> NAME/KEY: MOD_RES
<222> LOCATION: (1)..(88)
<223> OTHER INFORMATION: Deamidation N (2) [2?]
<220> FEATURE:
<221> NAME/KEY: MOD_RES
<222> LOCATION: (1)..(88)
<223> OTHER INFORMATION: Glycation (4) [4?]
<220> FEATURE:
<221> NAME/KEY: MOD_RES
```

<222> LOCATION: (9)..(53)
<223> OTHER INFORMATION: Oxidation M (2) [9 53]
<220> FEATURE:
<221> NAME/KEY: MOD_RES
<222> LOCATION: (81)..(81)
<223> OTHER INFORMATION: Carboxymethyl C [81]

<400> SEQUENCE: 29

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Thr Asn Ala Val Ala
        35                  40                  45

His Val Asp Asp Met Pro Asn Ala Leu Ser Ala Leu Ser Asp Leu His
    50                  55                  60

Ala His Lys Leu Arg Val Asp Pro Val Asn Phe Lys Leu Leu Ser His
65                  70                  75                  80

Cys Leu Leu Val Thr Leu Ala Ala
                85

<210> SEQ ID NO 30
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Oxidation M [9]
<220> FEATURE:
<221> NAME/KEY: MOD_RES
<222> LOCATION: (17)..(17)
<223> OTHER INFORMATION: Glycation [17]

<400> SEQUENCE: 30

Tyr Gly Ala Glu Ala Leu Glu Arg Met Phe Leu Ser Phe Pro Thr Thr
1               5                   10                  15

Lys Thr Tyr

<210> SEQ ID NO 31
<211> LENGTH: 83
<212> TYPE: PRT
<213> ORGANISM: Homo sapiens
<220> FEATURE:
<221> NAME/KEY: MOD_RES
<222> LOCATION: (1)..(83)
<223> OTHER INFORMATION: Oxidation M [?]
<220> FEATURE:
<221> NAME/KEY: MOD_RES
<222> LOCATION: (17)..(76)
<223> OTHER INFORMATION: Glycation (6) [17 33 37 38 67 76]
<220> FEATURE:
<221> NAME/KEY: MOD_RES
<222> LOCATION: (45)..(74)
<223> OTHER INFORMATION: Deamidation N (3) [45 55 74]
<220> FEATURE:
<221> NAME/KEY: MOD_RES
<222> LOCATION: (81)..(81)
<223> OTHER INFORMATION: Carboxymethyl C [81]

<400> SEQUENCE: 31

Tyr Gly Ala Glu Ala Leu Glu Arg Met Phe Leu Ser Phe Pro Thr Thr
1               5                   10                  15

Lys Thr Tyr Phe Pro His Phe Asp Leu Ser His Gly Ser Ala Gln Val
            20                  25                  30

Lys Gly His Gly Lys Lys Val Ala Asp Ala Leu Asn Ala Val Ala His

-continued

```
                35                  40                  45

Val Asp Asp Met Pro Asn Ala Leu Ser Ala Leu Ser Asp Leu His Ala
 50                  55                  60

His Lys Leu Arg Val Asp Pro Val Asn Phe Lys Leu Ser His Cys
 65                  70                  75                  80

Leu Leu Val

<210> SEQ ID NO 32
<211> LENGTH: 91
<212> TYPE: PRT
<213> ORGANISM: Homo sapiens
<220> FEATURE:
<221> NAME/KEY: MOD_RES
<222> LOCATION: (1)..(91)
<223> OTHER INFORMATION: Deamidation N (2) [2?]
<220> FEATURE:
<221> NAME/KEY: MOD_RES
<222> LOCATION: (1)..(91)
<223> OTHER INFORMATION: Glycation [?]
<220> FEATURE:
<221> NAME/KEY: MOD_RES
<222> LOCATION: (79)..(79)
<223> OTHER INFORMATION: Carboxymethyl C [79]

<400> SEQUENCE: 32

Ala Glu Ala Leu Glu Arg Met Phe Leu Ser Phe Pro Thr Thr Lys Thr
 1                5                  10                  15

Tyr Phe Pro His Phe Asp Leu Ser His Gly Ser Ala Gln Val Lys Gly
                 20                  25                  30

His Gly Lys Lys Val Ala Asp Ala Leu Thr Asn Ala Val Ala His Val
             35                  40                  45

Asp Asp Met Pro Asn Ala Leu Ser Ala Leu Ser Asp Leu His Ala His
 50                  55                  60

Lys Leu Arg Val Asp Pro Val Asn Phe Lys Leu Leu Ser His Cys Leu
 65                  70                  75                  80

Leu Val Thr Leu Ala Ala His Leu Pro Ala Glu
                 85                  90

<210> SEQ ID NO 33
<211> LENGTH: 114
<212> TYPE: PRT
<213> ORGANISM: Homo sapiens
<220> FEATURE:
<221> NAME/KEY: MOD_RES
<222> LOCATION: (1)..(114)
<223> OTHER INFORMATION: Glycation (4) [4?]
<220> FEATURE:
<221> NAME/KEY: MOD_RES
<222> LOCATION: (6)..(50)
<223> OTHER INFORMATION: Oxidation M (2) [6 50]
<220> FEATURE:
<221> NAME/KEY: MOD_RES
<222> LOCATION: (78)..(78)
<223> OTHER INFORMATION: Carboxymethyl C [78]

<400> SEQUENCE: 33

Glu Ala Leu Glu Arg Met Phe Leu Ser Phe Pro Thr Thr Lys Thr Tyr
 1                5                  10                  15

Phe Pro His Phe Asp Leu Ser His Gly Ser Ala Gln Val Lys Gly His
                 20                  25                  30

Gly Lys Lys Val Ala Asp Ala Leu Asn Ala Val Ala His Val Asp Asp
             35                  40                  45

Met Pro Asn Ala Leu Ser Ala Leu Ser Asp Leu His Ala His Lys Leu
 50                  55                  60
```

```
Arg Val Asp Pro Val Asn Phe Lys Leu Leu Ser His Cys Leu Leu Val
 65                  70                  75                  80

Thr Leu Ala Ala His Leu Pro Ala Glu Phe Thr Pro Ala Val His Ala
                 85                  90                  95

Ser Leu Asp Lys Phe Leu Ala Ser Val Ser Thr Val Leu Thr Ser Lys
            100                 105                 110

Tyr Arg

<210> SEQ ID NO 34
<211> LENGTH: 89
<212> TYPE: PRT
<213> ORGANISM: Homo sapiens
<220> FEATURE:
<221> NAME/KEY: MOD_RES
<222> LOCATION: (1)..(89)
<223> OTHER INFORMATION: Oxidation M [?]
<220> FEATURE:
<221> NAME/KEY: MOD_RES
<222> LOCATION: (1)..(89)
<223> OTHER INFORMATION: Deamidation N [?]
<220> FEATURE:
<221> NAME/KEY: MOD_RES
<222> LOCATION: (77)..(77)
<223> OTHER INFORMATION: Carboxymethyl C [77]

<400> SEQUENCE: 34

Ala Leu Glu Arg Met Phe Leu Ser Phe Pro Thr Thr Lys Thr Tyr Phe
  1               5                  10                  15

Pro His Phe Asp Leu Ser His Gly Ser Ala Gln Val Lys Gly His Gly
                 20                  25                  30

Lys Lys Val Ala Asp Ala Leu Thr Asn Ala Val Ala His Val Asp Asp
             35                  40                  45

Met Pro Asn Ala Leu Ser Ala Leu Ser Asp Leu His Ala His Lys Leu
         50                  55                  60

Arg Val Asp Pro Val Asn Phe Lys Leu Leu Ser His Cys Leu Leu Val
 65                  70                  75                  80

Thr Leu Ala Ala His Leu Pro Ala Glu
                 85

<210> SEQ ID NO 35
<211> LENGTH: 87
<212> TYPE: PRT
<213> ORGANISM: Homo sapiens
<220> FEATURE:
<221> NAME/KEY: MOD_RES
<222> LOCATION: (1)..(87)
<223> OTHER INFORMATION: Oxidation M [?]
<220> FEATURE:
<221> NAME/KEY: MOD_RES
<222> LOCATION: (1)..(87)
<223> OTHER INFORMATION: Glycation (2) [2?]
<220> FEATURE:
<221> NAME/KEY: MOD_RES
<222> LOCATION: (1)..(87)
<223> OTHER INFORMATION: Deamidation N [?]
<220> FEATURE:
<221> NAME/KEY: MOD_RES
<222> LOCATION: (77)..(77)
<223> OTHER INFORMATION: Carboxymethyl C [77]

<400> SEQUENCE: 35

Ala Leu Glu Arg Met Phe Leu Ser Phe Pro Thr Thr Lys Thr Tyr Phe
  1               5                  10                  15

Pro His Phe Asp Leu Ser His Gly Ser Ala Gln Val Lys Gly His Gly
                 20                  25                  30
```

```
Lys Lys Val Ala Asp Ala Leu Thr Asn Ala Val Ala His Val Asp Asp
        35                  40                  45

Met Pro Asn Ala Leu Ser Ala Leu Ser Asp Leu His Ala His Lys Leu
    50                  55                  60

Arg Val Asp Pro Val Asn Phe Lys Leu Leu Ser His Cys Leu Leu Val
65                  70                  75                  80

Thr Leu Ala Ala His Leu Pro
                85

<210> SEQ ID NO 36
<211> LENGTH: 69
<212> TYPE: PRT
<213> ORGANISM: Homo sapiens
<220> FEATURE:
<221> NAME/KEY: MOD_RES
<222> LOCATION: (1)..(69)
<223> OTHER INFORMATION: Glycation (4) [4?]
<220> FEATURE:
<221> NAME/KEY: MOD_RES
<222> LOCATION: (5)..(49)
<223> OTHER INFORMATION: Oxidation M (2) [5 49]

<400> SEQUENCE: 36

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
                20                  25                  30

Lys Lys Val Ala Asp Ala Leu Thr Asn Ala Val Ala His Val Asp Asp
        35                  40                  45

Met Pro Asn Ala Leu Ser Ala Leu Ser Asp Leu His Ala His Lys Leu
    50                  55                  60

Arg Val Asp Pro Val
65

<210> SEQ ID NO 37
<211> LENGTH: 65
<212> TYPE: PRT
<213> ORGANISM: Homo sapiens
<220> FEATURE:
<221> NAME/KEY: MOD_RES
<222> LOCATION: (1)..(65)
<223> OTHER INFORMATION: Glycation (4) [4?]
<220> FEATURE:
<221> NAME/KEY: MOD_RES
<222> LOCATION: (1)..(65)
<223> OTHER INFORMATION: Deamidation N [?]
<220> FEATURE:
<221> NAME/KEY: MOD_RES
<222> LOCATION: (5)..(49)
<223> OTHER INFORMATION: Oxidation M (2) [5 49]

<400> SEQUENCE: 37

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
                20                  25                  30

Lys Lys Val Ala Asp Ala Leu Thr Asn Ala Val Ala His Val Asp Asp
        35                  40                  45

Met Pro Asn Ala Leu Ser Ala Leu Ser Asp Leu His Ala His Lys Leu
    50                  55                  60

Arg
65
```

```
<210> SEQ ID NO 38
<211> LENGTH: 64
<212> TYPE: PRT
<213> ORGANISM: Homo sapiens
<220> FEATURE:
<221> NAME/KEY: MOD_RES
<222> LOCATION: (1)..(64)
<223> OTHER INFORMATION: Glycation [?]
<220> FEATURE:
<221> NAME/KEY: MOD_RES
<222> LOCATION: (1)..(64)
<223> OTHER INFORMATION: Deamidation N [?]

<400> SEQUENCE: 38

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
        35                  40                  45

Met Pro Asn Ala Leu Ser Ala Leu Ser Asp Leu His Ala His Lys Leu
    50                  55                  60

<210> SEQ ID NO 39
<211> LENGTH: 63
<212> TYPE: PRT
<213> ORGANISM: Homo sapiens
<220> FEATURE:
<221> NAME/KEY: MOD_RES
<222> LOCATION: (1)..(63)
<223> OTHER INFORMATION: Glycation (3) [3?]
<220> FEATURE:
<221> NAME/KEY: MOD_RES
<222> LOCATION: (1)..(63)
<223> OTHER INFORMATION: Deamidation N [?]

<400> SEQUENCE: 39

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
        35                  40                  45

Met Pro Asn Ala Leu Ser Ala Leu Ser Asp Leu His Ala His Lys
    50                  55                  60

<210> SEQ ID NO 40
<211> LENGTH: 62
<212> TYPE: PRT
<213> ORGANISM: Homo sapiens
<220> FEATURE:
<221> NAME/KEY: MOD_RES
<222> LOCATION: (1)..(62)
<223> OTHER INFORMATION: Oxidation M [?]
<220> FEATURE:
<221> NAME/KEY: MOD_RES
<222> LOCATION: (13)..(34)
<223> OTHER INFORMATION: Glycation (4) [13 29 33 34]

<400> SEQUENCE: 40

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
```

Met Pro Asn Ala Leu Ser Ala Leu Ser Asp Leu His Ala His
    50                  55                  60

<210> SEQ ID NO 41
<211> LENGTH: 60
<212> TYPE: PRT
<213> ORGANISM: Homo sapiens
<220> FEATURE:
<221> NAME/KEY: MOD_RES
<222> LOCATION: (1)..(60)
<223> OTHER INFORMATION: Glycation (3) [3?]

<400> SEQUENCE: 41

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
        35                  40                  45

Met Pro Asn Ala Leu Ser Ala Leu Ser Asp Leu His
    50                  55                  60

<210> SEQ ID NO 42
<211> LENGTH: 57
<212> TYPE: PRT
<213> ORGANISM: Homo sapiens
<220> FEATURE:
<221> NAME/KEY: MOD_RES
<222> LOCATION: (1)..(57)
<223> OTHER INFORMATION: Glycation (2) [2?]
<220> FEATURE:
<221> NAME/KEY: MOD_RES
<222> LOCATION: (41)..(51)
<223> OTHER INFORMATION: Deamidation N (2) [41 51]

<400> SEQUENCE: 42

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
        35                  40                  45

Met Pro Asn Ala Leu Ser Ala Leu Ser
    50                  55

<210> SEQ ID NO 43
<211> LENGTH: 53
<212> TYPE: PRT
<213> ORGANISM: Homo sapiens
<220> FEATURE:
<221> NAME/KEY: MOD_RES
<222> LOCATION: (1)..(53)
<223> OTHER INFORMATION: Oxidation M [?]
<220> FEATURE:
<221> NAME/KEY: MOD_RES
<222> LOCATION: (13)..(34)
<223> OTHER INFORMATION: Glycation (4) [13 29 33 34]
<220> FEATURE:
<221> NAME/KEY: MOD_RES
<222> LOCATION: (41)..(51)
<223> OTHER INFORMATION: Deamidation N (2) [41 51]

<400> SEQUENCE: 43

Ala Leu Glu Arg Met Phe Leu Ser Phe Pro Thr Thr Lys Thr Tyr Phe
1               5                   10                  15

-continued

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
        35                  40                  45

Met Pro Asn Ala Leu
    50

<210> SEQ ID NO 44
<211> LENGTH: 46
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]

<400> SEQUENCE: 44

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val
        35                  40                  45

<210> SEQ ID NO 45
<211> LENGTH: 43
<212> TYPE: PRT
<213> ORGANISM: Homo sapiens
<220> FEATURE:
<221> NAME/KEY: MOD_RES
<222> LOCATION: (1)..(43)
<223> OTHER INFORMATION: Glycation [?]
<220> FEATURE:
<221> NAME/KEY: MOD_RES
<222> LOCATION: (41)..(41)
<223> OTHER INFORMATION: Deamidation N [41]

<400> SEQUENCE: 45

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val
        35                  40

<210> SEQ ID NO 46
<211> LENGTH: 83
<212> TYPE: PRT
<213> ORGANISM: Homo sapiens
<220> FEATURE:
<221> NAME/KEY: MOD_RES
<222> LOCATION: (1)..(83)
<223> OTHER INFORMATION: Glycation (2) [2?]
<220> FEATURE:
<221> NAME/KEY: MOD_RES
<222> LOCATION: (41)..(70)
<223> OTHER INFORMATION: Deamidation N (3) [41 51 70]
<220> FEATURE:
<221> NAME/KEY: MOD_RES
<222> LOCATION: (77)..(77)
<223> OTHER INFORMATION: Carboxymethyl C [77]

<400> SEQUENCE: 46

Ala Leu Glu Arg Met Phe Leu Ser Phe Pro Thr Thr Lys Thr Tyr Phe
1               5                   10                  15

-continued

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
            35                  40                  45

Met Pro Asn Ala Leu Ser Ala Leu Ser Asp Leu His Ala His Lys Leu
        50                  55                  60

Arg Val Asp Pro Val Asn Phe Lys Leu Leu Ser His Cys Leu Leu Val
65                  70                  75                  80

Thr Leu Ala

<210> SEQ ID NO 47
<211> LENGTH: 21
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Glycation [13]

<400> SEQUENCE: 47

Ala Leu Glu Arg Met Phe Leu Ser Phe Pro Thr Thr Lys Thr Tyr Phe
1               5                   10                  15

Pro His Phe Asp Leu
            20

<210> SEQ ID NO 48
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]

<400> SEQUENCE: 48

Ala Leu Glu Arg Met Phe Leu Ser Phe Pro Thr
1               5                   10

<210> SEQ ID NO 49
<211> LENGTH: 80
<212> TYPE: PRT
<213> ORGANISM: Homo sapiens
<220> FEATURE:
<221> NAME/KEY: MOD_RES
<222> LOCATION: (1)..(80)
<223> OTHER INFORMATION: Deamidation N (2) [2?]
<220> FEATURE:
<221> NAME/KEY: MOD_RES
<222> LOCATION: (1)..(80)
<223> OTHER INFORMATION: Glycation (5) [5?]
<220> FEATURE:
<221> NAME/KEY: MOD_RES
<222> LOCATION: (1)..(80)
<223> OTHER INFORMATION: Oxidation M [?]
<220> FEATURE:
<221> NAME/KEY: MOD_RES
<222> LOCATION: (77)..(77)
<223> OTHER INFORMATION: Carboxymethyl C [77]

<400> SEQUENCE: 49

Ala Leu Glu Arg Met Phe Leu Ser Phe Pro Thr Thr Lys Thr Tyr Phe
1               5                   10                  15

Pro His Phe Asp Leu Ser His Gly Ser Ala Gln Val Lys Gly His Gly
            20                  25                  30

Lys Lys Val Ala Asp Ala Leu Thr Asn Ala Val Ala His Val Asp Asp
            35                  40                  45

```
Met Pro Asn Ala Leu Ser Ala Leu Ser Asp Leu His Ala His Lys Leu
        50                  55                  60

Arg Val Asp Pro Val Asn Phe Lys Leu Leu Ser His Cys Leu Leu Val
 65                  70                  75                  80

<210> SEQ ID NO 50
<211> LENGTH: 87
<212> TYPE: PRT
<213> ORGANISM: Homo sapiens
<220> FEATURE:
<221> NAME/KEY: MOD_RES
<222> LOCATION: (1)..(87)
<223> OTHER INFORMATION: Glycation (4) [4?]
<220> FEATURE:
<221> NAME/KEY: MOD_RES
<222> LOCATION: (75)..(75)
<223> OTHER INFORMATION: Carboxymethyl C [75]

<400> SEQUENCE: 50

Glu Arg Met Phe Leu Ser Phe Pro Thr Thr Lys Thr Tyr Phe Pro His
  1               5                  10                  15

Phe Asp Leu Ser His Gly Ser Ala Gln Val Lys Gly His Gly Lys Lys
             20                  25                  30

Val Ala Asp Ala Leu Thr Asn Ala Val Ala His Val Asp Asp Met Pro
         35                  40                  45

Asn Ala Leu Ser Ala Leu Ser Asp Leu His Ala His Lys Leu Arg Val
 50                  55                  60

Asp Pro Val Asn Phe Lys Leu Leu Ser His Cys Leu Leu Val Thr Leu
 65                  70                  75                  80

Ala Ala His Leu Pro Ala Glu
             85

<210> SEQ ID NO 51
<211> LENGTH: 114
<212> TYPE: PRT
<213> ORGANISM: Homo sapiens
<220> FEATURE:
<221> NAME/KEY: MOD_RES
<222> LOCATION: (1)..(114)
<223> OTHER INFORMATION: Oxidation M [?]
<220> FEATURE:
<221> NAME/KEY: MOD_RES
<222> LOCATION: (1)..(114)
<223> OTHER INFORMATION: Glycation (5) [5?]
<220> FEATURE:
<221> NAME/KEY: MOD_RES
<222> LOCATION: (41)..(70)
<223> OTHER INFORMATION: Deamidation N (3) [41 51 70]
<220> FEATURE:
<221> NAME/KEY: MOD_RES
<222> LOCATION: (77)..(77)
<223> OTHER INFORMATION: Carboxymethyl C [77]

<400> SEQUENCE: 51

Ala Leu Glu Arg Met Phe Leu Ser Phe Pro Thr Thr Lys Thr Tyr Phe
  1               5                  10                  15

Pro His Phe Asp Leu Ser His Gly Ser Ala Gln Val Lys Gly His Gly
             20                  25                  30

Lys Lys Val Ala Asp Ala Leu Thr Asn Ala Val Ala His Val Asp Asp
         35                  40                  45

Met Pro Asn Ala Leu Ser Ala Leu Ser Asp Leu His Ala His Lys Leu
 50                  55                  60

Arg Val Asp Pro Val Asn Phe Lys Leu Leu Ser His Cys Leu Leu Val
 65                  70                  75                  80
```

```
Thr Leu Ala Ala His Leu Pro Ala Glu Phe Thr Pro Ala Val His Ala
                85                  90                  95

Ser Leu Asp Lys Phe Leu Ala Ser Val Ser Leu Val Leu Thr Ser Lys
            100                 105                 110

Tyr Arg

<210> SEQ ID NO 52
<211> LENGTH: 86
<212> TYPE: PRT
<213> ORGANISM: Homo sapiens
<220> FEATURE:
<221> NAME/KEY: MOD_RES
<222> LOCATION: (1)..(86)
<223> OTHER INFORMATION: Glycation (3) [3?]
<220> FEATURE:
<221> NAME/KEY: MOD_RES
<222> LOCATION: (1)..(86)
<223> OTHER INFORMATION: Oxidation M [?]
<220> FEATURE:
<221> NAME/KEY: MOD_RES
<222> LOCATION: (1)..(86)
<223> OTHER INFORMATION: Deamidation N (2) [2?]
<220> FEATURE:
<221> NAME/KEY: MOD_RES
<222> LOCATION: (1)..(86)
<223> OTHER INFORMATION: Glycation [?]
<220> FEATURE:
<221> NAME/KEY: MOD_RES
<222> LOCATION: (2)..(46)
<223> OTHER INFORMATION: Oxidation M (2) [2 46]
<220> FEATURE:
<221> NAME/KEY: MOD_RES
<222> LOCATION: (74)..(74)
<223> OTHER INFORMATION: Carboxymethyl C [74]

<400> SEQUENCE: 52

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

Pro Val Asn Phe Lys Leu Leu Ser His Cys Leu Leu Val Thr Leu Ala
65                  70                  75                  80

Ala His Leu Pro Ala Glu
                85

<210> SEQ ID NO 53
<211> LENGTH: 100
<212> TYPE: PRT
<213> ORGANISM: Homo sapiens
<220> FEATURE:
<221> NAME/KEY: MOD_RES
<222> LOCATION: (1)..(100)
<223> OTHER INFORMATION: Glycation [?]
<220> FEATURE:
<221> NAME/KEY: MOD_RES
<222> LOCATION: (1)..(100)
<223> OTHER INFORMATION: Deamidation N (2) [2?]
<220> FEATURE:
<221> NAME/KEY: MOD_RES
<222> LOCATION: (35)..(35)
<223> OTHER INFORMATION: Oxidation M [35]
<220> FEATURE:
<221> NAME/KEY: MOD_RES
<222> LOCATION: (63)..(63)
```

<223> OTHER INFORMATION: Carboxymethyl C [63]

<400> SEQUENCE: 53

Tyr Phe Pro His Phe Asp Leu Ser His Gly Ser Ala Gln Val Lys Gly
1               5                   10                  15

His Gly Lys Lys Val Ala Asp Ala Leu Thr Asn Ala Val Ala His Val
            20                  25                  30

Asp Asp Met Pro Asn Ala Leu Ser Ala Leu Ser Asp Leu His Ala His
        35                  40                  45

Lys Leu Arg Val Asp Pro Val Asn Phe Lys Leu Leu Ser His Cys Leu
    50                  55                  60

Leu Val Thr Leu Ala Ala His Leu Pro Ala Glu Phe Thr Pro Ala Val
65                  70                  75                  80

His Ala Ser Leu Asp Lys Phe Leu Ala Ser Val Ser Thr Val Leu Thr
                85                  90                  95

Ser Lys Tyr Arg
            100

<210> SEQ ID NO 54
<211> LENGTH: 97
<212> TYPE: PRT
<213> ORGANISM: Homo sapiens
<220> FEATURE:
<221> NAME/KEY: MOD_RES
<222> LOCATION: (1)..(97)
<223> OTHER INFORMATION: Glycation (3) [3?]
<220> FEATURE:
<221> NAME/KEY: MOD_RES
<222> LOCATION: (12)..(95)
<223> OTHER INFORMATION: Glycation (7) [12 16 17 46 55 83 95]
<220> FEATURE:
<221> NAME/KEY: MOD_RES
<222> LOCATION: (32)..(32)
<223> OTHER INFORMATION: Oxidation M [32]
<220> FEATURE:
<221> NAME/KEY: MOD_RES
<222> LOCATION: (60)..(60)
<223> OTHER INFORMATION: Carboxymethyl C [60]

<400> SEQUENCE: 54

His Phe Asp Leu Ser His Gly Ser Ala Gln Val Lys Gly His Gly Lys
1               5                   10                  15

Lys Val Ala Asp Ala Leu Thr Asn Ala Val Ala His Val Asp Asp Met
            20                  25                  30

Pro Asn Ala Leu Ser Ala Leu Ser Asp Leu His Ala His Lys Leu Arg
        35                  40                  45

Val Asp Pro Val Asn Phe Lys Leu Leu Ser His Cys Leu Leu Val Thr
    50                  55                  60

Leu Ala Ala His Leu Pro Ala Glu Phe Thr Pro Ala Val His Ala Ser
65                  70                  75                  80

Leu Asp Lys Phe Leu Ala Ser Val Ser Thr Val Leu Thr Ser Lys Tyr
                85                  90                  95

Arg

<210> SEQ ID NO 55
<211> LENGTH: 94
<212> TYPE: PRT
<213> ORGANISM: Homo sapiens
<220> FEATURE:
<221> NAME/KEY: MOD_RES
<222> LOCATION: (1)..(94)
<223> OTHER INFORMATION: Deamidation N [?]
<220> FEATURE:

```
<221> NAME/KEY: MOD_RES
<222> LOCATION: (9)..(92)
<223> OTHER INFORMATION: Glycation (7) [9 13 14 43 52 80 92]
<220> FEATURE:
<221> NAME/KEY: MOD_RES
<222> LOCATION: (29)..(29)
<223> OTHER INFORMATION: Oxidation M [29]
<220> FEATURE:
<221> NAME/KEY: MOD_RES
<222> LOCATION: (57)..(57)
<223> OTHER INFORMATION: Carboxymethyl C [57]

<400> SEQUENCE: 55

Leu Ser His Gly Ser Ala Gln Val Lys Gly His Gly Lys Lys Val Ala
1               5                   10                  15

Asp Ala Leu Thr Asn Ala Val Ala His Val Asp Asp Met Pro Asn Ala
            20                  25                  30

Leu Ser Ala Leu Ser Asp Leu His Ala His Lys Leu Arg Val Asp Pro
        35                  40                  45

Val Asn Phe Lys Leu Leu Ser His Cys Leu Leu Val Thr Leu Ala Ala
    50                  55                  60

His Leu Pro Ala Glu Phe Thr Pro Ala Val His Ala Ser Leu Asp Lys
65                  70                  75                  80

Phe Leu Ala Ser Val Ser Thr Val Leu Thr Ser Lys Tyr Arg
                85                  90

<210> SEQ ID NO 56
<211> LENGTH: 93
<212> TYPE: PRT
<213> ORGANISM: Homo sapiens
<220> FEATURE:
<221> NAME/KEY: MOD_RES
<222> LOCATION: (1)..(93)
<223> OTHER INFORMATION: Glycation (4) [4?]
<220> FEATURE:
<221> NAME/KEY: MOD_RES
<222> LOCATION: (28)..(28)
<223> OTHER INFORMATION: Oxidation M [28]
<220> FEATURE:
<221> NAME/KEY: MOD_RES
<222> LOCATION: (56)..(56)
<223> OTHER INFORMATION: Carboxymethyl C [56]

<400> SEQUENCE: 56

Ser His Gly Ser Ala Gln Val Lys Gly His Gly Lys Lys Val Ala Asp
1               5                   10                  15

Ala Leu Thr Asn Ala Val Ala His Val Asp Asp Met Pro Asn Ala Leu
            20                  25                  30

Ser Ala Leu Ser Asp Leu His Ala His Lys Leu Arg Val Asp Pro Val
        35                  40                  45

Asn Phe Lys Leu Leu Ser His Cys Leu Leu Val Thr Leu Ala Ala His
    50                  55                  60

Leu Pro Ala Glu Phe Thr Pro Ala Val His Ala Ser Leu Asp Lys Phe
65                  70                  75                  80

Leu Ala Ser Val Ser Thr Val Leu Thr Ser Lys Tyr Arg
                85                  90

<210> SEQ ID NO 57
<211> LENGTH: 91
<212> TYPE: PRT
<213> ORGANISM: Homo sapiens
<220> FEATURE:
<221> NAME/KEY: MOD_RES
<222> LOCATION: (1)..(91)
<223> OTHER INFORMATION: Deamidation N [?]
```

-continued

```
<220> FEATURE:
<221> NAME/KEY: MOD_RES
<222> LOCATION: (1)..(91)
<223> OTHER INFORMATION: Glycation (2) [2 ?]
<220> FEATURE:
<221> NAME/KEY: MOD_RES
<222> LOCATION: (54)..(54)
<223> OTHER INFORMATION: Carboxymethyl C [54]

<400> SEQUENCE: 57

Gly Ser Ala Gln Val Lys Gly His Gly Lys Lys Val Ala Asp Ala Leu
1               5                   10                  15

Thr Asn Ala Val Ala His Val Asp Asp Met Pro Asn Ala Leu Ser Ala
            20                  25                  30

Leu Ser Asp Leu His Ala His Lys Leu Arg Val Asp Pro Val Asn Phe
        35                  40                  45

Lys Leu Leu Ser His Cys Leu Leu Val Thr Leu Ala Ala His Leu Pro
    50                  55                  60

Ala Glu Phe Thr Pro Ala Val His Ala Ser Leu Asp Lys Phe Leu Ala
65                  70                  75                  80

Ser Val Ser Thr Val Leu Thr Ser Lys Tyr Arg
                85                  90

<210> SEQ ID NO 58
<211> LENGTH: 90
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: Oxidation M [25]
<220> FEATURE:
<221> NAME/KEY: MOD_RES
<222> LOCATION: (53)..(53)
<223> OTHER INFORMATION: Carboxymethyl C [53]

<400> SEQUENCE: 58

Ser Ala Gln Val Lys Gly His Gly Lys Lys Val Ala Asp Ala Leu Thr
1               5                   10                  15

Asn Ala Val Ala His Val Asp Asp Met Pro Asn Ala Leu Ser Ala Leu
            20                  25                  30

Ser Asp Leu His Ala His Lys Leu Arg Val Asp Pro Val Asn Phe Lys
        35                  40                  45

Leu Leu Ser His Cys Leu Leu Val Thr Leu Ala Ala His Leu Pro Ala
    50                  55                  60

Glu Phe Thr Pro Ala Val His Ala Ser Leu Asp Lys Phe Leu Ala Ser
65                  70                  75                  80

Val Ser Thr Val Leu Thr Ser Lys Tyr Arg
                85                  90

<210> SEQ ID NO 59
<211> LENGTH: 89
<212> TYPE: PRT
<213> ORGANISM: Homo sapiens
<220> FEATURE:
<221> NAME/KEY: MOD_RES
<222> LOCATION: (1)..(89)
<223> OTHER INFORMATION: Glycation (5) [5?]
<220> FEATURE:
<221> NAME/KEY: MOD_RES
<222> LOCATION: (1)..(89)
<223> OTHER INFORMATION: Glycation (3) [3?]
<220> FEATURE:
<221> NAME/KEY: MOD_RES
<222> LOCATION: (16)..(45)
```

```
<223> OTHER INFORMATION: Deamidation N (3) [16 26 45]
<220> FEATURE:
<221> NAME/KEY: MOD_RES
<222> LOCATION: (24)..(24)
<223> OTHER INFORMATION: Oxidation M [24]
<220> FEATURE:
<221> NAME/KEY: MOD_RES
<222> LOCATION: (52)..(52)
<223> OTHER INFORMATION: Carboxymethyl C [52]

<400> SEQUENCE: 59

Ala Gln Val Lys Gly His Gly Lys Lys Val Ala Asp Ala Leu Thr Asn
1               5                   10                  15
Ala Val Ala His Val Asp Asp Met Pro Asn Ala Leu Ser Ala Leu Ser
                20                  25                  30
Asp Leu His Ala His Lys Leu Arg Val Asp Pro Val Asn Phe Lys Leu
            35                  40                  45
Leu Ser His Cys Leu Leu Val Thr Leu Ala Ala His Leu Pro Ala Glu
        50                  55                  60
Phe Thr Pro Ala Val His Ala Ser Leu Asp Lys Phe Leu Ala Ser Val
65                  70                  75                  80
Ser Thr Val Leu Thr Ser Lys Tyr Arg
                85

<210> SEQ ID NO 60
<211> LENGTH: 88
<212> TYPE: PRT
<213> ORGANISM: Homo sapiens
<220> FEATURE:
<221> NAME/KEY: MOD_RES
<222> LOCATION: (1)..(88)
<223> OTHER INFORMATION: Deamidation N (2) [2?]
<220> FEATURE:
<221> NAME/KEY: MOD_RES
<222> LOCATION: (1)..(88)
<223> OTHER INFORMATION: Glycation (5) [5?]
<220> FEATURE:
<221> NAME/KEY: MOD_RES
<222> LOCATION: (51)..(51)
<223> OTHER INFORMATION: Carboxymethyl C [51]

<400> SEQUENCE: 60

Gln Val Lys Gly His Gly Lys Lys Val Ala Asp Ala Leu Thr Asn Ala
1               5                   10                  15
Val Ala His Val Asp Asp Met Pro Asn Ala Leu Ser Ala Leu Ser Asp
                20                  25                  30
Leu His Ala His Lys Leu Arg Val Asp Pro Val Asn Phe Lys Leu Leu
            35                  40                  45
Ser His Cys Leu Leu Val Thr Leu Ala Ala His Leu Pro Ala Glu Phe
        50                  55                  60
Thr Pro Ala Val His Ala Ser Leu Asp Lys Phe Leu Ala Ser Val Ser
65                  70                  75                  80
Thr Val Leu Thr Ser Lys Tyr Arg
                85

<210> SEQ ID NO 61
<211> LENGTH: 83
<212> TYPE: PRT
<213> ORGANISM: Homo sapiens
<220> FEATURE:
<221> NAME/KEY: MOD_RES
<222> LOCATION: (1)..(83)
<223> OTHER INFORMATION: Glycation (4) [4?]
<220> FEATURE:
<221> NAME/KEY: MOD_RES
```

-continued

```
<222> LOCATION: (1)..(83)
<223> OTHER INFORMATION: Glycation (3) [3?]
<220> FEATURE:
<221> NAME/KEY: MOD_RES
<222> LOCATION: (1)..(83)
<223> OTHER INFORMATION: Deamidation N (2) [2?]
<220> FEATURE:
<221> NAME/KEY: MOD_RES
<222> LOCATION: (10)..(39)
<223> OTHER INFORMATION: Deamidation N (3) [10 20 39]
<220> FEATURE:
<221> NAME/KEY: MOD_RES
<222> LOCATION: (46)..(46)
<223> OTHER INFORMATION: Carboxymethyl C [46]

<400> SEQUENCE: 61

Gly Lys Lys Val Ala Asp Ala Leu Thr Asn Ala Val Ala His Val Asp
1               5                   10                  15

Asp Met Pro Asn Ala Leu Ser Ala Leu Ser Asp Leu His Ala His Lys
            20                  25                  30

Leu Arg Val Asp Pro Val Asn Phe Lys Leu Leu Ser His Cys Leu Leu
        35                  40                  45

Val Thr Leu Ala Ala His Leu Pro Ala Glu Phe Thr Pro Ala Val His
    50                  55                  60

Ala Ser Leu Asp Lys Phe Leu Ala Ser Val Ser Thr Val Leu Thr Ser
65                  70                  75                  80

Lys Tyr Arg

<210> SEQ ID NO 62
<211> LENGTH: 81
<212> TYPE: PRT
<213> ORGANISM: Homo sapiens
<220> FEATURE:
<221> NAME/KEY: MOD_RES
<222> LOCATION: (1)..(81)
<223> OTHER INFORMATION: Deamidation N (2) [2?]
<220> FEATURE:
<221> NAME/KEY: MOD_RES
<222> LOCATION: (16)..(16)
<223> OTHER INFORMATION: Oxidation M [16]
<220> FEATURE:
<221> NAME/KEY: MOD_RES
<222> LOCATION: (44)..(44)
<223> OTHER INFORMATION: Carboxymethyl C [44]

<400> SEQUENCE: 62

Lys Val Ala Asp Ala Leu Thr Asn Ala Val Ala His Val Asp Asp Met
1               5                   10                  15

Pro Asn Ala Leu Ser Ala Leu Ser Asp Leu His Ala His Lys Leu Arg
            20                  25                  30

Val Asp Pro Val Asn Phe Lys Leu Leu Ser His Cys Leu Leu Val Thr
        35                  40                  45

Leu Ala Ala His Leu Pro Ala Glu Phe Thr Pro Ala Val His Ala Ser
    50                  55                  60

Leu Asp Lys Phe Leu Ala Ser Val Ser Thr Val Leu Thr Ser Lys Tyr
65                  70                  75                  80

Arg

<210> SEQ ID NO 63
<211> LENGTH: 77
<212> TYPE: PRT
<213> ORGANISM: Homo sapiens
<220> FEATURE:
<221> NAME/KEY: MOD_RES
<222> LOCATION: (1)..(77)
```

-continued

```
<223> OTHER INFORMATION: Glycation [?]
<220> FEATURE:
<221> NAME/KEY: MOD_RES
<222> LOCATION: (1)..(77)
<223> OTHER INFORMATION: Deamidation N (2) [2?]
<220> FEATURE:
<221> NAME/KEY: MOD_RES
<222> LOCATION: (1)..(77)
<223> OTHER INFORMATION: Glycation (3) [3?]
<220> FEATURE:
<221> NAME/KEY: MOD_RES
<222> LOCATION: (1)..(77)
<223> OTHER INFORMATION: Deamidation N [?]
<220> FEATURE:
<221> NAME/KEY: MOD_RES
<222> LOCATION: (40)..(40)
<223> OTHER INFORMATION: Carboxymethyl C [40]

<400> SEQUENCE: 63

Ala Leu Thr Asn Ala Val Ala His Val Asp Asp Met Pro Asn Ala Leu
1               5                   10                  15

Ser Ala Leu Ser Asp Leu His Ala His Lys Leu Arg Val Asp Pro Val
                20                  25                  30

Asn Phe Lys Leu Leu Ser His Cys Leu Leu Val Thr Leu Ala Ala His
            35                  40                  45

Leu Pro Ala Glu Phe Thr Pro Ala Val His Ala Ser Leu Asp Lys Phe
        50                  55                  60

Leu Ala Ser Val Ser Thr Val Leu Thr Ser Lys Tyr Arg
65                  70                  75

<210> SEQ ID NO 64
<211> LENGTH: 76
<212> TYPE: PRT
<213> ORGANISM: Homo sapiens
<220> FEATURE:
<221> NAME/KEY: MOD_RES
<222> LOCATION: (1)..(76)
<223> OTHER INFORMATION: Glycation (2) [2?]
<220> FEATURE:
<221> NAME/KEY: MOD_RES
<222> LOCATION: (3)..(32)
<223> OTHER INFORMATION: Deamidation N (3) [3 13 32]
<220> FEATURE:
<221> NAME/KEY: MOD_RES
<222> LOCATION: (39)..(39)
<223> OTHER INFORMATION: Carboxymethyl C [39]

<400> SEQUENCE: 64

Leu Thr Asn Ala Val Ala His Val Asp Asp Met Pro Asn Ala Leu Ser
1               5                   10                  15

Ala Leu Ser Asp Leu His Ala His Lys Leu Arg Val Asp Pro Val Asn
                20                  25                  30

Phe Lys Leu Leu Ser His Cys Leu Leu Val Thr Leu Ala Ala His Leu
            35                  40                  45

Pro Ala Glu Phe Thr Pro Ala Val His Ala Ser Leu Asp Lys Phe Leu
        50                  55                  60

Ala Ser Val Ser Thr Val Leu Thr Ser Lys Tyr Arg
65                  70                  75

<210> SEQ ID NO 65
<211> LENGTH: 75
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Oxidation M [10]
```

```
<220> FEATURE:
<221> NAME/KEY: MOD_RES
<222> LOCATION: (38)..(38)
<223> OTHER INFORMATION: Carboxymethyl C [38]

<400> SEQUENCE: 65

Thr Asn Ala Val Ala His Val Asp Asp Met Pro Asn Ala Leu Ser Ala
1               5                   10                  15

Leu Ser Asp Leu His Ala His Lys Leu Arg Val Asp Pro Val Asn Phe
            20                  25                  30

Lys Leu Leu Ser His Cys Leu Leu Val Thr Leu Ala Ala His Leu Pro
        35                  40                  45

Ala Glu Phe Thr Pro Ala Val His Ala Ser Leu Asp Lys Phe Leu Ala
    50                  55                  60

Ser Val Ser Thr Val Leu Thr Ser Lys Tyr Arg
65                  70                  75

<210> SEQ ID NO 66
<211> LENGTH: 74
<212> TYPE: PRT
<213> ORGANISM: Homo sapiens
<220> FEATURE:
<221> NAME/KEY: MOD_RES
<222> LOCATION: (1)..(74)
<223> OTHER INFORMATION: Deamidation N (2) [2?]
<220> FEATURE:
<221> NAME/KEY: MOD_RES
<222> LOCATION: (1)..(74)
<223> OTHER INFORMATION: Glycation (2) [2?]
<220> FEATURE:
<221> NAME/KEY: MOD_RES
<222> LOCATION: (9)..(9)
<223> OTHER INFORMATION: Oxidation M [9]
<220> FEATURE:
<221> NAME/KEY: MOD_RES
<222> LOCATION: (37)..(37)
<223> OTHER INFORMATION: Carboxymethyl C [37]

<400> SEQUENCE: 66

Asn Ala Val Ala His Val Asp Asp Met Pro Asn Ala Leu Ser Ala Leu
1               5                   10                  15

Ser Asp Leu His Ala His Lys Leu Arg Val Asp Pro Val Asn Phe Lys
            20                  25                  30

Leu Leu Ser His Cys Leu Leu Val Thr Leu Ala Ala His Leu Pro Ala
        35                  40                  45

Glu Phe Thr Pro Ala Val His Ala Ser Leu Asp Lys Phe Leu Ala Ser
    50                  55                  60

Val Ser Thr Val Leu Thr Ser Lys Tyr Arg
65                  70

<210> SEQ ID NO 67
<211> LENGTH: 107
<212> TYPE: PRT
<213> ORGANISM: Homo sapiens
<220> FEATURE:
<221> NAME/KEY: MOD_RES
<222> LOCATION: (1)..(107)
<223> OTHER INFORMATION: Glycation (2) [2?]
<220> FEATURE:
<221> NAME/KEY: MOD_RES
<222> LOCATION: (70)..(70)
<223> OTHER INFORMATION: Carboxymethyl C [70]

<400> SEQUENCE: 67

Ser Phe Pro Thr Thr Lys Thr Tyr Phe Pro His Phe Asp Leu Ser His
1               5                   10                  15
```

```
Gly Ser Ala Gln Val Lys Gly His Gly Lys Lys Val Ala Asp Ala Leu
            20                  25                  30

Thr Asn Ala Val Ala His Val Asp Asp Met Pro Asn Ala Leu Ser Ala
                35                  40                  45

Leu Ser Asp Leu His Ala His Lys Leu Arg Val Asp Pro Val Asn Phe
 50                  55                  60

Lys Leu Leu Ser His Cys Leu Leu Val Thr Leu Ala Ala His Leu Pro
 65                  70                  75                  80

Ala Glu Phe Thr Pro Ala Val His Ala Ser Leu Asp Lys Phe Leu Ala
                85                  90                  95

Ser Val Ser Thr Val Leu Thr Ser Lys Tyr Arg
            100                 105

<210> SEQ ID NO 68
<211> LENGTH: 66
<212> TYPE: PRT
<213> ORGANISM: Homo sapiens
<220> FEATURE:
<221> NAME/KEY: MOD_RES
<222> LOCATION: (1)..(66)
<223> OTHER INFORMATION: Glycation (2) [2?]
<220> FEATURE:
<221> NAME/KEY: MOD_RES
<222> LOCATION: (3)..(22)
<223> OTHER INFORMATION: Deamidation N (2) [3 22]
<220> FEATURE:
<221> NAME/KEY: MOD_RES
<222> LOCATION: (29)..(29)
<223> OTHER INFORMATION: Carboxymethyl C [29]

<400> SEQUENCE: 68

Met Pro Asn Ala Leu Ser Ala Leu Ser Asp Leu His Ala His Lys Leu
 1               5                  10                  15

Arg Val Asp Pro Val Asn Phe Lys Leu Leu Ser His Cys Leu Leu Val
            20                  25                  30

Thr Leu Ala Ala His Leu Pro Ala Glu Phe Thr Pro Ala Val His Ala
                35                  40                  45

Ser Leu Asp Lys Phe Leu Ala Ser Val Ser Thr Val Leu Thr Ser Lys
 50                  55                  60

Tyr Arg
 65

<210> SEQ ID NO 69
<211> LENGTH: 62
<212> TYPE: PRT
<213> ORGANISM: Homo sapiens
<220> FEATURE:
<221> NAME/KEY: MOD_RES
<222> LOCATION: (1)..(62)
<223> OTHER INFORMATION: Glycation (3) [3?]
<220> FEATURE:
<221> NAME/KEY: MOD_RES
<222> LOCATION: (25)..(25)
<223> OTHER INFORMATION: Carboxymethyl C [25]

<400> SEQUENCE: 69

Leu Ser Ala Leu Ser Asp Leu His Ala His Lys Leu Arg Val Asp Pro
 1               5                  10                  15

Val Asn Phe Lys Leu Leu Ser His Cys Leu Leu Val Thr Leu Ala Ala
            20                  25                  30

His Leu Pro Ala Glu Phe Thr Pro Ala Val His Ala Ser Leu Asp Lys
                35                  40                  45
```

Phe Leu Ala Ser Val Ser Thr Val Leu Thr Ser Lys Tyr Arg
                    50                  55                  60

<210> SEQ ID NO 70
<211> LENGTH: 61
<212> TYPE: PRT
<213> ORGANISM: Homo sapiens
<220> FEATURE:
<221> NAME/KEY: MOD_RES
<222> LOCATION: (1)..(61)
<223> OTHER INFORMATION: Glycation (3) [3?]
<220> FEATURE:
<221> NAME/KEY: MOD_RES
<222> LOCATION: (1)..(61)
<223> OTHER INFORMATION: Glycation [?]
<220> FEATURE:
<221> NAME/KEY: MOD_RES
<222> LOCATION: (17)..(17)
<223> OTHER INFORMATION: Deamidation N [17]
<220> FEATURE:
<221> NAME/KEY: MOD_RES
<222> LOCATION: (24)..(24)
<223> OTHER INFORMATION: Carboxymethyl C [24]

<400> SEQUENCE: 70

Ser Ala Leu Ser Asp Leu His Ala His Lys Leu Arg Val Asp Pro Val
1               5                   10                  15

Asn Phe Lys Leu Leu Ser His Cys Leu Leu Val Thr Leu Ala Ala His
                20                  25                  30

Leu Pro Ala Glu Phe Thr Pro Ala Val His Ala Ser Leu Asp Lys Phe
            35                  40                  45

Leu Ala Ser Val Ser Thr Val Leu Thr Ser Lys Tyr Arg
        50                  55                  60

<210> SEQ ID NO 71
<211> LENGTH: 60
<212> TYPE: PRT
<213> ORGANISM: Homo sapiens
<220> FEATURE:
<221> NAME/KEY: MOD_RES
<222> LOCATION: (9)..(58)
<223> OTHER INFORMATION: Glycation (4) [9 18 46 58]
<220> FEATURE:
<221> NAME/KEY: MOD_RES
<222> LOCATION: (23)..(23)
<223> OTHER INFORMATION: Carboxymethyl C [23]

<400> SEQUENCE: 71

Ala Leu Ser Asp Leu His Ala His Lys Leu Arg Val Asp Pro Val Asn
1               5                   10                  15

Phe Lys Leu Leu Ser His Cys Leu Leu Val Thr Leu Ala Ala His Leu
                20                  25                  30

Pro Ala Glu Phe Thr Pro Ala Val His Ala Ser Leu Asp Lys Phe Leu
            35                  40                  45

Ala Ser Val Ser Thr Val Leu Thr Ser Lys Tyr Arg
        50                  55                  60

<210> SEQ ID NO 72
<211> LENGTH: 59
<212> TYPE: PRT
<213> ORGANISM: Homo sapiens
<220> FEATURE:
<221> NAME/KEY: MOD_RES
<222> LOCATION: (8)..(57)
<223> OTHER INFORMATION: Glycation (4) [8 17 45 57]
<220> FEATURE:
<221> NAME/KEY: MOD_RES
<222> LOCATION: (22)..(22)

```
<223> OTHER INFORMATION: Carboxymethyl C [22]

<400> SEQUENCE: 72

Leu Ser Asp Leu His Ala His Lys Leu Arg Val Asp Pro Val Asn Phe
1               5                   10                  15

Lys Leu Leu Ser His Cys Leu Leu Val Thr Leu Ala Ala His Leu Pro
            20                  25                  30

Ala Glu Phe Thr Pro Ala Val His Ala Ser Leu Asp Lys Phe Leu Ala
        35                  40                  45

Ser Val Ser Thr Val Leu Thr Ser Lys Tyr Arg
    50                  55

<210> SEQ ID NO 73
<211> LENGTH: 54
<212> TYPE: PRT
<213> ORGANISM: Homo sapiens
<220> FEATURE:
<221> NAME/KEY: MOD_RES
<222> LOCATION: (3)..(52)
<223> OTHER INFORMATION: Glycation (4) [3 12 40 52]
<220> FEATURE:
<221> NAME/KEY: MOD_RES
<222> LOCATION: (17)..(17)
<223> OTHER INFORMATION: Carboxymethyl C [17]

<400> SEQUENCE: 73

Ala His Lys Leu Arg Val Asp Pro Val Asn Phe Lys Leu Leu Ser His
1               5                   10                  15

Cys Leu Leu Val Thr Leu Ala Ala His Leu Pro Ala Glu Phe Thr Pro
            20                  25                  30

Ala Val His Ala Ser Leu Asp Lys Phe Leu Ala Ser Val Ser Thr Val
        35                  40                  45

Leu Thr Ser Lys Tyr Arg
    50

<210> SEQ ID NO 74
<211> LENGTH: 52
<212> TYPE: PRT
<213> ORGANISM: Homo sapiens
<220> FEATURE:
<221> NAME/KEY: MOD_RES
<222> LOCATION: (1)..(52)
<223> OTHER INFORMATION: Glycation (3) [3?]
<220> FEATURE:
<221> NAME/KEY: MOD_RES
<222> LOCATION: (15)..(15)
<223> OTHER INFORMATION: Carboxymethyl C [15]

<400> SEQUENCE: 74

Lys Leu Arg Val Asp Pro Val Asn Phe Lys Leu Leu Ser His Cys Leu
1               5                   10                  15

Leu Val Thr Leu Ala Ala His Leu Pro Ala Glu Phe Thr Pro Ala Val
            20                  25                  30

His Ala Ser Leu Asp Lys Phe Leu Ala Ser Val Ser Thr Val Leu Thr
        35                  40                  45

Ser Lys Tyr Arg
    50

<210> SEQ ID NO 75
<211> LENGTH: 51
<212> TYPE: PRT
<213> ORGANISM: Homo sapiens
<220> FEATURE:
<221> NAME/KEY: MOD_RES
```

```
<222> LOCATION: (7)..(7)
<223> OTHER INFORMATION: Deamidation N [7]
<220> FEATURE:
<221> NAME/KEY: MOD_RES
<222> LOCATION: (9)..(49)
<223> OTHER INFORMATION: Glycation (3) [9 37 49]
<220> FEATURE:
<221> NAME/KEY: MOD_RES
<222> LOCATION: (14)..(14)
<223> OTHER INFORMATION: Carboxymethyl C [14]

<400> SEQUENCE: 75

Leu Arg Val Asp Pro Val Asn Phe Lys Leu Leu Ser His Cys Leu Leu
1               5                   10                  15

Val Thr Leu Ala Ala His Leu Pro Ala Glu Phe Thr Pro Ala Val His
            20                  25                  30

Ala Ser Leu Asp Lys Phe Leu Ala Ser Val Ser Thr Val Leu Thr Ser
        35                  40                  45

Lys Tyr Arg
    50

<210> SEQ ID NO 76
<211> LENGTH: 48
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Carboxymethyl C [11]

<400> SEQUENCE: 76

Asp Pro Val Asn Phe Lys Leu Leu Ser His Cys Leu Leu Val Thr Leu
1               5                   10                  15

Ala Ala His Leu Pro Ala Glu Phe Thr Pro Ala Val His Ala Ser Leu
            20                  25                  30

Asp Lys Phe Leu Ala Ser Val Ser Thr Val Leu Thr Ser Lys Tyr Arg
        35                  40                  45

<210> SEQ ID NO 77
<211> LENGTH: 47
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Carboxymethyl C [10]

<400> SEQUENCE: 77

Pro Val Asn Phe Lys Leu Leu Ser His Cys Leu Leu Val Thr Leu Ala
1               5                   10                  15

Ala His Leu Pro Ala Glu Phe Thr Pro Ala Val His Ala Ser Leu Asp
            20                  25                  30

Lys Phe Leu Ala Ser Val Ser Thr Val Leu Thr Ser Lys Tyr Arg
        35                  40                  45

<210> SEQ ID NO 78
<211> LENGTH: 45
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Carboxymethyl C [8]

<400> SEQUENCE: 78
```

Asn Phe Lys Leu Leu Ser His Cys Leu Leu Val Thr Leu Ala Ala His Leu
1               5                   10                  15

Pro Ala Glu Phe Thr Pro Ala Val His Ala Ser Leu Asp Lys Phe Leu
            20                  25                  30

Ala Ser Val Ser Thr Val Leu Thr Ser Lys Tyr Arg
        35                  40                  45

<210> SEQ ID NO 79
<211> LENGTH: 44
<212> TYPE: PRT
<213> ORGANISM: Homo sapiens
<220> FEATURE:
<221> NAME/KEY: MOD_RES
<222> LOCATION: (2)..(42)
<223> OTHER INFORMATION: Glycation (3) [2 30 42]
<220> FEATURE:
<221> NAME/KEY: MOD_RES
<222> LOCATION: (7)..(7)
<223> OTHER INFORMATION: Carboxymethyl C [7]

<400> SEQUENCE: 79

Phe Lys Leu Leu Ser His Cys Leu Leu Val Thr Leu Ala Ala His Leu
1               5                   10                  15

Pro Ala Glu Phe Thr Pro Ala Val His Ala Ser Leu Asp Lys Phe Leu
            20                  25                  30

Ala Ser Val Ser Thr Val Leu Thr Ser Lys Tyr Arg
        35                  40

<210> SEQ ID NO 80
<211> LENGTH: 43
<212> TYPE: PRT
<213> ORGANISM: Homo sapiens
<220> FEATURE:
<221> NAME/KEY: MOD_RES
<222> LOCATION: (1)..(43)
<223> OTHER INFORMATION: Glycation [?]
<220> FEATURE:
<221> NAME/KEY: MOD_RES
<222> LOCATION: (6)..(6)
<223> OTHER INFORMATION: Carboxymethyl C [6]

<400> SEQUENCE: 80

Lys Leu Leu Ser His Cys Leu Leu Val Thr Leu Ala Ala His Leu Pro
1               5                   10                  15

Ala Glu Phe Thr Pro Ala Val His Ala Ser Leu Asp Lys Phe Leu Ala
            20                  25                  30

Ser Val Ser Thr Val Leu Thr Ser Lys Tyr Arg
        35                  40

<210> SEQ ID NO 81
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation [?]
<220> FEATURE:
<221> NAME/KEY: MOD_RES
<222> LOCATION: (2)..(2)
<223> OTHER INFORMATION: Carboxymethyl C [2]

<400> SEQUENCE: 81

His Cys Leu Leu Val Thr Leu Ala Ala His Leu Pro Ala Glu Phe Thr
1               5                   10                  15

Pro Ala Val His Ala Ser Leu Asp Lys Phe Leu Ala Ser Val Ser Thr

Val Leu Thr Ser Lys Tyr Arg
        35

<210> SEQ ID NO 82
<211> LENGTH: 35
<212> TYPE: PRT
<213> ORGANISM: Homo sapiens
<220> FEATURE:
<221> NAME/KEY: MOD_RES
<222> LOCATION: (21)..(33)
<223> OTHER INFORMATION: Glycation (2) [21 33]

<400> SEQUENCE: 82

Val Thr Leu Ala Ala His Leu Pro Ala Glu Phe Thr Pro Ala Val His
1               5                   10                  15

Ala Ser Leu Asp Lys Phe Leu Ala Ser Val Ser Thr Val Leu Thr Ser
            20                  25                  30

Lys Tyr Arg
        35

<210> SEQ ID NO 83
<211> LENGTH: 69
<212> TYPE: PRT
<213> ORGANISM: Homo sapiens
<220> FEATURE:
<221> NAME/KEY: MOD_RES
<222> LOCATION: (1)..(69)
<223> OTHER INFORMATION: Deamidation N (2) [2?]
<220> FEATURE:
<221> NAME/KEY: MOD_RES
<222> LOCATION: (1)..(69)
<223> OTHER INFORMATION: Glycation (2) [2?]
<220> FEATURE:
<221> NAME/KEY: MOD_RES
<222> LOCATION: (1)..(69)
<223> OTHER INFORMATION: Glycation (3) [3?]
<220> FEATURE:
<221> NAME/KEY: MOD_RES
<222> LOCATION: (2)..(46)
<223> OTHER INFORMATION: Oxidation M (2) [2 46]

<400> SEQUENCE: 83

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
            35                  40                  45

Ala Leu Ser Ala Leu Ser Asp Leu His Ala His Lys Leu Arg Val Asp
        50                  55                  60

Pro Val Asn Phe Lys
65

<210> SEQ ID NO 84
<211> LENGTH: 67
<212> TYPE: PRT
<213> ORGANISM: Homo sapiens
<220> FEATURE:
<221> NAME/KEY: MOD_RES
<222> LOCATION: (1)..(67)
<223> OTHER INFORMATION: Glycation [?]
<220> FEATURE:
<221> NAME/KEY: MOD_RES
<222> LOCATION: (1)..(67)
<223> OTHER INFORMATION: Deamidation N [?]
<220> FEATURE:

```
<221> NAME/KEY: MOD_RES
<222> LOCATION: (2)..(46)
<223> OTHER INFORMATION: Oxidation M (2) [2 46]

<400> SEQUENCE: 84

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

Pro Val Asn
65

<210> SEQ ID NO 85
<211> LENGTH: 66
<212> TYPE: PRT
<213> ORGANISM: Homo sapiens
<220> FEATURE:
<221> NAME/KEY: MOD_RES
<222> LOCATION: (1)..(66)
<223> OTHER INFORMATION: Glycation (3) [3?]
<220> FEATURE:
<221> NAME/KEY: MOD_RES
<222> LOCATION: (2)..(46)
<223> OTHER INFORMATION: Oxidation M (2) [2 46]
<220> FEATURE:
<221> NAME/KEY: MOD_RES
<222> LOCATION: (38)..(48)
<223> OTHER INFORMATION: Deamidation N (2) [38 48]

<400> SEQUENCE: 85

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

Pro Val
65

<210> SEQ ID NO 86
<211> LENGTH: 64
<212> TYPE: PRT
<213> ORGANISM: Homo sapiens
<220> FEATURE:
<221> NAME/KEY: MOD_RES
<222> LOCATION: (1)..(64)
<223> OTHER INFORMATION: Oxidation M [?]
<220> FEATURE:
<221> NAME/KEY: MOD_RES
<222> LOCATION: (1)..(64)
<223> OTHER INFORMATION: Glycation (3) [3?]
<220> FEATURE:
<221> NAME/KEY: MOD_RES
<222> LOCATION: (1)..(64)
<223> OTHER INFORMATION: Deamidation N [?]
<220> FEATURE:
<221> NAME/KEY: MOD_RES
<222> LOCATION: (1)..(64)
<223> OTHER INFORMATION: Glycation [?]
<220> FEATURE:
<221> NAME/KEY: MOD_RES
```

```
<222> LOCATION: (2)..(46)
<223> OTHER INFORMATION: Oxidation M (2) [2 46]
<220> FEATURE:
<221> NAME/KEY: MOD_RES
<222> LOCATION: (38)..(48)
<223> OTHER INFORMATION: Deamidation N (2) [38 48]

<400> SEQUENCE: 86
```

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

```
<210> SEQ ID NO 87
<211> LENGTH: 62
<212> TYPE: PRT
<213> ORGANISM: Homo sapiens
<220> FEATURE:
<221> NAME/KEY: MOD_RES
<222> LOCATION: (1)..(62)
<223> OTHER INFORMATION: Oxidation M [?]
<220> FEATURE:
<221> NAME/KEY: MOD_RES
<222> LOCATION: (1)..(62)
<223> OTHER INFORMATION: Glycation [?]

<400> SEQUENCE: 87
```

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg
    50                  55                  60

```
<210> SEQ ID NO 88
<211> LENGTH: 55
<212> TYPE: PRT
<213> ORGANISM: Homo sapiens
<220> FEATURE:
<221> NAME/KEY: MOD_RES
<222> LOCATION: (1)..(55)
<223> OTHER INFORMATION: Oxidation M [?]
<220> FEATURE:
<221> NAME/KEY: MOD_RES
<222> LOCATION: (1)..(55)
<223> OTHER INFORMATION: Glycation (3) [3?]
<220> FEATURE:
<221> NAME/KEY: MOD_RES
<222> LOCATION: (2)..(46)
<223> OTHER INFORMATION: Oxidation M (2) [2 46]
<220> FEATURE:
<221> NAME/KEY: MOD_RES
<222> LOCATION: (10)..(31)
<223> OTHER INFORMATION: Glycation (4) [10 26 30 31]
<220> FEATURE:
<221> NAME/KEY: MOD_RES
<222> LOCATION: (38)..(48)
<223> OTHER INFORMATION: Deamidation N (2) [38 48]

<400> SEQUENCE: 88
```

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Met Pro Asn
        35                  40                  45

Ala Leu Ser Ala Leu Ser Asp
    50                  55

<210> SEQ ID NO 89
<211> LENGTH: 53
<212> TYPE: PRT
<213> ORGANISM: Homo sapiens
<220> FEATURE:
<221> NAME/KEY: MOD_RES
<222> LOCATION: (1)..(53)
<223> OTHER INFORMATION: Deamidation N [?]
<220> FEATURE:
<221> NAME/KEY: MOD_RES
<222> LOCATION: (1)..(53)
<223> OTHER INFORMATION: Glycation [?]

<400> SEQUENCE: 89

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu
    50

<210> SEQ ID NO 90
<211> LENGTH: 52
<212> TYPE: PRT
<213> ORGANISM: Homo sapiens
<220> FEATURE:
<221> NAME/KEY: MOD_RES
<222> LOCATION: (1)..(52)
<223> OTHER INFORMATION: Oxidation M [?]
<220> FEATURE:
<221> NAME/KEY: MOD_RES
<222> LOCATION: (1)..(52)
<223> OTHER INFORMATION: Deamidation N [?]
<220> FEATURE:
<221> NAME/KEY: MOD_RES
<222> LOCATION: (1)..(52)
<223> OTHER INFORMATION: Glycation (3) [3?]

<400> SEQUENCE: 90

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala
    50

<210> SEQ ID NO 91
<211> LENGTH: 51
<212> TYPE: PRT
<213> ORGANISM: Homo sapiens
<220> FEATURE:
<221> NAME/KEY: MOD_RES
<222> LOCATION: (1)..(51)
<223> OTHER INFORMATION: Glycation (2) [2?]

-continued

```
<400> SEQUENCE: 91

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser
    50

<210> SEQ ID NO 92
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Oxidation M [?]
<220> FEATURE:
<221> NAME/KEY: MOD_RES
<222> LOCATION: (1)..(49)
<223> OTHER INFORMATION: Deamidation N [?]

<400> SEQUENCE: 92

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala

<210> SEQ ID NO 93
<211> LENGTH: 46
<212> TYPE: PRT
<213> ORGANISM: Homo sapiens
<220> FEATURE:
<221> NAME/KEY: MOD_RES
<222> LOCATION: (1)..(46)
<223> OTHER INFORMATION: Glycation [?]
<220> FEATURE:
<221> NAME/KEY: MOD_RES
<222> LOCATION: (38)..(38)
<223> OTHER INFORMATION: Deamidation N [38]

<400> SEQUENCE: 93

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met
        35                  40                  45

<210> SEQ ID NO 94
<211> LENGTH: 43
<212> TYPE: PRT
<213> ORGANISM: Homo sapiens
<220> FEATURE:
<221> NAME/KEY: MOD_RES
<222> LOCATION: (30)..(31)
<223> OTHER INFORMATION: Glycation (2) [30 31]

<400> SEQUENCE: 94
```

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val
        35                  40

<210> SEQ ID NO 95
<211> LENGTH: 40
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (38)..(38)
<223> OTHER INFORMATION: Deamidation N [38]

<400> SEQUENCE: 95

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val
        35                  40

<210> SEQ ID NO 96
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation (3) [3?]
<220> FEATURE:
<221> NAME/KEY: MOD_RES
<222> LOCATION: (38)..(38)
<223> OTHER INFORMATION: Deamidation N [38]

<400> SEQUENCE: 96

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala
        35

<210> SEQ ID NO 97
<211> LENGTH: 81
<212> TYPE: PRT
<213> ORGANISM: Homo sapiens
<220> FEATURE:
<221> NAME/KEY: MOD_RES
<222> LOCATION: (1)..(81)
<223> OTHER INFORMATION: Glycation (3) [3?]
<220> FEATURE:
<221> NAME/KEY: MOD_RES
<222> LOCATION: (2)..(46)
<223> OTHER INFORMATION: Oxidation M (2) [2 46]
<220> FEATURE:
<221> NAME/KEY: MOD_RES
<222> LOCATION: (38)..(67)
<223> OTHER INFORMATION: Deamidation N (3) [38 48 67]
<220> FEATURE:
<221> NAME/KEY: MOD_RES
<222> LOCATION: (74)..(74)

<223> OTHER INFORMATION: Carboxymethyl C [74]

<400> SEQUENCE: 97

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

Pro Val Asn Phe Lys Leu Leu Ser His Cys Leu Leu Val Thr Leu Ala
65                  70                  75                  80

Ala

<210> SEQ ID NO 98
<211> LENGTH: 33
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Glycation (3) [3?]
<220> FEATURE:
<221> NAME/KEY: MOD_RES
<222> LOCATION: (2)..(2)
<223> OTHER INFORMATION: Oxidation M [2]

<400> SEQUENCE: 98

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala

<210> SEQ ID NO 99
<211> LENGTH: 30
<212> TYPE: PRT
<213> ORGANISM: Homo sapiens
<220> FEATURE:
<221> NAME/KEY: MOD_RES
<222> LOCATION: (1)..(30)
<223> OTHER INFORMATION: Glycation [?]
<220> FEATURE:
<221> NAME/KEY: MOD_RES
<222> LOCATION: (2)..(2)
<223> OTHER INFORMATION: Oxidation M [2]

<400> SEQUENCE: 99

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys
            20                  25                  30

<210> SEQ ID NO 100
<211> LENGTH: 80
<212> TYPE: PRT
<213> ORGANISM: Homo sapiens
<220> FEATURE:
<221> NAME/KEY: MOD_RES
<222> LOCATION: (1)..(80)
<223> OTHER INFORMATION: Deamidation N (2) [2?]
<220> FEATURE:
<221> NAME/KEY: MOD_RES
<222> LOCATION: (1)..(80)

```
<223> OTHER INFORMATION: Glycation (5) [5?]
<220> FEATURE:
<221> NAME/KEY: MOD_RES
<222> LOCATION: (2)..(46)
<223> OTHER INFORMATION: Oxidation M (2) [2 46]
<220> FEATURE:
<221> NAME/KEY: MOD_RES
<222> LOCATION: (74)..(74)
<223> OTHER INFORMATION: Carboxymethyl C [74]

<400> SEQUENCE: 100

Arg Met Phe Leu Ser Phe Pro Thr Thr Lys Thr Tyr Phe Pro His Phe
1               5                   10                  15

Asp Leu Ser His Gly Ser Ala Gln Val Lys Gly His Gly Lys Lys Val
            20                  25                  30

Ala Asp Ala Leu Thr Asn Ala Val Ala His Val Asp Asp Met Pro Asn
        35                  40                  45

Ala Leu Ser Ala Leu Ser Asp Leu His Ala His Lys Leu Arg Val Asp
    50                  55                  60

Pro Val Asn Phe Lys Leu Leu Ser His Cys Leu Leu Val Thr Leu Ala
65                  70                  75                  80

<210> SEQ ID NO 101
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 101

Arg Met Phe Leu Ser Phe Pro
1               5

<210> SEQ ID NO 102
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 102

Arg Met Phe Leu Ser
1               5

<210> SEQ ID NO 103
<211> LENGTH: 85
<212> TYPE: PRT
<213> ORGANISM: Homo sapiens
<220> FEATURE:
<221> NAME/KEY: MOD_RES
<222> LOCATION: (1)..(85)
<223> OTHER INFORMATION: Oxidation M [?]
<220> FEATURE:
<221> NAME/KEY: MOD_RES
<222> LOCATION: (1)..(85)
<223> OTHER INFORMATION: Deamidation N [?]
<220> FEATURE:
<221> NAME/KEY: MOD_RES
<222> LOCATION: (1)..(85)
<223> OTHER INFORMATION: Glycation [?]
<220> FEATURE:
<221> NAME/KEY: MOD_RES
<222> LOCATION: (9)..(68)
<223> OTHER INFORMATION: Glycation (6) [9 25 29 30 59 68]
<220> FEATURE:
```

```
<221> NAME/KEY: MOD_RES
<222> LOCATION: (37)..(66)
<223> OTHER INFORMATION: Deamidation N (3) [37 47 66]
<220> FEATURE:
<221> NAME/KEY: MOD_RES
<222> LOCATION: (73)..(73)
<223> OTHER INFORMATION: Carboxymethyl C (73)

<400> SEQUENCE: 103

Met Phe Leu Ser Phe Pro Thr Thr Lys Thr Tyr Phe Pro His Phe Asp
1               5                   10                  15

Leu Ser His Gly Ser Ala Gln Val Lys Gly His Gly Lys Lys Val Ala
            20                  25                  30

Asp Ala Leu Thr Asn Ala Val Ala His Val Asp Met Pro Asn Ala
        35                  40                  45

Leu Ser Ala Leu Ser Asp Leu His Ala His Lys Leu Arg Val Asp Pro
    50                  55                  60

Val Asn Phe Lys Leu Leu Ser His Cys Leu Leu Val Thr Leu Ala Ala
65                  70                  75                  80

His Leu Pro Ala Glu
                85

<210> SEQ ID NO 104
<211> LENGTH: 76
<212> TYPE: PRT
<213> ORGANISM: Homo sapiens
<220> FEATURE:
<221> NAME/KEY: MOD_RES
<222> LOCATION: (1)..(76)
<223> OTHER INFORMATION: Glycation (2) [2?]
<220> FEATURE:
<221> NAME/KEY: MOD_RES
<222> LOCATION: (1)..(76)
<223> OTHER INFORMATION: Glycation (3) [3?]
<220> FEATURE:
<221> NAME/KEY: MOD_RES
<222> LOCATION: (28)..(57)
<223> OTHER INFORMATION: Deamidation N (3) [28 38 57]
<220> FEATURE:
<221> NAME/KEY: MOD_RES
<222> LOCATION: (36)..(36)
<223> OTHER INFORMATION: Oxidation M [36]
<220> FEATURE:
<221> NAME/KEY: MOD_RES
<222> LOCATION: (64)..(64)
<223> OTHER INFORMATION: Carboxymethyl C [64]

<400> SEQUENCE: 104

Thr Tyr Phe Pro His Phe Asp Leu Ser His Gly Ser Ala Gln Val Lys
1               5                   10                  15

Gly His Gly Lys Lys Val Ala Asp Ala Leu Thr Asn Ala Val Ala His
            20                  25                  30

Val Asp Asp Met Pro Asn Ala Leu Ser Ala Leu Ser Asp Leu His Ala
        35                  40                  45

His Lys Leu Arg Val Asp Pro Val Asn Phe Lys Leu Leu Ser His Cys
    50                  55                  60

Leu Leu Val Thr Leu Ala Ala His Leu Pro Ala Glu
65                  70                  75

<210> SEQ ID NO 105
<211> LENGTH: 75
<212> TYPE: PRT
<213> ORGANISM: Homo sapiens
<220> FEATURE:
<221> NAME/KEY: MOD_RES
<222> LOCATION: (1)..(75)
```

<223> OTHER INFORMATION: Glycation (2) [2?]
<220> FEATURE:
<221> NAME/KEY: MOD_RES
<222> LOCATION: (27)..(56)
<223> OTHER INFORMATION: Deamidation N (3) [27 37 56]
<220> FEATURE:
<221> NAME/KEY: MOD_RES
<222> LOCATION: (35)..(35)
<223> OTHER INFORMATION: Oxidation M [35]
<220> FEATURE:
<221> NAME/KEY: MOD_RES
<222> LOCATION: (63)..(63)
<223> OTHER INFORMATION: Carboxymethyl C [63]

<400> SEQUENCE: 105

Tyr Phe Pro His Phe Asp Leu Ser His Gly Ser Ala Gln Val Lys Gly
1               5                   10                  15

His Gly Lys Lys Val Ala Asp Ala Leu Thr Asn Ala Val Ala His Val
            20                  25                  30

Asp Asp Met Pro Asn Ala Leu Ser Ala Leu Ser Asp Leu His Ala His
        35                  40                  45

Lys Leu Arg Val Asp Pro Val Asn Phe Lys Leu Leu Ser His Cys Leu
    50                  55                  60

Leu Val Thr Leu Ala Ala His Leu Pro Ala Glu
65                  70                  75

<210> SEQ ID NO 106
<211> LENGTH: 74
<212> TYPE: PRT
<213> ORGANISM: Homo sapiens
<220> FEATURE:
<221> NAME/KEY: MOD_RES
<222> LOCATION: (26)..(55)
<223> OTHER INFORMATION: Deamidation N (3) [26 36 55]
<220> FEATURE:
<221> NAME/KEY: MOD_RES
<222> LOCATION: (34)..(34)
<223> OTHER INFORMATION: Oxidation M [34]
<220> FEATURE:
<221> NAME/KEY: MOD_RES
<222> LOCATION: (62)..(62)
<223> OTHER INFORMATION: Carboxymethyl C [62]

<400> SEQUENCE: 106

Phe Pro His Phe Asp Leu Ser His Gly Ser Ala Gln Val Lys Gly His
1               5                   10                  15

Gly Lys Lys Val Ala Asp Ala Leu Thr Asn Ala Val Ala His Val Asp
            20                  25                  30

Asp Met Pro Asn Ala Leu Ser Ala Leu Ser Asp Leu His Ala His Lys
        35                  40                  45

Leu Arg Val Asp Pro Val Asn Phe Lys Leu Leu Ser His Cys Leu Leu
    50                  55                  60

Val Thr Leu Ala Ala His Leu Pro Ala Glu
65                  70

<210> SEQ ID NO 107
<211> LENGTH: 72
<212> TYPE: PRT
<213> ORGANISM: Homo sapiens
<220> FEATURE:
<221> NAME/KEY: MOD_RES
<222> LOCATION: (32)..(32)
<223> OTHER INFORMATION: Oxidation M [32]
<220> FEATURE:
<221> NAME/KEY: MOD_RES
<222> LOCATION: (60)..(60)
<223> OTHER INFORMATION: Carboxymethyl C [60]

<400> SEQUENCE: 107

His Phe Asp Leu Ser His Gly Ser Ala Gln Val Lys Gly His Gly Lys
1               5                   10                  15

Lys Val Ala Asp Ala Leu Thr Asn Ala Val Ala His Val Asp Asp Met
            20                  25                  30

Pro Asn Ala Leu Ser Ala Leu Ser Asp Leu His Ala His Lys Leu Arg
        35                  40                  45

Val Asp Pro Val Asn Phe Lys Leu Leu Ser His Cys Leu Leu Val Thr
    50                  55                  60

Leu Ala Ala His Leu Pro Ala Glu
65                  70

<210> SEQ ID NO 108
<211> LENGTH: 69
<212> TYPE: PRT
<213> ORGANISM: Homo sapiens
<220> FEATURE:
<221> NAME/KEY: MOD_RES
<222> LOCATION: (1)..(69)
<223> OTHER INFORMATION: Glycation [?]
<220> FEATURE:
<221> NAME/KEY: MOD_RES
<222> LOCATION: (57)..(57)
<223> OTHER INFORMATION: Carboxymethyl C [57]

<400> SEQUENCE: 108

Leu Ser His Gly Ser Ala Gln Val Lys Gly His Gly Lys Lys Val Ala
1               5                   10                  15

Asp Ala Leu Thr Asn Ala Val Ala His Val Asp Asp Met Pro Asn Ala
            20                  25                  30

Leu Ser Ala Leu Ser Asp Leu His Ala His Lys Leu Arg Val Asp Pro
        35                  40                  45

Val Asn Phe Lys Leu Leu Ser His Cys Leu Leu Val Thr Leu Ala Ala
    50                  55                  60

His Leu Pro Ala Glu
65

<210> SEQ ID NO 109
<211> LENGTH: 67
<212> TYPE: PRT
<213> ORGANISM: Homo sapiens
<220> FEATURE:
<221> NAME/KEY: MOD_RES
<222> LOCATION: (1)..(67)
<223> OTHER INFORMATION: Glycation (4) [4?]
<220> FEATURE:
<221> NAME/KEY: MOD_RES
<222> LOCATION: (1)..(67)
<223> OTHER INFORMATION: Deamidation N (2) [2?]
<220> FEATURE:
<221> NAME/KEY: MOD_RES
<222> LOCATION: (7)..(50)
<223> OTHER INFORMATION: Glycation (5) [7 11 12 41 50]
<220> FEATURE:
<221> NAME/KEY: MOD_RES
<222> LOCATION: (55)..(55)
<223> OTHER INFORMATION: Carboxymethyl C [55]

<400> SEQUENCE: 109

His Gly Ser Ala Gln Val Lys Gly His Gly Lys Lys Val Ala Asp Ala
1               5                   10                  15

Leu Thr Asn Ala Val Ala His Val Asp Asp Met Pro Asn Ala Leu Ser
            20                  25                  30

```
Ala Leu Ser Asp Leu His Ala His Lys Leu Arg Val Asp Pro Val Asn
        35                  40                  45

Phe Lys Leu Leu Ser His Cys Leu Leu Val Thr Leu Ala Ala His Leu
 50                  55                  60

Pro Ala Glu
 65

<210> SEQ ID NO 110
<211> LENGTH: 84
<212> TYPE: PRT
<213> ORGANISM: Homo sapiens
<220> FEATURE:
<221> NAME/KEY: MOD_RES
<222> LOCATION: (36)..(65)
<223> OTHER INFORMATION: Deamidation N (3) [36 46 65]
<220> FEATURE:
<221> NAME/KEY: MOD_RES
<222> LOCATION: (72)..(72)
<223> OTHER INFORMATION: Carboxymethyl C [72]

<400> SEQUENCE: 110

Phe Leu Ser Phe Pro Thr Thr Lys Thr Tyr Phe Pro His Phe Asp Leu
 1               5                  10                  15

Ser His Gly Ser Ala Gln Val Lys Gly His Gly Lys Lys Val Ala Asp
            20                  25                  30

Ala Leu Thr Asn Ala Val Ala His Val Asp Asp Met Pro Asn Ala Leu
        35                  40                  45

Ser Ala Leu Ser Asp Leu His Ala His Lys Leu Arg Val Asp Pro Val
 50                  55                  60

Asn Phe Lys Leu Leu Ser His Cys Leu Leu Val Thr Leu Ala Ala His
 65                  70                  75                  80

Leu Pro Ala Glu

<210> SEQ ID NO 111
<211> LENGTH: 66
<212> TYPE: PRT
<213> ORGANISM: Homo sapiens
<220> FEATURE:
<221> NAME/KEY: MOD_RES
<222> LOCATION: (1)..(66)
<223> OTHER INFORMATION: Deamidation N [?]
<220> FEATURE:
<221> NAME/KEY: MOD_RES
<222> LOCATION: (6)..(49)
<223> OTHER INFORMATION: Glycation (5) [6 10 11 40 49]
<220> FEATURE:
<221> NAME/KEY: MOD_RES
<222> LOCATION: (54)..(54)
<223> OTHER INFORMATION: Carboxymethyl C [54]

<400> SEQUENCE: 111

Gly Ser Ala Gln Val Lys Gly His Gly Lys Lys Val Ala Asp Ala Leu
 1               5                  10                  15

Thr Asn Ala Val Ala His Val Asp Asp Met Pro Asn Ala Leu Ser Ala
            20                  25                  30

Leu Ser Asp Leu His Ala His Lys Leu Arg Val Asp Pro Val Asn Phe
        35                  40                  45

Lys Leu Leu Ser His Cys Leu Leu Val Thr Leu Ala Ala His Leu Pro
 50                  55                  60

Ala Glu
 65

<210> SEQ ID NO 112
```

```
<211> LENGTH: 63
<212> TYPE: PRT
<213> ORGANISM: Homo sapiens
<220> FEATURE:
<221> NAME/KEY: MOD_RES
<222> LOCATION: (15)..(44)
<223> OTHER INFORMATION: Deamidation N (3) [15 25 44]
<220> FEATURE:
<221> NAME/KEY: MOD_RES
<222> LOCATION: (51)..(51)
<223> OTHER INFORMATION: Carboxymethyl C [51]

<400> SEQUENCE: 112

Gln Val Lys Gly His Gly Lys Lys Val Ala Asp Ala Leu Thr Asn Ala
1               5                   10                  15

Val Ala His Val Asp Asp Met Pro Asn Ala Leu Ser Ala Leu Ser Asp
            20                  25                  30

Leu His Ala His Lys Leu Arg Val Asp Pro Val Asn Phe Lys Leu Leu
        35                  40                  45

Ser His Cys Leu Leu Val Thr Leu Ala Ala His Leu Pro Ala Glu
    50                  55                  60

<210> SEQ ID NO 113
<211> LENGTH: 62
<212> TYPE: PRT
<213> ORGANISM: Homo sapiens
<220> FEATURE:
<221> NAME/KEY: MOD_RES
<222> LOCATION: (1)..(62)
<223> OTHER INFORMATION: Glycation (3) [3?]
<220> FEATURE:
<221> NAME/KEY: MOD_RES
<222> LOCATION: (1)..(62)
<223> OTHER INFORMATION: Glycation (4) [4?]
<220> FEATURE:
<221> NAME/KEY: MOD_RES
<222> LOCATION: (1)..(62)
<223> OTHER INFORMATION: Deamidation N (2) [2?]
<220> FEATURE:
<221> NAME/KEY: MOD_RES
<222> LOCATION: (2)..(45)
<223> OTHER INFORMATION: Glycation (5) [2 6 7 36 45]
<220> FEATURE:
<221> NAME/KEY: MOD_RES
<222> LOCATION: (22)..(22)
<223> OTHER INFORMATION: Oxidation M [22]
<220> FEATURE:
<221> NAME/KEY: MOD_RES
<222> LOCATION: (50)..(50)
<223> OTHER INFORMATION: Carboxymethyl C [50]

<400> SEQUENCE: 113

Val Lys Gly His Gly Lys Lys Val Ala Asp Ala Leu Thr Asn Ala Val
1               5                   10                  15

Ala His Val Asp Asp Met Pro Asn Ala Leu Ser Ala Leu Ser Asp Leu
            20                  25                  30

His Ala His Lys Leu Arg Val Asp Pro Val Asn Phe Lys Leu Leu Ser
        35                  40                  45

His Cys Leu Leu Val Thr Leu Ala Ala His Leu Pro Ala Glu
    50                  55                  60

<210> SEQ ID NO 114
<211> LENGTH: 61
<212> TYPE: PRT
<213> ORGANISM: Homo sapiens
<220> FEATURE:
<221> NAME/KEY: MOD_RES
<222> LOCATION: (1)..(61)
<223> OTHER INFORMATION: Glycation (3) [3?]
```

```
<220> FEATURE:
<221> NAME/KEY: MOD_RES
<222> LOCATION: (1)..(44)
<223> OTHER INFORMATION: Glycation (5) [1 5 6 35 44]
<220> FEATURE:
<221> NAME/KEY: MOD_RES
<222> LOCATION: (1)..(61)
<223> OTHER INFORMATION: Deamidation N [?]
<220> FEATURE:
<221> NAME/KEY: MOD_RES
<222> LOCATION: (1)..(61)
<223> OTHER INFORMATION: Glycation (4) [4?]
<220> FEATURE:
<221> NAME/KEY: MOD_RES
<222> LOCATION: (1)..(61)
<223> OTHER INFORMATION: Deamidation N (2) [2?]
<220> FEATURE:
<221> NAME/KEY: MOD_RES
<222> LOCATION: (13)..(42)
<223> OTHER INFORMATION: Deamidation N (3) [13 23 42]
<220> FEATURE:
<221> NAME/KEY: MOD_RES
<222> LOCATION: (21)..(21)
<223> OTHER INFORMATION: Oxidation M [21]
<220> FEATURE:
<221> NAME/KEY: MOD_RES
<222> LOCATION: (49)..(49)
<223> OTHER INFORMATION: Carboxymethyl C [49]

<400> SEQUENCE: 114

Lys Gly His Gly Lys Lys Val Ala Asp Ala Leu Thr Asn Ala Val Ala
1               5                   10                  15

His Val Asp Asp Met Pro Asn Ala Leu Ser Ala Leu Ser Asp Leu His
                20                  25                  30

Ala His Lys Leu Arg Val Asp Pro Val Asn Phe Lys Leu Leu Ser His
            35                  40                  45

Cys Leu Leu Val Thr Leu Ala Ala His Leu Pro Ala Glu
    50                  55                  60

<210> SEQ ID NO 115
<211> LENGTH: 60
<212> TYPE: PRT
<213> ORGANISM: Homo sapiens
<220> FEATURE:
<221> NAME/KEY: MOD_RES
<222> LOCATION: (1)..(60)
<223> OTHER INFORMATION: Deamidation N (2) [2?]
<220> FEATURE:
<221> NAME/KEY: MOD_RES
<222> LOCATION: (1)..(60)
<223> OTHER INFORMATION: Glycation (3) [3?]
<220> FEATURE:
<221> NAME/KEY: MOD_RES
<222> LOCATION: (48)..(48)
<223> OTHER INFORMATION: Carboxymethyl C [48]

<400> SEQUENCE: 115

Gly His Gly Lys Lys Val Ala Asp Ala Leu Thr Asn Ala Val Ala His
1               5                   10                  15

Val Asp Asp Met Pro Asn Ala Leu Ser Ala Leu Ser Asp Leu His Ala
                20                  25                  30

His Lys Leu Arg Val Asp Pro Val Asn Phe Lys Leu Leu Ser His Cys
            35                  40                  45

Leu Leu Val Thr Leu Ala Ala His Leu Pro Ala Glu
    50                  55                  60

<210> SEQ ID NO 116
<211> LENGTH: 59
<212> TYPE: PRT
```

-continued

```
<213> ORGANISM: Homo sapiens
<220> FEATURE:
<221> NAME/KEY: MOD_RES
<222> LOCATION: (1)..(59)
<223> OTHER INFORMATION: Deamidation N (2) [2?]
<220> FEATURE:
<221> NAME/KEY: MOD_RES
<222> LOCATION: (1)..(59)
<223> OTHER INFORMATION: Deamidation N [?]
<220> FEATURE:
<221> NAME/KEY: MOD_RES
<222> LOCATION: (3)..(42)
<223> OTHER INFORMATION: Glycation (4) [3 4 33 42]
<220> FEATURE:
<221> NAME/KEY: MOD_RES
<222> LOCATION: (11)..(40)
<223> OTHER INFORMATION: Deamidation N (3) [11 21 40]
<220> FEATURE:
<221> NAME/KEY: MOD_RES
<222> LOCATION: (47)..(47)
<223> OTHER INFORMATION: Carboxymethyl C [47]

<400> SEQUENCE: 116

His Gly Lys Lys Val Ala Asp Ala Leu Thr Asn Ala Val Ala His Val
 1               5                  10                  15

Asp Asp Met Pro Asn Ala Leu Ser Ala Leu Ser Asp Leu His Ala His
             20                  25                  30

Lys Leu Arg Val Asp Pro Val Asn Phe Lys Leu Leu Ser His Cys Leu
         35                  40                  45

Leu Val Thr Leu Ala Ala His Leu Pro Ala Glu
     50                  55

<210> SEQ ID NO 117
<211> LENGTH: 58
<212> TYPE: PRT
<213> ORGANISM: Homo sapiens
<220> FEATURE:
<221> NAME/KEY: MOD_RES
<222> LOCATION: (1)..(58)
<223> OTHER INFORMATION: Deamidation N (2) [2?]
<220> FEATURE:
<221> NAME/KEY: MOD_RES
<222> LOCATION: (46)..(46)
<223> OTHER INFORMATION: Carboxymethyl C [46]

<400> SEQUENCE: 117

Gly Lys Lys Val Ala Asp Ala Leu Thr Asn Ala Val Ala His Val Asp
 1               5                  10                  15

Asp Met Pro Asn Ala Leu Ser Ala Leu Ser Asp Leu His Ala His Lys
             20                  25                  30

Leu Arg Val Asp Pro Val Asn Phe Lys Leu Leu Ser His Cys Leu Leu
         35                  40                  45

Val Thr Leu Ala Ala His Leu Pro Ala Glu
     50                  55

<210> SEQ ID NO 118
<211> LENGTH: 57
<212> TYPE: PRT
<213> ORGANISM: Homo sapiens
<220> FEATURE:
<221> NAME/KEY: MOD_RES
<222> LOCATION: (1)..(57)
<223> OTHER INFORMATION: Deamidation N (2) [2?]
<220> FEATURE:
<221> NAME/KEY: MOD_RES
<222> LOCATION: (1)..(57)
<223> OTHER INFORMATION: Glycation (3) [3?]
<220> FEATURE:
<221> NAME/KEY: MOD_RES
```

```
<222> LOCATION: (1)..(57)
<223> OTHER INFORMATION: Deamidation N [?]
<220> FEATURE:
<221> NAME/KEY: MOD_RES
<222> LOCATION: (17)..(17)
<223> OTHER INFORMATION: Oxidation M [17]
<220> FEATURE:
<221> NAME/KEY: MOD_RES
<222> LOCATION: (45)..(45)
<223> OTHER INFORMATION: Carboxymethyl C [45]

<400> SEQUENCE: 118

Lys Lys Val Ala Asp Ala Leu Thr Asn Ala Val Ala His Val Asp Asp
1               5                   10                  15

Met Pro Asn Ala Leu Ser Ala Leu Ser Asp Leu His Ala His Lys Leu
            20                  25                  30

Arg Val Asp Pro Val Asn Phe Lys Leu Leu Ser His Cys Leu Leu Val
        35                  40                  45

Thr Leu Ala Ala His Leu Pro Ala Glu
    50                  55

<210> SEQ ID NO 119
<211> LENGTH: 55
<212> TYPE: PRT
<213> ORGANISM: Homo sapiens
<220> FEATURE:
<221> NAME/KEY: MOD_RES
<222> LOCATION: (1)..(55)
<223> OTHER INFORMATION: Glycation [?]
<220> FEATURE:
<221> NAME/KEY: MOD_RES
<222> LOCATION: (16)..(16)
<223> OTHER INFORMATION: Oxidation M [16]
<220> FEATURE:
<221> NAME/KEY: MOD_RES
<222> LOCATION: (44)..(44)
<223> OTHER INFORMATION: Carboxymethyl C [44]

<400> SEQUENCE: 119

Lys Val Ala Asp Ala Leu Thr Asn Ala Val Ala His Val Asp Asp Met
1               5                   10                  15

Pro Asn Ala Leu Ser Ala Leu Ser Asp Leu His Ala His Lys Leu Arg
            20                  25                  30

Val Asp Pro Val Asn Phe Lys Leu Leu Ser His Cys Leu Leu Val Thr
        35                  40                  45

Leu Met His Leu Pro Ala Glu
    50                  55

<210> SEQ ID NO 120
<211> LENGTH: 55
<212> TYPE: PRT
<213> ORGANISM: Homo sapiens
<220> FEATURE:
<221> NAME/KEY: MOD_RES
<222> LOCATION: (1)..(54)
<223> OTHER INFORMATION: Glycation [?]
<220> FEATURE:
<221> NAME/KEY: MOD_RES
<222> LOCATION: (1)..(54)
<223> OTHER INFORMATION: Glycation [?]
<220> FEATURE:
<221> NAME/KEY: MOD_RES
<222> LOCATION: (1)..(54)
<223> OTHER INFORMATION: Deamidation N (2) [2?]
<220> FEATURE:
<221> NAME/KEY: MOD_RES
<222> LOCATION: (1)..(54)
<223> OTHER INFORMATION: Deamidation N [?]
<220> FEATURE:
```

```
<221> NAME/KEY: MOD_RES
<222> LOCATION: (15)..(15)
<223> OTHER INFORMATION: Oxidation M [15]
<220> FEATURE:
<221> NAME/KEY: MOD_RES
<222> LOCATION: (29)..(38)
<223> OTHER INFORMATION: Glycation (2) [29 38]
<220> FEATURE:
<221> NAME/KEY: MOD_RES
<222> LOCATION: (43)..(43)
<223> OTHER INFORMATION: Carboxymethyl C [43]

<400> SEQUENCE: 120

Val Ala Asp Ala Leu Thr Asn Ala Val Ala His Val Asp Asp Met Pro
1               5                   10                  15

Asn Ala Leu Ser Ala Leu Ser Asp Leu His Ala His Lys Leu Arg Val
            20                  25                  30

Asp Pro Val Asn Phe Lys Leu Leu Ser His Cys Leu Leu Val Thr Leu
        35                  40                  45

Ala Ala His Leu Pro Ala Glu
    50                  55

<210> SEQ ID NO 121
<211> LENGTH: 52
<212> TYPE: PRT
<213> ORGANISM: Homo sapiens
<220> FEATURE:
<221> NAME/KEY: MOD_RES
<222> LOCATION: (1)..(52)
<223> OTHER INFORMATION: Glycation [?]
<220> FEATURE:
<221> NAME/KEY: MOD_RES
<222> LOCATION: (1)..(52)
<223> OTHER INFORMATION: Deamidation N [?]
<220> FEATURE:
<221> NAME/KEY: MOD_RES
<222> LOCATION: (12)..(12)
<223> OTHER INFORMATION: Oxidation M [12]
<220> FEATURE:
<221> NAME/KEY: MOD_RES
<222> LOCATION: (40)..(40)
<223> OTHER INFORMATION: Carboxymethyl C [40]

<400> SEQUENCE: 121

Ala Leu Thr Asn Ala Val Ala His Val Asp Asp Met Pro Asn Ala Leu
1               5                   10                  15

Ser Ala Leu Ser Asp Leu His Ala His Lys Leu Arg Val Asp Pro Val
            20                  25                  30

Asn Phe Lys Leu Leu Ser His Cys Leu Leu Val Thr Leu Ala Ala His
        35                  40                  45

Leu Pro Ala Glu
    50

<210> SEQ ID NO 122
<211> LENGTH: 51
<212> TYPE: PRT
<213> ORGANISM: Homo sapiens
<220> FEATURE:
<221> NAME/KEY: MOD_RES
<222> LOCATION: (1)..(51)
<223> OTHER INFORMATION: Glycation [?]
<220> FEATURE:
<221> NAME/KEY: MOD_RES
<222> LOCATION: (11)..(11)
<223> OTHER INFORMATION: Oxidation M [11]
<220> FEATURE:
<221> NAME/KEY: MOD_RES
<222> LOCATION: (39)..(39)
<223> OTHER INFORMATION: Carboxymethyl C [39]
```

-continued

<400> SEQUENCE: 122

Leu Thr Asn Ala Val Ala His Val Asp Asp Met Pro Asn Ala Leu Ser
1               5                   10                  15

Ala Leu Ser Asp Leu His Ala His Lys Leu Arg Val Asp Pro Val Asn
            20                  25                  30

Phe Lys Leu Leu Ser His Cys Leu Leu Val Thr Leu Ala Ala His Leu
        35                  40                  45

Pro Ala Glu
    50

<210> SEQ ID NO 123
<211> LENGTH: 50
<212> TYPE: PRT
<213> ORGANISM: Homo sapiens
<220> FEATURE:
<221> NAME/KEY: MOD_RES
<222> LOCATION: (1)..(50)
<223> OTHER INFORMATION: Deamidation N (2) [2?]
<220> FEATURE:
<221> NAME/KEY: MOD_RES
<222> LOCATION: (2)..(31)
<223> OTHER INFORMATION: Deamidation N (3) [2 12 31]
<220> FEATURE:
<221> NAME/KEY: MOD_RES
<222> LOCATION: (10)..(10)
<223> OTHER INFORMATION: Oxidation M [10]
<220> FEATURE:
<221> NAME/KEY: MOD_RES
<222> LOCATION: (38)..(38)
<223> OTHER INFORMATION: Carboxymethyl C [38]

<400> SEQUENCE: 123

Thr Asn Ala Val Ala His Val Asp Asp Met Pro Asn Ala Leu Ser Ala
1               5                   10                  15

Leu Ser Asp Leu His Ala His Lys Leu Arg Val Asp Pro Val Asn Phe
            20                  25                  30

Lys Leu Leu Ser His Cys Leu Leu Val Thr Leu Ala Ala His Leu Pro
        35                  40                  45

Ala Glu
    50

<210> SEQ ID NO 124
<211> LENGTH: 48
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Oxidation M [8]
<220> FEATURE:
<221> NAME/KEY: MOD_RES
<222> LOCATION: (36)..(36)
<223> OTHER INFORMATION: Carboxymethyl C [36]

<400> SEQUENCE: 124

Ala Val Ala His Val Asp Asp Met Pro Asn Ala Leu Ser Ala Leu Ser
1               5                   10                  15

Asp Leu His Ala His Lys Leu Arg Val Asp Pro Val Asn Phe Lys Leu
            20                  25                  30

Leu Ser His Cys Leu Leu Val Thr Leu Ala Ala His Leu Pro Ala Glu
        35                  40                  45

<210> SEQ ID NO 125
<211> LENGTH: 82

```
<212> TYPE: PRT
<213> ORGANISM: Homo sapiens
<220> FEATURE:
<221> NAME/KEY: MOD_RES
<222> LOCATION: (1)..(82)
<223> OTHER INFORMATION: Glycation (5) [5?]
<220> FEATURE:
<221> NAME/KEY: MOD_RES
<222> LOCATION: (42)..(42)
<223> OTHER INFORMATION: Oxidation M [42]
<220> FEATURE:
<221> NAME/KEY: MOD_RES
<222> LOCATION: (70)..(70)
<223> OTHER INFORMATION: Carboxymethyl C [70]

<400> SEQUENCE: 125

Ser Phe Pro Thr Thr Lys Thr Tyr Phe Pro His Phe Asp Leu Ser His
1               5                   10                  15

Gly Ser Ala Gln Val Lys Gly His Gly Lys Lys Val Ala Asp Ala Leu
            20                  25                  30

Thr Asn Ala Val Ala His Val Asp Asp Met Pro Asn Ala Leu Ser Ala
        35                  40                  45

Leu Ser Asp Leu His Ala His Lys Leu Arg Val Asp Pro Val Asn Phe
    50                  55                  60

Lys Leu Leu Ser His Cys Leu Leu Val Thr Leu Ala Ala His Leu Pro
65                  70                  75                  80

Ala Glu

<210> SEQ ID NO 126
<211> LENGTH: 45
<212> TYPE: PRT
<213> ORGANISM: Homo sapiens
<220> FEATURE:
<221> NAME/KEY: MOD_RES
<222> LOCATION: (1)..(45)
<223> OTHER INFORMATION: Glycation [?]
<220> FEATURE:
<221> NAME/KEY: MOD_RES
<222> LOCATION: (1)..(45)
<223> OTHER INFORMATION: Deamidation N [?]
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (33)..(33)
<223> OTHER INFORMATION: Carboxymethyl C [33]

<400> SEQUENCE: 126

His Val Asp Asp Met Pro Asn Ala Leu Ser Ala Leu Ser Asp Leu His
1               5                   10                  15

Ala His Lys Leu Arg Val Asp Pro Val Asn Phe Lys Leu Leu Ser His
            20                  25                  30

Cys Leu Leu Val Thr Leu Ala Ala His Leu Pro Ala Glu
        35                  40                  45

<210> SEQ ID NO 127
<211> LENGTH: 42
<212> TYPE: PRT
<213> ORGANISM: Homo sapiens
<220> FEATURE:
<221> NAME/KEY: MOD_RES
<222> LOCATION: (1)..(42)
<223> OTHER INFORMATION: Glycation [?]
<220> FEATURE:
<221> NAME/KEY: MOD_RES
<222> LOCATION: (2)..(2)
```

```
<223> OTHER INFORMATION: Oxidation M [2]
<220> FEATURE:
<221> NAME/KEY: MOD_RES
<222> LOCATION: (4)..(23)
<223> OTHER INFORMATION: Deamidation N (2) [4 23]
<220> FEATURE:
<221> NAME/KEY: MOD_RES
<222> LOCATION: (30)..(30)
<223> OTHER INFORMATION: Carboxymethyl C [30]

<400> SEQUENCE: 127

Asp Met Pro Asn Ala Leu Ser Ala Leu Ser Asp Leu His Ala His Lys
1               5                   10                  15

Leu Arg Val Asp Pro Val Asn Phe Lys Leu Leu Ser His Cys Leu Leu
            20                  25                  30

Val Thr Leu Ala Ala His Leu Pro Ala Glu
        35                  40

<210> SEQ ID NO 128
<211> LENGTH: 40
<212> TYPE: PRT
<213> ORGANISM: Homo sapiens
<220> FEATURE:
<221> NAME/KEY: MOD_RES
<222> LOCATION: (14)..(23)
<223> OTHER INFORMATION: Glycation (2) [14 23]
<220> FEATURE:
<221> NAME/KEY: MOD_RES
<222> LOCATION: (28)..(28)
<223> OTHER INFORMATION: Carboxymethyl C [28]

<400> SEQUENCE: 128

Pro Asn Ala Leu Ser Ala Leu Ser Asp Leu His Ala His Lys Leu Arg
1               5                   10                  15

Val Asp Pro Val Asn Phe Lys Leu Leu Ser His Cys Leu Leu Val Thr
            20                  25                  30

Leu Ala Ala His Leu Pro Ala Glu
        35                  40

<210> SEQ ID NO 129
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation [?]
<220> FEATURE:
<221> NAME/KEY: MOD_RES
<222> LOCATION: (27)..(27)
<223> OTHER INFORMATION: Carboxymethyl C [27]

<400> SEQUENCE: 129

Asn Ala Leu Ser Ala Leu Ser Asp Leu His Ala His Lys Leu Arg Val
1               5                   10                  15

Asp Pro Val Asn Phe Lys Leu Leu Ser His Cys Leu Leu Val Thr Leu
            20                  25                  30

Ala Ala His Leu Pro Ala Glu
        35

<210> SEQ ID NO 130
<211> LENGTH: 81
<212> TYPE: PRT
<213> ORGANISM: Homo sapiens
<220> FEATURE:
<221> NAME/KEY: MOD_RES
<222> LOCATION: (1)..(81)
```

```
<223> OTHER INFORMATION: Glycation (3) [3?]
<220> FEATURE:
<221> NAME/KEY: MOD_RES
<222> LOCATION: (1)..(81)
<223> OTHER INFORMATION: Deamidation N (2) [2?]
<220> FEATURE:
<221> NAME/KEY: MOD_RES
<222> LOCATION: (33)..(62)
<223> OTHER INFORMATION: Deamidation N (3) [33 43 62]
<220> FEATURE:
<221> NAME/KEY: MOD_RES
<222> LOCATION: (69)..(69)
<223> OTHER INFORMATION: Carboxymethyl C [69]

<400> SEQUENCE: 130

Phe Pro Thr Thr Lys Thr Tyr Phe Pro His Phe Asp Leu Ser His Gly
 1               5                  10                  15

Ser Ala Gln Val Lys Gly His Gly Lys Lys Val Ala Asp Ala Leu Thr
            20                  25                  30

Asn Ala Val Ala His Val Asp Asp Met Pro Asn Ala Leu Ser Ala Leu
        35                  40                  45

Ser Asp Leu His Ala His Lys Leu Arg Val Asp Pro Val Asn Phe Lys
    50                  55                  60

Leu Leu Ser His Cys Leu Leu Val Thr Leu Ala Ala His Leu Pro Ala
65                  70                  75                  80

Glu

<210> SEQ ID NO 131
<211> LENGTH: 33
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Glycation [?]
<220> FEATURE:
<221> NAME/KEY: MOD_RES
<222> LOCATION: (21)..(21)
<223> OTHER INFORMATION: Carboxymethyl C [21]

<400> SEQUENCE: 131

Ser Asp Leu His Ala His Lys Leu Arg Val Asp Pro Val Asn Phe Lys
 1               5                  10                  15

Leu Leu Ser His Cys Leu Leu Val Thr Leu Ala Ala His Leu Pro Ala
            20                  25                  30

Glu

<210> SEQ ID NO 132
<211> LENGTH: 30
<212> TYPE: PRT
<213> ORGANISM: Homo sapiens
<220> FEATURE:
<221> NAME/KEY: MOD_RES
<222> LOCATION: (4)..(13)
<223> OTHER INFORMATION: Glycation (2) [4 13]
<220> FEATURE:
<221> NAME/KEY: MOD_RES
<222> LOCATION: (18)..(18)
<223> OTHER INFORMATION: Carboxymethyl C [18]

<400> SEQUENCE: 132

His Ala His Lys Leu Arg Val Asp Pro Val Asn Phe Lys Leu Leu Ser
 1               5                  10                  15

His Cys Leu Leu Val Thr Leu Ala Ala His Leu Pro Ala Glu
            20                  25                  30
```

```
<210> SEQ ID NO 133
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (7)..(7)
<223> OTHER INFORMATION: Carboxymethyl C [7]

<400> SEQUENCE: 133

Phe Lys Leu Leu Ser His Cys Leu Leu Val Thr Leu Ala Ala His Leu
 1               5                  10                  15

Pro Ala Glu

<210> SEQ ID NO 134
<211> LENGTH: 79
<212> TYPE: PRT
<213> ORGANISM: Homo sapiens
<220> FEATURE:
<221> NAME/KEY: MOD_RES
<222> LOCATION: (1)..(79)
<223> OTHER INFORMATION: Deamidation N (2) [2?]
<220> FEATURE:
<221> NAME/KEY: MOD_RES
<222> LOCATION: (67)..(67)
<223> OTHER INFORMATION: Carboxymethyl C [67]

<400> SEQUENCE: 134

Thr Thr Lys Thr Tyr Phe Pro His Phe Asp Leu Ser His Gly Ser Ala
 1               5                  10                  15

Gln Val Lys Gly His Gly Lys Lys Val Ala Asp Ala Leu Thr Asn Ala
            20                  25                  30

Val Ala His Val Asp Asp Met Pro Asn Ala Leu Ser Ala Leu Ser Asp
        35                  40                  45

Leu His Ala His Lys Leu Arg Val Asp Pro Val Asn Phe Lys Leu Leu
    50                  55                  60

Ser His Cys Leu Leu Val Thr Leu Ala Ala His Leu Pro Ala Glu
65                  70                  75

<210> SEQ ID NO 135
<211> LENGTH: 78
<212> TYPE: PRT
<213> ORGANISM: Homo sapiens
<220> FEATURE:
<221> NAME/KEY: MOD_RES
<222> LOCATION: (1)..(78)
<223> OTHER INFORMATION: Deamidation N [?]
<220> FEATURE:
<221> NAME/KEY: MOD_RES
<222> LOCATION: (1)..(78)
<223> OTHER INFORMATION: Glycation [?]
<220> FEATURE:
<221> NAME/KEY: MOD_RES
<222> LOCATION: (1)..(78)
<223> OTHER INFORMATION: Glycation (5) [5?]
<220> FEATURE:
<221> NAME/KEY: MOD_RES
<222> LOCATION: (38)..(38)
<223> OTHER INFORMATION: Oxidation M [38]
<220> FEATURE:
<221> NAME/KEY: MOD_RES
<222> LOCATION: (66)..(66)
<223> OTHER INFORMATION: Carboxymethyl C [66]

<400> SEQUENCE: 135
```

```
Thr Lys Thr Tyr Phe Pro His Phe Asp Leu Ser His Gly Ser Ala Gln
1               5                   10                  15

Val Lys Gly His Gly Lys Lys Val Ala Asp Ala Leu Thr Asn Ala Val
            20                  25                  30

Ala His Val Asp Asp Met Pro Asn Ala Leu Ser Ala Leu Ser Asp Leu
        35                  40                  45

His Ala His Lys Leu Arg Val Asp Pro Val Asn Phe Lys Leu Leu Ser
    50                  55                  60

His Cys Leu Leu Val Thr Leu Ala Ala His Leu Pro Ala Glu
65                  70                  75
```

<210> SEQ ID NO 136
<211> LENGTH: 76
<212> TYPE: PRT
<213> ORGANISM: Homo sapiens
<220> FEATURE:
<221> NAME/KEY: MOD_RES
<222> LOCATION: (1)..(76)
<223> OTHER INFORMATION: Deamidation N (2) [2?]
<220> FEATURE:
<221> NAME/KEY: MOD_RES
<222> LOCATION: (1)..(76)
<223> OTHER INFORMATION: Glycation (2) [2?]
<220> FEATURE:
<221> NAME/KEY: MOD_RES
<222> LOCATION: (1)..(76)
<223> OTHER INFORMATION: Glycation (3) [3?]
<220> FEATURE:
<221> NAME/KEY: MOD_RES
<222> LOCATION: (37)..(37)
<223> OTHER INFORMATION: Oxidation M [37]
<220> FEATURE:
<221> NAME/KEY: MOD_RES
<222> LOCATION: (65)..(65)
<223> OTHER INFORMATION: Carboxymethyl C [65]

<400> SEQUENCE: 136

```
Lys Thr Tyr Phe Pro His Phe Asp Leu Ser His Gly Ser Ala Gln Val
1               5                   10                  15

Lys Gly His Gly Lys Lys Val Ala Asp Ala Leu Thr Asn Ala Val Ala
            20                  25                  30

His Val Asp Asp Met Pro Asn Ala Leu Ser Ala Leu Ser Asp Leu His
        35                  40                  45

Ala His Lys Leu Arg Val Asp Pro Val Asn Phe Lys Leu Leu Ser His
    50                  55                  60

Cys Leu Leu Val Thr Leu Met His Leu Pro Ala Glu
65                  70                  75
```

<210> SEQ ID NO 137
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Glycation [12]
<220> FEATURE:
<221> NAME/KEY: MOD_RES
<222> LOCATION: (12)..(12)

<400> SEQUENCE: 137

```
Phe Leu Ala Ser Val Ser Thr Val Leu Thr Ser Lys Tyr Arg
1               5                   10
```

<210> SEQ ID NO 138

```
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]

<400> SEQUENCE: 138

Ser Thr Val Leu Thr Ser Lys Tyr Arg
1               5

<210> SEQ ID NO 139
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 139

Thr Ser Lys Tyr Arg
1               5

<210> SEQ ID NO 140
<211> LENGTH: 22
<212> TYPE: PRT
<213> ORGANISM: Homo sapiens
<220> FEATURE:
<221> NAME/KEY: MOD_RES
<222> LOCATION: (8)..(20)
<223> OTHER INFORMATION: Glycation (2) [8 20]

<400> SEQUENCE: 140

Ala Val His Ala Ser Leu Asp Lys Phe Leu Ala Ser Val Ser Thr Val
1               5                   10                  15

Leu Thr Ser Lys Tyr Arg
            20

<210> SEQ ID NO 141
<211> LENGTH: 29
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Deamidation N [19]

<400> SEQUENCE: 141

Tyr Pro Val Glu Pro Phe Thr Glu Ser Gln Ser Leu Thr Leu Thr Asp
1               5                   10                  15

Val Glu Asn Leu His Leu Pro Leu Pro Leu Leu Gln Ser
            20                  25

<210> SEQ ID NO 142
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 142

Asp Met Pro Ile Gln Ala Phe Leu Leu Tyr Gln Glu Pro Val Leu Gly
1               5                   10                  15
```

Pro Val

<210> SEQ ID NO 143
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 143

Asp Met Pro Ile Gln Ala Phe Leu Leu Tyr
1               5                   10

<210> SEQ ID NO 144
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Deamidation N [5]

<400> SEQUENCE: 144

Leu Glu Glu Leu Asn Val Pro Gly Glu Ile Val Glu Ser Leu Ser Ser
1               5                   10                  15

Ser Glu Glu Ser Ile Thr Arg
            20

<210> SEQ ID NO 145
<211> LENGTH: 19
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 145

Asn Val Pro Gly Glu Ile Val Glu Ser Leu Ser Ser Ser Glu Glu Ser
1               5                   10                  15

Ile Thr Arg

<210> SEQ ID NO 146
<211> LENGTH: 34
<212> TYPE: PRT
<213> ORGANISM: Homo sapiens
<220> FEATURE:
<221> NAME/KEY: MOD_RES
<222> LOCATION: (1)..(34)
<223> OTHER INFORMATION: Deamidation N I?]
<220> FEATURE:
<221> NAME/KEY: MOD_RES
<222> LOCATION: (30)..(30)
<223> OTHER INFORMATION: Oxidation M [30]

<400> SEQUENCE: 146

Gly Pro Ile Pro Asn Ser Leu Pro Gln Asn Ile Pro Pro Leu Thr Gln
1               5                   10                  15

Thr Pro Val Val Val Pro Pro Phe Leu Gln Pro Glu Val Met Gly Val
            20                  25                  30

Ser Lys

<210> SEQ ID NO 147
<211> LENGTH: 33

```
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Oxidation M [29]

<400> SEQUENCE: 147

Pro Ile Pro Asn Ser Leu Pro Gln Asn Ile Pro Pro Leu Thr Gln Thr
1               5                   10                  15

Pro Val Val Val Pro Pro Phe Leu Gln Pro Glu Val Met Gly Val Ser
            20                  25                  30

Lys

<210> SEQ ID NO 148
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Oxidation M [8]

<400> SEQUENCE: 148

Pro Phe Leu Gln Pro Glu Val Met Gly Val Ser Lys
1               5                   10

<210> SEQ ID NO 149
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]

<400> SEQUENCE: 149

Pro Glu Val Met Gly Val Ser Lys
1               5

<210> SEQ ID NO 150
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]

<400> SEQUENCE: 150

Met Gly Val Ser Lys
1               5

<210> SEQ ID NO 151
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]

<400> SEQUENCE: 151

Leu Val Asn Glu Leu Thr Glu Phe Ala
1               5

<210> SEQ ID NO 152
```

```
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]

<400> SEQUENCE: 152

Leu Val Asn Glu Leu Thr Glu Phe
1               5

<210> SEQ ID NO 153
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]

<400> SEQUENCE: 153

Leu Val Asn Glu Leu
1               5

<210> SEQ ID NO 154
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]

<400> SEQUENCE: 154

Val Asn Glu Leu Thr Glu Phe Ala Lys
1               5

<210> SEQ ID NO 155
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Carboxymethyl C [9]

<400> SEQUENCE: 155

Val Ala Asp Glu Ser His Ala Gly Cys Glu Lys
1               5                   10

<210> SEQ ID NO 156
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 156

Phe Gly Asp Glu Leu Cys Lys
1               5

<210> SEQ ID NO 157
<211> LENGTH: 8
<212> TYPE: PRT
<213> ORGANISM: Homo sapiens
<220> FEATURE:
```

```
<221> NAME/KEY: MOD_RES
<222> LOCATION: (6)..(6)
<223> OTHER INFORMATION: Deamidation N [6]

<400> SEQUENCE: 157

Leu Lys Pro Asp Pro Asn Thr Leu
1               5

<210> SEQ ID NO 158
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Deamidation N [11]

<400> SEQUENCE: 158

Phe Tyr Ala Pro Glu Leu Leu Tyr Tyr Ala Asn Lys
1               5                   10

<210> SEQ ID NO 159
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Deamidation N [8]

<400> SEQUENCE: 159

Pro Glu Leu Leu Tyr Tyr Ala Asn Lys
1               5

<210> SEQ ID NO 160
<211> LENGTH: 14
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 160

Tyr Asn Gly Val Phe Gln Glu Cys Cys Gln Ala Glu Asp Lys
1               5                   10

<210> SEQ ID NO 161
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 161

Tyr Ile Cys Asp Asn Gln Asp Thr Ile Ser Ser Lys
1               5                   10

<210> SEQ ID NO 162
<211> LENGTH: 9
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
```

```
<400> SEQUENCE: 162

Glu Cys Cys Asp Lys Pro Leu Leu Glu
1               5

<210> SEQ ID NO 163
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 163

Cys Asp Lys Pro Leu Leu Glu Lys
1               5

<210> SEQ ID NO 164
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 164

Asp Ala Ile Pro Glu Asn
1               5

<210> SEQ ID NO 165
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 165

Asp Ala Ile Pro Glu Asn Leu Pro Pro Leu Thr Ala Asp Phe Ala Glu
1               5                   10                  15

<210> SEQ ID NO 166
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 166

Asp Ala Ile Pro Glu Asn Leu Pro Pro Leu Thr Ala Asp Phe Ala
1               5                   10                  15

<210> SEQ ID NO 167
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 167

Asp Ala Ile Pro Glu Asn Leu Pro Pro Leu Thr Ala Asp Phe
1               5                   10
```

<210> SEQ ID NO 168
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 168

Asp Ala Ile Pro Glu Asn Leu Pro Pro Leu
1               5                   10

<210> SEQ ID NO 169
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 169

Val Asp Glu Pro Gln Asn Leu Ile Lys
1               5

<210> SEQ ID NO 170
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Deamidation N [8]

<400> SEQUENCE: 170

Leu Gly Glu Tyr Gly Phe Gln Asn Ala Leu
1               5                   10

<210> SEQ ID NO 171
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 171

Asn Ala Leu Ile Val Arg
1               5

<210> SEQ ID NO 172
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Deamidation N [9]

<400> SEQUENCE: 172

Glu Asp Tyr Leu Ser Leu Ile Leu Asn Arg
1               5                   10

<210> SEQ ID NO 173
<211> LENGTH: 12

```
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Carboxymethyl C [9]

<400> SEQUENCE: 173

Leu Phe Thr Phe His Ala Asp Ile Cys Thr Leu Pro
1               5                   10

<210> SEQ ID NO 174
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 174

Ala Asp Ile Cys Thr Leu Pro Asp Thr Glu Lys
1               5                   10

<210> SEQ ID NO 175
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Oxidation M [3]
<220> FEATURE:
<221> NAME/KEY: MOD_RES
<222> LOCATION: (5)..(5)
<223> OTHER INFORMATION: Deamidation N [5]

<400> SEQUENCE: 175

Thr Val Met Glu Asn Phe Val Ala Phe Val Asp Lys
1               5                   10

<210> SEQ ID NO 176
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Oxidation M [3]

<400> SEQUENCE: 176

Thr Val Met Glu Asn Phe
1               5

<210> SEQ ID NO 177
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 177

Val Met Glu Asn Phe Val Ala Phe Val Asp Lys
1               5                   10

<210> SEQ ID NO 178
<211> LENGTH: 9
```

```
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 178

Gln Cys Pro Phe Asp Glu His Val Lys
1               5

<210> SEQ ID NO 179
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Carboxymethyl C [8]

<400> SEQUENCE: 179

Phe Ser Gln Tyr Leu Gln Gln Cys Pro Phe Asp Glu His Val Lys
1               5                   10                  15

<210> SEQ ID NO 180
<211> LENGTH: 19
<212> TYPE: PRT
<213> ORGANISM: Homo sapiens
<220> FEATURE:
<221> NAME/KEY: MOD_RES
<222> LOCATION: (2)..(18)
<223> OTHER INFORMATION: Carboxymethyl C (3) [2 17 18]
<220> FEATURE:
<221> NAME/KEY: MOD_RES
<222> LOCATION: (3)..(3)
<223> OTHER INFORMATION: Glycation [3]
<220> FEATURE:
<221> NAME/KEY: MOD_RES
<222> LOCATION: (14)..(14)
<223> OTHER INFORMATION: Oxidation M [14]

<400> SEQUENCE: 180

Leu Cys Lys Val Ala Ser Leu Arg Glu Thr Tyr Gly Asp Met Ala Asp
1               5                   10                  15

Cys Cys Glu

<210> SEQ ID NO 181
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 181

Leu Cys Lys Val Ala Ser Leu Arg Glu Thr Tyr Gly
1               5                   10

<210> SEQ ID NO 182
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 182
```

```
Leu Cys Lys Val Ala Ser Leu Arg Glu Thr Tyr
1               5                   10

<210> SEQ ID NO 183
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 183

Leu Cys Lys Val Ala Ser Leu Arg Glu Thr
1               5                   10

<210> SEQ ID NO 184
<211> LENGTH: 18
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Carboxymethyl C (3) [1 16 17]
<220> FEATURE:
<221> NAME/KEY: MOD_RES
<222> LOCATION: (2)..(2)
<223> OTHER INFORMATION: Glycation I2]

<400> SEQUENCE: 184

Cys Lys Val Ala Ser Leu Arg Glu Thr Tyr Gly Asp Met Ala Asp Cys
1               5                   10                  15

Cys Glu

<210> SEQ ID NO 185
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Oxidation M [12]
<220> FEATURE:
<221> NAME/KEY: MOD_RES
<222> LOCATION: (15)..(16)
<223> OTHER INFORMATION: Carboxymethyl C (2) [15 16]

<400> SEQUENCE: 185

Lys Val Ala Ser Leu Arg Glu Thr Tyr Gly Asp Met Ala Asp Cys Cys
1               5                   10                  15

Glu

<210> SEQ ID NO 186
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (9)..(10)
<223> OTHER INFORMATION: Carboxymethyl C (2) [9 10]

<400> SEQUENCE: 186

Glu Thr Tyr Gly Asp Met Ala Asp Cys Cys Glu
1               5                   10
```

<210> SEQ ID NO 187
<211> LENGTH: 21
<212> TYPE: PRT
<213> ORGANISM: Homo sapiens
<220> FEATURE:
<221> NAME/KEY: MOD_RES
<222> LOCATION: (14)..(15)
<223> OTHER INFORMATION: Carboxymethyl C (2) [14 15]

<400> SEQUENCE: 187

Val Ala Ser Leu Arg Glu Thr Tyr Gly Asp Met Ala Asp Cys Cys Glu
1               5                   10                  15

Lys Gln Glu Pro Glu
            20

<210> SEQ ID NO 188
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Oxidation M [9]
<220> FEATURE:
<221> NAME/KEY: MOD_RES
<222> LOCATION: (12)..(13)
<223> OTHER INFORMATION: Carboxyrnethyl C (2) [12 13]
<220> FEATURE:
<221> NAME/KEY: MOD_RES
<222> LOCATION: (15)..(15)
<223> OTHER INFORMATION: Glycation [15]

<400> SEQUENCE: 188

Ser Leu Arg Glu Thr Tyr Gly Asp Met Ala Asp Cys Cys Glu Lys Gln
1               5                   10                  15

Glu Pro Glu

<210> SEQ ID NO 189
<211> LENGTH: 17
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Oxidation M [7]
<220> FEATURE:
<221> NAME/KEY: MOD_RES
<222> LOCATION: (10)..(11)
<223> OTHER INFORMATION: Carboxymethyl C (2) [10 11]
<220> FEATURE:
<221> NAME/KEY: MOD_RES
<222> LOCATION: (13)..(13)
<223> OTHER INFORMATION: Glycation [13]

<400> SEQUENCE: 189

Arg Glu Thr Tyr Gly Asp Met Ala Asp Cys Cys Glu Lys Gln Glu Pro
1               5                   10                  15

Glu

<210> SEQ ID NO 190
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES

```
<222> LOCATION: (9)..(10)
<223> OTHER INFORMATION: Carboxymethyl C (2) [9 10]
<220> FEATURE:
<221> NAME/KEY: MOD_RES
<222> LOCATION: (12)..(12)
<223> OTHER INFORMATION: Glycation [12]

<400> SEQUENCE: 190

Glu Thr Tyr Gly Asp Met Ala Asp Cys Cys Glu Lys Gln Glu Pro Glu
1               5                   10                  15

<210> SEQ ID NO 191
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation [?]
<220> FEATURE:
<221> NAME/KEY: MOD_RES
<222> LOCATION: (2)..(18)
<223> OTHER INFORMATION: Carboxymethyl C (3) [2 17 18]
<220> FEATURE:
<221> NAME/KEY: MOD_RES
<222> LOCATION: (26)..(26)
<223> OTHER INFORMATION: Deamidation N [26]

<400> SEQUENCE: 191

Leu Cys Lys Val Ala Ser Leu Arg Glu Thr Tyr Gly Asp Met Ala Asp
1               5                   10                  15

Cys Cys Glu Lys Gln Glu Pro Glu Arg Asn
            20                  25

<210> SEQ ID NO 192
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Oxidation M [8]
<220> FEATURE:
<221> NAME/KEY: MOD_RES
<222> LOCATION: (11)..(12)
<223> OTHER INFORMATION: Carboxymethyl C (2) [11 12]

<400> SEQUENCE: 192

Leu Arg Glu Thr Tyr Gly Asp Met Ala Asp Cys Cys Glu Lys Gln Glu
1               5                   10                  15

Pro Glu Arg Asn Glu
            20

<210> SEQ ID NO 193
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Oxidation M [7]
<220> FEATURE:
<221> NAME/KEY: MOD_RES
<222> LOCATION: (10)..(11)
<223> OTHER INFORMATION: Carboxymethyl C (2) [10 11]
<220> FEATURE:
<221> NAME/KEY: MOD_RES
<222> LOCATION: (13)..(13)
<223> OTHER INFORMATION: Glycation [13]
<220> FEATURE:
<221> NAME/KEY: MOD_RES
```

```
<222> LOCATION: (19)..(19)
<223> OTHER INFORMATION: Deamidation N [19]

<400> SEQUENCE: 193

Arg Glu Thr Tyr Gly Asp Met Ala Asp Cys Cys Glu Lys Gln Glu Pro
1               5                   10                  15

Glu Arg Asn Glu
            20

<210> SEQ ID NO 194
<211> LENGTH: 19
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (9)..(10)
<223> OTHER INFORMATION: Carboxymethyl C (2) [9 10]
<220> FEATURE:
<221> NAME/KEY: MOD_RES
<222> LOCATION: (18)..(18)
<223> OTHER INFORMATION: Deamidation N [18]

<400> SEQUENCE: 194

Glu Thr Tyr Gly Asp Met Ala Asp Cys Cys Glu Lys Gln Glu Pro Glu
1               5                   10                  15

Arg Asn Glu

<210> SEQ ID NO 195
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]
<220> FEATURE:
<221> NAME/KEY: MOD_RES
<222> LOCATION: (3)..(3)
<223> OTHER INFORMATION: Glycation [3]

<400> SEQUENCE: 195

Leu Cys Lys Val Ala Ser
1               5

<210> SEQ ID NO 196
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 196

Thr Tyr Gly Asp Met Ala Asp Cys Cys Glu
1               5                   10

<210> SEQ ID NO 197
<211> LENGTH: 14
<212> TYPE: PRT
<213> ORGANISM: Homo sapiens
```

```
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
<222> LOCATION: (11)..(11)
<223> OTHER INFORMATION: Glycation [11]

<400> SEQUENCE: 197

Thr Tyr Gly Asp Met Ala Asp Cys Cys Glu Lys Gln Glu Pro
1               5                   10

<210> SEQ ID NO 198
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
<222> LOCATION: (11)..(11)
<223> OTHER INFORMATION: Glycation [11]

<400> SEQUENCE: 198

Thr Tyr Gly Asp Met Ala Asp Cys Cys Glu Lys Gln Glu
1               5                   10

<210> SEQ ID NO 199
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
<222> LOCATION: (11)..(11)
<223> OTHER INFORMATION: Glycation [11]

<400> SEQUENCE: 199

Thr Tyr Gly Asp Met Ala Asp Cys Cys Glu Lys Gln
1               5                   10

<210> SEQ ID NO 200
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 200
```

Thr Tyr Gly Asp Met Ala Asp Cys Cys Glu Lys
1               5                   10

<210> SEQ ID NO 201
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Oxidation M [3]
<220> FEATURE:
<221> NAME/KEY: MOD_RES
<222> LOCATION: (6)..(7)
<223> OTHER INFORMATION: Carboxymethyl C (2) [6 7]

<400> SEQUENCE: 201

Gly Asp Met Ala Asp Cys Cys Glu Lys Gln Glu Pro Glu
1               5                   10

<210> SEQ ID NO 202
<211> LENGTH: 11
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Carboxymethyl C (2) [4 5]

<400> SEQUENCE: 202

Met Ala Asp Cys Cys Glu Lys Gln Glu Pro Glu
1               5                   10

<210> SEQ ID NO 203
<211> LENGTH: 10
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Carboxymethyl C (2) [3 4]
<220> FEATURE:
<221> NAME/KEY: MOD_RES
<222> LOCATION: (6)..(6)
<223> OTHER INFORMATION: Glycation [6]

<400> SEQUENCE: 203

Ala Asp Cys Cys Glu Lys Gln Glu Pro Glu
1               5                   10

<210> SEQ ID NO 204
<211> LENGTH: 8
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 204

Cys Cys Glu Lys Gln Glu Pro Glu
1               5

<210> SEQ ID NO 205
<211> LENGTH: 18

```
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
<222> LOCATION: (17)..(17)
<223> OTHER INFORMATION: Deamidation N [17]

<400> SEQUENCE: 205

Thr Tyr Gly Asp Met Ala Asp Cys Cys Glu Lys Gln Glu Pro Glu Arg
1               5                   10                  15

Asn Glu

<210> SEQ ID NO 206
<211> LENGTH: 17
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
<222> LOCATION: (11)..(11)
<223> OTHER INFORMATION: Glycation [11]
<220> FEATURE:
<221> NAME/KEY: MOD_RES
<222> LOCATION: (17)..(17)
<223> OTHER INFORMATION: Deamidation N [17]

<400> SEQUENCE: 206

Thr Tyr Gly Asp Met Ala Asp Cys Cys Glu Lys Gln Glu Pro Glu Arg
1               5                   10                  15

Asn

<210> SEQ ID NO 207
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 207

Thr Tyr Gly Asp Met Ala Asp Cys Cys Glu Lys Gln Glu Pro Glu Arg
1               5                   10                  15

<210> SEQ ID NO 208
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (7)..(8)
<223> OTHER INFORMATION: Carboxymethyl C (2) [7 8]
```

```
<220> FEATURE:
<221> NAME/KEY: MOD_RES
<222> LOCATION: (10)..(10)
<223> OTHER INFORMATION: Glycation [10]
<220> FEATURE:
<221> NAME/KEY: MOD_RES
<222> LOCATION: (16)..(16)
<223> OTHER INFORMATION: Deamidation N [16]

<400> SEQUENCE: 208

Tyr Gly Asp Met Ala Asp Cys Cys Glu Lys Gln Glu Pro Glu Arg Asn
1               5                   10                  15

Glu

<210> SEQ ID NO 209
<211> LENGTH: 16
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Carboxymethyl C (2) [6 7]
<220> FEATURE:
<221> NAME/KEY: MOD_RES
<222> LOCATION: (9)..(9)
<223> OTHER INFORMATION: Glycation [9]
<220> FEATURE:
<221> NAME/KEY: MOD_RES
<222> LOCATION: (15)..(15)
<223> OTHER INFORMATION: Deamidation N [15]

<400> SEQUENCE: 209

Gly Asp Met Ala Asp Cys Cys Glu Lys Gln Glu Pro Glu Arg Asn Glu
1               5                   10                  15

<210> SEQ ID NO 210
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (5)..(6)
<223> OTHER INFORMATION: Carboxymethyl C (2) [5 6]
<220> FEATURE:
<221> NAME/KEY: MOD_RES
<222> LOCATION: (8)..(8)
<223> OTHER INFORMATION: Glycation [8]
<220> FEATURE:
<221> NAME/KEY: MOD_RES
<222> LOCATION: (14)..(14)
<223> OTHER INFORMATION: Deamidation N [14]

<400> SEQUENCE: 210

Asp Met Ala Asp Cys Cys Glu Lys Gln Glu Pro Glu Arg Asn Glu
1               5                   10                  15

<210> SEQ ID NO 211
<211> LENGTH: 14
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Carboxymethyl C (2) [4 5]
<220> FEATURE:
<221> NAME/KEY: MOD_RES
<222> LOCATION: (7)..(7)
<223> OTHER INFORMATION: Glycation [7]
```

```
<220> FEATURE:
<221> NAME/KEY: MOD_RES
<222> LOCATION: (13)..(13)
<223> OTHER INFORMATION: Deamidation N [13]

<400> SEQUENCE: 211

Met Ala Asp Cys Cys Glu Lys Gln Glu Pro Glu Arg Asn Glu
1               5                   10

<210> SEQ ID NO 212
<211> LENGTH: 13
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Carboxymethyl C (2) [3 4]
<220> FEATURE:
<221> NAME/KEY: MOD_RES
<222> LOCATION: (6)..(6)
<223> OTHER INFORMATION: Glycation [6]
<220> FEATURE:
<221> NAME/KEY: MOD_RES
<222> LOCATION: (12)..(12)
<223> OTHER INFORMATION: Deamidation N [12]

<400> SEQUENCE: 212

Ala Asp Cys Cys Glu Lys Gln Glu Pro Glu Arg Asn Glu
1               5                   10

<210> SEQ ID NO 213
<211> LENGTH: 11
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]
<220> FEATURE:
<221> NAME/KEY: MOD_RES
<222> LOCATION: (10)..(10)
<223> OTHER INFORMATION: Deamidation N [10]

<400> SEQUENCE: 213

Cys Cys Glu Lys Gln Glu Pro Glu Arg Asn Glu
1               5                   10

<210> SEQ ID NO 214
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (9)..(9)
<223> OTHER INFORMATION: Deamidation N [9]

<400> SEQUENCE: 214

Cys Glu Lys Gln Glu Pro Glu Arg Asn Glu
1               5                   10

<210> SEQ ID NO 215
<211> LENGTH: 43
<212> TYPE: PRT
```

```
<213> ORGANISM: Homo sapiens
<220> FEATURE:
<221> NAME/KEY: MOD_RES
<222> LOCATION: (1)..(43)
<223> OTHER INFORMATION: Glycation (2) [2 ?]
<220> FEATURE:
<221> NAME/KEY: MOD_RES
<222> LOCATION: (1)..(43)
<223> OTHER INFORMATION: Deamidation N [?]
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(41)
<223> OTHER INFORMATION: Carboxymethyl C (4) [8 9 19 41]

<400> SEQUENCE: 215

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro Lys
            20                  25                  30

Leu Lys Pro Asp Pro Asn Thr Leu Cys Asp Glu
        35                  40

<210> SEQ ID NO 216
<211> LENGTH: 32
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(32)
<223> OTHER INFORMATION: Glycation (3) [11 24 32]

<400> SEQUENCE: 216

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro Lys
            20                  25                  30

<210> SEQ ID NO 217
<211> LENGTH: 31
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxyrnethyl C (3) [8 9 19]
<220> FEATURE:
<221> NAME/KEY: MOD_RES
<222> LOCATION: (17)..(17)
<223> OTHER INFORMATION: Deamidation N [17]

<400> SEQUENCE: 217

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro
            20                  25                  30
```

```
                     20                  25                  30

<210> SEQ ID NO 218
<211> LENGTH: 30
<212> TYPE: PRT
<213> ORGANISM: Homo sapiens
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (17)..(17)
<223> OTHER INFORMATION: Deamidation N [17]

<400> SEQUENCE: 218

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu
            20                  25                  30

<210> SEQ ID NO 219
<211> LENGTH: 27
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Glycation [?]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(24)
<223> OTHER INFORMATION: Glycation (2) [11 24]
<220> FEATURE:
<221> NAME/KEY: MOD_RES
<222> LOCATION: (17)..(17)
<223> OTHER INFORMATION: Deamidation N [17]

<400> SEQUENCE: 219

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser
            20                  25

<210> SEQ ID NO 220
<211> LENGTH: 25
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation [?]
<220> FEATURE:
<221> NAME/KEY: MOD_RES
<222> LOCATION: (8)..(19)
<223> OTHER INFORMATION: Carboxymethyl C (3) [8 9 19]

<400> SEQUENCE: 220

Thr Tyr Gly Asp Met Ala Asp Cys Cys Glu Lys Gln Glu Pro Glu Arg
1               5                   10                  15

Asn Glu Cys Phe Leu Ser His Lys Asp
            20                  25

<210> SEQ ID NO 221
<211> LENGTH: 41
```

```
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(41)
<223> OTHER INFORMATION: Carboxymethyl C [8 9 19 41]
<220> FEATURE:
<221> NAME/KEY: MOD_RES
<222> LOCATION: (11)..(34)
<223> OTHER INFORMATION: Glycation (4) [11 24 32 34]
<220> FEATURE:
<221> NAME/KEY: MOD_RES
<222> LOCATION: (17)..(38)
<223> OTHER INFORMATION: Deamidation N (2) [17 38]

<400> SEQUENCE: 221

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro Lys
            20                  25                  30

Leu Lys Pro Asp Pro Asn Thr Leu Cys
        35                  40

<210> SEQ ID NO 222
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(11)
<223> OTHER INFORMATION: Glycation [11]

<400> SEQUENCE: 222

Thr Tyr Gly Asp Met Ala Asp Cys Cys Glu Lys Gln Glu Pro Glu Arg
1               5                   10                  15

Asn Glu Cys Phe Leu Ser His
            20

<210> SEQ ID NO 223
<211> LENGTH: 22
<212> TYPE: PRT
<213> ORGANISM: Homo sapiens
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (17)..(17)
<223> OTHER INFORMATION: Deamidation N [17]

<400> SEQUENCE: 223

Thr Tyr Gly Asp Met Ala Asp Cys Cys Glu Lys Gln Glu Pro Glu Arg
1               5                   10                  15

Asn Glu Cys Phe Leu Ser
            20
```

```
<210> SEQ ID NO 224
<211> LENGTH: 21
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(11)
<223> OTHER INFORMATION: Glycation [11]

<400> SEQUENCE: 224

Thr Tyr Gly Asp Met Ala Asp Cys Cys Glu Lys Gln Glu Pro Glu Arg
1               5                   10                  15

Asn Glu Cys Phe Leu
            20

<210> SEQ ID NO 225
<211> LENGTH: 20
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(11)
<223> OTHER INFORMATION: Glycation [11]
<220> FEATURE:
<221> NAME/KEY: MOD_RES
<222> LOCATION: (17)..(17)
<223> OTHER INFORMATION: Deamidation N [17]

<400> SEQUENCE: 225

Thr Tyr Gly Asp Met Ala Asp Cys Cys Glu Lys Gln Glu Pro Glu Arg
1               5                   10                  15

Asn Glu Cys Phe
            20

<210> SEQ ID NO 226
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Deamidation N [?]
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxyrnethyl C (3) [8 9 19]
<220> FEATURE:
<221> NAME/KEY: MOD_RES
<222> LOCATION: (11)..(34)
<223> OTHER INFORMATION: Glycation (4) [11 24 32 34]
<220> FEATURE:
<221> NAME/KEY: MOD_RES
<222> LOCATION: (17)..(38)
```

<223> OTHER INFORMATION: Deamidation N (2) [17 38]

<400> SEQUENCE: 226

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro Lys
            20                  25                  30

Leu Lys Pro Asp Pro Asn Thr
        35

<210> SEQ ID NO 227
<211> LENGTH: 38
<212> TYPE: PRT
<213> ORGANISM: Homo sapiens
<220> FEATURE:
<221> NAME/KEY: MOD_RES
<222> LOCATION: (1)..(38)
<223> OTHER INFORMATION: Glycation (3) [3?]
<220> FEATURE:
<221> NAME/KEY: MOD_RES
<222> LOCATION: (1)..(38)
<223> OTHER INFORMATION: Deamidation N [?]
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(19)
<223> OTHER INFORMATION: Carboxymethyl C (3) [8 9 19]
<220> FEATURE:
<221> NAME/KEY: MOD_RES
<222> LOCATION: (11)..(34)
<223> OTHER INFORMATION: Glycation (4) [11 24 32 34]

<400> SEQUENCE: 227

Thr Tyr Gly Asp Met Ala Asp Cys Cys Glu Lys Gln Glu Pro Glu Arg
1               5                   10                  15

Asn Glu Cys Phe Leu Ser His Lys Asp Asp Ser Pro Asp Leu Pro Lys
            20                  25                  30

Leu Lys Pro Asp Pro Asn
        35

<210> SEQ ID NO 228
<211> LENGTH: 42
<212> TYPE: PRT
<213> ORGANISM: Homo sapiens
<220> FEATURE:
<221> NAME/KEY: MOD_RES
<222> LOCATION: (1)..(42)
<223> OTHER INFORMATION: Glycation (3) [3?]
<220> FEATURE:
<221> NAME/KEY: MOD_RES
<222> LOCATION: (1)..(42)
<223> OTHER INFORMATION: Dearnidation N [?]
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (7)..(40)
<223> OTHER INFORMATION: Carboxymethyl C (4) [7 8 18 40]
<220> FEATURE:
<221> NAME/KEY: MOD_RES
<222> LOCATION: (10)..(33)
<223> OTHER INFORMATION: Glycation (4) [10 23 31 33]
<220> FEATURE:
<221> NAME/KEY: MOD_RES
<222> LOCATION: (16)..(37)
<223> OTHER INFORMATION: Deamidation N (2) [16 37]

```
<400> SEQUENCE: 228

Tyr Gly Asp Met Ala Asp Cys Cys Glu Lys Gln Glu Pro Glu Arg Asn
1               5                   10                  15

Glu Cys Phe Leu Ser His Lys Asp Asp Ser Pro Asp Leu Pro Lys Leu
            20                  25                  30

Lys Pro Asp Pro Asn Thr Leu Cys Asp Glu
        35                  40

<210> SEQ ID NO 229
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Glycation (2) [2?]
<220> FEATURE:
<221> NAME/KEY: MOD_RES
<222> LOCATION: (5)..(38)
<223> OTHER INFORMATION: Carboxymethyl C [5 6 16 38]
<220> FEATURE:
<221> NAME/KEY: MOD_RES
<222> LOCATION: (14)..(35)
<223> OTHER INFORMATION: Deamidation N (2) [14 35]

<400> SEQUENCE: 229

Asp Met Ala Asp Cys Cys Glu Lys Gln Glu Pro Glu Arg Asn Glu Cys
1               5                   10                  15

Phe Leu Ser His Lys Asp Asp Ser Pro Asp Leu Pro Lys Leu Lys Pro
            20                  25                  30

Asp Pro Asn Thr Leu Cys Asp Glu
        35                  40

<210> SEQ ID NO 230
<211> LENGTH: 37
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Glycation (3) [3 ?]
<220> FEATURE:
<221> NAME/KEY: MOD_RES
<222> LOCATION: (1)..(37)
<223> OTHER INFORMATION: Deamidation N [?]
<220> FEATURE:
<221> NAME/KEY: MOD_RES
<222> LOCATION: (2)..(35)
<223> OTHER INFORMATION: Carboxymethyl C (4) [2 3 13 35]
<220> FEATURE:
<221> NAME/KEY: MOD_RES
<222> LOCATION: (11)..(32)
<223> OTHER INFORMATION: Deamidation N (2) [11 32]

<400> SEQUENCE: 230

Asp Cys Cys Glu Lys Gln Glu Pro Glu Arg Asn Glu Cys Phe Leu Ser
1               5                   10                  15

His Lys Asp Asp Ser Pro Asp Leu Pro Lys Leu Lys Pro Asp Pro Asn
            20                  25                  30

Thr Leu Cys Asp Glu
        35

<210> SEQ ID NO 231
<211> LENGTH: 9
<212> TYPE: PRT
<213> ORGANISM: Homo sapiens
```

```
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 231

Thr Tyr Gly Asp Met Ala Asp Cys Cys
1               5

<210> SEQ ID NO 232
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M [5]
<220> FEATURE:
<221> NAME/KEY: MOD_RES
<222> LOCATION: (8)..(8)
<223> OTHER INFORMATION: Carboxymethyl C [8]

<400> SEQUENCE: 232

Thr Tyr Gly Asp Met Ala Asp Cys
1               5

<210> SEQ ID NO 233
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M[5]

<400> SEQUENCE: 233

Thr Tyr Gly Asp Met Ala
1               5

<210> SEQ ID NO 234
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Oxidation M[5]

<400> SEQUENCE: 234

Thr Tyr Gly Asp Met
1               5

<210> SEQ ID NO 235
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (7)..(8)
<223> OTHER INFORMATION: Carboxymethyl C (2) [7 8]

<400> SEQUENCE: 235
```

Tyr Gly Asp Met Ala Asp Cys Cys Glu
1               5

<210> SEQ ID NO 236
<211> LENGTH: 7
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 236

Asp Met Ala Asp Cys Cys Glu
1               5

<210> SEQ ID NO 237
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (4)..(5)
<223> OTHER INFORMATION: Carboxymethyl C (2) [4 5]

<400> SEQUENCE: 237

Met Ala Asp Cys Cys Glu
1               5

<210> SEQ ID NO 238
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 238

Lys Gln Glu Pro Glu Arg Asn Glu
1               5

<210> SEQ ID NO 239
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: GlycatIon [1]
<220> FEATURE:
<221> NAME/KEY: MOD_RES
<222> LOCATION: (7)..(7)
<223> OTHER INFORMATION: Deamidation N [7]

<400> SEQUENCE: 239

Lys Gln Glu Pro Glu Arg Asn
1               5

<210> SEQ ID NO 240
<211> LENGTH: 6
<212> TYPE: PRT
<213> ORGANISM: Homo sapiens
<220> FEATURE:
<221> NAME/KEY: MOD_RES
<222> LOCATION: (5)..(5)

<223> OTHER INFORMATION: Deamidation N [5]

<400> SEQUENCE: 240

Glu Pro Glu Arg Asn Glu
1               5

<210> SEQ ID NO 241
<211> LENGTH: 4
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]

<400> SEQUENCE: 241

Glu Arg Asn Glu
1

<210> SEQ ID NO 242
<211> LENGTH: 33
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Glycation (3) [3 ?]
<220> FEATURE:
<221> NAME/KEY: MOD_RES
<222> LOCATION: (1)..(33)
<223> OTHER INFORMATION: Deamidation N [?]
<220> FEATURE:
<221> NAME/KEY: MOD_RES
<222> LOCATION: (9)..(31)
<223> OTHER INFORMATION: Carboxymethyl C (2) [9 31]

<400> SEQUENCE: 242

Lys Gln Glu Pro Glu Arg Asn Glu Cys Phe Leu Ser His Lys Asp Asp
1               5                   10                  15

Ser Pro Asp Leu Pro Lys Leu Lys Pro Asp Pro Asn Thr Leu Cys Asp
            20                  25                  30

Glu

<210> SEQ ID NO 243
<211> LENGTH: 19
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: Glycation (2) [1 14]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (9)..(9)
<223> OTHER INFORMATION: Carboxymethyl C [9]

<400> SEQUENCE: 243

Lys Gln Glu Pro Glu Arg Asn Glu Cys Phe Leu Ser His Lys Asp Asp
1               5                   10                  15

Ser Pro Asp

<210> SEQ ID NO 244
<211> LENGTH: 18
<212> TYPE: PRT

```
<213> ORGANISM: Homo sapiens
<220> FEATURE:
<221> NAME/KEY: MOD_RES
<222> LOCATION: (1)..(14)
<223> OTHER INFORMATION: Glycation (2) [1 14]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (9)..(9)
<223> OTHER INFORMATION: Carboxymethyl C [9]

<400> SEQUENCE: 244

Lys Gln Glu Pro Glu Arg Asn Glu Cys Phe Leu Ser His Lys Asp Asp
1               5                   10                  15

Ser Pro

<210> SEQ ID NO 245
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (9)..(9)
<223> OTHER INFORMATION: Carboxymethyl C [9]

<400> SEQUENCE: 245

Lys Gln Glu Pro Glu Arg Asn Glu Cys
1               5

<210> SEQ ID NO 246
<211> LENGTH: 34
<212> TYPE: PRT
<213> ORGANISM: Homo sapiens
<220> FEATURE:
<221> NAME/KEY: MOD_RES
<222> LOCATION: (1)..(34)
<223> OTHER INFORMATION: Deamidation N [?]
<220> FEATURE:
<221> NAME/KEY: MOD_RES
<222> LOCATION: (1)..(34)
<223> OTHER INFORMATION: Glycation (3) [3 ?]
<220> FEATURE:
<221> NAME/KEY: MOD_RES
<222> LOCATION: (5)..(27)
<223> OTHER INFORMATION: Carboxymethyl C (2) [5 27]

<400> SEQUENCE: 246

Glu Arg Asn Glu Cys Phe Leu Ser His Lys Asp Asp Ser Pro Asp Leu
1               5                   10                  15

Pro Lys Leu Lys Pro Asp Pro Asn Thr Leu Cys Asp Glu Phe Lys Ala
                20                  25                  30

Asp Glu

<210> SEQ ID NO 247
<211> LENGTH: 4
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: Glycation [1]

<400> SEQUENCE: 247

Lys Gln Glu Pro
1

<210> SEQ ID NO 248
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation [?]

<400> SEQUENCE: 248

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly
        35

<210> SEQ ID NO 249
<211> LENGTH: 38
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (1)..(38)
<223> OTHER INFORMATION: Glycation [?]

<400> SEQUENCE: 249

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu
        35

<210> SEQ ID NO 250
<211> LENGTH: 37
<212> TYPE: PRT
<213> ORGANISM: Homo sapiens
<220> FEATURE:
<221> NAME/KEY: MOD_RES
<222> LOCATION: (2)..(35)
<223> OTHER INFORMATION: Glycation (3) [2 28 35]

<400> SEQUENCE: 250

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp
        35

<210> SEQ ID NO 251
<211> LENGTH: 36
<212> TYPE: PRT
```

```
<213> ORGANISM: Homo sapiens
<220> FEATURE:
<221> NAME/KEY: MOD_RES
<222> LOCATION: (1)..(1)
<223> OTHER INFORMATION: Oxidation M [1]

<400> SEQUENCE: 251

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys
        35

<210> SEQ ID NO 252
<211> LENGTH: 39
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation (3) [1 27 35]

<400> SEQUENCE: 252

Lys Trp Val Thr Phe Ile Ser Leu Leu Leu Phe Ser Ser Ala Tyr
1               5                   10                  15

Ser Arg Gly Val Phe Arg Arg Asp Thr His Lys Ser Glu Ile Ala His
            20                  25                  30

Arg Phe Lys Asp Leu Gly Glu
        35

<210> SEQ ID NO 253
<211> LENGTH: 13
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Glycation [?]

<400> SEQUENCE: 253

Lys Ser Glu Ile Ala His Arg Phe Lys Asp Leu Gly Glu
1               5                   10

<210> SEQ ID NO 254
<211> LENGTH: 41
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]

<400> SEQUENCE: 254

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu
        35                  40

<210> SEQ ID NO 255
<211> LENGTH: 28
<212> TYPE: PRT
<213> ORGANISM: Homo sapiens
```

```
<220> FEATURE:
<221> NAME/KEY: MOD_RES
<222> LOCATION: (1)..(28)
<223> OTHER INFORMATION: Deamidation N [?]
<220> FEATURE:
<221> NAME/KEY: MOD_RES
<222> LOCATION: (4)..(26)
<223> OTHER INFORMATION: Carboxymethyl C (2) [4 26]

<400> SEQUENCE: 255

Arg Asn Glu Cys Phe Leu Ser His Lys Asp Asp Ser Pro Asp Leu Pro
1               5                   10                  15

Lys Leu Lys Pro Asp Pro Asn Thr Leu Cys Asp Glu
            20                  25

<210> SEQ ID NO 256
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(9)
<223> OTHER INFORMATION: Glycation [9]

<400> SEQUENCE: 256

Arg Asn Glu Cys Phe Leu Ser His Lys Asp Asp Ser Pro Asp
1               5                   10

<210> SEQ ID NO 257
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 257

Arg Asn Glu Cys Phe Leu Ser His Lys Asp Asp Ser Pro
1               5                   10

<210> SEQ ID NO 258
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(9)
<223> OTHER INFORMATION: Glycation [9]

<400> SEQUENCE: 258

Arg Asn Glu Cys Phe Leu Ser His Lys Asp
1               5                   10
```

-continued

```
<210> SEQ ID NO 259
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(9)
<223> OTHER INFORMATION: Glycation [9]

<400> SEQUENCE: 259

Arg Asn Glu Cys Phe Leu Ser His Lys
1               5

<210> SEQ ID NO 260
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]

<400> SEQUENCE: 260

Arg Asn Glu Cys Phe
1               5

<210> SEQ ID NO 261
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 261

Arg Asn Glu Cys
1

<210> SEQ ID NO 262
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Deamidation N [?]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(19)
<223> OTHER INFORMATION: Glycation (3) [9 17 19]

<400> SEQUENCE: 262

Arg Asn Glu Cys Phe Leu Ser His Lys Asp Asp Ser Pro Asp Leu Pro
1               5                   10                  15
```

Lys Leu Lys Pro Asp Pro Asn
            20

<210> SEQ ID NO 263
<211> LENGTH: 22
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(19)
<223> OTHER INFORMATION: Glycation (3) [9 17 19]

<400> SEQUENCE: 263

Arg Asn Glu Cys Phe Leu Ser His Lys Asp Asp Ser Pro Asp Leu Pro
1               5                   10                  15

Lys Leu Lys Pro Asp Pro
            20

<210> SEQ ID NO 264
<211> LENGTH: 21
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (9)..(19)
<223> OTHER INFORMATION: Glycation (3) [9 17 19]

<400> SEQUENCE: 264

Arg Asn Glu Cys Phe Leu Ser His Lys Asp Asp Ser Pro Asp Leu Pro
1               5                   10                  15

Lys Leu Lys Pro Asp
            20

<210> SEQ ID NO 265
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (4)..(4)
<223> OTHER INFORMATION: Carboxymethyl C [4]

<400> SEQUENCE: 265

Arg Asn Glu Cys Phe Leu Ser His Lys Asp Asp Ser Pro Asp Leu Pro
1               5                   10                  15

Lys Leu Lys

<210> SEQ ID NO 266
<211> LENGTH: 30
<212> TYPE: PRT
<213> ORGANISM: Homo sapiens
<220> FEATURE:
<221> NAME/KEY: MOD_RES

```
<222> LOCATION: (1)..(30)
<223> OTHER INFORMATION: Deamidation N[?]
<220> FEATURE:
<221> NAME/KEY: MOD_RES
<222> LOCATION: (1)..(30)
<223> OTHER INFORMATION: Glycation [?]
<220> FEATURE:
<221> NAME/KEY: MOD_RES
<222> LOCATION: (4)..(26)
<223> OTHER INFORMATION: Carboxymethyl C (2) [4 26]

<400> SEQUENCE: 266

Arg Asn Glu Cys Phe Leu Ser His Lys Asp Asp Ser Pro Asp Leu Pro
1               5                   10                  15

Lys Leu Lys Pro Asp Pro Asn Thr Leu Cys Asp Glu Phe Lys
            20                  25                  30

<210> SEQ ID NO 267
<211> LENGTH: 32
<212> TYPE: PRT
<213> ORGANISM: Homo sapiens
<220> FEATURE:
<221> NAME/KEY: MOD_RES
<222> LOCATION: (1)..(22)
<223> OTHER INFORMATION: Deamidation N (2) [1 22]
<220> FEATURE:
<221> NAME/KEY: MOD_RES
<222> LOCATION: (1)..(32)
<223> OTHER INFORMATION: Glycation [?]
<220> FEATURE:
<221> NAME/KEY: MOD_RES
<222> LOCATION: (3)..(25)
<223> OTHER INFORMATION: Carboxymethyl C (2) [3 25]
<220> FEATURE:
<221> NAME/KEY: MOD_RES
<222> LOCATION: (8)..(29)
<223> OTHER INFORMATION: Glycation (4) [8 16 18 29]

<400> SEQUENCE: 267

Asn Glu Cys Phe Leu Ser His Lys Asp Asp Ser Pro Asp Leu Pro Lys
1               5                   10                  15

Leu Lys Pro Asp Pro Asn Thr Leu Cys Asp Glu Phe Lys Ala Asp Glu
            20                  25                  30

<210> SEQ ID NO 268
<211> LENGTH: 44
<212> TYPE: PRT
<213> ORGANISM: Homo sapiens
<220> FEATURE:
<221> NAME/KEY: MOD_RES
<222> LOCATION: (2)..(23)
<223> OTHER INFORMATION: Deamidation N (2) [2 23]
<220> FEATURE:
<221> NAME/KEY: MOD_RES
<222> LOCATION: (4)..(26)
<223> OTHER INFORMATION: Carboxymethyl C (2) [4 26]

<400> SEQUENCE: 268

Arg Asn Glu Cys Phe Leu Ser His Lys Asp Asp Ser Pro Asp Leu Pro
1               5                   10                  15

Lys Leu Lys Pro Asp Pro Asn Thr Leu Cys Asp Glu Phe Phe Lys Ala
            20                  25                  30

Asp Glu Lys Lys Phe Trp Gly Lys Tyr Leu Tyr Glu
            35                  40

<210> SEQ ID NO 269
<211> LENGTH: 42
<212> TYPE: PRT
<213> ORGANISM: Homo sapiens
```

```
<220> FEATURE:
<221> NAME/KEY: MOD_RES
<222> LOCATION: (1)..(22)
<223> OTHER INFORMATION: Deamidation N (2) [1 22]
<220> FEATURE:
<221> NAME/KEY: MOD_RES
<222> LOCATION: (1)..(42)
<223> OTHER INFORMATION: Glycation (5) [5?]
<220> FEATURE:
<221> NAME/KEY: MOD_RES
<222> LOCATION: (3)..(25)
<223> OTHER INFORMATION: Carboxymethyl C (2) [3 25]

<400> SEQUENCE: 269

Asn Glu Cys Phe Leu Ser His Lys Asp Asp Ser Pro Asp Leu Pro Lys
1               5                   10                  15

Leu Lys Pro Asp Pro Asn Thr Leu Cys Asp Glu Phe Lys Ala Asp Glu
            20                  25                  30

Lys Lys Phe Trp Gly Lys Tyr Leu Tyr Glu
        35                  40

<210> SEQ ID NO 270
<211> LENGTH: 16
<212> TYPE: PRT
<213> ORGANISM: Homo sapiens
<220> FEATURE:
<221> NAME/KEY: MOD_RES
<222> LOCATION: (3)..(11)
<223> OTHER INFORMATION: Glycation (2) [3 11]

<400> SEQUENCE: 270

Thr His Lys Ser Glu Ile Ala His Arg Phe Lys Asp Leu Gly Glu Glu
1               5                   10                  15

<210> SEQ ID NO 271
<211> LENGTH: 25
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (6)..(16)
<223> OTHER INFORMATION: Glycation (3) [6 14 16]

<400> SEQUENCE: 271

Cys Phe Leu Ser His Lys Asp Asp Ser Pro Asp Leu Pro Lys Leu Lys
1               5                   10                  15

Pro Asp Pro Asn Thr Leu Cys Asp Glu
            20                  25

<210> SEQ ID NO 272
<211> LENGTH: 58
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (1)..(58)
<223> OTHER INFORMATION: Glycation (2) [2?]
<220> FEATURE:
<221> NAME/KEY: MOD_RES
<222> LOCATION: (58)..(58)
<223> OTHER INFORMATION: Carboxymethyl C [58]
```

-continued

<400> SEQUENCE: 272

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys
        50                  55

<210> SEQ ID NO 273
<211> LENGTH: 29
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (20)..(20)
<223> OTHER INFORMATION: Deamidation N [20]

<400> SEQUENCE: 273

Cys Phe Leu Ser His Lys Asp Asp Ser Pro Asp Leu Pro Lys Leu Lys
1               5                   10                  15

Pro Asp Pro Asn Thr Leu Cys Asp Glu Phe Lys Ala Asp
            20                  25

<210> SEQ ID NO 274
<211> LENGTH: 17
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: Glycation (3) [1 3 14]
<220> FEATURE:
<221> NAME/KEY: MOD_RES
<222> LOCATION: (10)..(10)
<223> OTHER INFORMATION: Carboxymethyl C [10]

<400> SEQUENCE: 274

Lys Leu Lys Pro Asp Pro Asn Thr Leu Cys Asp Glu Phe Lys Ala Asp
1               5                   10                  15

Glu

<210> SEQ ID NO 275
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 275

Asp Pro Asn Thr Leu Cys Asp Glu Phe Lys Ala Asp Glu
1               5                   10

<210> SEQ ID NO 276
<211> LENGTH: 12
<212> TYPE: PRT
<213> ORGANISM: Homo sapiens
<220> FEATURE:
<221> NAME/KEY: MOD_RES

```
<222> LOCATION: (5)..(5)
<223> OTHER INFORMATION: Carboxymethyl C [5]
<220> FEATURE:
<221> NAME/KEY: MOD_RES
<222> LOCATION: (9)..(9)
<223> OTHER INFORMATION: Glycation [9]

<400> SEQUENCE: 276

Pro Asn Thr Leu Cys Asp Glu Phe Lys Ala Asp Glu
1               5                   10

<210> SEQ ID NO 277
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 277

Asn Thr Leu Cys Asp Glu Phe Lys Ala Asp Glu
1               5                   10

<210> SEQ ID NO 278
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (5)..(5)
<223> OTHER INFORMATION: Glycation [5]

<400> SEQUENCE: 278

Cys Asp Glu Phe Lys Ala Asp Glu
1               5

<210> SEQ ID NO 279
<211> LENGTH: 22
<212> TYPE: PRT
<213> ORGANISM: Homo sapiens
<220> FEATURE:
<221> NAME/KEY: MOD_RES
<222> LOCATION: (6)..(19)
<223> OTHER INFORMATION: Glycation (3) [6 8 19]
<220> FEATURE:
<221> NAME/KEY: MOD_RES
<222> LOCATION: (15)..(15)
<223> OTHER INFORMATION: Carboxymethyl C [15]

<400> SEQUENCE: 279

Ser Pro Asp Leu Pro Lys Leu Lys Pro Asp Pro Asn Thr Leu Cys Asp
1               5                   10                  15

Glu Phe Lys Ala Asp Glu
                20

<210> SEQ ID NO 280
<211> LENGTH: 21
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Carboxymethyl C [14]

<400> SEQUENCE: 280
```

```
Pro Asp Leu Pro Lys Leu Lys Pro Asp Pro Asn Thr Leu Cys Asp Glu
1               5                   10                  15

Phe Lys Ala Asp Glu
            20
```

<210> SEQ ID NO 281
<211> LENGTH: 40
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (20)..(20)
<223> OTHER INFORMATION: Deamidation N [20]

<400> SEQUENCE: 281

```
Cys Phe Leu Ser His Lys Asp Asp Ser Pro Asp Leu Pro Lys Leu Lys
1               5                   10                  15

Pro Asp Pro Asn Thr Leu Cys Asp Glu Phe Lys Ala Asp Glu Lys Lys
            20                  25                  30

Phe Trp Gly Lys Tyr Leu Tyr Glu
            35                  40
```

<210> SEQ ID NO 282
<211> LENGTH: 35
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]

<400> SEQUENCE: 282

```
Cys Phe Leu Ser His Lys Asp Asp Ser Pro Asp Leu Pro Lys Leu Lys
1               5                   10                  15

Pro Asp Pro Asn Thr Leu Cys Asp Glu Phe Lys Ala Asp Glu Lys Lys
            20                  25                  30

Phe Trp Gly
        35
```

<210> SEQ ID NO 283
<211> LENGTH: 32
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (1)..(32)
<223> OTHER INFORMATION: Glycation (4) [4?]

<400> SEQUENCE: 283

```
Cys Phe Leu Ser His Lys Asp Asp Ser Pro Asp Leu Pro Lys Leu Lys
1               5                   10                  15

Pro Asp Pro Asn Thr Leu Cys Asp Glu Phe Lys Ala Asp Glu Lys Lys
            20                  25                  30
```

<210> SEQ ID NO 284
<211> LENGTH: 37
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Glycation [?]
<220> FEATURE:
<221> NAME/KEY: MOD_RES
<222> LOCATION: (20)..(20)
<223> OTHER INFORMATION: Carboxymethyl C [20]

<400> SEQUENCE: 284

Ser His Lys Asp Asp Ser Pro Asp Leu Pro Lys Leu Lys Pro Asp Pro
1               5                   10                  15

Asn Thr Leu Cys Asp Glu Phe Lys Ala Asp Glu Lys Lys Phe Trp Gly
            20                  25                  30

Lys Tyr Leu Tyr Glu
        35

<210> SEQ ID NO 285
<211> LENGTH: 50
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (1)..(50)
<223> OTHER INFORMATION: Glycation (3) [3 ?]
<220> FEATURE:
<221> NAME/KEY: MOD_RES
<222> LOCATION: (20)..(20)
<223> OTHER INFORMATION: Deamidation N [20]

<400> SEQUENCE: 285

Cys Phe Leu Ser His Lys Asp Asp Ser Pro Asp Leu Pro Lys Leu Lys
1               5                   10                  15

Pro Asp Pro Asn Thr Leu Cys Asp Glu Phe Lys Ala Asp Glu Lys Lys
            20                  25                  30

Phe Trp Gly Lys Tyr Leu Tyr Glu Ile Ala Arg Arg His Pro Tyr Phe
        35                  40                  45

Tyr Ala
    50

<210> SEQ ID NO 286
<211> LENGTH: 48
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Carboxymethyl C (2) [1 23]
<220> FEATURE:
<221> NAME/KEY: MOD_RES
<222> LOCATION: (6)..(36)
<223> OTHER INFORMATION: Glycation (7) [6 14 16 27 31 32 36]
<220> FEATURE:
<221> NAME/KEY: MOD_RES
<222> LOCATION: (6)..(36)
<223> OTHER INFORMATION: Glycation (7) [6 14 16 27 31 32 36]

<400> SEQUENCE: 286

Cys Phe Leu Ser His Lys Asp Asp Ser Pro Asp Leu Pro Lys Leu Lys
1               5                   10                  15

```
Pro Asp Pro Asn Thr Leu Cys Asp Glu Phe Lys Ala Asp Glu Lys Lys
        20                  25                  30

Phe Trp Gly Lys Tyr Leu Tyr Glu Ile Ala Arg Arg His Pro Tyr Phe
        35                  40                  45
```

<210> SEQ ID NO 287
<211> LENGTH: 38
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Carboxymethyl C [9]

<400> SEQUENCE: 287

```
Leu Lys Pro Asp Pro Asn Thr Leu Cys Asp Glu Phe Lys Ala Asp Glu
1               5                   10                  15

Lys Lys Phe Trp Gly Lys Tyr Leu Tyr Glu Ile Ala Arg Arg His Pro
            20                  25                  30

Tyr Phe Tyr Ala Pro Glu
        35
```

<210> SEQ ID NO 288
<211> LENGTH: 36
<212> TYPE: PRT
<213> ORGANISM: Homo sapiens
<220> FEATURE:
<221> NAME/KEY: MOD_RES
<222> LOCATION: (1)..(36)
<223> OTHER INFORMATION: Glycation (2) [2 ?]
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (7)..(7)
<223> OTHER INFORMATION: Carboxymethyl C [7]

<400> SEQUENCE: 288

```
Pro Asp Pro Asn Thr Leu Cys Asp Glu Phe Lys Ala Asp Glu Lys Lys
1               5                   10                  15

Phe Trp Gly Lys Tyr Leu Tyr Glu Ile Ala Arg Arg His Pro Tyr Phe
            20                  25                  30

Tyr Ala Pro Glu
        35
```

<210> SEQ ID NO 289
<211> LENGTH: 48
<212> TYPE: PRT
<213> ORGANISM: Homo sapiens
<220> FEATURE:
<221> NAME/KEY: MOD_RES
<222> LOCATION: (1)..(48)
<223> OTHER INFORMATION: Glycation (6) [6 ?]
<220> FEATURE:
<221> NAME/KEY: MOD_RES
<222> LOCATION: (19)..(19)
<223> OTHER INFORMATION: Carboxymethyl C [19]

<400> SEQUENCE: 289

```
His Lys Asp Asp Ser Pro Asp Leu Pro Lys Leu Lys Pro Asp Pro Asn
1               5                   10                  15

Thr Leu Cys Asp Glu Phe Lys Ala Asp Glu Lys Lys Phe Trp Gly Lys
            20                  25                  30
```

Tyr Leu Tyr Glu Ile Ala Arg Arg His Pro Tyr Phe Tyr Ala Pro Glu
            35                  40                  45

<210> SEQ ID NO 290
<211> LENGTH: 51
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (1)..(51)
<223> OTHER INFORMATION: Glycation [?]
<220> FEATURE:
<221> NAME/KEY: MOD_RES
<222> LOCATION: (2)..(44)
<223> OTHER INFORMATION: Glycation (4) [2 28 36 44]

<400> SEQUENCE: 290

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
            35                  40                  45

Ile Ala Phe
    50

<210> SEQ ID NO 291
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (6)..(6)
<223> OTHER INFORMATION: Glycation [6]

<400> SEQUENCE: 291

Cys Phe Leu Ser His Lys Asp Asp Ser Pro Asp Leu Pro
1               5                   10

<210> SEQ ID NO 292
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (6)..(6)
<223> OTHER INFORMATION: Glycation [6]

<400> SEQUENCE: 292

Cys Phe Leu Ser His Lys Asp Asp Ser Pro Asp Leu
1               5                   10

<210> SEQ ID NO 293
<211> LENGTH: 11
<212> TYPE: PRT
<213> ORGANISM: Homo sapiens
<220> FEATURE:

-continued

```
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (6)..(6)
<223> OTHER INFORMATION: Glycation [6]

<400> SEQUENCE: 293

Cys Phe Leu Ser His Lys Asp Asp Ser Pro Asp
1               5                   10

<210> SEQ ID NO 294
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 294

Cys Phe Leu Ser His Lys Asp Asp Ser Pro
1               5                   10

<210> SEQ ID NO 295
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (6)..(6)
<223> OTHER INFORMATION: Glycation [6]

<400> SEQUENCE: 295

Cys Phe Leu Ser His Lys Asp Asp Ser
1               5

<210> SEQ ID NO 296
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 296

Cys Phe Leu Ser His
1               5

<210> SEQ ID NO 297
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (20)..(20)
<223> OTHER INFORMATION: Deamidation N [20]

<400> SEQUENCE: 297

Cys Phe Leu Ser His Lys Asp Asp Ser Pro Asp Leu Pro Lys Leu Lys
```

```
                   1               5                  10                  15

Pro Asp Pro Asn Thr
                20

<210> SEQ ID NO 298
<211> LENGTH: 15
<212> TYPE: PRT
<213> ORGANISM: Homo sapiens
<220> FEATURE:
<221> NAME/KEY: MOD_RES
<222> LOCATION: (1)..(15)
<223> OTHER INFORMATION: Glycation [?]
<220> FEATURE:
<221> NAME/KEY: MOD_RES
<222> LOCATION: (13)..(13)
<223> OTHER INFORMATION: Carboxymethyl C [13]

<400> SEQUENCE: 298

Asp Leu Pro Lys Leu Lys Pro Asp Pro Asn Thr Leu Cys Asp Glu
1               5                  10                  15

<210> SEQ ID NO 299
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (5)..(5)
<223> OTHER INFORMATION: Deamidation N [5]
<220> FEATURE:
<221> NAME/KEY: MOD_RES
<222> LOCATION: (8)..(8)
<223> OTHER INFORMATION: Carboxymethyl C [8]

<400> SEQUENCE: 299

Lys Pro Asp Pro Asn Thr Leu Cys Asp Glu
1               5                  10

<210> SEQ ID NO 300
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (7)..(7)
<223> OTHER INFORMATION: Carboxymethyl C [7]

<400> SEQUENCE: 300

Pro Asp Pro Asn Thr Leu Cys Asp Glu
1               5

<210> SEQ ID NO 301
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]
<220> FEATURE:
<221> NAME/KEY: MOD_RES
<222> LOCATION: (3)..(3)
<223> OTHER INFORMATION: Deamidation N [3]
```

<220> FEATURE:
<221> NAME/KEY: MOD_RES
<222> LOCATION: (6)..(6)
<223> OTHER INFORMATION: Carboxymethyl C [6]

<400> SEQUENCE: 301

Asp Pro Asn Thr Leu Cys Asp Glu
1               5

<210> SEQ ID NO 302
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (2)..(2)
<223> OTHER INFORMATION: Deamidation N [2]
<220> FEATURE:
<221> NAME/KEY: MOD_RES
<222> LOCATION: (5)..(5)
<223> OTHER INFORMATION: Carboxymethyl C [5]

<400> SEQUENCE: 302

Pro Asn Thr Leu Cys Asp Glu
1               5

<210> SEQ ID NO 303
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (4)..(4)
<223> OTHER INFORMATION: Carboxymethyl C [4]

<400> SEQUENCE: 303

Asn Thr Leu Cys Asp Glu
1               5

<210> SEQ ID NO 304
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 304

Leu Cys Asp Glu
1

<210> SEQ ID NO 305
<211> LENGTH: 39
<212> TYPE: PRT
<213> ORGANISM: Homo sapiens
<220> FEATURE:
<221> NAME/KEY: MOD_RES
<222> LOCATION: (5)..(21)
<223> OTHER INFORMATION: Glycation (3) [5 13 21]
<220> FEATURE:
<221> NAME/KEY: MOD_RES
<222> LOCATION: (35)..(35)

<223> OTHER INFORMATION: Carboxymethyl C [35]

<400> SEQUENCE: 305

Arg Asp Thr His Lys Ser Glu Ile Ala His Arg Phe Lys Asp Leu Gly
1               5                   10                  15

Glu Glu His Phe Lys Gly Leu Val Leu Ile Ala Phe Ser Gln Tyr Leu
            20                  25                  30

Gln Gln Cys Pro Phe Asp Glu
        35

<210> SEQ ID NO 306
<211> LENGTH: 21
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Glycation [?]
<220> FEATURE:
<221> NAME/KEY: MOD_RES
<222> LOCATION: (16)..(16)
<223> OTHER INFORMATION: Deamidation N [16]
<220> FEATURE:
<221> NAME/KEY: MOD_RES
<222> LOCATION: (19)..(19)
<223> OTHER INFORMATION: Carboxymethyl C [19]

<400> SEQUENCE: 306

His Lys Asp Asp Ser Pro Asp Leu Pro Lys Leu Lys Pro Asp Pro Asn
1               5                   10                  15

Thr Leu Cys Asp Glu
            20

<210> SEQ ID NO 307
<211> LENGTH: 19
<212> TYPE: PRT
<213> ORGANISM: Homo sapiens
<220> FEATURE:
<221> NAME/KEY: MOD_RES
<222> LOCATION: (8)..(10)
<223> OTHER INFORMATION: Glycation (2) [8 10]
<220> FEATURE:
<221> NAME/KEY: MOD_RES
<222> LOCATION: (17)..(17)
<223> OTHER INFORMATION: Carboxymethyl C [17]

<400> SEQUENCE: 307

Asp Asp Ser Pro Asp Leu Pro Lys Leu Lys Pro Asp Pro Asn Thr Leu
1               5                   10                  15

Cys Asp Glu

<210> SEQ ID NO 308
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 308

Phe Lys Ala Asp Glu
1               5

<210> SEQ ID NO 309
<211> LENGTH: 14
<212> TYPE: PRT

```
<213> ORGANISM: Homo sapiens
<220> FEATURE:
<221> NAME/KEY: MOD_RES
<222> LOCATION: (1)..(14)
<223> OTHER INFORMATION: Glycation (3) [3 ?]

<400> SEQUENCE: 309

Lys Ala Asp Glu Lys Lys Phe Trp Gly Lys Tyr Leu Tyr Glu
1               5                   10

<210> SEQ ID NO 310
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation [?]

<400> SEQUENCE: 310

Phe Lys Ala Asp Glu Lys Lys Phe Trp Gly Lys Tyr Leu Tyr Glu Ile
1               5                   10                  15

Ala Arg Arg His Pro Tyr Phe Tyr Ala Pro
            20                  25

<210> SEQ ID NO 311
<211> LENGTH: 25
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation (3) [3 ?]
<220> FEATURE:
<221> NAME/KEY: MOD_RES
<222> LOCATION: (1)..(25)
<223> OTHER INFORMATION: Glycation (2) [2 ?]

<400> SEQUENCE: 311

Phe Lys Ala Asp Glu Lys Lys Phe Trp Gly Lys Tyr Leu Tyr Glu Ile
1               5                   10                  15

Ala Arg Arg His Pro Tyr Phe Tyr Ala
            20                  25

<210> SEQ ID NO 312
<211> LENGTH: 23
<212> TYPE: PRT
<213> ORGANISM: Homo sapiens
<220> FEATURE:
<221> NAME/KEY: MOD_RES
<222> LOCATION: (2)..(7)
<223> OTHER INFORMATION: Glycation (3) [2 3 7]

<400> SEQUENCE: 312

Glu Lys Lys Phe Trp Gly Lys Tyr Leu Tyr Glu Ile Ala Arg Arg His
1               5                   10                  15

Pro Tyr Phe Tyr Ala Pro Glu
            20

<210> SEQ ID NO 313
<211> LENGTH: 36
<212> TYPE: PRT
<213> ORGANISM: Homo sapiens
<220> FEATURE:
<221> NAME/KEY: MOD_RES
<222> LOCATION: (2)..(34)
<223> OTHER INFORMATION: Glycation (5) [2 6 7 11 34]
<220> FEATURE:
```

```
<221> NAME/KEY: MOD_RES
<222> LOCATION: (33)..(36)
<223> OTHER INFORMATION: Deamidation N (2) [33 36]

<400> SEQUENCE: 313

Phe Lys Ala Asp Glu Lys Lys Phe Trp Gly Lys Tyr Leu Tyr Glu Ile
1               5                   10                  15

Ala Arg Arg His Pro Tyr Phe Tyr Ala Pro Glu Leu Leu Tyr Tyr Ala
                20                  25                  30

Asn Lys Tyr Asn
            35

<210> SEQ ID NO 314
<211> LENGTH: 40
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Glycation (5) [1 5 6 10 33]
<220> FEATURE:
<221> NAME/KEY: MOD_RES
<222> LOCATION: (1)..(40)
<223> OTHER INFORMATION: Deamidation N [?]

<400> SEQUENCE: 314

Lys Ala Asp Glu Lys Lys Phe Trp Gly Lys Tyr Leu Tyr Glu Ile Ala
1               5                   10                  15

Arg Arg His Pro Tyr Phe Tyr Ala Pro Glu Leu Leu Tyr Tyr Ala Asn
                20                  25                  30

Lys Tyr Asn Gly Val Phe Gln Glu
            35                  40

<210> SEQ ID NO 315
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 315

Lys Ala Asp Glu
1

<210> SEQ ID NO 316
<211> LENGTH: 22
<212> TYPE: PRT
<213> ORGANISM: Homo sapiens
<220> FEATURE:
<221> NAME/KEY: MOD_RES
<222> LOCATION: (1)..(22)
<223> OTHER INFORMATION: Glycation [?]

<400> SEQUENCE: 316

Lys Lys Phe Trp Gly Lys Tyr Leu Tyr Glu Ile Ala Arg Arg His Pro
1               5                   10                  15

Tyr Phe Tyr Ala Pro Glu
                20

<210> SEQ ID NO 317
<211> LENGTH: 36
<212> TYPE: PRT
<213> ORGANISM: Homo sapiens
<220> FEATURE:
```

```
<221> NAME/KEY: MOD_RES
<222> LOCATION: (1)..(36)
<223> OTHER INFORMATION: Glycation (3) [3 ?]
<220> FEATURE:
<221> NAME/KEY: MOD_RES
<222> LOCATION: (1)..(36)
<223> OTHER INFORMATION: Deamidation N [?]
<220> FEATURE:
<221> NAME/KEY: MOD_RES
<222> LOCATION: (28)..(31)
<223> OTHER INFORMATION: Deamidation N (2) [28 31]

<400> SEQUENCE: 317

Lys Lys Phe Trp Gly Lys Tyr Leu Tyr Glu Ile Ala Arg Arg His Pro
1               5                   10                  15

Tyr Phe Tyr Ala Pro Glu Leu Leu Tyr Tyr Ala Asn Lys Tyr Asn Gly
            20                  25                  30

Val Phe Gln Glu
        35

<210> SEQ ID NO 318
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation (2) [2 ?]
<220> FEATURE:
<221> NAME/KEY: MOD_RES
<222> LOCATION: (27)..(30)
<223> OTHER INFORMATION: Deamidation N (2) [27 30]

<400> SEQUENCE: 318

Lys Phe Trp Gly Lys Tyr Leu Tyr Glu Ile Ala Arg Arg His Pro Tyr
1               5                   10                  15

Phe Tyr Ala Pro Glu Leu Leu Tyr Tyr Ala Asn Lys Tyr Asn Gly Val
            20                  25                  30

Phe Gln Glu
        35

<210> SEQ ID NO 319
<211> LENGTH: 32
<212> TYPE: PRT
<213> ORGANISM: Homo sapiens
<220> FEATURE:
<221> NAME/KEY: MOD_RES
<222> LOCATION: (2)..(25)
<223> OTHER INFORMATION: Glycation (2) [2 25]
<220> FEATURE:
<221> NAME/KEY: MOD_RES
<222> LOCATION: (24)..(27)
<223> OTHER INFORMATION: Deamidation N (2) [24 27]

<400> SEQUENCE: 319

Gly Lys Tyr Leu Tyr Glu Ile Ala Arg Arg His Pro Tyr Phe Tyr Ala
1               5                   10                  15

Pro Glu Leu Leu Tyr Tyr Ala Asn Lys Tyr Asn Gly Val Phe Gln Glu
            20                  25                  30

<210> SEQ ID NO 320
<211> LENGTH: 36
<212> TYPE: PRT
<213> ORGANISM: Homo sapiens
<220> FEATURE:
<221> NAME/KEY: MOD_RES
<222> LOCATION: (1)..(36)
<223> OTHER INFORMATION: Glycation [?]
```

-continued

```
<220> FEATURE:
<221> NAME/KEY: MOD_RES
<222> LOCATION: (23)..(26)
<223> OTHER INFORMATION: Deamidation N (2) [23 26]
<220> FEATURE:
<221> NAME/KEY: MOD_RES
<222> LOCATION: (32)..(33)
<223> OTHER INFORMATION: Carboxymethyl C (2) [32 33]

<400> SEQUENCE: 320

Lys Tyr Leu Tyr Glu Ile Ala Arg Arg His Pro Tyr Phe Tyr Ala Pro
1               5                   10                  15

Glu Leu Leu Tyr Tyr Ala Asn Lys Tyr Asn Gly Val Phe Gln Glu Cys
            20                  25                  30

Cys Gln Ala Glu
        35

<210> SEQ ID NO 321
<211> LENGTH: 7
<212> TYPE: PRT
<213> ORGANISM: Homo sapiens
<220> FEATURE:
<221> NAME/KEY: MOD_RES
<222> LOCATION: (1)..(7)
<223> OTHER INFORMATION: Glycation [?]

<400> SEQUENCE: 321

Lys Lys Phe Trp Gly Lys Tyr
1               5

<210> SEQ ID NO 322
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 322

Lys Tyr Leu Tyr Glu
1               5

<210> SEQ ID NO 323
<211> LENGTH: 20
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Glycation [19]

<400> SEQUENCE: 323

Ile Ala Arg Arg His Pro Tyr Phe Tyr Ala Pro Glu Leu Leu Tyr Tyr
1               5                   10                  15

Ala Asn Lys Tyr
            20

<210> SEQ ID NO 324
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: Deamidation N [?]
<220> FEATURE:
<221> NAME/KEY: MOD_RES
```

```
<222> LOCATION: (9)..(9)
<223> OTHER INFORMATION: Glycation [9]

<400> SEQUENCE: 324

Pro Glu Leu Leu Tyr Tyr Ala Asn Lys Tyr Asn Gly Val Phe Gln Glu
1               5                   10                  15

<210> SEQ ID NO 325
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Deamidation N [?]
<220> FEATURE:
<221> NAME/KEY: MOD_RES
<222> LOCATION: (11)..(11)
<223> OTHER INFORMATION: Glycation [11]

<400> SEQUENCE: 325

Tyr Ala Pro Glu Leu Leu Tyr Tyr Ala Asn Lys Tyr Asn Gly Val Phe
1               5                   10                  15

Gln Glu

<210> SEQ ID NO 326
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Deamidation N [?]

<400> SEQUENCE: 326

Ala Pro Glu Leu Leu Tyr Tyr Ala Asn Lys Tyr Asn Gly Val Phe Gln
1               5                   10                  15

Glu

<210> SEQ ID NO 327
<211> LENGTH: 31
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Glycation [19]
<220> FEATURE:
<221> NAME/KEY: MOD_RES
<222> LOCATION: (27)..(28)
<223> OTHER INFORMATION: Carboxymethyl C (2) [27 28]

<400> SEQUENCE: 327

Ile Ala Arg Arg His Pro Tyr Phe Tyr Ala Pro Glu Leu Leu Tyr Tyr
1               5                   10                  15

Ala Asn Lys Tyr Asn Gly Val Phe Gln Glu Cys Cys Gln Ala Glu
            20                  25                  30

<210> SEQ ID NO 328
<211> LENGTH: 21
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Deamidation N [?]
<220> FEATURE:
<221> NAME/KEY: MOD_RES
```

```
<222> LOCATION: (9)..(9)
<223> OTHER INFORMATION: Glycation [9]
<220> FEATURE:
<221> NAME/KEY: MOD_RES
<222> LOCATION: (17)..(18)
<223> OTHER INFORMATION: Carboxymethyl C (2) [17 18]

<400> SEQUENCE: 328

Pro Glu Leu Leu Tyr Tyr Ala Asn Lys Tyr Asn Gly Val Phe Gln Glu
1               5                   10                  15

Cys Cys Gln Ala Glu
            20

<210> SEQ ID NO 329
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Deamidation N [?]
<220> FEATURE:
<221> NAME/KEY: MOD_RES
<222> LOCATION: (7)..(10)
<223> OTHER INFORMATION: Deamidation N (2) [7 10]
<220> FEATURE:
<221> NAME/KEY: MOD_RES
<222> LOCATION: (16)..(17)
<223> OTHER INFORMATION: Carboxymethyl C (2) [16 17]

<400> SEQUENCE: 329

Glu Leu Leu Tyr Tyr Ala Asn Lys Tyr Asn Gly Val Phe Gln Glu Cys
1               5                   10                  15

Cys Gln Ala Glu
            20

<210> SEQ ID NO 330
<211> LENGTH: 27
<212> TYPE: PRT
<213> ORGANISM: Homo sapiens
<220> FEATURE:
<221> NAME/KEY: MOD_RES
<222> LOCATION: (14)..(17)
<223> OTHER INFORMATION: Deamidation N (2) [14 17]
<220> FEATURE:
<221> NAME/KEY: MOD_RES
<222> LOCATION: (15)..(15)
<223> OTHER INFORMATION: Glycation [15]
<220> FEATURE:
<221> NAME/KEY: MOD_RES
<222> LOCATION: (23)..(24)
<223> OTHER INFORMATION: Carboxymethyl C (2) [23 24]

<400> SEQUENCE: 330

His Pro Tyr Phe Tyr Ala Pro Glu Leu Ile Tyr Tyr Ala Asn Lys Tyr
1               5                   10                  15

Asn Gly Val Phe Gln Glu Cys Cys Gln Ala Glu
            20                  25

<210> SEQ ID NO 331
<211> LENGTH: 22
<212> TYPE: PRT
<213> ORGANISM: Homo sapiens
<220> FEATURE:
<221> NAME/KEY: MOD_RES
<222> LOCATION: (9)..(12)
<223> OTHER INFORMATION: Deamidation N (2) [9 12]
<220> FEATURE:
<221> NAME/KEY: MOD_RES
<222> LOCATION: (18)..(19)
```

<223> OTHER INFORMATION: Carboxymethyl C (2) [18 19]

<400> SEQUENCE: 331

Ala Pro Glu Leu Leu Tyr Tyr Ala Asn Lys Tyr Asn Gly Val Phe Gln
1               5                   10                  15

Glu Cys Cys Gln Ala Glu
            20

<210> SEQ ID NO 332
<211> LENGTH: 42
<212> TYPE: PRT
<213> ORGANISM: Homo sapiens
<220> FEATURE:
<221> NAME/KEY: MOD_RES
<222> LOCATION: (1)..(42)
<223> OTHER INFORMATION: Deamidation N [?]
<220> FEATURE:
<221> NAME/KEY: MOD_RES
<222> LOCATION: (1)..(42)
<223> OTHER INFORMATION: Glycation (2) [2 ?]
<220> FEATURE:
<221> NAME/KEY: MOD_RES
<222> LOCATION: (27)..(36)
<223> OTHER INFORMATION: Carboxymethyl C (3) [27 28 36]

<400> SEQUENCE: 332

Ile Ala Arg Arg His Pro Tyr Phe Tyr Ala Pro Glu Leu Leu Tyr Tyr
1               5                   10                  15

Ala Asn Lys Tyr Asn Gly Val Phe Gln Glu Cys Cys Gln Ala Glu Asp
            20                  25                  30

Lys Gly Ala Cys Leu Leu Pro Lys Ile Glu
        35                  40

<210> SEQ ID NO 333
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Deamidation N [?]
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (27)..(36)
<223> OTHER INFORMATION: Carboxymethyl C (3) [27 28 36]

<400> SEQUENCE: 333

Ile Ala Arg Arg His Pro Tyr Phe Tyr Ala Pro Glu Leu Leu Tyr Tyr
1               5                   10                  15

Ala Asn Lys Tyr Asn Gly Val Phe Gln Glu Cys Cys Gln Ala Glu Asp
            20                  25                  30

Lys Gly Ala Cys Leu Leu Pro Lys
        35                  40

<210> SEQ ID NO 334
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Deamidation N [?]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (15)..(16)
<223> OTHER INFORMATION: Carboxymethyl C (2) [15 16]

<400> SEQUENCE: 334

Leu Leu Tyr Tyr Ala Asn Lys Tyr Asn Gly Val Phe Gln Glu Cys Cys
1               5                   10                  15

Gln Ala

<210> SEQ ID NO 335
<211> LENGTH: 16
<212> TYPE: PRT
<213> ORGANISM: Homo sapiens
<220> FEATURE:
<221> NAME/KEY: MOD_RES
<222> LOCATION: (6)..(9)
<223> OTHER INFORMATION: Deamidation N (2) [6 9]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (15)..(16)
<223> OTHER INFORMATION: Carboxymethyl C (2) [15 16]

<400> SEQUENCE: 335

Leu Leu Tyr Tyr Ala Asn Lys Tyr Asn Gly Val Phe Gln Glu Cys Cys
1               5                   10                  15

<210> SEQ ID NO 336
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Deamidation N [?]
<220> FEATURE:
<221> NAME/KEY: MOD_RES
<222> LOCATION: (6)..(6)
<223> OTHER INFORMATION: Glycation [6]
<220> FEATURE:
<221> NAME/KEY: MOD_RES
<222> LOCATION: (14)..(15)
<223> OTHER INFORMATION: Carboxymethyl C (2) [14 15]

<400> SEQUENCE: 336

Leu Tyr Tyr Ala Asn Lys Tyr Asn Gly Val Phe Gln Glu Cys Cys Gln
1               5                   10                  15

Ala Glu

<210> SEQ ID NO 337
<211> LENGTH: 9
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 337

Val Phe Gln Glu Cys Cys Gln Ala Glu
1               5

<210> SEQ ID NO 338

```
<211> LENGTH: 8
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Carboxymethyl C (2) [4 5]

<400> SEQUENCE: 338

Phe Gln Glu Cys Cys Gln Ala Glu
1               5

<210> SEQ ID NO 339
<211> LENGTH: 7
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Carboxymethyl C (2) [3 4]

<400> SEQUENCE: 339

Gln Glu Cys Cys Gln Ala Glu
1               5

<210> SEQ ID NO 340
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]

<400> SEQUENCE: 340

Glu Cys Cys Gln Ala Glu
1               5

<210> SEQ ID NO 341
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: Deamidation N [?]
<220> FEATURE:
<221> NAME/KEY: MOD_RES
<222> LOCATION: (3)..(6)
<223> OTHER INFORMATION: Deamidation N (2) [3 6]
<220> FEATURE:
<221> NAME/KEY: MOD_RES
<222> LOCATION: (4)..(4)
<223> OTHER INFORMATION: Glycation [4]
<220> FEATURE:
<221> NAME/KEY: MOD_RES
<222> LOCATION: (12)..(13)
<223> OTHER INFORMATION: Carboxymethyl C (2) [12 13]

<400> SEQUENCE: 341

Tyr Ala Asn Lys Tyr Asn Gly Val Phe Gln Glu Cys Cys Gln Ala Glu
1               5                   10                  15

<210> SEQ ID NO 342
<211> LENGTH: 15
<212> TYPE: PRT
<213> ORGANISM: Homo sapiens
<220> FEATURE:
<221> NAME/KEY: MOD_RES
<222> LOCATION: (11)..(12)
<223> OTHER INFORMATION: Carboxymethyl C (2) [11 12]
```

<400> SEQUENCE: 342

Ala Asn Lys Tyr Asn Gly Val Phe Gln Glu Cys Cys Gln Ala Glu
1               5                   10                  15

<210> SEQ ID NO 343
<211> LENGTH: 14
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: Deamidation N [?]
<220> FEATURE:
<221> NAME/KEY: MOD_RES
<222> LOCATION: (1)..(4)
<223> OTHER INFORMATION: Deamidation N (2) [1 4]
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (10)..(11)
<223> OTHER INFORMATION: Carboxymethyl C (2) [10 11]

<400> SEQUENCE: 343

Asn Lys Tyr Asn Gly Val Phe Gln Glu Cys Cys Gln Ala Glu
1               5                   10

<210> SEQ ID NO 344
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (3)..(3)
<223> OTHER INFORMATION: Deamidation N [3]
<220> FEATURE:
<221> NAME/KEY: MOD_RES
<222> LOCATION: (9)..(10)
<223> OTHER INFORMATION: Carboxymethyl C (2) [9 10]

<400> SEQUENCE: 344

Lys Tyr Asn Gly Val Phe Gln Glu Cys Gln Ala Glu
1               5                   10

<210> SEQ ID NO 345
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (7)..(8)
<223> OTHER INFORMATION: Carboxymethyl C (2) [7 8]

<400> SEQUENCE: 345

Asn Gly Val Phe Gln Glu Cys Cys Gln Ala Glu
1               5                   10

<210> SEQ ID NO 346
<211> LENGTH: 10
<212> TYPE: PRT

```
<213> ORGANISM: Homo sapiens
<220> FEATURE:
<221> NAME/KEY: MOD_RES
<222> LOCATION: (6)..(7)
<223> OTHER INFORMATION: Carboxymethyl C (2)[6 7]

<400> SEQUENCE: 346

Gly Val Phe Gln Glu Cys Cys Gln Ala Glu
1               5                   10

<210> SEQ ID NO 347
<211> LENGTH: 27
<212> TYPE: PRT
<213> ORGANISM: Homo sapiens
<220> FEATURE:
<221> NAME/KEY: MOD_RES
<222> LOCATION: (6)..(9)
<223> OTHER INFORMATION: Deamidation N (2) [6 9]
<220> FEATURE:
<221> NAME/KEY: MOD_RES
<222> LOCATION: (15)..(24)
<223> OTHER INFORMATION: Carboxymethyl C (3) [15 16 24]

<400> SEQUENCE: 347

Leu Leu Tyr Tyr Ala Asn Lys Tyr Asn Gly Val Phe Gln Glu Cys Cys
1               5                   10                  15

Gln Ala Glu Asp Lys Gly Ala Cys Leu Leu Pro
            20                  25

<210> SEQ ID NO 348
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation [?]
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 348

Glu Cys Cys Gln Ala Glu Asp Lys Gly Ala Cys Leu Leu Pro Lys Ile
1               5                   10                  15

Glu

<210> SEQ ID NO 349
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation [?]
<220> FEATURE:
<221> NAME/KEY: MOD_RES
<222> LOCATION: (8)..(17)
<223> OTHER INFORMATION: Carboxymethyl C (3) [8 9 17]

<400> SEQUENCE: 349

Tyr Asn Gly Val Phe Gln Glu Cys Cys Gln Ala Glu Asp Lys Gly Ala
1               5                   10                  15

Cys Leu Leu Pro Lys Ile Glu
            20

<210> SEQ ID NO 350
<211> LENGTH: 23
```

```
<212> TYPE: PRT
<213> ORGANISM: Homo sapiens
<220> FEATURE:
<221> NAME/KEY: MOD_RES
<222> LOCATION: (4)..(13)
<223> OTHER INFORMATION: Carboxymethyl C (3) [4 5 13]
<220> FEATURE:
<221> NAME/KEY: MOD_RES
<222> LOCATION: (10)..(17)
<223> OTHER INFORMATION: Glycation (2) [10 17]

<400> SEQUENCE: 350

Phe Gln Glu Cys Cys Gln Ala Glu Asp Lys Gly Ala Cys Leu Leu Pro
1               5                   10                  15

Lys Ile Glu Thr Met Arg Glu
            20

<210> SEQ ID NO 351
<211> LENGTH: 21
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 351

Glu Cys Cys Gln Ala Glu Asp Lys Gly Ala Cys Leu Leu Pro Lys Ile
1               5                   10                  15

Glu Thr Met Arg Glu
            20

<210> SEQ ID NO 352
<211> LENGTH: 29
<212> TYPE: PRT
<213> ORGANISM: Homo sapiens
<220> FEATURE:
<221> NAME/KEY: MOD_RES
<222> LOCATION: (1)..(29)
<223> OTHER INFORMATION: Deamidation N [?]
<220> FEATURE:
<221> NAME/KEY: MOD_RES
<222> LOCATION: (1)..(29)
<223> OTHER INFORMATION: Oxidation M [?]
<220> FEATURE:
<221> NAME/KEY: MOD_RES
<222> LOCATION: (10)..(19)
<223> OTHER INFORMATION: Carboxymethyl C (3) [10 11 19]

<400> SEQUENCE: 352

Asn Lys Tyr Asn Gly Val Phe Gln Glu Cys Cys Gln Ala Glu Asp Lys
1               5                   10                  15

Gly Ala Cys Leu Leu Pro Lys Ile Glu Thr Met Arg Glu
            20                  25

<210> SEQ ID NO 353
<211> LENGTH: 28
<212> TYPE: PRT
<213> ORGANISM: Homo sapiens
<220> FEATURE:
<221> NAME/KEY: MOD_RES
<222> LOCATION: (9)..(18)
<223> OTHER INFORMATION: Carboxymethyl C (3) [9 10 18]

<400> SEQUENCE: 353

Lys Tyr Asn Gly Val Phe Gln Glu Cys Cys Gln Ala Glu Asp Lys Gly
1               5                   10                  15

Ala Cys Leu Leu Pro Lys Ile Glu Thr Met Arg Glu
```

```
                20                  25
```

<210> SEQ ID NO 354
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 354

```
Leu Leu Tyr Tyr Ala Asn
1               5
```

<210> SEQ ID NO 355
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: Deamidation N [?]

<400> SEQUENCE: 355

```
Tyr Ala Asn Lys Tyr Asn Gly Val Phe Gln Glu
1               5                   10
```

<210> SEQ ID NO 356
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Deamidation [?]
<220> FEATURE:
<221> NAME/KEY: MOD_RES
<222> LOCATION: (2)..(5)
<223> OTHER INFORMATION: Deamidation N (2) [2 5]
<220> FEATURE:
<221> NAME/KEY: MOD_RES
<222> LOCATION: (3)..(3)
<223> OTHER INFORMATION: Glycation [3]

<400> SEQUENCE: 356

```
Ala Asn Lys Tyr Asn Gly Val Phe Gln Glu
1               5                   10
```

<210> SEQ ID NO 357
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 357

```
Asn Lys Tyr Asn Gly Val Phe Gln Glu
1               5
```

<210> SEQ ID NO 358
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

```
<220> FEATURE:
<221> NAME/KEY: MOD_RES
<222> LOCATION: (3)..(3)
<223> OTHER INFORMATION: Deamidation N [3]

<400> SEQUENCE: 358

Lys Tyr Asn Gly Val Phe Gln Glu
1               5

<210> SEQ ID NO 359
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Deamidation N [2]

<400> SEQUENCE: 359

Tyr Asn Gly Val Phe Gln Glu
1               5

<210> SEQ ID NO 360
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]

<400> SEQUENCE: 360

Cys Cys Gln Ala Glu Asp
1               5

<210> SEQ ID NO 361
<211> LENGTH: 11
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (7)..(7)
<223> OTHER INFORMATION: Glycation [7]

<400> SEQUENCE: 361

Cys Cys Gln Ala Glu Asp Lys Gly Ala Cys Leu
1               5                   10

<210> SEQ ID NO 362
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]

<400> SEQUENCE: 362

Cys Cys Gln Ala Glu Asp Lys Gly Ala Cys
1               5                   10

<210> SEQ ID NO 363
<211> LENGTH: 8
<212> TYPE: PRT
<213> ORGANISM: Homo sapiens
```

-continued

```
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (7)..(7)
<223> OTHER INFORMATION: Glycation [7]

<400> SEQUENCE: 363

Cys Cys Gln Ala Glu Asp Lys Gly
1               5

<210> SEQ ID NO 364
<211> LENGTH: 7
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (7)..(7)
<223> OTHER INFORMATION: Glycation [7]

<400> SEQUENCE: 364

Cys Cys Gln Ala Glu Asp Lys
1               5

<210> SEQ ID NO 365
<211> LENGTH: 18
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (1)..(18)
<223> OTHER INFORMATION: Glycation [?]
<220> FEATURE:
<221> NAME/KEY: MOD_RES
<222> LOCATION: (18)..(18)
<223> OTHER INFORMATION: Oxidation M [18]

<400> SEQUENCE: 365

Cys Cys Gln Ala Glu Asp Lys Gly Ala Cys Leu Leu Pro Lys Ile Glu
1               5                   10                  15

Thr Met

<210> SEQ ID NO 366
<211> LENGTH: 38
<212> TYPE: PRT
<213> ORGANISM: Homo sapiens
<220> FEATURE:
<221> NAME/KEY: MOD_RES
<222> LOCATION: (1)..(38)
<223> OTHER INFORMATION: Glycation (3) [3 ?]
<220> FEATURE:
<221> NAME/KEY: MOD_RES
<222> LOCATION: (7)..(30)
<223> OTHER INFORMATION: Carboxymethyl C (2) [7 30]

<400> SEQUENCE: 366

Ala Glu Asp Lys Gly Ala Cys Leu Leu Pro Lys Ile Glu Thr Met Arg
1               5                   10                  15

Glu Lys Val Leu Ala Ser Ser Ala Arg Gln Arg Leu Arg Cys Ala Ser
            20                  25                  30
```

-continued

```
Ile Gln Lys Phe Gly Glu
        35

<210> SEQ ID NO 367
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 367

Cys Gln Ala Glu
1

<210> SEQ ID NO 368
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]

<400> SEQUENCE: 368

Met Lys Trp Val Thr Phe Ile Ser Leu Leu
1               5                   10

<210> SEQ ID NO 369
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 369

Met Lys Trp Val Thr Phe
1               5

<210> SEQ ID NO 370
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (2)..(2)
<223> OTHER INFORMATION: Glycation [2]

<400> SEQUENCE: 370

Met Lys Trp Val Thr
1               5

<210> SEQ ID NO 371
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
```

<222> LOCATION: (2)..(2)
<223> OTHER INFORMATION: Glycation [2]

<400> SEQUENCE: 371

Met Lys Trp Val
1

<210> SEQ ID NO 372
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]

<400> SEQUENCE: 372

Met Lys Trp Val Thr Phe Ile Ser Leu Leu Leu Phe Ser Ser Ala
1               5                   10                  15

Tyr Ser Arg Gly Val Phe
            20

<210> SEQ ID NO 373
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Glycation [16]

<400> SEQUENCE: 373

Phe Ser Ser Ala Tyr Ser Arg Gly Val Phe Arg Arg Asp Thr His Lys
1               5                   10                  15

Ser Glu

<210> SEQ ID NO 374
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]

<400> SEQUENCE: 374

Phe Arg Arg Asp Thr His Lys Ser Glu
1               5

<210> SEQ ID NO 375
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 375

His Lys Ser Glu
1

<210> SEQ ID NO 376
<211> LENGTH: 10
<212> TYPE: PRT
<213> ORGANISM: Homo sapiens
<220> FEATURE:

```
<221> NAME/KEY: MOD_RES
<222> LOCATION: (4)..(4)
<223> OTHER INFORMATION: Glycation [4]
<220> FEATURE:
<221> NAME/KEY: MOD_RES
<222> LOCATION: (8)..(8)
<223> OTHER INFORMATION: Oxidation M [8]

<400> SEQUENCE: 376

Leu Leu Pro Lys Ile Glu Thr Met Arg Glu
1               5                   10

<210> SEQ ID NO 377
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]

<400> SEQUENCE: 377

Ile Glu Thr Met Arg Glu
1               5

<210> SEQ ID NO 378
<211> LENGTH: 36
<212> TYPE: PRT
<213> ORGANISM: Homo sapiens
<220> FEATURE:
<221> NAME/KEY: MOD_RES
<222> LOCATION: (1)..(36)
<223> OTHER INFORMATION: Glycation (3) [3 ?]
<220> FEATURE:
<221> NAME/KEY: MOD_RES
<222> LOCATION: (2)..(33)
<223> OTHER INFORMATION: Glycation (4) [2 9 16 33]
<220> FEATURE:
<221> NAME/KEY: MOD_RES
<222> LOCATION: (5)..(28)
<223> OTHER INFORMATION: Carboxymethyl C (2) [5 28]
<220> FEATURE:
<221> NAME/KEY: MOD_RES
<222> LOCATION: (13)..(13)
<223> OTHER INFORMATION: Oxidation M [13]

<400> SEQUENCE: 378

Asp Lys Gly Ala Cys Leu Leu Pro Lys Ile Glu Thr Met Arg Glu Lys
1               5                   10                  15

Val Leu Ala Ser Ser Ala Arg Gln Arg Leu Arg Cys Ala Ser Ile Gln
            20                  25                  30

Lys Phe Gly Glu
        35

<210> SEQ ID NO 379
<211> LENGTH: 27
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (13)..(13)
<223> OTHER INFORMATION: Oxidation M [13]

<400> SEQUENCE: 379

Asp Lys Gly Ala Cys Leu Leu Pro Lys Ile Glu Thr Met Arg Glu Lys
1               5                   10                  15
```

```
Val Leu Ala Ser Ser Ala Arg Gln Arg Leu Arg
        20                  25
```

<210> SEQ ID NO 380
<211> LENGTH: 47
<212> TYPE: PRT
<213> ORGANISM: Homo sapiens
<220> FEATURE:
<221> NAME/KEY: MOD_RES
<222> LOCATION: (1)..(47)
<223> OTHER INFORMATION: Glycation (2) [2 ?]
<220> FEATURE:
<221> NAME/KEY: MOD_RES
<222> LOCATION: (20)..(20)
<223> OTHER INFORMATION: Carboxymethyl C [20]

<400> SEQUENCE: 380

```
Lys Ile Glu Thr Met Arg Glu Lys Val Leu Ala Ser Ser Ala Arg Gln
1               5                   10                  15
Arg Leu Arg Cys Ala Ser Ile Gln Lys Phe Gly Glu Arg Ala Leu Lys
            20                  25                  30
Ala Trp Ser Val Ala Arg Leu Ser Gln Lys Phe Pro Lys Ala Glu
        35                  40                  45
```

<210> SEQ ID NO 381
<211> LENGTH: 45
<212> TYPE: PRT
<213> ORGANISM: Homo sapiens
<220> FEATURE:
<221> NAME/KEY: MOD_RES
<222> LOCATION: (1)..(45)
<223> OTHER INFORMATION: Glycation [?]
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (19)..(19)
<223> OTHER INFORMATION: Carboxymethyl C [19]

<400> SEQUENCE: 381

```
Ile Glu Thr Met Arg Glu Lys Leu Ala Ser Ser Ala Arg Gln Arg Leu
1               5                   10                  15
Arg Cys Ala Ser Ile Gln Lys Phe Gly Glu Arg Ala Leu Lys Ala Trp
            20                  25                  30
Ser Val Ala Arg Leu Ser Gln Lys Phe Pro Lys Ala Glu
        35                  40                  45
```

<210> SEQ ID NO 382
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 382

```
Asp Lys Gly Ala Cys Leu Leu Pro Lys Ile
1               5                   10
```

<210> SEQ ID NO 383
<211> LENGTH: 8
<212> TYPE: PRT
<213> ORGANISM: Homo sapiens
<220> FEATURE:

-continued

```
<221> NAME/KEY: MOD_RES
<222> LOCATION: (5)..(5)
<223> OTHER INFORMATION: Carboxymethyl C [5]

<400> SEQUENCE: 383

Asp Lys Gly Ala Cys Leu Leu Pro
1               5

<210> SEQ ID NO 384
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (5)..(5)
<223> OTHER INFORMATION: Carboxyrnethyl C [5]

<400> SEQUENCE: 384

Asp Lys Gly Ala Cys Leu
1               5

<210> SEQ ID NO 385
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (5)..(5)
<223> OTHER INFORMATION: Carboxymethyl C [5]

<400> SEQUENCE: 385

Asp Lys Gly Ala Cys
1               5

<210> SEQ ID NO 386
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Glycation [?]
<220> FEATURE:
<221> NAME/KEY: MOD_RES
<222> LOCATION: (4)..(4)
<223> OTHER INFORMATION: Carboxymethyl C [4]

<400> SEQUENCE: 386

Lys Gly Ala Cys Leu Leu Pro Lys Ile Glu
1               5                   10

<210> SEQ ID NO 387
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 387

Gly Ala Cys Leu Leu Pro Lys Ile Glu
```

<210> SEQ ID NO 388
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 388

Thr Met Arg Glu Lys Val Leu Ala Ser Ser Ala Arg
1               5                   10

<210> SEQ ID NO 389
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (5)..(5)
<223> OTHER INFORMATION: Glycation [5]

<400> SEQUENCE: 389

Thr Met Arg Glu Lys Val Leu Ala Ser Ser
1               5                   10

<210> SEQ ID NO 390
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]

<400> SEQUENCE: 390

Thr Met Arg Glu Lys Val Leu Ala Ser
1               5

<210> SEQ ID NO 391
<211> LENGTH: 44
<212> TYPE: PRT
<213> ORGANISM: Homo sapiens
<220> FEATURE:
<221> NAME/KEY: MOD_RES
<222> LOCATION: (1)..(44)
<223> OTHER INFORMATION: Glycation [?]
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (17)..(17)
<223> OTHER INFORMATION: Carboxymethyl C [17]

<400> SEQUENCE: 391

Thr Met Arg Glu Lys Val Leu Ala Ser Ser Ala Arg Gln Arg Leu Arg
1               5                   10                  15

Cys Ala Ser Ile Gln Lys Phe Gly Glu Arg Ala Leu Lys Ala Trp Ser
            20                  25                  30

Val Ala Arg Leu Ser Gln Lys Phe Pro Lys Ala Glu
        35                  40

```
<210> SEQ ID NO 392
<211> LENGTH: 46
<212> TYPE: PRT
<213> ORGANISM: Homo sapiens
<220> FEATURE:
<221> NAME/KEY: MOD_RES
<222> LOCATION: (1)..(46)
<223> OTHER INFORMATION: Glycation (2) [2 ?]
<220> FEATURE:
<221> NAME/KEY: MOD_RES
<222> LOCATION: (16)..(16)
<223> OTHER INFORMATION: Carboxymethyl C [16]

<400> SEQUENCE: 392

Met Arg Glu Lys Val Leu Ala Ser Ser Ala Arg Gln Arg Leu Arg Cys
1               5                   10                  15

Ala Ser Ile Gln Lys Phe Gly Glu Arg Ala Leu Lys Ala Trp Ser Val
            20                  25                  30

Ala Arg Leu Ser Gln Lys Phe Pro Lys Ala Glu Phe Val Glu
        35                  40                  45

<210> SEQ ID NO 393
<211> LENGTH: 21
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation (2) [1 18]
<220> FEATURE:
<221> NAME/KEY: MOD_RES
<222> LOCATION: (13)..(13)
<223> OTHER INFORMATION: Carboxymethyl C [13]

<400> SEQUENCE: 393

Lys Val Leu Ala Ser Ser Ala Arg Gln Arg Leu Arg Cys Ala Ser Ile
1               5                   10                  15

Gln Lys Phe Gly Glu
            20

<210> SEQ ID NO 394
<211> LENGTH: 30
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation (3) [1 18 25]
<220> FEATURE:
<221> NAME/KEY: MOD_RES
<222> LOCATION: (13)..(13)
<223> OTHER INFORMATION: Carboxymethyl C [13]

<400> SEQUENCE: 394

Lys Val Leu Ala Ser Ser Ala Arg Gln Arg Leu Arg Cys Ala Ser Ile
1               5                   10                  15

Gln Lys Phe Gly Glu Arg Ala Leu Lys Ala Trp Ser Val Ala
            20                  25                  30

<210> SEQ ID NO 395
<211> LENGTH: 36
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Carboxymethyl C [13]
```

-continued

<400> SEQUENCE: 395

Lys Val Leu Ala Ser Ser Ala Arg Gln Arg Leu Arg Cys Ala Ser Ile
1               5                   10                  15

Gln Lys Phe Gly Glu Arg Ala Leu Lys Ala Trp Ser Val Ala Arg Leu
            20                  25                  30

Ser Gln Lys Phe
        35

<210> SEQ ID NO 396
<211> LENGTH: 30
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]
<220> FEATURE:
<221> NAME/KEY: MOD_RES
<222> LOCATION: (8)..(28)
<223> OTHER INFORMATION: Glycation (4) [8 15 25 28]

<400> SEQUENCE: 396

Leu Arg Cys Ala Ser Ile Gln Lys Phe Gly Glu Arg Ala Leu Lys Ala
1               5                   10                  15

Trp Ser Val Ala Arg Leu Ser Gln Lys Phe Pro Lys Ala Glu
            20                  25                  30

<210> SEQ ID NO 397
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation (3) [3 ?]
<220> FEATURE:
<221> NAME/KEY: MOD_RES
<222> LOCATION: (8)..(8)
<223> OTHER INFORMATION: Carboxymethyl C [8]

<400> SEQUENCE: 397

Ser Ala Arg Gln Arg Leu Arg Cys Ala Ser Ile Gln Lys Phe Gly Glu
1               5                   10                  15

Arg Ala Leu Lys Ala Trp Ser Val Ala Arg Leu Ser Gln Lys Phe Pro
            20                  25                  30

Lys Ala Glu
        35

<210> SEQ ID NO 398
<211> LENGTH: 42
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Carboxymethyl C [12]

<400> SEQUENCE: 398

Val Leu Ala Ser Ser Ala Arg Gln Arg Leu Arg Cys Ala Ser Ile Gln
1               5                   10                  15

Lys Phe Gly Glu Arg Ala Leu Lys Ala Trp Ser Val Ala Arg Leu Ser
            20                  25                  30

Gln Lys Phe Pro Lys Ala Glu Phe Val Glu
        35                  40

-continued

<210> SEQ ID NO 399
<211> LENGTH: 56
<212> TYPE: PRT
<213> ORGANISM: Homo sapiens
<220> FEATURE:
<221> NAME/KEY: MOD_RES
<222> LOCATION: (1)..(56)
<223> OTHER INFORMATION: Glycation (6) [6 ?]
<220> FEATURE:
<221> NAME/KEY: MOD_RES
<222> LOCATION: (13)..(13)
<223> OTHER INFORMATION: Carboxymethyl C [13]

<400> SEQUENCE: 399

Lys Val Leu Ala Ser Ser Ala Arg Gln Arg Leu Arg Cys Ala Ser Ile
1               5                   10                  15

Gln Lys Phe Gly Glu Arg Ala Leu Lys Ala Trp Ser Val Ala Arg Leu
            20                  25                  30

Ser Gln Lys Phe Pro Lys Ala Glu Phe Val Glu Val Thr Lys Leu Val
        35                  40                  45

Thr Asp Leu Thr Lys Val His Ile
    50                  55

<210> SEQ ID NO 400
<211> LENGTH: 53
<212> TYPE: PRT
<213> ORGANISM: Homo sapiens
<220> FEATURE:
<221> NAME/KEY: MOD_RES
<222> LOCATION: (1)..(53)
<223> OTHER INFORMATION: Glycation (2) [2 ?]
<220> FEATURE:
<221> NAME/KEY: MOD_RES
<222> LOCATION: (13)..(13)
<223> OTHER INFORMATION: Carboxymethyl C [13]

<400> SEQUENCE: 400

Lys Val Leu Ala Ser Ser Ala Arg Gln Arg Leu Arg Cys Ala Ser Ile
1               5                   10                  15

Gln Lys Phe Gly Glu Arg Ala Leu Lys Ala Trp Ser Val Ala Arg Leu
            20                  25                  30

Ser Gln Lys Phe Pro Lys Ala Glu Phe Val Glu Val Thr Lys Leu Val
        35                  40                  45

Thr Asp Leu Thr Lys
    50

<210> SEQ ID NO 401
<211> LENGTH: 56
<212> TYPE: PRT
<213> ORGANISM: Homo sapiens
<220> FEATURE:
<221> NAME/KEY: MOD_RES
<222> LOCATION: (1)..(56)
<223> OTHER INFORMATION: Glycation (4) [4 ?]
<220> FEATURE:
<221> NAME/KEY: MOD_RES
<222> LOCATION: (12)..(12)
<223> OTHER INFORMATION: Carboxymethyl C [12]

<400> SEQUENCE: 401

Val Leu Ala Ser Ser Ala Arg Gln Arg Leu Arg Cys Ala Ser Ile Gln
1               5                   10                  15

Lys Phe Gly Glu Arg Ala Leu Lys Ala Trp Ser Val Ala Arg Leu Ser
            20                  25                  30

Gln Lys Phe Pro Lys Ala Glu Phe Val Glu Val Thr Lys Leu Val Thr
 35                  40                  45

Asp Leu Thr Lys Val His Lys Ile
 50                  55

<210> SEQ ID NO 402
<211> LENGTH: 47
<212> TYPE: PRT
<213> ORGANISM: Homo sapiens
<220> FEATURE:
<221> NAME/KEY: MOD_RES
<222> LOCATION: (1)..(47)
<223> OTHER INFORMATION: Glycation (4) [4 ?]
<220> FEATURE:
<221> NAME/KEY: MOD_RES
<222> LOCATION: (3)..(3)
<223> OTHER INFORMATION: Carboxymethyl C [3]

<400> SEQUENCE: 402

Leu Arg Cys Ala Ser Ile Gln Lys Phe Gly Glu Arg Ala Leu Lys Ala
1               5                  10                  15

Trp Ser Val Ala Arg Leu Ser Gln Lys Phe Pro Lys Ala Glu Phe Val
             20                  25                  30

Glu Val Thr Lys Leu Val Thr Asp Leu Thr Lys Val His Lys Glu
         35                  40                  45

<210> SEQ ID NO 403
<211> LENGTH: 43
<212> TYPE: PRT
<213> ORGANISM: Homo sapiens
<220> FEATURE:
<221> NAME/KEY: MOD_RES
<222> LOCATION: (1)..(43)
<223> OTHER INFORMATION: Glycation [?]

<400> SEQUENCE: 403

Ser Ile Gln Lys Phe Gly Glu Arg Ala Leu Lys Ala Trp Ser Val Ala
1               5                  10                  15

Arg Leu Ser Gln Lys Phe Pro Lys Ala Glu Phe Val Glu Val Thr Lys
             20                  25                  30

Leu Val Thr Asp Leu Thr Lys Val His Lys Glu
         35                  40

<210> SEQ ID NO 404
<211> LENGTH: 37
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Glycation (2) [2 ?]

<400> SEQUENCE: 404

Glu Arg Ala Leu Lys Ala Trp Ser Val Ala Arg Leu Ser Gln Lys Phe
1               5                  10                  15

Pro Lys Ala Glu Phe Val Glu Val Thr Lys Leu Val Thr Asp Leu Thr
             20                  25                  30

Lys Val His Lys Glu
         35

<210> SEQ ID NO 405
<211> LENGTH: 50
<212> TYPE: PRT
<213> ORGANISM: Homo sapiens
<220> FEATURE:

```
<221> NAME/KEY: MOD_RES
<222> LOCATION: (6)..(6)
<223> OTHER INFORMATION: Carboxymethyl C [6]

<400> SEQUENCE: 405

Arg Gln Arg Leu Arg Cys Ala Ser Ile Gln Lys Phe Gly Glu Arg Ala
1               5                   10                  15

Leu Lys Ala Trp Ser Val Ala Arg Leu Ser Gln Lys Phe Pro Lys Ala
            20                  25                  30

Glu Phe Val Glu Val Thr Lys Leu Val Thr Asp Leu Thr Lys Val His
        35                  40                  45

Lys Glu
    50

<210> SEQ ID NO 406
<211> LENGTH: 20
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation (2) [1 18]
<220> FEATURE:
<221> NAME/KEY: MOD_RES
<222> LOCATION: (13)..(13)
<223> OTHER INFORMATION: Carboxymethyl C [13]

<400> SEQUENCE: 406

Lys Val Leu Ala Ser Ser Ala Arg Gln Arg Leu Arg Cys Ala Ser Ile
1               5                   10                  15

Gln Lys Phe Gly
            20

<210> SEQ ID NO 407
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Carboxymethyl C [12]

<400> SEQUENCE: 407

Val Leu Ala Ser Ser Ala Arg Gln Arg Leu Arg Cys Ala Ser Ile Gln
1               5                   10                  15

Lys Phe Gly Glu
            20

<210> SEQ ID NO 408
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 408

Cys Ala Ser Ile Gln Lys Phe Gly Glu
1               5

<210> SEQ ID NO 409
<211> LENGTH: 6
<212> TYPE: PRT
<213> ORGANISM: Homo sapiens
<220> FEATURE:
```

```
<221> NAME/KEY: MOD_RES
<222> LOCATION: (3)..(3)
<223> OTHER INFORMATION: Glycation [3]

<400> SEQUENCE: 409

Ile Gln Lys Phe Gly Glu
1               5

<210> SEQ ID NO 410
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Glycation [?]

<400> SEQUENCE: 410

Lys Phe Pro Lys Ala Glu Phe Val Glu
1               5

<210> SEQ ID NO 411
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 411

Lys Ala Glu Phe Val Glu
1               5

<210> SEQ ID NO 412
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation (2) [2 ?]
<220> FEATURE:
<221> NAME/KEY: MOD_RES
<222> LOCATION: (1)..(26)
<223> OTHER INFORMATION: Glycation (4) [4 ?]

<400> SEQUENCE: 412

Leu Ser Gln Lys Phe Pro Lys Ala Glu Phe Val Glu Val Thr Lys Leu
1               5                   10                  15

Val Thr Asp Leu Thr Lys Val His Lys Glu
            20                  25

<210> SEQ ID NO 413
<211> LENGTH: 30
<212> TYPE: PRT
<213> ORGANISM: Homo sapiens
<220> FEATURE:
<221> NAME/KEY: MOD_RES
<222> LOCATION: (1)..(30)
<223> OTHER INFORMATION: Glycation (2) [2 ?]
<220> FEATURE:
<221> NAME/KEY: MOD_RES
<222> LOCATION: (23)..(24)
<223> OTHER INFORMATION: Carboxymethyl C (2) [23 24]

<400> SEQUENCE: 413

Phe Pro Lys Ala Glu Phe Val Glu Val Thr Lys Leu Val Thr Asp Leu
1               5                   10                  15
```

Thr Lys Val His Lys Glu Cys Cys His Gly Asp Leu Leu Glu
            20                  25                  30

<210> SEQ ID NO 414
<211> LENGTH: 36
<212> TYPE: PRT
<213> ORGANISM: Homo sapiens
<220> FEATURE:
<221> NAME/KEY: MOD_RES
<222> LOCATION: (29)..(30)
<223> OTHER INFORMATION: Carboxymethyl C (2) [29 30]

<400> SEQUENCE: 414

Ala Arg Leu Ser Gln Lys Phe Pro Lys Ala Glu Phe Val Glu Val Thr
1               5                   10                  15

Lys Leu Val Thr Asp Leu Thr Lys Val His Lys Glu Cys Cys His Gly
            20                  25                  30

Asp Leu Leu Glu
        35

<210> SEQ ID NO 415
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 415

Arg Ala Leu Lys Ala
1               5

<210> SEQ ID NO 416
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 416

Arg Ala Leu Lys Ala Trp Ser Val Ala Arg Leu Ser
1               5                   10

<210> SEQ ID NO 417
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Glycation [5]

<400> SEQUENCE: 417

Ala His Arg Phe Lys Asp Leu Gly Glu Glu
1               5                   10

<210> SEQ ID NO 418
<211> LENGTH: 7
<212> TYPE: PRT
<213> ORGANISM: Homo sapiens
<220> FEATURE:
<221> NAME/KEY: MOD_RES
<222> LOCATION: (1)..(7)
<223> OTHER INFORMATION: Glycation [?]

```
<400> SEQUENCE: 418

Gln Lys Phe Pro Lys Ala Glu
1               5

<210> SEQ ID NO 419
<211> LENGTH: 13
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Glycation [?]

<400> SEQUENCE: 419

Ser Val Ala Arg Leu Ser Gln Lys Phe Pro Lys Ala Glu
1               5                   10

<210> SEQ ID NO 420
<211> LENGTH: 10
<212> TYPE: PRT
<213> ORGANISM: Homo sapiens
<220> FEATURE:
<221> NAME/KEY: MOD_RES
<222> LOCATION: (5)..(8)
<223> OTHER INFORMATION: Glycation (2) [5 8]

<400> SEQUENCE: 420

Arg Leu Ser Gln Lys Phe Pro Lys Ala Glu
1               5                   10

<210> SEQ ID NO 421
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Glycation [6]

<400> SEQUENCE: 421

Phe Val Glu Val Thr Lys
1               5

<210> SEQ ID NO 422
<211> LENGTH: 37
<212> TYPE: PRT
<213> ORGANISM: Homo sapiens
<220> FEATURE:
<221> NAME/KEY: MOD_RES
<222> LOCATION: (6)..(35)
<223> OTHER INFORMATION: Glycation (4) [6 13 16 35]
<220> FEATURE:
<221> NAME/KEY: MOD_RES
<222> LOCATION: (18)..(26)
<223> OTHER INFORMATION: Carboxymethyl C (3) [18 19 26]

<400> SEQUENCE: 422

Phe Val Glu Val Thr Lys Leu Val Thr Asp Leu Thr Lys Val His Lys
1               5                   10                  15

Glu Cys Cys His Gly Asp Leu Leu Glu Cys Ala Asp Asp Arg Ala Asp
            20                  25                  30

Leu Ala Lys Tyr Ile
            35

<210> SEQ ID NO 423
<211> LENGTH: 48
```

```
<212> TYPE: PRT
<213> ORGANISM: Homo sapiens
<220> FEATURE:
<221> NAME/KEY: MOD_RES
<222> LOCATION: (1)..(48)
<223> OTHER INFORMATION: Glycation (4) [4?]
<220> FEATURE:
<221> NAME/KEY: MOD_RES
<222> LOCATION: (18)..(38)
<223> OTHER INFORMATION: Carboxyrnethyl C (4) [18 19 26 38]
<220> FEATURE:
<221> NAME/KEY: MOD_RES
<222> LOCATION: (40)..(40)
<223> OTHER INFORMATION: Deamidation N [40]

<400> SEQUENCE: 423

Phe Val Glu Val Thr Lys Leu Val Thr Asp Leu Thr Lys Val His Lys
1               5                   10                  15

Glu Cys Cys His Gly Asp Leu Leu Glu Cys Ala Asp Asp Arg Ala Asp
            20                  25                  30

Leu Ala Lys Tyr Ile Cys Asp Asn Gln Asp Thr Ile Ser Ser Lys Leu
        35                  40                  45

<210> SEQ ID NO 424
<211> LENGTH: 47
<212> TYPE: PRT
<213> ORGANISM: Homo sapiens
<220> FEATURE:
<221> NAME/KEY: MOD_RES
<222> LOCATION: (1)..(47)
<223> OTHER INFORMATION: Glycation (4) [4 ?]
<220> FEATURE:
<221> NAME/KEY: MOD_RES
<222> LOCATION: (18)..(38)
<223> OTHER INFORMATION: Carboxymethyl C (4) [18 19 26 38]
<220> FEATURE:
<221> NAME/KEY: MOD_RES
<222> LOCATION: (40)..(40)
<223> OTHER INFORMATION: Deamidation N [40]

<400> SEQUENCE: 424

Phe Val Glu Val Thr Lys Leu Val Thr Asp Leu Thr Lys Val His Lys
1               5                   10                  15

Glu Cys Cys His Gly Asp Leu Leu Glu Cys Ala Asp Asp Arg Ala Asp
            20                  25                  30

Leu Ala Lys Tyr Ile Cys Asp Asn Gln Asp Thr Ile Ser Ser Lys
        35                  40                  45

<210> SEQ ID NO 425
<211> LENGTH: 44
<212> TYPE: PRT
<213> ORGANISM: Homo sapiens
<220> FEATURE:
<221> NAME/KEY: MOD_RES
<222> LOCATION: (1)..(44)
<223> OTHER INFORMATION: Glycation [?]
<220> FEATURE:
<221> NAME/KEY: MOD_RES
<222> LOCATION: (18)..(38)
<223> OTHER INFORMATION: Carboxymethyl C(4) [18 19 26 38]
<220> FEATURE:
<221> NAME/KEY: MOD_RES
<222> LOCATION: (40)..(40)
<223> OTHER INFORMATION: Deamidation N [40]

<400> SEQUENCE: 425

Phe Val Glu Val Thr Lys Leu Val Thr Asp Leu Thr Lys Val His Lys
1               5                   10                  15

Glu Cys Cys His Gly Asp Leu Leu Glu Cys Ala Asp Asp Arg Ala Asp
```

Leu Ala Lys Tyr Ile Cys Asp Asn Gln Asp Thr Ile
                35                  40

<210> SEQ ID NO 426
<211> LENGTH: 20
<212> TYPE: PRT
<213> ORGANISM: Homo sapiens
<220> FEATURE:
<221> NAME/KEY: MOD_RES
<222> LOCATION: (15)..(16)
<223> OTHER INFORMATION: Carboxymethyl C (2) [15 16]

<400> SEQUENCE: 426

Val Thr Lys Leu Val Thr Asp Leu Thr Lys Val His Lys Glu Cys Cys
1               5                   10                  15

His Gly Asp Leu
            20

<210> SEQ ID NO 427
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (3)..(4)
<223> OTHER INFORMATION: Carboxymethyl C (2) [3 4]

<400> SEQUENCE: 427

Lys Glu Cys Cys His Gly Asp Leu Leu Glu
1               5                   10

<210> SEQ ID NO 428
<211> LENGTH: 43
<212> TYPE: PRT
<213> ORGANISM: Homo sapiens
<220> FEATURE:
<221> NAME/KEY: MOD_RES
<222> LOCATION: (1)..(43)
<223> OTHER INFORMATION: Glycation (2) [2 ?]
<220> FEATURE:
<221> NAME/KEY: MOD_RES
<222> LOCATION: (15)..(35)
<223> OTHER INFORMATION: Carboxymethyl C (4) [15 16 23 35]

<400> SEQUENCE: 428

Val Thr Lys Leu Val Thr Asp Leu Thr Lys Val His Lys Glu Cys Cys
1               5                   10                  15

His Gly Asp Leu Leu Glu Cys Ala Asp Asp Arg Ala Asp Leu Ala Lys
            20                  25                  30

Tyr Ile Cys Asp Asn Gln Asp Thr Ile Ser Ser
            35                  40

<210> SEQ ID NO 429
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation [?]
<220> FEATURE:
<221> NAME/KEY: MOD_RES
<222> LOCATION: (3)..(23)

<223> OTHER INFORMATION: Carboxymethyl C (4) [3 4 11 23]

<400> SEQUENCE: 429

Lys Glu Cys Cys His Gly Asp Leu Leu Glu Cys Ala Asp Asp Arg Ala
1               5                   10                  15

Asp Leu Ala Lys Tyr Ile Cys Asp Asn Gln Asp Thr Ile Ser Ser Lys
            20                  25                  30

Leu Lys Glu
        35

<210> SEQ ID NO 430
<211> LENGTH: 45
<212> TYPE: PRT
<213> ORGANISM: Homo sapiens
<220> FEATURE:
<221> NAME/KEY: MOD_RES
<222> LOCATION: (1)..(44)
<223> OTHER INFORMATION: Glycation (6) [1 8 11 30 42 44]
<220> FEATURE:
<221> NAME/KEY: MOD_RES
<222> LOCATION: (13)..(33)
<223> OTHER INFORMATION: Carboxymethyl C (4) [13 14 21 33]

<400> SEQUENCE: 430

Lys Leu Val Thr Asp Leu Thr Lys Val His Lys Glu Cys Cys His Gly
1               5                   10                  15

Asp Leu Leu Glu Cys Ala Asp Asp Arg Ala Asp Leu Ala Lys Tyr Ile
            20                  25                  30

Cys Asp Asn Gln Asp Thr Ile Ser Ser Lys Leu Lys Glu
            35                  40                  45

<210> SEQ ID NO 431
<211> LENGTH: 41
<212> TYPE: PRT
<213> ORGANISM: Homo sapiens
<220> FEATURE:
<221> NAME/KEY: MOD_RES
<222> LOCATION: (1)..(41)
<223> OTHER INFORMATION: Glycation (4) [4 ?]
<220> FEATURE:
<221> NAME/KEY: MOD_RES
<222> LOCATION: (9)..(29)
<223> OTHER INFORMATION: Carboxymethyl C (4) [9 10 17 29]
<220> FEATURE:
<221> NAME/KEY: MOD_RES
<222> LOCATION: (31)..(31)
<223> OTHER INFORMATION: Deamidation N [31]

<400> SEQUENCE: 431

Asp Leu Thr Lys Val His Lys Glu Cys Cys His Gly Asp Leu Leu Glu
1               5                   10                  15

Cys Ala Asp Asp Arg Ala Asp Leu Ala Lys Tyr Ile Cys Asp Asn Gln
            20                  25                  30

Asp Thr Ile Ser Ser Lys Leu Lys Glu
            35                  40

<210> SEQ ID NO 432
<211> LENGTH: 38
<212> TYPE: PRT
<213> ORGANISM: Homo sapiens
<220> FEATURE:
<221> NAME/KEY: MOD_RES
<222> LOCATION: (1)..(38)
<223> OTHER INFORMATION: Glycation [?]
<220> FEATURE:
<221> NAME/KEY: MOD_RES
<222> LOCATION: (6)..(26)

```
<223> OTHER INFORMATION: Carboxymethyl C (4) [6 7 14 26]
<220> FEATURE:
<221> NAME/KEY: MOD_RES
<222> LOCATION: (28)..(28)
<223> OTHER INFORMATION: Deamidation N [28]

<400> SEQUENCE: 432
```

Lys Val His Lys Glu Cys Cys His Gly Asp Leu Leu Glu Cys Ala Asp
1               5                   10                  15

Asp Arg Ala Asp Leu Ala Lys Tyr Ile Cys Asp Asn Gln Asp Thr Ile
            20                  25                  30

Ser Ser Lys Leu Lys Glu
        35

```
<210> SEQ ID NO 433
<211> LENGTH: 50
<212> TYPE: PRT
<213> ORGANISM: Homo sapiens
<220> FEATURE:
<221> NAME/KEY: MOD_RES
<222> LOCATION: (1)..(50)
<223> OTHER INFORMATION: Glycation (3) [3?]
<220> FEATURE:
<221> NAME/KEY: MOD_RES
<222> LOCATION: (15)..(49)
<223> OTHER INFORMATION: Carboxymethyl C (6) [15 16 23 35 48 49]

<400> SEQUENCE: 433
```

Val Thr Lys Leu Val Thr Asp Leu Thr Lys Val His Lys Glu Cys Cys
1               5                   10                  15

His Gly Asp Leu Leu Glu Cys Ala Asp Asp Arg Ala Asp Leu Ala Lys
            20                  25                  30

Tyr Ile Cys Asp Asn Gln Asp Thr Ile Ser Ser Lys Leu Lys Glu Cys
        35                  40                  45

Cys Asp
    50

```
<210> SEQ ID NO 434
<211> LENGTH: 53
<212> TYPE: PRT
<213> ORGANISM: Homo sapiens
<220> FEATURE:
<221> NAME/KEY: MOD_RES
<222> LOCATION: (1)..(53)
<223> OTHER INFORMATION: Glycation (5) [5 ?]
<220> FEATURE:
<221> NAME/KEY: MOD_RES
<222> LOCATION: (13)..(47)
<223> OTHER INFORMATION: Carboxymethyl C (6) [13 14 21 33 46 47]

<400> SEQUENCE: 434
```

Lys Leu Val Thr Asp Leu Thr Lys Val His Lys Glu Cys Cys His Gly
1               5                   10                  15

Asp Leu Leu Glu Cys Ala Asp Asp Arg Ala Asp Leu Ala Lys Tyr Ile
            20                  25                  30

Cys Asp Asn Gln Asp Thr Ile Ser Ser Lys Leu Lys Glu Cys Cys Asp
        35                  40                  45

Lys Pro Leu Leu Glu
    50

```
<210> SEQ ID NO 435
<211> LENGTH: 52
<212> TYPE: PRT
<213> ORGANISM: Homo sapiens
<220> FEATURE:
```

```
<221> NAME/KEY: MOD_RES
<222> LOCATION: (1)..(52)
<223> OTHER INFORMATION: Glycation (2) [2 ?]
<220> FEATURE:
<221> NAME/KEY: MOD_RES
<222> LOCATION: (12)..(46)
<223> OTHER INFORMATION: Carboxymethyl C (6) [12 13 20 32 45 46]
<220> FEATURE:
<221> NAME/KEY: MOD_RES
<222> LOCATION: (34)..(34)
<223> OTHER INFORMATION: Deamidation N [34]

<400> SEQUENCE: 435

Leu Val Thr Asp Leu Thr Lys Val His Lys Glu Cys Cys His Gly Asp
1               5                   10                  15

Leu Leu Glu Cys Ala Asp Asp Arg Ala Asp Leu Ala Lys Tyr Ile Cys
            20                  25                  30

Asp Asn Gln Asp Thr Ile Ser Ser Lys Leu Lys Glu Cys Cys Asp Lys
        35                  40                  45

Pro Leu Leu Glu
    50

<210> SEQ ID NO 436
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Glycation [?]
<220> FEATURE:
<221> NAME/KEY: MOD_RES
<222> LOCATION: (9)..(43)
<223> OTHER INFORMATION: Carboxymethyl C (6) [9 10 17 29 42 43]
<220> FEATURE:
<221> NAME/KEY: MOD_RES
<222> LOCATION: (31)..(31)
<223> OTHER INFORMATION: Deamidation N [31]

<400> SEQUENCE: 436

Asp Leu Thr Lys Val His Lys Glu Cys Cys His Gly Asp Leu Leu Glu
1               5                   10                  15

Cys Ala Asp Asp Arg Ala Asp Leu Ala Lys Tyr Ile Cys Asp Asn Gln
            20                  25                  30

Asp Thr Ile Ser Ser Lys Leu Lys Glu Cys Cys Asp Lys Pro Leu Leu
        35                  40                  45

Glu

<210> SEQ ID NO 437
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 437

Val Thr Lys Leu Val Thr Asp Leu
1               5

<210> SEQ ID NO 438
<211> LENGTH: 6
<212> TYPE: PRT
<213> ORGANISM: Homo sapiens
<220> FEATURE:
<221> NAME/KEY: MOD_RES
```

```
<222> LOCATION: (3)..(3)
<223> OTHER INFORMATION: Glycation [3]

<400> SEQUENCE: 438

Val Thr Lys Leu Val Thr
1               5

<210> SEQ ID NO 439
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 439

Val Thr Lys Leu Val
1               5

<210> SEQ ID NO 440
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Carboxymethyl C [23]
<220> FEATURE:
<221> NAME/KEY: MOD_RES
<222> LOCATION: (33)..(33)
<223> OTHER INFORMATION: Deamidation N [33]

<400> SEQUENCE: 440

Lys Asp Leu Gly Glu Glu His Phe Lys Gly Leu Val Leu Ile Ala Phe
1               5                   10                  15

Ser Gln Tyr Leu Gln Gln Cys Pro Phe Asp Glu His Val Lys Leu Val
            20                  25                  30

Asn Glu

<210> SEQ ID NO 441
<211> LENGTH: 8
<212> TYPE: PRT
<213> ORGANISM: Homo sapiens
<220> FEATURE:
<221> NAME/KEY: MOD_RES
<222> LOCATION: (4)..(7)
<223> OTHER INFORMATION: Glycation (2) [4 7]

<400> SEQUENCE: 441

Asp Leu Thr Lys Val His Lys Glu
1               5

<210> SEQ ID NO 442
<211> LENGTH: 6
<212> TYPE: PRT
<213> ORGANISM: Homo sapiens
<220> FEATURE:
<221> NAME/KEY: MOD_RES
<222> LOCATION: (2)..(5)
<223> OTHER INFORMATION: Glycation (2) [2 5]

<400> SEQUENCE: 442

Thr Lys Val His Lys Glu
1               5

<210> SEQ ID NO 443
```

```
<211> LENGTH: 31
<212> TYPE: PRT
<213> ORGANISM: Homo sapiens
<220> FEATURE:
<221> NAME/KEY: MOD_RES
<222> LOCATION: (5)..(27)
<223> OTHER INFORMATION: Glycation (2) [5 27]
<220> FEATURE:
<221> NAME/KEY: MOD_RES
<222> LOCATION: (20)..(20)
<223> OTHER INFORMATION: Carboxymethyl C [20]
<220> FEATURE:
<221> NAME/KEY: MOD_RES
<222> LOCATION: (30)..(30)
<223> OTHER INFORMATION: Deamidation N [30]

<400> SEQUENCE: 443

Gly Glu Glu His Phe Lys Gly Leu Val Leu Ile Ala Phe Ser Gln Tyr
1               5                   10                  15

Leu Gln Gln Cys Pro Phe Asp Glu His Val Lys Leu Val Asn Glu
            20                  25                  30

<210> SEQ ID NO 444
<211> LENGTH: 5
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Glycation [?]
<220> FEATURE:
<221> NAME/KEY: MOD_RES
<222> LOCATION: (1)..(4)
<223> OTHER INFORMATION: Glycation (2) [1 4]

<400> SEQUENCE: 444

Lys Val His Lys Glu
1               5

<210> SEQ ID NO 445
<211> LENGTH: 30
<212> TYPE: PRT
<213> ORGANISM: Homo sapiens
<220> FEATURE:
<221> NAME/KEY: MOD_RES
<222> LOCATION: (1)..(30)
<223> OTHER INFORMATION: Glycation [?]
<220> FEATURE:
<221> NAME/KEY: MOD_RES
<222> LOCATION: (19)..(19)
<223> OTHER INFORMATION: Carboxymethyl C [19]
<220> FEATURE:
<221> NAME/KEY: MOD_RES
<222> LOCATION: (29)..(29)
<223> OTHER INFORMATION: Deamidation N [29]

<400> SEQUENCE: 445

Glu Glu His Phe Lys Gly Leu Val Leu Ile Ala Phe Ser Gln Tyr Leu
1               5                   10                  15

Gln Gln Cys Pro Phe Asp Glu His Val Lys Leu Val Asn Glu
            20                  25                  30

<210> SEQ ID NO 446
<211> LENGTH: 8
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
```

```
<400> SEQUENCE: 446

Cys Cys His Gly Asp Leu Leu Glu
1               5

<210> SEQ ID NO 447
<211> LENGTH: 23
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Carboxymethyl C (4) [1 2 9 21]

<400> SEQUENCE: 447

Cys Cys His Gly Asp Leu Leu Glu Cys Ala Asp Asp Arg Ala Asp Leu
1               5                   10                  15

Ala Lys Tyr Ile Cys Asp Asn
            20

<210> SEQ ID NO 448
<211> LENGTH: 15
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Carboxymethyl C (3) [1 2 9]

<400> SEQUENCE: 448

Cys Cys His Gly Asp Leu Leu Glu Cys Ala Asp Asp Arg Ala Asp
1               5                   10                  15

<210> SEQ ID NO 449
<211> LENGTH: 12
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Carboxymethyl C (3) [1 2 9]

<400> SEQUENCE: 449

Cys Cys His Gly Asp Leu Leu Glu Cys Ala Asp Asp
1               5                   10

<210> SEQ ID NO 450
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Carboxymethyl C (3) [1 2 9]

<400> SEQUENCE: 450

Cys Cys His Gly Asp Leu Leu Glu Cys
1               5

<210> SEQ ID NO 451
<211> LENGTH: 30
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Carboxymethyl C (4) [1 2 9 21]
<220> FEATURE:
<221> NAME/KEY: MOD_RES
```

```
<222> LOCATION: (1)..(30)
<223> OTHER INFORMATION: Glycation [?]

<400> SEQUENCE: 451

Cys Cys His Gly Asp Leu Leu Glu Cys Ala Asp Asp Arg Ala Asp Leu
 1               5                  10                  15

Ala Lys Tyr Ile Cys Asp Asn Gln Asp Thr Ile Ser Ser Lys
             20                  25                  30

<210> SEQ ID NO 452
<211> LENGTH: 30
<212> TYPE: PRT
<213> ORGANISM: Homo sapiens
<220> FEATURE:
<221> NAME/KEY: MOD_RES
<222> LOCATION: (6)..(18)
<223> OTHER INFORMATION: Carboxymethyl C (2) [6 18]
<220> FEATURE:
<221> NAME/KEY: MOD_RES
<222> LOCATION: (15)..(29)
<223> OTHER INFORMATION: Glycation (3) [15 27 29]

<400> SEQUENCE: 452

Gly Asp Leu Leu Glu Cys Ala Asp Asp Arg Ala Asp Leu Ala Lys Tyr
 1               5                  10                  15

Ile Cys Asp Asn Gln Asp Thr Ile Ser Ser Lys Leu Lys Glu
             20                  25                  30

<210> SEQ ID NO 453
<211> LENGTH: 36
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Carboxymethyl C (5) [1 2 9 21 34 35]
<220> FEATURE:
<221> NAME/KEY: MOD_RES
<222> LOCATION: (1)..(36)
<223> OTHER INFORMATION: Glycation (2) [2 ?]
<220> FEATURE:
<221> NAME/KEY: MOD_RES
<222> LOCATION: (23)..(23)
<223> OTHER INFORMATION: Deamidation N [23]

<400> SEQUENCE: 453

Cys Cys His Gly Asp Leu Leu Glu Cys Ala Asp Asp Arg Ala Asp Leu
 1               5                  10                  15

Ala Lys Tyr Ile Cys Asp Asn Gln Asp Thr Ile Ser Ser Lys Leu Lys
             20                  25                  30

Glu Cys Cys Asp
         35

<210> SEQ ID NO 454
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Carboxymethyl C (5) [1 2 9 21 34 35]
<220> FEATURE:
<221> NAME/KEY: MOD_RES
<222> LOCATION: (1)..(35)
<223> OTHER INFORMATION: Glycation (2) [2 ?]
<220> FEATURE:
<221> NAME/KEY: MOD_RES
<222> LOCATION: (23)..(23)
<223> OTHER INFORMATION: Deamidation N [23]
```

<400> SEQUENCE: 454

Cys Cys His Gly Asp Leu Leu Glu Cys Ala Asp Asp Arg Ala Asp Leu
1               5                   10                  15

Ala Lys Tyr Ile Cys Asp Asn Gln Asp Thr Ile Ser Ser Lys Leu Lys
            20                  25                  30

Glu Cys Cys
        35

<210> SEQ ID NO 455
<211> LENGTH: 37
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Glycation (3) [3 ?]
<220> FEATURE:
<221> NAME/KEY: MOD_RES
<222> LOCATION: (5)..(31)
<223> OTHER INFORMATION: Carboxymethyl C (4) [5 17 30 31]
<220> FEATURE:
<221> NAME/KEY: MOD_RES
<222> LOCATION: (19)..(19)
<223> OTHER INFORMATION: Deamidation N [19]

<400> SEQUENCE: 455

Asp Leu Leu Glu Cys Ala Asp Asp Arg Ala Leu Ala Lys Tyr Ile
1               5                   10                  15

Cys Asp Asn Gln Asp Thr Ile Ser Ser Lys Leu Lys Glu Cys Cys Asp
            20                  25                  30

Lys Pro Leu Leu Glu
        35

<210> SEQ ID NO 456
<211> LENGTH: 46
<212> TYPE: PRT
<213> ORGANISM: Homo sapiens
<220> FEATURE:
<221> NAME/KEY: MOD_RES
<222> LOCATION: (1)..(45)
<223> OTHER INFORMATION: Carboxymethyl C (7) [1 2 9 21 34 35 45]
<220> FEATURE:
<221> NAME/KEY: MOD_RES
<222> LOCATION: (1)..(46)
<223> OTHER INFORMATION: Glycation (3) [3 ?]
<220> FEATURE:
<221> NAME/KEY: MOD_RES
<222> LOCATION: (23)..(23)
<223> OTHER INFORMATION: Deamidation N [23]

<400> SEQUENCE: 456

Cys Cys His Gly Asp Leu Leu Glu Cys Ala Asp Asp Arg Ala Asp Leu
1               5                   10                  15

Ala Lys Tyr Ile Cys Asp Asn Gln Asp Thr Ile Ser Ser Lys Leu Lys
            20                  25                  30

Glu Cys Cys Asp Lys Pro Leu Leu Glu Lys Ser His Cys Ile
        35                  40                  45

<210> SEQ ID NO 457
<211> LENGTH: 7
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]

-continued

```
<400> SEQUENCE: 457

Cys Cys His Gly Asp Leu Leu
1               5

<210> SEQ ID NO 458
<211> LENGTH: 32
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Carboxymethyl C (4) [1 13 26 27]
<220> FEATURE:
<221> NAME/KEY: MOD_RES
<222> LOCATION: (1)..(32)
<223> OTHER INFORMATION: Glycation (3) [3 ?]

<400> SEQUENCE: 458

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp Lys Pro Leu Leu
            20                  25                  30

<210> SEQ ID NO 459
<211> LENGTH: 29
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Carboxymethyl C (4) [1 13 26 27]
<220> FEATURE:
<221> NAME/KEY: MOD_RES
<222> LOCATION: (1)..(29)
<223> OTHER INFORMATION: Glycation [?]

<400> SEQUENCE: 459

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp Lys
            20                  25

<210> SEQ ID NO 460
<211> LENGTH: 28
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Carboxymethyl C (4) [1 13 26 27]
<220> FEATURE:
<221> NAME/KEY: MOD_RES
<222> LOCATION: (10)..(24)
<223> OTHER INFORMATION: Glycation (3) [10 22 24]

<400> SEQUENCE: 460

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp
            20                  25

<210> SEQ ID NO 461
<211> LENGTH: 9
<212> TYPE: PRT
<213> ORGANISM: Homo sapiens
<220> FEATURE:
<221> NAME/KEY: MOD_RES
```

```
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 461

Glu Cys Cys Asp Lys Pro Leu Leu Glu
1               5

<210> SEQ ID NO 462
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation (3) [3 ?]
<220> FEATURE:
<221> NAME/KEY: MOD_RES
<222> LOCATION: (6)..(20)
<223> OTHER INFORMATION: Carboxymethyl C (3) [6 19 20]

<400> SEQUENCE: 462

Leu Ala Lys Tyr Ile Cys Asp Asn Gln Asp Thr Ile Ser Ser Lys Leu
1               5                   10                  15

Lys Glu Cys Cys Asp Lys Pro Leu Leu Glu
            20                  25

<210> SEQ ID NO 463
<211> LENGTH: 25
<212> TYPE: PRT
<213> ORGANISM: Homo sapiens
<220> FEATURE:
<221> NAME/KEY: MOD_RES
<222> LOCATION: (2)..(21)
<223> OTHER INFORMATION: Glycation (4) [2 14 16 21]
<220> FEATURE:
<221> NAME/KEY: MOD_RES
<222> LOCATION: (5)..(19)
<223> OTHER INFORMATION: Carboxymethyl C (3) [5 18 19]

<400> SEQUENCE: 463

Ala Lys Tyr Ile Cys Asp Asn Gln Asp Thr Ile Ser Ser Lys Leu Lys
1               5                   10                  15

Glu Cys Cys Asp Lys Pro Leu Leu Glu
            20                  25

<210> SEQ ID NO 464
<211> LENGTH: 40
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Carboxymethyl C (5) [1 13 26 27 37]
<220> FEATURE:
<221> NAME/KEY: MOD_RES
<222> LOCATION: (15)..(15)
<223> OTHER INFORMATION: DeamIdatIon N [15]

<400> SEQUENCE: 464

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp Lys Pro Leu Leu
            20                  25                  30

Glu Lys Ser His Cys Ile Ala Glu
```

```
              35                  40

<210> SEQ ID NO 465
<211> LENGTH: 34
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Carboxymethyl C (4) [1 13 26 27]
<220> FEATURE:
<221> NAME/KEY: MOD_RES
<222> LOCATION: (10)..(34)
<223> OTHER INFORMATION: Glycation (5) [10 22 24 29 34]
<220> FEATURE:
<221> NAME/KEY: MOD_RES
<222> LOCATION: (15)..(15)
<223> OTHER INFORMATION: Deamidation N [15]

<400> SEQUENCE: 465

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp Lys Pro Leu Leu
            20                  25                  30

Glu Lys

<210> SEQ ID NO 466
<211> LENGTH: 26
<212> TYPE: PRT
<213> ORGANISM: Homo sapiens
<220> FEATURE:
<221> NAME/KEY: MOD_RES
<222> LOCATION: (8)..(20)
<223> OTHER INFORMATION: Glycation (4) [8 10 15 20]
<220> FEATURE:
<221> NAME/KEY: MOD_RES
<222> LOCATION: (12)..(23)
<223> OTHER INFORMATION: Carboxymethyl C (3) [12 13 23]

<400> SEQUENCE: 466

Asn Gln Asp Thr Ile Ser Ser Lys Leu Lys Glu Cys Cys Asp Lys Pro
1               5                   10                  15

Leu Leu Glu Lys Ser His Cys Ile Ala Glu
            20                  25

<210> SEQ ID NO 467
<211> LENGTH: 32
<212> TYPE: PRT
<213> ORGANISM: Homo sapiens
<220> FEATURE:
<221> NAME/KEY: MOD_RES
<222> LOCATION: (1)..(32)
<223> OTHER INFORMATION: Glycation (4) [4 ?]
<220> FEATURE:
<221> NAME/KEY: MOD_RES
<222> LOCATION: (5)..(29)
<223> OTHER INFORMATION: Carboxymethyl C (4) [5 18 19 29]
<220> FEATURE:
<221> NAME/KEY: MOD_RES
<222> LOCATION: (7)..(7)
<223> OTHER INFORMATION: Deamidation N [7]

<400> SEQUENCE: 467

Ala Lys Tyr Ile Cys Asp Asn Gln Asp Thr Ile Ser Ser Lys Leu Lys
1               5                   10                  15

Glu Cys Cys Asp Lys Pro Leu Leu Glu Lys Ser His Cys Ile Ala Glu
            20                  25                  30
```

-continued

```
<210> SEQ ID NO 468
<211> LENGTH: 42
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Carboxymethyl C (5) [1 13 26 27 37]
<220> FEATURE:
<221> NAME/KEY: MOD_RES
<222> LOCATION: (1)..(42)
<223> OTHER INFORMATION: Glycation [?]

<400> SEQUENCE: 468

Cys Ala Asp Asp Arg Ala Asp Leu Ala Lys Tyr Ile Cys Asp Asn Gln
1               5                   10                  15

Asp Thr Ile Ser Ser Lys Leu Lys Glu Cys Cys Asp Lys Pro Leu Leu
            20                  25                  30

Glu Lys Ser His Cys Ile Ala Glu Val Glu
        35                  40

<210> SEQ ID NO 469
<211> LENGTH: 37
<212> TYPE: PRT
<213> ORGANISM: Homo sapiens
<220> FEATURE:
<221> NAME/KEY: MOD_RES
<222> LOCATION: (1)..(37)
<223> OTHER INFORMATION: Glycation (3) [3 ?]
<220> FEATURE:
<221> NAME/KEY: MOD_RES
<222> LOCATION: (8)..(32)
<223> OTHER INFORMATION: Carboxymethyl C (4) [8 21 22 32]

<400> SEQUENCE: 469

Ala Asp Leu Ala Lys Tyr Ile Cys Asp Asn Gln Asp Thr Ile Ser Ser
1               5                   10                  15

Lys Leu Lys Glu Cys Cys Asp Lys Pro Leu Leu Glu Lys Ser His Cys
            20                  25                  30

Ile Ala Glu Val Glu
        35

<210> SEQ ID NO 470
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 470

Cys Ala Asp Asp Arg Ala Asp Leu Ala Lys Tyr
1               5                   10

<210> SEQ ID NO 471
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (10)..(10)
<223> OTHER INFORMATION: Glycation [10]

<400> SEQUENCE: 471
```

```
Cys Ala Asp Asp Arg Ala Asp Leu Ala Lys
1               5                   10

<210> SEQ ID NO 472
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 472

Cys Ala Asp Asp Arg Ala Asp
1               5

<210> SEQ ID NO 473
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 473

Cys Ala Asp Asp Arg Ala
1               5

<210> SEQ ID NO 474
<211> LENGTH: 23
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Carboxymethyl C (2) [1 13]
<220> FEATURE:
<221> NAME/KEY: MOD_RES
<222> LOCATION: (10)..(22)
<223> OTHER INFORMATION: Glycation (2) [10 22]

<400> SEQUENCE: 474

Cys Ala Asp Asp Arg Ala Asp Leu Ala Lys Tyr Ile Cys Asp Asn Gln
1               5                   10                  15

Asp Thr Ile Ser Ser Lys Leu
            20

<210> SEQ ID NO 475
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 475

Cys Ala Asp Asp Arg
1               5

<210> SEQ ID NO 476
<211> LENGTH: 4
<212> TYPE: PRT
<213> ORGANISM: Homo sapiens
<220> FEATURE:
<221> NAME/KEY: MOD_RES
<222> LOCATION: (1)..(1)
```

<223> OTHER INFORMATION: Carboxymethyl C [1]

<400> SEQUENCE: 476

Cys Ala Asp Asp
1

<210> SEQ ID NO 477
<211> LENGTH: 22
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Carboxymethyl C (2) [1 13]
<220> FEATURE:
<221> NAME/KEY: MOD_RES
<222> LOCATION: (10)..(22)
<223> OTHER INFORMATION: Glycation (2) [10 22]

<400> SEQUENCE: 477

Cys Ala Asp Asp Arg Ala Asp Leu Ala Lys Tyr Ile Cys Asp Asn Gln
1               5                   10                  15

Asp Thr Ile Ser Ser Lys
            20

<210> SEQ ID NO 478
<211> LENGTH: 17
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Carboxymethyl C (2) [1 13]
<220> FEATURE:
<221> NAME/KEY: MOD_RES
<222> LOCATION: (15)..(15)
<223> OTHER INFORMATION: Deamidation N [15]

<400> SEQUENCE: 478

Cys Ala Asp Asp Arg Ala Asp Leu Ala Lys Tyr Ile Cys Asp Asn Gln
1               5                   10                  15

Asp

<210> SEQ ID NO 479
<211> LENGTH: 16
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Carboxymethyl C (2) [1 13]
<220> FEATURE:
<221> NAME/KEY: MOD_RES
<222> LOCATION: (15)..(15)
<223> OTHER INFORMATION: Deamidation N [15]

<400> SEQUENCE: 479

Cys Ala Asp Asp Arg Ala Asp Leu Ala Lys Tyr Ile Cys Asp Asn Gln
1               5                   10                  15

<210> SEQ ID NO 480
<211> LENGTH: 7
<212> TYPE: PRT
<213> ORGANISM: Homo sapiens
<220> FEATURE:
<221> NAME/KEY: MOD_RES
<222> LOCATION: (4)..(6)
<223> OTHER INFORMATION: Glycation (2) [4 6]

```
<400> SEQUENCE: 480

Ile Ser Ser Lys Leu Lys Glu
1               5

<210> SEQ ID NO 481
<211> LENGTH: 5
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Glycation [?]

<400> SEQUENCE: 481

Ser Lys Leu Lys Glu
1               5

<210> SEQ ID NO 482
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Carboxymethyl C [7]

<400> SEQUENCE: 482

Leu Leu Glu Lys Ser His Cys Ile Ala Glu
1               5                   10

<210> SEQ ID NO 483
<211> LENGTH: 17
<212> TYPE: PRT
<213> ORGANISM: Homo sapiens
<220> FEATURE:
<221> NAME/KEY: MOD_RES
<222> LOCATION: (1)..(12)
<223> OTHER INFORMATION: Carboxymethyl C (3) [1 2 12]

<400> SEQUENCE: 483

Cys Cys Asp Lys Pro Leu Leu Glu Lys Ser His Cys Ile Ala Glu Val
1               5                   10                  15

Glu

<210> SEQ ID NO 484
<211> LENGTH: 4
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]

<400> SEQUENCE: 484

Cys Cys Asp Lys
1

<210> SEQ ID NO 485
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (3)..(3)
```

```
<223> OTHER INFORMATION: Glycation [3]

<400> SEQUENCE: 485

Cys Asp Lys Pro Leu Leu Glu
1               5

<210> SEQ ID NO 486
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 486

Cys Ile Ala Glu Val Glu
1               5

<210> SEQ ID NO 487
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Glycation (2) [1 10]
<220> FEATURE:
<221> NAME/KEY: MOD_RES
<222> LOCATION: (4)..(4)
<223> OTHER INFORMATION: Carboxymethyl C [4]

<400> SEQUENCE: 487

Lys Ser His Cys Ile Ala Glu Val Glu Lys
1               5                   10

<210> SEQ ID NO 488
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Glycation [5]

<400> SEQUENCE: 488

Ala Glu Val Glu Lys Asp Ala Ile Pro Glu
1               5                   10

<210> SEQ ID NO 489
<211> LENGTH: 26
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Glycation (2) [1 10]
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (4)..(4)
<223> OTHER INFORMATION: Carboxymethyl C [4]

<400> SEQUENCE: 489

Lys Ser His Cys Ile Ala Glu Val Glu Lys Asp Ala Ile Pro Glu Asn
1               5                   10                  15
```

Leu Pro Pro Leu Thr Ala Asp Phe Ala Glu
            20                  25

<210> SEQ ID NO 490
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Glycation [?]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (16)..(16)
<223> OTHER INFORMATION: Deamidation N [16]

<400> SEQUENCE: 490

Lys Ser His Cys Ile Ala Glu Val Glu Lys Asp Ala Ile Pro Glu Asn
1               5                   10                  15
Leu Pro Pro Leu
            20

<210> SEQ ID NO 491
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 491

Lys Ser His Cys Ile Ala
1               5

<210> SEQ ID NO 492
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (4)..(4)
<223> OTHER INFORMATION: Carboxymethyl C [4]

<400> SEQUENCE: 492

Lys Ser His Cys
1

<210> SEQ ID NO 493
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 493

His Cys Ile Ala Glu
1               5

-continued

```
<210> SEQ ID NO 494
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 494

Cys Ile Ala Glu
1

<210> SEQ ID NO 495
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 495

His Arg Phe Lys Asp Leu Gly Glu
1               5

<210> SEQ ID NO 496
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 496

Lys Asp Leu Gly Glu
1               5

<210> SEQ ID NO 497
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 497

Val Glu Lys Asp Ala Ile Pro Glu
1               5

<210> SEQ ID NO 498
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 498

Val Glu Lys Asp Ala Ile
1               5

<210> SEQ ID NO 499
<211> LENGTH: 9
<212> TYPE: PRT
<213> ORGANISM: Homo sapiens
```

```
<220> FEATURE:
<221> NAME/KEY: MOD_RES
<222> LOCATION: (3)..(3)
<223> OTHER INFORMATION: Glycation [3]
<220> FEATURE:
<221> NAME/KEY: MOD_RES
<222> LOCATION: (9)..(9)
<223> OTHER INFORMATION: DearnIdatIon N [9]

<400> SEQUENCE: 499

Val Glu Lys Asp Ala Ile Pro Glu Asn
1               5

<210> SEQ ID NO 500
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Deamidation N [9]

<400> SEQUENCE: 500

Val Glu Lys Asp Ala Ile Pro Glu Asn Leu Pro Pro Leu
1               5                   10

<210> SEQ ID NO 501
<211> LENGTH: 29
<212> TYPE: PRT
<213> ORGANISM: Homo sapiens
<220> FEATURE:
<221> NAME/KEY: MOD_RES
<222> LOCATION: (1)..(29)
<223> OTHER INFORMATION: Glycation [?]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (24)..(24)
<223> OTHER INFORMATION: Carboxymethyl C [24]

<400> SEQUENCE: 501

Val Glu Lys Asp Ala Ile Pro Glu Asn Leu Pro Pro Leu Thr Ala Asp
1               5                   10                  15

Phe Ala Glu Asp Lys Asp Val Cys Lys Asn Tyr Gln Glu
            20                  25

<210> SEQ ID NO 502
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 502

Lys Asp Ala Ile Pro Glu Asn Leu Pro
1               5

<210> SEQ ID NO 503
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
```

```
<220> FEATURE:
<221> NAME/KEY: MOD_RES
<222> LOCATION: (7)..(7)
<223> OTHER INFORMATION: Deamidation N [7]

<400> SEQUENCE: 503

Asn Leu Pro Pro Leu Thr Ala Asp Phe Ala Glu
1               5                   10

<210> SEQ ID NO 504
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Deamidation N [?]
<220> FEATURE:
<221> NAME/KEY: MOD_RES
<222> LOCATION: (1)..(20)
<223> OTHER INFORMATION: Glycation [?]
<220> FEATURE:
<221> NAME/KEY: MOD_RES
<222> LOCATION: (16)..(16)
<223> OTHER INFORMATION: Carboxymethyl C [16]

<400> SEQUENCE: 504

Asn Leu Pro Pro Leu Thr Ala Asp Phe Ala Glu Asp Lys Asp Val Cys
1               5                   10                  15

Lys Asn Tyr Gln
            20

<210> SEQ ID NO 505
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Deamidation N (2) [1 18]
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (16)..(16)
<223> OTHER INFORMATION: Carboxymethyl C [16]

<400> SEQUENCE: 505

Asn Leu Pro Pro Leu Thr Ala Asp Phe Ala Glu Asp Lys Asp Val Cys
1               5                   10                  15

Lys Asn

<210> SEQ ID NO 506
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]
<220> FEATURE:
<221> NAME/KEY: MOD_RES
<222> LOCATION: (8)..(8)
<223> OTHER INFORMATION: Deamidation N [8]

<400> SEQUENCE: 506

Glu Asp Lys Asp Val Cys Lys Asn Tyr Gln Glu
1               5                   10
```

```
<210> SEQ ID NO 507
<211> LENGTH: 19
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation [1]
<220> FEATURE:
<221> NAME/KEY: MOD_RES
<222> LOCATION: (11)..(15)
<223> OTHER INFORMATION: Glycation (2) [11 15]
<220> FEATURE:
<221> NAME/KEY: MOD_RES
<222> LOCATION: (14)..(14)
<223> OTHER INFORMATION: Carboxymethyl C [14]

<400> SEQUENCE: 507

Pro Pro Leu Thr Ala Asp Phe Ala Glu Asp Lys Asp Val Cys Lys Asn
1               5                   10                  15

Tyr Gln Glu

<210> SEQ ID NO 508
<211> LENGTH: 15
<212> TYPE: PRT
<213> ORGANISM: Homo sapiens
<220> FEATURE:
<221> NAME/KEY: MOD_RES
<222> LOCATION: (7)..(11)
<223> OTHER INFORMATION: Glycation (2) [7 11]
<220> FEATURE:
<221> NAME/KEY: MOD_RES
<222> LOCATION: (10)..(10)
<223> OTHER INFORMATION: Carboxymethyl C [10]

<400> SEQUENCE: 508

Ala Asp Phe Ala Glu Asp Lys Asp Val Cys Lys Asn Tyr Gln Glu
1               5                   10                  15

<210> SEQ ID NO 509
<211> LENGTH: 13
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Glycation [?]
<220> FEATURE:
<221> NAME/KEY: MOD_RES
<222> LOCATION: (8)..(8)
<223> OTHER INFORMATION: Carboxymethyl C [8]

<400> SEQUENCE: 509

Phe Ala Glu Asp Lys Asp Val Cys Lys Asn Tyr Gln Glu
1               5                   10

<210> SEQ ID NO 510
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Carboxymethyl C [7]
<220> FEATURE:
<221> NAME/KEY: MOD_RES
<222> LOCATION: (9)..(9)
<223> OTHER INFORMATION: Deamidation N [9]

<400> SEQUENCE: 510
```

Ala Glu Asp Lys Asp Val Cys Lys Asn Tyr Gln Glu
1               5                   10

<210> SEQ ID NO 511
<211> LENGTH: 27
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Deamidation N (2) [1 18]
<220> FEATURE:
<221> NAME/KEY: MOD_RES
<222> LOCATION: (15)..(15)
<223> OTHER INFORMATION: Carboxymethyl C [15]

<400> SEQUENCE: 511

Asn Leu Pro Pro Leu Thr Ala Asp Phe Ala Glu Asp Lys Asp Val Cys
1               5                   10                  15

Lys Asn Tyr Gln Glu Ala Lys Asp Ala Phe Leu
            20                  25

<210> SEQ ID NO 512
<211> LENGTH: 30
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Carboxymethyl C [13]

<400> SEQUENCE: 512

Pro Leu Thr Ala Asp Phe Ala Glu Asp Lys Asp Val Cys Lys Asn Tyr
1               5                   10                  15

Gln Glu Ala Lys Asp Ala Phe Leu Gly Ser Phe Leu Tyr Glu
            20                  25                  30

<210> SEQ ID NO 513
<211> LENGTH: 31
<212> TYPE: PRT
<213> ORGANISM: Homo sapiens
<220> FEATURE:
<221> NAME/KEY: MOD_RES
<222> LOCATION: (4)..(18)
<223> OTHER INFORMATION: Glycation (3) [4 8 14]
<220> FEATURE:
<221> NAME/KEY: MOD_RES
<222> LOCATION: (7)..(7)
<223> OTHER INFORMATION: Carboxymethyl C [7]
<220> FEATURE:
<221> NAME/KEY: MOD_RES
<222> LOCATION: (9)..(9)
<223> OTHER INFORMATION: Deamidation N [9]

<400> SEQUENCE: 513

Ala Glu Asp Lys Asp Val Cys Lys Asn Tyr Gln Glu Ala Lys Asp Ala
1               5                   10                  15

Phe Leu Gly Ser Phe Leu Tyr Glu Tyr Ser Arg Arg His Pro Glu
            20                  25                  30

<210> SEQ ID NO 514
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

-continued

```
<400> SEQUENCE: 514

Asn Leu Pro Pro Leu Thr Ala
1               5

<210> SEQ ID NO 515
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 515

Asn Leu Pro Pro Leu
1               5

<210> SEQ ID NO 516
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 516

Asn Leu Pro Pro
1

<210> SEQ ID NO 517
<211> LENGTH: 22
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 517

Asp Lys Asp Val Cys Lys Asn Tyr Gln Glu Ala Lys Asp Ala Phe Leu
1               5                   10                  15

Gly Ser Phe Leu Tyr Glu
            20

<210> SEQ ID NO 518
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 518

Asp Lys Asp Val Cys Lys Asn Tyr Gln Glu Ala
1               5                   10

<210> SEQ ID NO 519
<211> LENGTH: 13
<212> TYPE: PRT
<213> ORGANISM: Homo sapiens
<220> FEATURE:
<221> NAME/KEY: MOD_RES
<222> LOCATION: (1)..(13)
<223> OTHER INFORMATION: Glycation (2) [2 ?]
<220> FEATURE:
```

```
<221> NAME/KEY: MOD_RES
<222> LOCATION: (5)..(5)
<223> OTHER INFORMATION: Carboxymethyl C [5]

<400> SEQUENCE: 519

Asp Lys Asp Val Cys Lys Asn Tyr Gln Glu Ala Lys Asp
1               5                   10

<210> SEQ ID NO 520
<211> LENGTH: 20
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]
<220> FEATURE:
<221> NAME/KEY: MOD_RES
<222> LOCATION: (4)..(10)
<223> OTHER INFORMATION: Glycation (2) [4 10]
<220> FEATURE:
<221> NAME/KEY: MOD_RES
<222> LOCATION: (4)..(10)
<223> OTHER INFORMATION: Glycation (2) [4 10]

<400> SEQUENCE: 520

Asp Val Cys Lys Asn Tyr Gln Glu Ala Lys Asp Ala Phe Leu Gly Ser
1               5                   10                  15

Phe Leu Tyr Glu
            20

<210> SEQ ID NO 521
<211> LENGTH: 27
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]
<220> FEATURE:
<221> NAME/KEY: MOD_RES
<222> LOCATION: (5)..(5)
<223> OTHER INFORMATION: Deamidation N [5]

<400> SEQUENCE: 521

Asp Val Cys Lys Asn Tyr Gln Glu Ala Lys Asp Ala Phe Leu Gly Ser
1               5                   10                  15

Phe Leu Tyr Glu Tyr Ser Arg Arg His Pro Glu
            20                  25

<210> SEQ ID NO 522
<211> LENGTH: 23
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 522

Asn Tyr Gln Glu Ala Lys Asp Ala Phe Leu Gly Ser Phe Leu Tyr Glu
1               5                   10                  15

Tyr Ser Arg Arg His Pro Glu
            20

<210> SEQ ID NO 523
<211> LENGTH: 9
<212> TYPE: PRT
```

```
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (7)..(7)
<223> OTHER INFORMATION: Deamidation N [7]

<400> SEQUENCE: 523

Asp Lys Asp Val Cys Lys Asn Tyr Gln
1               5

<210> SEQ ID NO 524
<211> LENGTH: 8
<212> TYPE: PRT
<213> ORGANISM: Homo sapiens
<220> FEATURE:
<221> NAME/KEY: MOD_RES
<222> LOCATION: (1)..(8)
<223> OTHER INFORMATION: Glycation [?]
<220> FEATURE:
<221> NAME/KEY: MOD_RES
<222> LOCATION: (5)..(5)
<223> OTHER INFORMATION: Carboxymethyl C (5]
<220> FEATURE:
<221> NAME/KEY: MOD_RES
<222> LOCATION: (7)..(7)
<223> OTHER INFORMATION: Deamidation N {7]

<400> SEQUENCE: 524

Asp Lys Asp Val Cys Lys Asn Tyr
1               5

<210> SEQ ID NO 525
<211> LENGTH: 7
<212> TYPE: PRT
<213> ORGANISM: Homo sapiens
<220> FEATURE:
<221> NAME/KEY: MOD_RES
<222> LOCATION: (1)..(7)
<223> OTHER INFORMATION: Glycation [?]
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (7)..(7)
<223> OTHER INFORMATION: Deamidation N [7]

<400> SEQUENCE: 525

Asp Lys Asp Val Cys Lys Asn
1               5

<210> SEQ ID NO 526
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 526

Asp Lys Asp Val Cys
1               5

<210> SEQ ID NO 527
<211> LENGTH: 4
```

```
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (2)..(2)
<223> OTHER INFORMATION: Glycation [2]

<400> SEQUENCE: 527

Asp Lys Asp Val
1

<210> SEQ ID NO 528
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]
<220> FEATURE:
<221> NAME/KEY: MOD_RES
<222> LOCATION: (4)..(4)
<223> OTHER INFORMATION: Glycation [4]
<220> FEATURE:
<221> NAME/KEY: MOD_RES
<222> LOCATION: (5)..(5)
<223> OTHER INFORMATION: Deamidation N [5]

<400> SEQUENCE: 528

Asp Val Cys Lys Asn Tyr Gln Glu
1               5

<210> SEQ ID NO 529
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (3)..(3)
<223> OTHER INFORMATION: Deamidation N [3]

<400> SEQUENCE: 529

Cys Lys Asn Tyr Gln Glu
1               5

<210> SEQ ID NO 530
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (2)..(2)
<223> OTHER INFORMATION: Deamidation N [2]

<400> SEQUENCE: 530

Lys Asn Tyr Gln Glu
```

```
<210> SEQ ID NO 531
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 531

Asn Tyr Gln Glu
1

<210> SEQ ID NO 532
<211> LENGTH: 30
<212> TYPE: PRT
<213> ORGANISM: Homo sapiens
<220> FEATURE:
<221> NAME/KEY: MOD_RES
<222> LOCATION: (1)..(29)
<223> OTHER INFORMATION: Glycation (2) [1 29]

<400> SEQUENCE: 532

Lys Asp Ala Phe Leu Gly Ser Phe Leu Tyr Glu Tyr Ser Arg Arg His
1               5                   10                  15

Pro Glu Tyr Ala Val Ser Val Leu Leu Arg Leu Ala Lys Glu
            20                  25                  30

<210> SEQ ID NO 533
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 533

Ala Lys Asp Ala Phe Leu
1               5

<210> SEQ ID NO 534
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 534

Ala Lys Glu Tyr Glu
1               5

<210> SEQ ID NO 535
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 535

Lys Glu Tyr Glu Ala Thr Leu Glu
1               5
```

```
<210> SEQ ID NO 536
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Glycation [6]

<400> SEQUENCE: 536

Leu Leu Arg Leu Ala Lys Glu
1               5

<210> SEQ ID NO 537
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 537

Arg Leu Ala Lys Glu
1               5

<210> SEQ ID NO 538
<211> LENGTH: 44
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (8)..(40)
<223> OTHER INFORMATION: Carboxymethyl C (4) [8 9 17 40]

<400> SEQUENCE: 538

Tyr Glu Ala Thr Leu Glu Glu Cys Cys Ala Lys Asp Asp Pro His Ala
1               5                   10                  15

Cys Tyr Ser Thr Val Phe Asp Lys Leu Lys His Leu Val Asp Glu Pro
            20                  25                  30

Gln Asn Leu Ile Lys Gln Asn Cys Asp Gln Phe Glu
        35                  40

<210> SEQ ID NO 539
<211> LENGTH: 25
<212> TYPE: PRT
<213> ORGANISM: Homo sapiens
<220> FEATURE:
<221> NAME/KEY: MOD_RES
<222> LOCATION: (8)..(17)
<223> OTHER INFORMATION: Carboxymethyl C (3) [8 9 17]

<400> SEQUENCE: 539

Tyr Glu Ala Thr Leu Glu Glu Cys Cys Ala Lys Asp Asp Pro His Ala
1               5                   10                  15

Cys Tyr Ser Thr Val Phe Asp Lys Leu
            20                  25
```

-continued

```
<210> SEQ ID NO 540
<211> LENGTH: 20
<212> TYPE: PRT
<213> ORGANISM: Homo sapiens
<220> FEATURE:
<221> NAME/KEY: MOD_RES
<222> LOCATION: (8)..(17)
<223> OTHER INFORMATION: Carboxymethyl C (3) [8 9 17]
<220> FEATURE:
<221> NAME/KEY: MOD_RES
<222> LOCATION: (11)..(11)
<223> OTHER INFORMATION: Glycation [11]

<400> SEQUENCE: 540

Tyr Glu Ala Thr Leu Glu Glu Cys Cys Ala Lys Asp Asp Pro His Ala
1               5                   10                  15

Cys Tyr Ser Thr
            20

<210> SEQ ID NO 541
<211> LENGTH: 19
<212> TYPE: PRT
<213> ORGANISM: Homo sapiens
<220> FEATURE:
<221> NAME/KEY: MOD_RES
<222> LOCATION: (8)..(17)
<223> OTHER INFORMATION: Carboxymethyl C (3) [8 9 17]

<400> SEQUENCE: 541

Tyr Glu Ala Thr Leu Glu Glu Cys Cys Ala Lys Asp Asp Pro His Ala
1               5                   10                  15

Cys Tyr Ser

<210> SEQ ID NO 542
<211> LENGTH: 15
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 542

Tyr Glu Ala Thr Leu Glu Glu Cys Cys Ala Lys Asp Asp Pro His
1               5                   10                  15

<210> SEQ ID NO 543
<211> LENGTH: 14
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 543

Tyr Glu Ala Thr Leu Glu Glu Cys Cys Ala Lys Asp Asp Pro
1               5                   10

<210> SEQ ID NO 544
<211> LENGTH: 13
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]
<220> FEATURE:
<221> NAME/KEY: MOD_RES
```

```
<222> LOCATION: (11)..(11)
<223> OTHER INFORMATION: Glycation [11]

<400> SEQUENCE: 544

Tyr Glu Ala Thr Leu Glu Glu Cys Cys Ala Lys Asp Asp
1               5                   10

<210> SEQ ID NO 545
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Deamidation N [?]
<220> FEATURE:
<221> NAME/KEY: MOD_RES
<222> LOCATION: (8)..(40)
<223> OTHER INFORMATION: Carboxymethyl C (4) [8 9 17 40]

<400> SEQUENCE: 545

Tyr Glu Ala Thr Leu Glu Glu Cys Cys Ala Lys Asp Asp Pro His Ala
1               5                   10                  15

Cys Tyr Ser Thr Val Phe Asp Lys Leu Lys His Leu Val Asp Glu Pro
            20                  25                  30

Gln Asn Leu Ile Lys Gln Asn Cys
        35                  40

<210> SEQ ID NO 546
<211> LENGTH: 19
<212> TYPE: PRT
<213> ORGANISM: Homo sapiens
<220> FEATURE:
<221> NAME/KEY: MOD_RES
<222> LOCATION: (6)..(15)
<223> OTHER INFORMATION: Carboxymethyl C (3) [6 7 15]

<400> SEQUENCE: 546

Ala Thr Leu Glu Glu Cys Cys Ala Lys Asp Asp Pro His Ala Cys Tyr
1               5                   10                  15

Ser Thr Val

<210> SEQ ID NO 547
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation (3) [3?]
<220> FEATURE:
<221> NAME/KEY: MOD_RES
<222> LOCATION: (6)..(38)
<223> OTHER INFORMATION: Carboxymethyl C (4) [6 7 15 38]
<220> FEATURE:
<221> NAME/KEY: MOD_RES
<222> LOCATION: (32)..(37)
<223> OTHER INFORMATION: Deamidation N (2) [32 37]

<400> SEQUENCE: 547

Ala Thr Leu Glu Glu Cys Cys Ala Lys Asp Asp Pro His Ala Cys Tyr
1               5                   10                  15

Ser Thr Val Phe Asp Lys Leu Lys His Leu Val Asp Glu Pro Gln Asn
            20                  25                  30

Leu Ile Lys Gln Asn Cys Asp
        35
```

```
<210> SEQ ID NO 548
<211> LENGTH: 11
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Carboxymethyl C (2) [6 7]

<400> SEQUENCE: 548

Ala Thr Leu Glu Glu Cys Cys Ala Lys Asp Asp
1               5                   10

<210> SEQ ID NO 549
<211> LENGTH: 10
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Carboxymethyl C (2) [6 7]
<220> FEATURE:
<221> NAME/KEY: MOD_RES
<222> LOCATION: (9)..(9)
<223> OTHER INFORMATION: Glycation [9]

<400> SEQUENCE: 549

Ala Thr Leu Glu Glu Cys Cys Ala Lys Asp
1               5                   10

<210> SEQ ID NO 550
<211> LENGTH: 8
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Carboxymethyl C (2) [6 7]

<400> SEQUENCE: 550

Ala Thr Leu Glu Glu Cys Cys Ala
1               5

<210> SEQ ID NO 551
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 551

Ala Thr Leu Glu Glu Cys
1               5

<210> SEQ ID NO 552
<211> LENGTH: 37
<212> TYPE: PRT
<213> ORGANISM: Homo sapiens
<220> FEATURE:
<221> NAME/KEY: MOD_RES
<222> LOCATION: (6)..(15)
<223> OTHER INFORMATION: Carboxymethyl C (3) [6 7 15]
<220> FEATURE:
<221> NAME/KEY: MOD_RES
<222> LOCATION: (9)..(35)
<223> OTHER INFORMATION: Glycation (4) [9 22 24 35]
<220> FEATURE:
<221> NAME/KEY: MOD_RES
```

```
<222> LOCATION: (32)..(37)
<223> OTHER INFORMATION: Deamidation N (2) [32 37]

<400> SEQUENCE: 552

Ala Thr Leu Glu Glu Cys Cys Ala Lys Asp Asp Pro His Ala Cys Tyr
1               5                   10                  15

Ser Thr Val Phe Asp Lys Leu Lys His Leu Val Asp Glu Pro Gln Asn
            20                  25                  30

Leu Ile Lys Gln Asn
        35

<210> SEQ ID NO 553
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation (3) [3?]
<220> FEATURE:
<221> NAME/KEY: MOD_RES
<222> LOCATION: (3)..(35)
<223> OTHER INFORMATION: Carboxymethyl C (4) [3 4 12 35]

<400> SEQUENCE: 553

Glu Glu Cys Cys Ala Lys Asp Asp Pro His Ala Cys Tyr Ser Thr Val
1               5                   10                  15

Phe Asp Lys Leu Lys His Leu Val Asp Glu Pro Gln Asn Leu Ile Lys
            20                  25                  30

Gln Asn Cys Asp Gln Phe Glu
        35

<210> SEQ ID NO 554
<211> LENGTH: 46
<212> TYPE: PRT
<213> ORGANISM: Homo sapiens
<220> FEATURE:
<221> NAME/KEY: MOD_RES
<222> LOCATION: (1)..(46)
<223> OTHER INFORMATION: Deamidation N [?]
<220> FEATURE:
<221> NAME/KEY: MOD_RES
<222> LOCATION: (1)..(46)
<223> OTHER INFORMATION: Glycation (2) [2?]
<220> FEATURE:
<221> NAME/KEY: MOD_RES
<222> LOCATION: (6)..(38)
<223> OTHER INFORMATION: Carboxymethyl C (4) [6 7 15 38]
<220> FEATURE:
<221> NAME/KEY: MOD_RES
<222> LOCATION: (9)..(43)
<223> OTHER INFORMATION: Glycation (5) [9 22 24 35 43]
<220> FEATURE:
<221> NAME/KEY: MOD_RES
<222> LOCATION: (32)..(37)
<223> OTHER INFORMATION: Deamidation N (2) [32 37]

<400> SEQUENCE: 554

Ala Thr Leu Glu Glu Cys Cys Ala Lys Asp Asp Pro His Ala Cys Tyr
1               5                   10                  15

Ser Thr Val Phe Asp Lys Leu Lys His Leu Val Asp Glu Pro Gln Asn
            20                  25                  30

Leu Ile Lys Gln Asn Cys Asp Gln Phe Glu Lys Leu Gly Glu
        35                  40                  45

<210> SEQ ID NO 555
<211> LENGTH: 44
```

```
<212> TYPE: PRT
<213> ORGANISM: Homo sapiens
<220> FEATURE:
<221> NAME/KEY: MOD_RES
<222> LOCATION: (1)..(44)
<223> OTHER INFORMATION: Glycation (3) [3?]
<220> FEATURE:
<221> NAME/KEY: MOD_RES
<222> LOCATION: (4)..(36)
<223> OTHER INFORMATION: Carboxymethyl C (4) [4 5 13 36]

<400> SEQUENCE: 555

Leu Glu Glu Cys Cys Ala Lys Asp Asp Pro His Ala Cys Tyr Ser Thr
1               5                   10                  15

Val Phe Asp Lys Leu Lys His Leu Val Asp Glu Pro Gln Asn Leu Ile
            20                  25                  30

Lys Gln Asn Cys Asp Gln Phe Glu Lys Leu Gly Glu
        35                  40

<210> SEQ ID NO 556
<211> LENGTH: 38
<212> TYPE: PRT
<213> ORGANISM: Homo sapiens
<220> FEATURE:
<221> NAME/KEY: MOD_RES
<222> LOCATION: (1)..(38)
<223> OTHER INFORMATION: Glycation (2) [2?]
<220> FEATURE:
<221> NAME/KEY: MOD_RES
<222> LOCATION: (2)..(34)
<223> OTHER INFORMATION: Carboxymethyl C (4) [2 3 11 34]

<400> SEQUENCE: 556

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu
        35

<210> SEQ ID NO 557
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation [?]
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 557

Glu Cys Cys Ala Lys Asp Asp Pro His Ala Cys Tyr Ser Thr Val Phe
1               5                   10                  15

Asp Lys

<210> SEQ ID NO 558
<211> LENGTH: 15
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]
<220> FEATURE:
<221> NAME/KEY: MOD_RES
```

```
<222> LOCATION: (5)..(5)
<223> OTHER INFORMATION: Glycation [5]

<400> SEQUENCE: 558

Glu Cys Cys Ala Lys Asp Asp Pro His Ala Cys Tyr Ser Thr Val
1               5                   10                  15

<210> SEQ ID NO 559
<211> LENGTH: 14
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]
<220> FEATURE:
<221> NAME/KEY: MOD_RES
<222> LOCATION: (5)..(5)
<223> OTHER INFORMATION: Glycation [5]

<400> SEQUENCE: 559

Glu Cys Cys Ala Lys Asp Asp Pro His Ala Cys Tyr Ser Thr
1               5                   10

<210> SEQ ID NO 560
<211> LENGTH: 12
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 560

Glu Cys Cys Ala Lys Asp Asp Pro His Ala Cys Tyr
1               5                   10

<210> SEQ ID NO 561
<211> LENGTH: 11
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 561

Glu Cys Cys Ala Lys Asp Asp Pro His Ala Cys
1               5                   10

<210> SEQ ID NO 562
<211> LENGTH: 10
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 562

Glu Cys Cys Ala Lys Asp Asp Pro His Ala
1               5                   10

<210> SEQ ID NO 563
<211> LENGTH: 9
```

```
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 563

Glu Cys Cys Ala Lys Asp Asp Pro His
1               5

<210> SEQ ID NO 564
<211> LENGTH: 8
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 564

Glu Cys Cys Ala Lys Asp Asp Pro
1               5

<210> SEQ ID NO 565
<211> LENGTH: 7
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 565

Glu Cys Cys Ala Lys Asp Asp
1               5

<210> SEQ ID NO 566
<211> LENGTH: 5
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 566

Glu Cys Cys Ala Lys
1               5

<210> SEQ ID NO 567
<211> LENGTH: 30
<212> TYPE: PRT
<213> ORGANISM: Homo sapiens
<220> FEATURE:
```

<221> NAME/KEY: MOD_RES
<222> LOCATION: (2)..(11)
<223> OTHER INFORMATION: Carboxymethyl C (3) [2 3 11]
<220> FEATURE:
<221> NAME/KEY: MOD_RES
<222> LOCATION: (5)..(20)
<223> OTHER INFORMATION: Glycation (3) [5 18 20]
<220> FEATURE:
<221> NAME/KEY: MOD_RES
<222> LOCATION: (28)..(28)
<223> OTHER INFORMATION: Deamidation N [28]

<400> SEQUENCE: 567

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile
            20                  25                  30

<210> SEQ ID NO 568
<211> LENGTH: 67
<212> TYPE: PRT
<213> ORGANISM: Homo sapiens
<220> FEATURE:
<221> NAME/KEY: MOD_RES
<222> LOCATION: (1)..(67)
<223> OTHER INFORMATION: Deamidation N [?]
<220> FEATURE:
<221> NAME/KEY: MOD_RES
<222> LOCATION: (1)..(67)
<223> OTHER INFORMATION: Deamidation N (2) [2?]
<220> FEATURE:
<221> NAME/KEY: MOD_RES
<222> LOCATION: (1)..(67)
<223> OTHER INFORMATION: Glycation (3) [3?]
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (5)..(56)
<223> OTHER INFORMATION: Glycation (6) [5 18 20 31 39 56]

<400> SEQUENCE: 568

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln Val Ser Thr Pro Thr
    50                  55                  60

Leu Val Glu
65

<210> SEQ ID NO 569
<211> LENGTH: 55
<212> TYPE: PRT
<213> ORGANISM: Homo sapiens
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (28)..(47)
<223> OTHER INFORMATION: Deamidation N (3) [28 33 47]

<400> SEQUENCE: 569

```
Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg
50                  55
```

<210> SEQ ID NO 570
<211> LENGTH: 53
<212> TYPE: PRT
<213> ORGANISM: Homo sapiens
<220> FEATURE:
<221> NAME/KEY: MOD_RES
<222> LOCATION: (1)..(53)
<223> OTHER INFORMATION: Glycation [?]
<220> FEATURE:
<221> NAME/KEY: MOD_RES
<222> LOCATION: (1)..(53)
<223> OTHER INFORMATION: Deamidation N [?]
<220> FEATURE:
<221> NAME/KEY: MOD_RES
<222> LOCATION: (2)..(34)
<223> OTHER INFORMATION: Carboxymethyl C (4) [2 3 11 34]

<400> SEQUENCE: 570

```
Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr
    50
```

<210> SEQ ID NO 571
<211> LENGTH: 50
<212> TYPE: PRT
<213> ORGANISM: Homo sapiens
<220> FEATURE:
<221> NAME/KEY: MOD_RES
<222> LOCATION: (1)..(51)
<223> OTHER INFORMATION: Deamidation N [?]
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (5)..(39)
<223> OTHER INFORMATION: Glycation (5) [5 18 20 31 39]

<400> SEQUENCE: 571

```
Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile
    50
```

<210> SEQ ID NO 572
<211> LENGTH: 65

```
<212> TYPE: PRT
<213> ORGANISM: Homo sapiens
<220> FEATURE:
<221> NAME/KEY: MOD_RES
<222> LOCATION: (1)..(65)
<223> OTHER INFORMATION: Deamidation N [?]
<220> FEATURE:
<221> NAME/KEY: MOD_RES
<222> LOCATION: (1)..(65)
<223> OTHER INFORMATION: Glycation (5) [5?]
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (5)..(56)
<223> OTHER INFORMATION: Glycation (6) [5 18 20 31 39 56]
<220> FEATURE:
<221> NAME/KEY: MOD_RES
<222> LOCATION: (28)..(47)
<223> OTHER INFORMATION: Deamidation N (3) [28 33 47]

<400> SEQUENCE: 572

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln Val Ser Thr Pro Thr
    50                  55                  60

Leu
65

<210> SEQ ID NO 573
<211> LENGTH: 64
<212> TYPE: PRT
<213> ORGANISM: Homo sapiens
<220> FEATURE:
<221> NAME/KEY: MOD_RES
<222> LOCATION: (1)..(64)
<223> OTHER INFORMATION: Deamidation N (2) [2?]
<220> FEATURE:
<221> NAME/KEY: MOD_RES
<222> LOCATION: (1)..(64)
<223> OTHER INFORMATION: Glycation (2) [2?]
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (5)..(56)
<223> OTHER INFORMATION: Glycation (6) [5 18 20 31 39 56]
<220> FEATURE:
<221> NAME/KEY: MOD_RES
<222> LOCATION: (28)..(47)
<223> OTHER INFORMATION: Deamidation N (3) [28 33 47]

<400> SEQUENCE: 573

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln Val Ser Thr Pro Thr
    50                  55                  60
```

```
<210> SEQ ID NO 574
<211> LENGTH: 63
<212> TYPE: PRT
<213> ORGANISM: Homo sapiens
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
<221> NAME/KEY: MOD_RES
<222> LOCATION: (5)..(56)
<223> OTHER INFORMATION: Glycation (6) [5 18 20 31 39 56]
<220> FEATURE:
<221> NAME/KEY: MOD_RES
<222> LOCATION: (28)..(47)
<223> OTHER INFORMATION: Deamidation N (3) [28 33 47]

<400> SEQUENCE: 574

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln Val Ser Thr Pro
    50                  55                  60

<210> SEQ ID NO 575
<211> LENGTH: 62
<212> TYPE: PRT
<213> ORGANISM: Homo sapiens
<220> FEATURE:
<221> NAME/KEY: MOD_RES
<222> LOCATION: (1)..(62)
<223> OTHER INFORMATION: Glycation [?]
<220> FEATURE:
<221> NAME/KEY: MOD_RES
<222> LOCATION: (1)..(62)
<223> OTHER INFORMATION: Deamidation N [?]
<220> FEATURE:
<221> NAME/KEY: MOD_RES
<222> LOCATION: (2)..(34)
<223> OTHER INFORMATION: Carboxymethyl C (4) [2 3 11 34]

<400> SEQUENCE: 575

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln Val Ser Thr
    50                  55                  60

<210> SEQ ID NO 576
<211> LENGTH: 59
<212> TYPE: PRT
<213> ORGANISM: Homo sapiens
<220> FEATURE:
<221> NAME/KEY: MOD_RES
<222> LOCATION: (1)..(59)
<223> OTHER INFORMATION: Glycation (5) [5?]
<220> FEATURE:
<221> NAME/KEY: MOD_RES
<222> LOCATION: (2)..(34)
<223> OTHER INFORMATION: Carboxymethyl C (4) [2 3 11 34]
<220> FEATURE:
```

```
<221> NAME/KEY: MOD_RES
<222> LOCATION: (28)..(47)
<223> OTHER INFORMATION: Deamidation N (3) [28 33 47]

<400> SEQUENCE: 576

Glu Cys Cys Ala Lys Asp Asp Pro His Ala Cys Tyr Ser Thr Val Phe
1               5                   10                  15

Asp Lys Leu Lys His Leu Val Asp Glu Pro Gln Asn Leu Ile Lys Gln
            20                  25                  30

Asn Cys Asp Gln Phe Glu Lys Leu Gly Glu Tyr Gly Phe Gln Asn Ala
        35                  40                  45

Leu Ile Val Arg Tyr Thr Arg Lys Val Pro Gln
    50                  55

<210> SEQ ID NO 577
<211> LENGTH: 37
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(37)
<223> OTHER INFORMATION: Glycation (3) [3?]
<220> FEATURE:
<221> NAME/KEY: MOD_RES
<222> LOCATION: (27)..(32)
<223> OTHER INFORMATION: Deamidation N (2) [27 32]

<400> SEQUENCE: 577

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu
        35

<210> SEQ ID NO 578
<211> LENGTH: 40
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (1)..(40)
<223> OTHER INFORMATION: Deamidation N [?]

<400> SEQUENCE: 578

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu Lys Leu Gly
        35                  40

<210> SEQ ID NO 579
<211> LENGTH: 39
```

```
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(39)
<223> OTHER INFORMATION: Glycation [?]
<220> FEATURE:
<221> NAME/KEY: MOD_RES
<222> LOCATION: (27)..(32)
<223> OTHER INFORMATION: Deamidation N (2) [27 32]

<400> SEQUENCE: 579

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu Lys Leu
            35

<210> SEQ ID NO 580
<211> LENGTH: 40
<212> TYPE: PRT
<213> ORGANISM: Homo sapiens
<220> FEATURE:
<221> NAME/KEY: MOD_RES
<222> LOCATION: (1)..(32)
<223> OTHER INFORMATION: Carboxymethyl C (3) [1 9 32]
<220> FEATURE:
<221> NAME/KEY: MOD_RES
<222> LOCATION: (1)..(40)
<223> OTHER INFORMATION: Deamidation N [?]
<220> FEATURE:
<221> NAME/KEY: MOD_RES
<222> LOCATION: (26)..(31)
<223> OTHER INFORMATION: Deamidation N (2) [26 31]

<400> SEQUENCE: 580

Cys Ala Lys Asp Asp Pro His Ala Cys Tyr Ser Thr Val Phe Asp Lys
1               5                   10                  15

Leu Lys His Leu Val Asp Glu Pro Gln Asn Leu Ile Lys Gln Asn Cys
            20                  25                  30

Asp Gln Phe Glu Lys Leu Gly Glu
            35                  40

<210> SEQ ID NO 581
<211> LENGTH: 28
<212> TYPE: PRT
<213> ORGANISM: Homo sapiens
<220> FEATURE:
<221> NAME/KEY: MOD_RES
<222> LOCATION: (1)..(28)
<223> OTHER INFORMATION: Glycation (2) [2?]
<220> FEATURE:
<221> NAME/KEY: MOD_RES
<222> LOCATION: (1)..(28)
<223> OTHER INFORMATION: Deamidation N [?]
<220> FEATURE:
<221> NAME/KEY: MOD_RES
<222> LOCATION: (20)..(20)
<223> OTHER INFORMATION: Carboxymethyl C [20]

<400> SEQUENCE: 581

Val Phe Asp Lys Leu Lys His Leu Val Asp Glu Pro Gln Asn Leu Ile
1               5                   10                  15

Lys Gln Asn Cys Asp Gln Phe Glu Lys Leu Gly Glu
```

```
                        20                  25

<210> SEQ ID NO 582
<211> LENGTH: 24
<212> TYPE: PRT
<213> ORGANISM: Homo sapiens
<220> FEATURE:
<221> NAME/KEY: MOD_RES
<222> LOCATION: (10)..(15)
<223> OTHER INFORMATION: Deamidation N (2) [10 15]
<220> FEATURE:
<221> NAME/KEY: MOD_RES
<222> LOCATION: (16)..(16)
<223> OTHER INFORMATION: Carboxymethyl C [16]

<400> SEQUENCE: 582

Leu Lys His Leu Val Asp Glu Pro Gln Asn Leu Ile Lys Gln Asn Cys
1               5                   10                  15

Asp Gln Phe Glu Lys Leu Gly Glu
            20

<210> SEQ ID NO 583
<211> LENGTH: 23
<212> TYPE: PRT
<213> ORGANISM: Homo sapiens
<220> FEATURE:
<221> NAME/KEY: MOD_RES
<222> LOCATION: (2)..(14)
<223> OTHER INFORMATION: Deamidation N (2) [9 14]
<220> FEATURE:
<221> NAME/KEY: MOD_RES
<222> LOCATION: (15)..(15)
<223> OTHER INFORMATION: Carboxymethyl C [15]

<400> SEQUENCE: 583

Lys His Leu Val Asp Glu Pro Gln Asn Leu Ile Lys Gln Asn Cys Asp
1               5                   10                  15

Gln Phe Glu Lys Leu Gly Glu
            20

<210> SEQ ID NO 584
<211> LENGTH: 39
<212> TYPE: PRT
<213> ORGANISM: Homo sapiens
<220> FEATURE:
<221> NAME/KEY: MOD_RES
<222> LOCATION: (8)..(31)
<223> OTHER INFORMATION: Carboxymethyl C (2) [8 31]
<220> FEATURE:
<221> NAME/KEY: MOD_RES
<222> LOCATION: (25)..(30)
<223> OTHER INFORMATION: Deamidation N (2) [25 30]

<400> SEQUENCE: 584

Ala Lys Asp Asp Pro His Ala Cys Tyr Ser Thr Val Phe Asp Lys Leu
1               5                   10                  15

Lys His Leu Val Asp Glu Pro Gln Asn Leu Ile Lys Gln Asn Cys Asp
            20                  25                  30

Gln Phe Glu Lys Leu Gly Glu
        35

<210> SEQ ID NO 585
<211> LENGTH: 17
<212> TYPE: PRT
<213> ORGANISM: Homo sapiens
<220> FEATURE:
<221> NAME/KEY: MOD_RES
<222> LOCATION: (3)..(8)
```

```
<223> OTHER INFORMATION: Deamidation N (2) [3 8]
<220> FEATURE:
<221> NAME/KEY: MOD_RES
<222> LOCATION: (6)..(14)
<223> OTHER INFORMATION: Glycation (2) [6 14]
<220> FEATURE:
<221> NAME/KEY: MOD_RES
<222> LOCATION: (9)..(9)
<223> OTHER INFORMATION: Carboxymethyl C [9]

<400> SEQUENCE: 585

Pro Gln Asn Leu Ile Lys Gln Asn Cys Asp Gln Phe Glu Lys Leu Gly
1               5                   10                  15

Glu

<210> SEQ ID NO 586
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 586

Gln Asn Cys Asp Gln Phe Glu Lys Leu Gly Glu
1               5                   10

<210> SEQ ID NO 587
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (2)..(2)
<223> OTHER INFORMATION: Carboxymethyl C [2]
<220> FEATURE:
<221> NAME/KEY: MOD_RES
<222> LOCATION: (7)..(7)
<223> OTHER INFORMATION: Glycation [7]

<400> SEQUENCE: 587

Asn Cys Asp Gln Phe Glu Lys Leu Gly Glu
1               5                   10

<210> SEQ ID NO 588
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]
<220> FEATURE:
<221> NAME/KEY: MOD_RES
<222> LOCATION: (6)..(6)
<223> OTHER INFORMATION: Glycation [6]

<400> SEQUENCE: 588

Cys Asp Gln Phe Glu Lys Leu Gly Glu
1               5

<210> SEQ ID NO 589
<211> LENGTH: 37
<212> TYPE: PRT
<213> ORGANISM: Homo sapiens
```

```
<220> FEATURE:
<221> NAME/KEY: MOD_RES
<222> LOCATION: (1)..(37)
<223> OTHER INFORMATION: Glycation (3) [3?]
<220> FEATURE:
<221> NAME/KEY: MOD_RES
<222> LOCATION: (6)..(29)
<223> OTHER INFORMATION: Carboxymethyl C (2) [6 29]
<220> FEATURE:
<221> NAME/KEY: MOD_RES
<222> LOCATION: (23)..(28)
<223> OTHER INFORMATION: Deamidation N (2) [23 28]

<400> SEQUENCE: 589

Asp Asp Pro His Ala Cys Tyr Ser Thr Val Phe Asp Lys Leu Lys His
1               5                   10                  15

Leu Val Asp Glu Pro Gln Asn Leu Ile Lys Gln Asn Cys Asp Gln Phe
            20                  25                  30

Glu Lys Leu Gly Glu
        35

<210> SEQ ID NO 590
<211> LENGTH: 33
<212> TYPE: PRT
<213> ORGANISM: Homo sapiens
<220> FEATURE:
<221> NAME/KEY: MOD_RES
<222> LOCATION: (2)..(25)
<223> OTHER INFORMATION: Carboxymethyl C (2) [2 25]

<400> SEQUENCE: 590

Ala Cys Tyr Ser Thr Val Phe Asp Lys Leu Lys His Leu Val Asp Glu
1               5                   10                  15

Pro Gln Asn Leu Ile Lys Gln Asn Cys Asp Gln Phe Glu Lys Leu Gly
            20                  25                  30

Glu

<210> SEQ ID NO 591
<211> LENGTH: 48
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(48)
<223> OTHER INFORMATION: Carboxymethyl C (4) [1 2 10 33 48]
<220> FEATURE:
<221> NAME/KEY: MOD_RES
<222> LOCATION: (1)..(48)
<223> OTHER INFORMATION: Glycation (5) [5?]
<220> FEATURE:
<221> NAME/KEY: MOD_RES
<222> LOCATION: (1)..(48)
<223> OTHER INFORMATION: Glycation (6) [6?]
<220> FEATURE:
<221> NAME/KEY: MOD_RES
<222> LOCATION: (1)..(48)
<223> OTHER INFORMATION: Glycation (4) [4?]
<220> FEATURE:
<221> NAME/KEY: MOD_RES
<222> LOCATION: (1)..(48)
<223> OTHER INFORMATION: Glycation (3) [3?]
<220> FEATURE:
<221> NAME/KEY: MOD_RES
<222> LOCATION: (1)..(48)
<223> OTHER INFORMATION: Deamidation N [?]
<220> FEATURE:
<221> NAME/KEY: MOD_RES
```

```
<222> LOCATION: (1)..(48)
<223> OTHER INFORMATION: Deamidation N (2) [2?]
<220> FEATURE:
<221> NAME/KEY: MOD_RES
<222> LOCATION: (1)..(48)
<223> OTHER INFORMATION: Glycation [?]
<220> FEATURE:
<221> NAME/KEY: MOD_RES
<222> LOCATION: (1)..(48)
<223> OTHER INFORMATION: Deamidation N (2) [2?]
<220> FEATURE:
<221> NAME/KEY: MOD_RES
<222> LOCATION: (4)..(48)
<223> OTHER INFORMATION: Glycation (6) [4 17 10 30 38 48]
<220> FEATURE:
<221> NAME/KEY: MOD_RES
<222> LOCATION: (4)..(38)
<223> OTHER INFORMATION: Glycation (5) [4 17 19 30 38)
<220> FEATURE:
<221> NAME/KEY: MOD_RES
<222> LOCATION: (27)..(32)
<223> OTHER INFORMATION: Deamidation N (2) [27 32]
<220> FEATURE:
<221> NAME/KEY: MOD_RES
<222> LOCATION: (27)..(46)
<223> OTHER INFORMATION: Deamidation N (3) [27 32 46]

<400> SEQUENCE: 591

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu Lys Leu Gly Glu Tyr Gly Phe Gln Asn Ala Leu
        35                  40                  45

<210> SEQ ID NO 592
<211> LENGTH: 46
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(46)
<223> OTHER INFORMATION: Glycation (3) [3?]

<400> SEQUENCE: 592

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu Lys Leu Gly Glu Tyr Gly Phe Gln Asn
        35                  40                  45

<210> SEQ ID NO 593
<211> LENGTH: 43
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(43)
<223> OTHER INFORMATION: Glycation [?]
<220> FEATURE:
<221> NAME/KEY: MOD_RES
<222> LOCATION: (27)..(32)
```

```
<223> OTHER INFORMATION: Deamidation N (2) [27 32]

<400> SEQUENCE: 593

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys Asp Gln Phe Glu Lys Leu Gly Glu Tyr Gly
        35                  40

<210> SEQ ID NO 594
<211> LENGTH: 49
<212> TYPE: PRT
<213> ORGANISM: Homo sapiens
<220> FEATURE:
<221> NAME/KEY: MOD_RES
<222> LOCATION: (5)..(43)
<223> OTHER INFORMATION: Glycation (5) [5 7 18 26 43]
<220> FEATURE:
<221> NAME/KEY: MOD_RES
<222> LOCATION: (15)..(34)
<223> OTHER INFORMATION: Deamidation N (3) [15 20 34]
<220> FEATURE:
<221> NAME/KEY: MOD_RES
<222> LOCATION: (21)..(21)
<223> OTHER INFORMATION: Carboxymethyl C [21]

<400> SEQUENCE: 594

Thr Val Phe Asp Lys Leu Lys His Leu Val Asp Glu Pro Gln Asn Leu
1               5                   10                  15

Ile Lys Gln Asn Cys Asp Gln Phe Glu Lys Leu Gly Glu Tyr Gly Phe
            20                  25                  30

Gln Asn Ala Leu Ile Val Arg Tyr Thr Arg Lys Val Pro Gln Val Ser
        35                  40                  45

Thr

<210> SEQ ID NO 595
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Deamidation N [?]
<220> FEATURE:
<221> NAME/KEY: MOD_RES
<222> LOCATION: (1)..(49)
<223> OTHER INFORMATION: Glycation (3) [3?]
<220> FEATURE:
<221> NAME/KEY: MOD_RES
<222> LOCATION: (1)..(49)
<223> OTHER INFORMATION: Glycation (2) [2?]
<220> FEATURE:
<221> NAME/KEY: MOD_RES
<222> LOCATION: (12)..(31)
<223> OTHER INFORMATION: Deamidation N (3) [12 17 31]
<220> FEATURE:
<221> NAME/KEY: MOD_RES
<222> LOCATION: (18)..(18)
<223> OTHER INFORMATION: Carboxymethyl C [18]

<400> SEQUENCE: 595

Asp Lys Leu Lys His Leu Val Asp Glu Pro Gln Asn Leu Ile Lys Gln
1               5                   10                  15

Asn Cys Asp Gln Phe Glu Lys Leu Gly Glu Tyr Gly Phe Gln Asn Ala
            20                  25                  30

Leu Ile Val Arg Tyr Thr Arg Lys Val Pro Gln Val Ser Thr Pro Thr
```

```
                    35                  40                  45

Leu

<210> SEQ ID NO 596
<211> LENGTH: 39
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Glycation [?]
<220> FEATURE:
<221> NAME/KEY: MOD_RES
<222> LOCATION: (1)..(39)
<223> OTHER INFORMATION: Deamidation N [?]
<220> FEATURE:
<221> NAME/KEY: MOD_RES
<222> LOCATION: (6)..(6)
<223> OTHER INFORMATION: Carboxymethyl C [6]

<400> SEQUENCE: 596

Leu Ile Lys Gln Asn Cys Asp Gln Phe Glu Lys Leu Gly Glu Tyr Gly
1               5                   10                  15

Phe Gln Asn Ala Leu Ile Val Arg Tyr Thr Arg Lys Val Pro Gln Val
            20                  25                  30

Ser Thr Pro Thr Leu Val Glu
        35

<210> SEQ ID NO 597
<211> LENGTH: 32
<212> TYPE: PRT
<213> ORGANISM: Homo sapiens
<220> FEATURE:
<221> NAME/KEY: MOD_RES
<222> LOCATION: (4)..(21)
<223> OTHER INFORMATION: Glycation (2) [4 21]

<400> SEQUENCE: 597

Gln Phe Glu Lys Leu Gly Glu Tyr Gly Phe Gln Asn Ala Leu Ile Val
1               5                   10                  15

Arg Tyr Thr Arg Lys Val Pro Gln Val Ser Thr Pro Thr Leu Val Glu
            20                  25                  30

<210> SEQ ID NO 598
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Deamidation N (2) [2?]
<220> FEATURE:
<221> NAME/KEY: MOD_RES
<222> LOCATION: (1)..(49)
<223> OTHER INFORMATION: Glycation (4) [4?]
<220> FEATURE:
<221> NAME/KEY: MOD_RES
<222> LOCATION: (2)..(25)
<223> OTHER INFORMATION: Carboxymethyl C (2) [2 25]

<400> SEQUENCE: 598

Ala Cys Tyr Ser Thr Val Phe Asp Lys Leu Lys His Leu Val Asp Glu
1               5                   10                  15

Pro Gln Asn Leu Ile Lys Gln Asn Cys Asp Gln Phe Glu Lys Leu Gly
            20                  25                  30

Glu Tyr Gly Phe Gln Asn Ala Leu Ile Val Arg Tyr Thr Arg Lys Val
        35                  40                  45
```

Pro

<210> SEQ ID NO 599
<211> LENGTH: 49
<212> TYPE: PRT
<213> ORGANISM: Homo sapiens
<220> FEATURE:
<221> NAME/KEY: MOD_RES
<222> LOCATION: (1)..(24)
<223> OTHER INFORMATION: Carboxymethyl C (2) [1 24]
<220> FEATURE:
<221> NAME/KEY: MOD_RES
<222> LOCATION: (1)..(49)
<223> OTHER INFORMATION: Glycation (3) [3?]
<220> FEATURE:
<221> NAME/KEY: MOD_RES
<222> LOCATION: (1)..(49)
<223> OTHER INFORMATION: Deamidation N [?]

<400> SEQUENCE: 599

Cys Tyr Ser Thr Val Phe Asp Lys Leu Lys His Leu Val Asp Glu Pro
1               5                   10                  15

Gln Asn Leu Ile Lys Gln Asn Cys Asp Gln Phe Glu Lys Leu Gly Glu
            20                  25                  30

Tyr Gly Phe Gln Asn Ala Leu Ile Val Arg Tyr Thr Arg Lys Val Pro
        35                  40                  45

Cys

<210> SEQ ID NO 600
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Deamidation N [?]
<220> FEATURE:
<221> NAME/KEY: MOD_RES
<222> LOCATION: (9)..(49)
<223> OTHER INFORMATION: Glycation (4) [9 17 34 49]
<220> FEATURE:
<221> NAME/KEY: MOD_RES
<222> LOCATION: (12)..(49)
<223> OTHER INFORMATION: Carboxymethyl C (2) [12 49]

<400> SEQUENCE: 600

Val Asp Glu Pro Gln Asn Leu Ile Lys Gln Asn Cys Asp Gln Phe Glu
1               5                   10                  15

Lys Leu Gly Glu Tyr Gly Phe Gln Asn Ala Leu Ile Val Arg Tyr Thr
            20                  25                  30

Arg Lys Val Pro Gln Val Ser Thr Pro Thr Leu Val Glu Val Ser Arg
        35                  40                  45

Ser

<210> SEQ ID NO 601
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Deamidation N [?]
<220> FEATURE:
<221> NAME/KEY: MOD_RES
<222> LOCATION: (10)..(49)
<223> OTHER INFORMATION: Carboxymethyl C (2) [10 49]

-continued

```
<400> SEQUENCE: 601

Glu Pro Gln Asn Leu Ile Lys Gln Asn Cys Asp Gln Phe Glu Lys Leu
1               5                   10                  15

Gly Glu Tyr Gly Phe Gln Asn Ala Leu Ile Val Arg Tyr Thr Arg Lys
            20                  25                  30

Val Pro Gln Val Ser Thr Pro Thr Leu Val Glu Val Ser Arg Ser Leu
        35                  40                  45

Gly

<210> SEQ ID NO 602
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Glycation (4) [4?]
<220> FEATURE:
<221> NAME/KEY: MOD_RES
<222> LOCATION: (1)..(20)
<223> OTHER INFORMATION: Deamidation N (3) [1 6 20]
<220> FEATURE:
<221> NAME/KEY: MOD_RES
<222> LOCATION: (7)..(49)
<223> OTHER INFORMATION: Carboxymethyl C (2) [7 49]

<400> SEQUENCE: 602

Asn Leu Ile Lys Gln Asn Cys Asp Gln Phe Glu Lys Leu Gly Glu Tyr
1               5                   10                  15

Gly Phe Gln Asn Ala Leu Ile Val Arg Tyr Thr Arg Lys Val Pro Gln
            20                  25                  30

Val Ser Thr Pro Thr Leu Val Glu Val Ser Arg Ser Leu Gly Lys Val
        35                  40                  45

Gly

<210> SEQ ID NO 603
<211> LENGTH: 49
<212> TYPE: PRT
<213> ORGANISM: Homo sapiens
<220> FEATURE:
<221> NAME/KEY: MOD_RES
<222> LOCATION: (1)..(49)
<223> OTHER INFORMATION: Glycation (3) [3?]
<220> FEATURE:
<221> NAME/KEY: MOD_RES
<222> LOCATION: (4)..(18)
<223> OTHER INFORMATION: Deamidation N (2) [4 18]
<220> FEATURE:
<221> NAME/KEY: MOD_RES
<222> LOCATION: (5)..(49)
<223> OTHER INFORMATION: Carboxymethyl C (2) [5 49]

<400> SEQUENCE: 603

Ile Lys Gln Asn Cys Asp Gln Phe Glu Lys Leu Gly Glu Tyr Gly Phe
1               5                   10                  15

Gln Asn Ala Leu Ile Val Arg Tyr Thr Arg Lys Val Pro Gln Val Ser
            20                  25                  30

Thr Pro Thr Leu Val Glu Val Ser Arg Ser Leu Gly Lys Val Gly Thr
        35                  40                  45

Arg

<210> SEQ ID NO 604
<211> LENGTH: 17
<212> TYPE: PRT
```

```
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (4)..(17)
<223> OTHER INFORMATION: Glycation (2) [4 17]

<400> SEQUENCE: 604

Cys Cys Ala Lys Asp Asp Pro His Ala Cys Tyr Ser Thr Val Phe Asp
1               5                   10                  15

Lys

<210> SEQ ID NO 605
<211> LENGTH: 16
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (4)..(4)
<223> OTHER INFORMATION: Glycation [4]

<400> SEQUENCE: 605

Cys Cys Ala Lys Asp Asp Pro His Ala Cys Tyr Ser Thr Val Phe Asp
1               5                   10                  15

<210> SEQ ID NO 606
<211> LENGTH: 14
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]

<400> SEQUENCE: 606

Cys Cys Ala Lys Asp Asp Pro His Ala Cys Tyr Ser Thr Val
1               5                   10

<210> SEQ ID NO 607
<211> LENGTH: 13
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]

<400> SEQUENCE: 607

Cys Cys Ala Lys Asp Asp Pro His Ala Cys Tyr Ser Thr
1               5                   10

<210> SEQ ID NO 608
<211> LENGTH: 12
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]

<400> SEQUENCE: 608

Cys Cys Ala Lys Asp Asp Pro His Ala Cys Tyr Ser
```

1               5               10

<210> SEQ ID NO 609
<211> LENGTH: 8
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 609

Cys Cys Ala Lys Asp Asp Pro His
1               5

<210> SEQ ID NO 610
<211> LENGTH: 7
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]

<400> SEQUENCE: 610

Cys Cys Ala Lys Asp Asp Pro
1               5

<210> SEQ ID NO 611
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 611

Cys Cys Ala Lys Asp Asp
1               5

<210> SEQ ID NO 612
<211> LENGTH: 5
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 612

Cys Cys Ala Lys Asp
1               5

<210> SEQ ID NO 613
<211> LENGTH: 4
<212> TYPE: PRT
<213> ORGANISM: Homo sapiens

```
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 613

Cys Cys Ala Lys
1

<210> SEQ ID NO 614
<211> LENGTH: 33
<212> TYPE: PRT
<213> ORGANISM: Homo sapiens
<220> FEATURE:
<221> NAME/KEY: MOD_RES
<222> LOCATION: (1)..(33)
<223> OTHER INFORMATION: Carboxymethyl C (4) [1 2 10 33]
<220> FEATURE:
<221> NAME/KEY: MOD_RES
<222> LOCATION: (1)..(33)
<223> OTHER INFORMATION: Glycation (3) [3?]
<220> FEATURE:
<221> NAME/KEY: MOD_RES
<222> LOCATION: (1)..(33)
<223> OTHER INFORMATION: Deamidation N [?]

<400> SEQUENCE: 614

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile Lys Gln Asn
            20                  25                  30

Cys

<210> SEQ ID NO 615
<211> LENGTH: 29
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (1)..(29)
<223> OTHER INFORMATION: Glycation [?]

<400> SEQUENCE: 615

Cys Cys Ala Lys Asp Asp Pro His Ala Cys Tyr Ser Thr Val Phe Asp
1               5                   10                  15

Lys Leu Lys His Leu Val Asp Glu Pro Gln Asn Leu Ile
            20                  25

<210> SEQ ID NO 616
<211> LENGTH: 36
<212> TYPE: PRT
<213> ORGANISM: Homo sapiens
<220> FEATURE:
<221> NAME/KEY: MOD_RES
<222> LOCATION: (1)..(32)
<223> OTHER INFORMATION: Carboxymethyl C (3) [1 9 32]
<220> FEATURE:
<221> NAME/KEY: MOD_RES
<222> LOCATION: (1)..(36)
<223> OTHER INFORMATION: Glycation [?]
<220> FEATURE:
<221> NAME/KEY: MOD_RES
```

```
<222> LOCATION: (26)..(31)
<223> OTHER INFORMATION: Deamidation N (2) [26 31]

<400> SEQUENCE: 616

Cys Ala Lys Asp Asp Pro His Ala Cys Tyr Ser Thr Val Phe Asp Lys
1               5                   10                  15

Leu Lys His Leu Val Asp Glu Pro Gln Asn Leu Ile Lys Gln Asn Cys
            20                  25                  30

Asp Gln Phe Glu
        35

<210> SEQ ID NO 617
<211> LENGTH: 21
<212> TYPE: PRT
<213> ORGANISM: Homo sapiens
<220> FEATURE:
<221> NAME/KEY: MOD_RES
<222> LOCATION: (11)..(16)
<223> OTHER INFORMATION: Deamidation N (2) [11 16]
<220> FEATURE:
<221> NAME/KEY: MOD_RES
<222> LOCATION: (17)..(17)
<223> OTHER INFORMATION: Carboxymethyl C [17]

<400> SEQUENCE: 617

Lys Leu Lys His Leu Val Asp Glu Pro Gln Asn Leu Ile Lys Gln Asn
1               5                   10                  15

Cys Asp Gln Phe Glu
            20

<210> SEQ ID NO 618
<211> LENGTH: 20
<212> TYPE: PRT
<213> ORGANISM: Homo sapiens
<220> FEATURE:
<221> NAME/KEY: MOD_RES
<222> LOCATION: (2)..(13)
<223> OTHER INFORMATION: Glycation (2) [2 13]
<220> FEATURE:
<221> NAME/KEY: MOD_RES
<222> LOCATION: (10)..(15)
<223> OTHER INFORMATION: Deamidation N (2) [10 15]
<220> FEATURE:
<221> NAME/KEY: MOD_RES
<222> LOCATION: (16)..(16)
<223> OTHER INFORMATION: Carboxymethyl C [16]

<400> SEQUENCE: 618

Leu Lys His Leu Val Asp Glu Pro Gln Asn Leu Ile Lys Gln Asn Cys
1               5                   10                  15

Asp Gln Phe Glu
        20

<210> SEQ ID NO 619
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation [?]
<220> FEATURE:
<221> NAME/KEY: MOD_RES
<222> LOCATION: (9)..(14)
<223> OTHER INFORMATION: Deamidation N (2) [9 14]
<220> FEATURE:
<221> NAME/KEY: MOD_RES
<222> LOCATION: (15)..(15)
<223> OTHER INFORMATION: Carboxymethyl C [15]
```

<400> SEQUENCE: 619

Lys His Leu Val Asp Glu Pro Gln Asn Leu Ile Lys Gln Asn Cys Asp
1               5                   10                  15

Gln Phe Glu

<210> SEQ ID NO 620
<211> LENGTH: 14
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: Deamidation N [?]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (10)..(10)
<223> OTHER INFORMATION: Carboxymethyl C [10]

<400> SEQUENCE: 620

Glu Pro Gln Asn Leu Ile Lys Gln Asn Cys Asp Gln Phe Glu
1               5                   10

<210> SEQ ID NO 621
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Carboxymethyl C [9]

<400> SEQUENCE: 621

Pro Gln Asn Leu Ile Lys Gln Asn Cys Asp Gln Phe Glu
1               5                   10

<210> SEQ ID NO 622
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Glycation [5]
<220> FEATURE:
<221> NAME/KEY: MOD_RES
<222> LOCATION: (8)..(8)
<223> OTHER INFORMATION: Carboxymethyl C [8]

<400> SEQUENCE: 622

Gln Asn Leu Ile Lys Gln Asn Cys Asp Gln Phe Glu
1               5                   10

<210> SEQ ID NO 623
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 623

Ile Lys Gln Asn Cys Asp Gln Phe Glu
1               5

<210> SEQ ID NO 624
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (3)..(3)
<223> OTHER INFORMATION: Deamidation N [3]
<220> FEATURE:
<221> NAME/KEY: MOD_RES
<222> LOCATION: (4)..(4)
<223> OTHER INFORMATION: Carboxymethyl C [4]

<400> SEQUENCE: 624

Lys Gln Asn Cys Asp Gln Phe Glu
1               5

<210> SEQ ID NO 625
<211> LENGTH: 30
<212> TYPE: PRT
<213> ORGANISM: Homo sapiens
<220> FEATURE:
<221> NAME/KEY: MOD_RES
<222> LOCATION: (1)..(30)
<223> OTHER INFORMATION: Glycation (2) [2?]
<220> FEATURE:
<221> NAME/KEY: MOD_RES
<222> LOCATION: (3)..(26)
<223> OTHER INFORMATION: Carboxymethyl C (2) [3 26]
<220> FEATURE:
<221> NAME/KEY: MOD_RES
<222> LOCATION: (20)..(25)
<223> OTHER INFORMATION: Deamidation N (2) [20 25]

<400> SEQUENCE: 625

His Ala Cys Tyr Ser Thr Val Phe Asp Lys Leu Lys His Leu Val Asp
1               5                   10                  15

Glu Pro Gln Asn Leu Ile Lys Gln Asn Cys Asp Gln Phe Glu
            20                  25                  30

<210> SEQ ID NO 626
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (9)..(9)
<223> OTHER INFORMATION: Deamidation N [9]

<400> SEQUENCE: 626

Lys Leu Gly Glu Tyr Gly Phe Gln Asn Ala
1               5                   10

<210> SEQ ID NO 627
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

```
<400> SEQUENCE: 627

Lys Leu Gly Glu Tyr Gly
1               5

<210> SEQ ID NO 628
<211> LENGTH: 23
<212> TYPE: PRT
<213> ORGANISM: Homo sapiens

<400> SEQUENCE: 628

Lys Leu Gly Glu Tyr Gly Phe Gln Asn Ala Leu Ile Val Arg Tyr Thr
1               5                   10                  15

Arg Lys Val Pro Gln Val Ser
            20

<210> SEQ ID NO 629
<211> LENGTH: 46
<212> TYPE: PRT
<213> ORGANISM: Homo sapiens
<220> FEATURE:
<221> NAME/KEY: MOD_RES
<222> LOCATION: (1)..(46)
<223> OTHER INFORMATION: Glycation (3) [3?]
<220> FEATURE:
<221> NAME/KEY: MOD_RES
<222> LOCATION: (1)..(46)
<223> OTHER INFORMATION: Glycation [?]
<220> FEATURE:
<221> NAME/KEY: MOD_RES
<222> LOCATION: (9)..(9)
<223> OTHER INFORMATION: Deamidation N [9]
<220> FEATURE:
<221> NAME/KEY: MOD_RES
<222> LOCATION: (41)..(42)
<223> OTHER INFORMATION: Carboxymethyl C (2) [41 42]

<400> SEQUENCE: 629

Lys Leu Gly Glu Tyr Gly Phe Gln Asn Ala Leu Ile Val Arg Tyr Thr
1               5                   10                  15

Arg Lys Val Pro Gln Val Ser Thr Pro Thr Leu Val Glu Val Ser Arg
            20                  25                  30

Ser Leu Gly Lys Val Gly Thr Arg Cys Cys Thr Lys Pro Glu
        35                  40                  45

<210> SEQ ID NO 630
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (9)..(9)
<223> OTHER INFORMATION: Deamidation N [9]

<400> SEQUENCE: 630

Lys Leu Gly Glu Tyr Gly Phe Gln Asn Ala Leu Ile Val Arg Tyr Thr
1               5                   10                  15

Arg Lys Val Pro Gln Val Ser Thr Pro Thr Leu Val Glu Val Ser Arg
            20                  25                  30

Ser Leu Gly Lys Val Gly Thr Arg
        35                  40

<210> SEQ ID NO 631
```

```
<211> LENGTH: 44
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (16)..(42)
<223> OTHER INFORMATION: Glycation (3) [16 34 42]
<220> FEATURE:
<221> NAME/KEY: MOD_RES
<222> LOCATION: (39)..(40)
<223> OTHER INFORMATION: Carboxymethyl C (2) [39 40]

<400> SEQUENCE: 631

Gly Glu Tyr Gly Phe Gln Asn Ala Leu Ile Val Arg Tyr Thr Arg Lys
1               5                   10                  15

Val Pro Gln Val Ser Thr Pro Thr Leu Val Glu Val Ser Arg Ser Leu
            20                  25                  30

Gly Lys Val Gly Thr Arg Cys Cys Thr Lys Pro Glu
        35                  40

<210> SEQ ID NO 632
<211> LENGTH: 48
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Deamidation N [9]
<220> FEATURE:
<221> NAME/KEY: MOD_RES
<222> LOCATION: (41)..(42)
<223> OTHER INFORMATION: Carboxymethyl C (2) [41 42]

<400> SEQUENCE: 632

Lys Leu Gly Glu Tyr Gly Phe Gln Asn Ala Leu Ile Val Arg Tyr Thr
1               5                   10                  15

Arg Lys Val Pro Gln Val Ser Thr Pro Thr Leu Val Glu Val Ser Arg
            20                  25                  30

Ser Leu Gly Lys Val Gly Thr Arg Cys Cys Thr Lys Pro Glu Ser Glu
        35                  40                  45

<210> SEQ ID NO 633
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation [?]

<400> SEQUENCE: 633

Tyr Gly Phe Gln Asn Ala Leu Ile Val Arg Tyr Thr Arg Lys Val Pro
1               5                   10                  15

Gln Val Ser Thr Pro Thr Leu Val Glu Val Ser Arg Ser Leu Gly Lys
            20                  25                  30

Val Gly Thr
        35

<210> SEQ ID NO 634
<211> LENGTH: 40
<212> TYPE: PRT
<213> ORGANISM: Homo sapiens
<220> FEATURE:
```

-continued

```
<221> NAME/KEY: MOD_RES
<222> LOCATION: (12)..(38)
<223> OTHER INFORMATION: Glycation (3) [12 30 38]
<220> FEATURE:
<221> NAME/KEY: MOD_RES
<222> LOCATION: (35)..(36)
<223> OTHER INFORMATION: Carboxymethyl C (2) [35 36]

<400> SEQUENCE: 634

Phe Gln Asn Ala Leu Ile Val Arg Tyr Thr Arg Lys Val Pro Gln Val
1               5                   10                  15

Ser Thr Pro Thr Leu Val Glu Val Ser Arg Ser Leu Gly Lys Val Gly
            20                  25                  30

Thr Arg Cys Cys Thr Lys Pro Glu
            35                  40

<210> SEQ ID NO 635
<211> LENGTH: 39
<212> TYPE: PRT
<213> ORGANISM: Homo sapiens
<220> FEATURE:
<221> NAME/KEY: MOD_RES
<222> LOCATION: (34)..(35)
<223> OTHER INFORMATION: Carboxymethyl C (2) [34 35]

<400> SEQUENCE: 635

Gln Asn Ala Leu Ile Val Arg Tyr Thr Arg Lys Val Pro Gln Val Ser
1               5                   10                  15

Thr Pro Thr Leu Val Glu Val Ser Arg Ser Leu Gly Lys Val Gly Thr
            20                  25                  30

Arg Cys Cys Thr Lys Pro Glu
            35

<210> SEQ ID NO 636
<211> LENGTH: 44
<212> TYPE: PRT
<213> ORGANISM: Homo sapiens
<220> FEATURE:
<221> NAME/KEY: MOD_RES
<222> LOCATION: (1)..(44)
<223> OTHER INFORMATION: Glycation [?]
<220> FEATURE:
<221> NAME/KEY: MOD_RES
<222> LOCATION: (5)..(5)
<223> OTHER INFORMATION: Deamidation N [5]
<220> FEATURE:
<221> NAME/KEY: MOD_RES
<222> LOCATION: (37)..(38)
<223> OTHER INFORMATION: Carboxymethyl C (2) [37 38]

<400> SEQUENCE: 636

Tyr Gly Phe Gln Asn Ala Leu Ile Val Arg Tyr Thr Arg Lys Val Pro
1               5                   10                  15

Gln Val Ser Thr Pro Thr Leu Val Glu Val Ser Arg Ser Leu Gly Lys
            20                  25                  30

Val Gly Thr Arg Cys Cys Thr Lys Pro Glu Ser Glu
            35                  40

<210> SEQ ID NO 637
<211> LENGTH: 33
<212> TYPE: PRT
<213> ORGANISM: Homo sapiens
<220> FEATURE:
<221> NAME/KEY: MOD_RES
<222> LOCATION: (26)..(27)
<223> OTHER INFORMATION: Carboxymethyl C (2) [26 27]
```

```
<400> SEQUENCE: 637

Thr Arg Lys Val Pro Gln Val Ser Thr Pro Thr Leu Val Glu Val Ser
1               5                  10                  15

Arg Ser Leu Gly Lys Val Gly Thr Arg Cys Cys Thr Lys Pro Glu Ser
            20                  25                  30

Glu

<210> SEQ ID NO 638
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (33)..(34)
<223> OTHER INFORMATION: Carboxymethyl C (2) [33 34]

<400> SEQUENCE: 638

Asn Ala Leu Ile Val Arg Tyr Thr Arg Lys Val Pro Gln Val Ser Thr
1               5                  10                  15

Pro Thr Leu Val Glu Val Ser Arg Ser Leu Gly Lys Val Gly Thr Arg
            20                  25                  30

Cys Cys Thr Lys Pro Glu Ser Glu
        35                  40

<210> SEQ ID NO 639
<211> LENGTH: 35
<212> TYPE: PRT
<213> ORGANISM: Homo sapiens
<220> FEATURE:
<221> NAME/KEY: MOD_RES
<222> LOCATION: (22)..(33)
<223> OTHER INFORMATION: Carboxymethyl C (3) [22 23 33]

<400> SEQUENCE: 639

Pro Gln Val Ser Thr Pro Thr Leu Val Glu Val Ser Arg Ser Leu Gly
1               5                  10                  15

Lys Val Gly Thr Arg Cys Cys Thr Lys Pro Glu Ser Glu Arg Met Pro
            20                  25                  30

Cys Thr Glu
        35

<210> SEQ ID NO 640
<211> LENGTH: 45
<212> TYPE: PRT
<213> ORGANISM: Homo sapiens
<220> FEATURE:
<221> NAME/KEY: MOD_RES
<222> LOCATION: (1)..(45)
<223> OTHER INFORMATION: Glycation [?]
<220> FEATURE:
<221> NAME/KEY: MOD_RES
<222> LOCATION: (32)..(43)
<223> OTHER INFORMATION: Carboxymethyl C (3) [32 33 43]

<400> SEQUENCE: 640

Ala Leu Ile Val Arg Tyr Thr Arg Lys Val Pro Gln Val Ser Thr Pro
1               5                  10                  15

Thr Leu Val Glu Val Ser Arg Ser Leu Gly Lys Val Gly Thr Arg Cys
            20                  25                  30

Cys Thr Lys Pro Glu Ser Glu Arg Met Pro Cys Thr Glu
```

```
<210> SEQ ID NO 641
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Deamidation N [5]

<400> SEQUENCE: 641

Tyr Gly Phe Gln Asn
1               5

<210> SEQ ID NO 642
<211> LENGTH: 9
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 642

Arg Cys Cys Thr Lys Pro Glu Ser Glu
1               5

<210> SEQ ID NO 643
<211> LENGTH: 8
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]
<220> FEATURE:
<221> NAME/KEY: MOD_RES
<222> LOCATION: (4)..(4)
<223> OTHER INFORMATION: Glycation [4]

<400> SEQUENCE: 643

Cys Cys Thr Lys Pro Glu Ser Glu
1               5

<210> SEQ ID NO 644
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 644

Cys Thr Lys Pro Glu Ser Glu
1               5

<210> SEQ ID NO 645
<211> LENGTH: 14
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Carboxymethyl C (2) [7 8]
```

<400> SEQUENCE: 645

Gly Lys Val Gly Thr Arg Cys Cys Thr Lys Pro Glu Ser Glu
1               5                   10

<210> SEQ ID NO 646
<211> LENGTH: 12
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 646

Val Gly Thr Arg Cys Cys Thr Lys Pro Glu Ser Glu
1               5                   10

<210> SEQ ID NO 647
<211> LENGTH: 15
<212> TYPE: PRT
<213> ORGANISM: Homo sapiens
<220> FEATURE:
<221> NAME/KEY: MOD_RES
<222> LOCATION: (2)..(13)
<223> OTHER INFORMATION: Carboxymethyl C (3) [2 3 13]
<220> FEATURE:
<221> NAME/KEY: MOD_RES
<222> LOCATION: (5)..(5)
<223> OTHER INFORMATION: Glycation [5]
<220> FEATURE:
<221> NAME/KEY: MOD_RES
<222> LOCATION: (11)..(11)
<223> OTHER INFORMATION: Oxidation M [11]

<400> SEQUENCE: 647

Arg Cys Cys Thr Lys Pro Glu Ser Glu Arg Met Pro Cys Thr Glu
1               5                   10                  15

<210> SEQ ID NO 648
<211> LENGTH: 14
<212> TYPE: PRT
<213> ORGANISM: Homo sapiens
<220> FEATURE:
<221> NAME/KEY: MOD_RES
<222> LOCATION: (1)..(12)
<223> OTHER INFORMATION: Carboxymethyl C (3) [1 2 12]

<400> SEQUENCE: 648

Cys Cys Thr Lys Pro Glu Ser Glu Arg Met Pro Cys Thr Glu
1               5                   10

<210> SEQ ID NO 649
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (8)..(8)
<223> OTHER INFORMATION: Oxidation M [8]
<220> FEATURE:
<221> NAME/KEY: MOD_RES
<222> LOCATION: (10)..(10)
<223> OTHER INFORMATION: Carboxymethyl C [10]

<400> SEQUENCE: 649

```
Thr Lys Pro Glu Ser Glu Arg Met Pro Cys Thr Glu
1               5                  10

<210> SEQ ID NO 650
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (8)..(8)
<223> OTHER INFORMATION: Carboxymethyl C [8]

<400> SEQUENCE: 650

Pro Glu Ser Glu Arg Met Pro Cys Thr Glu
1               5                  10

<210> SEQ ID NO 651
<211> LENGTH: 18
<212> TYPE: PRT
<213> ORGANISM: Homo sapiens
<220> FEATURE:
<221> NAME/KEY: MOD_RES
<222> LOCATION: (5)..(16)
<223> OTHER INFORMATION: Carboxymethyl C (3) [5 6 16]
<220> FEATURE:
<221> NAME/KEY: MOD_RES
<222> LOCATION: (8)..(8)
<223> OTHER INFORMATION: Glycation [8]
<220> FEATURE:
<221> NAME/KEY: MOD_RES
<222> LOCATION: (14)..(14)
<223> OTHER INFORMATION: Oxidation M [14]

<400> SEQUENCE: 651

Val Gly Thr Arg Cys Cys Thr Lys Pro Glu Ser Glu Arg Met Pro Cys
1               5                  10                  15
Thr Glu

<210> SEQ ID NO 652
<211> LENGTH: 16
<212> TYPE: PRT
<213> ORGANISM: Homo sapiens
<220> FEATURE:
<221> NAME/KEY: MOD_RES
<222> LOCATION: (3)..(14)
<223> OTHER INFORMATION: Carboxymethyl C (3) [3 4 14]

<400> SEQUENCE: 652

Thr Arg Cys Cys Thr Lys Pro Glu Ser Glu Arg Met Pro Cys Thr Glu
1               5                  10                  15

<210> SEQ ID NO 653
<211> LENGTH: 39
<212> TYPE: PRT
<213> ORGANISM: Homo sapiens
<220> FEATURE:
<221> NAME/KEY: MOD_RES
<222> LOCATION: (6)..(14)
<223> OTHER INFORMATION: Glycation (2) [6 14]
<220> FEATURE:
<221> NAME/KEY: MOD_RES
<222> LOCATION: (11)..(35)
<223> OTHER INFORMATION: Carboxymethyl C (4) [11 12 22 35]

<400> SEQUENCE: 653

Ser Arg Ser Leu Gly Lys Val Gly Thr Arg Cys Cys Thr Lys Pro Glu
```

-continued

```
                1               5                  10                  15
Ser Glu Arg Met Pro Cys Thr Glu Asp Tyr Leu Ser Leu Ile Leu Asn
            20                  25                  30

Arg Leu Cys Val Leu His Glu
            35

<210> SEQ ID NO 654
<211> LENGTH: 27
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Oxidation M [8]
<220> FEATURE:
<221> NAME/KEY: MOD_RES
<222> LOCATION: (10)..(23)
<223> OTHER INFORMATION: Carboxymethyl C (2) [10 23]
<220> FEATURE:
<221> NAME/KEY: MOD_RES
<222> LOCATION: (20)..(20)
<223> OTHER INFORMATION: Deamidation N [20]

<400> SEQUENCE: 654

Thr Lys Pro Glu Ser Glu Arg Met Pro Cys Thr Glu Asp Tyr Leu Ser
1               5                  10                  15

Leu Ile Leu Asn Arg Leu Cys Val Leu His Glu
            20                  25

<210> SEQ ID NO 655
<211> LENGTH: 36
<212> TYPE: PRT
<213> ORGANISM: Homo sapiens
<220> FEATURE:
<221> NAME/KEY: MOD_RES
<222> LOCATION: (8)..(32)
<223> OTHER INFORMATION: Carboxymethyl C (4) [8 9 19 32]

<400> SEQUENCE: 655

Leu Gly Lys Val Gly Thr Arg Cys Cys Thr Lys Pro Glu Ser Glu Arg
1               5                  10                  15

Met Pro Cys Thr Glu Asp Tyr Leu Ser Leu Ile Leu Asn Arg Leu Cys
            20                  25                  30

Val Leu His Glu
            35

<210> SEQ ID NO 656
<211> LENGTH: 35
<212> TYPE: PRT
<213> ORGANISM: Homo sapiens
<220> FEATURE:
<221> NAME/KEY: MOD_RES
<222> LOCATION: (2)..(10)
<223> OTHER INFORMATION: Glycation (2) [2 10]
<220> FEATURE:
<221> NAME/KEY: MOD_RES
<222> LOCATION: (7)..(31)
<223> OTHER INFORMATION: Carboxymethyl C (4) [7 8 18 31]
<220> FEATURE:
<221> NAME/KEY: MOD_RES
<222> LOCATION: (28)..(28)
<223> OTHER INFORMATION: Deamidation N [28]

<400> SEQUENCE: 656

Gly Lys Val Gly Thr Arg Cys Cys Thr Lys Pro Glu Ser Glu Arg Met
1               5                  10                  15

Pro Cys Thr Glu Asp Tyr Leu Ser Leu Ile Leu Asn Arg Leu Cys Val
```

```
                  20                  25                  30

Leu His Glu
        35

<210> SEQ ID NO 657
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Glycation [7]

<400> SEQUENCE: 657

Val Ser Arg Ser Leu Gly Lys Val Gly Thr
1               5                   10

<210> SEQ ID NO 658
<211> LENGTH: 7
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Carboxymethyl C (2) [2 3]
<220> FEATURE:
<221> NAME/KEY: MOD_RES
<222> LOCATION: (5)..(5)
<223> OTHER INFORMATION: Glycation [5]

<400> SEQUENCE: 658

Arg Cys Cys Thr Lys Pro Glu
1               5

<210> SEQ ID NO 659
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Carboxymethyl C (2) [1 2]

<400> SEQUENCE: 659

Cys Cys Thr Lys Pro Glu
1               5

<210> SEQ ID NO 660
<211> LENGTH: 10
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 660

Val Gly Thr Arg Cys Cys Thr Lys Pro Glu
1               5                   10

<210> SEQ ID NO 661
<211> LENGTH: 9
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Carboxymethyl C (2) [4 5]
<220> FEATURE:
```

```
<221> NAME/KEY: MOD_RES
<222> LOCATION: (7)..(7)
<223> OTHER INFORMATION: Glycation [7]

<400> SEQUENCE: 661

Gly Thr Arg Cys Cys Thr Lys Pro Glu
1               5

<210> SEQ ID NO 662
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 662

Ser Glu Arg Met Pro Cys Thr Glu
1               5

<210> SEQ ID NO 663
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (6)..(6)
<223> OTHER INFORMATION: Carboxymethyl C [6]

<400> SEQUENCE: 663

Ser Glu Arg Met Pro Cys Thr
1               5

<210> SEQ ID NO 664
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Oxidation M [3]
<220> FEATURE:
<221> NAME/KEY: MOD_RES
<222> LOCATION: (5)..(5)
<223> OTHER INFORMATION: Carboxymethyl C [5]

<400> SEQUENCE: 664

Glu Arg Met Pro Cys Thr Glu
1               5

<210> SEQ ID NO 665
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (6)..(6)
<223> OTHER INFORMATION: Carboxymethyl C [6]

<400> SEQUENCE: 665

Ser Glu Arg Met Pro Cys Thr Glu Asp Tyr
```

```
                1               5                    10
```

<210> SEQ ID NO 666
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 666

```
Ser Glu Arg Met Pro Cys Thr Glu Asp
1               5
```

<210> SEQ ID NO 667
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Carboxymethyl C [4]

<400> SEQUENCE: 667

```
Arg Met Pro Cys Thr Glu
1               5
```

<210> SEQ ID NO 668
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Carboxymethyl C [4]

<400> SEQUENCE: 668

```
Arg Met Pro Cys Thr Glu Asp Tyr Leu Ser
1               5                   10
```

<210> SEQ ID NO 669
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 669

```
Arg Met Pro Cys Thr Glu Asp Tyr Leu
1               5
```

<210> SEQ ID NO 670
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

```
<400> SEQUENCE: 670

Arg Met Pro Cys Thr Glu Asp Tyr
1               5

<210> SEQ ID NO 671
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 671

Arg Met Pro Cys Thr Glu Asp
1               5

<210> SEQ ID NO 672
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(17)
<223> OTHER INFORMATION: Carboxymethyl C (2) [4 17]
<220> FEATURE:
<221> NAME/KEY: MOD_RES
<222> LOCATION: (14)..(14)
<223> OTHER INFORMATION: Deamidation N [14]

<400> SEQUENCE: 672

Arg Met Pro Cys Thr Glu Asp Tyr Leu Ser Leu Ile Leu Asn Arg Leu
1               5                   10                  15

Cys Val

<210> SEQ ID NO 673
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Carboxymethyl C [4]
<220> FEATURE:
<221> NAME/KEY: MOD_RES
<222> LOCATION: (14)..(14)
<223> OTHER INFORMATION: Deamidation N [14]

<400> SEQUENCE: 673

Arg Met Pro Cys Thr Glu Asp Tyr Leu Ser Leu Ile Leu Asn
1               5                   10

<210> SEQ ID NO 674
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
```

```
<221> NAME/KEY: MOD_RES
<222> LOCATION: (1)..(34)
<223> OTHER INFORMATION: Glycation (2) [2 ?]
<220> FEATURE:
<221> NAME/KEY: MOD_RES
<222> LOCATION: (3)..(32)
<223> OTHER INFORMATION: Carboxymethyl C (4) [3 16 31 32]
<220> FEATURE:
<221> NAME/KEY: MOD_RES
<222> LOCATION: (13)..(13)
<223> OTHER INFORMATION: Deamidation N [13]

<400> SEQUENCE: 674

Met Pro Cys Thr Glu Asp Tyr Leu Ser Leu Ile Leu Asn Arg Leu Cys
1               5                   10                  15

Val Leu His Glu Lys Thr Pro Val Ser Glu Lys Val Thr Lys Cys Cys
            20                  25                  30

Thr Glu

<210> SEQ ID NO 675
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 675

Arg Met Pro Cys Thr
1               5

<210> SEQ ID NO 676
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Carboxymethyl C [4]

<400> SEQUENCE: 676

Arg Met Pro Cys
1

<210> SEQ ID NO 677
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (3)..(3)
<223> OTHER INFORMATION: Carboxymethyl C [3]

<400> SEQUENCE: 677

Met Pro Cys Thr Glu
1               5

<210> SEQ ID NO 678
<211> LENGTH: 14
<212> TYPE: PRT
```

```
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 678

Gln Gln Cys Pro Phe Asp Glu His Val Lys Leu Val Asn Glu
1               5                   10

<210> SEQ ID NO 679
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 679

Pro Cys Thr Glu
1

<210> SEQ ID NO 680
<211> LENGTH: 19
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Carboxymethyl C [8]

<400> SEQUENCE: 680

Phe Ser Gln Tyr Leu Gln Gln Cys Pro Phe Asp Glu His Val Lys Leu
1               5                   10                  15

Val Asn Glu

<210> SEQ ID NO 681
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Deamidation N [8]
<220> FEATURE:
<221> NAME/KEY: MOD_RES
<222> LOCATION: (11)..(11)
<223> OTHER INFORMATION: Carboxymethyl C [11]
<220> FEATURE:
<221> NAME/KEY: MOD_RES
<222> LOCATION: (16)..(16)
<223> OTHER INFORMATION: Glycation [16]

<400> SEQUENCE: 681

Asp Tyr Leu Ser Leu Ile Leu Asn Arg Leu Cys Val Leu His Glu Lys
1               5                   10                  15

Thr Pro Val Ser Glu
            20

<210> SEQ ID NO 682
<211> LENGTH: 41
<212> TYPE: PRT
<213> ORGANISM: Homo sapiens
<220> FEATURE:
<221> NAME/KEY: MOD_RES
<222> LOCATION: (1)..(41)
<223> OTHER INFORMATION: Glycation (2) [2 ?]
<220> FEATURE:
```

-continued

```
<221> NAME/KEY: MOD_RES
<222> LOCATION: (8)..(33)
<223> OTHER INFORMATION: Deamidation N (2) [8 33]
<220> FEATURE:
<221> NAME/KEY: MOD_RES
<222> LOCATION: (11)..(37)
<223> OTHER INFORMATION: Carboxymethyl C(4) [11 26 27 37]

<400> SEQUENCE: 682

Asp Tyr Leu Ser Leu Ile Leu Asn Arg Leu Cys Val Leu His Glu Lys
1               5                   10                  15

Thr Pro Val Ser Glu Lys Val Thr Lys Cys Cys Thr Glu Ser Leu Val
            20                  25                  30

Asn Arg Arg Pro Cys Phe Ser Ala Leu
            35                  40

<210> SEQ ID NO 683
<211> LENGTH: 44
<212> TYPE: PRT
<213> ORGANISM: Homo sapiens
<220> FEATURE:
<221> NAME/KEY: MOD_RES
<222> LOCATION: (7)..(32)
<223> OTHER INFORMATION: Deamidation N (2) [7 32]
<220> FEATURE:
<221> NAME/KEY: MOD_RES
<222> LOCATION: (10)..(36)
<223> OTHER INFORMATION: Carboxymethyl C (4) [10 25 26 36]
<220> FEATURE:
<221> NAME/KEY: MOD_RES
<222> LOCATION: (15)..(24)
<223> OTHER INFORMATION: Glycation (3) [15 21 24]

<400> SEQUENCE: 683

Tyr Leu Ser Leu Ile Leu Asn Arg Leu Cys Val Leu His Glu Lys Thr
1               5                   10                  15

Pro Val Ser Glu Lys Val Thr Lys Cys Cys Thr Glu Ser Leu Val Asn
            20                  25                  30

Arg Arg Pro Cys Phe Ser Ala Leu Thr Pro Asp Glu
            35                  40

<210> SEQ ID NO 684
<211> LENGTH: 32
<212> TYPE: PRT
<213> ORGANISM: Homo sapiens
<220> FEATURE:
<221> NAME/KEY: MOD_RES
<222> LOCATION: (1)..(32)
<223> OTHER INFORMATION: Glycation [?]
<220> FEATURE:
<221> NAME/KEY: MOD_RES
<222> LOCATION: (13)..(24)
<223> OTHER INFORMATION: Carboxymethyl C (3) [13 14 24]
<220> FEATURE:
<221> NAME/KEY: MOD_RES
<222> LOCATION: (20)..(20)
<223> OTHER INFORMATION: Deamidation N [20]

<400> SEQUENCE: 684

His Glu Lys Thr Pro Val Ser Glu Lys Val Thr Lys Cys Cys Thr Glu
1               5                   10                  15

Ser Leu Val Asn Arg Arg Pro Cys Phe Ser Ala Leu Thr Pro Asp Glu
            20                  25                  30

<210> SEQ ID NO 685
<211> LENGTH: 43
<212> TYPE: PRT
<213> ORGANISM: Homo sapiens
```

```
<220> FEATURE:
<221> NAME/KEY: MOD_RES
<222> LOCATION: (1)..(43)
<223> OTHER INFORMATION: Glycation [?]
<220> FEATURE:
<221> NAME/KEY: MOD_RES
<222> LOCATION: (9)..(35)
<223> OTHER INFORMATION: Carboxymethyl C (9) [9 24 25 35]

<400> SEQUENCE: 685

Leu Ser Leu Ile Leu Asn Arg Leu Cys Val Leu His Glu Lys Thr Pro
1               5                   10                  15

Val Ser Glu Lys Val Thr Lys Cys Cys Thr Glu Ser Leu Val Asn Arg
            20                  25                  30

Arg Pro Cys Phe Ser Ala Leu Thr Pro Asp Glu
        35                  40

<210> SEQ ID NO 686
<211> LENGTH: 42
<212> TYPE: PRT
<213> ORGANISM: Homo sapiens
<220> FEATURE:
<221> NAME/KEY: MOD_RES
<222> LOCATION: (5)..(30)
<223> OTHER INFORMATION: Deamidation N (2) [5 30]
<220> FEATURE:
<221> NAME/KEY: MOD_RES
<222> LOCATION: (8)..(34)
<223> OTHER INFORMATION: Carboxymethyl C (9) [8 23 29 34]

<400> SEQUENCE: 686

Ser Leu Ile Leu Asn Arg Leu Cys Val Leu His Glu Lys Thr Pro Val
1               5                   10                  15

Ser Glu Lys Val Thr Lys Cys Cys Thr Glu Ser Leu Val Asn Arg Arg
            20                  25                  30

Pro Cys Phe Ser Ala Leu Thr Pro Asp Glu
        35                  40

<210> SEQ ID NO 687
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Deamidation N [8]

<400> SEQUENCE: 687

Asp Tyr Leu Ser Leu Ile Leu Asn Arg
1               5

<210> SEQ ID NO 688
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 688

Leu Asn Arg Leu Cys Val Leu His Glu
1               5

<210> SEQ ID NO 689
<211> LENGTH: 8
<212> TYPE: PRT
```

```
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 689

Asn Arg Leu Cys Val Leu His Glu
1               5

<210> SEQ ID NO 690
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 690

Leu Cys Val Leu His Glu
1               5

<210> SEQ ID NO 691
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 691

Lys Thr Pro Val Ser Glu
1               5

<210> SEQ ID NO 692
<211> LENGTH: 8
<212> TYPE: PRT
<213> ORGANISM: Homo sapiens
<220> FEATURE:
<221> NAME/KEY: MOD_RES
<222> LOCATION: (1)..(8)
<223> OTHER INFORMATION: Glycation [?]
<220> FEATURE:
<221> NAME/KEY: MOD_RES
<222> LOCATION: (1)..(7)
<223> OTHER INFORMATION: Glycation (2) [1 7]

<400> SEQUENCE: 692

Lys Thr Pro Val Ser Glu Lys Val
1               5

<210> SEQ ID NO 693
<211> LENGTH: 7
<212> TYPE: PRT
<213> ORGANISM: Homo sapiens
<220> FEATURE:
<221> NAME/KEY: MOD_RES
<222> LOCATION: (1)..(7)
<223> OTHER INFORMATION: Glycation (2) [1 7]

<400> SEQUENCE: 693

Lys Thr Pro Val Ser Glu Lys
1               5

<210> SEQ ID NO 694
<211> LENGTH: 11
<212> TYPE: PRT
```

```
<213> ORGANISM: Homo sapiens
<220> FEATURE:
<221> NAME/KEY: MOD_RES
<222> LOCATION: (4)..(7)
<223> OTHER INFORMATION: Glycation(2) [4 7]
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 694

Val Ser Glu Lys Val Thr Lys Cys Cys Thr Glu
1               5                  10

<210> SEQ ID NO 695
<211> LENGTH: 10
<212> TYPE: PRT
<213> ORGANISM: Homo sapiens
<220> FEATURE:
<221> NAME/KEY: MOD_RES
<222> LOCATION: (3)..(6)
<223> OTHER INFORMATION: Glycation (2) [3 6]
<220> FEATURE:
<221> NAME/KEY: MOD_RES
<222> LOCATION: (7)..(8)
<223> OTHER INFORMATION: Carboxymethyl C (2) [7 8]

<400> SEQUENCE: 695

Ser Glu Lys Val Thr Lys Cys Cys Thr Glu
1               5                  10

<210> SEQ ID NO 696
<211> LENGTH: 9
<212> TYPE: PRT
<213> ORGANISM: Homo sapiens
<220> FEATURE:
<221> NAME/KEY: MOD_RES
<222> LOCATION: (2)..(5)
<223> OTHER INFORMATION: Glycation (2) [2 5]
<220> FEATURE:
<221> NAME/KEY: MOD_RES
<222> LOCATION: (6)..(7)
<223> OTHER INFORMATION: Carboxymethyl C (2) [6 7]

<400> SEQUENCE: 696

Glu Lys Val Thr Lys Cys Cys Thr Glu
1               5

<210> SEQ ID NO 697
<211> LENGTH: 30
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Glycation (3) [1 7 10]
<220> FEATURE:
<221> NAME/KEY: MOD_RES
<222> LOCATION: (11)..(22)
<223> OTHER INFORMATION: Carboxymethyl C (3) [11 12 22]
<220> FEATURE:
<221> NAME/KEY: MOD_RES
<222> LOCATION: (18)..(18)
<223> OTHER INFORMATION: Deamidation N [18]

<400> SEQUENCE: 697

Lys Thr Pro Val Ser Glu Lys Val Thr Lys Cys Cys Thr Glu Ser Leu
1               5                  10                  15

Val Asn Arg Arg Pro Cys Phe Ser Ala Leu Thr Pro Asp Glu
            20                  25                  30
```

-continued

```
<210> SEQ ID NO 698
<211> LENGTH: 26
<212> TYPE: PRT
<213> ORGANISM: Homo sapiens
<220> FEATURE:
<221> NAME/KEY: MOD_RES
<222> LOCATION: (3)..(6)
<223> OTHER INFORMATION: Glycation (2) [3 6]
<220> FEATURE:
<221> NAME/KEY: MOD_RES
<222> LOCATION: (7)..(18)
<223> OTHER INFORMATION: Carboxymethyl C (3) [7 8 18]

<400> SEQUENCE: 698

Ser Glu Lys Val Thr Lys Cys Cys Thr Glu Ser Leu Val Asn Arg Arg
1               5                   10                  15

Pro Cys Phe Ser Ala Leu Thr Pro Asp Glu
            20                  25

<210> SEQ ID NO 699
<211> LENGTH: 30
<212> TYPE: PRT
<213> ORGANISM: Homo sapiens
<220> FEATURE:
<221> NAME/KEY: MOD_RES
<222> LOCATION: (1)..(30)
<223> OTHER INFORMATION: Glycation [?]
<220> FEATURE:
<221> NAME/KEY: MOD_RES
<222> LOCATION: (7)..(26)
<223> OTHER INFORMATION: Carboxymethyl C (2) [7 26]

<400> SEQUENCE: 699

Ser Gln Tyr Leu Gln Gln Cys Pro Phe Asp Glu His Val Lys Leu Val
1               5                   10                  15

Asn Glu Leu Thr Glu Phe Ala Lys Thr Cys Val Ala Asp Glu
            20                  25                  30

<210> SEQ ID NO 700
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Glycation [?]
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (16)..(16)
<223> OTHER INFORMATION: Carboxymethyl C [16]

<400> SEQUENCE: 700

Glu His Val Lys Leu Val Asn Glu Leu Thr Glu Phe Ala Lys Thr Cys
1               5                   10                  15

Val Ala Asp Glu
            20

<210> SEQ ID NO 701
<211> LENGTH: 8
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]
```

<400> SEQUENCE: 701

Lys Val Thr Lys Cys Cys Thr Glu
1               5

<210> SEQ ID NO 702
<211> LENGTH: 11
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 702

Lys Val Thr Lys Cys Cys Thr Glu Ser Leu Val
1               5                   10

<210> SEQ ID NO 703
<211> LENGTH: 10
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 703

Lys Val Thr Lys Cys Cys Thr Glu Ser Leu
1               5                   10

<210> SEQ ID NO 704
<211> LENGTH: 9
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 704

Lys Val Thr Lys Cys Cys Thr Glu Ser
1               5

<210> SEQ ID NO 705
<211> LENGTH: 30
<212> TYPE: PRT
<213> ORGANISM: Homo sapiens
<220> FEATURE:
<221> NAME/KEY: MOD_RES
<222> LOCATION: (5)..(16)
<223> OTHER INFORMATION: Carboxymethyl C (3) [5 6 16]

<400> SEQUENCE: 705

Lys Val Thr Lys Cys Cys Thr Glu Ser Leu Val Asn Arg Arg Pro Cys
1               5                   10                  15

Phe Ser Ala Leu Thr Pro Asp Glu Thr Tyr Val Pro Lys Ala
            20                  25                  30

<210> SEQ ID NO 706
<211> LENGTH: 29
<212> TYPE: PRT
<213> ORGANISM: Homo sapiens
<220> FEATURE:
<221> NAME/KEY: MOD_RES
<222> LOCATION: (5)..(16)
<223> OTHER INFORMATION: Carboxymethyl C (3) [5 6 16]
<220> FEATURE:

```
<221> NAME/KEY: MOD_RES
<222> LOCATION: (12)..(12)
<223> OTHER INFORMATION: Deamidation N [12]

<400> SEQUENCE: 706

Lys Val Thr Lys Cys Cys Thr Glu Ser Leu Val Asn Arg Arg Pro Cys
1               5                   10                  15

Phe Ser Ala Leu Thr Pro Asp Glu Thr Tyr Val Pro Lys
            20                  25

<210> SEQ ID NO 707
<211> LENGTH: 49
<212> TYPE: PRT
<213> ORGANISM: Homo sapiens
<220> FEATURE:
<221> NAME/KEY: MOD_RES
<222> LOCATION: (1)..(34)
<223> OTHER INFORMATION: Glycation (4) [1 4 29 34]
<220> FEATURE:
<221> NAME/KEY: MOD_RES
<222> LOCATION: (5)..(43)
<223> OTHER INFORMATION: Carboxymethyl C (9) [5 6 16 43]
<220> FEATURE:
<221> NAME/KEY: MOD_RES
<222> LOCATION: (12)..(12)
<223> OTHER INFORMATION: Deamidation N [12]

<400> SEQUENCE: 707

Lys Val Thr Lys Cys Cys Thr Glu Ser Leu Val Asn Arg Arg Pro Cys
1               5                   10                  15

Phe Ser Ala Leu Thr Pro Asp Glu Thr Tyr Val Pro Lys Ala Phe Asp
            20                  25                  30

Glu Lys Leu Phe Thr Phe His Ala Asp Ile Cys Thr Leu Pro Asp Thr
        35                  40                  45

Glu

<210> SEQ ID NO 708
<211> LENGTH: 47
<212> TYPE: PRT
<213> ORGANISM: Homo sapiens
<220> FEATURE:
<221> NAME/KEY: MOD_RES
<222> LOCATION: (1)..(47)
<223> OTHER INFORMATION: Glycation [?]
<220> FEATURE:
<221> NAME/KEY: MOD_RES
<222> LOCATION: (1)..(47)
<223> OTHER INFORMATION: Glycation (2) [2 ?]
<220> FEATURE:
<221> NAME/KEY: MOD_RES
<222> LOCATION: (5)..(43)
<223> OTHER INFORMATION: Carboxymethyl C (4) [5 6 16 43]
<220> FEATURE:
<221> NAME/KEY: MOD_RES
<222> LOCATION: (12)..(12)
<223> OTHER INFORMATION: Deamidation N [12]

<400> SEQUENCE: 708

Lys Val Thr Lys Cys Cys Thr Glu Ser Leu Val Asn Arg Arg Pro Cys
1               5                   10                  15

Phe Ser Ala Leu Thr Pro Asp Glu Thr Tyr Val Pro Lys Ala Phe Asp
            20                  25                  30

Glu Lys Leu Phe Thr Phe His Ala Asp Ile Cys Thr Leu Pro Asp
        35                  40                  45

<210> SEQ ID NO 709
<211> LENGTH: 45
```

```
<212> TYPE: PRT
<213> ORGANISM: Homo sapiens
<220> FEATURE:
<221> NAME/KEY: MOD_RES
<222> LOCATION: (1)..(39)
<223> OTHER INFORMATION: Carboxymethyl C (4) [1 2 12 39]
<220> FEATURE:
<221> NAME/KEY: MOD_RES
<222> LOCATION: (1)..(45)
<223> OTHER INFORMATION: Glycation [?]
<220> FEATURE:
<221> NAME/KEY: MOD_RES
<222> LOCATION: (8)..(8)
<223> OTHER INFORMATION: Deamidation N [8]

<400> SEQUENCE: 709

Cys Cys Thr Glu Ser Leu Val Asn Arg Arg Pro Cys Phe Ser Ala Leu
1               5                   10                  15

Thr Pro Asp Glu Thr Tyr Val Pro Lys Ala Phe Asp Glu Lys Leu Phe
            20                  25                  30

Thr Phe His Ala Asp Ile Cys Thr Leu Pro Asp Thr Glu
        35                  40                  45

<210> SEQ ID NO 710
<211> LENGTH: 7
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Glycation (2) [1 4]
<220> FEATURE:
<221> NAME/KEY: MOD_RES
<222> LOCATION: (5)..(6)
<223> OTHER INFORMATION: Carboxymethyl C(2) [5 6]

<400> SEQUENCE: 710

Lys Val Thr Lys Cys Cys Thr
1               5

<210> SEQ ID NO 711
<211> LENGTH: 5
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Glycation [?]
<220> FEATURE:
<221> NAME/KEY: MOD_RES
<222> LOCATION: (5)..(5)
<223> OTHER INFORMATION: Carboxymethyl C [5]

<400> SEQUENCE: 711

Lys Val Thr Lys Cys
1               5

<210> SEQ ID NO 712
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (3)..(4)
<223> OTHER INFORMATION: Carboxymethyl C (2) [3 4]

<400> SEQUENCE: 712
```

```
Thr Lys Cys Cys Thr Glu
1               5

<210> SEQ ID NO 713
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (2)..(3)
<223> OTHER INFORMATION: Carboxymethyl C (2) [2 3]

<400> SEQUENCE: 713

Lys Cys Cys Thr Glu
1               5

<210> SEQ ID NO 714
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Glycation [?]
<220> FEATURE:
<221> NAME/KEY: MOD_RES
<222> LOCATION: (8)..(35)
<223> OTHER INFORMATION: Carboxymethyl C (2) [8 35]

<400> SEQUENCE: 714

Ser Leu Val Asn Arg Arg Pro Cys Phe Ser Ala Leu Thr Pro Asp Glu
1               5                   10                  15

Thr Tyr Val Pro Lys Ala Phe Asp Glu Lys Leu Phe Thr Phe His Ala
            20                  25                  30

Asp Ile Cys Thr Leu Pro Asp Thr
            35                  40

<210> SEQ ID NO 715
<211> LENGTH: 32
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (8)..(8)
<223> OTHER INFORMATION: Carboxymethyl C [8]

<400> SEQUENCE: 715

Ser Leu Val Asn Arg Arg Pro Cys Phe Ser Ala Leu Thr Pro Asp Glu
1               5                   10                  15

Thr Tyr Val Pro Lys Ala Phe Asp Glu Lys Leu Phe Thr Phe His Ala
            20                  25                  30

<210> SEQ ID NO 716
<211> LENGTH: 40
<212> TYPE: PRT
<213> ORGANISM: Homo sapiens
<220> FEATURE:
<221> NAME/KEY: MOD_RES
<222> LOCATION: (1)..(40)
<223> OTHER INFORMATION: Glycation [?]
```

```
<220> FEATURE:
<221> NAME/KEY: MOD_RES
<222> LOCATION: (3)..(3)
<223> OTHER INFORMATION: Deamidation N[3]
<220> FEATURE:
<221> NAME/KEY: MOD_RES
<222> LOCATION: (7)..(34)
<223> OTHER INFORMATION: Carboxymethyl C (2) [7 34]
<220> FEATURE:
<221> NAME/KEY: MOD_RES
<222> LOCATION: (20)..(25)
<223> OTHER INFORMATION: Glycation (2) [20 25]

<400> SEQUENCE: 716

Leu Val Asn Arg Arg Pro Cys Phe Ser Ala Leu Thr Pro Asp Glu Thr
1               5                   10                  15

Tyr Val Pro Lys Ala Phe Asp Glu Lys Leu Phe Thr Phe His Ala Asp
            20                  25                  30

Ile Cys Thr Leu Pro Asp Thr Glu
            35                  40

<210> SEQ ID NO 717
<211> LENGTH: 33
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Carboxymethyl C [27]

<400> SEQUENCE: 717

Phe Ser Ala Leu Thr Pro Asp Glu Thr Tyr Val Pro Lys Ala Phe Asp
1               5                   10                  15

Glu Lys Leu Phe Thr Phe His Ala Asp Ile Cys Thr Leu Pro Asp Thr
            20                  25                  30

Glu

<210> SEQ ID NO 718
<211> LENGTH: 46
<212> TYPE: PRT
<213> ORGANISM: Homo sapiens
<220> FEATURE:
<221> NAME/KEY: MOD_RES
<222> LOCATION: (1)..(46)
<223> OTHER INFORMATION: Glycation (4) [4 ?]
<220> FEATURE:
<221> NAME/KEY: MOD_RES
<222> LOCATION: (3)..(3)
<223> OTHER INFORMATION: Deamidation N [3]
<220> FEATURE:
<221> NAME/KEY: MOD_RES
<222> LOCATION: (7)..(34)
<223> OTHER INFORMATION: Carboxymethyl C (2) [7 34]
<220> FEATURE:
<221> NAME/KEY: MOD_RES
<222> LOCATION: (20)..(45)
<223> OTHER INFORMATION: Glycation (5) [20 25 41 44 45]

<400> SEQUENCE: 718

Leu Val Asn Arg Arg Pro Cys Phe Ser Ala Leu Thr Pro Asp Glu Thr
1               5                   10                  15

Tyr Val Pro Lys Ala Phe Asp Glu Lys Leu Phe Thr Phe His Ala Asp
            20                  25                  30

Ile Cys Thr Leu Pro Asp Thr Glu Lys Gln Ile Lys Lys Gln
            35                  40                  45

<210> SEQ ID NO 719
```

```
<211> LENGTH: 46
<212> TYPE: PRT
<213> ORGANISM: Homo sapiens
<220> FEATURE:
<221> NAME/KEY: MOD_RES
<222> LOCATION: (6)..(33)
<223> OTHER INFORMATION: Carboxymethyl C (2) [6 33]
<220> FEATURE:
<221> NAME/KEY: MOD_RES
<222> LOCATION: (19)..(44)
<223> OTHER INFORMATION: Glycation (5) [19 24 40 43 44]

<400> SEQUENCE: 719

Val Asn Arg Arg Pro Cys Phe Ser Ala Leu Thr Pro Asp Glu Thr Tyr
1               5                   10                  15

Val Pro Lys Ala Phe Asp Glu Lys Leu Phe Thr Phe His Ala Asp Ile
                20                  25                  30

Cys Thr Leu Pro Asp Thr Glu Lys Gln Ile Lys Lys Gln Thr
                35                  40                  45

<210> SEQ ID NO 720
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (8)..(8)
<223> OTHER INFORMATION: Carboxymethyl C [8]

<400> SEQUENCE: 720

Ser Leu Val Asn Arg Arg Pro Cys
1               5

<210> SEQ ID NO 721
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 721

His Phe Lys Gly Leu Val
1               5

<210> SEQ ID NO 722
<211> LENGTH: 4
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 722

His Phe Lys Gly
1

<210> SEQ ID NO 723
<211> LENGTH: 10
<212> TYPE: PRT
<213> ORGANISM: Homo sapiens
<220> FEATURE:
<221> NAME/KEY: MOD_RES
```

```
<222> LOCATION: (6)..(6)
<223> OTHER INFORMATION: Carboxymethyl C [6]

<400> SEQUENCE: 723

Gln Tyr Leu Gln Gln Cys Pro Phe Asp Glu
1               5                   10

<210> SEQ ID NO 724
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Carboxymethyl C [4]

<400> SEQUENCE: 724

Leu Gln Gln Cys Pro Phe Asp Glu
1               5

<210> SEQ ID NO 725
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C (2)

<400> SEQUENCE: 725

Gln Cys Pro Phe Asp Glu
1               5

<210> SEQ ID NO 726
<211> LENGTH: 21
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Carboxymethyl C [19]

<400> SEQUENCE: 726

Thr Tyr Val Pro Lys Ala Phe Asp Glu Lys Leu Phe Thr Phe His Ala
1               5                   10                  15

Asp Ile Cys Thr Leu
            20

<210> SEQ ID NO 727
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation [?]

<400> SEQUENCE: 727

Thr Tyr Val Pro Lys Ala Phe Asp Glu Lys Leu Phe Thr Phe His Ala
1               5                   10                  15

Asp Ile

<210> SEQ ID NO 728
<211> LENGTH: 21
<212> TYPE: PRT
<213> ORGANISM: Homo sapiens
<220> FEATURE:
```

```
<221> NAME/KEY: MOD_RES
<222> LOCATION: (1)..(16)
<223> OTHER INFORMATION: Glycation (2) [1 6]
<220> FEATURE:
<221> NAME/KEY: MOD_RES
<222> LOCATION: (15)..(15)
<223> OTHER INFORMATION: Carboxymethyl C [15]

<400> SEQUENCE: 728

Lys Ala Phe Asp Glu Lys Leu Phe Thr Phe His Ala Asp Ile Cys Thr
1               5                   10                  15

Leu Pro Asp Thr Glu
            20

<210> SEQ ID NO 729
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Carboxymethyl C [14]

<400> SEQUENCE: 729

Ala Phe Asp Glu Lys Leu Phe Thr Phe His Ala Asp Ile Cys Thr Leu
1               5                   10                  15

Pro Asp Thr Glu
            20

<210> SEQ ID NO 730
<211> LENGTH: 43
<212> TYPE: PRT
<213> ORGANISM: Homo sapiens
<220> FEATURE:
<221> NAME/KEY: MOD_RES
<222> LOCATION: (2)..(43)
<223> OTHER INFORMATION: Glycation (2) [2 ?]
<220> FEATURE:
<221> NAME/KEY: MOD_RES
<222> LOCATION: (19)..(19)
<223> OTHER INFORMATION: Carboxymethyl C (19)

<400> SEQUENCE: 730

Thr Tyr Val Pro Lys Ala Phe Asp Glu Lys Leu Phe Thr Phe His Ala
1               5                   10                  15

Asp Ile Cys Thr Leu Pro Asp Thr Glu Lys Gln Ile Lys Gln Thr
                20                  25                  30

Ala Leu Val Glu Leu Leu Lys His Lys Pro Lys
        35                  40

<210> SEQ ID NO 731
<211> LENGTH: 39
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Carboxymethyl C (19)

<400> SEQUENCE: 731

Thr Tyr Val Pro Lys Ala Phe Asp Glu Lys Leu Phe Thr Phe His Ala
1               5                   10                  15

Asp Ile Cys Thr Leu Pro Asp Thr Glu Lys Gln Ile Lys Gln Thr
                20                  25                  30

Ala Leu Val Glu Leu Leu Lys
        35
```

```
<210> SEQ ID NO 732
<211> LENGTH: 45
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Carboxymethyl C [18]
<220> FEATURE:
<221> NAME/KEY: MOD_RES
<222> LOCATION: (45)..(45)
<223> OTHER INFORMATION: Glycation [?]

<400> SEQUENCE: 732

Tyr Val Pro Lys Ala Phe Asp Glu Lys Leu Phe Thr Phe His Ala Asp
1               5                   10                  15

Ile Cys Thr Leu Pro Asp Thr Glu Lys Gln Ile Lys Lys Gln Thr Ala
            20                  25                  30

Leu Val Glu Leu Leu Lys His Lys Pro Lys Ala Thr Glu
        35                  40                  45

<210> SEQ ID NO 733
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Glycation [5]

<400> SEQUENCE: 733

Thr Tyr Val Pro Lys Ala
1               5

<210> SEQ ID NO 734
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 734

Val Pro Lys Ala Phe Asp Glu
1               5

<210> SEQ ID NO 735
<211> LENGTH: 27
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Glycation (3) [3?]
<220> FEATURE:
<221> NAME/KEY: MOD_RES
<222> LOCATION: (10)..(10)
<223> OTHER INFORMATION: Carboxymethyl C [10]

<400> SEQUENCE: 735

Lys Leu Phe Thr Phe His Ala Asp Ile Cys Thr Leu Pro Asp Thr Glu
1               5                   10                  15

Lys Gln Ile Lys Lys Gln Thr Ala Leu Val Glu
            20                  25
```

```
<210> SEQ ID NO 736
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation (2) [2 ?]

<400> SEQUENCE: 736

Thr Leu Pro Asp Thr Glu Lys Gln Ile Lys Lys Gln Thr Ala Leu Val
1               5                   10                  15

Glu

<210> SEQ ID NO 737
<211> LENGTH: 37
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Carboxymethyl C (10]

<400> SEQUENCE: 737

Lys Leu Phe Thr Phe His Ala Asp Ile Cys Thr Leu Pro Asp Thr Glu
1               5                   10                  15

Lys Gln Ile Lys Lys Gln Thr Ala Leu Val Glu Leu Leu Lys His Lys
            20                  25                  30

Pro Lys Ala Thr Glu
            35

<210> SEQ ID NO 738
<211> LENGTH: 36
<212> TYPE: PRT
<213> ORGANISM: Homo sapiens
<220> FEATURE:
<221> NAME/KEY: MOD_RES
<222> LOCATION: (1)..(36)
<223> OTHER INFORMATION: Glycation (4) [4 ?]
<220> FEATURE:
<221> NAME/KEY: MOD_RES
<222> LOCATION: (10)..(10)
<223> OTHER INFORMATION: Carboxymethyl C [10]

<400> SEQUENCE: 738

Lys Leu Phe Thr Phe His Ala Asp Ile Cys Thr Leu Pro Asp Thr Glu
1               5                   10                  15

Lys Gln Ile Lys Lys Gln Thr Ala Leu Val Glu Leu Leu Lys His Lys
            20                  25                  30

Pro Lys Ala Thr
            35

<210> SEQ ID NO 739
<211> LENGTH: 30
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Carboxymethyl C [10]

<400> SEQUENCE: 739

Lys Leu Phe Thr Phe His Ala Asp Ile Cys Thr Leu Pro Asp Thr Glu
1               5                   10                  15

Lys Gln Ile Lys Lys Gln Thr Ala Leu Val Glu Leu Leu Lys
            20                  25                  30
```

```
<210> SEQ ID NO 740
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation (5) [5 ?]

<400> SEQUENCE: 740

Thr Glu Lys Gln Ile Lys Lys Gln Thr Ala Leu Val Glu Leu Leu Lys
1               5                   10                  15

His Lys Pro Lys Ala Thr Glu
            20

<210> SEQ ID NO 741
<211> LENGTH: 31
<212> TYPE: PRT
<213> ORGANISM: Homo sapiens
<220> FEATURE:
<221> NAME/KEY: MOD_RES
<222> LOCATION: (1)..(31)
<223> OTHER INFORMATION: Glycation (3) [3 ?]
<220> FEATURE:
<221> NAME/KEY: MOD_RES
<222> LOCATION: (4)..(4)
<223> OTHER INFORMATION: Carboxymethyl C [4]

<400> SEQUENCE: 741

Ala Asp Ile Cys Thr Leu Pro Asp Thr Glu Lys Gln Ile Lys Lys Gln
1               5                   10                  15

Thr Ala Leu Val Glu Leu Leu Lys His Lys Pro Lys Ala Thr Glu
            20                  25                  30

<210> SEQ ID NO 742
<211> LENGTH: 38
<212> TYPE: PRT
<213> ORGANISM: Homo sapiens
<220> FEATURE:
<221> NAME/KEY: MOD_RES
<222> LOCATION: (1)..(38)
<223> OTHER INFORMATION: Glycation (6) [6 ?]
<220> FEATURE:
<221> NAME/KEY: MOD_RES
<222> LOCATION: (1)..(34)
<223> OTHER INFORMATION: Glycation (7) [1 17 20 21 30 32 34]
<220> FEATURE:
<221> NAME/KEY: MOD_RES
<222> LOCATION: (10)..(10)
<223> OTHER INFORMATION: Carboxymethyl C (10)

<400> SEQUENCE: 742

Lys Leu Phe Thr Phe His Ala Asp Ile Cys Thr Leu Pro Asp Thr Glu
1               5                   10                  15

Lys Gln Ile Lys Lys Gln Thr Ala Leu Val Glu Leu Leu Lys His Lys
            20                  25                  30

Pro Lys Ala Thr Glu Glu
        35

<210> SEQ ID NO 743
<211> LENGTH: 24
<212> TYPE: PRT
<213> ORGANISM: Homo sapiens
<220> FEATURE:
<221> NAME/KEY: MOD_RES
<222> LOCATION: (1)..(24)
<223> OTHER INFORMATION: Glycation (4) [4 ?]
```

```
<400> SEQUENCE: 743

Thr Glu Lys Gln Ile Lys Lys Gln Thr Ala Leu Val Glu Leu Leu Lys
1               5                   10                  15

His Lys Pro Lys Ala Thr Glu Glu
            20

<210> SEQ ID NO 744
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation (4) [4 ?]

<400> SEQUENCE: 744

Glu Lys Gln Ile Lys Lys Gln Thr Ala Leu Val Glu Leu Leu Lys His
1               5                   10                  15

Lys Pro Lys Ala Thr Glu Glu
            20

<210> SEQ ID NO 745
<211> LENGTH: 35
<212> TYPE: PRT
<213> ORGANISM: Homo sapiens
<220> FEATURE:
<221> NAME/KEY: MOD_RES
<222> LOCATION: (1)..(35)
<223> OTHER INFORMATION: Glycation [?]
<220> FEATURE:
<221> NAME/KEY: MOD_RES
<222> LOCATION: (7)..(7)
<223> OTHER INFORMATION: Carboxymethyl C [7]

<400> SEQUENCE: 745

Thr Phe His Ala Asp Ile Cys Thr Leu Pro Asp Thr Glu Lys Gln Ile
1               5                   10                  15

Lys Lys Gln Thr Ala Leu Val Glu Leu Leu Lys His Lys Pro Lys Ala
            20                  25                  30

Thr Glu Glu
        35

<210> SEQ ID NO 746
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 746

Lys Leu Phe Thr
1

<210> SEQ ID NO 747
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 747
```

```
Phe Thr Phe His Ala Asp Ile Cys Thr Leu Pro Asp Thr Glu
1               5                   10
```

<210> SEQ ID NO 748
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 748

```
His Ala Asp Ile Cys Thr Leu Pro Asp Thr Glu
1               5                   10
```

<210> SEQ ID NO 749
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 749

```
Asp Ile Cys Thr Leu Pro Asp Thr Glu
1               5
```

<210> SEQ ID NO 750
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: Glycation (4) [2 ?]

<400> SEQUENCE: 750

```
Lys Gln Ile Lys Lys Gln Thr Ala Leu Val Glu
1               5                   10
```

<210> SEQ ID NO 751
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Glycation (?]

<400> SEQUENCE: 751

```
Lys Gln Ile Lys Lys Gln Thr Ala Leu Val Glu Leu Leu Lys His Lys
1               5                   10                  15

Pro Lys Ala Thr
            20
```

<210> SEQ ID NO 752
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation (4) [?]

<400> SEQUENCE: 752

```
Lys Gln Ile Lys Lys Gln Thr Ala Leu Val Glu Leu Leu Lys His Lys
1               5                   10                  15
```

-continued

```
                1               5                  10                 15

Pro Lys Ala

<210> SEQ ID NO 753
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation (4) [4 ?]

<400> SEQUENCE: 753

Lys Gln Ile Lys Lys Gln Thr Ala Leu Val Glu Leu Leu Lys His Lys
1               5                  10                 15

Pro

<210> SEQ ID NO 754
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: Glycation (3) [3 ?]

<400> SEQUENCE: 754

Lys Gln Ile Lys Lys Gln Thr Ala Leu Val Glu Leu Leu Lys His Lys
1               5                  10                 15

<210> SEQ ID NO 755
<211> LENGTH: 15
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: Glycation (4) [1 4 5 14]

<400> SEQUENCE: 755

Lys Gln Ile Lys Lys Gln Thr Ala Leu Val Glu Leu Leu Lys His
1               5                  10                 15

<210> SEQ ID NO 756
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation (2) [2 ?]

<400> SEQUENCE: 756

Ile Lys Lys Gln Thr Ala Leu Val Glu Leu Leu Lys His Lys Pro Lys
1               5                  10                 15

Ala Thr Glu

<210> SEQ ID NO 757
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation (3) [3 ?]

<400> SEQUENCE: 757
```

```
Lys Gln Thr Ala Leu Val Glu Leu Leu Lys His Lys Pro Lys Ala Thr
1               5                   10                  15

Glu

<210> SEQ ID NO 758
<211> LENGTH: 16
<212> TYPE: PRT
<213> ORGANISM: Homo sapiens
<220> FEATURE:
<221> NAME/KEY: MOD_RES
<222> LOCATION: (9)..(13)
<223> OTHER INFORMATION: Glycation (3) [9 11 13]

<400> SEQUENCE: 758

Gln Thr Ala Leu Val Glu Leu Leu Lys His Lys Pro Lys Ala Thr Glu
1               5                   10                  15

<210> SEQ ID NO 759
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation [?]

<400> SEQUENCE: 759

Lys Lys Gln Thr Ala Leu Val Glu Leu Leu Lys His Lys Pro Lys Ala
1               5                   10                  15

Thr Glu Glu

<210> SEQ ID NO 760
<211> LENGTH: 28
<212> TYPE: PRT
<213> ORGANISM: Homo sapiens
<220> FEATURE:
<221> NAME/KEY: MOD_RES
<222> LOCATION: (1)..(28)
<223> OTHER INFORMATION: Glycation (?)
<220> FEATURE:
<221> NAME/KEY: MOD_RES
<222> LOCATION: (28)..(28)
<223> OTHER INFORMATION: Oxidation M [28]

<400> SEQUENCE: 760

Lys Gln Ile Lys Lys Gln Thr Ala Leu Val Glu Leu Leu Lys His Lys
1               5                   10                  15

Pro Lys Ala Thr Glu Glu Gln Leu Lys Thr Val Met
            20                  25

<210> SEQ ID NO 761
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation (4) [4 ?]

<400> SEQUENCE: 761

Lys Gln Ile Lys Lys Gln Thr Ala Leu Val Glu Leu Leu Lys His Lys
1               5                   10                  15

Pro Lys Ala Thr Glu Glu Gln Leu Lys Thr
            20                  25
```

```
<210> SEQ ID NO 762
<211> LENGTH: 25
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation (5) [5 ?]

<400> SEQUENCE: 762

Lys Gln Ile Lys Lys Gln Thr Ala Leu Val Glu Leu Leu Lys His Lys
1               5                   10                  15

Pro Lys Ala Thr Glu Glu Gln Leu Lys
            20                  25

<210> SEQ ID NO 763
<211> LENGTH: 28
<212> TYPE: PRT
<213> ORGANISM: Homo sapiens
<220> FEATURE:
<221> NAME/KEY: MOD_RES
<222> LOCATION: (1)..(28)
<223> OTHER INFORMATION: Glycation (?]
<220> FEATURE:
<221> NAME/KEY: MOD_RES
<222> LOCATION: (27)..(27)
<223> OTHER INFORMATION: Oxidation M [27]

<400> SEQUENCE: 763

Gln Ile Lys Lys Gln Thr Ala Leu Val Glu Leu Leu Lys His Lys Pro
1               5                   10                  15

Lys Ala Thr Glu Glu Gln Leu Lys Thr Val Met Glu
            20                  25

<210> SEQ ID NO 764
<211> LENGTH: 27
<212> TYPE: PRT
<213> ORGANISM: Homo sapiens
<220> FEATURE:
<221> NAME/KEY: MOD_RES
<222> LOCATION: (1)..(27)
<223> OTHER INFORMATION: Glycation [?]
<220> FEATURE:
<221> NAME/KEY: MOD_RES
<222> LOCATION: (26)..(26)
<223> OTHER INFORMATION: Oxidation M [26]

<400> SEQUENCE: 764

Ile Lys Lys Gln Thr Ala Leu Val Glu Leu Leu Lys His Lys Pro Lys
1               5                   10                  15

Ala Thr Glu Glu Gln Leu Lys Thr Val Met Glu
            20                  25

<210> SEQ ID NO 765
<211> LENGTH: 24
<212> TYPE: PRT
<213> ORGANISM: Homo sapiens
<220> FEATURE:
<221> NAME/KEY: MOD_RES
<222> LOCATION: (9)..(20)
<223> OTHER INFORMATION: Glycation (4) [9 11 13 20]
<220> FEATURE:
<221> NAME/KEY: MOD_RES
<222> LOCATION: (23)..(23)
<223> OTHER INFORMATION: Oxidation M [23]

<400> SEQUENCE: 765

Gln Thr Ala Leu Val Glu Leu Leu Lys His Lys Pro Lys Ala Thr Glu
1               5                   10                  15
```

Glu Gln Leu Lys Thr Val Met Glu
            20

<210> SEQ ID NO 766
<211> LENGTH: 21
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Glycation (2) [2 ?]
<220> FEATURE:
<221> NAME/KEY: MOD_RES
<222> LOCATION: (20)..(20)
<223> OTHER INFORMATION: Oxidation M [20]

<400> SEQUENCE: 766

Leu Val Glu Leu Leu Lys His Lys Pro Lys Ala Thr Glu Glu Gln Leu
1               5                   10                  15

Lys Thr Val Met Glu
            20

<210> SEQ ID NO 767
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Glycation [?]

<400> SEQUENCE: 767

Val Glu Leu Leu Lys His Lys Pro Lys Ala Thr Glu Glu Gln Leu Lys
1               5                   10                  15

Thr Val Met Glu
            20

<210> SEQ ID NO 768
<211> LENGTH: 5
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Glycation (2) [2 ?]

<400> SEQUENCE: 768

Lys Gln Ile Lys Lys
1               5

<210> SEQ ID NO 769
<211> LENGTH: 4
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Glycation [?]

<400> SEQUENCE: 769

Lys Gln Ile Lys
1

<210> SEQ ID NO 770
<211> LENGTH: 8
<212> TYPE: PRT
<213> ORGANISM: Homo sapiens

```
<220> FEATURE:
<221> NAME/KEY: MOD_RES
<222> LOCATION: (1)..(8)
<223> OTHER INFORMATION: Glycation [?]

<400> SEQUENCE: 770

Lys Lys Gln Thr Ala Leu Val Glu
1               5

<210> SEQ ID NO 771
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: Glycation [?]

<400> SEQUENCE: 771

Leu Leu Lys His Lys Pro Lys Ala Thr Glu Glu
1               5                   10

<210> SEQ ID NO 772
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation (2) [2 ?]
<220> FEATURE:
<221> NAME/KEY: MOD_RES
<222> LOCATION: (17)..(17)
<223> OTHER INFORMATION: Oxidation M (17]

<400> SEQUENCE: 772

Leu Leu Lys His Lys Pro Lys Ala Thr Glu Glu Gln Leu Lys Thr Val
1               5                   10                  15

Met Glu

<210> SEQ ID NO 773
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation (3) [3 ?]
<220> FEATURE:
<221> NAME/KEY: MOD_RES
<222> LOCATION: (2)..(13)
<223> OTHER INFORMATION: Glycation (4) [2 4 6 13]
<220> FEATURE:
<221> NAME/KEY: MOD_RES
<222> LOCATION: (16)..(16)
<223> OTHER INFORMATION: Oxidation M (16]

<400> SEQUENCE: 773

Leu Lys His Lys Pro Lys Ala Thr Glu Glu Gln Leu Lys Thr Val Met
1               5                   10                  15

Glu

<210> SEQ ID NO 774
<211> LENGTH: 9
<212> TYPE: PRT
<213> ORGANISM: Homo sapiens
<220> FEATURE:
<221> NAME/KEY: MOD_RES
<222> LOCATION: (5)..(5)
```

```
<223> OTHER INFORMATION: Glycation [5]
<220> FEATURE:
<221> NAME/KEY: MOD_RES
<222> LOCATION: (8)..(8)
<223> OTHER INFORMATION: Oxidation M [8]

<400> SEQUENCE: 774

Glu Glu Gln Leu Lys Thr Val Met Glu
1               5

<210> SEQ ID NO 775
<211> LENGTH: 21
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Glycation [?]
<220> FEATURE:
<221> NAME/KEY: MOD_RES
<222> LOCATION: (17)..(17)
<223> OTHER INFORMATION: Oxidation M [17]
<220> FEATURE:
<221> NAME/KEY: MOD_RES
<222> LOCATION: (19)..(19)
<223> OTHER INFORMATION: Deamidation N [19]

<400> SEQUENCE: 775

Leu Leu Lys His Lys Pro Lys Ala Thr Glu Glu Gln Leu Lys Thr Val
1               5                   10                  15

Met Glu Asn Phe Val
            20

<210> SEQ ID NO 776
<211> LENGTH: 28
<212> TYPE: PRT
<213> ORGANISM: Homo sapiens
<220> FEATURE:
<221> NAME/KEY: MOD_RES
<222> LOCATION: (1)..(28)
<223> OTHER INFORMATION: Glycation (4) [4 ?]
<220> FEATURE:
<221> NAME/KEY: MOD_RES
<222> LOCATION: (17)..(17)
<223> OTHER INFORMATION: Oxidation M [17]
<220> FEATURE:
<221> NAME/KEY: MOD_RES
<222> LOCATION: (27)..(28)
<223> OTHER INFORMATION: Carboxymethyl C (2) [27 28]

<400> SEQUENCE: 776

Leu Leu Lys His Lys Pro Lys Ala Thr Glu Glu Gln Leu Lys Thr Val
1               5                   10                  15

Met Glu Asn Phe Val Ala Phe Val Asp Lys Cys Cys
            20                  25

<210> SEQ ID NO 777
<211> LENGTH: 26
<212> TYPE: PRT
<213> ORGANISM: Homo sapiens
<220> FEATURE:
<221> NAME/KEY: MOD_RES
<222> LOCATION: (1)..(26)
<223> OTHER INFORMATION: Glycation (3) [3 ?]

<400> SEQUENCE: 777

Leu Leu Lys His Lys Pro Lys Ala Thr Glu Glu Gln Leu Lys Thr Val
1               5                   10                  15

Met Glu Asn Phe Val Ala Phe Val Asp Lys
```

```
                    20                  25

<210> SEQ ID NO 778
<211> LENGTH: 28
<212> TYPE: PRT
<213> ORGANISM: Homo sapiens
<220> FEATURE:
<221> NAME/KEY: MOD_RES
<222> LOCATION: (1)..(28)
<223> OTHER INFORMATION: Glycation (3) [3 ?]
<220> FEATURE:
<221> NAME/KEY: MOD_RES
<222> LOCATION: (11)..(11)
<223> OTHER INFORMATION: Oxidation M [11]
<220> FEATURE:
<221> NAME/KEY: MOD_RES
<222> LOCATION: (21)..(22)
<223> OTHER INFORMATION: Carboxymethyl C (2) [21 22]

<400> SEQUENCE: 778

Lys Ala Thr Glu Glu Gln Leu Lys Thr Val Met Glu Asn Phe Val Ala
1               5                   10                  15

Phe Val Asp Lys Cys Cys Ala Ala Asp Asp Lys Glu
            20                  25

<210> SEQ ID NO 779
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Glycation [?]

<400> SEQUENCE: 779

Leu Leu Lys His Lys Pro Lys Ala Thr
1               5

<210> SEQ ID NO 780
<211> LENGTH: 4
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 780

Leu Leu Lys His
1

<210> SEQ ID NO 781
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Glycation [?]

<400> SEQUENCE: 781

Leu Lys His Lys Pro Lys Ala Thr Glu
1               5

<210> SEQ ID NO 782
<211> LENGTH: 7
<212> TYPE: PRT
<213> ORGANISM: Homo sapiens
<220> FEATURE:
```

```
<221> NAME/KEY: MOD_RES
<222> LOCATION: (1)..(7)
<223> OTHER INFORMATION: Glycation [?]

<400> SEQUENCE: 782

His Lys Pro Lys Ala Thr Glu
1               5

<210> SEQ ID NO 783
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 783

Lys Ala Thr Glu
1

<210> SEQ ID NO 784
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 784

Glu Gln Leu Lys Thr
1               5

<210> SEQ ID NO 785
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 785

Glu Gln Leu Lys Thr Val Met Glu Asn
1               5

<210> SEQ ID NO 786
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation [?]
<220> FEATURE:
<221> NAME/KEY: MOD_RES
<222> LOCATION: (9)..(9)
<223> OTHER INFORMATION: Deamidation N [9]
<220> FEATURE:
<221> NAME/KEY: MOD_RES
<222> LOCATION: (17)..(18)
<223> OTHER INFORMATION: Carboxymethyl C (2) [17 18]

<400> SEQUENCE: 786

Glu Gln Leu Lys Thr Val Met Glu Asn Phe Val Ala Phe Val Asp Lys
1               5                   10                  15

Cys Cys Ala
```

<210> SEQ ID NO 787
<211> LENGTH: 30
<212> TYPE: PRT
<213> ORGANISM: Homo sapiens
<220> FEATURE:
<221> NAME/KEY: MOD_RES
<222> LOCATION: (17)..(26)
<223> OTHER INFORMATION: Carboxymethyl C (3) [17 18 26]

<400> SEQUENCE: 787

Glu Gln Leu Lys Thr Val Met Glu Asn Phe Val Ala Phe Val Asp Lys
1               5                   10                  15

Cys Cys Ala Ala Asp Asp Lys Glu Ala Cys Phe Ala Val Glu
            20                  25                  30

<210> SEQ ID NO 788
<211> LENGTH: 26
<212> TYPE: PRT
<213> ORGANISM: Homo sapiens
<220> FEATURE:
<221> NAME/KEY: MOD_RES
<222> LOCATION: (4)..(23)
<223> OTHER INFORMATION: Glycation (3) [4 16 23]
<220> FEATURE:
<221> NAME/KEY: MOD_RES
<222> LOCATION: (9)..(9)
<223> OTHER INFORMATION: Deamidation N [9]
<220> FEATURE:
<221> NAME/KEY: MOD_RES
<222> LOCATION: (17)..(26)
<223> OTHER INFORMATION: Carboxymethyl C (3) [17 18 26]

<400> SEQUENCE: 788

Glu Gln Leu Lys Thr Val Met Glu Asn Phe Val Ala Phe Val Asp Lys
1               5                   10                  15

Cys Cys Ala Ala Asp Asp Lys Glu Ala Cys
            20                  25

<210> SEQ ID NO 789
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation (2) [2 ?]
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (16)..(17)
<223> OTHER INFORMATION: Carboxymethyl C (2) [16 17]

<400> SEQUENCE: 789

Gln Leu Lys Thr Val Met Glu Asn Phe Val Ala Phe Val Asp Lys Cys
1               5                   10                  15

Cys Ala Ala Asp Asp Lys Glu
            20

<210> SEQ ID NO 790
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

```
<220> FEATURE:
<221> NAME/KEY: MOD_RES
<222> LOCATION: (6)..(6)
<223> OTHER INFORMATION: Oxidation M [6]

<400> SEQUENCE: 790

Gln Leu Lys Thr Val Met Glu
1               5

<210> SEQ ID NO 791
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation (2) [2 ?]
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (16)..(17)
<223> OTHER INFORMATION: Carboxymethyl C (2) [16 17]

<400> SEQUENCE: 791

Gln Leu Lys Thr Val Met Glu Asn Phe Val Ala Phe Val Asp Lys Cys
1               5                   10                  15

Cys Ala Ala Asp Asp Lys Glu
            20

<210> SEQ ID NO 792
<211> LENGTH: 23
<212> TYPE: PRT
<213> ORGANISM: Homo sapiens
<220> FEATURE:
<221> NAME/KEY: MOD_RES
<222> LOCATION: (1)..(23)
<223> OTHER INFORMATION: Glycation [2 ?]
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (16)..(17)
<223> OTHER INFORMATION: Carboxymethyl [16 17]

<400> SEQUENCE: 792

Gln Leu Lys Thr Val Met Glu Asn Phe Val Ala Phe Val Asp Lys Cys
1               5                   10                  15

Cys Ala Ala Asp Asp Lys Glu
            20

<210> SEQ ID NO 793
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation (3)
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (8)..(8)
<223> OTHER INFORMATION: Deamidation N [8]
```

```
<400> SEQUENCE: 793

Gln Leu Lys Thr Val Met Glu Asn
1               5

<210> SEQ ID NO 794
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: Glycation [?]
<220> FEATURE:
<221> NAME/KEY: MOD_RES
<222> LOCATION: (16)..(17)
<223> OTHER INFORMATION: Carboxymethyl C (2) [16 17]

<400> SEQUENCE: 794

Gln Leu Lys Thr Val Met Glu Asn Phe Val Ala Phe Val Asp Lys Cys
1               5                   10                  15
Cys Ala

<210> SEQ ID NO 795
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation M [6]
<220> FEATURE:
<221> NAME/KEY: MOD_RES
<222> LOCATION: (7)..(7)
<223> OTHER INFORMATION: GIycation [7]
<220> FEATURE:
<221> NAME/KEY: MOD_RES
<222> LOCATION: (8)..(8)
<223> OTHER INFORMATION: Deamidation N [8]
<220> FEATURE:
<221> NAME/KEY: MOD_RES
<222> LOCATION: (16)..(17)
<223> OTHER INFORMATION: Carboxymethyl C (2) [16 17]

<400> SEQUENCE: 795

Gln Leu Lys Thr Val Met Glu Asn Phe Val Ala Phe Val Asp Lys Cys
1               5                   10                  15
Cys

<210> SEQ ID NO 796
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Deamidation N [7]
<220> FEATURE:
<221> NAME/KEY: MOD_RES
<222> LOCATION: (15)..(16)
<223> OTHER INFORMATION: Carboxymethyl C (2) [15 16]

<400> SEQUENCE: 796

Leu Lys Thr Val Met Glu Asn Phe Val Ala Phe Val Asp Lys Cys Cys
1               5                   10                  15
Ala Ala Asp Asp Lys Glu
                20
```

```
<210> SEQ ID NO 797
<211> LENGTH: 21
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Oxidation M [4]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (14)..(15)
<223> OTHER INFORMATION: Carboxymethyl C (2) [14 15]

<400> SEQUENCE: 797

Lys Thr Val Met Glu Asn Phe Val Ala Phe Val Asp Lys Cys Cys Ala
1               5                   10                  15

Ala Asp Asp Lys Glu
            20

<210> SEQ ID NO 798
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: Glycation [?]
<220> FEATURE:
<221> NAME/KEY: MOD_RES
<222> LOCATION: (1)..(19)
<223> OTHER INFORMATION: Glycation [?], Glycation (2) [11 18]
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (11)..(18)
<223> OTHER INFORMATION: GIycation (2) [11 18]
<220> FEATURE:
<221> NAME/KEY: MOD_RES
<222> LOCATION: (12)..(13)
<223> OTHER INFORMATION: Carboxymethyl C (2) [12 13]

<400> SEQUENCE: 798

Val Met Glu Asn Phe Val Ala Phe Val Asp Lys Cys Cys Ala Ala Asp
1               5                   10                  15

Asp Lys Glu

<210> SEQ ID NO 799
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Deamidation N [3]
<220> FEATURE:
<221> NAME/KEY: MOD_RES
<222> LOCATION: (10)..(17)
<223> OTHER INFORMATION: Glycation (2) [10 17]
```

-continued

```
<220> FEATURE:
<221> NAME/KEY: MOD_RES
<222> LOCATION: (11)..(12)
<223> OTHER INFORMATION: Carboxymethyl C (2) [11 12]

<400> SEQUENCE: 799

Met Glu Asn Phe Val Ala Phe Val Asp Lys Cys Cys Ala Ala Asp Asp
1               5                   10                  15

Lys Glu

<210> SEQ ID NO 800
<211> LENGTH: 17
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Deamidation N [2]
<220> FEATURE:
<221> NAME/KEY: MOD_RES
<222> LOCATION: (9)..(16)
<223> OTHER INFORMATION: Glycation (2) [9 16]
<220> FEATURE:
<221> NAME/KEY: MOD_RES
<222> LOCATION: (10)..(11)
<223> OTHER INFORMATION: Carboxymethyl C (2) [10 11]

<400> SEQUENCE: 800

Glu Asn Phe Val Ala Phe Val Asp Lys Cys Cys Ala Ala Asp Asp Lys
1               5                   10                  15

Glu

<210> SEQ ID NO 801
<211> LENGTH: 27
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: Glycation (3) [1 13 20]
<220> FEATURE:
<221> NAME/KEY: MOD_RES
<222> LOCATION: (6)..(6)
<223> OTHER INFORMATION: Deamidation N [6]
<220> FEATURE:
<221> NAME/KEY: MOD_RES
<222> LOCATION: (14)..(23)
<223> OTHER INFORMATION: Carboxymethyl C (3) [14 15 23]

<400> SEQUENCE: 801

Lys Thr Val Met Glu Asn Phe Val Ala Phe Val Asp Lys Cys Cys Ala
1               5                   10                  15

Ala Asp Asp Lys Glu Ala Cys Phe Ala Val Glu
            20                  25

<210> SEQ ID NO 802
<211> LENGTH: 26
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Oxidation M [3]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (13)..(22)
```

-continued

<223> OTHER INFORMATION: Carboxymethyl C (3) [13 14 22]

<400> SEQUENCE: 802

Thr Val Met Glu Asn Phe Val Ala Phe Val Asp Lys Cys Cys Ala Ala
1               5                   10                  15

Asp Asp Lys Glu Ala Cys Phe Ala Val Glu
            20                  25

<210> SEQ ID NO 803
<211> LENGTH: 25
<212> TYPE: PRT
<213> ORGANISM: Homo sapiens
<220> FEATURE:
<221> NAME/KEY: MOD_RES
<222> LOCATION: (1)..(25)
<223> OTHER INFORMATION: Glycation (2) [11 18], Glycation [7 ?]
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (11)..(18)
<223> OTHER INFORMATION: Glycation (2) [11 18]
<220> FEATURE:
<221> NAME/KEY: MOD_RES
<222> LOCATION: (12)..(21)
<223> OTHER INFORMATION: Carboxymethyl C (3) [12 13 21]

<400> SEQUENCE: 803

Val Met Glu Asn Phe Val Ala Phe Val Asp Lys Cys Cys Ala Ala Asp
1               5                   10                  15

Asp Lys Glu Ala Cys Phe Ala Val Glu
            20                  25

<210> SEQ ID NO 804
<211> LENGTH: 35
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Deamidation N [8]
<220> FEATURE:
<221> NAME/KEY: MOD_RES
<222> LOCATION: (16)..(25)
<223> OTHER INFORMATION: Carboxymethyl C (3) [16 17 25]

<400> SEQUENCE: 804

Gln Leu Lys Thr Val Met Glu Asn Phe Val Ala Phe Val Asp Lys Cys
1               5                   10                  15

Cys Ala Ala Asp Asp Lys Glu Ala Cys Phe Ala Val Glu Gly Pro Lys
            20                  25                  30

Leu Val Val
        35

<210> SEQ ID NO 805
<211> LENGTH: 41
<212> TYPE: PRT
<213> ORGANISM: Homo sapiens
<220> FEATURE:
<221> NAME/KEY: MOD_RES
<222> LOCATION: (1)..(41)
<223> OTHER INFORMATION: Glycation (2) [2 ?]
<220> FEATURE:
<221> NAME/KEY: MOD_RES
<222> LOCATION: (7)..(7)
<223> OTHER INFORMATION: Deamidation N [7]
<220> FEATURE:

<221> NAME/KEY: MOD_RES
<222> LOCATION: (15)..(24)
<223> OTHER INFORMATION: Carboxymethyl C (3) [15 16 24]

<400> SEQUENCE: 805

Leu Lys Thr Val Met Glu Asn Phe Val Ala Phe Val Asp Lys Cys Cys
1               5                   10                  15

Ala Ala Asp Asp Lys Glu Ala Cys Phe Ala Val Glu Gly Pro Lys Leu
                20                  25                  30

Val Val Ser Thr Gln Thr Ala Leu Ala
            35                  40

<210> SEQ ID NO 806
<211> LENGTH: 41
<212> TYPE: PRT
<213> ORGANISM: Homo sapiens
<220> FEATURE:
<221> NAME/KEY: MOD_RES
<222> LOCATION: (1)..(41)
<223> OTHER INFORMATION: Glycation (2) [2 ?
<220> FEATURE:
<221> NAME/KEY: MOD_RES
<222> LOCATION: (1)..(41)
<223> OTHER INFORMATION: Glycation (2) [2 ?], Glycation (3) [11 18 28]
<220> FEATURE:
<221> NAME/KEY: MOD_RES
<222> LOCATION: (2)..(2)
<223> OTHER INFORMATION: Oxidation M [2]
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (12)..(21)
<223> OTHER INFORMATION: Carboxymethyl C (3) [12 13 21]

<400> SEQUENCE: 806

Leu Lys Thr Val Met Glu Asn Phe Val Ala Phe Val Asp Lys Cys Cys
1               5                   10                  15

Ala Ala Asp Asp Lys Glu Ala Cys Phe Ala Val Glu Gly Pro Lys Leu
                20                  25                  30

Val Val Ser Thr Gln Thr Ala Leu Ala
            35                  40

<210> SEQ ID NO 807
<211> LENGTH: 38
<212> TYPE: PRT
<213> ORGANISM: Homo sapiens

<400> SEQUENCE: 807

Val Met Glu Asn Phe Val Ala Phe Val Asp Lys Cys Cys Ala Ala Asp
1               5                   10                  15

Asp Lys Glu Ala Cys Phe Ala Val Glu Gly Pro Lys Leu Val Val Ser
                20                  25                  30

Thr Gln Thr Ala Leu Ala
            35

<210> SEQ ID NO 808
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation M [6]

```
<400> SEQUENCE: 808

Gln Leu Lys Thr Val Met
1               5

<210> SEQ ID NO 809
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 809

Gln Leu Lys Thr Val
1               5

<210> SEQ ID NO 810
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]

<400> SEQUENCE: 810

Leu Lys Thr Val Met Glu
1               5

<210> SEQ ID NO 811
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation (1)
<220> FEATURE:
<221> NAME/KEY: MOD_RES
<222> LOCATION: (4)..(4)
<223> OTHER INFORMATION: Oxidation M [4]

<400> SEQUENCE: 811

Lys Thr Val Met Glu
1               5

<210> SEQ ID NO 812
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: Glycation [?]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (9)..(10)
<223> OTHER INFORMATION: Carboxymethyl C (2) [9 10]

<400> SEQUENCE: 812

Asn Phe Val Ala Phe Val Asp Lys Cys Cys Ala Ala Asp Asp Lys Glu
1               5                   10                  15

<210> SEQ ID NO 813
```

```
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 813

His Val Lys Leu Val Asn Glu Leu Thr Glu
1               5                   10

<210> SEQ ID NO 814
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (8)..(15)
<223> OTHER INFORMATION: Glycation (2) [8 15]
<220> FEATURE:
<221> NAME/KEY: MOD_RES
<222> LOCATION: (9)..(18)
<223> OTHER INFORMATION: Carboxymethyl C (3) [9 10 18]

<400> SEQUENCE: 814

Asn Phe Val Ala Phe Val Asp Lys Cys Cys Ala Ala Asp Asp Lys Glu
1               5                   10                  15

Ala Cys Phe Ala Val Glu
            20

<210> SEQ ID NO 815
<211> LENGTH: 19
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
<222> LOCATION: (1)..(19)
<223> OTHER INFORMATION: Glycation [?], Glycation (2) [8 15]
<220> FEATURE:
<221> NAME/KEY: MOD_RES
<222> LOCATION: (9)..(18)
<223> OTHER INFORMATION: Carboxymethyl C (3) [9 10 18]

<400> SEQUENCE: 815

Asn Phe Val Ala Phe Val Asp Lys Cys Cys Ala Ala Asp Asp Lys Glu
1               5                   10                  15

Ala Cys Phe

<210> SEQ ID NO 816
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: Glycation [?]
<220> FEATURE:
<221> NAME/KEY: MOD_RES
<222> LOCATION: (1)..(1)
<223> OTHER INFORMATION: Deamidation N [1]
<220> FEATURE:
<221> NAME/KEY: MOD_RES
```

```
<222> LOCATION: (9)..(10)
<223> OTHER INFORMATION: Carboxymethyl C (2) [9 10]

<400> SEQUENCE: 816

Asn Phe Val Ala Phe Val Asp Lys Cys Cys Ala Ala Asp Asp Lys Glu
1               5                   10                  15

Ala

<210> SEQ ID NO 817
<211> LENGTH: 21
<212> TYPE: PRT
<213> ORGANISM: Homo sapiens
<220> FEATURE:
<221> NAME/KEY: MOD_RES
<222> LOCATION: (1)..(21)
<223> OTHER INFORMATION: Glycation [?]
<220> FEATURE:
<221> NAME/KEY: MOD_RES
<222> LOCATION: (8)..(17)
<223> OTHER INFORMATION: Carboxymethyl C (3) [8 9 17]

<400> SEQUENCE: 817

Phe Val Ala Phe Val Asp Lys Cys Cys Ala Ala Asp Asp Lys Glu Ala
1               5                   10                  15

Cys Phe Ala Val Glu
            20

<210> SEQ ID NO 818
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Carboxymethyl C [7]

<400> SEQUENCE: 818

Ala Asp Asp Lys Glu Ala Cys Phe Ala Val Glu
1               5                   10

<210> SEQ ID NO 819
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 819

Asp Asp Lys Glu Ala Cys Phe Ala Val Glu
1               5                   10

<210> SEQ ID NO 820
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (4)..(4)
<223> OTHER INFORMATION: Carboxymethyl C [4]

<400> SEQUENCE: 820

Lys Glu Ala Cys Phe Ala Val Glu
```

```
<210> SEQ ID NO 821
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Carboxymethyl C [3]

<400> SEQUENCE: 821

Glu Ala Cys Phe Ala Val Glu
1               5

<210> SEQ ID NO 822
<211> LENGTH: 17
<212> TYPE: PRT
<213> ORGANISM: Homo sapiens
<220> FEATURE:
<221> NAME/KEY: MOD_RES
<222> LOCATION: (3)..(10)
<223> OTHER INFORMATION: Glycation (2) [3 10]
<220> FEATURE:
<221> NAME/KEY: MOD_RES
<222> LOCATION: (4)..(13)
<223> OTHER INFORMATION: Carboxymethyl C (3) [4 5 13]

<400> SEQUENCE: 822

Val Asp Lys Cys Cys Ala Ala Asp Asp Lys Glu Ala Cys Phe Ala Val
1               5                   10                  15

Glu

<210> SEQ ID NO 823
<211> LENGTH: 15
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (3) [2 3 11]

<400> SEQUENCE: 823

Lys Cys Cys Ala Ala Asp Asp Lys Glu Ala Cys Phe Ala Val Glu
1               5                   10                  15

<210> SEQ ID NO 824
<211> LENGTH: 14
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Carboxymethyl C (3) [1 2 10]
<220> FEATURE:
<221> NAME/KEY: MOD_RES
<222> LOCATION: (7)..(7)
<223> OTHER INFORMATION: Glycation [7]

<400> SEQUENCE: 824

Cys Cys Ala Ala Asp Asp Lys Glu Ala Cys Phe Ala Val Glu
1               5                   10

<210> SEQ ID NO 825
<211> LENGTH: 13
<212> TYPE: PRT
<213> ORGANISM: Homo sapiens
<220> FEATURE:
<221> NAME/KEY: MOD_RES
```

```
<222> LOCATION: (1)..(9)
<223> OTHER INFORMATION: Carboxymethyl C (2) [1 9]

<400> SEQUENCE: 825

Cys Ala Ala Asp Asp Lys Glu Ala Cys Phe Ala Val Glu
1               5                   10

<210> SEQ ID NO 826
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 826

His Val Lys Leu Val Asn Glu Leu Thr
1               5

<210> SEQ ID NO 827
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Deamidation N [1]

<400> SEQUENCE: 827

Asn Phe Val Ala Phe Val
1               5

<210> SEQ ID NO 828
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Glycation [8]
<220> FEATURE:
<221> NAME/KEY: MOD_RES
<222> LOCATION: (9)..(10)
<223> OTHER INFORMATION: Carboxymethyl C (2) [9 10]

<400> SEQUENCE: 828

Asn Phe Val Ala Phe Val Asp Lys Cys Cys Ala Ala Asp Asp
1               5                   10

<210> SEQ ID NO 829
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Deamidation N [6]

<400> SEQUENCE: 829

His Val Lys Leu Val Asn Glu Leu
1               5

<210> SEQ ID NO 830
<211> LENGTH: 13
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: Deamidation N [1]
<220> FEATURE:
<221> NAME/KEY: MOD_RES
<222> LOCATION: (8)..(8)
<223> OTHER INFORMATION: Glycation [8]
<220> FEATURE:
<221> NAME/KEY: MOD_RES
<222> LOCATION: (9)..(10)
<223> OTHER INFORMATION: Carboxymethyl C (2) [9 10]

<400> SEQUENCE: 830

Asn Phe Val Ala Phe Val Asp Lys Cys Cys Ala Ala Asp
1               5                   10

<210> SEQ ID NO 831
<211> LENGTH: 15
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Carboxymethyl C (2) [8 9]

<400> SEQUENCE: 831

Phe Val Ala Phe Val Asp Lys Cys Cys Ala Ala Asp Asp Lys Glu
1               5                   10                  15

<210> SEQ ID NO 832
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Glycation [5]

<400> SEQUENCE: 832

Ala Ala Asp Asp Lys Glu
1               5

<210> SEQ ID NO 833
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glycation [4]

<400> SEQUENCE: 833

Ala Asp Asp Lys Glu
1               5

<210> SEQ ID NO 834
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 834

Lys Leu Val Asn Glu Leu Thr Glu
1               5

<210> SEQ ID NO 835
<211> LENGTH: 12
```

```
<212> TYPE: PRT
<213> ORGANISM: Homo sapiens
<220> FEATURE:
<221> NAME/KEY: MOD_RES
<222> LOCATION: (1)..(12)
<223> OTHER INFORMATION: Glycation [?]
<220> FEATURE:
<221> NAME/KEY: MOD_RES
<222> LOCATION: (1)..(12)
<223> OTHER INFORMATION: Glycation [?], Glycation (2) [4 11]
<220> FEATURE:
<221> NAME/KEY: MOD_RES
<222> LOCATION: (5)..(6)
<223> OTHER INFORMATION: Carboxymethyl C (2) [5 6]

<400> SEQUENCE: 835

Phe Val Asp Lys Cys Cys Ala Ala Asp Asp Lys Glu
1               5                   10

<210> SEQ ID NO 836
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Glycation [?]
<220> FEATURE:
<221> NAME/KEY: MOD_RES
<222> LOCATION: (3)..(4)
<223> OTHER INFORMATION: Carboxymethyl C (2) [3 4]

<400> SEQUENCE: 836

Asp Lys Cys Cys Ala Ala Asp Asp Lys Glu
1               5                   10

<210> SEQ ID NO 837
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 837

Cys Ala Ala Asp Asp Lys Glu
1               5

<210> SEQ ID NO 838
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 838

Ala Cys Phe Ala Val Glu
1               5

<210> SEQ ID NO 839
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]
<220> FEATURE:
```

```
<221> NAME/KEY: MOD_RES
<222> LOCATION: (9)..(9)
<223> OTHER INFORMATION: Glycation [9]

<400> SEQUENCE: 839

Ala Cys Phe Ala Val Glu Gly Pro Lys
1               5

<210> SEQ ID NO 840
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 840

Ala Cys Phe Ala Val Glu Gly Pro
1               5

<210> SEQ ID NO 841
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]
<220> FEATURE:
<221> NAME/KEY: MOD_RES
<222> LOCATION: (9)..(9)
<223> OTHER INFORMATION: Glycation [9]

<400> SEQUENCE: 841

Ala Cys Phe Ala Val Glu Gly Pro Lys Leu Val Val
1               5                   10

<210> SEQ ID NO 842
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Glycation [6]

<400> SEQUENCE: 842

Ala Val Glu Gly Pro Lys Leu Val Val Ser Thr Gln Thr Ala Leu Ala
1               5                   10                  15

<210> SEQ ID NO 843
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 843

Ala Cys Phe Ala
1

<210> SEQ ID NO 844
<211> LENGTH: 5
<212> TYPE: PRT
<213> ORGANISM: Homo sapiens
<220> FEATURE:
```

```
<221> NAME/KEY: MOD_RES
<222> LOCATION: (1)..(1)
<223> OTHER INFORMATION: Carboxymethyl C [1]

<400> SEQUENCE: 844

Cys Phe Ala Val Glu
1               5

<210> SEQ ID NO 845
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Deamidation N [4]
<220> FEATURE:
<221> NAME/KEY: MOD_RES
<222> LOCATION: (7)..(7)
<223> OTHER INFORMATION: Glycation [7]
<220> FEATURE:
<221> NAME/KEY: MOD_RES
<222> LOCATION: (13)..(13)
<223> OTHER INFORMATION: Carboxymethyl C [13]

<400> SEQUENCE: 845

Lys Leu Val Asn Glu Leu Thr Glu Phe Ala Lys Thr Cys Val Ala Asp
1               5                   10                  15

Glu

<210> SEQ ID NO 846
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 846

Gly Pro Lys Leu Val Val
1               5

<210> SEQ ID NO 847
<211> LENGTH: 20
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Glycation [8]
<220> FEATURE:
<221> NAME/KEY: MOD_RES
<222> LOCATION: (10)..(19)
<223> OTHER INFORMATION: Carboxymethyl C (2) [10 19]

<400> SEQUENCE: 847

Asn Glu Leu Thr Glu Phe Ala Lys Thr Cys Val Ala Asp Glu Ser His
1               5                   10                  15

Ala Gly Cys Glu
            20

<210> SEQ ID NO 848
<211> LENGTH: 6
<212> TYPE: PRT
<213> ORGANISM: Homo sapiens
<220> FEATURE:
<221> NAME/KEY: MOD_RES
<222> LOCATION: (3)..(3)
```

```
<223> OTHER INFORMATION: Glycation [3]
<220> FEATURE:
<221> NAME/KEY: MOD_RES
<222> LOCATION: (6)..(6)
<223> OTHER INFORMATION: Deamidation N [6]

<400> SEQUENCE: 848

His Val Lys Leu Val Asn
1               5

<210> SEQ ID NO 849
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]

<400> SEQUENCE: 849

His Val Lys Leu Val
1               5

<210> SEQ ID NO 850
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Deamidation N [5]

<400> SEQUENCE: 850

Val Lys Leu Val Asn Glu
1               5

<210> SEQ ID NO 851
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (4)..(4)
<223> OTHER INFORMATION: Deamidation N [4]

<400> SEQUENCE: 851

Lys Leu Val Asn Glu
1               5

<210> SEQ ID NO 852
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Carboxymethyl C [8]

<400> SEQUENCE: 852

Leu Thr Glu Phe Ala Lys Thr Cys Val Ala Asp
1               5                   10

<210> SEQ ID NO 853
<211> LENGTH: 8
<212> TYPE: PRT
```

```
<213> ORGANISM: Homo sapiens
<220> FEATURE:
<221> NAME/KEY: MOD_RES
<222> LOCATION: (6)..(6)
<223> OTHER INFORMATION: Glycation [6]
<220> FEATURE:
<221> NAME/KEY: MOD_RES
<222> LOCATION: (8)..(8)
<223> OTHER INFORMATION: Carboxymethyl C [8]

<400> SEQUENCE: 853

Leu Thr Glu Phe Ala Lys Thr Cys
1               5

<210> SEQ ID NO 854
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Glycation [6]

<400> SEQUENCE: 854

Leu Thr Glu Phe Ala Lys Thr
1               5

<210> SEQ ID NO 855
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Glycation [6]

<400> SEQUENCE: 855

Leu Thr Glu Phe Ala Lys
1               5

<210> SEQ ID NO 856
<211> LENGTH: 16
<212> TYPE: PRT
<213> ORGANISM: Homo sapiens
<220> FEATURE:
<221> NAME/KEY: MOD_RES
<222> LOCATION: (6)..(15)
<223> OTHER INFORMATION: Carboxymethyl C (2) [6 15]

<400> SEQUENCE: 856

Glu Phe Ala Lys Thr Cys Val Ala Asp Glu Ser His Ala Gly Cys Glu
1               5                   10                  15

<210> SEQ ID NO 857
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 857

Phe Ala Lys Thr Cys Val Ala Asp Glu Ser His
1               5                   10

<210> SEQ ID NO 858
<211> LENGTH: 13
<212> TYPE: PRT
```

```
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (3)..(12)
<223> OTHER INFORMATION: Carboxymethyl C (2) [3 12]

<400> SEQUENCE: 858

Lys Thr Cys Val Ala Asp Glu Ser His Ala Gly Cys Glu
1               5                   10

<210> SEQ ID NO 859
<211> LENGTH: 12
<212> TYPE: PRT
<213> ORGANISM: Homo sapiens
<220> FEATURE:
<221> NAME/KEY: MOD_RES
<222> LOCATION: (2)..(11)
<223> OTHER INFORMATION: Carboxymethyl C (2) [2 11]

<400> SEQUENCE: 859

Thr Cys Val Ala Asp Glu Ser His Ala Gly Cys Glu
1               5                   10

<210> SEQ ID NO 860
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Carboxymethyl C [9]

<400> SEQUENCE: 860

Val Ala Asp Glu Ser His Ala Gly Cys Glu
1               5                   10

<210> SEQ ID NO 861
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Carboxymethyl C [7]

<400> SEQUENCE: 861

Asp Glu Ser His Ala Gly Cys Glu
1               5

<210> SEQ ID NO 862
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Carboxymethyl C [6]

<400> SEQUENCE: 862

Glu Ser His Ala Gly Cys Glu
1               5

<210> SEQ ID NO 863
<211> LENGTH: 21
<212> TYPE: PRT
```

```
<213> ORGANISM: Homo sapiens
<220> FEATURE:
<221> NAME/KEY: MOD_RES
<222> LOCATION: (1)..(21)
<223> OTHER INFORMATION: Glycation [?]
<220> FEATURE:
<221> NAME/KEY: MOD_RES
<222> LOCATION: (5)..(14)
<223> OTHER INFORMATION: Carboxymethyl C (2) [5 14]

<400> SEQUENCE: 863

Phe Ala Lys Thr Cys Val Ala Asp Glu Ser His Ala Gly Cys Glu Lys
1               5                   10                  15

Ser Leu His Thr Leu
            20

<210> SEQ ID NO 864
<211> LENGTH: 16
<212> TYPE: PRT
<213> ORGANISM: Homo sapiens
<220> FEATURE:
<221> NAME/KEY: MOD_RES
<222> LOCATION: (3)..(16)
<223> OTHER INFORMATION: Glycation (2) [3 16]
<220> FEATURE:
<221> NAME/KEY: MOD_RES
<222> LOCATION: (5)..(14)
<223> OTHER INFORMATION: Carboxymethyl C (2) [5 14]

<400> SEQUENCE: 864

Phe Ala Lys Thr Cys Val Ala Asp Glu Ser His Ala Gly Cys Glu Lys
1               5                   10                  15

<210> SEQ ID NO 865
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]
<220> FEATURE:
<221> NAME/KEY: MOD_RES
<222> LOCATION: (5)..(5)
<223> OTHER INFORMATION: Carboxymethyl C [5]

<400> SEQUENCE: 865

Phe Ala Lys Thr Cys Val Ala Asp
1               5

<210> SEQ ID NO 866
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glycation [3]
<220> FEATURE:
<221> NAME/KEY: MOD_RES
<222> LOCATION: (5)..(5)
<223> OTHER INFORMATION: Carboxymethyl C [5]

<400> SEQUENCE: 866

Phe Ala Lys Thr Cys Val
1               5

<210> SEQ ID NO 867
<211> LENGTH: 5
<212> TYPE: PRT
```

-continued

```
<213> ORGANISM: Homo sapiens
<220> FEATURE:
<221> NAME/KEY: MOD_RES
<222> LOCATION: (3)..(3)
<223> OTHER INFORMATION: Glycation [3]
<220> FEATURE:
<221> NAME/KEY: MOD_RES
<222> LOCATION: (5)..(5)
<223> OTHER INFORMATION: Carboxymethyl C [5]

<400> SEQUENCE: 867

Phe Ala Lys Thr Cys
1               5

<210> SEQ ID NO 868
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycation [2]
<220> FEATURE:
<221> NAME/KEY: MOD_RES
<222> LOCATION: (4)..(4)
<223> OTHER INFORMATION: Carboxymethyl C [4]

<400> SEQUENCE: 868

Ala Lys Thr Cys Val Ala Asp Glu
1               5

<210> SEQ ID NO 869
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]
<220> FEATURE:
<221> NAME/KEY: MOD_RES
<222> LOCATION: (3)..(3)
<223> OTHER INFORMATION: Carboxymethyl C [3]

<400> SEQUENCE: 869

Lys Thr Cys Val Ala Asp Glu
1               5

<210> SEQ ID NO 870
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Carboxymethyl C [2]

<400> SEQUENCE: 870

Thr Cys Val Ala Asp Glu
1               5

<210> SEQ ID NO 871
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Carboxymethyl C [1]

<400> SEQUENCE: 871
```

```
Cys Val Ala Asp Glu
1               5

<210> SEQ ID NO 872
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 872

Ser His Ala Gly Cys Glu
1               5

<210> SEQ ID NO 873
<211> LENGTH: 34
<212> TYPE: PRT
<213> ORGANISM: Homo sapiens
<220> FEATURE:
<221> NAME/KEY: MOD_RES
<222> LOCATION: (1)..(34)
<223> OTHER INFORMATION: Oxidation M [?]
<220> FEATURE:
<221> NAME/KEY: MOD_RES
<222> LOCATION: (1)..(34)
<223> OTHER INFORMATION: Glycation [?]
<220> FEATURE:
<221> NAME/KEY: MOD_RES
<222> LOCATION: (5)..(34)
<223> OTHER INFORMATION: Carboxymethyl C (4) [5 18 33 34]

<400> SEQUENCE: 873

Ser His Ala Gly Cys Glu Lys Ser Leu His Thr Leu Phe Gly Asp Glu
1               5                   10                  15

Leu Cys Lys Val Ala Ser Leu Arg Glu Thr Tyr Gly Asp Met Ala Asp
            20                  25                  30

Cys Cys

<210> SEQ ID NO 874
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 874

Ser His Ala Gly Cys Glu Lys Ser Leu His Thr
1               5                   10

<210> SEQ ID NO 875
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (7)..(7)
<223> OTHER INFORMATION: Glycation [7]

<400> SEQUENCE: 875

Ser His Ala Gly Cys Glu Lys Ser Leu His
```

-continued

```
1               5                   10

<210> SEQ ID NO 876
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (7)..(7)
<223> OTHER INFORMATION: Glycation [7]

<400> SEQUENCE: 876

Ser His Ala Gly Cys Glu Lys Ser
1               5

<210> SEQ ID NO 877
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]
<220> FEATURE:
<221> NAME/KEY: MOD_RES
<222> LOCATION: (7)..(7)
<223> OTHER INFORMATION: Glycation [7]

<400> SEQUENCE: 877

Ser His Ala Gly Cys Glu Lys
1               5

<210> SEQ ID NO 878
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Carboxymethyl C [5]

<400> SEQUENCE: 878

Ser His Ala Gly Cys
1               5

<210> SEQ ID NO 879
<211> LENGTH: 29
<212> TYPE: PRT
<213> ORGANISM: Homo sapiens
<220> FEATURE:
<221> NAME/KEY: MOD_RES
<222> LOCATION: (12)..(28)
<223> OTHER INFORMATION: Carboxymethyl C (3) [12 27 28]
<220> FEATURE:
<221> NAME/KEY: MOD_RES
<222> LOCATION: (24)..(24)
<223> OTHER INFORMATION: Oxidation M [24]

<400> SEQUENCE: 879

Lys Ser Leu His Thr Leu Phe Gly Asp Glu Leu Cys Lys Val Ala Ser
1               5                   10                  15

Leu Arg Glu Thr Tyr Gly Asp Met Ala Asp Cys Cys Glu
            20                  25

<210> SEQ ID NO 880
```

```
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (5)..(21)
<223> OTHER INFORMATION: Carboxymethyl C (3) [5 20 21]
<220> FEATURE:
<221> NAME/KEY: MOD_RES
<222> LOCATION: (6)..(6)
<223> OTHER INFORMATION: Glycation [6]

<400> SEQUENCE: 880

Gly Asp Glu Leu Cys Lys Val Ala Ser Leu Arg Glu Thr Tyr Gly Asp
1               5                   10                  15

Met Ala Asp Cys Cys Glu
            20

<210> SEQ ID NO 881
<211> LENGTH: 21
<212> TYPE: PRT
<213> ORGANISM: Homo sapiens
<220> FEATURE:
<221> NAME/KEY: MOD_RES
<222> LOCATION: (4)..(20)
<223> OTHER INFORMATION: Carboxymethyl C (3) [4 19 20]
<220> FEATURE:
<221> NAME/KEY: MOD_RES
<222> LOCATION: (16)..(16)
<223> OTHER INFORMATION: Oxidation M [16]

<400> SEQUENCE: 881

Asp Glu Leu Cys Lys Val Ala Ser Leu Arg Glu Thr Tyr Gly Asp Met
1               5                   10                  15

Ala Asp Cys Cys Glu
            20

<210> SEQ ID NO 882
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation M [1]
<220> FEATURE:
<221> NAME/KEY: MOD_RES
<222> LOCATION: (3)..(19)
<223> OTHER INFORMATION: Carboxymethyl C (3) [3 18 19]
<220> FEATURE:
<221> NAME/KEY: MOD_RES
<222> LOCATION: (4)..(4)
<223> OTHER INFORMATION: Glycation [4]

<400> SEQUENCE: 882

Glu Leu Cys Lys Val Ala Ser Leu Arg Glu Thr Tyr Gly Asp Met Ala
1               5                   10                  15

Asp Cys Cys Glu
            20

<210> SEQ ID NO 883
<211> LENGTH: 28
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: Oxidation M [1]
<220> FEATURE:
<221> NAME/KEY: MOD_RES
<222> LOCATION: (1)..(28)
<223> OTHER INFORMATION: Glycation [?]
<220> FEATURE:
<221> NAME/KEY: MOD_RES
<222> LOCATION: (6)..(22)
<223> OTHER INFORMATION: Carboxymethyl C (3) [6 21 22]

<400> SEQUENCE: 883

Phe Gly Asp Glu Leu Cys Lys Val Ala Ser Leu Arg Glu Thr Tyr Gly
1               5                   10                  15

Asp Met Ala Asp Cys Cys Glu Lys Gln Glu Pro Glu
            20                  25

<210> SEQ ID NO 884
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 884

Lys Ser Leu His Thr Leu Phe Gly
1               5

<210> SEQ ID NO 885
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 885

Lys Ser Leu His Thr Leu Phe
1               5

<210> SEQ ID NO 886
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glycation [1]

<400> SEQUENCE: 886

Lys Ser Leu His Thr Leu
1               5

<210> SEQ ID NO 887
<211> LENGTH: 14
<212> TYPE: PRT
<213> ORGANISM: Homo sapiens

<400> SEQUENCE: 887

Ile Thr Pro Asn Leu Ala Glu Phe Ala Phe Ser Leu Tyr Arg
1               5                   10

<210> SEQ ID NO 888
<211> LENGTH: 10
<212> TYPE: PRT
```

```
<213> ORGANISM: Homo sapiens

<400> SEQUENCE: 888

Leu Glu Val Ala Glu Ser Glu Phe Thr His
1               5                   10
```